US006632921B1

(12) United States Patent
Sikorski et al.

(10) Patent No.: US 6,632,921 B1
(45) Date of Patent: Oct. 14, 2003

(54) SERYL-LYSYL-BASED PEPTIDE AND PEPTIDOMIMETIC INHIBITORS OF N-MYRISTOYL TRANSFERASE AS ANTI-INFECTIVE AGENTS

(75) Inventors: James A. Sikorski, Des Peres, MO (US); Devadas Balekudru, Chesterfield, MO (US); Daniel P. Getman, Chesterfield, MO (US); David L. Brown, Chesterfield, MO (US); Srinivasan Nagarajan, Chesterfield, MO (US); Mark E. Zupec, O'Fallon, IL (US); Jeffrey I. Gordon, St. Louis, MO (US)

(73) Assignee: G. D Searle & Co, Skokie, IL (US)

( * ) Notice: Subject to any disclaimer, the term of this patent is extended or adjusted under 35 U.S.C. 154(b) by 0 days.

(21) Appl. No.: 09/277,573

(22) Filed: Mar. 26, 1999

Related U.S. Application Data

(63) Continuation of application No. 08/823,101, filed on Mar. 24, 1997, now Pat. No. 5,942,600, which is a continuation of application No. 08/450,607, filed on May 25, 1995, now abandoned.

(51) Int. Cl.$^7$ .................................................. C07K 5/08

(52) U.S. Cl. ........................ 530/331; 562/562; 562/567; 514/18; 514/19

(58) Field of Search .......................... 530/331; 562/562, 562/567; 514/18, 19

(56) References Cited

U.S. PATENT DOCUMENTS 5,486,503 A * 1/1996 Oppenheim et al. ........... 514/2

* cited by examiner

*Primary Examiner*—Christopher S. F. Low
*Assistant Examiner*—David Lukton
(74) *Attorney, Agent, or Firm*—J. Timothy Keane; Joseph R. Schuh

(57) ABSTRACT

Seryl-lysyl-based peptide and peptidomimetic compounds are described as inhibitors of the enzyme N-myristoyl transferase to provide selective control of the fungal organism *Candida albicans*. Peptidomimetic compounds of particular interest are those of the formula:

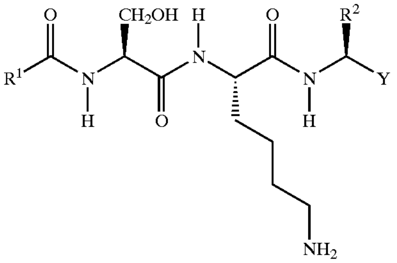

wherein $R^1$ is selected form aminoalkyl, p-aminoalkylphenylalkyl, imidazolylalkylphenylalkyl, 2-alkylimidazolylalkylphenylalkyl, benzimidazolylalkylphenylalkyl and 2-alkylbenzimidazolylalkylphenylalkyl; wherein $R^2$ is selected from hydrido, alkyl, cycloalkyl, akenyl, alkynyl, haloalkyl, benzyl, alkylphenylalkyl, alkoxyphenylalkyl, halophenylalkyl, phenethyl, cycloalkylalkyl, halocycloalkylalkyl, alkylcycloalkylalkyl, alkoxycycloalkylalkyl and naphthylalkyl; wherein Y is selected from carboxylic acid, hydroxamic acid, phosphonic acid and tetrazolyl; or a pharmaceutically-acceptable salt, amide or ester thereof. Compounds of the formula are species-specific inhibitors of *C. albicans* with little effect on human NMT enzyme and thus would.be useful in treating *C. albicans* fungal infections in humans.

12 Claims, No Drawings

SEQUENCE LISTING

```
<160> NUMBER OF SEQ ID NOS: 5

<210> SEQ ID NO 1
<211> LENGTH: 10
<212> TYPE: PRT
<213> ORGANISM: Candida albicans

<400> SEQUENCE: 1

Gly Cys Gly Ala Ser Val Pro Val Asp Asp
1               5                   10


<210> SEQ ID NO 2
<211> LENGTH: 8
<212> TYPE: PRT
<213> ORGANISM: Saccharomyces cerevisiae

<400> SEQUENCE: 2

Gly Leu Tyr Ala Ser Lys Leu Ser
1               5


<210> SEQ ID NO 3
<211> LENGTH: 8
<212> TYPE: PRT
<213> ORGANISM: Saccharomyces cerevisiae

<400> SEQUENCE: 3

Ala Leu Tyr Ala Ser Lys Leu Ser
1               5


<210> SEQ ID NO 4
<211> LENGTH: 8
<212> TYPE: PRT
<213> ORGANISM: Saccharomyces cerevisiae

<400> SEQUENCE: 4

Gly Asn Ala Ala Ser Ala Arg Arg
1               5


<210> SEQ ID NO 5
<211> LENGTH: 8
<212> TYPE: PRT
<213> ORGANISM: Saccharomyces cerevisiae

<400> SEQUENCE: 5

Ser Asn Ser Leu Lys Asn Ser Thr
1               5
```

SERYL-LYSYL-BASED PEPTIDE AND PEPTIDOMIMETIC INHIBITORS OF N-MYRISTOYL TRANSFERASE AS ANTI-INFECTIVE AGENTS

This is a continuation of application Ser. No. 08/823,101 filed on Mar. 24, 1997, now U.S. Pat. No. 5,942,600 which is a continuation of application Ser. No. 08/450,607 filed on May 25, 1995, which is now abandoned.

FIELD OF THE INVENTION

Compounds and methods are known for control of pathogenic fungi. Of particular interest herein are certain peptidomimetic compounds useful to inhibit the enzyme N-myristoyl transferase which, in turn, is useful for selective control of the fungal organism *Candida albicans.*

BACKGROUND OF THE INVENTION

*Candida albicans*, a diploid asexual yeast, is a major cause of systemic fungal infections, particularly in patients with acquired immunodeficiency syndrome (AIDS).

Species of the genus Candida are part of the normal human flora and are the most common yeast pathogens. *Candida albicans*, a dimorphic, asexual yeast, is the most frequently identified pathogen among Candida species. Systemic Candida infections commonly occur in patients who have been immunocompromised by treatment with immunosuppressive medication and broad spectrum antibiotics.

At the present time, therapy for a patient afflicted with systemic *C. albicans* infection is treatment with amphotericin B alone or in combination with the nucleoside analog 5-fluorocytosine. Alternatively, lanosterol 14α-demethylase inhibitors such as the imidazole ketoconazole or the triazole fluconazole are used. While amphotericin B is an effective fungicidal agent, it is nephrotoxic, does not penetrate into the cerebrospinal fluid, and must be given intravenously. Ketoconazole and the newer azoles are fungistatic rather than fungicidal.

A series of n-alkoxyacetic acids has been tested for effects on the growth of a variety of fungal species, including *C. albicans*, in Sabouraud dextrose agar, with 3-oxaundecanoic acid showing the broadest spectrum and highest potency and several other compounds, including 3-oxatetradecanoic acid, inhibiting growth [Gerson et al, *J. Pharmaceut. Sci.*, 68, 82–84 (1979)].

U.S. Pat. No. 5,073,571 describes ether containing fatty acid compounds such as 13-oxatetradecanoic acid which have been evaluated as antiviral agents, e.g. against retroviruses such as HIV-1. The compound 13-oxatetradecanoic acid, which is a substrate for human acyl CoA synthetase and human myristoylCoA:protein N-myristoyltransferase (NMT), inhibits HIV-1 replication in acutely and chronically infected human T-lymphocyte cell lines at doses which do not cause cellular toxicity [B. Devadas et al, *J. Biol. Chem.*, 267, 7224–7239 (1992)]. Studies with tritiated 13-oxatetradecanoic acid indicate that this fatty acid analog is incorporated into HIV-1 $Pr55^{gag}$ and nef and some, but not all, cellular proteins [Bryant et al, *Proc. Nat'l. Acad. Sci. USA*, 88, 2055–2059 (1991)].

N-myristoylation of proteins is catalyzed by myristoyl-CoA:protein N-myristoyltransferase (NMT[1], N-myristoyltransferase). NMT transfers myristate (C14:0) from myristoylCoA to the amino-terminal Gly residue of proteins in such diverse eukaryotic species as animals, plants, and fungi [J. K. Lodge et al, *J. Biol. Chem.*, 269, 2996–3000 (1994)]. This modification is required for the biological functions of a variety of cellular and viral proteins [D. R. Johnson et al, *Ann. Rev. Biochem.*, in press, (1994)]. The NMT1 gene is essential for vegetative growth of *S. cerevisiae*. Moreover, haploid strains of *S. cerevisiae* containing a nmt1 null allele are not viable [R. J. Duronio et al, *Proteins, Structure, Function, and Genetics*, 13, 41–56 (1992c)]. Metabolic labeling studies indicate that *S. cerevisiae* produces at least 12 N-myristoylproteins during exponential growth [R. J. Duronio et al, *J. Cell. Biol.*, 113, 1313–1330 (1991)]. Two functionally interchangeable ADP ribosylation factors, Arf1p and Arf2p, have been identified as N-myristoylproteins [T. Stearns et al, *Mol. Cell. Biol.*, 10, 6690–6699 (1990)]. Metabolic labeling studies have shown that a laboratory strain of *C.albicans* (B311) synthesizes a small number of cellular N-myristoylproteins during exponential growth in rich media The *C.albicans* NMT gene has been isolated. Its 451 amino acid protein product shares 55% identity with the *S. cerevisiae* acyltransferase [R. C. Wiegand et al, *J. Biol. Chem.*, 267, 8591–8598 (1992)]. Two ARF genes have also been indentified in *C. albicans* [C. A. Langner et al, *J. Biol. Chem.*, 267, 17159–17169 (1992)]. At least one of them is a substrate for NMT [J. K. Lodge et al, *J. Biol. Chem.*, 269, 2996–3000 (1994)]. Although *C. albicans* does not have a known sexual pathway, nonetheless it synthesizes a protein, Cag1, which is homologous to *S. cervisiae* Gpa1p [C. Sadhu et al, *Mol. Cell. Biol.*, 12, 1977–1985 (1992)]. The amino termirnal sequence of Cag1 (GCGASVPVDD) makes it a likely substrate for *S. cerevisiae* Nmt1p [D. A. Towler et al, *Ann. Rev. Biochem.*, 57, 69–99 (1988b)]. Moreover, CAG1 can complement the growth arrest and mating defects found in strains of *S. cerevisiae* with gpa1 null alleles [C. Sadhu et al, *Mol. Cell. Biol.*, 12, 1977–1985 (1992)].

The peptide substrate specificities of *C. albicans* and *S. cerevisiae* NMTs are considerably different than that of human NMT [W. J. Rocque et al, *J. Biol. Chem.*, 268, 9964–9971 (1993)]. However, surveys of a large panel of myristic acid analogs indicate that the acylCoA binding sites of the orthologous enzymes are quite similar [N. S. Kishore et al, *J. Biol. Chem.*, 268, 4889–4902 (1993) footnote 2]. This apparent divergence in the peptide but not acylCoA binding sites undoubtedly reflects the similar requirements of these NMT enzymes for myristoylCoA and the marked differences in the numbers and types of protein substrates they must acylate in vivo [D. A. Rudnick et al, *Adv. Enzvmol.*, 67, 375–430 (1993)].

Interaction between *Saccharomyces-cerevisiae*-derived myristoyl-CoA:protein N-myristoyltransferase (Nmt1p) and photoactivatable $^{125}I$-labeled octapeptides has been studied in the presence of other high-affinity peptide substrates and competitive inhibitors of such labeled octapeptides, such other peptide substrates and competitive inhibitors being the peptides GLYASKLS-$NH_2$ and ALYASKLS-$NH_2$, respectively [D. A. Rudnick et al, *Proc. Natl. Acad. Sci.*, 90(3), 1087–1091 (1993)]

DESCRIPTION OF THE INVENTION

Peptidomimetic compounds, and pharmaceutical compositions thereof, for inhibition of the enzyme N-myristoyl transferase, provide selective control of the fungal organism *Candida albicans*, where such peptidomimetic compounds are selected from a class of compounds of Formula I:

(I)

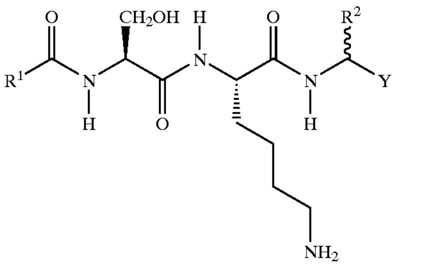

wherein $R^1$ is selected from aminoalkyl, aminoalkylcycloalkyl, aminoalkylcycloalkylalkyl, monoalkylaminoalkyl, dialkylaminoalkyl, monoalkylaminocycloalkylalkyl, dialkylaminocycloalkylalkyl, aminoalkylarylalkyl, monoalkylaminoalkylarylalkyl, dialkylaminoalkylarylalkyl, aminocycloalkyl, monocycloalkylaminoalkyl, monoalkylaminocycloalkyl, monocycloalkylaminocycloalkyl, dialkylaminocycloalkyl, aminocycloalkylarylalkyl, aminoalkylarylcycloalkyl, aminocycloalkylarylcycloalkyl, monocycloalkylaminoalkylarylalkyl, monoalkylaminocycloalkylarylalkyl, monoalkylaminoalkylarylcycloalkyl, monocycloalkylaminocycloalkylarylalkyl, monocycloalkylaminoalkylarylcycloalkyl, monoalkylaminocycloalkylarylcycloalkyl, monocycloalkylaminocycloalkylarylcycloalkyl, dialkylaminocycloalkylarylalkyl, dialkylaminoalkylarylcycloalkyl, dialkylaminocycloalkylarylcycloalkyl, heterocyclic-A-alkyl, heterocyclic-A-alkylarylalkyl, heterocyclic-A-cycloalkyl, heterocyclic-A-cycloalkylarylalkyl, heterocyclic-A-alkylarylcycloalkyl, heterocyclic-A-cycloalkylarylcycloalkyl, heteroaryl-A-alkyl, heteroaryl-A-alkylarylalkyl, heteroaryl-A-cycloalkyl, heteroaryl-A-cycloalkylarylalkyl, heteroaryl-A-alkylarylcycloalkyl and heteroaryl-A-cycloalkylarylcycloalkyl, wherein A is either a covalent bond or is a moiety selected from

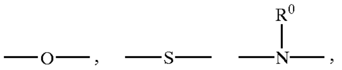

wherein $R^0$ is selected from hydrido, alkyl, cycloalkyl and cycloalkylalkyl; wherein any foregoing heterocyclic-containing moiety may be fused to an aryl ring to form an arylheterocyclic moiety, and wherein any foregoing heteroaryl-containing moiety may be fused to an aryl ring to form an arylheteroaryl moiety, and wherein any of said heterocyclic moiety, heteroaryl moiety, arylheterocyclic moiety and arylheteroaryl moiety may be independently substituted at one or more substitutable positions with one or more radicals selected from halo, alkyl, haloalkyl, cycloalkyl, cycloalkylalkyl, amino, aminoacyl, aminocarbonylalkoxy, monoalkylamino, dialkylamino, alkoxy, alkylthio, aralkyl and aryl, with the proviso that said heterocyclic moiety is selected from morpholino, thiomorpholino, piperazinyl, piperidinyl and pyrrolidinyl, and with the further proviso that said heteroaryl moiety is selected from imidazolyl and pyridinyl;

wherein $R^2$ is a radical selected from hydrido, alkyl, cycloalkyl, cycloalkylalkyl, bicycloalkyl, alkenyl, cycloalkenyl, fused bicycloalkenyl, cycloalkyl fused to cycloalkenyl, alkenylalkyl, alkynyl, aralkyl and aryl, wherein any of said $R^2$ radicals having a substitutable position may be substituted by one or more radicals selected from alkyl, cycloalkyl, cycloalkylalkyl, alkenyl, cycloalkenyl, fused bicycloalkenyl, cycloalkyl fused to cycloalkenyl, alkenylalkyl, alkynyl, halo, haloalkyl, alkoxy, alkoxyalkyl, alkylthio, aralkoxy, aryloxy, arylthio, aralkyl, aryl, alkoxycarbonyl, cycloalkoxycarbonyl, alkoxycarbonylalkyl and cycloalkoxycarbonylcycloalkyl;

wherein Y is an alkylol group or is an acidic group selected to contain at least one acidic hydrogen atom so as to impart a pKa less than about 5.0 to compound of Formula I;

or a pharmaceutically-acceptable ester, amide, or salt thereof.

Compounds of Formula I would be primarily useful in treating fungal infections caused by *Candida albicans*, particularly where selective inhibition of the NMT enzyme of this fungal organism is desirable over general NMT inhibition of the host, e.g., human subject. These compounds would also be useful as adjunctive therapies. For example, compounds of Formula I may be used in combination with other drugs, such as another anti-infective, e.g., metronidazole, to treat fungal infections.

The phrase "acidic group selected to contain at least one acidic hydrogen atom", as used to define the —Y moiety, is intended to embrace chemical groups which, when attached at the "C-terminus" position of Formula I, confers acidic character to the compound of Formula I. "Acidic character" means proton-donor capability, that is, the capacity of the compound of Formula I to be a proton donor in the presence of a proton-receiving substance such as water. Typically, the acidic group should be selected to have proton-donor capability such that the product compound of Formula I has a $PK_a$ in a range from about one to about six. More typically, the Formula I compound would have a $pK_a$ in a range from about one to about five. An example of an acidic group containing at least one acidic hydrogen atom is carboxyl group (—COOH) attached directly to the "C-terminus" position. There are many examples of acidic groups other than carboxyl group, selectable to contain at least one acidic hydrogen atom. Such other acidic groups may be collectively referred to as "bioisosteres of carboxylic acid" or referred to as "acidic bioisosteres". Specific examples of such acidic bioisosteres are described hereinafter. Compounds of Formula I may have one or more acidic protons and, therefore, may have one or more pKa values. It is preferred, however, that at least one of these $pK_a$ values of the Formula I compound as conferred by the —Y moiety be in a range from about one to about five. The —Y moiety may be attached to the C-terminus position through any portion of the —Y moiety which results in a Formula I compound being relatively stable and also having a labile or acidic proton to meet the foregoing $pK_a$ criteria. For example, where the —Y acid moiety is tetrazole, the tetrazole is attached at the ring carbon atom.

A class of preferred peptidomimetic compounds are those compounds of Formula II:

(II)

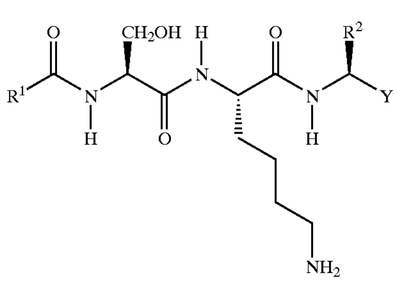

wherein $R^1$ is selected from aminoalkyl, aminoalkylcycloalkyl, aminoalkylcycloalkylalkyl, monoalkylaminoalkyl, dialkylaminoalkyl, monoalkylaminocycloalkylalkyl, dialkylaminocycloalkylalkyl, aminoalkylarylalkyl, monoalkylaminoalkylarylalkyl, dialkylaminoalkylarylalkyl, aminocycloalkyl, monocycloalkylaminoalkyl, monoalkylaminocycloalkyl, monocycloalkylaminocycloalkyl, dialkylaminocycloalkyl, aminocycloalkylarylalkyl, aminoalkylarylcycloalkyl, aminocycloalkylarylcycloalkyl, monocycloalkylaminoalkylarylalkyl, monoalkylaminocycloalkylarylalkyl, monoalkylaminoalkylarylcycloalkyl, monocycloalkylaminocycloalkylarylalkyl, monocycloalkylaminoalkylarylcycloalkyl, monoalkylaminocycloalkylarylcycloalkyl, monocycloalkylaminocycloalkylarylcycloalkyl, dialkylaminocycloalkylarylalkyl, dialkylaminoalkylarylcycloalkyl, dialkylaminocycloalkylarylcycloalkyl, heterocyclic-A-alkyl, heterocyclic-A-alkylarylalkyl, heterocyclic-A-cycloalkyl, heterocyclic-A-cycloalkylarylalkyl, heterocyclic-A-alkylarylcycloalkyl, heterocyclic-A-cycloalkylarylcycloalkyl, heteroaryl-A-alkyl, heeroaryl-A-alkylarylalkyl, heteroaryl- A-cycloalkyl, heteroaryl-A-cycloalkylarylalkyl, heteroaryl-A-alkylarylcycloalkyl and heteroaryl-A-cycloalkylarylcycloalkyl, wherein A is either a covalent bond or is a moiety selected from

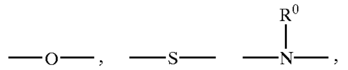

wherein $R^0$ is selected from hydrido, alkyl, cycloalkyl and cycloalkylalkyl; wherein any foregoing heterocyclic-containing moiety may be fused to an aryl ring to form an arylheterocyclic moiety, and wherein any foregoing heteroaryl-containing moiety may be fused to an aryl ring to form an arylheteroaryl moiety, and wherein any of said heterocyclic moiety, heteroaryl moiety, arylheterocyclic moiety and arylheteroaryl moiety may be independently substituted at one or more substitutable positions with one or more radicals selected from halo, alkyl, haloalkyl, cycloalkyl, cycloalkylalkyl, amino, aminoacyl, aminocarbonylalkoxy, monoalkylamino, dialkylamino, alkoxy, alkylthio, aralkyl and aryl, with the proviso that said heterocyclic moiety is selected from morpholino, thiomorpholino, piperazinyl, piperidinyl and pyrrolidinyl, and with the further proviso that said heteroaryl moiety is selected from imidazolyl and pyridinyl;

wherein $R^2$ is a radical selected from hydrido, alkyl, cycloalkyl, cycloalkylalkyl, bicycloalkyl, alkenyl, cycloalkenyl, fused bicycloalkenyl, cycloalkyl fused to cycloalkenyl, alkenylalkyl, alkynyl, aralkyl and aryl, wherein any of said $R^2$ radicals having a substitutable position may be substituted by one or more radicals selected from alkyl, cycloalkyl, cycloalkylalkyl, alkenyl, cycloalkenyl, fused bicycloalkenyl, cycloalkyl fused to cycloalkenyl, alkenylalkyl, alkynyl, halo, haloalkyl, alkoxy, alkoxyalkyl, alkylthio, aralkoxy, aryloxy, arylthio, aralkyl, aryl, alkoxycarbonyl, cycloalkoxycarbonyl, alkoxycarbonylalkyl and cycloalkoxycarbonylcycloalkyl;

wherein Y is selected from hydroxyalkyl, hydroxycycloalkyl, hydroxycycloalkylalkyl, hydroxyaryl, hydroxyaminocarbonylaralkyl, hydroxyaminocarbonyl, hydroxyaminocarbonylalkyl, hydroxyaminocarbonylcycloalkyl, hydroxyaminocarbonylcycloalkylalkyl, hydroxyaminocarbonylaryl, carboxyl, carboxyalkyl, carboxycycloalkyl, carboxycyloalkylalkyl, tetrazolyl, tetrazolylalkyl, tetrazolylcycloalkyl, tetrazolylcycloalkylalkyl, phosphinic acid, monoalkylphosphinic acid, dialkylphosphinic acid, monocycloalkylphosphinic acid, dicycloalkylphosphinic acid, monocycloalkylalkylphosphinic acid, dicycloalkylalkylphosphinic acid, mixed monoalkylmonocycloalkylphosphinic acid, mixed monoalkylmonocycloalkylalkylphosphinic acid, mixed monocycloalkylmonocycloalkylalkylphosphinic acid, monoarylphosphinic acid, diarylphosphinic acid, mixed monoalkylmonoarylphosphinic acid, mixed monocycloalkylmonoarylphosphinic acid, mixed monocycloalkylalkylmonoarylphosphinic acid, phosphonic acid, alkylphosphonic acid, cycloalkylphosphonic acid, cycloalkylalkylphosphonic acid, aralkylphosphonic acid and arylphosphonic acid;

or a pharmaceutically-acceptable ester, amide, or salt thereof.

A more preferred class of peptidomimetic compounds consists of those compounds of Formula II wherein $R^1$ is selected from aminoalkyl, monoalkylaminoalkyl, dialkylaminoalkyl, aminoalkylphenylalkyl, monoalkylaminoalkylphenylalkyl, dialkylaminoalkylphenylalkyl, heterocyclicalkyl, heterocyclicalkylphenylalkyl, heteroarylalkyl, heteroarylalkylphenylalkyl, heterocycliccylcoalkyl, heterocycliccycloalkylalkyl, heteroarylcycloalkyl and heteroarylcycloalkylalkyl wherein any foregoing heterocyclic moiety may be fused to a phenyl ring to form a benzoheterocyclic moiety and wherein any foregoing heteroaryl moiety may be fused to a phenyl ring to form a benzoheteroaryl moiety, and wherein any of said heterocyclic moiety, benzoheterocyclic moiety, heteroaryl moiety and benzoheteroaryl moiety may be substituted at one or more substitutable positions with one or more radicals selected from halo, alkyl, haloalkyl, cycloalkyl, cycloalkylalkyl, alkoxy, alkylthio, phenylalkyl and phenyl; with the proviso that said heterocyclic moiety is selected from morpholino, thiomorpholino, piperazinyl, piperidinyl and pyrrolidinyl, and with the further proviso that said heteroaryl is selected from imidazolyl and pyridinyl;

wherein $R^2$ is a radical selected from hydrido, alkyl, cycloalkyl, cycloalkylalkyl, phenylalkyl and phenyl, wherein any of said $R^2$ radicals having a substitutable position may be substituted by one or more radicals selected from alkyl, cycloalkyl, cycloalkylalkyl, alkenyl, alkynyl, halo, haloalkyl, alkoxy, alkylthio, phenylalkyl, phenyl, naphthyl, tetrahydronaphthyl, decahydronaphthyl, naphthylalkyl, tetrahydronaphthylalkyl, decahydronaphthylalkyl, naphthylcycloalkyl, tetrahydronaphthylcycloalkyl, decahydronaphthylalkyl, alkoxycarbonyl and alkoxycarbonylalkyl;

wherein Y is selected from

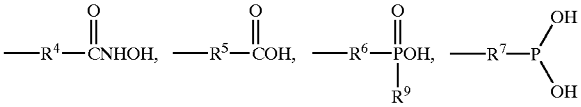

and

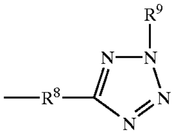

wherein each of $R^4$ through $R^8$ is either a covalent bond or is a divalent radical of the general structure $$-[X]-$$

wherein X is selected from alkyl, cycloalkyl, cycloalkylalkyl, phenylalkyl and phenyl;

wherein $R^9$ is selected from hydrido, alkyl, cycloalkyl, cycloalkylalkyl, phenylalkyl and phenyl;

or a pharmaceutically-acceptable ester, amide, or salt thereof.

An even more preferred class of peptidomimetic compounds consists of those compounds of Formula II wherein $R^1$ is selected from

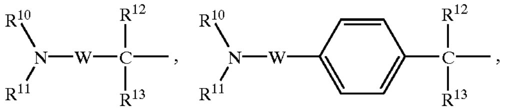

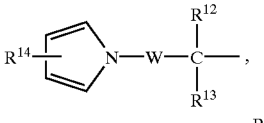

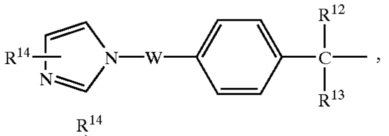

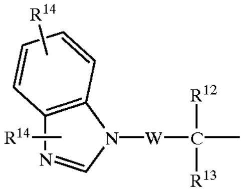

and

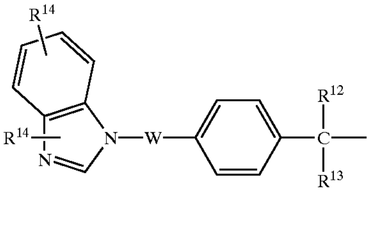

wherein W is a divalent radical of the general structure $$-[W]-$$

wherein W is selected from alkyl and cycloalkyl;

wherein each of $R^{10}$ and $R^{11}$ is independently selected from hydrido, alkyl, cycloalkyl, cycloalkylalkyl, phenylalkyl and phenyl; wherein further $R^{10}$ and $R^{11}$ may be taken together to form a saturated heterocyclic ring system having five or six ring members and having at least one nitrogen atom as a ring member and optionally having a second heteroatom selected from an oxygen, nitrogen or sulfur atom as a ring member, said heterocyclic ring system selected from morpholino, thiomorpholino, piperazinyl, piperidinyl and pyrrolidinyl; wherein each of $R^{12}$ and $R^{13}$ is independently selected from hydrido, alkyl and haloalkyl; wherein $R^{14}$ is selected from hydrido, alkyl, haloalkyl, halo, cycloalkyl, alkoxy, alkylthio, phenylalkyl and phenyl;

wherein $R^2$ is a moiety selected from hydrido, alkyl, cycloalkyl, cycloalkylalkyl, alkenyl, alkynyl, haloalkyl, naphthyl, tetrahydronaphthyl, decahydronaphthyl, naphthylalkyl, tetrahydronaphthylalkyl, decahydronaphthylalkyl, naphthylcycloalkyl, tetrahydronaphthylcycloalkyl, decahydronaphthylalkyl, phenylalkyl and phenyl, wherein any said $R^2$ moiety may be substituted at a substitutable position by one or more radicals selected from alkyl, halo and alkoxy;

wherein Y is selected from

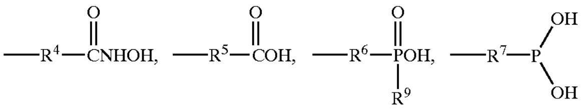

and

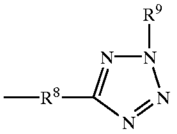

wherein each of $R^4$ through $R^8$ is either a covalent bond or is a divalent radical of the general structure $$-[X]-$$

with each of $R^4$ through $R^8$ independently selected from $-CH_2-$, $-CH_2CH_2-$ and $-CH_2CH_2CH_2-$;

wherein $R^9$ is selected from hydrido, alkyl, cycloalkyl, cycloalkylalkyl, phenylalkyl and phenyl;

or a pharmaceutically-acceptable ester, amide, or salt thereof.

A highly preferred class of peptidomimetic compounds consists of those compounds of Formula II wherein $R^1$ is selected from

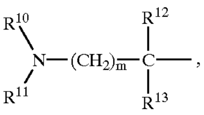

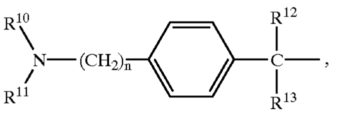

-continued

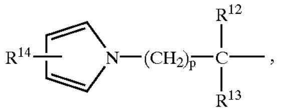

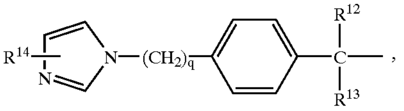

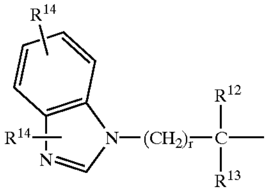

and

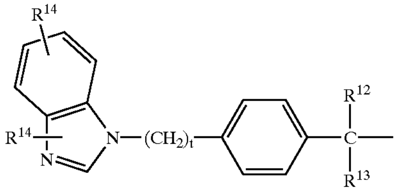

wherein each of $R^{10}$ and $R^{11}$ is independently selected from hydrido, alkyl, cycloalkyl, cycloalkylalkyl, phenylalkyl and phenyl; wherein further $R^{10}$ and $R^{11}$ may be taken together to form a saturated heterocyclic ring system having five or six ring members and having at least one nitrogen atom as a ring member and optionally having a second heteroatom selected from an oxygen, nitrogen or sulfur atom as a ring member, said heterocyclic ring system selected from morpholino, thiomorpholino, piperazinyl, piperidinyl and pyrrolidinyl; wherein each of $R^{12}$ and $R^{13}$ is independently selected from hydrido, alkyl and haloalkyl; wherein $R^{14}$ is selected from hydrido, alkyl, haloalkyl, halo, cycloalkyl, alkoxy, alkylthio, phenylalkyl and phenyl;

wherein each of m, n, p and r is a whole number independently selected from 3 through 15; wherein each of q and t is a whole number independently selected from 1 through 6;

wherein $R^2$ is a moiety selected from hydrido, alkyl, cycloalkyl, cycloalkylalkyl, alkenyl, alkynyl, haloalkyl, naphthyl, tetrahydronaphthyl, decahydronaphthyl, naphthylalkyl, tetrahydronaphthylalkyl, decahydronaphthylalkyl, naphthylcycloalkyl, tetrahydronaphthylcycloalkyl, decahydronaphthylalkyl, phenylalkyl, and phenyl, wherein any said $R^2$ moiety may be substituted at a substitutable position by one or more radicals selected from alkyl, halo and alkoxy;

wherein Y is selected from

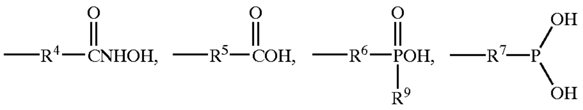

and

-continued

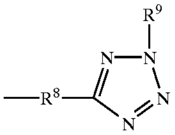

wherein each of $R^4$ through $R^8$ is either a covalent bond or is a divalent radical of the general structure $$-[X]-$$

with each of $R^4$ through $R^8$ independently selected from $-CH_2-$, $-CH_2CH_2-$ and $-CH_2CH_2CH_2$;

wherein $R^9$ is selected from hydrido, alkyl, cycloalkyl, cycloalkylalkyl and benzyl;

or a pharmaceutically-acceptable ester, amide, or salt thereof.

A more highly preferred class of peptidomimetic compounds consists of those compounds of Formula II wherein $R^1$ is selected from

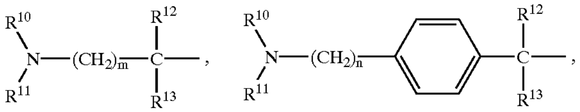

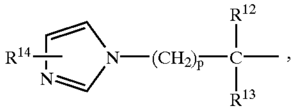

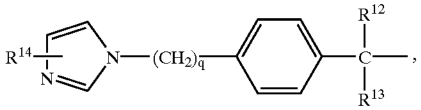

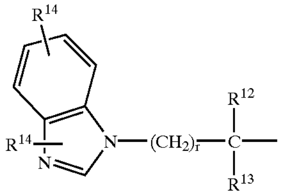

and

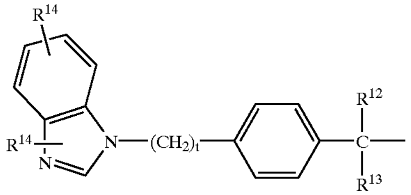

wherein each of $R^{10}$ and $R^{11}$ is independently selected from hydrido and alkyl; wherein further $R^{10}$ and $R^{11}$ may be taken together to form a saturated heterocyclic ring system having five or six ring members and having at least one nitrogen atom as a ring member and optionally having a second hetero atom selected from an oxygen, nitrogen or sulfur atom as a ring member, said heterocyclic ring system selected from morpholino, thiomorpholino, piperazinyl, piperidinyl and pyrrolidinyl; wherein each of $R^{12}$ and $R^{13}$ is independently selected from hydrido, alkyl and haloalkyl; wherein $R^{14}$ is selected from hydrido, alkyl, haloalkyl, halo, cycloalkyl, alkoxy, alkylthio, phenylalkyl and phenyl;

wherein each of m, n, p and r is a whole number independently selected from 6 through 14; wherein each of q and t is a whole number independently selected from 3 through 6;

wherein $R^2$ is a moiety selected from hydrido, alkyl, cycloalkyl, cycloalkylalkyl, alkenyl, alkynyl, haloalkyl, naphthyl, tetrahydronaphthyl, decahydronaphthyl, naphthylalkyl, tetrahydronaphthylalkyl, decahydronaphthylalkyl, naphthylcycloalkyl, tetrahydronaphthylcycloalkyl, decahydronaphthylalkyl, phenylalkyl, and phenyl, wherein any said $R^2$ moiety may be substituted at a substitutable position by one or more radicals selected from alkyl, halo and alkoxy;

wherein Y is selected from

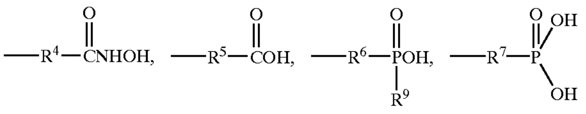

and

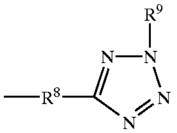

wherein each of $R^4$ through $R^8$ is either a covalent bond or is a divalent radical of the general structure

—[X]— with each of $R^4$ through $R^8$ independently selected from $—CH_2—$, $—CH_2CH_2—$ and $—CH_2CH_2CH_2$;

wherein $R^9$ is selected from hydrido, alkyl and benzyl;

or a pharmaceutically-acceptable ester, amide, or salt thereof.

An even more highly preferred class of peptidomimetic compounds consists of those compounds of Formula II wherein $R^1$ is selected from

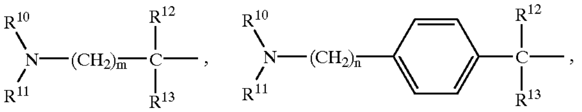

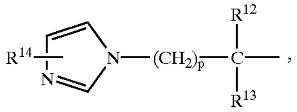

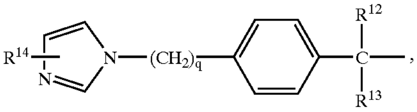

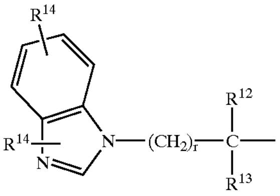

and

-continued

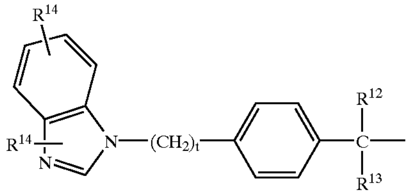

wherein each of $R^{10}$ and $R^{11}$ is independently selected from hydrido and alkyl; wherein each of $R^{12}$ and $R^{13}$ is independently selected from hydrido and alkyl; wherein $R^{14}$ is selected from hydrido, alkyl, haloalkyl, alkoxy and alkylthio;

wherein each of m, n, p and r is a whole number independently selected from 6 through 14; wherein each of q and t is a whole number independently selected from 3 through 6;

wherein $R^2$ is a moiety selected from hydrido, alkyl, cycloalkyl, cycloalkylalkyl, alkenyl, alkynyl, haloalkyl, naphthyl, naphthylalkyl, phenylalkyl, and phenyl, wherein any said $R^2$ moiety may be substituted at a substitutable position by one or more radicals selected from alkyl, halo and alkoxy;

wherein Y is selected from

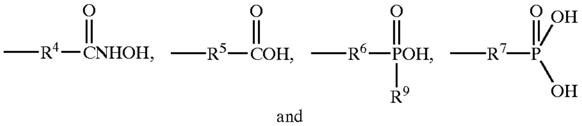

and

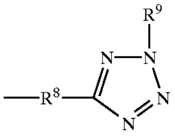

wherein each of $R^4$ through $R^8$ is either a covalent bond or is $—CH_2$;

wherein $R^9$ is selected from hydrido, alkyl and benzyl;

or a pharmaceutically-acceptable ester, amide, or salt thereof.

A very highly preferred class of peptidomimetic compounds consists of those compounds of Formula II wherein $R^1$ is selected from $H_2N(CH_2)_9—$, $H_2N(CH_2)_{10}—$, $H_2N(CH_2)_{11}—$, $CH_3NH(CH_2)_{10}—$, $(CH_3)_2N(CH_2)_{10}—$, $p\text{-}[H_2N(CH_2)_6]C_6H_4CH_2—$, $p\text{-}[H_2N(CH_2)_8]C_6H_4CH_2—$, $p\text{-}[H_2N(CH_2)_9]C_6H_4CH_2—$, $p\text{-}[H_2N(CH_2)_{10}]C_6H_4CH_2—$, $p\text{-}[H_2N(CH_2)_6]C_6H_4CH(CH_3)—$, $p\text{-}[H_2N(CH_2)_8]C_6H_4CH(CH_3)—$, $p\text{-}[H_2N(CH_2)_9]C_6H_4CH(CH_3)—$, $p\text{-}[H_2N(CH_2)_{10}]C_6H_4CH(CH_3)—$,

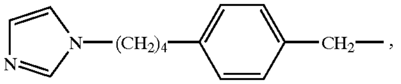

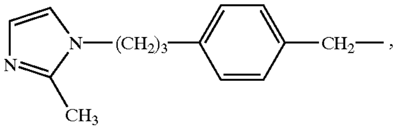

-continued

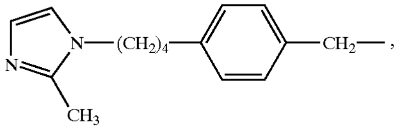,

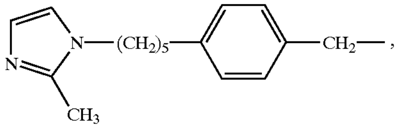,

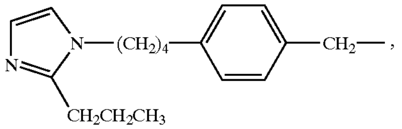,

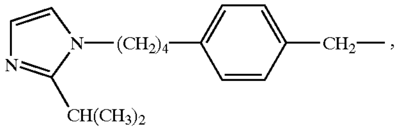,

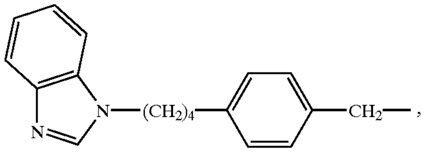,

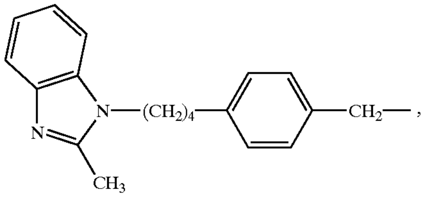,

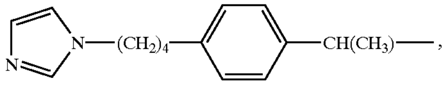,

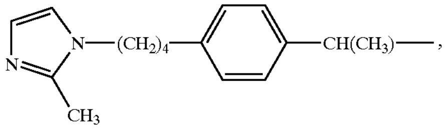,

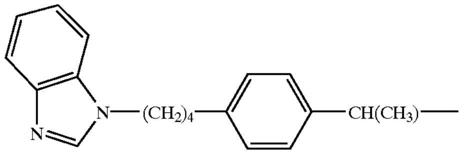 and

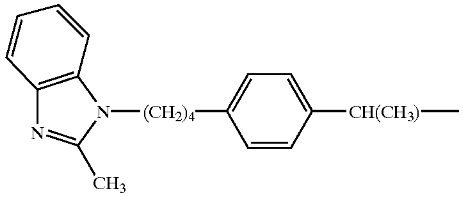;

wherein $R^2$ is selected from —H, —$CH_3$, —$CH_2CH_3$, —$CH_2CH_2CH_3$, —$CH_2CH_2CH_2CH_3$, —$CH_2CH_2CH_2CH_2CH_3$, —$CH_2CH_2CH_2CH_2CH_2CH_3$, —$CH(CH_3)_2$, —$CH_2CH(CH_3)_2$, —$CH_2CH_2CH(CH_3)_2$, -cyclo-$C_3H_5$, -cyclo-$C_4H_7$, -cyclo-$C_5H_9$, -cyclo-$C_6H_{11}$, -Cyclo-$C_7H_{13}$, -cyclo-$C_8H_{15}$, —$CH(CH_3)(CH_2CH_3)$, —$CH(CH_2CH_3)_2$, —$CH(CH_3)(CH_2CH_2CH_3)$, —$C(CH_3)_3$, $HC{\equiv}CCH_2$—, $H_2C{=}CH$—, $H_2C{=}CHCH_2$—, —$CH_2F$, —$CH_2C_6H_5$, —$CH_2C_6H_4$-p-$OCH_3$, —$CH_2C_6H_4$-p-$CH_3$, —$CH_2C_6H_4$-p-F, —$CH_2CH_2C_6H_5$, —$CH_2$-cyclo-$C_6H_{11}$, —$CH_2$-cyclo-$C_6H_{10}$-4-F, —$CH_2$-cyclo-$C_6H_{10}$-4-$CH_3$, —$CH_2$-cyclo-$C_6H_{10}$-4-$OCH_3$, —$CH_2CH_2$-cyclo-$C_6H_{11}$, —$CH_2$-cyclo-$C_5H_9$, —$CH_2CH_2$-cyclo-$C_5H_9$ and —$CH_2$-2-naphthyl;

wherein Y is selected from —$CO_2H$, —$CH_2CO_2H$, —CONHOH, —$PO_3H_2$, and

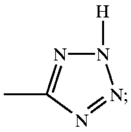;

or a pharmaceutically-acceptable ester, amide, or salt thereof.

A very highly preferred class of peptidomimetic compounds of Formula II of particular interest consists of compounds and their diastereoisomers of the group consisting of L-Alanine, 3-cyclohexyl-N-[$N^2$-[N-[2-[4-[4-(2-methyl-1H-imidazol-1-yl)butyl]phenyl]oxopropyl]-L-seryl]-L-lysyl]-, (±), bis-trifluoroacetate;

L-Alanine, 3-cyclohexyl-N-[$N^2$-[N-[[4-[4-(2-methyl-1H-imidazol-1-yl)butyl]phenyllacetyl]-L-seryl]-L-lysyl]-, bis-trifluoroacetate;

L-Alanine, 3-cyclohexyl-N-[[(11-amino-undecanoyl)-L-seryl]-L-lysyl]-, bis-trifluoroacetate;

L-Leucine, N-[[(11-amino-undecanoyl)-L-seryl]-L-lysyl]-, bis-trifluoroacetate;

L-Alanine, N-[$N^2$-[N-[[4-[4-(2-methyl-1H-imidazol-1-yl)butyl]phenyl]acetyl]-L-seryl]-L-lysyl]-, bis-trifluoroacetate;

L-Alanine, 3-phenyl-N-[$N^2$-[N-[[4-[4-(2-methyl-1H-imidazol-1-yl)butyl]phenyl]acetyl]-L-seryl]-L-lysyl]-, bis-trifluoroacetate;

L-iso-Leucine, N-[$N^2$-[N-[[4-[4-(2-methyl-1H-imidazol-1-yl)butyl]phenyl]acetyl]-L-seryl]-L-lysyl]-, bis-trifluoroacetate;

L-Leucine, N-[$N^2$-[N-[[4-[4-(2-methyl-1H-imidazol-1-yl)butyl]phenyl]acetyl]-L-seryl]-L-lysyl]-, bis-trifluoroacetate;

Lysinamide, N-[1-cyclohexyl-2-carboxyethyl]-$N^2$-[N-[[4-[4-(2-methyl-1H-imidazol-1-yl)butyl]phenyl]acetyl]-L-seryl]-, ±, bis-trifluoroacetate;

Lysinamide, N-[1-cyclooctyl-2-carboxyethyl]-$N^2$-[N-[[4-[4-(2-methyl-1H-imidazol-1-yl)butyl]phenyl]acetyl]-L-seryl]-, ±, bis-trifluoroacetate; and D-Alanine, 3-cyclohexyl-N-[$N^2$-[N-[[4-[4-(2-methyl-1H-imidazol-1-yl)butyl]phenyl]acetyl]-L-seryl]-L-lysyl]-, bis-trifluoroacetate.

The term "hydridol" denotes a single hydrogen atom (H). This hydrido group may be attached, for example, to an oxygen atom to form a hydroxyl group; or, as another example, one hydrido group may be attached to a carbon atom to form a

group; or, as another example, two hydrido groups may be attached to a carbon atom to form a —$CH_2$— group. Where the term "alkyl" is used, either alone or within other terms such as "haloalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The term "haloalkyl", embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluoro-chloromethyl group. Examples of a polyhaloalkyl are trifluoromethyl, 1,1-difluoroethyl, 2,2,2-trifluoroethyl, perfluoroethyl and 2,2,3,3-tetrafluoropropyl groups. The term "difluoroalkyl" embraces alkyl groups having two fluoro atoms substituted on any one or two of the alkyl group carbon atoms. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The term "cycloalkenyl" embraces cyclic radicals having three to about ten ring carbon atoms including one or more double bonds involving adjacent ring carbons. The terms "alkoxy" and "alkoxyalkyl" embrace linear or branched oxy-containing radicals each having alkyl portions of one to about ten carbon atoms, such as a methoxy group. The term "alkoxyalkyl" also embraces alkyl radicals having two or more alkoxy groups attached to the alkyl radical, that is, to form monoalkoxyalkyl and dialkoxyalkyl groups. The "alkoxy" or "alkoxyalkyl" radicals may be further substituted with one or more halo atoms, such as fluoro, chloro or bromo, to provide haloalkoxy or haloalkoxyalkyl.groups. The term "alkylthio" embraces radicals containing a linear or branched alkyl group, of one to about ten carbon atoms attached to a divalent sulfur atom, such as a methythio group. The term "aryl" embraces aromatic radicals such as phenyl, naphthyl and biphenyl. A preferred aryl group is phenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "aryloxy" and "arylthio" denote radical respectively, aryl groups having an oxygen or sulfur atom through which the radical is attached to a nucleus, examples of which are phenoxy and phenylthio. The term "aralkoxy", alone or within another term, embraces an aryl group attached to an alkoxy group to form, for example, benzyloxy. The term "alkenylalkyll" denotes a radical having a double-bond unsaturation site between two carbons, and which radical may consist of only two carbons or may be further substituted with alkyl groups which may optionally contain additional double-bond unsaturation. The term "acyl" whether used alone, or within a term such as acyloxy, denotes a radical provided by the residue after removal of hydroxyl from an organic acid, examples of such radical being acetyl and benzoyl. "Lower alkanoyl" is an example of a more prefered sub-class of acyl. A group embraced by the term "heterocyclic ring system" or "heteroaryl ring system", or "heterocyclic", or "heteroaryl" may be attached to the backbone of Formula I as a substituent at $R^1$ through a carbon atom of the hetero ring system, or may be attached through a carbon iatom of a moiety substituted on a hetero ring-member carbon atom. Also, such hetero-containing group may be attached through a ring nitrogen atom, where a bond is formable with such nitrogen atom. For any of the foregoing defined radicals, preferred radicals are those containing from one to about ten carbon atoms.

The term "monoalkylphosphinic acid" is intended to describe an acidic moiety having one alkyl group attached to the phosphorus atom through which alkyl group the phosphinic moiety is attached to the Formula I nucleus at "Y". In such cases, this alkyl group will be "divalent" in character as shown below:

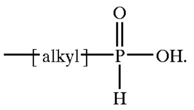

Another phospinic acid moiety described for use as "Y" substituent is characterized by the term "dialkylphosphinic acid" moiety, which term is intended to describe an acidic moiety having two alkyl groups attached to the phosphorous atom, one of such alkyl groups being "divalent" in character and through which this dialkylphosphinic acid moiety is attached at "Y", as shown below:

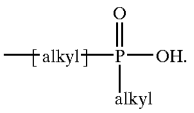

The phrase "mixed monoalkylmonocycloalkylphosphinic acid" is intended to describe a phosphinic acid moiety having both a monoalkyl moiety and a monocycloalkyl moiety attached to the phosphorus atom, either of which may provide a "linking" divalent group to the nucleus of Formula I at the "Y" position.

Specific examples of alkyl groups are methyl, ethyl, n-propyl, isopropyl-, n-butyl, sec-butyl, isobutyl, tert-butyl, n-pentyl, isopentyl, methylbutyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Also included in the family of compounds of Formula I, are isomeric forms including regioisomers, optical isomers, diastereoisomers and epimers, as well as the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicylic, phenylacetic, trifluoroacetic, mandelic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

Nomenclature used to define the peptides of Formula I is that specified by the IUPAC [published in *European Journal of Biochemistry*, 138, 9–37 (1984)], wherein conventional representation of the peptides stipulates that in a peptide sequence the amino group appears to the left and the carboxyl group to the right. When the amino acid has enantiomeric forms, it is the L form of the amino acid which is represented unless otherwise stated. In the amino acid structural formulas, each residue is generally represented by a single or 3-letter designation, corresponding to the trivial name of the amino acid in accordance with the following list:

| TRIVIAL NAME | SYMBOL | ONE-LETTER SYMBOL |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Homocysteine | Hcy | — |
| Isoleucine | Ile | I |
| Leucine | Leu | L |
| Lysine | Lys | K |
| Methionine | Met | M |
| Norvaline | Nva | — |
| Penicillamine | Pen | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Unspecified Amino Acid | Xaa | X |

Another name for norvaline in n-propylglycine. The group $^{125}$I-Tyr indicates a radioactive mono-iodinated tyrosine residue.

GENERAL SYNTHETIC SCHEMES

The compounds of the present invention represented by Formula I above can be prepared utilizing the following general procedures as schematically shown in Schemes I–VIII.

Scheme I

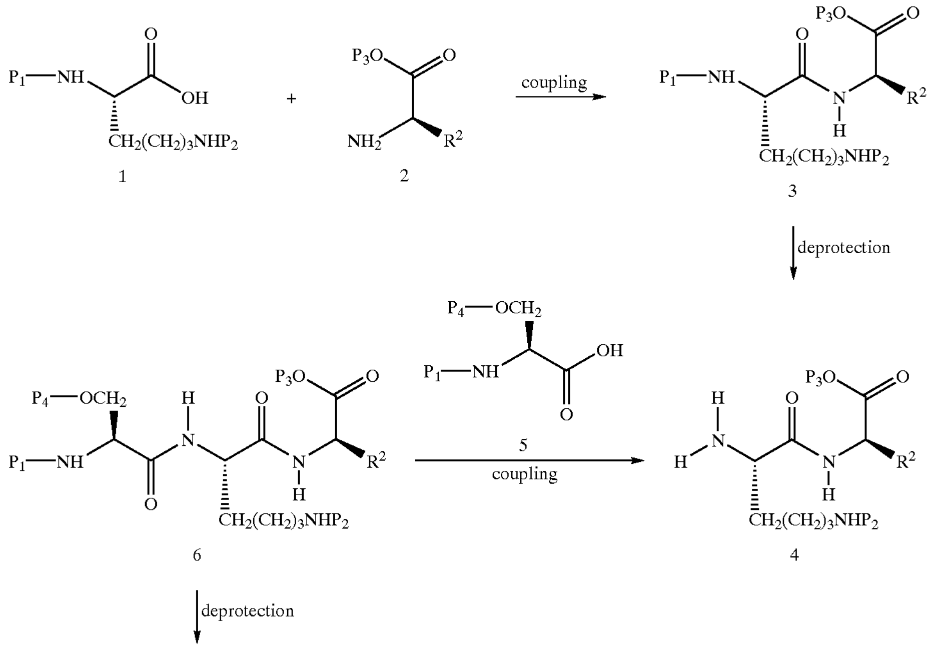

1 2 3 4 5 6

-continued

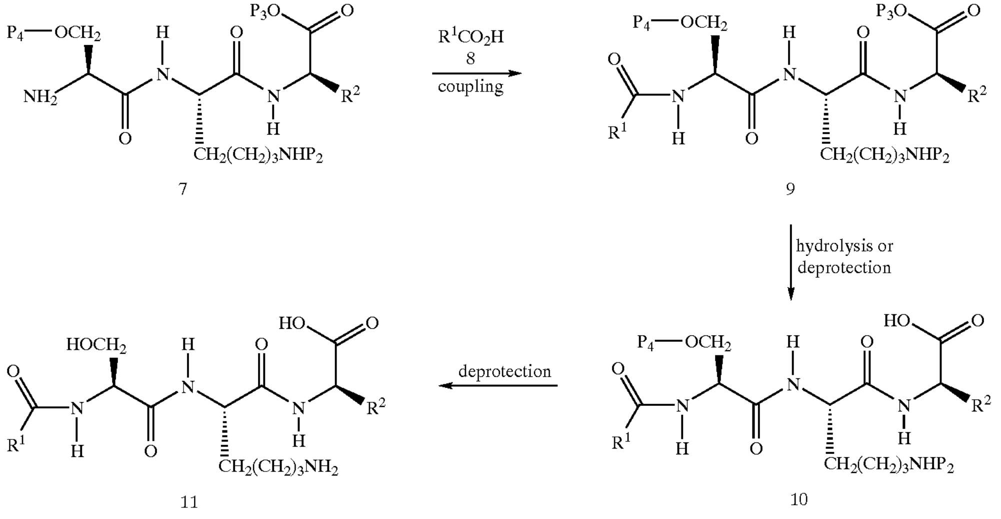

7 9 10 11

An appropriate DL-, D-, or L-lysine derivative 1 which has been differentially protected at both the alpha and omega amino groups with a suitable amine protecting group designated $P_1$ or $P_2$ is coupled to a suitably protected DL-, D-, or L-amino acid ester 2 containing an appropriate amino acid carboxyl-protecting group designated $P_3$ in a suitable solvent to produce a protected lysinamide of formula 3, wherein $R^2$, $P_1$, $P_2$, and $P_3$ are as defined above. Such reactions are well-known to those skilled in the art of solution-based peptide synthesis and generally employ methods such as those described by Bodanszky, M. and Bodanszky, A. in "The Practice of Peptide Synthesis" (1984), Springer-Verlag, New York, N.Y. or by Bodanszky, M. in "Principles of Peptide Synthesis" (1984), Springer-Verlag, New York, N.Y., and references cited therein.

Alternatively, the compounds of Formula I can be prepared according to Scheme I using well-known methods in solid-phase peptide synthesis such as those described by Barany, G. and Merrifield, R. B. in "The Peptides" (Gross, E. and Meienhofer, J., Eds.), vol.2, pp.1–284, (1979), Academic Press, New York, N.Y., and references cited therein. In this case, the carboxyl-protecting group designated $P_3$ is covalently attached, usually by an ester bond, to an appropriate solid phase resin, such as a hydroxymethyl-resin composed of styrene/1% divinylbenzene (Peninsula Laboratories) or an O-methlyphenylacetamidomethyl-resin (Sigma). Such resins are commercially available or can be readily prepared by one skilled in the art of solid-phase peptide synthesis.

Suitable amino protecting groups are well known in the art and include carbobenzoxy, 4-chloro-benzoxycarbonyl, t-butoxycarbonyl, and the like. $P_1$ and $P_2$ independently are selected from amine protecting groups, including but not limited to, aralkyl, substituted aralkyl, cycloalkenylalkyl, and substituted cycloalkenylalkyl, allyl, substituted allyl, acyl, alkoxy-carbonyl, aralkoxy-carbonyl and silyl. Examples of aralkyl include, but are not limited to benzyl, orthomethyl-benzyl, trityl and benzhydryl, which can be optionally substituted with halogen, alkyl of $C_1$–$C_8$, alkoxy, hydroxy, nitro, alkylene, amino, alkylamino, acylamino, and acyl, or their salts, such as phosphonium and ammonium salts. Examples of aryl groups include phenyl, naphthalenyl, indanyl, anthracenyl, durenyl, 9-phenylfluorenyl, and phenanthrenyl, cycloalkenylalkyl or substituted cycloalkenylalkyl radicals containing cycloalkyls of $C_6$–$C_{10}$. Suitable acyl groups include carbobenzoxy, 4-chloro-benzoxycarbonyl, t-butoxycarbonyl, iso-butoxycarbonyl, benzoyl, substituted benzoyl, butyryl, acetyl, trifluoroacetyl, trichloroacetyl, phthaloyl and the like.

One skilled in the art can choose appropriate combinations of $P_1$ and $P_2$. For example, a preferred amino protecting group for $P_1$ is carbobenzoxy and a preferred amino protecting group for $P_2$ is t-butoxycarbonyl. Alternatively, a preferred amino protecting group for $P_1$ is t-butoxycarbonyl and a preferred amino protecting group for $P_2$ is carbobenzoxy.

Additionally, the $P_1$ and/or $P_2$ protecting groups can form a heterocyclic ring with the nitrogen to which they are attached, for example, 1,2-bis-(methylene)benzene, phthalimidyl, succinimidyl, maleimidyl, and the like, and where these heterocyclic groups can further include adjoining aryl and cycloalkyl rings. In addition, the heterocyclic groups can be mon-. di-, or tri-substituted e.g., nitrophthalimidyl.

The term silyl refers to a silicon atom optionally substituted by one or more alkyl, aryl and aralkyl groups. Suitable silyl protecting groups include, but are not limited to trimethylsilyl, triethylsilyl, triisopropylsilyl, tert-butyldimethylsilyl, dimethylphenylsilyl, 1,2-bis(dimethylsilyl)benzene, 1,2-bis-(dimethylsilyl)ethane, and diphenylmethylsilyl.

Suitable carboxyl-protecting groups $P_3$ are well known in the art and include methyl, ethyl, benzyl, tertiary-butyl, 4-methoxyphenylmethyl, and the like.

The DL-, D-, or L-amino acid ester corresponding to formula 2 wherein $R^2$ and $P_3$ is as defined above are commercially available (Sigma Chemical Co.), or are readily prepared using standard methods well known in the art from readily available starting materials. Methods of preparing these amino acid derivatives from the corresponding amino acids are well known to those skilled in the art of organic chemistry including amino acid/amino acid ester chemistry using methods such as those described by R. M. Williams in "Synthesis of Optically Active α-Amino Acids," (1989) Pergamon Press, New York, N.Y.

Standard coupling procedures can be used to couple the amino acids and amines. The carboxylic acid group is reacted to form an anhydride, mixed anhydride, acid halide, such as chloride or bromide, or active ester, such as esters of N-hydroxysuccinimide, HOBT (W. König, R. Geiger, *Chem. Ber.* 103, 788 (1970), and the like, using well known procedures and conditions. This reaction is usually facilitated by adding an acid scavenger such as a teritary amine base. Suitable acid scavengers include, but are not limited to triethylamine, tributylamine, tri-iso-propylamine, DBU, N-methylmorpholine, di-iso-propylethylamine, pyridine, 2,2,6,6-tetramethylpiperidine, N,N-dimethylaminopyridine, and the like, including mixtures of these bases. A preferred tertiary amine base is N-methylmorpholine. Appropriate solvent systems include tetrahydrofuran, ethylether, methyl-tert-butylether, methylene chloride, N,N-dimethylformamide, N,N-dimethylacetamide, and the like, including mixtures thereof.

Following preparation of the lysinamide drivative 3, the amino protecting group $P_1$ is removed under conditions which will not effect the remaining portion of the molecule to produce the lysinamide 4, where $R^2$, $P_2$, and $P_3$ are as defined above. These methods are well known in the art and include acid hydrolysis, hydrogenolysis and the like. A preferred method (W. H. Hartung, and R. Simonoff, *Organic Reactions*, 7, 263–326, (1953)) involves removal of the protecting group, e.g., removal of a carbobenzoxy group, by hydrogenolysis utilizing palladium on carbon in a suitable solvent system such as an alcohol, acetic acid, and the like or mixtures thereof. When the $P_1$ protecting group is a t-butoxycarbonyl group, it can be removed utilizing an inorganic or organic acid, e.g., HF, HCl or trifluoroacetic acid (H. Kappeler, and R. Schwyzer, *Helv. Chim. Acta*, 43, 1453, (1960)), in a suitable solvent system such as dioxane or methylene chloride. The resulting product is the lysine salt derivative.

Following neutralization of the salt, the amine 4 is then coupled to a suitably protected DL-, D-, or L-serine derivative 5, where $P_4$ is an appropriate hydroxyl-protecting group and $P_1$ is a suitable amino protecting group, as defined above, in an appropriate solvent to provide the desired protected serine-lysine dipeptide derivatives6, where $R^2$, $P_1$, $P_2$, $P_3$, and $P_4$ are as defined above. Examples of a suitable $P_4$ hydroxyl-protecting group include, but are not limited to tert-butyl and benzyl, and the like. In general, tert-butyl is preferred for $P_4$ under solution conditions, while benzyl is preferred for $P_4$ using solid phase synthetic methods.

Following preparation of the protected serine-lysine dipeptide 6, the amino protecting group $P_1$ is then removed under conditions that will not effect the rest of the molecule, using the general methods described above for the deprotection of 3, to provide the amine 7.

The resulting amine 7 is then coupled under standard conditions with an appropriate carboxylic acid 8, where $R^1$ is as defined above, in a suitable solvent to provide the protected amide 9. General procedures for the synthesis of these carboxylic acids 8 containing the appropriate $R^1$ groups are shown schematically in Schemes VII and VIII.

Following preparation of the protected amide 9, the carboxyl-protecting group $P_3$ is removed by base hydrolysis under standard conditions, using a solution of an appropriate metal hydroxide, such as lithium or sodium hydroxide, in an appropriate aprotic or protic solvent system such as an alcohol or water and the like or mixtures thereof, to provide the free carboxylic acid 10 after acidification. Alternatively, when $P_3$ is a benzyl or other aralkyl group, it may be removed by hydrogenolysis under standard conditions, using palladium on carbon in a suitable solvent system such as an alcohol, acetic acid, and the like or mixtures thereof. Alternatively, when $P_3$ is a tert-butyl group, it can be removed utilizing an organic or inorganic acid, e.g., HF, HCl or trifluoroacetic acid, in an appropriate solvent system such as dioxane or methylene chloride.

Following preparation of the protected carboxylic acid 10, the remaining $P_2$ and $P_4$ protecting groups can be removed under standard conditions as described above under conditions which do not effect the rest of the molecule to provide the deprotected dipeptide carboxylic acid derivatives 11. Alternatively, the sequence of reactions leading from 9 to 11 can be reversed, wherein the protecting groups $P_2$ and $P_4$ are removed first under conditions which do not effect the rest of the molecule, and then the carboxyl-protecting group $P_3$ can be removed subsequently, under suitable conditions as described above. Alternatively under solid phase conditions, the protecting group $P_2$ is removed first under conditions which do not effect the rest of the molecule, and then the carboxyl-protecting group $P_3$ and hydroxyl-protecting group $P_4$ can be removed subsequently, under suitable conditions using HF, as described above. In either case, the resulting final products 11 or their derivatives or salts can be crystallized or purified chromatographically using either a chiral or achiral column as is well known to those skilled in the art.

Alternatively, the sequence of coupling and deprotection reactions leading to intermediate 9 can be altered as depicted in Scheme II.

Starting from a suitable ϵ-amino protected lysine derivative 12, subsequent coupling to the protected serine derivative 5 produces the protected dipeptide 13, wherein $P_1$, $P_2$, $P_3$, and $P_4$ are as defined above. The amino protecting group $P_1$ in 13 is then removed under conditions which do not alter the rest of the molecule, and the resulting amine 14 is then coupled under standard conditions with 8 to provide 15. Subsequent removal from 15 of the carboxyl-protecting group $P_3$, usually by hydrolysis, provides the free carboxylic acid 16, which can be subsequently activated and coupled with 2 under standard conditions to provide intermediate 9, wherein $R^1$, $R^2$, $P_2$, $P_3$, and $P_4$ are as defined above. Similar methods to those described previously in the reactions in Scheme I can then be used to convert 9 to 11 under standard conditions.

Scheme II.

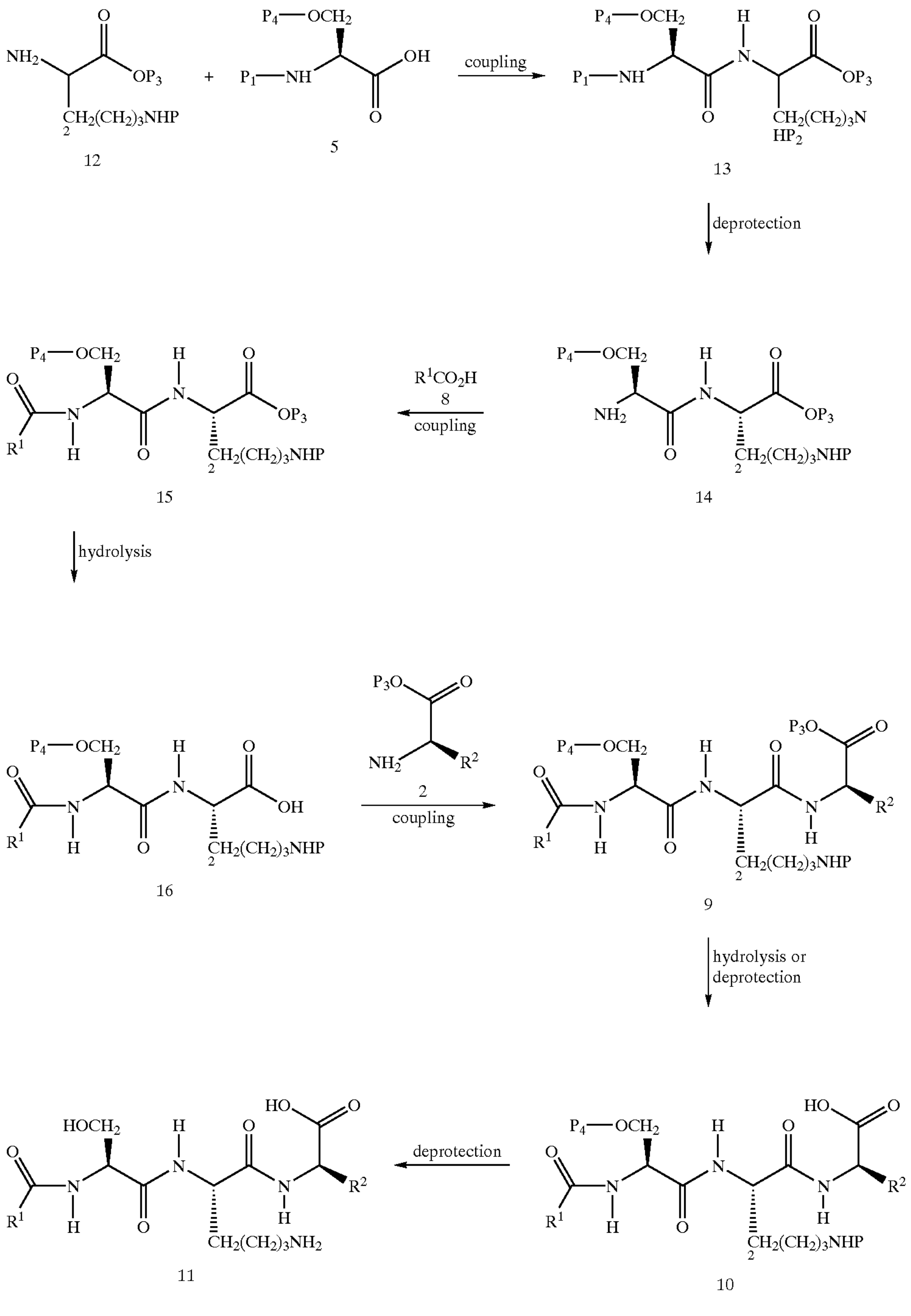

Alternatively, as depicted in Scheme III, intermediate 16 can be activated and coupled under standard conditions with a suitably protected DL-, D-, or L-beta-amino acid ester 17 to provide the protected intermediate 18. Representative N-protected beta-amino acid esters are well known to those skilled in the art of amino acid ester chemistry and can be readily prepared using the methods described by E. Juaristi, D. Quintana and J. Escalante in *Aldrichimica Acta*, 27, 3–11 (1994), and references cited therein. Subsequent deprotection or hydrolysis removes the carboyl-protecting group $P_3$ from 18 to provide the free carboxylic acid derivative 19, which can be subsequently deprotected under the conditions described above for Scheme I to provide the homologated DL-, D-, or L-beta-amino acid analog 20.

Scheme III.

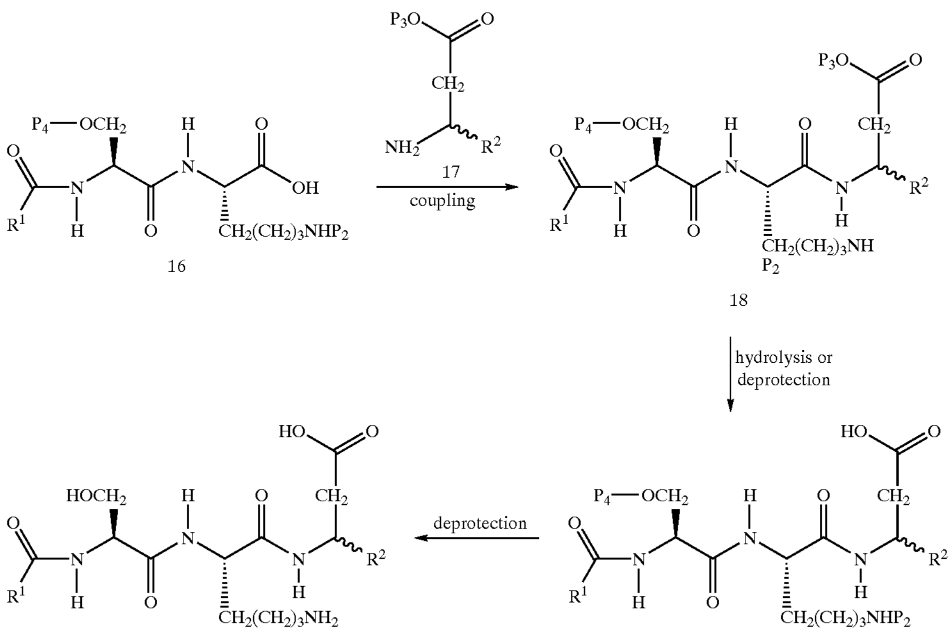

16 17 18 19 20

Alternatively, intermediate 16 can be activated and coupled with a suitably protected phosphono-amino acid ester 21 to provide the coupled phosphonate ester product 22. Representative protected phosphono-amino acid esters 21 are well know to those skilled in the art of organophosphorus chemistry and can be readily prepared using the methods described by G. Osapay and A. Csiba in *Eur. J. Med. Chem.* 28, 355–61 (1993), R. G. Almquist, W.-R. Chao, and C. Jennings-White in *J. Med. Chem.* 28, 1064, (1985), T. Yokomatsu and S. Shibuya in *Tetrahedron: Asymmetry,* 3, 377–8 (1992), and M. C. Allen, W. Fuhrer, B. Tuck, R. Wade and J. M. Wood in *J. Med. Chem.* 32, 1652–61 (1989), and references cited therein. Subsequent hydrolysis removes the $P_3$ phosphonate-protecting groups from 22 to produce the phosphonic acids 23, which can be further deprotected under standard conditions as described previously to provide the fully-deprotected phosphonic acids 24.

Scheme IV.

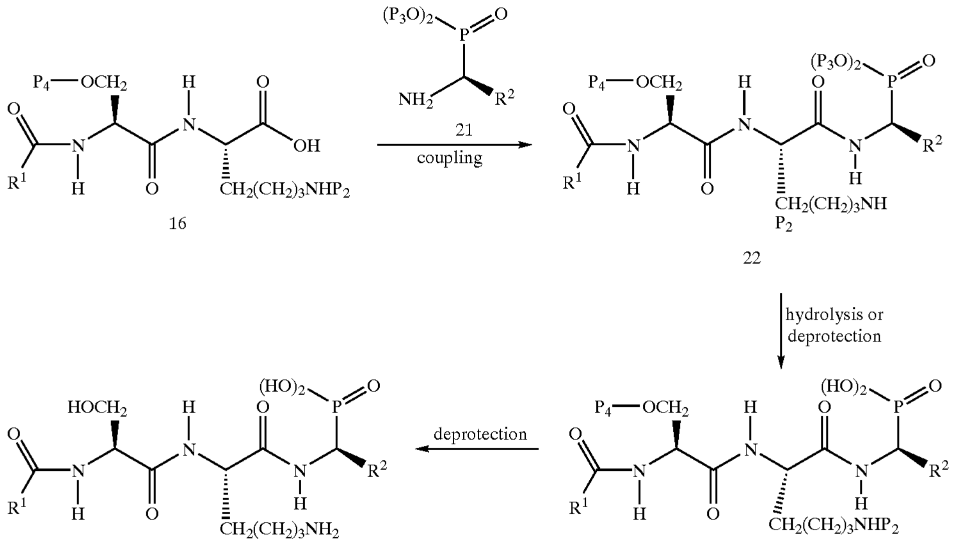

16 21 22 23 24

Alternatively, intermediate 16 can be activated and coupled with a suitably N-protected tetrazole 25 to provide the coupled protected tetrazole product 26. Representative N-protected tetrazoles 25 are well known to those skilled in the art of amino acid chemistry and can be readily prepared from the corresponding protected aminoalkyl tetrazoles as described by Z. Grzonka, E. Bekowskas, and B. Liberek in *Tetrahedron*, 27, 1783 (1971), and by L. R. Hughes, J. Oldfield, S. J. Pegg, A. J. Barker and P. R. Marsham in European Patent EP 373891. Subsequent deprotection of 27 under standard conditions, as described previously, provides the fully deprotected tetrazoles 28.

Scheme V.

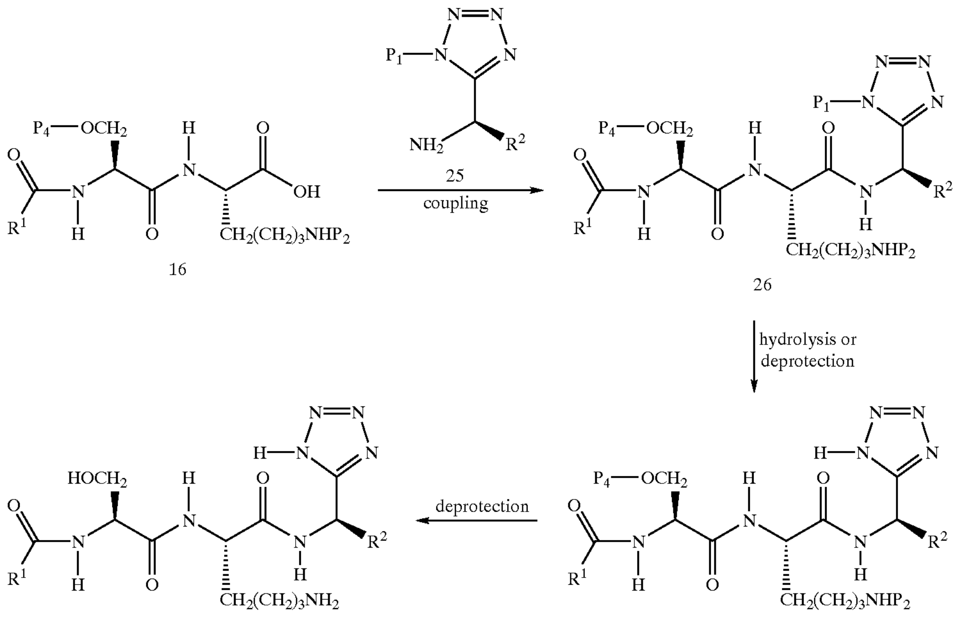

16 26 27 28

Alternatively, intermediate ester 9 can be reacted with a suitably protected hydroxylamine derivative in a suitable solvent to provide the coupled hydroxyl-protected hydroxamic acid product 29, as described by E. W. Petrillo and M. A. Ondetti in U.S. Pat. No. 4,284,561 (1981). Representative oxygen-protected hydroxylamines are commercially available or readily prepared by those skilled in the art. Subsequent deprotection of 29 can be accomplished under standard conditions either stepwise through intermediate 30 or directly to provide the fully deprotected hydroxamic acid analogs 31.

Scheme VI.

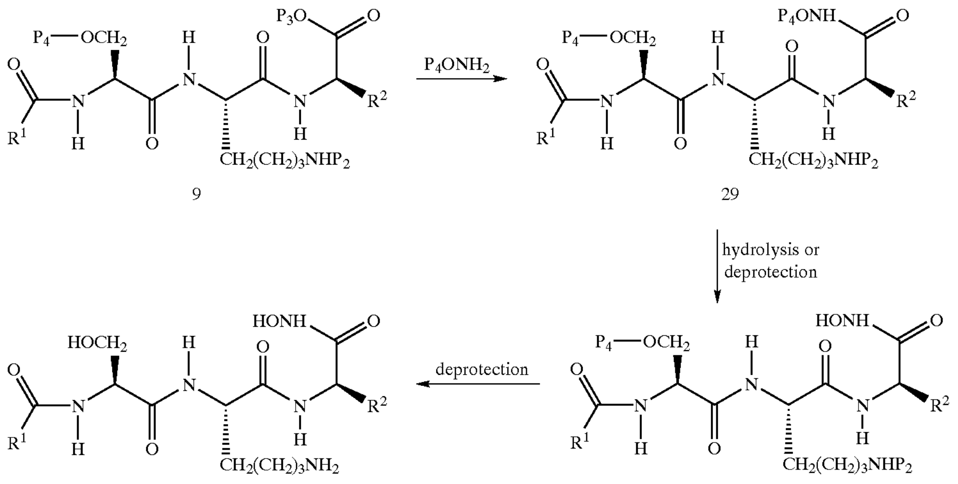

9 29 30 31

The intermediate carboxylic acids 8 required for the syntheses depicted in Schemes I–VI are either commercially available or readily prepared by those skilled in the art of organic synthesis. Representative general procedures for the preparation of these intermediates 8 are depicted in Schemes VII and VIII.

Commercially available p-iodophenyl acetic acid 32 is esterified with an alcohol, preferably methanol, under standard conditions to provide the corresponding methyl p-iodophenylacetate 33. The iodoester 33 is then coupled with an appropriate acetylenic alcohol 34 to provide the coupled alcohol product 35 under conditions utilizing a palladium catalyst as described by K. Sonogashira, Y. Tohda and N. Hagihara in *Tetrahedron Letters*, 50, 4467–70 (1975). This reaction may be applied to a variety of acetylenic alcohols where the number of methylene units defined by x may be varied between 1 and 9. The resulting unsaturated alcohol 35 is then reduced by hydrogenolysis in the presence of a suitable catalyst such as palladium on carbon to provide the saturated alcohol product 36, which can be cleanly converted to the corresponding saturated iodide 37, under standard conditions using known alcohol group manipulations.

Scheme VII.

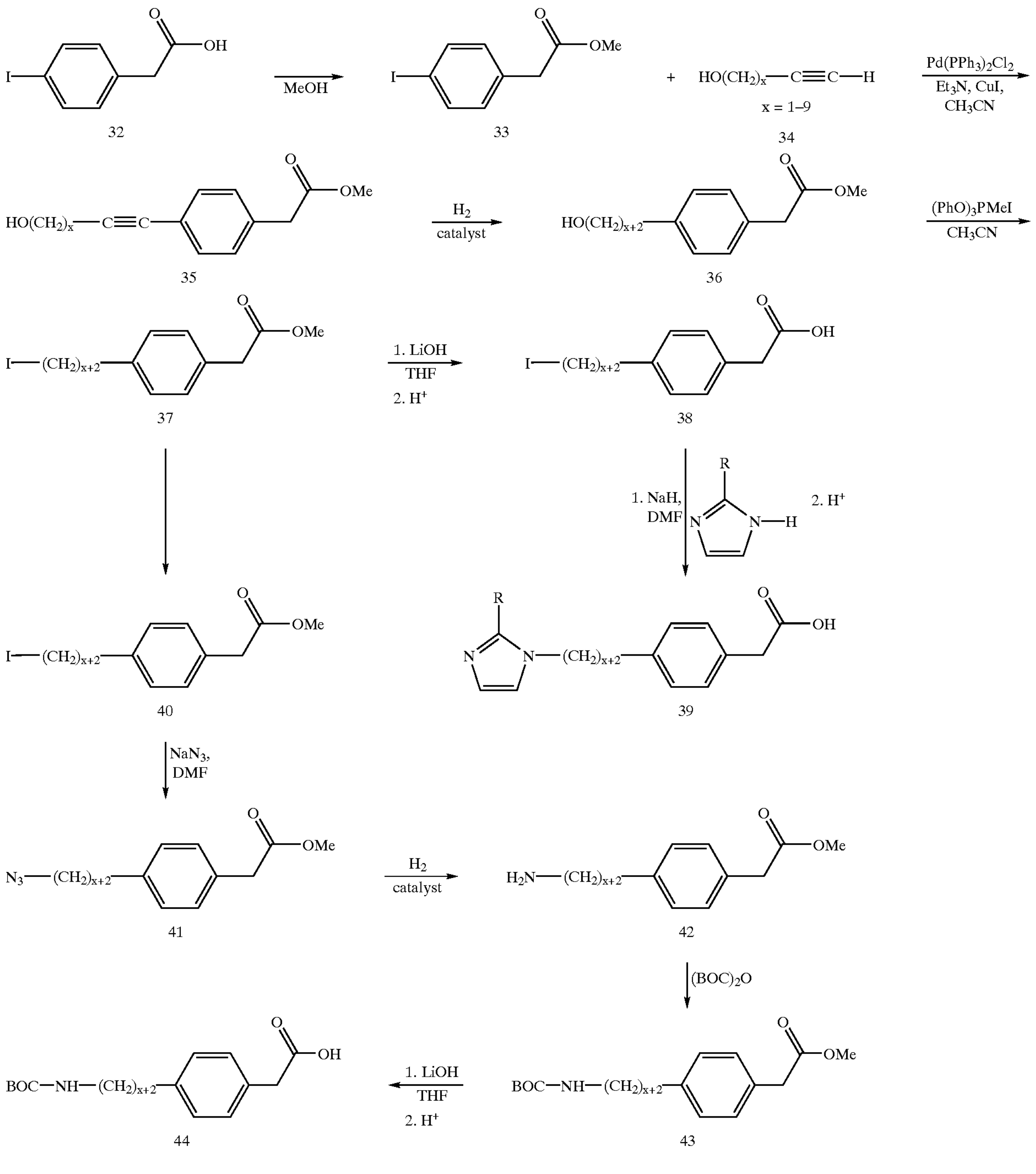

The iodide ester 37 may be hydrolyzed with base to provide the corresponding free carboxylic acid 38, after acidification, which is then reacted with a suitable nitrogen heterocycle in the presence of base and in a suitable aprotic solvent to give the coupled carboxylic acid product 39, after acidification. Essentially any acid scavenger, such as sodium hydride or a tertiary amine as previously defined, may be used in this reaction. Sodium hydride is the preferred base. Examples of suitable heterocycles include, but are not limited to, 1,2,4-triazole, 1,2,3-triazole, imidazole, benzimidazole, 2-mercapto-pyridine, N-methyl-2-mercaptoimidazole, 2-mercaptobenzimidazole, or 1,2,4-triazole, 1,2,3-triazole, imidazole, or benzimidazole systems substituted with halo, alkyl or alkoxy groups. Preferably, the heterocycle is an imidazole or benzimidazole ring; most preferred is a 2-methylimidazole.

Alternatively, the iodide ester 37 can be converted stepwise to the corresponding amino ester 42 after formation and reduction of the corresponding azide intermediate 41. Amino ester 42 is then N-protected with a suitable amino protecting group, $P_1$, as defined above, to provide 43. Preferably, $P_1$ is a t-butoxycarbonyl (BOC) group, as depicted in Scheme VII. The resulting N-protected amino ester 43 is then hydrolyzed under standard conditions to give the N-protected amino acid 44, after acidification.

Alternatively as shown in Scheme VIII, the iodophenylacetate ester 33 can be alkylated α to the ester group with a suitable alkyl halide R'X in an aprotic solvent and in the presence of base such as sodium hydride to provide the racemic iodophenyl alkanoate esters 45. Preferably R' is a primary lower alkyl group such as methyl. The resulting product 45 can then be carried through the same sequence of reactions as previously described for those in Scheme VII to provide the a-alkyl substituted intermediates 46–55.

Scheme VIII.

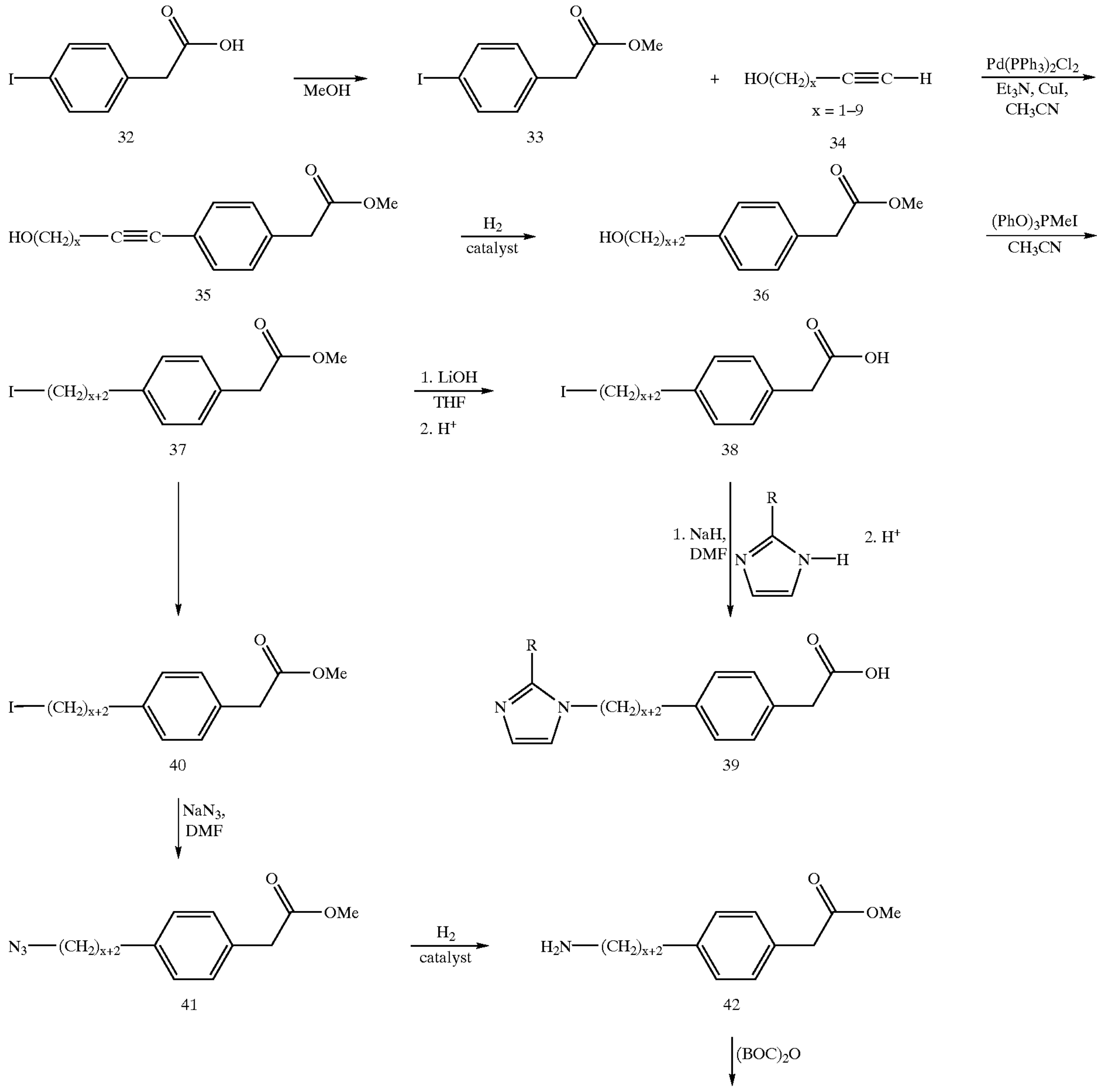

-continued

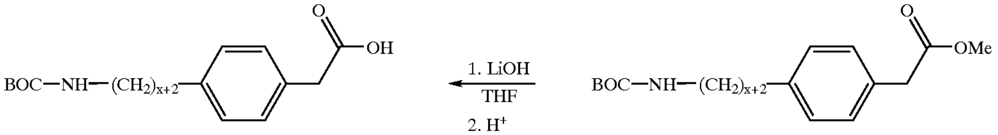

44 43

The following is a description of preparation of a compound (Comparator Compound “A”) which is not part of the present invention. Following this synthesis description is a table of data obtained by evaluation of Comparator Compound “A” in accordance with the methods described in the “Biological Evaluation” section.

Synthesis of Comparator Compound A.

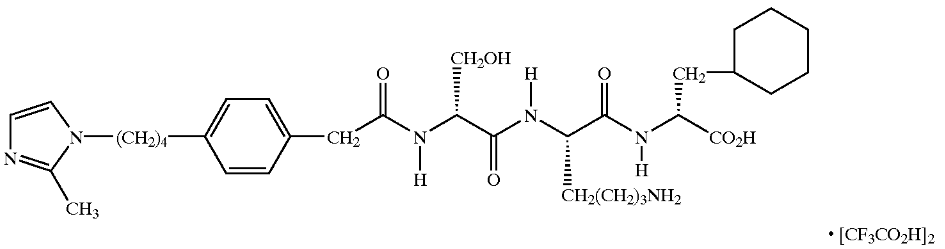

Preparation of D-Alanine, 3-cyclohexyl-N-[N[2]-[N-[[4-[4-(2-methyl-1H-imidazol-1-yl)butyl]phenyl] acetyl]-D-seryl]-D-lysyl]-, bis-trifluoroacetate.

Part A:

To commercially available (Peninsula Laboratories) hydroxymethyl-resin of styrene/1% divinylbenzene (0.67 g, 0.75 mequiv/g) in 10 mL of dichloromethane was added N-BOC-(3-cyclohexyl)-D-alanine (0.55 g, 2.0 mmoles), dicyclohexylcarbodiimide (DCC, 0.4 g, 2.0 mmoles), and 4-dimethyl-aminopyridine (DMAP, 0.02 g, 0.2 mmoles). After stirring for 18 hours at room temperature, the amino acid-resin was separated by filtration and treated with 20 mL of 50% trifluoroacetic acid in dichloromethane for 30 minutes, and separated by filtration. The resulting amino acid-resin was washed sequentially with dichloromethane (3x20 mL), isopropanol (3x20 mL), diisopropylethylamine 10% (v/v) in dichloromethane (3x20 mL), and dichloromethane (3x20 mL).

Part B:

N-α-BOC-N-ε-(2-chloro-benzyloxycarbonyl)-D-lysine (0.83 g, 2.0 mmoles) was activated with dicyclohexylcarbodiimide (0.20 g, 1.0 mmoles) in dichloromethane and coupled to the resin product from Part A for 60 minutes at room temperature. The dipeptide-resin was separated by filtration, the N-α-BOC group was removed with trifluoroacetic acid in dichloromethane, and the resulting resin was washed as described in Part A.

Part C:

N-BOC-(O-benzyl)-D-serine (0.59 g, 2.0 mmoles) was activated with dicyclohexylcarbodiimide (0.20 g, 1.0 mmoles) in dichloromethane and coupled to the resin product from Part B for 60 minutes at room temperature. The tripeptide-resin was separated by filtration, the N-α-BOC group was removed with trifluoroacetic acid in dichloromethane, and the resulting resin was washed as described in Part A.

Part D:

To 4-[(2-methyl-1H-imidazol-1-yl)butyl]phenylacetic acid hydrochloride (0.08 g, 0.26 nmoles) in 2 mL of dimethylformamide (DMF) was added diisopropyl-ethylamine (0.04 mL, 0.26 mmoles). The resulting mixture was added to a suspension of the tripeptide-resin product from Part C in 5 mL of dichloromethane, followed by the addition of dicyclohexylcarbodiimide (0.05 g, 0.26 nmoles). After 18 hours at room temperature, the solvent was removed by filtration, and the resulting resin was washed with dichloromethane.

Part E:

The resin product from Part D was treated with 10 mL of 90% hydrogen fluoride in anisole (v/v) for 60 minutes at 0° C. The hydrogen fluoride was removed by evaporation, the resulting residue was extracted with 30% acetic acid in water and lyophilized. The crude material was purified by reverse phase HPLC on a Waters Deltapak RPC-18 column using a linear gradient of 1% to 35% acetonitrile (0.05% trifluoroacetic acid) in water (0.05% trifluoroacetic acid) over 30 minutes at 15 mL/min, which after lyophilization, gave 53 mg of 95% pure (by HPLC) D-alanine, 3-cyclohexyl-N-[N[2]-[N-[[4-[4-(2-methyl-1H-imidazol-1-yl)butyl]phenyl]acetyl]-D-seryl]-D-lysyl]-, bis-trifluoroacetate; HRMS: (M+H) calcd. 641.4027, found 641.4038.

| Amino acid analyses: | | |
|---|---|---|
| | theory | obs. |
| serine | 1.00 | 0.98 |
| lysine | 1.00 | 1.02 |
| D-cyclohexylalanine: observed but not quantitated. | | |

-continued

| $IC_{50}$ caNMT (μM) | $IC_{50}$ hNMT (μM) | Selectivity | $caEC_{50}$ 24 hours (μM) |
|---|---|---|---|
| >1000 | >1000 | ND | >400 |

caNMT = *Candida albicans* NMT;
hNMT = human NMT;
ca = *Candida albicans*
ND = not determined.

The following procedures constitute specific exemplification of methods to prepare starting materials, intermediates and product compounds embraced by the foregoing General Synthetic Schemes. Those skilled in the art will readily understand that known variations of the conditions and processes of the following preparative procedures can be used to prepare the compounds of the invention. All temperatures expressed are in degrees Centigrade.

EXAMPLE 1

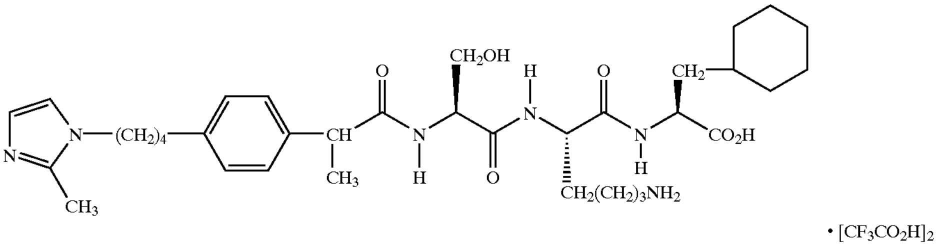

Part A: Preparation of L-Alanine, 3-cyclohexyl-, Methyl Ester, Trifluroacetate.

To a solution of L-alanine, 3-cyclohexyl-N-BOC-, methyl ester (1.0 g, 3.5 mmol) in $CH_2Cl_2$ (4.00 mL), trifluoroacetic acid (1.00 mL) was added, and the mixture was stirred at room temperature for 1 hour. The trifluoroacetic acid was removed under reduced pressure, the residue was triturated with ether, and filtered. The solid material thus obtained was washed thoroughly with ether and dried in a dessicator under vacuum over NaOH pellets to give 0.87 g of L-alanine, 3-cyclohexyl-, methyl ester trifluroacetate, which was used without further purification in Part B.

Part B: Preparation of L-Alanine, 3-cyclohexyl-N-[N-α-Carbobenzoxy-N-ε-BOC-L-Lysyl]-, Methyl Ester.

N-α-Carbobenzoxy-N-ε-BOC-L-lysine (1.3 g, 3.4 mmol) and HOBt (0.6 g, 4.0 mmol) were dissolved in $CH_2Cl_2$ (8.00 mL) and dimethylacetamide (2.0 mL), and the solution was cooled to 0° C. To this cooled solution, DCC (0.74 g, 3.6 mmol) in $CH_2Cl_2$ (10 mL) was added dropwise, and the reaction was stirred at 0° C. for 1 hour, and filtered. The filtrate was added to a solution of the L-alanine, 3-cyclohexyl-, methyl ester trifluroacetate from Part A in $CH_2Cl_2$ (3.0 mL) containing N-methylmorpholine (0.37 g, 3.68 mmol). The resulting mixture was stirred at room temperature for 16 hours and concentrated under vacuum. The residue was partitioned between EtOAc (40 mL) and 5% citric acid (20 mL). The organic phase was washed successively with 5% citric acid (2x20 mL), water (2x20 mL), 0.25 N NaOH (2x20 mL), brine, dried ($Na_2SO_4$), and filtered. After the removal of the solvent, the product was crystallized from EtOAc/hexane to give 1.4 g (73%) of L-alanine, 3-cyclohexyl-N-[N-α-carbobenzoxy-N-ε-BOC-L-lysyl]]-, methyl ester as a pale yellow powder. FAB-MS m/z=554 (M+Li); HRMS calcd. for $C_{29}H_{45}N_3O_7Li$ (M+Li) 554.3418, found 554.3447.

Part C: Preparation of L-Alanine, 3-cyclohexyl-N-[N-ε-BOC-L-Lysyl]-, Methyl Ester Acetate.

A solution of L-alanine, 3-cyclohexyl-N-[N-α-carbobenzoxy-N-ε-BOC-L-lysyl]]-, methyl ester (0.6 g, 1.1 mmol) from Part B in MeOH (15 mL) and acetic acid (0.07 mL) was hydrogenated at atmospheric pressure in the presence of 5% Pd/C (0.2 g) for 1 hour and filtered. The filtrate was concentrated under reduced pressure, and the resulting L-alanine, 3-cyclohexyl-N-[N-ε-BOC-L-lysyl]-, methyl ester acetate salt [FAB-MS: m/z=420 (M+Li)] was used without further purification in Part D.

Part D: Preparation of L-Alanine, 3-cyclohexyl-N-[[N-ε-BOC-L-Lysyl]-L-(O-t-butyl)-N-carbobenzoxy-seryl]-, Methyl Ester.

To a solution of N-carbobenzoxy-(O-t-butyl)-L-serine (0.4 g, 1.35 mmol) in dimethylacetamide (1 mL) and dichloromethane (5 mL) at 0° C., was added HOBt (0.23 g, 1.53 mmol) and DCC (0.3 g, 1.45 mmol), and the resulting mixture was stirred for 1 hour, then filtered. The filtrate was added to a solution of L-alanine, 3-cyclohexyl-N-[N-ε-BOC-L-lysyl]-, methyl ester acetate salt from Part C, in dimethylacetamide (1 mL) containing N-methyl-morpholine (0.14 g, 1.36 mmol), and the stirring was continued at room temperature for 16 hours. After the removal of the solvent in vacuo, the residue was partitioned between cold 0.25 N NaOH (25 mL) and EtOAc (25 mL). The organic phase was washed successively with cold 0.25 N NaOH (2x25 mL), water, 5% citric acid (2x15 mL), water, dried ($Na_2SO_4$), filtered, and concentrated under reduced pressure. The resulting material was crystallized from EtOAc/hexane to give 0.48 g (63%) of L-alanine, 3-cyclohexyl-N-[[N-ε-BOC-L-lysyl]-L-(O-t-butyl)-N-carbobenzoxy-seryl]-, methyl ester as a white powder. FAB-MS m/z=697 (M+Li), 641, & 597. HRMS calcd. for $C_{36}H_{59}N_4O_9$ (M+H), 691.4282, found 691.4266.

Part E: Preparation of L-Alanine, 3-cyclohexyl-N-[N-ε-BOC-L-Lysyl]-L-(O-t-butyl)seryl]-, Methyl Ester.

A solution of L-alanine, 3-cyclohexyl-N-[[N-ε-BOC-L-lysyl]-L-(O-t-butyl)-N-carbobenzoxy-seryl]-, methyl ester from Part D (0.18 g, 0.26 mmol) in MeOH (10.0 mL) was hydrogenated at atmospheric pressure in the presence of 5% Pd/C (0.05 g) at room temperature for 1 hour. The catalyst was removed by filtration, the filtrate concentrated, and the residue dried in a desiccator for 1 hour to give L-alanine, 3-cyclohexyl-N-[N-ε-BOC-L-lysyl]-L-(O-t-butyl)seryl]-, methyl ester [FAB-MS m/z=563 (M+Li)], which was used without purification in Part M below.

Part F: Preparation of Methyl 4-iodophenylacetate.

4-iodophenylacetic acid (5.2 g, 0.02 mol) and DMAP (0.25 g, 0.002 mol) was dissolved in dichloromethane (40 mL) and methanol (3.2 mL), and the solution was cooled to 0° C. Then a solution of DCC (4.32 g, 0.021 mol) in dichloromethane was added dropwise over a period of 15 minutes. The reaction mixture was stirred at 0° C. for 1 hour and at room temperature for 16 hours, then filtered. The filtrate was diluted with dichloromethane (40 mL) and washed with 5% citric acid (4×25 mL), water (2×50 mL), dried ($Na_2SO_4$), filtered, and concentrated. The residual liquid was purified by silica gel flash column chromatography eluting with 20% EtOAc in hexane to give methyl 4-iodophenylacetate (4.5 g, 82%) as a colorless liquid: $^1$H-NMR ($CDCl_3$) δ: 7.64 (d, 2H, J=8.4 Hz), 7.01 (2H, J=8.4 Hz), 3.69 (s, 3H), 3.57 (s, 2H); FAB-MS m/z=283 (M+Li). HRMS calcd. for $C_9H_{10}IO_2$ (M+H), 276.9725, found 276.9726.

Part G: Preparation of Methyl±2-(4-iodophenyl)propionate.

To a solution of methyl 4-iodophenylacetate (1.0 g, 3.62 mmol) in dry THF (10 mL) was added sodium hydride (0.095 g, 3.96 mmol, 80% suspension), stirring continued at 5° C. for 30 minutes, followed by the addition of iodomethane (0.68 g, 4.8 mmol). After stirring for 2 hours at room temperature, additional iodomethane (0.46 g, 3.2 mmol) was added, and the reaction mixture was stirred at room temperature overnight for 16 hours. Acetic acid (0.2 mL) was added, and the reaction mixture was concentrated under reduced pressure. The residue was partitioned between EtOAc (30 mL) and 5% citric acid (25 mL). The organic phase was washed with water (2×20 mL), dried ($Na_2SO_4$), filtered and concentrated. The resulting substance was purified by silica gel flash column chromatography eluting with 20% EtOAc in hexane to give methyl±2-(4-iodophenyl)propionate (0.7 g, 70%) as a pale yellow liquid. $^1$H-NMR ($CDCl_3$) δ: 7.64 (d, 2H, J=8.4 Hz), 7.03 (2H, J=8.4 Hz), 3.66 (m over s, 4H), 1.46 (d, 3H, J=7.2 Hz); FAB-MS m/z=291 (M+H); HRMS calcd for $C_{10}H_{12}IO_2$ (M+H) 290.9882, found 290.9861.

Part H: Preparation of Methyl±2-[4-(4-hydroxy-1-butynyl) phenyl]-propionate.

To a mixture of methyl±2-(4-iodophenyl)propionate (0.9 g, 3.1 mmol), butyn-1-ol (0.4 g, 5.7 mmol), and triethylamine (0.43 g, 4.3 mmol) in acetonitrile (15 mL) at 0° C. was added bistriphenylphosphine palladium chloride (0.2 g, 0.28 mmol) and CuI (0.025,g). The reaction mixture was stirred at 0° C. under argon atmosphere for 30 minutes and at room temperature for 2.5 hours. The dark colored reaction mixture was concentrated under reduced pressure, and the residue was partitioned between 5% citric acid (50 mL) and EtOAc (50 mL). The organic phase was washed with 5% citric acid (3×15 mL), water, dried ($Na_2SO_4$), filtered, and concentrated. The resulting material was purified by silica gel flash column chromatography eluting with 40% EtOAc in hexane to afford methyl±2-[4-(4-hydroxy-1-butynyl) phenyl]propionate (0.69 g, 96%) as an orange colored liquid. FAB-MS m/z=233 (M+H); HRMS calcd for $C_{14}H_{17}O_3$ (M+H) 233.1178, found 233.1149.

Part I: Preparation of Methyl±2-[4-(4-hydroxybutyl)phenyl] propionate.

Methyl±2-[4-(4-hydroxy-1-butynyl)phenyl]propionate (0.6 g, 2.31 mmol) was dissolved in MeOH (10 mL) and hydrogenated at 40 psi for 4.5 hours in the presence of 5% Pd/C (0.3 g) and filtered. The filtrate was concentrated to dryness to give methyl±2-[4-(4-hydroxybutyl)phenyl] propionate (0.6 g, 98%) as a pale yellow viscous liquid. FAB-MS m/z=237 (M+H); HRMS calcd for $C_{14}H_{21}O_3$ (M+H) 237.1491, found 237.1491.

Part J: Preparation of Methyl±2-[4-(4-iodobutyl)phenyl] propionate.

To a solution of methyl±2-[4-(4-hydroxybutyl)phenyl] propionate (0.8 g, 3.4 mmol) in acetonitrile (15 mL) was added methyltriphenoxyphosphonium iodide (2.0 g, 4.4 mmol), and the mixture was stirred at room temperature for 16 hours. Methanol (5 mL) was added, and the reaction mixture was concentrated under reduced pressure. The resulting residue was partitioned between cold 0.25 N NaOH (50 mL) and dichloromethane (50 mL), the organic phase was washed with 0.25 N NaOH (2×25 mL), water (3×25 mL) dried ($Na_2SO_4$), filtered, and concentrated. The residual material was purified by silica gel flash column chromatography eluting with 20% EtOAc in hexane to furnish methyl±2-[4-(4-iodobutyl)phenyl]propionate (1.0 g, 85%) as a pale yellow viscous liquid. $^1$H NMR ($CDCl_3$) δ: 7.2 (m, 2H), 7.14 (m, 2H), 3.66 (s over m, 4H), 3.2 (t, 2H), 2.6 (t, 2H), 1.85 (m, 2H), 1.7 (m, 2H), 1.48 (d, 3H, J=7.2 Hz); FAB-MS m/z=353 (M+Li); HRMS calcd for $C_{14}H_{20}IO_2$ (M+H) 347.0508, found 347.0509.

Part K: Preparation of ±2-[4-(4-iodobutyl)phenyl]propionic Acid.

A solution of methyl±2-[4-(4-iodobutyl)phenyl] propionate (1.0 g, 2.9 mmol) in 1M LiOH (5.00 mL) containing MeOH (3.75 mL) was heated to 60° C. for 1 hour under a nitrogen atmosphere. The reaction mixture was concentrated under reduced pressure, water (25 mL) was added and the mixture was extracted with ether (3×15 mL). The combined ether extracts were washed with water (3×15 mL), dried ($Na_2SO_4$), filtered, and concentrated to give ±2-[4-(4-iodobutyl)phenyl]propionic acid (0.7 g, 73%) as a colorless liquid. $^1$H NMR ($CDCl_3$) δ: 7.22 (m, 2H), 7.15 (m, 2H), 3.7 (m, 1H), 3.4 & 3.2 (t, 2H), 2.6 (t, 2H), 1.85 (m, 2H), 1.7 (m, 2H), 1.5 (d, 3H, J=6.9 Hz); FAB-MS m/z=339 (M+Li).

Part L: Preparation of ±2-[4-(2-methyl-1H-imidazol-1-yl)-butyl]phenyl]-propionic Acid Hydrochloride.

To a solution of ±2-[4-(4-iodobutyl)phenyl]propionic acid (0.25 g, 0.75 mmol) in DMF (1.5 mL) at 0° C. was added NaH (0.95 g, 80% suspension, 2.1 mmol), and the mixture was stirred at 0° C. for 30 minutes and at room temperature for 1.5 hours under an argon atmosphere. The DMF was distilled away in vacuo. The resulting residue was treated with 2N HCl (3 mL) and water (10 ml) and washed with EtOAc (3×5 mL). The aqueous phase was freeze dried and the residue was washed with 10% $CH_3CN$ in EtOAc (20 mL) and dried to afford ±2-[[4-(2-methyl-1H-imidazol-1-yl)-butyl]phenyl]propionic acid hydrochloride (0.14 g, 58%). $^1$H-NMR (DMSO-d6) δ: 7.64 (d, 1H, J=2.1 Hz), 7.54 (d, 1H, J=2.1 Hz), 7.15 (m, 4H), 4.1 (t, 2H, J=7.2 Hz), 3.6 (q, 1H), 2.57 (s over m, 5H), 1.75 (m, 2H), 1.55 (m, 2H), 1.32 (d, 3H, J=6.9 Hz); FAB-MS m/z=287 (M+H); HRMS calcd for $C_{17}H_{23}N_2O_2$ (M+H) 287.1760, found 287.1754.

Part M: Preparation of L-Alanine, 3-cyclohexyl-N-[N$^2$-[N-[2-[4-[4-(2-methyl-1H-imidazol-1-yl)butyl]phenyl] oxopropyl]-L-(Q-t-butyl)seryl]-N-ϵ-BOC-L-lysyl]-, (±), Methyl Ester.

The ±[2-[4-(2-methyl-1H-imidazol-1-yl)-butyl]phenyl]] propionic acid hydrochloride (0.12 g, 0.38 mmol) from Part L and HOBt (0.065 g, 0.43 mmol) were dissolved in dimethylacetamide (1.00 mL) and dichloromethane (1.00 mL). The mixture was cooled to 0° C., DCC (0.08 g, 0.39 mmol) was added, stirred for 45 minutes, then added to a solution of L-alanine, 3-cyclohexyl-N-[N-ϵ-BOC-L-lysyl]-L-(O-t-butyl) seryl]-, methyl ester from Part E in dimethylacetamide (0.5 mL) containing N-methylmorpholine (0.028 g, 0.27 mmol) and DMAP (0.005 g). The reaction mixture was stirred at room temperature for 16 hours, and concentrated in vacuo. The resulting residue was partitioned between dichloromethane (25 mL) and cold 0.25 N NaOH (10 mL). The organic phase was washed successively with cold 0.25 N NaOH (10 mL), water (3×10 mL), dried ($Na_2SO_4$), filtered, and concentrated. The resulting solid was washed with cold 15% ethyl acetate in hexane and dried to give 0.14 g (65%) of L-alanine, 3-cyclohexyl-N-[$N^2$-[N-[2-[4-[4-(2-methyl-1H-imidazol-1-yl)butyl]-phenyl]-oxopropyl]-L-(O-t-butyl)seryl]-N-ε-BOC-L-lysyl]-, (±), methyl ester as an amorphous material, which was used without further purification in Part N. FAB-MS m/z=825 (M+H), HRMS calcd for $C_{45}H_{73}N_6O_8Li$ (M+Li): 831.5572, found 831.5597.

Part N: Preparation of L-Alanine, 3-cyclohexyl-N-[$N^2$-[N-[2-[4-[4-(2-methyl-1H-imidazol-1-yl)butyl]phenyl] oxopropyl]-L-(O-t-butyl)seryl]-N-ε-BOC-L-lysyl]-, (±), bis-trifluoroacetate.

A solution of L-alanine, 3-cyclohexyl-N-[$N^2$-[N-[2-[4-[4-(2-methyl-1H-imidazol-1-yl)butyl]phenyl]-oxopropyl]-L-(O-t-butyl)seryl]-N-ε-BOC-L-lysyl]-, (±), methyl ester from Part M (0.14 g, 0.17 mmol) in 1M LIOH (0.4 mL, 0.4 mmol) and THF (0.3 mL) was stirred at room temperature for 2.5 hours. The reaction mixture was diluted with water (20 mL) and washed with EtOAc (2x20 mL). The aqueous phase was acidified with 5% citric acid, and extracted with dichloromethane (2x15 mL). The combined organic phases were washed with water (2x10 mL), dried ($Na_2SO_4$), filtered, and concentrated under reduced pressure. The residue, which contained the desired L-alanine, 3-cyclohexyl-N-[$N^2$-[N-[2-[4-[4-(2-methyl)-1H-imidazol-1-yl)butyl]phenyl]-oxopropyl]-L-(O-t-butyl)seryl]-N-ε-BOC-L-lysyl]-, (±), [FAB-MS m/z=811 (M+H), HRMS calcd. for $C_{44}H_{71}N_6O_8$ (M+H), 811.5333, found 811.5328], was treated with trifluoroacetic acid (0.8 mL) and stirred at room temperature for 3.5 hours. After the removal of trifluoroacetic acid under reduced pressure, the residue was purified by reverse phase HPLC using a 5–70% $CH_3CN/H_20$ gradient (30 min) at a flow rate of 70 mL/min. The appropriate fractions were pooled and freeze dried to give 0.035 g (23%) of pure L-alanine, 3-cyclohexyl-N-[$N^2$-[N-[2-[4-[4-(2-methyl-1H-imidazol-1-yl)butyl]phenyl]-oxopropyl]-L-seryl]-L-lysyl]l-, (±), bis-trifluoroacetate as a white powder. FAB-MS m/z=655 (M+H); HRMS calcd for $C_{35}H_{55}N_6O_8$ (M+H): 655.4183, found 655.4210. Amino acid analyses: calcd serine 1.00, lysine 1.00; found serine 1.00, lysine 1.00.

EXAMPLE 2

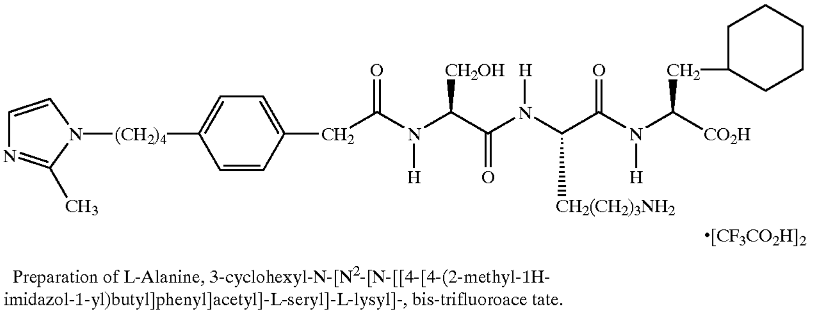

Preparation of L-Alanine, 3-cyclohexyl-N-[$N^2$-[N-[[4-[4-(2-methyl-1H-imidazol-1-yl)butyl]phenyl]acetyl]-L-seryl]-L-lysyl]-, bis-trifluoroace tate.

Part A: Preparation of Methyl 4-(4-Hydroxy-1-butynyl) phenylacetate.

To a solution of butyn-1-ol (0.76 g, 0.11 mol) and methyl 4-iodophenylacetate (1.5 g, 0.0054 mol) in acetonitrile (10 mL) at 0° C., triethylamine (1.5 mL, 0.01 mol) was added, followed by the addition of bistriphenylphosphine palladium chloride (0.25 g, 0.36 mmol) and CuI (0.025 g). The reaction mixture was stirred at 0° C. under an argon atmosphere for 30 minutes and at room temperature for 3 hours. The dark colored reaction mixture was concentrated under reduced pressure, and the residue was partitioned between 5% citric acid (50 mL) and EtOAc (50 mL). The organic phase was washed with 5% citric acid (3x15 mL), water, dried ($Na_2SO_4$), filtered, and concentrated. The resulting material was purified by silica gel flash column chromatography eluting with 35% EtOAc in hexane to afford methyl 4-(4-hydroxy-1-butynyl)phenylacetate (1 g, 85%) as a dark colored liquid. FAB-MS m/z=219 (M+H), HRMS calcd. for $C_{13}H_{15}O_3$ (M+H), 219.1021, found 219.1008. Calcd for $C_{13}H_{14}O_3$: C, 71.54, H 6.46; found: C, 71.04, H, 6.41.

Part B: Preparation of Methyl 4-(4-Hydroxy-1-butyl) phenylacetate.

Methyl 4-(4-hydroxy-1-butynyl)phenylacetate (10.6 g, 0.0485 mol) was dissolved in methanol (200 mL), then 10% palladium on carbon (1.1 g) was added, and the mixture was stirred under hydrogen (50 psi). After 6 hours, additonal 10% palladium on carbon (1 g) was added, and the mixture was stirred overnight. The catalyst was filtered through celite, the filtrate was concentrated and dried in vacuo to give 10.20 g (94.5%) of methyl 4-(4-hydroxy-1-butyl) phenylacetate as a yellow liquid. FAB-MS m/z=223 (M+H); HRMS calcd for $C_{13}H_{19}O_3$ (M+H) 223.1334, found 223.1328.

Part C: Preparation of Methyl 4-(4-Iodo-1-butyl) phenylacetate.

To a solution of methyl 4-(4-hydroxy-1-butyl) phenylacetate (3.88 g, 17 mmol) in dry acetonitrile (10 mL), a solution of methyl triphenoxyphosphonium iodide (10.26 g, 23 mmol) in dry acetonitrile (100 mL) was added, and the reaction was stirred at 0° C. The reaction mixture was warmed up to room temperature over several hours and stirred at room temperature overnight. The reaction mixture was quenched with excess methanol at 0° C. The solvents were removed under reduced pressure, the residue was dissolved in ethyl acetate (500 mL), and washed successively with cold 0.2N NaOH (2x500 mL), water (2x500 mL), saturated brine (2x500 mL), dried over $MgSO_4$, filtered, and concentrated. The crude material thus obtained was purified by silica gel flash column chromatography eluting with 10% EtOAc in hexane to give 4.12 g (71%) of pure methyl 4-(4-iodo-1-butyl)phenylacetate as a clear liquid. $^1H$ NMR (400 MHz, $CDCl_3$) δ: 1.70–1.89 (m, 4H), 2.62 (t, 2H, J=7.52 Hz), 3.20 (t, 2H, J=6.86 Hz), 3.60 (s, 2H), 3.69 (s, 3H), 7.17 (ab quartet, 4H, J=7.92 Hz). FAB-MS m/z=333 (M+H); HRMS calcd for $C_{13}H_{18}O_2I$ (M+H) 333.0351, found 333.0347.

Part D: Preparation of 4-(4-Iodo-1-butyl)phenylacetic Acid.

Methyl 4-(4-iodo-1-butyl)phenylacetate (21.28 g, 0.064 mol) was dissolved in methanol (160 mL). Lithium hydroxide (6.72 g, 0.16 mol) and water (10 mL) were added, and the reaction mixture was stirred for 18 hours at room temperature. The solvents were removed under reduced pressure, the residue was treated with ethyl acetate (600 mL), and the organic solution was washed with 1N HCl (3x300 mL), brine (3x300 mL), dried over $MgSO_4$, and filtered. The filtrate was concentrated and dried in vacuo to give 17.5 g (85.9%) of 4-(4-iodo-1-butyl)phenylacetic acid as a yellow solid. $^1H$ NMR (300 MHz, $CD_3OD$) δ: 1.68–1.84 (m, 4H), 2.61 (t, 2H, J=7.35 Hz), 3.24 (t, 2H, J=6.75 Hz), 3.55 (s, 2H), 7.16 (ab quartet, 4H, J=8.26 Hz). FAB-MS m/z=319 (M+H); HRMS calcd for $C_{12}H_{16}O_2I$ (M+H) 319.0194, found 319.0208.

Part E: Preparation of [[4-[4-(2-Methyl-1H-imidazol-1-yl]-butyl]-phenylacetic Acid Hydrochloride.

To a suspension of sodium hydride (3.17 g, 0.132 mol) in dry DMF (30 mL) at 5° C., a solution of 2-methylimidazole (10.11 g, 0.123 mol) in dry DMF (50 mL) was added. The reaction mixture was stirred for 30 minutes at 5° C., then a solution of 4-(4-iodo-1-butyl)phenylacetic acid (14 g, 0.044 mol) was added in dry DMF (15 mL), and stirring continued for 1.5 hours. The reaction mixture was allowed to warm to room temperature and stirred for 5 hours, cooled to 0° C., and quenched with 1N HCl. The solution was concentrated, the residue dissolved in water, and washed several times with ethyl acetate. Water was removed under reduced pressure, the residue was dried in vacuo, and treated with ethyl acetate/acetonitrile (1:1, v/v). The solid was filtered, and washed with ethyl acetate several times. The solid thus obtained was then washed with absolute ethanol. The ethanol washings were concentrated and dried to give 7.63 g (64%) of 4-[4-(2-methyl-1H-imidazol-1-yl)-butyl]-phenylacetic acid hydrochloride. $^1H$ NMR (300 MHz, $CD_3OD$) δ: 1.65–1.88 (m, 4H), 2.58 (s, 3H), 2.67 (t, 2H, J=7.35 Hz), 3.56 (s, 2H), 4.12 (t, 2H, J=7.25 Hz), 7.17 (ab quartet, 4H, J=8.16 Hz), 7.40 (d, 1H, J=2.01 Hz), 7.47 (d, 1H, J=2.01 Hz). FAB-MS m/z=273 (M+H); HRMS calcd for $C_{16}H_{21}N_2O_2$ (M+H): 273.1603, found 273.1635.

Part F: Preparation of L-Alanine, 3-cyclohexyl-N-[$N^2$-[N-[[4-[4-(2-Methyl-1H-imidazol-1-yl)butyl]phenyl]acetyl]-L-(Q-t-butyl)seryl]-N-ϵ-BOC-L-lysyl]-, Methyl Ester.

To a solution of 4-[4-(2-methyl-1H-imidazol-1-yl)-butyl] phenylacetic acid hydrochloride (0.12 g, 0.39 mmol) and HOBt (0.065 g, 0.43 mmol) in dimethylacetamide (2.5 mL), DCC (0.085 g, 0.41 mmol) was added, and the mixture was stirred at 0° C. for 2 hours. Then a solution of L-alanine, 3-cyclohexyl-N-[N-ϵ-BOC-L-lysyl]-L-(O-t-butyl)seryl]-, methyl ester in dimethylacetamide (0.5 mL) containing N-methylmorpholine (0.041 g, 0.41 mmol) and DMAP (0.005 g) was added. The reaction mixture was stirred at room temperature for 24 hours, and concentrated in vacuo. The residue was partitioned between EtOAc (25 mL) and cold 0.25 N NaOH (10 mL). The organic phase was washed with water (3x15 mL), dried ($Na_2SO_4$), filtered, and concentrated under reduced pressure to give an amorphous substance which was crystallized from ether/hexane to afford 0.15 g (65%) of L-alanine, 3-cyclohexyl-N-[$N^2$-[N-[[4-[4-(2-methyl-1H-imidazol-1-yl)butyl]phenyl]-acetyl]-L-(O-t-butyl)seryl]-N-ϵ-BOC-L-lysyl]-, methyl ester as a pale yellow powder. FAB-MS m/z=811 (M+H), HRMS calcd. for $C_{44}H_{71}N_6O_8$ (M+H), 811.5337, found 811.5324.

Part G: Preparation of L-Alanine, 3-cyclohexyl-N-[$N^2$-[N-[[4-[4-(2-Methyl-1H-imidazol-1-yl)butyl]phenyl]acetyl]-L-seryl]-L-lysyl]-, bis-trifluoroacetate.

The L-alanine, 3-cyclohexyl-N-[$N^2$-[N-[[4-[4-(2-methyl-1H-imidazol-1-yl)butyl]phenyl]acetyl]-L-(O-t-butyl)seryl]-N-ϵ-BOC-L-lysyl]-, methyl ester (0.15 g, 0.19 mmol) from Part F, was stirred with 1 M LiOH, (0.3 mL) containing MeOH (0.2 mL), for 2 hours at room temperature. The mixture was acidified with 5% citric acid and extracted with EtOAc (3x15 mL). The combined organic phases were washed with water (3x10 mL), dried ($Na_2SO_4$), filtered, and concentrated. The resulting residue was dried in vacuo for 16 hours and then treated with trifluoroacetic acid (1.5 mL). After stirring for 4 hours at room temperature, the solution was concentrated under reduced pressure, and the residue was purified by reverse-phase HPLC using a 5–70% $CH_3CN/H_2O$ gradient (30 min) at 70 mL/min flow rate. The appropriate fractions were combined and freeze dried to afford 0.053 g (34%) of L-alanine, 3-cyclohexyl-N-[$N^2$-[N-[[4-[4-(2-methyl-1H-imidazol-1-yl)butyl]-phenyl]acetyl]-L-seryl]-L-lysyl]-, bis-trifluoroacetate as a white powder. FAB-MS m/z=641 (M+H), HRMS calcd. for $C_{34}H_{53}N_6O_6$ (M+H), 641.4027, found 641.4041. Amino acid analyses: calcd for serine 1.00, lysine 1.00, found serine 1.02; lysine 1.00.

EXAMPLE 3

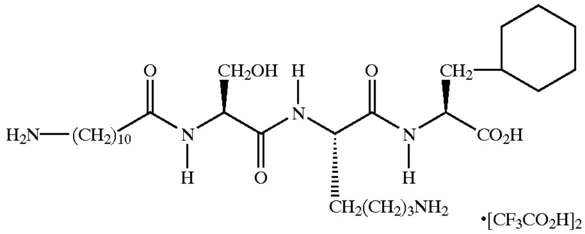

Preparation of L-Alanine, 3-cyclohexyl-N-[[(11-amino-undecanoyl-L-seryl]-L-lysyl]-, bis-trifluoroacetate.

Part A:

To commercially available (Peninsula Laboratories) hydroxymethyl-resin of styrene/1% divinylbenzene (0.67 g, 0.75 mequiv/g) in 10 mL of dichloro-methane was added N-BOC-(3-cyclohexyl)-L-alanine (0.55 g, 2.0 mmoles), dicyclohexylcarbodiimide (0.4 g, 2.0 mmoles), and 4-dimethylaminopyridine (0.02 g, 0.2 nmoles). After stirring for 18 hours at room temperature, the amino acid resin was separated by filtration and treated with 50% trifluoroacetic acid in dichloromethane for 30 minutes. Then the amino acid resin was again separated by filtration, and was washed with dichloro-methane (3x20 mL), isopropanol (3x20 mL), diisopropylethylamine (10%, v/v) in dichloromethane (3x20 mL), and dichloromethane (3x20 mL).

Part B:

N-α-BOC-N-ϵ-(2-chloro-benzyloxycarbonyl)-L-lysine (0.83 g, 2.0 mmoles) was activated with dicyclohexylcarbodiimide (0.20g, 1.0 mmoles) in dichloromethane and coupled to the resin product from Part A for 60 minutes. The dipeptide-resin was separated by filtration, the N-α-BOC group was removed with trifluoroacetic acid, and the resulting resin was washed as described in Part A.

Part C:

N-BOC-(O-benzyl)-L-serine (0.59 g, 2.0 mmoles) was activated with dicyclohexylcarbodiimide (0.20 g, 1.0 mmoles) in dichloromethane and coupled to the resin product from Part B for 60 minutes at room temperature. The tripeptide-resin was separated by filtration, the N-α-BOC group was removed with trifluoroacetic acid in dichloromethane, and the resulting resin was washed as described in Part A.

Part D:

N-BOC-11-aminoundecanoic acid (Bachem, 0.60 g, 2.0 mmoles) was activated with disuccinimidylcarbonate (0.56 g, 2.2 mmoles) and 4-dimethylamino-pyridine (0.02 g, 0.2 mmoles) in dimethylformamide/pyridine (2/1, v/v) and reacted with the resin product from Part C for 60 minutes at room temperature. The resulting resin was separated by filtration, the N-α-BOC group was removed with trifluoroacetic acid in dichloromethane, and the resulting resin was treated with 90% hydrogen fluoride/anisole (v/v) for 60 minutes at 0° C. The hydrogen fluoride was removed by evaporation, and the product was extracted into 30% acetic acid/water and then lyophilized. The crude material was purified by reverse phase HPLC on a Waters Deltapak RPC-18 column using a linear gradient of 1% to 35% acetonitrile (0.05% trifluoroacetic acid) in water (0.05% trifluoroacetic acid) over 30 minutes at 15 mL/min, which after lyophilization, gave 137 mg of 95% pure (by HPLC) L-alanine, 3-cyclohexyl-N-[[(il-amino-undecanoyl)-L-seryl]-L-lysyl]-, bis-trifluoroacetate. HRMS: (M+H) calcd 570.4231, found 570.4262. Amino acid analyses: calcd serine 1.00, lysine 1.00; found: serine 0.99, lysine 1.01.

EXAMPLE 4

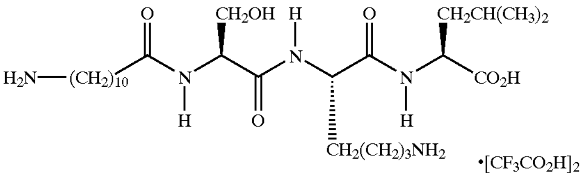

Preparation of L-Leucine, N-[[(11-amino-undecanoyl-L-seryl]-L-lysyl]-, bis-trifluoroacetate.

Part A:

Commercially available (Sigma) N-BOC-L-leucyl-O-methylphenylacetamido-methyl-resin (1.0 g, 0.5 mmoles Leu/g; resin: polystyrene/1% divinylbenzene) was treated with 20 mL of 50% trifluoroacetic acid in dichloromethane for 30 minutes. The amino acid-resin was then separated by filtration, and washed with dichloromethane (3x20 mL), isopropanol (3x20 mL), diisopropylethyl-amine (10%, v/v) in dichloromethane (3x20 mL), and dichloromethane (3x20 mL).

Part B:

N-α-BOC-N-ε-(2-chloro-benzyloxycarbonyl)-L-lysine (0.83 g, 2.0 mmoles) was activated with dicyclohexylcarbodiimide (0.20 g, 1.0 mmoles) in dichloromethane and coupled to the resin product from Part A for 60 minutes at room temperature. The dipeptide-resin was separated by filtration, the N-α-BOC group was removed with trifluoroacetic acid in dichloromethane, and the resulting resin was washed as described in Part A.

Part C:

N-BOC-(O-benzyl)-L-serine (0.59 g, 2.0 mmoles) was activated with dicyclohexylcarbodiimide (0.20 g, 1.0 mmoles) in dichloromethane and coupled to the resin product from Part B for 60 minutes at room temperature. The tripeptide-resin was separated by filtration, the N-α-BOC group was removed with trifluoroacetic acid in dichloromethane and the resulting resin was washed as described in Part A.

Part D:

N-BOC-11-aminoundecanoic acid (Bachem, 0.60 g, 2.0 mmoles) was activated with disuccinimidylcarbonate (0.56 g, 2.2 mmoles) and 4-dimethylamino-pyridine (0.02 g, 0.2 mmoles) in 10 mL of dimethylformamide/pyridine (2/1, v/v) and reacted with the resin product from Part C for 60 minutes at room temperature. The resulting resin was separated by filtration, the N-α-BOC group was removed with trifluoroacetic acid in dichloromethane, and the resulting resin was treated with 90% hydrogen fluoride/anisole (v/v) for 60 minutes at 0° C. The hydrogen fluoride was removed by evaporation, and the product was extracted into 30% acetic acid/water and then lyophilized. The crude material was purified by reverse phase HPLC on a Waters Deltapak RPC-18 column using a linear gradient of 1% to 35% acetonitrile (0.05% trifluoroacetic acid) in water (0.05% trifluoroacetic acid) over 30 minutes at 15 mL/min, which after lyophilization, gave 84.8 mg of 98% pure (by HPLC) L-leucine, N-[[(11-amino-undecanoyl)-L-seryl]-L-lysyl]-, bis-trifluoroacetate.

HRMS: (M+H) calcd 530.3918, found 530.3919. Amino acid analyses: calcd serine 1.00, lysine 1.00, leucine 1.00; found: serine 1.05, lysine 1.00, leucine 1.05.

EXAMPLE 5

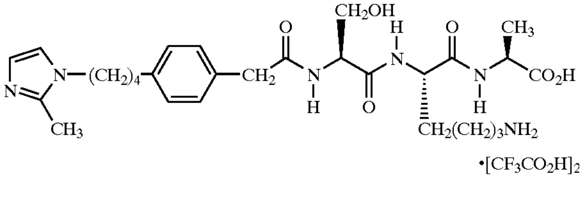

Preparation of L-Alanine, N-[N[2]-[N-[[4-[4-(2-methyl-1H-imidazol-1-yl)butyl]phenyl]acetyl]-L-seryl]-L-lysyl]-, bis-trifluoroacetate.

Part A:

To commercially available (Peninsula Laboratories) hydroxymethyl-resin of styrene/1% divinylbenzene (0.22 g, 0.75 mequiv/g) in 10 mL of dichloro-methane was added N-BOC-L-alanine (0.035 g, 0.183 mmoles), dicyclohexylcarbodiimide (0.034 g, 0.167 mmoles), and 4-dimethylaminopyridine (0.007 g, 0.06 mmoles). After stirring for 18 hours at room temperature, the amino acid-resin was separated by filtration, treated with 10 mL of 50% trifluoroacetic acid in dichloromethane for 30 minutes, and separated by filtration. The resulting amino acid-resin was washed with dichloromethane (3x10 mL), isopropanol (3x10 mL), diisopropylethylamine (10%, v/v) in dichloromethane (3x10 mL), and dichloromethane (3x10 mL).

Part B:

N-α-BOC-N-ε-(2-chloro-benzyloxycarbonyl)-L-lysine (0.83 g, 2.0 mmoles) was activated with dicyclohexylcarbodiimide (0.20 g, 1.0 mmoles) in dichloromethane and coupled to the resin product from Part A for 60 minutes at room temperature. The dipeptide-resin was separated by filtration, the N-α-BOC group was removed with trifluoroacetic acid in dichloromethane, and the resulting resin was washed as described in Part A.

Part C:

N-BOC-(O-benzyl)-L-serine (0.59 g, 2.0 mmoles) was activated with dicyclohexylcarbodiimide (0.20 g, 1.0 mmoles) in dichloromethane and coupled to the resin product from Part B for 60 minutes at room temperature. The tripeptide-resin was separated by filtration, the N-α-BOC group was removed with trifluoroacetic acid in dichloromethane, and the resulting resin was washed as described in Part A.

Part D:

To 4-[4-(2-methyl-1H-imidazol-1-yl)-butyl]phenylacetic acid hydrochloride (0.053 g, 0.17 mmoles) in 2 mL of dimethylformamide/dichloromethane (1/1) was added diisopropylethylamine (0.03 mL, 0.17 nmoles). The mixture was then added to a suspension of the tripeptide-resin product from Part C in 5 mL of dichloromethane, followed by dicyclohexylcarbodiimide (0.034 g, 0.17 mmoles). After 18 hours at room temperature, the solvent was removed by filtration and the resulting resin was washed with dichloromethane.

Part E:

The resin product from part D was treated with 3 mL of 90% hydrogen fluoride in anisole (v/v) for 60 minutes at 0° C. The hydrogen fluoride was removed by evaporation, and the product was extracted into 30% acetic acid/water and then lyophilized. The crude material was purified by reverse phase HPLC on a Waters Deltapak RPC-18 column using a linear gradient of 1% to 35% acetonitrile (0.05% trifluoro-acetic acid) in water (0.05% trifluoro-acetic acid) over 30 minutes at 15 mL/min, which after lyophilization, gave 16.7 mg of 99% pure (by HPLC) L-alanine, N-[$N^2$-[N-[[4-[4-(2-methyl-1H-imidazol-1-yl)butyl]phenyl]acetyl]-L-seryl]-L-lysyl]-, bis-trifluoroacetate. HRMS: (M+H) calcd 559.3244, found 559.3254. Amino acid analyses: calcd serine 1.00, lysine 1.00, alanine 1.00; found: serine 0.99, lysine 0.99, alanine 1.01.

EXAMPLE 6 group was removed with trifluoroacetic acid in dichloromethane, and the resulting resin was washed as described in Part A.

Part D:

To 4-[4-(2-methyl-1H-imidazol-1-yl)butyl]phenylacetic acid hydrochloride (0.053 g, 0.17 mmoles) in 2 mL of dimethylformamide/dichloromethane (1/1) was added diisopropylethylamine (0.03 mL, 0.17 mmoles). The mixture was then added to a suspension of the tripeptide-resin from Part C in 5 mL of dichloromethane, followed by dicyclohexylcarbodiimide (0.034 g, 0.17 mmoles). After 18 hours at room temperature, the solvent was removed by filtration and the resulting resin product was washed with dichloromethane.

Part E:

The resin product from Part D was treated with 3 mL of 90% hydrogen fluoride/anisole (v/v) for 60 minutes at 0° C. The hydrogen fluoride was removed by evaporation, and the product was extracted into 30% acetic acid/water and then lyophilized. The crude material was purified by reverse phase HPLC on a Waters Deltapak RPC-18 column using a linear gradient of 1% to 35% acetonitrile (0.05% trifluoro-

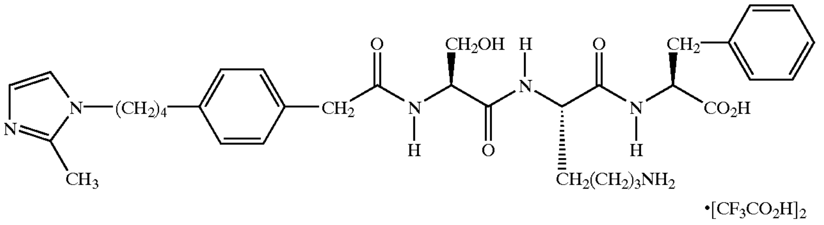

Preparation of L-Alanine, 3-phenyl-N-[$N^2$-[N-[[4-[4-(2-methyl-1H-imidazol-1-yl)butyl]phenyl]acetyl]-L-seryl]-L-lysyl]-, bis-trifluoroace tate.

Part A:

To commercially available (Peninsula Laboratories) hydroxymethyl-resin of styrene/1% divinylbenzene (0.22 g, 0.75 mequiv/g) in 10 mL of dichloro-methane was added N-BOC-L-phenylalanine (0.048 g, 0.183 mmoles), dicyclohexylcarbodiimide (0.034 g, 0.167 mmoles), and 4-dimethylamino-pyridine (0.007 g, 0.06 mmoles). After stirring for 18 hours at room temperature, the amino acid-resin was separated by filtration and treated with 10 mL of 50% trifluoroacetic acid in dichloromethane for 30 minutes, then again separated by filtration. The resulting amino acid-resin was washed with dichloromethane (3x10 mL), isopropanol (3x10 mL), diisopropylethylamine (10%, v/v) in dichloromethane (3x10 mL), and dichloromethane (3x10 mL).

Part B:

N-α-BOC-N-ε-(2-chloro-benzyloxycarbonyl)-L-lysine (0.83 g, 2.0 mmoles) was activated with dicyclohexylcarbodiimide (0.20 g, 1.0 mmoles) in dichloro-methane and coupled to the resin product from Part A for 60 minutes at room temperature. The dipeptide-resin was separated by filtration, the N-α-BOC group was removed with trifluoro-acetic acid in dichloromethane, and the resulting resin was washed as described in Part A.

Part C:

N-BOC-(O-benzyl)-L-serine (0.59 g, 2.0 mmoles) was activated with dicyclohexylcarbodiimide (0.20 g, 1.0 nmoles) in dichloromethane and coupled to the resin product from Part B for 60 minutes at room temperature. The tripeptide-resin was separated by filtration, the N-α-BOC acetic acid) in water (0.05% trifluoroacetic acid) over 30 minutes at 15 mL/min, which after lyophilization, gave 17.7 mg of 97% pure (by HPLC) L- alanine, 3-phenyl-N-[$N^2$-[N-[[4-[4-(2-methyl-1H-imidazol-1-yl)butyl]phenyl]acetyl]-L-seryl]-L-lysyl]-, bis-trifluoroacetate. HRMS: (M+H) cal. 635.3557, found 635.3565. Amino acid analyses: calcd serine 1.00, lysine 1.00, phenylalanine 1.00; found: serine 1.02, lysine 1.02, phenylalanine 0.96.

EXAMPLE 7

Part A:

To commercially available (Peninsula Laboratories) hydroxymethyl-resin of styrene/1% divinylbenzene (0.22 g, 0.75 mequiv/g) in 10 mL of dichloro-methane was added N-BOC-L-isoleucine (0.042 g, 0.183 mmoles), dicyclohexylcarbodiimide (0.034 g, 0.167 mmoles), and 4-dimethylamino-pyridine (0.007 g, 0.06 mmoles). After stirring for 18 hours at room temperature, the amino acid-resin was separated by filtration and treated with 10 mL of 50% trifluoroacetic acid in dichloromethane for 30 minutes, then again separated by filtration. The resulting amino acid-resin was washed with dichloromethane (3x10 mL), isopropanol (3x10 mL), diisopropylethylamine (10%, v/v) in dichloromethane (3x10 mL), and dichloromethane (3x10 mL).

Part B:

N-α-BOC-N-ε-(2-chloro-benzyloxycarbonyl)-L-lysine (0.83 g, 2.0 mmoles) was activated with dicyclohexylcarbodiimide (0.20 g, 1.0 mmoles) in dichloro-methane and coupled to the resin product from Part A for 60 minutes at room temperature. The dipeptide-resin was separated by filtration, the N-α-BOC group was removed with trifluoroacetic acid in dichloromethane, and the resulting resin was washed as described in Part A.

Part C:

N-BOC-(O-benzyl)-L-serine (0.59 g, 2.0 mmoles) was activated with dicyclohexylcarbodiimide (0.20 g, 1.0 mmoles) in dichloromethane and coupled to the resin product from Part B for 60 minutes at room temperature. The tripeptide-resin was separated by filtration, the N-α-BOC group was removed with trifluoroacetic acid in dichloromethane, and the resulting resin was washed as described in Part A.

Part D:

To 4-[4-(2-methyl-1H-imidazol-1-yl)-butyl]phenylacetic acid hydrochloride (0.053 g, 0.17 mmoles) in 2 mL of dimethylformamide/dichloromethane (1/1) was added diisopropylethylamine (0.03 mL. 0.17 mmoles). The mixture was then added to a suspension of the tripeptide-resin from Part C in 5 mL of dichloromethane, followed by dicyclohexylcarbodiimide (0.034 g, 0.17 mmoles). After 18 hours at room temperature, the solvent was removed by filtration, and the resulting resin product was washed with dichloromethane.

Part E:

The resin product from Part D was treated with 3 mL of 90% hydrogen fluoride/anisole (v/v) for 60 minutes at 0° C. The hydrogen fluoride was removed by evaporation, and the product was extracted into 30% acetic acid/water and then lyophilized. The crude material was purified by reverse phase HPLC on a Waters Deltapak RPC-18 column using a linear gradient of 1% to 35% acetonitrile (0.05% trifluoroacetic acid) in water (0.05% trifluoroacetic acid) over 30 minutes at 15 mL/min, which after lyophilization, gave 5.4 mg of 95% pure (by HPLC) L-iso-leucine, N-[$N^2$-[N-[[4-[4-(2-methyl-1H-imidazol-1-yl)butyl]phenyl]acetyl]-L-seryl]-L-lysyl]-, bis-trifluoroacetate. ESMS: (M+H) m/z=601. Amino acid analyses: calcd serine 1.00, lysine 1.00, iso-leucine 1.00; found: serine 1.07, lysine 1.05, iso-leucine 0.88.

EXAMPLE 8

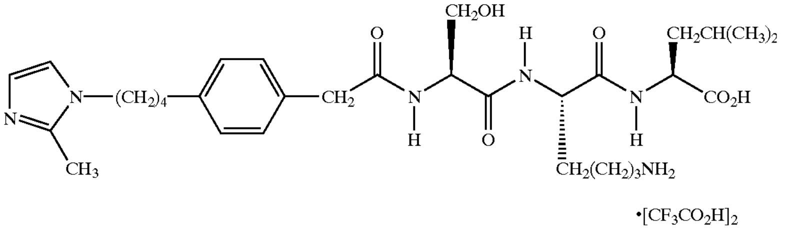

Preparation of L-Leucine, N-[$N^2$-[N-[[4-[4-(2-methyl-1H-imidazol-1-yl)butyl]phenyl]acetyl]-L-seryl]-L-lysyl]-, bis-trifluoroacetate.

Part A: Preparation of L-Lysine, [N-ε-(Carbobenzoxy)]-N-α-(L-[N-BOC-(O-benzyl)seryl]]-, Methyl Ester.

A mixture of EDC (8.0 g, 41,73 mmol), HOBt (5.63 g, 41.73 mmol), N-BOC-(O-benzyl)-L-serine (12.45 g, 41.73 mmol) was stirred in DMF (300 mL) at room temperature for 2 hours. To this reaction mixture was added N-ε-(carbobenzoxy)-L-lysine-, methyl ester hydrochloride (13.80 g, 41.73 mmol), followed by triethylamine (5.81 mL), and the stirring was continued for 18 hours. The mixture was dissolved in dichloromethane (1 L), and the organic phase was washed with dilute hydrochloric acid (1N, 500 mL), saturated sodium bicarbonate (500 mL), and brine. The organic layer was dried ($MgSO_4$), filtered, and concentrated to afford 23 g of L-lysine, [N-ε-(carbobenzoxy)]-N-α-[L-[N-BOC-(O-benzyl)seryl]]-, methyl ester.

Part B: Preparation of L-Lysine, [N-ε-(Carbobenzoxy)]-N-α-[L- (O-benzyl)-seryl]-, Methyl Ester Hydrochloride.

HCl (4N) in dioxane (80 mL) was added to L-lysine, [N-ε-(carbobenzoxy)]-N-α-[L-[N-BOC-(O-benzyl)seryl]]-, methyl ester (23.0 g, 40.23 mmol) from Part A, and the mixture was stirred for 2 hours. The solvent was removed in vacuo, and the excess HCl was removed by evaporationg with toluene to afford 20.0 g of L-lysine, [N-ε-(carbobenzoxy)]-N-α-[L-(O-benzyl)-seryl]-, methyl ester hydrochloride.

Part C: Preparation of L-Lysine, N-ε-(carbobenzoxy)-[N-α-[N-[4-[4-(2-Methyl-1H-imidazol-1-yl)butyl]phenyl]acetyl]-L-(O-benzyl)-seryl]-, Methyl Ester.

A mixture of 4-[(2-methyl-1H-imidazol-1-yl)butyl]phenylacetic acid hydrochloride (2.43 g, 7.878 nmol), HOBt (1.046 g, 7.878 mmol), EDC (1.51 g, 7.878 mmol) in DMF (100 mL) was stirred at room temperature for 1 hour. To this mixture, was added L-lysine, [N-ε-(carbobenzoxy)]-N-α-[L-(O-benzyl)-seryl]-, methyl ester hydrochloride from Part B (4.00 g, 7.878 mmol), followed by triethylamine (1.60 g, 15.75 mmol), and the stirring was continued for 18 hours. The DMF was removed by distillation in vacuo. The residue was dissolved in dichloromethane, washed with citric acid (100 mL), sodium bicarbonate (100 mL), brine, dried, filtered, and concentrated to afford 5.7 g of L-lysine, N-ε-(carbobenzoxy)-[N-α-[N-[4-[4-(2-methyl-1H-imidazol-1-yl)-butyl]phenyl]acetyl]-L-(O-benzyl)-seryl]-, methyl ester as a solid.

Part D: Preparation of L-Lysine, N-ε-(Carbobenzoxy)-[N-α-[N-[4-[4-(2-methyl-1H-imidazol-1-yl)butyl]phenyl]acetyl]-L-(O-benzyl)-seryl]-,.

Lithium hydroxide (0.227 g, 9.458 mmol) was added to a solution of L-lysine, N-e-(carbobenzoxy)-[N-α-[N-[4-[4-(2-methyl-1H-imidazol-1-yl)butyl]phenyl]-acetyl]-L-(O-benzyl)-seryl]-, methyl ester (4.55 g, 6.27 mmol) from Part C in methanol (150 mL) and water (10 mL), and the reaction mixture was stirred for 20 hours, then concentrated. The residue was dissolved in water and was neutralized with potassiun bisulfate (0.25 M) solution. The aqueous solution was extracted with dichloromethane, dried and concentrated to afford 4.2 g (94%) of L-lysine, N-ε-(carbobenzoxy)-[N-α-[N-[4-[4-(2-methyl-1H-imidazol-1-yl)butyl]phenyl]acetyl]-L-(O-benzyl)-seryl]-,.

Part E: Preparation of L-Leucine, N-[$N^2$-[N-[[4-[4-(2-Methyl-1H-imidazol-1-yl)butyl]phenyl]acetyl]-L-(O-benzyl)-seryl]-N-ε-(carbobenzoxy)-L-lysyl]-, Methyl Ester.

L-Lysine, N-e-(carbobenzoxy)-[N-α-[N-[4-[4-(2-methyl-1H-imidazol-1-yl)-butyl]phenyl]acetyl]-L-(O-benzyl)- seryl]-, (0.46 g. 6.46 mmol), HOBT (0.089 g, 6.78 mmol), and EDC (0.13 g, 6.78 mmol) were dissolved in 15 mL of DMF. The solution was stirred for 40 minutes at room temperature. L-Leucine methyl ester (0.13 g, 7.11 mmol) was dissolved in 5 mL of DMF containing N-methylmopholine (0.20g, 1.94 mol) and then added to this solution. The reaction mixture was stirred overnight at room temperature, and the DMF was removed in vacuo. The concentrated residue was brought up in 150 mL of dichloromethane, and the organic phase was washed with saturated aqueous $NaHCO_3$ (2×100 mL), brine (2×100 mL), dried over $MgSO_4$, filtered and concentrated. The concentrated residue was purified by silica gel flash column chromatography eluting with 5% methanol in methylene chloride to give 0.27g (49.8%) of L-leucine, N-[N$^2$-[N-[[4-[4-(2-methyl-1H-imidazol-1-yl)butyl]phenyl]acetyl]-L-(O-benzyl)-seryl]-N-ε-(carbobenzoxy)-L-lysyl]-, methyl ester as a white solid. FAB-MS m/z=839 (M+H). HRMS: calcd for $C_{47}H_{63}N_6O_8$ (M+H) 839.4707, found: 839.4706.

Part F: Preparation of L-Leucine, N-[N$^2$-[N-[[4-[4-(2-Methyl-1H-imidazol-1-yl)butyl]phenyl]acetyl]-L-(O-benzyl)-seryl]-N-ε-(carbobenzoxy)-L-lysyl]-,.

The L-leucine, N-[N$^2$-[N-[[4-[4-(2-methyl-1H-imidazol-1-yl)butyl]phenyl]-acetyl]-L-(O-benzyl)-seryl]-N-ε-(carbobenzoxy)-L-lysyl]-, methyl ester (0.17 g, 2.03 mmol) from Part E and lithium hydroxide (0.022 g, 5.24 mmol) were dissolved in methanol (5 mL) and water (0.5 mL). The reaction mixture was stirred overnight at room tempterature, and then quenched with 0.25 M $KHSO_4$ until the pH=3. The methanol and water were removed in vacuo, and the concentrated residue was pumped dry. The resulting white solid was washed with ethanol. The filterate was concentrated and pumped dry to give 0.18 g of L-leucine, N-[N$^2$-[N-[[4-[4-(2-methyl-1H-imidazol-1-yl)butyl]-phenyl]-acetyl]-L-(O-benzyl)-seryl]-N-ε-(carbobenzoxy)-L-lysyl]-, as a white foaming solid. FAB-MS m/z=825 (M+H). HRMS: calcd for $C_{46}H_{61}N_6O_8$ (M+H) 825.4551, found: 825.4561.

Part G: Preparation of L-Leucine, N-[N$^2$-[N-[[4-[4-(2-Methyl-1H-imidazol-1-yl)butyl]phenyl]acetyl]-L-seryl]-L-lysyl]-, bis-trifluoroacetate.

The L-leucine, N-[N$^2$-[N-[[4-[4-(2-methyl-1H-imidazol-1-yl)butyl]phenyl]-acetyl]-L-(O-benzyl)-seryl]-N-ε-(carbobenzoxy)-L-lysyl]-, from Part F was dissolved in 10 mL of methanol. Palladium on carbon (100 mg) and 1N trifluoroacetic acid in water (0.1 mL) were added to this solution. The solution was then stirred under a hydrogen atmosphere (50 psi) for 16 hours. The reaction mixture was filtered through celite and washed with excess methanol. The filtrate was concentrated. The concentrated residue was purified by reverse phase HPLC using a linear gradient of 10% to 90% acetonitrile in water (each containing 0.1% trifluoroacetic acid) to give 22 mg (17.8%) of L-leucine, N-[N$^2$-[N-[[4-[4-(2-methyl-1H-imidazol-1-yl)butyl]-phenyl]acetyl]-L-seryl]-L-lysyl]-, bis-trifluoroacetate as a pale yellow solid. HRMS: calcd for $C_{31}H_{48}N_6O_6$ 601.3714, found 601.3707.

EXAMPLE 9

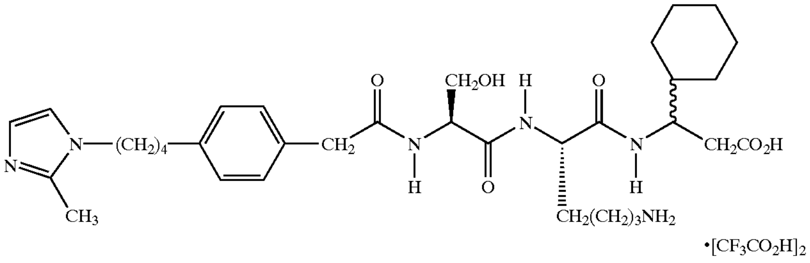

Preparation of Lysinamide, N-[1-cyclohexyl-2-carboxyethyl]-N$^2$-[N-[[4-[4-(2-methyl-1H-imidazol-1-yl)butyl]phenyl]acetyl]-L-seryl]-, ±, bis-trifluoro-aceta te.

Part A: Preparation of L-Lysinamide, N-[1-Cyclohexyl-2-carbomethoxyethyl]-N-ε-(carbobenzoxy)-[N-α-[N-[4-[4-(2-methyl-1H-imidazol-1-yl)-butyl]phenyl]-acetyl]-L- (O-benzyl)-seryl]-, ±.

L-Lysine, N-e-(carbobenzoxy)-[N-α-[N-[4-[4-(2-methyl-1H-imidazol-1-yl)-butyl]phenyl]acetyl]-L-(O-benzyl)-seryl]-, (150.0 mg, 0.21 mmol), 1-hydroxy-benzotriazole hydrate (31.1 mg, 0.21 mmol), and 1-(3-dimethylaminopropyl)-3-ethylcarbodiimide hydrochloride (40.1 mg, 0.21 mmol) were mixed in dimethylformamide (2.0 mL) at 0° C. for 15 minutes. N-Methylmorpholine (60.0 mg, 0.60 mmol) and methyl (R,S)-3-amino-3-cyclohexylpropionate (46 mg, 0.21 nmol) were added, and the solution was stirred at room temperature for 16 hours. The solvent was removed at reduced pressure, and the residue taken up in methanol (1.00 mL). The product was isolated as a waxy solid by preparative HPLC to give 136 mg (73%) of L-lysinamide, N-[1-cyclohexyl-2-carbomethoxyethyl]-N-ε-(carbobenzoxy)-[N-α-[N-[4-[4-(2-methyl-1H-imidazol-1-yl)-butyl]phenyl]-acetyl]-L-(O-benzyl)-seryl]-, ±. HRMS calcd for $C_{50}H_{67}N_6O_8$ (M+H) 879.5020, found 879.5030.

Part B: Preparation of Lysinamide, N-[1-Cyclohexyl-2-carbomethoxyethyl]-N$^2$-[N-[[4-[4-(2-methyl-1H-imidazol-1-yl)butyl]phenyl]acetyl]-L-seryl]-, ±, bis-trifluoroacetate.

The L-lysinamide, N-[1-cyclohexyl-2-carbomethoxyethyl]-N-ε-(carbobenzoxy)-[N-α-[N-[4-[4-(2-methyl-1H-imidazol-1-yl)-butyl]phenyl]-acetyl]-L-(O-benzyl)-seryl]-, from Part A (89 mg, 0.101 mmol) was mixed in methanol (3.0 mL) with trifluoroacetic acid (60 μL). Then palladium on carbon (15 mg of 10%) was added, and the solution was stirred under an atmosphere of hydrogen (50 psi) at room temperature for 16 hours. The catalyst was removed by filtration though a 0.2 micron nylon mesh filter, and the filter was washed with methanol (2×3.0 mL). The solvent was removed at reduced pressure to afford 76.0 mg (88% yield) of lysinamide, N-[1-cyclohexyl-2-carbomethoxy-ethyl]-N$^2$-[N-[[4-[4-(2-methyl-1H-imidazol-1-yl)butyl]phenyl]acetyl]-L-seryl]-, ±, bis-trifluoroacetate as an oil. HRMS calcd for $C_{35}H_{55}N_6O_6$ (M+H) 655.4183, found 655.4188.

Part C: Preparation of Lysinamide, N-[1-Cyclohexyl-2-carboxyethyl]-N$^2$-[N-[[4-[4-(2-methyl-1H-imidazol-1-yl) butyl]phenyl]acetyl]-L-seryl]-, ±, bis-trifluoroacetate.

The lysinamide, N-[1-cyclohexyl-2-(carbomethoxy) ethyl]-$N^2$-[N-[[4-[4-(2-methyl-1H-imidazol-1-yl)butyl] phenyl]acetyl]-L-seryl]-, ±, bis-trifluoroacetate from Part B (50 mg, 0.056 mmol) was dissolved in methanol/water (3.0 mL, 5:1). Lithium hydroxide monohydrate (15 mg, 0.366 mmol) was added, and the solution mixed for 3 hours at room temperature. The solvent was removed at reduced pressure, and the residue taken up in methanol (1.0 mL) and trifluoroacetic acid (30 μL). The product was isolated as a semi-solid by preparative HPLC to give 37.4 mg (77%) of lysinamide, N-[1-cyclohexyl-2-carboxyethyl]-$N^2$-[N-[[4-[4-(2-methyl-1H-imidazol-1-yl)butyl]phenyl]acetyl]-L-seryl]-, ±, bis-trifluoroacetate. HRMS calcd for $C_{34}H_{53}N_6O_6$ (M+H) 641.4027, found 641.4067.

EXAMPLE 10

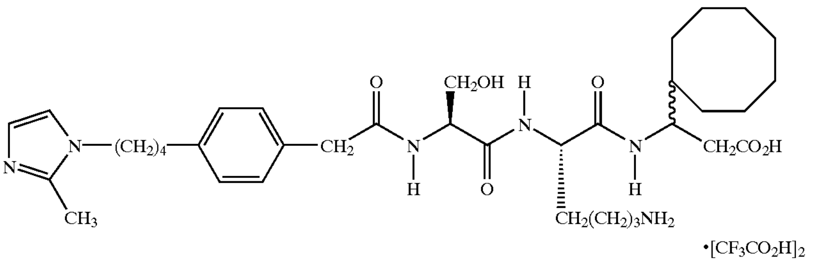

Preparation of Lysinamide, N-[1-cyclooctyl-2-carboxyethyl]-$N^2$-[N-[[4-[4-(2-methyl-1H-imidazol-1-yl)butyl]phenyl]acetyl]-L-seryl]-, ±, bis-trifluoro-aceta te.

Part A: Preparation of L-Lysinamide, N-[1-Cyclooctyl-2-carbomethoxyethyl]-N-ε-(carbobenzoxy)-[N-α-[N-[4-[4-(2-methyl-1H-imidazol-1-yl)-butyl]phenyl]-acetyl]-L-(O-benzyl)-seryl]-, ±.

L-Lysine, N-E-(carbobenzoxy)-[N-α-[N-[4-[4-(2-methyl-1H-imidazol-1-yl)-butyl]phenyl]acetyl]-L-(O-benzyl)-seryl]-, (156.0 mg, 0.21 mmol), 1-hydroxybenzotriazole hydrate (31.1 mg, 0.21 mmol), and 1-(3-dimethylaminopropyl)-3-ethylcarbodiimide hydrochloride (40.1 mg, 0.21 mmol) were mixed in dimethylformamide (2.0 mL) at 0° C. for 15 minutes. Then N-methylmorpholine (60.0 mg, 0.60 nmol) and methyl (R,S)-3-amino-3-cyclooctyl-propionate (46 mg, 0.21 mmol) were added, and the solution was stirred at room temperature for 16 hours. The solvent was removed at reduced pressure, and the residue taken up in methanol (1.00 mL) The product was isolated as a waxy solid by preparative HPLC to give 145 mg (76%) of L-lysinamide, N-[1-cyclooctyl-2-carbomethoxyethyl]-N-ε-(carbobenzoxy)-[N-α-[N-[4-[4-(2-methyl-1H-imidazol-1-yl)-butyl]phenyl]-acetyl]-L-(O-benzyl)-seryl]-, ±. HRMS calcd for $C_{52}H_{71}N_6O_8$ (M+H) 907.5333, found 907.5354.

Part B: Preparation of Lysinamide, N-[1-Cyclooctyl-2-carbomethoxyethyl]-$N^2$-[N-[[4-[4-(2-methyl-1H-imidazol-1-yl)butyl]phenyl]acetyl]-L-seryl]-, ±, bis-trifluoroacetate.

The L-lysinamide, N-[1-cyclooctyl-2-carbomethoxyethyl]-N-ε-(carbobenzoxy)-[N-α-[N-[4-[4-(2-methyl-1H-imidazol-1-yl)-butyl]phenyl]-acetyl]-L-(O-benzyl)-seryl]-, ± from Part A (135.0 mg, 0.149 mmol) was mixed in methanol (3.0 mL) with trifluoroacetic acid (60 μL). Then palladium on carbon (15 mg of 10%) was added, and the solution was stirred under an atmosphere of hydrogen (50 psi) at room temperature for 16 hours. The catalyst was removed by filtration though a 0.2 micron nylon mesh filter. The filter was washed with methanol (2x3.0 mL). The solvent was removed at reduced pressure to afford 102.0 mg (74%) of lysinamide, N-[1-cyclooctyl-2-carbomethoxyethyl]-$N^2$-[N-[[4-[4-(2-methyl-1H-imidazol-1-yl)butyl]phenyl]acetyl]-L-seryl]-, ±, bis-trifluoroacetate as an oil. HRMS calcd for $C_{37}H_{59}N_6O_6$ (M+H) 683.4496, found 683.4534.

Part C: Preparation of Lysinamide, N-[1-Cyclooctyl-2-carboxyethyl]-N$^2$-[N-[[4-[4-(2-methyl-1H-imidazol-1-yl)butyl]phenyl]acetyl]-L-seryl]-, ±, bis-trifluoroacetate.

The lysinamide, N-[1-cyclooctyl-2-carbo-methoxyethyl]-N$^2$-[N-[[4-[4-(2-methyl-1H-imidazol-1-yl)butyl]phenyl]acetyl]-L-seryl]-, ±, bis-trifluoroacetate from Part B (45 mg, 0.049 mmol) was mixed in tetrahydrofuran/methanol/water (3.0 mL, 8:2:1). Lithium hydroxide monohydrate (15 mg, 0.366 mmol) was added, and the solution was mixed for 3 hours at room temperature. The solvent was removed at reduced pressure, and the residue taken up in methanol (1.0 mL) and trifluoroacetic acid (30 μL). The product was isolated as a semi-solid by preparative HPLC to give 26.3 mg (78%) of lysinamide, N-[1-cyclooctyl-2-carboxyethyl]-N$^2$-[N-[[4-[4-(2-methyl-1H-imidazol-1-yl)butyl]-phenyl]acetyl]-L-seryl]-, ±, bis-trifluoroacetate. HRMS calcd for $C_{36}H_{57}N_6O_6$ (M+H) 669.4340, found 669.4342.

EXAMPLE 11

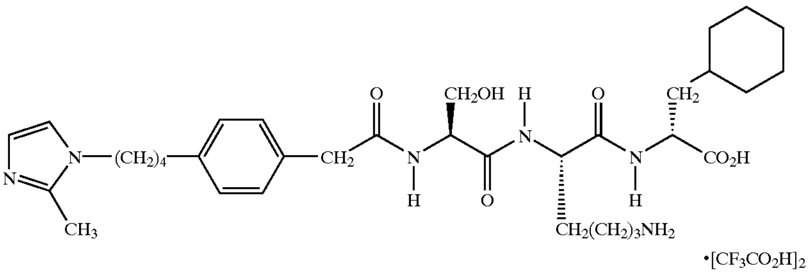

Preparation of D-Alanine, 3-cyclohexyl-N-[N$^2$-[N-[[4-[4-(2-methyl-1H-imidazol-1-yl)butyl]phenyl]acetyl]-L-seryl]-L-lysyl]-, bis-trifluoroace tate.

Part A:

To commercially available (Peninsula Laboratories) hydroxymethyl-resin of styrene/1% divinylbenzene (0.66 g, 0.75 mequiv/g) in 10 mL of dichloromethane was added N-BOC-(3-cyclohexyl)-D-alanine (0.55 g, 2.0 mmoles), dicyclohexylcarbodiimide (0.4 g, 2.0 mmoles), and 4-dimethyl-aminopyridine (0.02 g, 0.2 mmoles). After stirring for 18 hours at room temperature, the amino acid-resin was separated by filtration and treated with 20 mL of 50% trifluoroacetic acid in dichloromethane for 30 minutes, and again separated by filtration. The resulting amino acid-resin was washed sequentially with dichloromethane (3x20 mL), isopropanol (3x20 mL), diisopropylethylamine 10% (v/v) in dichloromethane (3 x20 mL), and dichloromethane (3x20 mL).

Part B:

N-α-BOC-N-ε-(2-chloro-benzyloxycarbonyl)-L-lysine (0.83 g, 2.0 mmoles) was activated with dicyclohexylcarbodiimide (0.20 g, 1.0 mmoles) in dichloromethane and coupled to the resin product from Part A for 60 minutes at room temperature. The dipeptide-resin was separated by filtration, the N-α-BOC group was removed with trifluoroacetic acid in dichloromethane, and the resulting resin was washed as described in Part A.

Part C:

N-BOC-(O-benzyl)-D-serine (0.59 g, 2.0 mmoles) was activated with dicyclohexylcarbodiimide (0.20 g, 1.0 mmoles) in dichloromethane and coupled to the resin product from Part B for 60 minutes at room temperature. The tripeptide-resin was separated by filtration, the N-A-BOC group was removed with trifluoroacetic acid in dichloromethane, and the resulting resin was washed as described in Part A.

Part D:

To 4-[(2-methyl-1H-imidazol-1-yl)butyl]phenylacetic acid hydrochloride (0.04 g, 0.13 mmoles) in 2 mL of dimethylformamide/dichloromethane (1/1) was added diisopropylethylamine (0.02 mL, 0.13 mmoles). The resulting mixture was added to a suspension of one third of the tripeptide-resin product from Part C in 5 mL of dichloromethane, followed by the addition of dicyclohexylcarbodiimide (0.05 g, 0.26 mmoles). After 18 hours at room temperature, the solvent was removed by filtration, and the resulting resin was washed with dichloromethane.

Part E:

The resin product from Part D was treated with 10 mL of 90% hydrogen fluoride in anisole (v/v) for 60 minutes at 0° C. The hydrogen fluoride was removed by evaporation, the resulting residue was extracted with 30% acetic acid in water and then lyophilized. The crude material was purified by reverse phase HPLC on a Waters Deltapak RPC-18 column using a linear gradient of 1% to 35% acetonitrile (0.05% trifluoroacetic acid) in water (0.05% trifluoroacetic acid) over 30 minutes at 15 mL/min, which after lyophilization, gave 11.4 mg of 95% pure (by HPLC) D-alanine, 3-cyclohexyl-N-[$N^2$-[N-[[4-[4-(2-methyl-1H-imidazol-1-yl)butyl]phenyl]acetyl]-L-seryl]-L-lysyl]-, bis-trifluoroacetate; HRMS: (M+H) calcd. 641.4027, found 641.4046. Amino acid analyses: calcd serine 1.00, lysine 1.00; found: serine 1.00, lysine 1.00.

Using analagous starting materials, methods and procedures as described in the foregoing General Synthetic Schemes and in the specific preparations of Examples #1-11, the compounds of Example #12-2786, as shown in Table I, may be prepared.

TABLE I

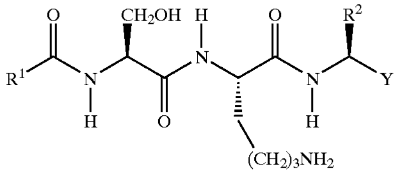

| Ex. No. | $R^1$ | $R^2$ | Y |
|---|---|---|---|
| 12 | $H_2N(CH_2)_9$— | -cyclo-$C_4H_7$ | —$CO_2H$ |
| 13 | $H_2N(CH_2)_9$— | -cyclo-$C_5H_9$ | —$CO_2H$ |
| 14 | $H_2N(CH_2)_9$— | -cyclo-$C_6H_{11}$ | —$CO_2H$ |
| 15 | $H_2N(CH_2)_9$— | -cyclo-$C_7H_{13}$ | —$CO_2H$ |
| 16 | $H_2N(CH_2)_9$— | -cyclo-$C_8H_{15}$ | —$CO_2H$ |
| 17 | $H_2N(CH_2)_9$— | —$CH(CH_3)(CH_2CH_3)$ | —$CO_2H$ |
| 18 | $H_2N(CH_2)_9$— | —$CH(CH_2CH_3)_2$ | —$CO_2H$ |
| 19 | $H_2N(CH_2)_9$— | —$CH(CH_3)(CH_2CH_2CH_3)$ | —$CO_2H$ |
| 20 | $H_2N(CH_2)_9$— | —$C(CH_3)_3$ | —$CO_2H$ |
| 21 | $H_2N(CH_2)_9$— | $HC{\equiv}CCH_2$— | —$CO_2H$ |
| 22 | $H_2N(CH_2)_9$— | $H_2C{=}CH$— | —$CO_2H$ |
| 23 | $H_2N(CH_2)_9$— | $H_2C{=}CHCH_2$— | —$CO_2H$ |
| 24 | $H_2N(CH_2)_9$— | —$CH_2F$ | —$CO_2H$ |
| 25 | $H_2N(CH_2)_9$— | —$CH_2C_6H_5$ | —$CO_2H$ |
| 26 | $H_2N(CH_2)_9$— | —$CH_2C_6H_4$-p-$OCH_3$ | —$CO_2H$ |
| 27 | $H_2N(CH_2)_9$— | —$CH_2C_6H_4$-p-$CH_3$ | —$CO_2H$ |
| 28 | $H_2N(CH_2)_9$— | —$CH_2C_6H_4$-p-F | —$CO_2H$ |
| 29 | $H_2N(CH_2)_9$— | —$CH_2CH_2C_6H_5$ | —$CO_2H$ |
| 30 | $H_2N(CH_2)_9$— | —$CH_2$-cyclo-$C_6H_{11}$ | —$CO_2H$ |
| 31 | $H_2N(CH_2)_9$— | —$CH_2$-cyclo-$C_6H_{10}$-4-F | —$CO_2H$ |
| 32 | $H_2N(CH_2)_9$— | —$CH_2$-cyclo-$C_6H_{10}$-4-$CH_3$ | —$CO_2H$ |
| 33 | $H_2N(CH_2)_9$— | —$CH_2$-cyclo-$C_6H_{10}$-4-$OCH_3$ | —$CO_2H$ |
| 34 | $H_2N(CH_2)_9$— | —$CH_2CH_2$-cyclo-$C_6H_{11}$ | —$CO_2H$ |
| 35 | $H_2N(CH_2)_9$— | —$CH_2$-cyclo-$C_5H_9$ | —$CO_2H$ |
| 36 | $H_2N(CH_2)_9$— | —$CH_2CH_2$-cyclo-$C_5H_9$ | —$CO_2H$ |
| 37 | $H_2N(CH_2)_9$— | —$CH_2$-2-naphthyl | —$CO_2H$ |
| 38 | $H_2N(CH_2)_9$— | —H | —$PO_3H_2$ |
| 39 | $H_2N(CH_2)_9$— | —$CH_3$ | —$PO_3H_2$ |
| 40 | $H_2N(CH_2)_9$— | —$CH_2CH_3$ | —$PO_3H_2$ |
| 41 | $H_2N(CH_2)_9$— | —$CH_2CH_2CH_3$ | —$PO_3H_2$ |
| 42 | $H_2N(CH_2)_9$— | —$CH_2CH_2CH_2CH_3$ | —$PO_3H_2$ |
| 43 | $H_2N(CH_2)_9$— | —$CH_2CH_2CH_2CH_2CH_3$ | —$PO_3H_2$ |
| 44 | $H_2N(CH_2)_9$— | —$CH_2CH_2CH_2CH_2CH_2CH_3$ | —$PO_3H_2$ |
| 45 | $H_2N(CH_2)_9$— | —$CH(CH_3)_2$ | —$PO_3H_2$ |
| 46 | $H_2N(CH_2)_9$— | —$CH_2CH(CH_3)_2$ | —$PO_3H_2$ |
| 47 | $H_2N(CH_2)_9$— | —$CH_2CH_2CH(CH_3)_2$ | —$PO_3H_2$ |
| 48 | $H_2N(CH_2)_9$— | -cyclo-$C_3H_5$ | —$PO_3H_2$ |
| 49 | $H_2N(CH_2)_9$— | -cyclo-$C_4H_7$ | —$PO_3H_2$ |
| 50 | $H_2N(CH_2)_9$— | -cyclo-$C_5H_9$ | —$PO_3H_2$ |
| 51 | $H_2N(CH_2)_9$— | -cyclo-$C_6H_{11}$ | —$PO_3H_2$ |
| 52 | $H_2N(CH_2)_9$— | -cyclo-$C_7H_{13}$ | —$PO_3H_2$ |
| 53 | $H_2N(CH_2)_9$— | -cyclo-$C_8H_{15}$ | —$PO_3H_2$ |
| 54 | $H_2N(CH_2)_9$— | —$CH(CH_3)(CH_2CH_3)$ | —$PO_3H_2$ |
| 55 | $H_2N(CH_2)_9$— | —$CH(CH_2CH_3)_2$ | —$PO_3H_2$ |
| 56 | $H_2N(CH_2)_9$— | —$CH(CH_3)(CH_2CH_2CH_3)$ | —$PO_3H_2$ |
| 57 | $H_2N(CH_2)_9$— | —$C(CH_3)_3$ | —$PO_3H_2$ |

TABLE I-continued

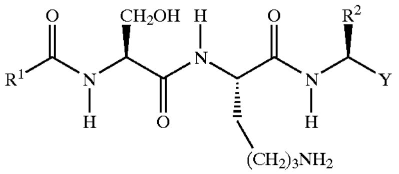

| Ex. No. | $R^1$ | $R^2$ | Y |
|---|---|---|---|
| 58 | $H_2N(CH_2)_9$— | HC≡$CCH_2$— | —$PO_3H_2$ |
| 59 | $H_2N(CH_2)_9$— | $H_2C$═CH— | —$PO_3H_2$ |
| 60 | $H_2N(CH_2)_9$— | $H_2C$═$CHCH_2$— | —$PO_3H_2$ |
| 61 | $H_2N(CH_2)_9$— | —$CH_2F$ | —$PO_3H_2$ |
| 62 | $H_2N(CH_2)_9$— | —$CH_2C_6H_5$ | —$PO_3H_2$ |
| 63 | $H_2N(CH_2)_9$— | —$CH_2C_6H_4$-p-$OCH_3$ | —$PO_3H_2$ |
| 64 | $H_2N(CH_2)_9$— | —$CH_2C_6H_4$-p-$CH_3$ | —$PO_3H_2$ |
| 65 | $H_2N(CH_2)_9$— | —$CH_2C_6H_4$-p-F | —$PO_3H_2$ |
| 66 | $H_2N(CH_2)_9$— | —$CH_2CH_2C_6H_5$ | —$PO_3H_2$ |
| 67 | $H_2N(CH_2)_9$— | —$CH_2$-cyclo-$C_6H_{11}$ | —$PO_3H_2$ |
| 68 | $H_2N(CH_2)_9$— | —$CH_2$-cyclo-$C_6H_{10}$-4-F | —$PO_3H_2$ |
| 69 | $H_2N(CH_2)_9$— | —$CH_2$-cyclo-$C_6H_{10}$-4-$CH_3$ | —$PO_3H_2$ |
| 70 | $H_2N(CH_2)_9$— | —$CH_2$-cyclo-$C_6H_{10}$-4-$OCH_3$ | —$PO_3H_2$ |
| 71 | $H_2N(CH_2)_9$— | —$CH_2CH_2$-cyclo-$C_6H_{11}$ | —$PO_3H_2$ |
| 72 | $H_2N(CH_2)_9$— | —$CH_2$-cyclo-$C_5H_9$ | —$PO_3H_2$ |
| 73 | $H_2N(CH_2)_9$— | —$CH_2CH_2$-cyclo-$C_5H_9$ | —$PO_3H_2$ |
| 74 | $H_2N(CH_2)_9$— | —$CH_2$-2-naphthyl | —$PO_3H_2$ |
| 75 | $H_2N(CH_2)_9$— | —H | -5-Tet |
| 76 | $H_2N(CH_2)_9$— | —$CH_3$ | -5-Tet |
| 77 | $H_2N(CH_2)_9$— | —$CH_2CH_3$ | -5-Tet |
| 78 | $H_2N(CH_2)_9$— | —$CH_2CH_2CH_3$ | -5-Tet |
| 79 | $H_2N(CH_2)_9$— | —$CH_2CH_2CH_2CH_3$ | -5-Tet |
| 80 | $H_2N(CH_2)_9$— | —$CH_2CH_2CH_2CH_2CH_3$ | -5-Tet |
| 81 | $H_2N(CH_2)_9$— | —$CH_2CH_2CH_2CH_2CH_2CH_3$ | -5-Tet |
| 82 | $H_2N(CH_2)_9$— | —$CH(CH_3)_2$ | -5-Tet |
| 83 | $H_2N(CH_2)_9$— | —$CH_2CH(CH_3)_2$ | -5-Tet |
| 84 | $H_2N(CH_2)_9$— | —$CH_2CH_2CH(CH_3)_2$ | -5-Tet |
| 85 | $H_2N(CH_2)_9$— | -cyclo-$C_3H_5$ | -5-Tet |
| 86 | $H_2N(CH_2)_9$— | -cyclo-$C_4H_7$ | -5-Tet |
| 87 | $H_2N(CH_2)_9$— | -cyclo-$C_5H_9$ | -5-Tet |
| 88 | $H_2N(CH_2)_9$— | -cyclo-$C_6H_{11}$ | -5-Tet |
| 89 | $H_2N(CH_2)_9$— | -cyclo-$C_7H_{13}$ | -5-Tet |
| 90 | $H_2N(CH_2)_9$— | -cyclo-$C_8H_{15}$ | -5-Tet |
| 91 | $H_2N(CH_2)_9$— | —$CH(CH_3)(CH_2CH_3)$ | -5-Tet |
| 92 | $H_2N(CH_2)_9$— | —$CH(CH_2CH_3)_2$ | -5-Tet |
| 93 | $H_2N(CH_2)_9$— | —$CH(CH_3)(CH_2CH_2CH_3)$ | -5-Tet |
| 94 | $H_2N(CH_2)_9$— | —$C(CH_3)_3$ | -5-Tet |
| 95 | $H_2N(CH_2)_9$— | HC≡$CCH_2$— | -5-Tet |
| 96 | $H_2N(CH_2)_9$— | $H_2C$═CH— | -5-Tet |
| 97 | $H_2N(CH_2)_9$— | $H_2C$═$CHCH_2$— | -5-Tet |
| 98 | $H_2N(CH_2)_9$— | —$CH_2F$ | -5-Tet |
| 99 | $H_2N(CH_2)_9$— | —$CH_2C_6H_5$ | -5-Tet |
| 100 | $H_2N(CH_2)_9$— | —$CH_2C_6H_4$-p-$OCH_3$ | -5-Tet |
| 101 | $H_2N(CH_2)_9$— | —$CH_2C_6H_4$-p-$CH_3$ | -5-Tet |
| 102 | $H_2N(CH_2)_9$— | —$CH_2C_6H_4$-p-F | -5-Tet |
| 103 | $H_2N(CH_2)_9$— | —$CH_2CH_2C_6H_5$ | -5-Tet |
| 104 | $H_2N(CH_2)_9$— | —$CH_2$-cyclo-$C_6H_{11}$ | -5-Tet |
| 105 | $H_2N(CH_2)_9$— | —$CH_2$-cyclo-$C_6H_{10}$-4-F | -5-Tet |
| 106 | $H_2N(CH_2)_9$— | —$CH_2$-cyclo-$C_6H_{10}$-4-$CH_3$ | -5-Tet |
| 107 | $H_2N(CH_2)_9$— | —$CH_2$-cyclo-$C_6H_{10}$-4-$OCH_3$ | -5-Tet |
| 108 | $H_2N(CH_2)_9$— | —$CH_2CH_2$-cyclo-$C_6H_{11}$ | -5-Tet |
| 109 | $H_2N(CH_2)_9$— | —$CH_2$-cyclo-$C_5H_9$ | -5-Tet |
| 110 | $H_2N(CH_2)_9$— | —$CH_2CH_2$-cyclo-$C_5H_9$ | -5-Tet |
| 111 | $H_2N(CH_2)_9$— | —$CH_2$-2-naphthyl | -5-Tet |
| 112 | $H_2N(CH_2)_{10}$— | —H | —$CO_2H$ |
| 113 | $H_2N(CH_2)_{10}$— | —$CH_3$ | —$CO_2H$ |
| 114 | $H_2N(CH_2)_{10}$— | —$CH_2CH_3$ | —$CO_2H$ |
| 115 | $H_2N(CH_2)_{10}$— | —$CH_2CH_2CH_3$ | —$CO_2H$ |
| 116 | $H_2N(CH_2)_{10}$— | —$CH_2CH_2CH_2CH_3$ | —$CO_2H$ |
| 117 | $H_2N(CH_2)_{10}$— | —$CH_2CH_2CH_2CH_2CH_3$ | —$CO_2H$ |
| 118 | $H_2N(CH_2)_{10}$— | —$CH_2CH_2CH_2CH_2CH_2CH_3$ | —$CO_2H$ |
| 119 | $H_2N(CH_2)_{10}$— | —$CH(CH_3)_2$ | —$CO_2H$ |
| 120 | $H_2N(CH_2)_{10}$— | —$CH_2CH(CH_3)_2$ | —CONHOH |
| 121 | $H_2N(CH_2)_{10}$— | —$CH_2CH_2CH(CH_3)_2$ | —$CO_2H$ |
| 122 | $H_2N(CH_2)_{10}$— | -cyclo-$C_3H_5$ | —$CO_2H$ |
| 123 | $H_2N(CH_2)_{10}$— | -cyclo-$C_4H_7$ | —$CO_2H$ |

TABLE I-continued

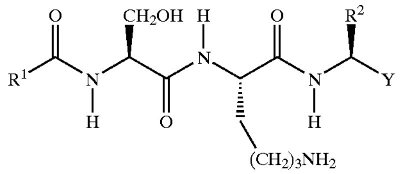

| Ex. No. | $R^1$ | $R^2$ | Y |
|---|---|---|---|
| 124 | $H_2N(CH_2)_{10}$— | -cyclo-$C_5H_9$ | —$CO_2H$ |
| 125 | $H_2N(CH_2)_{10}$— | -cyclo-$C_6H_{11}$ | —$CO_2H$ |
| 126 | $H_2N(CH_2)_{10}$— | -cyclo-$C_7H_{13}$ | —$CO_2H$ |
| 127 | $H_2N(CH_2)_{10}$— | -cyclo-$C_8H_{15}$ | —$CO_2H$ |
| 128 | $H_2N(CH_2)_{10}$— | —$CH(CH_3)(CH_2CH_3)$ | —$CO_2H$ |
| 129 | $H_2N(CH_2)_{10}$— | —$CH(CH_2CH_3)_2$ | —$CO_2H$ |
| 130 | $H_2N(CH_2)_{10}$— | —$CH(CH_3)(CH_2CH_2CH_3)$ | —$CO_2H$ |
| 131 | $H_2N(CH_2)_{10}$— | —$C(CH_3)_3$ | —$CO_2H$ |
| 132 | $H_2N(CH_2)_{10}$— | $HC\equiv CCH_2$— | —$CO_2H$ |
| 133 | $H_2N(CH_2)_{10}$— | $H_2C=CH$— | —$CO_2H$ |
| 134 | $H_2N(CH_2)_{10}$— | $H_2C=CHCH_2$— | —$CO_2H$ |
| 135 | $H_2N(CH_2)_{10}$— | —$CH_2F$ | —$CO_2H$ |
| 136 | $H_2N(CH_2)_{10}$— | —$CH_2C_6H_5$ | —$CO_2H$ |
| 137 | $H_2N(CH_2)_{10}$— | —$CH_2C_6H_4$-p-$OCH_3$ | —$CO_2H$ |
| 138 | $H_2N(CH_2)_{10}$— | —$CH_2C_6H_4$-p-$CH_3$ | —$CO_2H$ |
| 139 | $H_2N(CH_2)_{10}$— | —$CH_2C_6H_4$-p-F | —$CO_2H$ |
| 140 | $H_2N(CH_2)_{10}$— | —$CH_2CH_2C_6H_5$ | —$CO_2H$ |
| 141 | $H_2N(CH_2)_{10}$— | —$CH_2$-cyclo-$C_6H_{11}$ | —CONHOH |
| 142 | $H_2N(CH_2)_{10}$— | —$CH_2$-cyclo-$C_6H_{10}$-4-F | —$CO_2H$ |
| 143 | $H_2N(CH_2)_{10}$— | —$CH_2$-cyclo-$C_6H_{10}$-4-$CH_3$ | —$CO_2H$ |
| 144 | $H_2N(CH_2)_{10}$— | —$CH_2$-cyclo-$C_6H_{10}$-4-$OCH_3$ | —$CO_2H$ |
| 145 | $H_2N(CH_2)_{10}$— | —$CH_2CH_2$-cyclo-$C_6H_{11}$ | —$CO_2H$ |
| 146 | $H_2N(CH_2)_{10}$— | —$CH_2$-cyclo-$C_5H_9$ | —$CO_2H$ |
| 147 | $H_2N(CH_2)_{10}$— | —$CH_2CH_2$-cyclo-$C_5H_9$ | —$CO_2H$ |
| 148 | $H_2N(CH_2)_{10}$— | —$CH_2$-2-naphthyl | —$CO_2H$ |
| 149 | $H_2N(CH_2)_{10}$— | —H | —$PO_3H_2$ |
| 150 | $H_2N(CH_2)_{10}$— | —$CH_3$ | —$PO_3H_2$ |
| 151 | $H_2N(CH_2)_{10}$— | —$CH_2CH_3$ | —$PO_3H_2$ |
| 152 | $H_2N(CH_2)_{10}$— | —$CH_2CH_2CH_3$ | —$PO_3H_2$ |
| 153 | $H_2N(CH_2)_{10}$— | —$CH_2CH_2CH_2CH_3$ | —$PO_3H_2$ |
| 154 | $H_2N(CH_2)_{10}$— | —$CH_2CH_2CH_2CH_2CH_3$ | —$PO_3H_2$ |
| 155 | $H_2N(CH_2)_{10}$— | —$CH_2CH_2CH_2CH_2CH_2CH_3$ | —$PO_3H_2$ |
| 156 | $H_2N(CH_2)_{10}$— | —$CH(CH_3)_2$ | —$PO_3H_2$ |
| 157 | $H_2N(CH_2)_{10}$— | —$CH_2CH(CH_3)_2$ | —$PO_3H_2$ |
| 158 | $H_2N(CH_2)_{10}$— | —$CH_2CH_2CH(CH_3)_2$ | —$PO_3H_2$ |
| 159 | $H_2N(CH_2)_{10}$— | -cyclo-$C_3H_5$ | —$PO_3H_2$ |
| 160 | $H_2N(CH_2)_{10}$— | -cyclo-$C_4H_7$ | —$PO_3H_2$ |
| 161 | $H_2N(CH_2)_{10}$— | -cyclo-$C_5H_9$ | —$PO_3H_2$ |
| 162 | $H_2N(CH_2)_{10}$— | -cyclo-$C_6H_{11}$ | —$PO_3H_2$ |
| 163 | $H_2N(CH_2)_{10}$— | -cyclo-$C_7H_{13}$ | —$PO_3H_2$ |
| 164 | $H_2N(CH_2)_{10}$— | -cyclo-$C_8H_{15}$ | —$PO_3H_2$ |
| 165 | $H_2N(CH_2)_{10}$— | —$CH(CH_3)(CH_2CH_3)$ | —$PO_3H_2$ |
| 166 | $H_2N(CH_2)_{10}$— | —$CH(CH_2CH_3)_2$ | —$PO_3H_2$ |
| 167 | $H_2N(CH_2)_{10}$— | —$CH(CH_3)(CH_2CH_2CH_3)$ | —$PO_3H_2$ |
| 168 | $H_2N(CH_2)_{10}$— | —$C(CH_3)_3$ | —$PO_3H_2$ |
| 169 | $H_2N(CH_2)_{10}$— | $HC\equiv CCH_2$— | —$PO_3H_2$ |
| 170 | $H_2N(CH_2)_{10}$— | $H_2C=CH$— | —$PO_3H_2$ |
| 171 | $H_2N(CH_2)_{10}$— | $H_2C=CHCH_2$— | —$PO_3H_2$ |
| 172 | $H_2N(CH_2)_{10}$— | —$CH_2F$ | —$PO_3H_2$ |
| 173 | $H_2N(CH_2)_{10}$— | —$CH_2C_6H_5$ | —$PO_3H_2$ |
| 174 | $H_2N(CH_2)_{10}$— | —$CH_2C_6H_4$-p-$OCH_3$ | —$PO_3H_2$ |
| 175 | $H_2N(CH_2)_{10}$— | —$CH_2C_6H_4$-p-$CH_3$ | —$PO_3H_2$ |
| 176 | $H_2N(CH_2)_{10}$— | —$CH_2C_6H_4$-p-F | —$PO_3H_2$ |
| 177 | $H_2N(CH_2)_{10}$— | —$CH_2CH_2C_6H_5$ | —$PO_3H_2$ |
| 178 | $H_2N(CH_2)_{10}$— | —$CH_2$-cyclo-$C_6H_{11}$ | —$PO_3H_2$ |
| 179 | $H_2N(CH_2)_{10}$— | —$CH_2$-cyclo-$C_6H_{10}$-4-F | —$PO_3H_2$ |
| 180 | $H_2N(CH_2)_{10}$— | —$CH_2$-cyclo-$C_6H_{10}$-4-$CH_3$ | —$PO_3H_2$ |
| 181 | $H_2N(CH_2)_{10}$— | —$CH_2$-cyclo-$C_6H_{10}$-4-$OCH_3$ | —$PO_3H_2$ |
| 182 | $H_2N(CH_2)_{10}$— | —$CH_2CH_2$-cyclo-$C_6H_{11}$ | —$PO_3H_2$ |
| 183 | $H_2N(CH_2)_{10}$— | —$CH_2$-cyclo-$C_5H_9$ | —$PO_3H_2$ |
| 184 | $H_2N(CH_2)_{10}$— | —$CH_2CH_2$-cyclo-$C_5H_9$ | —$PO_3H_2$ |
| 185 | $H_2N(CH_2)_{10}$— | —$CH_2$-2-naphthyl | —$PO_3H_2$ |
| 186 | $H_2N(CH_2)_{10}$— | —H | -5-Tet |
| 187 | $H_2N(CH_2)_{10}$— | —$CH_3$ | -5-Tet |
| 188 | $H_2N(CH_2)_{10}$— | —$CH_2CH_3$ | -5-Tet |
| 189 | $H_2N(CH_2)_{10}$— | —$CH_2CH_2CH_3$ | -5-Tet |

TABLE I-continued

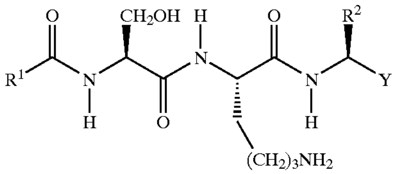

| Ex. No. | $R^1$ | $R^2$ | Y |
|---|---|---|---|
| 190 | $H_2N(CH_2)_{10}$— | —$CH_2CH_2CH_2CH_3$ | -5-Tet |
| 191 | $H_2N(CH_2)_{10}$— | —$CH_2CH_2CH_2CH_2CH_3$ | -5-Tet |
| 192 | $H_2N(CH_2)_{10}$— | —$CH_2CH_2CH_2CH_2CH_2CH_3$ | -5-Tet |
| 193 | $H_2N(CH_2)_{10}$— | —$CH(CH_3)_2$ | -5-Tet |
| 194 | $H_2N(CH_2)_{10}$— | —$CH_2CH(CH_3)_2$ | -5-Tet |
| 195 | $H_2N(CH_2)_{10}$— | —$CH_2CH_2CH(CH_3)_2$ | -5-Tet |
| 196 | $H_2N(CH_2)_{10}$— | -cyclo-$C_3H_5$ | -5-Tet |
| 197 | $H_2N(CH_2)_{10}$— | -cyclo-$C_4H_7$ | -5-Tet |
| 198 | $H_2N(CH_2)_{10}$— | -cyclo-$C_5H_9$ | -5-Tet |
| 199 | $H_2N(CH_2)_{10}$— | -cyclo-$C_6H_{11}$ | -5-Tet |
| 200 | $H_2N(CH_2)_{10}$— | -cyclo-$C_7H_{13}$ | -5-Tet |
| 201 | $H_2N(CH_2)_{10}$— | -cyclo-$C_8H_{15}$ | -5-Tet |
| 202 | $H_2N(CH_2)_{10}$— | —$CH(CH_3)(CH_2CH_3)$ | -5-Tet |
| 203 | $H_2N(CH_2)_{10}$— | —$CH(CH_2CH_3)_2$ | -5-Tet |
| 204 | $H_2N(CH_2)_{10}$— | —$CH(CH_3)(CH_2CH_2CH_3)$ | -5-Tet |
| 205 | $H_2N(CH_2)_{10}$— | —$C(CH_3)_3$ | -5-Tet |
| 206 | $H_2N(CH_2)_{10}$— | $HC{\equiv}CCH_2$— | -5-Tet |
| 207 | $H_2N(CH_2)_{10}$— | $H_2C{=}CH$— | -5-Tet |
| 208 | $H_2N(CH_2)_{10}$— | $H_2C{=}CHCH_2$— | -5-Tet |
| 209 | $H_2N(CH_2)_{10}$— | —$CH_2F$ | -5-Tet |
| 210 | $H_2N(CH_2)_{10}$— | —$CH_2C_6H_5$ | -5-Tet |
| 211 | $H_2N(CH_2)_{10}$— | —$CH_2C_6H_4$-p-$OCH_3$ | -5-Tet |
| 212 | $H_2N(CH_2)_{10}$— | —$CH_2C_6H_4$-p-$CH_3$ | -5-Tet |
| 213 | $H_2N(CH_2)_{10}$— | —$CH_2C_6H_4$-p-F | -5-Tet |
| 214 | $H_2N(CH_2)_{10}$— | —$CH_2CH_2C_6H_5$ | -5-Tet |
| 215 | $H_2N(CH_2)_{10}$— | —$CH_2$-cyclo-$C_6H_{11}$ | -5-Tet |
| 216 | $H_2N(CH_2)_{10}$— | —$CH_2$-cyclo-$C_6H_{10}$-4-F | -5-Tet |
| 217 | $H_2N(CH_2)_{10}$— | —$CH_2$-cyclo-$C_6H_{10}$-4-$CH_3$ | -5-Tet |
| 218 | $H_2N(CH_2)_{10}$— | —$CH_2$-cyclo-$C_6H_{10}$-4-$OCH_3$ | -5-Tet |
| 219 | $H_2N(CH_2)_{10}$— | —$CH_2CH_2$-cyclo-$C_6H_{11}$ | -5-Tet |
| 220 | $H_2N(CH_2)_{10}$— | —$CH_2$-cyclo-$C_5H_9$ | -5-Tet |
| 221 | $H_2N(CH_2)_{10}$— | —$CH_2CH_2$-cyclo-$C_5H_9$ | -5-Tet |
| 222 | $H_2N(CH_2)_{10}$— | —$CH_2$-2-naphthyl | -5-Tet |
| 223 | $H_2N(CH_2)_{11}$— | —H | —$CO_2H$ |
| 224 | $H_2N(CH_2)_{11}$— | —$CH_3$ | —$CO_2H$ |
| 225 | $H_2N(CH_2)_{11}$— | —$CH_2CH_3$ | —$CO_2H$ |
| 226 | $H_2N(CH_2)_{11}$— | —$CH_2CH_2CH_3$ | —$CO_2H$ |
| 227 | $H_2N(CH_2)_{11}$— | —$CH_2CH_2CH_2CH_3$ | —$CO_2H$ |
| 228 | $H_2N(CH_2)_{11}$— | —$CH_2CH_2CH_2CH_2CH_3$ | —$CO_2H$ |
| 229 | $H_2N(CH_2)_{11}$— | —$CH_2CH_2CH_2CH_2CH_2CH_3$ | —$CO_2H$ |
| 230 | $H_2N(CH_2)_{11}$— | —$CH(CH_3)_2$ | —$CO_2H$ |
| 231 | $H_2N(CH_2)_{11}$— | —$CH_2CH(CH_3)_2$ | —$CO_2H$ |
| 232 | $H_2N(CH_2)_{11}$— | —$CH_2CH_2CH(CH_3)_2$ | —$CO_2H$ |
| 233 | $H_2N(CH_2)_{11}$— | -cyclo-$C_3H_5$ | —$CO_2H$ |
| 234 | $H_2N(CH_2)_{11}$— | -cyclo-$C_4H_7$ | —$CO_2H$ |
| 235 | $H_2N(CH_2)_{11}$— | -cyclo-$C_5H_9$ | —$CO_2H$ |
| 236 | $H_2N(CH_2)_{11}$— | -cyclo-$C_6H_{11}$ | —$CO_2H$ |
| 237 | $H_2N(CH_2)_{11}$— | -cyclo-$C_7H_{13}$ | —$CO_2H$ |
| 238 | $H_2N(CH_2)_{11}$— | -cyclo-$C_8H_{15}$ | —$CO_2H$ |
| 239 | $H_2N(CH_2)_{11}$— | —$CH(CH_3)(CH_2CH_3)$ | —$CO_2H$ |
| 240 | $H_2N(CH_2)_{11}$— | —$CH(CH_2CH_3)_2$ | —$CO_2H$ |
| 241 | $H_2N(CH_2)_{11}$— | —$CH(CH_3)(CH_2CH_2CH_3)$ | —$CO_2H$ |
| 242 | $H_2N(CH_2)_{11}$— | —$C(CH_3)_3$ | —$CO_2H$ |
| 243 | $H_2N(CH_2)_{11}$— | $HC{\equiv}CCH_2$— | —$CO_2H$ |
| 244 | $H_2N(CH_2)_{11}$— | $H_2C{=}CH$— | —$CO_2H$ |
| 245 | $H_2N(CH_2)_{11}$— | $H_2C{=}CHCH_2$— | —$CO_2H$ |
| 246 | $H_2N(CH_2)_{11}$— | —$CH_2F$ | —$CO_2H$ |
| 247 | $H_2N(CH_2)_{11}$— | —$CH_2C_6H_5$ | —$CO_2H$ |
| 248 | $H_2N(CH_2)_{11}$— | —$CH_2C_6H_4$-p-$OCH_3$ | —$CO_2H$ |
| 249 | $H_2N(CH_2)_{11}$— | —$CH_2C_6H_4$-p-$CH_3$ | —$CO_2H$ |
| 250 | $H_2N(CH_2)_{11}$— | —$CH_2C_6H_4$-p-F | —$CO_2H$ |
| 251 | $H_2N(CH_2)_{11}$— | —$CH_2CH_2C_6H_5$ | —$CO_2H$ |
| 252 | $H_2N(CH_2)_{11}$— | —$CH_2$-cyclo-$C_6H_{11}$ | —$CO_2H$ |
| 253 | $H_2N(CH_2)_{11}$— | —$CH_2$-cyclo-$C_6H_{10}$-4-F | —$CO_2H$ |
| 254 | $H_2N(CH_2)_{11}$— | —$CH_2$-cyclo-$C_6H_{10}$-4-$CH_3$ | —$CO_2H$ |
| 255 | $H_2N(CH_2)_{11}$— | —$CH_2$-cyclo-$C_6H_{10}$-4-$OCH_3$ | —$CO_2H$ |

TABLE I-continued

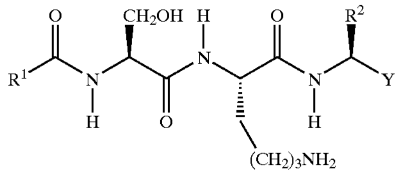

| Ex. No. | $R^1$ | $R^2$ | Y |
|---|---|---|---|
| 256 | $H_2N(CH_2)_{11}$— | —$CH_2CH_2$-cyclo-$C_6H_{11}$ | —$CO_2H$ |
| 257 | $H_2N(CH_2)_{11}$— | —$CH_2$-cyclo-$C_5H_9$ | —$CO_2H$ |
| 258 | $H_2N(CH_2)_{11}$— | —$CH_2CH_2$-cyclo-$C_5H_9$ | —$CO_2H$ |
| 259 | $H_2N(CH_2)_{11}$— | —$CH_2$-2-naphthyl | —$CO_2H$ |
| 260 | $H_2N(CH_2)_{11}$— | —H | —$PO_3H_2$ |
| 261 | $H_2N(CH_2)_{11}$— | —$CH_3$ | —$PO_3H_2$ |
| 262 | $H_2N(CH_2)_{11}$— | —$CH_2CH_3$ | —$PO_3H_2$ |
| 263 | $H_2N(CH_2)_{11}$— | —$CH_2CH_2CH_3$ | —$PO_3H_2$ |
| 264 | $H_2N(CH_2)_{11}$— | —$CH_2CH_2CH_2CH_3$ | —$PO_3H_2$ |
| 265 | $H_2N(CH_2)_{11}$— | —$CH_2CH_2CH_2CH_2CH_3$ | —$PO_3H_2$ |
| 266 | $H_2N(CH_2)_{11}$— | —$CH_2CH_2CH_2CH_2CH_2CH_3$ | —$PO_3H_2$ |
| 267 | $H_2N(CH_2)_{11}$— | —$CH(CH_3)_2$ | —$PO_3H_2$ |
| 268 | $H_2N(CH_2)_{11}$— | —$CH_2CH(CH_3)_2$ | —$PO_3H_2$ |
| 269 | $H_2N(CH_2)_{11}$— | —$CH_2CH_2CH(CH_3)_2$ | —$PO_3H_2$ |
| 270 | $H_2N(CH_2)_{11}$— | -cyclo-$C_3H_5$ | —$PO_3H_2$ |
| 271 | $H_2N(CH_2)_{11}$— | -cyclo-$C_4H_7$ | —$PO_3H_2$ |
| 272 | $H_2N(CH_2)_{11}$— | -cyclo-$C_5H_9$ | —$PO_3H_2$ |
| 273 | $H_2N(CH_2)_{11}$— | -cyclo-$C_6H_{11}$ | —$PO_3H_2$ |
| 274 | $H_2N(CH_2)_{11}$— | -cyclo-$C_7H_{13}$ | —$PO_3H_2$ |
| 275 | $H_2N(CH_2)_{11}$— | -cyclo-$C_8H_{15}$ | —$PO_3H_2$ |
| 276 | $H_2N(CH_2)_{11}$— | —$CH(CH_3)(CH_2CH_3)$ | —$PO_3H_2$ |
| 277 | $H_2N(CH_2)_{11}$— | —$CH(CH_2CH_3)_2$ | —$PO_3H_2$ |
| 278 | $H_2N(CH_2)_{11}$— | —$CH(CH_3)(CH_2CH_2CH_3)$ | —$PO_3H_2$ |
| 279 | $H_2N(CH_2)_{11}$— | —$C(CH_3)_3$ | —$PO_3H_2$ |
| 280 | $H_2N(CH_2)_{11}$— | $HC{\equiv}CCH_2$— | —$PO_3H_2$ |
| 281 | $H_2N(CH_2)_{11}$— | $H_2C{=}CH$— | —$PO_3H_2$ |
| 282 | $H_2N(CH_2)_{11}$— | $H_2C{=}CHCH_2$— | —$PO_3H_2$ |
| 283 | $H_2N(CH_2)_{11}$— | —$CH_2F$ | —$PO_3H_2$ |
| 284 | $H_2N(CH_2)_{11}$— | —$CH_2C_6H_5$ | —$PO_3H_2$ |
| 285 | $H_2N(CH_2)_{11}$— | —$CH_2C_6H_4$-p-$OCH_3$ | —$PO_3H_2$ |
| 286 | $H_2N(CH_2)_{11}$— | —$CH_2C_6H_4$-p-$CH_3$ | —$PO_3H_2$ |
| 287 | $H_2N(CH_2)_{11}$— | —$CH_2C_6H_4$-p-F | —$PO_3H_2$ |
| 288 | $H_2N(CH_2)_{11}$— | —$CH_2CH_2C_6H_5$ | —$PO_3H_2$ |
| 289 | $H_2N(CH_2)_{11}$— | —$CH_2$-cyclo-$C_6H_{11}$ | —$PO_3H_2$ |
| 290 | $H_2N(CH_2)_{11}$— | —$CH_2$-cyclo-$C_6H_{10}$-4-F | —$PO_3H_2$ |
| 291 | $H_2N(CH_2)_{11}$— | —$CH_2$-cyclo-$C_6H_{10}$-4-$CH_3$ | —$PO_3H_2$ |
| 292 | $H_2N(CH_2)_{11}$— | —$CH_2$-cyclo-$C_6H_{10}$-4-$OCH_3$ | —$PO_3H_2$ |
| 293 | $H_2N(CH_2)_{11}$— | —$CH_2CH_2$-cyclo-$C_6H_{11}$ | —$PO_3H_2$ |
| 294 | $H_2N(CH_2)_{11}$— | —$CH_2$-cyclo-$C_5H_9$ | —$PO_3H_2$ |
| 295 | $H_2N(CH_2)_{11}$— | —$CH_2CH_2$-cyclo-$C_5H_9$ | —$PO_3H_2$ |
| 296 | $H_2N(CH_2)_{11}$— | —$CH_2$-2-naphthyl | —$PO_3H_2$ |
| 297 | $H_2N(CH_2)_{11}$— | —H | -5-Tet |
| 298 | $H_2N(CH_2)_{11}$— | —$CH_3$ | -5-Tet |
| 199 | $H_2N(CH_2)_{11}$— | —$CH_2CH_3$ | -5-Tet |
| 300 | $H_2N(CH_2)_{11}$— | —$CH_2CH_2CH_3$ | -5-Tet |
| 301 | $H_2N(CH_2)_{11}$— | —$CH_2CH_2CH_2CH_3$ | -5-Tet |
| 302 | $H_2N(CH_2)_{11}$— | —$CH_2CH_2CH_2CH_2CH_3$ | -5-Tet |
| 303 | $H_2N(CH_2)_{11}$— | —$CH_2CH_2CH_2CH_2CH_2CH_3$ | -5-Tet |
| 304 | $H_2N(CH_2)_{11}$— | —$CH(CH_3)_2$ | -5-Tet |
| 305 | $H_2N(CH_2)_{11}$— | —$CH_2CH(CH_3)_2$ | -5-Tet |
| 306 | $H_2N(CH_2)_{11}$— | —$CH_2CH_2CH(CH_3)_2$ | -5-Tet |
| 307 | $H_2N(CH_2)_{11}$— | -cyclo-$C_3H_5$ | -5-Tet |
| 308 | $H_2N(CH_2)_{11}$— | -cyclo-$C_4H_7$ | -5-Tet |
| 309 | $H_2N(CH_2)_{11}$— | -cyclo-$C_5H_9$ | -5-Tet |
| 310 | $H_2N(CH_2)_{11}$— | -cyclo-$C_6H_{11}$ | -5-Tet |
| 311 | $H_2N(CH_2)_{11}$— | -cyclo-$C_7H_{13}$ | -5-Tet |
| 312 | $H_2N(CH_2)_{11}$— | -cyclo-$C_8H_{15}$ | -5-Tet |
| 313 | $H_2N(CH_2)_{11}$— | —$CH(CH_3)(CH_2CH_3)$ | -5-Tet |
| 314 | $H_2N(CH_2)_{11}$— | —$CH(CH_2CH_3)_2$ | -5-Tet |
| 315 | $H_2N(CH_2)_{11}$— | —$CH(CH_3)(CH_2CH_2CH_3)$ | -5-Tet |
| 316 | $H_2N(CH_2)_{11}$— | —$C(CH_3)_3$ | -5-Tet |
| 317 | $H_2N(CH_2)_{11}$— | $HC{\equiv}CCH_2$— | -5-Tet |
| 318 | $H_2N(CH_2)_{11}$— | $H_2C{=}CH$— | -5-Tet |
| 319 | $H_2N(CH_2)_{11}$— | $H_2C{=}CHCH_2$— | -5-Tet |
| 320 | $H_2N(CH_2)_{11}$— | —$CH_2F$ | -5-Tet |
| 321 | $H_2N(CH_2)_{11}$— | —$CH_2C_6H_5$ | -5-Tet |

TABLE I-continued

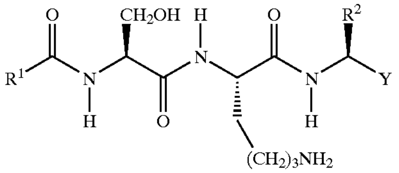

| Ex. No. | $R^1$ | $R^2$ | Y |
|---|---|---|---|
| 322 | $H_2N(CH_2)_{11}$— | —$CH_2C_6H_4$-p-$OCH_3$ | -5-Tet |
| 323 | $H_2N(CH_2)_{11}$— | —$CH_2C_6H_4$-p-$CH_3$ | -5-Tet |
| 324 | $H_2N(CH_2)_{11}$— | —$CH_2C_6H_4$-p-F | -5-Tet |
| 325 | $H_2N(CH_2)_{11}$— | —$CH_2CH_2C_6H_5$ | -5-Tet |
| 326 | $H_2N(CH_2)_{11}$— | —$CH_2$-cyclo-$C_6H_{11}$ | -5-Tet |
| 327 | $H_2N(CH_2)_{11}$— | —$CH_2$-cyclo-$C_6H_{10}$-4-F | -5-Tet |
| 328 | $H_2N(CH_2)_{11}$— | —$CH_2$-cyclo-$C_6H_{10}$-4-$CH_3$ | -5-Tet |
| 329 | $H_2N(CH_2)_{11}$— | —$CH_2$-cyclo-$C_6H_{10}$-4-$OCH_3$ | -5-Tet |
| 330 | $H_2N(CH_2)_{11}$— | —$CH_2CH_2$-cyclo-$C_6H_{11}$ | -5-Tet |
| 331 | $H_2N(CH_2)_{11}$— | —$CH_2$-cyclo-$C_5H_9$ | -5-Tet |
| 332 | $H_2N(CH_2)_{11}$— | —$CH_2CH_2$-cyclo-$C_5H_9$ | -5-Tet |
| 333 | $H_2N(CH_2)_{11}$— | —$CH_2$-2-naphthyl | -5-Tet |
| 334 | $CH_3NH(CH_2)_{10}$— | —H | —$CO_2H$ |
| 335 | $CH_3NH(CH_2)_{10}$— | —$CH_3$ | —$CO_2H$ |
| 336 | $CH_3NH(CH_2)_{10}$— | —$CH_2CH_3$ | —$CO_2H$ |
| 337 | $CH_3NH(CH_2)_{10}$— | —$CH_2CH_2CH_3$ | —$CO_2H$ |
| 338 | $CH_3NH(CH_2)_{10}$— | —$CH_2CH_2CH_2CH_3$ | —$CO_2H$ |
| 339 | $CH_3NH(CH_2)_{10}$— | —$CH_2CH_2CH_2CH_2CH_3$ | —$CO_2H$ |
| 340 | $CH_3NH(CH_2)_{10}$— | —$CH_2CH_2CH_2CH_2CH_2CH_3$ | —$CO_2H$ |
| 341 | $CH_3NH(CH_2)_{10}$— | —$CH(CH_3)_2$ | —$CO_2H$ |
| 342 | $CH_3NH(CH_2)_{10}$— | —$CH_2CH(CH_3)_2$ | —$CO_2H$ |
| 343 | $CH_3NH(CH_2)_{10}$— | —$CH_2CH_2CH(CH_3)_2$ | —$CO_2H$ |
| 344 | $CH_3NH(CH_2)_{10}$— | -cyclo-$C_3H_5$ | —$CO_2H$ |
| 345 | $CH_3NH(CH_2)_{10}$— | -cyclo-$C_4H_7$ | —$CO_2H$ |
| 346 | $CH_3NH(CH_2)_{10}$— | -cyclo-$C_5H_9$ | —$CO_2H$ |
| 347 | $CH_3NH(CH_2)_{10}$— | -cyclo-$C_6H_{11}$ | —$CO_2H$ |
| 348 | $CH_3NH(CH_2)_{10}$— | -cyclo-$C_7H_{13}$ | —$CO_2H$ |
| 349 | $CH_3NH(CH_2)_{10}$— | -cyclo-$C_8H_{15}$ | —$CO_2H$ |
| 350 | $CH_3NH(CH_2)_{10}$— | —$CH(CH_3)(CH_2CH_3)$ | —$CO_2H$ |
| 351 | $CH_3NH(CH_2)_{10}$— | —$CH(CH_2CH_3)_2$ | —$CO_2H$ |
| 352 | $CH_3NH(CH_2)_{10}$— | —$CH(CH_3)(CH_2CH_2CH_3)$ | —$CO_2H$ |
| 353 | $CH_3NH(CH_2)_{10}$— | —$C(CH_3)_3$ | —$CO_2H$ |
| 354 | $CH_3NH(CH_2)_{10}$— | $HC{\equiv}CCH_2$— | —$CO_2H$ |
| 355 | $CH_3NH(CH_2)_{10}$— | $H_2C{=}CH$— | —$CO_2H$ |
| 356 | $CH_3NH(CH_2)_{10}$— | $H_2C{=}CHCH_2$— | —$CO_2H$ |
| 357 | $CH_3NH(CH_2)_{10}$— | —$CH_2F$ | —$CO_2H$ |
| 358 | $CH_3NH(CH_2)_{10}$— | —$CH_2C_6H_5$ | —$CO_2H$ |
| 359 | $CH_3NH(CH_2)_{10}$— | —$CH_2C_6H_4$-p-$OCH_3$ | —$CO_2H$ |
| 360 | $CH_3NH(CH_2)_{10}$— | —$CH_2C_6H_4$-p-$CH_3$ | —$CO_2H$ |
| 361 | $CH_3NH(CH_2)_{10}$— | —$CH_2C_6H_4$-p-F | —$CO_2H$ |
| 362 | $CH_3NH(CH_2)_{10}$— | —$CH_2CH_2C_6H_5$ | —$CO_2H$ |
| 363 | $CH_3NH(CH_2)_{10}$— | —$CH_2$-cyclo-$C_6H_{11}$ | —$CO_2H$ |
| 364 | $CH_3NH(CH_2)_{10}$— | —$CH_2$-cyclo-$C_6H_{10}$-4-F | —$CO_2H$ |
| 365 | $CH_3NH(CH_2)_{10}$— | —$CH_2$-cyclo-$C_6H_{10}$-4-$CH_3$ | —$CO_2H$ |
| 366 | $CH_3NH(CH_2)_{10}$— | —$CH_2$-cyclo-$C_6H_{10}$-4-$OCH_3$ | —$CO_2H$ |
| 367 | $CH_3NH(CH_2)_{10}$— | —$CH_2CH_2$-cyclo-$C_6H_{11}$ | —$CO_2H$ |
| 368 | $CH_3NH(CH_2)_{10}$— | —$CH_2$-cyclo-$C_5H_9$ | —$CO_2H$ |
| 369 | $CH_3NH(CH_2)_{10}$— | —$CH_2CH_2$-cyclo-$C_5H_9$ | —$CO_2H$ |
| 370 | $CH_3NH(CH_2)_{10}$— | —$CH_2$-2-naphthyl | —$CO_2H$ |
| 371 | $CH_3NH(CH_2)_{10}$— | —H | —$PO_3H_2$ |
| 372 | $CH_3NH(CH_2)_{10}$— | —$CH_3$ | —$PO_3H_2$ |
| 373 | $CH_3NH(CH_2)_{10}$— | —$CH_2CH_3$ | —$PO_3H_2$ |
| 374 | $CH_3NH(CH_2)_{10}$— | —$CH_2CH_2CH_3$ | —$PO_3H_2$ |
| 375 | $CH_3NH(CH_2)_{10}$— | —$CH_2CH_2CH_2CH_3$ | —$PO_3H_2$ |
| 376 | $CH_3NH(CH_2)_{10}$— | —$CH_2CH_2CH_2CH_2CH_3$ | —$PO_3H_2$ |
| 377 | $CH_3NH(CH_2)_{10}$— | —$CH_2CH_2CH_2CH_2CH_2CH_3$ | —$PO_3H_2$ |
| 378 | $CH_3NH(CH_2)_{10}$— | —$CH(CH_3)_2$ | —$PO_3H_2$ |
| 379 | $CH_3NH(CH_2)_{10}$— | —$CH_2CH(CH_3)_2$ | —$PO_3H_2$ |
| 380 | $CH_3NH(CH_2)_{10}$— | —$CH_2CH_2CH(CH_3)_2$ | —$PO_3H_2$ |
| 381 | $CH_3NH(CH_2)_{10}$— | -cyclo-$C_3H_5$ | —$PO_3H_2$ |
| 382 | $CH_3NH(CH_2)_{10}$— | -cyclo-$C_4H_7$ | —$PO_3H_2$ |
| 383 | $CH_3NH(CH_2)_{10}$— | -cyclo-$C_5H_9$ | —$PO_3H_2$ |
| 384 | $CH_3NH(CH_2)_{10}$— | -cyclo-$C_6H_{11}$ | —$PO_3H_2$ |
| 385 | $CH_3NH(CH_2)_{10}$— | -cyclo-$C_7H_{13}$ | —$PO_3H_2$ |
| 386 | $CH_3NH(CH_2)_{10}$— | -cyclo-$C_8H_{15}$ | —$PO_3H_2$ |
| 387 | $CH_3NH(CH_2)_{10}$— | —$CH(CH_3)(CH_2CH_3)$ | —$PO_3H_2$ |

TABLE I-continued

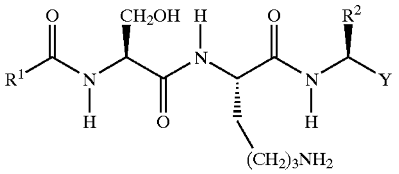

| Ex. No. | $R^1$ | $R^2$ | Y |
|---|---|---|---|
| 388 | $CH_3NH(CH_2)_{10}$— | —$CH(CH_2CH_3)_2$ | —$PO_3H_2$ |
| 389 | $CH_3NH(CH_2)_{10}$— | —$CH(CH_3)(CH_2CH_2CH_3)$ | —$PO_3H_2$ |
| 390 | $CH_3NH(CH_2)_{10}$— | —$C(CH_3)_3$ | —$PO_3H_2$ |
| 391 | $CH_3NH(CH_2)_{10}$— | $HC{\equiv}CCH_2$— | —$PO_3H_2$ |
| 392 | $CH_3NH(CH_2)_{10}$— | $H_2C{=}CH$— | —$PO_3H_2$ |
| 393 | $CH_3NH(CH_2)_{10}$— | $H_2C{=}CHCH_2$— | —$PO_3H_2$ |
| 394 | $CH_3NH(CH_2)_{10}$— | —$CH_2F$ | —$PO_3H_2$ |
| 395 | $CH_3NH(CH_2)_{10}$— | —$CH_2C_6H_5$ | —$PO_3H_2$ |
| 396 | $CH_3NH(CH_2)_{10}$— | —$CH_2C_6H_4$-p-$OCH_3$ | —$PO_3H_2$ |
| 397 | $CH_3NH(CH_2)_{10}$— | —$CH_2C_6H_4$-p-$CH_3$ | —$PO_3H_2$ |
| 398 | $CH_3NH(CH_2)_{10}$— | —$CH_2C_6H_4$-p-F | —$PO_3H_2$ |
| 399 | $CH_3NH(CH_2)_{10}$— | —$CH_2CH_2C_6H_5$ | —$PO_3H_2$ |
| 400 | $CH_3NH(CH_2)_{10}$— | —$CH_2$-cyclo-$C_6H_{11}$ | —$PO_3H_2$ |
| 401 | $CH_3NH(CH_2)_{10}$— | —$CH_2$-cyclo-$C_6H_{10}$-4-F | —$PO_3H_2$ |
| 402 | $CH_3NH(CH_2)_{10}$— | —$CH_2$-cyclo-$C_6H_{10}$-4-$CH_3$ | —$PO_3H_2$ |
| 403 | $CH_3NH(CH_2)_{10}$— | —$CH_2$-cyclo-$C_6H_{10}$-4-$OCH_3$ | —$PO_3H_2$ |
| 404 | $CH_3NH(CH_2)_{10}$— | —$CH_2CH_2$-cyclo-$C_6H_{11}$ | —$PO_3H_2$ |
| 405 | $CH_3NH(CH_2)_{10}$— | —$CH_2$-cyclo-$C_5H_9$ | —$PO_3H_2$ |
| 406 | $CH_3NH(CH_2)_{10}$— | —$CH_2CH_2$-cyclo-$C_5H_9$ | —$PO_3H_2$ |
| 407 | $CH_3NH(CH_2)_{10}$— | —$CH_2$-2-naphthyl | —$PO_3H_2$ |
| 408 | $CH_3NH(CH_2)_{10}$— | —H | -5-Tet |
| 409 | $CH_3NH(CH_2)_{10}$— | —$CH_3$ | -5-Tet |
| 410 | $CH_3NH(CH_2)_{10}$— | —$CH_2CH_3$ | -5-Tet |
| 411 | $CH_3NH(CH_2)_{10}$— | —$CH_2CH_2CH_3$ | -5-Tet |
| 412 | $CH_3NH(CH_2)_{10}$— | —$CH_2CH_2CH_2CH_3$ | -5-Tet |
| 413 | $CH_3NH(CH_2)_{10}$— | —$CH_2CH_2CH_2CH_2CH_3$ | -5-Tet |
| 414 | $CH_3NH(CH_2)_{10}$— | —$CH_2CH_2CH_2CH_2CH_2CH_3$ | -5-Tet |
| 415 | $CH_3NH(CH_2)_{10}$— | —$CH(CH_3)_2$ | -5-Tet |
| 416 | $CH_3NH(CH_2)_{10}$— | —$CH_2CH(CH_3)_2$ | -5-Tet |
| 417 | $CH_3NH(CH_2)_{10}$— | —$CH_2CH_2CH(CH_3)_2$ | -5-Tet |
| 418 | $CH_3NH(CH_2)_{10}$— | -cyclo-$C_3H_5$ | -5-Tet |
| 419 | $CH_3NH(CH_2)_{10}$— | -cyclo-$C_4H_7$ | -5-Tet |
| 420 | $CH_3NH(CH_2)_{10}$— | -cyclo-$C_5H_9$ | -5-Tet |
| 421 | $CH_3NH(CH_2)_{10}$— | -cyclo-$C_6H_{11}$ | -5-Tet |
| 422 | $CH_3NH(CH_2)_{10}$— | -cyclo-$C_7H_{13}$ | -5-Tet |
| 423 | $CH_3NH(CH_2)_{10}$— | -cyclo-$C_8H_{15}$ | -5-Tet |
| 424 | $CH_3NH(CH_2)_{10}$— | —$CH(CH_3)(CH_2CH_3)$ | -5-Tet |
| 425 | $CH_3NH(CH_2)_{10}$— | —$CH(CH_2CH_3)_2$ | -5-Tet |
| 426 | $CH_3NH(CH_2)_{10}$— | —$CH(CH_3)(CH_2CH_2CH_3)$ | -5-Tet |
| 427 | $CH_3NH(CH_2)_{10}$— | —$C(CH_3)_3$ | -5-Tet |
| 428 | $CH_3NH(CH_2)_{10}$— | $HC{\equiv}CCH_2$— | -5-Tet |
| 429 | $CH_3NH(CH_2)_{10}$— | $H_2C{=}CH$— | -5-Tet |
| 430 | $CH_3NH(CH_2)_{10}$— | $H_2C{=}CHCH_2$— | -5-Tet |
| 431 | $CH_3NH(CH_2)_{10}$— | —$CH_2F$ | -5-Tet |
| 432 | $CH_3NH(CH_2)_{10}$— | —$CH_2C_6H_5$ | -5-Tet |
| 433 | $CH_3NH(CH_2)_{10}$— | —$CH_2C_6H_4$-p-$OCH_3$ | -5-Tet |
| 434 | $CH_3NH(CH_2)_{10}$— | —$CH_2C_6H_4$-p-$CH_3$ | -5-Tet |
| 435 | $CH_3NH(CH_2)_{10}$— | —$CH_2C_6H_4$-p-F | -5-Tet |
| 436 | $CH_3NH(CH_2)_{10}$— | —$CH_2CH_2C_6H_5$ | -5-Tet |
| 437 | $CH_3NH(CH_2)_{10}$— | —$CH_2$-cyclo-$C_6H_{11}$ | -5-Tet |
| 438 | $CH_3NH(CH_2)_{10}$— | —$CH_2$-cyclo-$C_6H_{10}$-4-F | -5-Tet |
| 439 | $CH_3NH(CH_2)_{10}$— | —$CH_2$-cyclo-$C_6H_{10}$-4-$CH_3$ | -5-Tet |
| 440 | $CH_3NH(CH_2)_{10}$— | —$CH_2$-cyclo-$C_6H_{10}$-4-$OCH_3$ | -5-Tet |
| 441 | $CH_3NH(CH_2)_{10}$— | —$CH_2CH_2$-cyclo-$C_6H_{11}$ | -5-Tet |
| 442 | $CH_3NH(CH_2)_{10}$— | —$CH_2$-cyclo-$C_5H_9$ | -5-Tet |
| 443 | $CH_3NH(CH_2)_{10}$— | —$CH_2CH_2$-cyclo-$C_5H_9$ | -5-Tet |
| 444 | $CH_3NH(CH_2)_{10}$— | —$CH_2$-2-naphthyl | -5-Tet |
| 445 | $(CH_3)_2N(CH_2)_{10}$— | —H | —$CO_2H$ |
| 446 | $(CH_3)_2N(CH_2)_{10}$— | —$CH_3$ | —$CO_2H$ |
| 447 | $(CH_3)_2N(CH_2)_{10}$— | —$CH_2CH_3$ | —$CO_2H$ |
| 448 | $(CH_3)_2N(CH_2)_{10}$— | —$CH_2CH_2CH_3$ | —$CO_2H$ |
| 449 | $(CH_3)_2N(CH_2)_{10}$— | —$CH_2CH_2CH_2CH_3$ | —$CO_2H$ |
| 450 | $(CH_3)_2N(CH_2)_{10}$— | —$CH_2CH_2CH_2CH_2CH_3$ | —$CO_2H$ |
| 451 | $(CH_3)_2N(CH_2)_{10}$— | —$CH_2CH_2CH_2CH_2CH_2CH_3$ | —$CO_2H$ |
| 452 | $(CH_3)_2N(CH_2)_{10}$— | —$CH(CH_3)_2$ | —$CO_2H$ |
| 453 | $(CH_3)_2N(CH_2)_{10}$— | —$CH_2CH(CH_3)_2$ | —$CO_2H$ |

TABLE I-continued

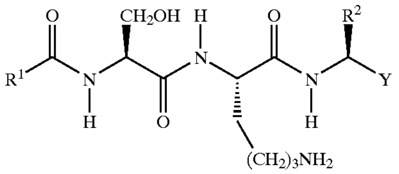

| Ex. No. | $R^1$ | $R^2$ | Y |
|---|---|---|---|
| 454 | $(CH_3)_2N(CH_2)_{10}$— | —$CH_2CH_2CH(CH_3)_2$ | —$CO_2H$ |
| 455 | $(CH_3)_2N(CH_2)_{10}$— | -cyclo-$C_3H_5$ | —$CO_2H$ |
| 456 | $(CH_3)_2N(CH_2)_{10}$— | -cyclo-$C_4H_7$ | —$CO_2H$ |
| 457 | $(CH_3)_2N(CH_2)_{10}$— | -cyclo-$C_5H_9$ | —$CO_2H$ |
| 458 | $(CH_3)_2N(CH_2)_{10}$— | -cyclo-$C_6H_{11}$ | —$CO_2H$ |
| 459 | $(CH_3)_2N(CH_2)_{10}$— | -cyclo-$C_7H_{13}$ | —$CO_2H$ |
| 460 | $(CH_3)_2N(CH_2)_{10}$— | -cyclo-$C_8H_{15}$ | —$CO_2H$ |
| 461 | $(CH_3)_2N(CH_2)_{10}$— | —$CH(CH_3)(CH_2CH_3)$ | —$CO_2H$ |
| 462 | $(CH_3)_2N(CH_2)_{10}$— | —$CH(CH_2CH_3)_2$ | —$CO_2H$ |
| 463 | $(CH_3)_2N(CH_2)_{10}$— | —$CH(CH_3)(CH_2CH_2CH_3)$ | —$CO_2H$ |
| 464 | $(CH_3)_2N(CH_2)_{10}$— | —$C(CH_3)_3$ | —$CO_2H$ |
| 465 | $(CH_3)_2N(CH_2)_{10}$— | $HC{\equiv}CCH_2$— | —$CO_2H$ |
| 466 | $(CH_3)_2N(CH_2)_{10}$— | $H_2C{=}CH$— | —$CO_2H$ |
| 467 | $(CH_3)_2N(CH_2)_{10}$— | $H_2C{=}CHCH_2$— | —$CO_2H$ |
| 468 | $(CH_3)_2N(CH_2)_{10}$— | —$CH_2F$ | —$CO_2H$ |
| 469 | $(CH_3)_2N(CH_2)_{10}$— | —$CH_2C_6H_5$ | —$CO_2H$ |
| 470 | $(CH_3)_2N(CH_2)_{10}$— | —$CH_2C_6H_4$-p-$OCH_3$ | —$CO_2H$ |
| 471 | $(CH_3)_2N(CH_2)_{10}$— | —$CH_2C_6H_4$-p-$CH_3$ | —$CO_2H$ |
| 472 | $(CH_3)_2N(CH_2)_{10}$— | —$CH_2C_6H_4$-p-F | —$CO_2H$ |
| 473 | $(CH_3)_2N(CH_2)_{10}$— | —$CH_2CH_2C_6H_5$ | —$CO_2H$ |
| 474 | $(CH_3)_2N(CH_2)_{10}$— | —$CH_2$-cyclo-$C_6H_{11}$ | —$CO_2H$ |
| 475 | $(CH_3)_2N(CH_2)_{10}$— | —$CH_2$-cyclo-$C_6H_{10}$-4-F | —$CO_2H$ |
| 476 | $(CH_3)_2N(CH_2)_{10}$— | —$CH_2$-cyclo-$C_6H_{10}$-4-$CH_3$ | —$CO_2H$ |
| 477 | $(CH_3)_2N(CH_2)_{10}$— | —$CH_2$-cyclo-$C_6H_{10}$-4-$OCH_3$ | —$CO_2H$ |
| 478 | $(CH_3)_2N(CH_2)_{10}$— | —$CH_2CH_2$-cyclo-$C_6H_{11}$ | —$CO_2H$ |
| 479 | $(CH_3)_2N(CH_2)_{10}$— | —$CH_2$-cyclo-$C_5H_9$ | —$CO_2H$ |
| 480 | $(CH_3)_2N(CH_2)_{10}$— | —$CH_2CH_2$-cyclo-$C_5H_9$ | —$CO_2H$ |
| 481 | $(CH_3)_2N(CH_2)_{10}$— | —$CH_2$-2-naphthyl | —$CO_2H$ |
| 482 | $(CH_3)_2N(CH_2)_{10}$— | —H | —$PO_3H_2$ |
| 483 | $(CH_3)_2N(CH_2)_{10}$— | —$CH_3$ | —$PO_3H_2$ |
| 484 | $(CH_3)_2N(CH_2)_{10}$— | —$CH_2CH_3$ | —$PO_3H_2$ |
| 485 | $(CH_3)_2N(CH_2)_{10}$— | —$CH_2CH_2CH_3$ | —$PO_3H_2$ |
| 486 | $(CH_3)_2N(CH_2)_{10}$— | —$CH_2CH_2CH_2CH_3$ | —$PO_3H_2$ |
| 487 | $(CH_3)_2N(CH_2)_{10}$— | —$CH_2CH_2CH_2CH_2CH_3$ | —$PO_3H_2$ |
| 488 | $(CH_3)_2N(CH_2)_{10}$— | —$CH_2CH_2CH_2CH_2CH_2CH_3$ | —$PO_3H_2$ |
| 489 | $(CH_3)_2N(CH_2)_{10}$— | —$CH(CH_3)_2$ | —$PO_3H_2$ |
| 490 | $(CH_3)_2N(CH_2)_{10}$— | —$CH_2CH(CH_3)_2$ | —$PO_3H_2$ |
| 491 | $(CH_3)_2N(CH_2)_{10}$— | —$CH_2CH_2CH(CH_3)_2$ | —$PO_3H_2$ |
| 492 | $(CH_3)_2N(CH_2)_{10}$— | -cyclo-$C_3H_5$ | —$PO_3H_2$ |
| 493 | $(CH_3)_2N(CH_2)_{10}$— | -cyclo-$C_4H_7$ | —$PO_3H_2$ |
| 494 | $(CH_3)_2N(CH_2)_{10}$— | -cyclo-$C_5H_9$ | —$PO_3H_2$ |
| 495 | $(CH_3)_2N(CH_2)_{10}$— | -cyclo-$C_6H_{11}$ | —$PO_3H_2$ |
| 496 | $(CH_3)_2N(CH_2)_{10}$— | -cyclo-$C_7H_{13}$ | —$PO_3H_2$ |
| 497 | $(CH_3)_2N(CH_2)_{10}$— | -cyclo-$C_8H_{15}$ | —$PO_3H_2$ |
| 498 | $(CH_3)_2N(CH_2)_{10}$— | —$CH(CH_3)(CH_2CH_3)$ | —$PO_3H_2$ |
| 499 | $(CH_3)_2N(CH_2)_{10}$— | —$CH(CH_2CH_3)_2$ | —$PO_3H_2$ |
| 500 | $(CH_3)_2N(CH_2)_{10}$— | —$CH(CH_3)(CH_2CH_2CH_3)$ | —$PO_3H_2$ |
| 501 | $(CH_3)_2N(CH_2)_{10}$— | —$C(CH_3)_3$ | —$PO_3H_2$ |
| 502 | $(CH_3)_2N(CH_2)_{10}$— | $HC{\equiv}CCH_2$— | —$PO_3H_2$ |
| 503 | $(CH_3)_2N(CH_2)_{10}$— | $H_2C{=}CH$— | —$PO_3H_2$ |
| 504 | $(CH_3)_2N(CH_2)_{10}$— | $H_2C{=}CHCH_2$— | —$PO_3H_2$ |
| 505 | $(CH_3)_2N(CH_2)_{10}$— | —$CH_2F$ | —$PO_3H_2$ |
| 506 | $(CH_3)_2N(CH_2)_{10}$— | —$CH_2C_6H_5$ | —$PO_3H_2$ |
| 507 | $(CH_3)_2N(CH_2)_{10}$— | —$CH_2C_6H_4$-p-$OCH_3$ | —$PO_3H_2$ |
| 508 | $(CH_3)_2N(CH_2)_{10}$— | —$CH_2C_6H_4$-p-$CH_3$ | —$PO_3H_2$ |
| 509 | $(CH_3)_2N(CH_2)_{10}$— | —$CH_2C_6H_4$-p-F | —$PO_3H_2$ |
| 510 | $(CH_3)_2N(CH_2)_{10}$— | —$CH_2CH_2C_6H_5$ | —$PO_3H_2$ |
| 511 | $(CH_3)_2N(CH_2)_{10}$— | —$CH_2$-cyclo-$C_6H_{11}$ | —$PO_3H_2$ |
| 512 | $(CH_3)_2N(CH_2)_{10}$— | —$CH_2$-cyclo-$C_6H_{10}$-4-F | —$PO_3H_2$ |
| 513 | $(CH_3)_2N(CH_2)_{10}$— | —$CH_2$-cyclo-$C_6H_{10}$-4-$CH_3$ | —$PO_3H_2$ |
| 514 | $(CH_3)_2N(CH_2)_{10}$— | —$CH_2$-cyclo-$C_6H_{10}$-4-$OCH_3$ | —$PO_3H_2$ |
| 515 | $(CH_3)_2N(CH_2)_{10}$— | —$CH_2CH_2$-cyclo-$C_6H_{11}$ | —$PO_3H_2$ |
| 516 | $(CH_3)_2N(CH_2)_{10}$— | —$CH_2$-cyclo-$C_5H_9$ | —$PO_3H_2$ |
| 517 | $(CH_3)_2N(CH_2)_{10}$— | —$CH_2CH_2$-cyclo-$C_5H_9$ | —$PO_3H_2$ |
| 518 | $(CH_3)_2N(CH_2)_{10}$— | —$CH_2$-2-naphthyl | —$PO_3H_2$ |
| 519 | $(CH_3)_2N(CH_2)_{10}$— | —H | -5-Tet |

TABLE I-continued

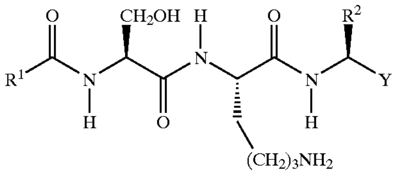

| Ex. No. | $R^1$ | $R^2$ | Y |
|---|---|---|---|
| 520 | $(CH_3)_2N(CH_2)_{10}$— | —$CH_3$ | -5-Tet |
| 521 | $(CH_3)_2N(CH_2)_{10}$— | —$CH_2CH_3$ | -5-Tet |
| 522 | $(CH_3)_2N(CH_2)_{10}$— | —$CH_2CH_2CH_3$ | -5-Tet |
| 523 | $(CH_3)_2N(CH_2)_{10}$— | —$CH_2CH_2CH_2CH_3$ | -5-Tet |
| 524 | $(CH_3)_2N(CH_2)_{10}$— | —$CH_2CH_2CH_2CH_2CH_3$ | -5-Tet |
| 525 | $(CH_3)_2N(CH_2)_{10}$— | —$CH_2CH_2CH_2CH_2CH_2CH_3$ | -5-Tet |
| 526 | $(CH_3)_2N(CH_2)_{10}$— | —$CH(CH_3)_2$ | -5-Tet |
| 527 | $(CH_3)_2N(CH_2)_{10}$— | —$CH_2CH(CH_3)_2$ | -5-Tet |
| 528 | $(CH_3)_2N(CH_2)_{10}$— | —$CH_2CH_2CH(CH_3)_2$ | -5-Tet |
| 529 | $(CH_3)_2N(CH_2)_{10}$— | -cyclo-$C_3H_5$ | -5-Tet |
| 530 | $(CH_3)_2N(CH_2)_{10}$— | -cyclo-$C_4H_7$ | -5-Tet |
| 531 | $(CH_3)_2N(CH_2)_{10}$— | -cyclo-$C_5H_9$ | -5-Tet |
| 532 | $(CH_3)_2N(CH_2)_{10}$— | -cyclo-$C_6H_{11}$ | -5-Tet |
| 533 | $(CH_3)_2N(CH_2)_{10}$— | -cyclo-$C_7H_{13}$ | -5-Tet |
| 534 | $(CH_3)_2N(CH_2)_{10}$— | -cyclo-$C_8H_{15}$ | -5-Tet |
| 535 | $(CH_3)_2N(CH_2)_{10}$— | —$CH(CH_3)(CH_2CH_3)$ | -5-Tet |
| 536 | $(CH_3)_2N(CH_2)_{10}$— | —$CH(CH_2CH_3)_2$ | -5-Tet |
| 537 | $(CH_3)_2N(CH_2)_{10}$— | —$CH(CH_3)(CH_2CH_2CH_3)$ | -5-Tet |
| 538 | $(CH_3)_2N(CH_2)_{10}$— | —$C(CH_3)_3$ | -5-Tet |
| 539 | $(CH_3)_2N(CH_2)_{10}$— | $HC{\equiv}CCH_2$— | -5-Tet |
| 540 | $(CH_3)_2N(CH_2)_{10}$— | $H_2C{=}CH$— | -5-Tet |
| 541 | $(CH_3)_2N(CH_2)_{10}$— | $H_2C{=}CHCH_2$— | -5-Tet |
| 542 | $(CH_3)_2N(CH_2)_{10}$— | —$CH_2F$ | -5-Tet |
| 543 | $(CH_3)_2N(CH_2)_{10}$— | —$CH_2C_6H_5$ | -5-Tet |
| 544 | $(CH_3)_2N(CH_2)_{10}$— | —$CH_2C_6H_4$-p-$OCH_3$ | -5-Tet |
| 545 | $(CH_3)_2N(CH_2)_{10}$— | —$CH_2C_6H_4$-p-$CH_3$ | -5-Tet |
| 546 | $(CH_3)_2N(CH_2)_{10}$— | —$CH_2C_6H_4$-p-F | -5-Tet |
| 547 | $(CH_3)_2N(CH_2)_{10}$— | —$CH_2CH_2C_6H_5$ | -5-Tet |
| 548 | $(CH_3)_2N(CH_2)_{10}$— | —$CH_2$-cyclo-$C_6H_{11}$ | -5-Tet |
| 549 | $(CH_3)_2N(CH_2)_{10}$— | —$CH_2$-cyclo-$C_6H_{10}$-4-F | -5-Tet |
| 550 | $(CH_3)_2N(CH_2)_{10}$— | —$CH_2$-cyclo-$C_6H_{10}$-4-$CH_3$ | -5-Tet |
| 551 | $(CH_3)_2N(CH_2)_{10}$— | —$CH_2$-cyclo-$C_6H_{10}$-4-$OCH_3$ | -5-Tet |
| 552 | $(CH_3)_2N(CH_2)_{10}$— | —$CH_2CH_2$-cyclo-$C_6H_{11}$ | -5-Tet |
| 553 | $(CH_3)_2N(CH_2)_{10}$— | —$CH_2$-cyclo-$C_5H_9$ | -5-Tet |
| 554 | $(CH_3)_2N(CH_2)_{10}$— | —$CH_2CH_2$-cyclo-$C_5H_9$ | -5-Tet |
| 555 | $(CH_3)_2N(CH_2)_{10}$— | —$CH_2$-2-naphthyl | -5-Tet |
| 556 | p-$[H_2N(CH_2)_6]C_6H_4CH_2$— | —H | —$CO_2H$ |
| 557 | p-$[H_2N(CH_2)_6]C_6H_4CH_2$— | —$CH_3$ | —$CO_2H$ |
| 558 | p-$[H_2N(CH_2)_6]C_6H_4CH_2$— | —$CH_2CH_3$ | —$CO_2H$ |
| 559 | p-$[H_2N(CH_2)_6]C_6H_4CH_2$— | —$CH_2CH_2CH_3$ | —$CO_2H$ |
| 560 | p-$[H_2N(CH_2)_6]C_6H_4CH_2$— | —$CH_2CH_2CH_2CH_3$ | —$CO_2H$ |
| 561 | p-$[H_2N(CH_2)_6]C_6H_4CH_2$— | —$CH_2CH_2CH_2CH_2CH_3$ | —$CO_2H$ |
| 562 | p-$[H_2N(CH_2)_6]C_6H_4CH_2$— | —$CH_2CH_2CH_2CH_2CH_2CH_3$ | —$CO_2H$ |
| 563 | p-$[H_2N(CH_2)_6]C_6H_4CH_2$— | —$CH(CH_3)_2$ | —$CO_2H$ |
| 564 | p-$[H_2N(CH_2)_6]C_6H_4CH_2$— | —$CH_2CH(CH_3)_2$ | —$CO_2H$ |
| 565 | p-$[H_2N(CH_2)_6]C_6H_4CH_2$— | —$CH_2CH_2CH(CH_3)_2$ | —$CO_2H$ |
| 566 | p-$[H_2N(CH_2)_6]C_6H_4CH_2$— | -cyclo-$C_3H_5$ | —$CO_2H$ |
| 567 | p-$[H_2N(CH_2)_6]C_6H_4CH_2$— | -cyclo-$C_4H_7$ | —$CO_2H$ |
| 568 | p-$[H_2N(CH_2)_6]C_6H_4CH_2$— | -cyclo-$C_5H_9$ | —$CO_2H$ |
| 569 | p-$[H_2N(CH_2)_6]C_6H_4CH_2$— | -cyclo-$C_6H_{11}$ | —$CO_2H$ |
| 570 | p-$[H_2N(CH_2)_6]C_6H_4CH_2$— | -cyclo-$C_7H_{13}$ | —$CO_2H$ |
| 571 | p-$[H_2N(CH_2)_6]C_6H_4CH_2$— | -cyclo-$C_8H_{15}$ | —$CO_2H$ |
| 572 | p-$[H_2N(CH_2)_6]C_6H_4CH_2$— | —$CH(CH_3)(CH_2CH_3)$ | —$CO_2H$ |
| 573 | p-$[H_2N(CH_2)_6]C_6H_4CH_2$— | —$CH(CH_2CH_3)_2$ | —$CO_2H$ |
| 574 | p-$[H_2N(CH_2)_6]C_6H_4CH_2$— | —$CH(CH_3)(CH_2CH_2CH_3)$ | —$CO_2H$ |
| 575 | p-$[H_2N(CH_2)_6]C_6H_4CH_2$— | —$C(CH_3)_3$ | —$CO_2H$ |
| 576 | p-$[H_2N(CH_2)_6]C_6H_4CH_2$— | $HC{\equiv}CCH_2$— | —$CO_2H$ |
| 577 | p-$[H_2N(CH_2)_6]C_6H_4CH_2$— | $H_2C{=}CH$— | —$CO_2H$ |
| 578 | p-$[H_2N(CH_2)_6]C_6H_4CH_2$— | $H_2C{=}CHCH_2$— | —$CO_2H$ |
| 579 | p-$[H_2N(CH_2)_6]C_6H_4CH_2$— | —$CH_2F$ | —$CO_2H$ |
| 580 | p-$[H_2N(CH_2)_6]C_6H_4CH_2$— | —$CH_2C_6H_5$ | —$CO_2H$ |
| 581 | p-$[H_2N(CH_2)_6]C_6H_4CH_2$— | —$CH_2C_6H_4$-p-$OCH_3$ | —$CO_2H$ |
| 582 | p-$[H_2N(CH_2)_6]C_6H_4CH_2$— | —$CH_2C_6H_4$-p-$CH_3$ | —$CO_2H$ |
| 583 | p-$[H_2N(CH_2)_6]C_6H_4CH_2$— | —$CH_2C_6H_4$-p-F | —$CO_2H$ |
| 584 | p-$[H_2N(CH_2)_6]C_6H_4CH_2$— | —$CH_2CH_2C_6H_5$ | —$CO_2H$ |
| 585 | p-$[H_2N(CH_2)_6]C_6H_4CH_2$— | —$CH_2$-cyclo-$C_6H_{11}$ | —$CO_2H$ |

TABLE I-continued

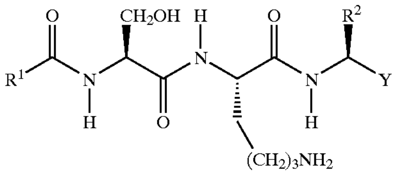

| Ex. No. | $R^1$ | $R^2$ | Y |
|---|---|---|---|
| 586 | p-$[H_2N(CH_2)_6]C_6H_4CH_2$— | —$CH_2$-cyclo-$C_6H_{10}$-4-F | —$CO_2H$ |
| 587 | p-$[H_2N(CH_2)_6]C_6H_4CH_2$— | —$CH_2$-cyclo-$C_6H_{10}$-4-$CH_3$ | —$CO_2H$ |
| 588 | p-$[H_2N(CH_2)_6]C_6H_4CH_2$— | —$CH_2$-cyclo-$C_6H_{10}$-4-$OCH_3$ | —$CO_2H$ |
| 589 | p-$[H_2N(CH_2)_6]C_6H_4CH_2$— | —$CH_2CH_2$-cyclo-$C_6H_{11}$ | —$CO_2H$ |
| 590 | p-$[H_2N(CH_2)_6]C_6H_4CH_2$— | —$CH_2$-cyclo-$C_5H_9$ | —$CO_2H$ |
| 591 | p-$[H_2N(CH_2)_6]C_6H_4CH_2$— | —$CH_2CH_2$-cyclo-$C_5H_9$ | —$CO_2H$ |
| 592 | p-$[H_2N(CH_2)_6]C_6H_4CH_2$— | —$CH_2$-2-naphthyl | —$CO_2H$ |
| 593 | p-$[H_2N(CH_2)_6]C_6H_4CH_2$— | —H | —$PO_3H_2$ |
| 594 | p-$[H_2N(CH_2)_6]C_6H_4CH_2$— | —$CH_3$ | —$PO_3H_2$ |
| 595 | p-$[H_2N(CH_2)_6]C_6H_4CH_2$— | —$CH_2CH_3$ | —$PO_3H_2$ |
| 596 | p-$[H_2N(CH_2)_6]C_6H_4CH_2$— | —$CH_2CH_2CH_3$ | —$PO_3H_2$ |
| 597 | p-$[H_2N(CH_2)_6]C_6H_4CH_2$— | —$CH_2CH_2CH_2CH_3$ | —$PO_3H_2$ |
| 598 | p-$[H_2N(CH_2)_6]C_6H_4CH_2$— | —$CH_2CH_2CH_2CH_2CH_3$ | —$PO_3H_2$ |
| 599 | p-$[H_2N(CH_2)_6]C_6H_4CH_2$— | —$CH_2CH_2CH_2CH_2CH_2CH_3$ | —$PO_3H_2$ |
| 600 | p-$[H_2N(CH_2)_6]C_6H_4CH_2$— | —$CH(CH_3)_2$ | —$PO_3H_2$ |
| 601 | p-$[H_2N(CH_2)_6]C_6H_4CH_2$— | —$CH_2CH(CH_3)_2$ | —$PO_3H_2$ |
| 602 | p-$[H_2N(CH_2)_6]C_6H_4CH_2$— | —$CH_2CH_2CH(CH_3)_2$ | —$PO_3H_2$ |
| 603 | p-$[H_2N(CH_2)_6]C_6H_4CH_2$— | -cyclo-$C_3H_5$ | —$PO_3H_2$ |
| 604 | p-$[H_2N(CH_2)_6]C_6H_4CH_2$— | -cyclo-$C_4H_7$ | —$PO_3H_2$ |
| 605 | p-$[H_2N(CH_2)_6]C_6H_4CH_2$— | -cyclo-$C_5H_9$ | —$PO_3H_2$ |
| 606 | p-$[H_2N(CH_2)_6]C_6H_4CH_2$— | -cyclo-$C_6H_{11}$ | —$PO_3H_2$ |
| 607 | p-$[H_2N(CH_2)_6]C_6H_4CH_2$— | -cyclo-$C_7H_{13}$ | —$PO_3H_2$ |
| 608 | p-$[H_2N(CH_2)_6]C_6H_4CH_2$— | -cyclo-$C_8H_{15}$ | —$PO_3H_2$ |
| 609 | p-$[H_2N(CH_2)_6]C_6H_4CH_2$— | —$CH(CH_3)(CH_2CH_3)$ | —$PO_3H_2$ |
| 610 | p-$[H_2N(CH_2)_6]C_6H_4CH_2$— | —$CH(CH_2CH_3)_2$ | —$PO_3H_2$ |
| 611 | p-$[H_2N(CH_2)_6]C_6H_4CH_2$— | —$CH(CH_3)(CH_2CH_2CH_3)$ | —$PO_3H_2$ |
| 612 | p-$[H_2N(CH_2)_6]C_6H_4CH_2$— | —$C(CH_3)_3$ | —$PO_3H_2$ |
| 613 | p-$[H_2N(CH_2)_6]C_6H_4CH_2$— | $HC{\equiv}CCH_2$— | —$PO_3H_2$ |
| 614 | p-$[H_2N(CH_2)_6]C_6H_4CH_2$— | $H_2C{=}CH$— | —$PO_3H_2$ |
| 615 | p-$[H_2N(CH_2)_6]C_6H_4CH_2$— | $H_2C{=}CHCH_2$— | —$PO_3H_2$ |
| 616 | p-$[H_2N(CH_2)_6]C_6H_4CH_2$— | —$CH_2F$ | —$PO_3H_2$ |
| 617 | p-$[H_2N(CH_2)_6]C_6H_4CH_2$— | —$CH_2C_6H_5$ | —$PO_3H_2$ |
| 618 | p-$[H_2N(CH_2)_6]C_6H_4CH_2$— | —$CH_2C_6H_4$-p-$OCH_3$ | —$PO_3H_2$ |
| 619 | p-$[H_2N(CH_2)_6]C_6H_4CH_2$— | —$CH_2C_6H_4$-p-$CH_3$ | —$PO_3H_2$ |
| 620 | p-$[H_2N(CH_2)_6]C_6H_4CH_2$— | —$CH_2C_6H_4$-p-F | —$PO_3H_2$ |
| 621 | p-$[H_2N(CH_2)_6]C_6H_4CH_2$— | —$CH_2CH_2C_6H_5$ | —$PO_3H_2$ |
| 622 | p-$[H_2N(CH_2)_6]C_6H_4CH_2$— | —$CH_2$-cyclo-$C_6H_{11}$ | —$PO_3H_2$ |
| 623 | p-$[H_2N(CH_2)_6]C_6H_4CH_2$— | —$CH_2$-cyclo-$C_6H_{10}$-4-F | —$PO_3H_2$ |
| 624 | p-$[H_2N(CH_2)_6]C_6H_4CH_2$— | —$CH_2$-cyclo-$C_6H_{10}$-4-$CH_3$ | —$PO_3H_2$ |
| 625 | p-$[H_2N(CH_2)_6]C_6H_4CH_2$— | —$CH_2$-cyclo-$C_6H_{10}$-4-$OCH_3$ | —$PO_3H_2$ |
| 626 | p-$[H_2N(CH_2)_6]C_6H_4CH_2$— | —$CH_2CH_2$-cyclo-$C_6H_{11}$ | —$PO_3H_2$ |
| 627 | p-$[H_2N(CH_2)_6]C_6H_4CH_2$— | —$CH_2$-cyclo-$C_5H_9$ | —$PO_3H_2$ |
| 628 | p-$[H_2N(CH_2)_6]C_6H_4CH_2$— | —$CH_2CH_2$-cyclo-$C_5H_9$ | —$PO_3H_2$ |
| 629 | p-$[H_2N(CH_2)_6]C_6H_4CH_2$— | —$CH_2$-2-naphthyl | —$PO_3H_2$ |
| 630 | p-$[H_2N(CH_2)_6]C_6H_4CH_2$— | —H | -5-Tet |
| 631 | p-$[H_2N(CH_2)_6]C_6H_4CH_2$— | —$CH_3$ | -5-Tet |
| 632 | p-$[H_2N(CH_2)_6]C_6H_4CH_2$— | —$CH_2CH_3$ | -5-Tet |
| 633 | p-$[H_2N(CH_2)_6]C_6H_4CH_2$— | —$CH_2CH_2CH_3$ | -5-Tet |
| 634 | p-$[H_2N(CH_2)_6]C_6H_4CH_2$— | —$CH_2CH_2CH_2CH_3$ | -5-Tet |
| 635 | p-$[H_2N(CH_2)_6]C_6H_4CH_2$— | —$CH_2CH_2CH_2CH_2CH_3$ | -5-Tet |
| 636 | p-$[H_2N(CH_2)_6]C_6H_4CH_2$— | —$CH_2CH_2CH_2CH_2CH_2CH_3$ | -5-Tet |
| 637 | p-$[H_2N(CH_2)_6]C_6H_4CH_2$— | —$CH(CH_3)_2$ | -5-Tet |
| 638 | p-$[H_2N(CH_2)_6]C_6H_4CH_2$— | —$CH_2CH(CH_3)_2$ | -5-Tet |
| 639 | p-$[H_2N(CH_2)_6]C_6H_4CH_2$— | —$CH_2CH_2CH(CH_3)_2$ | -5-Tet |
| 640 | p-$[H_2N(CH_2)_6]C_6H_4CH_2$— | -cyclo-$C_3H_5$ | -5-Tet |
| 641 | p-$[H_2N(CH_2)_6]C_6H_4CH_2$— | -cyclo-$C_4H_7$ | -5-Tet |
| 642 | p-$[H_2N(CH_2)_6]C_6H_4CH_2$— | -cyclo-$C_5H_9$ | -5-Tet |
| 643 | p-$[H_2N(CH_2)_6]C_6H_4CH_2$— | -cyclo-$C_6H_{11}$ | -5-Tet |
| 644 | p-$[H_2N(CH_2)_6]C_6H_4CH_2$— | -cyclo-$C_7H_{13}$ | -5-Tet |
| 645 | p-$[H_2N(CH_2)_6]C_6H_4CH_2$— | -cyclo-$C_8H_{15}$ | -5-Tet |
| 646 | p-$[H_2N(CH_2)_6]C_6H_4CH_2$— | —$CH(CH_3)(CH_2CH_3)$ | -5-Tet |
| 647 | p-$[H_2N(CH_2)_6]C_6H_4CH_2$— | —$CH(CH_2CH_3)_2$ | -5-Tet |
| 648 | p-$[H_2N(CH_2)_6]C_6H_4CH_2$— | —$CH(CH_3)(CH_2CH_2CH_3)$ | -5-Tet |
| 649 | p-$[H_2N(CH_2)_6]C_6H_4CH_2$— | —$C(CH_3)_3$ | -5-Tet |
| 650 | p-$[H_2N(CH_2)_6]C_6H_4CH_2$— | $HC{\equiv}CCH_2$— | -5-Tet |
| 651 | p-$[H_2N(CH_2)_6]C_6H_4CH_2$— | $H_2C{=}CH$— | -5-Tet |

TABLE I-continued

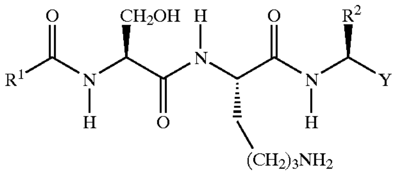

| Ex. No. | $R^1$ | $R^2$ | Y |
|---|---|---|---|
| 652 | p-$[H_2N(CH_2)_6]C_6H_4CH_2$— | $H_2C{=}CHCH_2$— | -5-Tet |
| 653 | p-$[H_2N(CH_2)_6]C_6H_4CH_2$— | —$CH_2F$ | -5-Tet |
| 654 | p-$[H_2N(CH_2)_6]C_6H_4CH_2$— | —$CH_2C_6H_5$ | -5-Tet |
| 655 | p-$[H_2N(CH_2)_6]C_6H_4CH_2$— | —$CH_2C_6H_4$-p-$OCH_3$ | -5-Tet |
| 656 | p-$[H_2N(CH_2)_6]C_6H_4CH_2$— | —$CH_2C_6H_4$-p-$CH_3$ | -5-Tet |
| 657 | p-$[H_2N(CH_2)_6]C_6H_4CH_2$— | —$CH_2C_6H_4$-p-F | -5-Tet |
| 658 | p-$[H_2N(CH_2)_6]C_6H_4CH_2$— | —$CH_2CH_2C_6H_5$ | -5-Tet |
| 659 | p-$[H_2N(CH_2)_6]C_6H_4CH_2$— | —$CH_2$-cyclo-$C_6H_{11}$ | -5-Tet |
| 660 | p-$[H_2N(CH_2)_6]C_6H_4CH_2$— | —$CH_2$-cyclo-$C_6H_{10}$-4-F | -5-Tet |
| 661 | p-$[H_2N(CH_2)_6]C_6H_4CH_2$— | —$CH_2$-cyclo-$C_6H_{10}$-4-$CH_3$ | -5-Tet |
| 662 | p-$[H_2N(CH_2)_6]C_6H_4CH_2$— | —$CH_2$-cyclo-$C_6H_{10}$-4-$OCH_3$ | -5-Tet |
| 663 | p-$[H_2N(CH_2)_6]C_6H_4CH_2$— | —$CH_2CH_2$-cyclo-$C_6H_{11}$ | -5-Tet |
| 664 | p-$[H_2N(CH_2)_6]C_6H_4CH_2$— | —$CH_2$-cyclo-$C_5H_9$ | -5-Tet |
| 665 | p-$[H_2N(CH_2)_6]C_6H_4CH_2$— | —$CH_2CH_2$-cyclo-$C_5H_9$ | -5-Tet |
| 666 | p-$[H_2N(CH_2)_6]C_6H_4CH_2$— | —$CH_2$-2-naphthyl | -5-Tet |
| 667 | p-$[H_2N(CH_2)_8]C_6H_4CH_2$— | —H | —$CO_2H$ |
| 668 | p-$[H_2N(CH_2)_8]C_6H_4CH_2$— | —$CH_3$ | —$CO_2H$ |
| 669 | p-$[H_2N(CH_2)_8]C_6H_4CH_2$— | —$CH_2CH_3$ | —$CO_2H$ |
| 670 | p-$[H_2N(CH_2)_8]C_6H_4CH_2$— | —$CH_2CH_2CH_3$ | —$CO_2H$ |
| 671 | p-$[H_2N(CH_2)_8]C_6H_4CH_2$— | —$CH_2CH_2CH_2CH_3$ | —$CO_2H$ |
| 672 | p-$[H_2N(CH_2)_8]C_6H_4CH_2$— | —$CH_2CH_2CH_2CH_2CH_3$ | —$CO_2H$ |
| 673 | p-$[H_2N(CH_2)_8]C_6H_4CH_2$— | —$CH_2CH_2CH_2CH_2CH_2CH_3$ | —$CO_2H$ |
| 674 | p-$[H_2N(CH_2)_8]C_6H_4CH_2$— | —$CH(CH_3)_2$ | —$CO_2H$ |
| 675 | p-$[H_2N(CH_2)_8]C_6H_4CH_2$— | —$CH_2CH(CH_3)_2$ | —$CO_2H$ |
| 676 | p-$[H_2N(CH_2)_8]C_6H_4CH_2$— | —$CH_2CH_2CH(CH_3)_2$ | —$CO_2H$ |
| 677 | p-$[H_2N(CH_2)_8]C_6H_4CH_2$— | -cyclo-$C_3H_5$ | —$CO_2H$ |
| 678 | p-$[H_2N(CH_2)_8]C_6H_4CH_2$— | -cyclo-$C_4H_7$ | —$CO_2H$ |
| 679 | p-$[H_2N(CH_2)_8]C_6H_4CH_2$— | -cyclo-$C_5H_9$ | —$CO_2H$ |
| 680 | p-$[H_2N(CH_2)_8]C_6H_4CH_2$— | -cyclo-$C_6H_{11}$ | —$CO_2H$ |
| 681 | p-$[H_2N(CH_2)_8]C_6H_4CH_2$— | -cyclo-$C_7H_{13}$ | —$CO_2H$ |
| 682 | p-$[H_2N(CH_2)_8]C_6H_4CH_2$— | -cyclo-$C_8H_{15}$ | —$CO_2H$ |
| 683 | p-$[H_2N(CH_2)_8]C_6H_4CH_2$— | —$CH(CH_3)(CH_2CH_3)$ | —$CO_2H$ |
| 684 | p-$[H_2N(CH_2)_8]C_6H_4CH_2$— | —$CH(CH_2CH_3)_2$ | —$CO_2H$ |
| 685 | p-$[H_2N(CH_2)_8]C_6H_4CH_2$— | —$CH(CH_3)(CH_2CH_2CH_3)$ | —$CO_2H$ |
| 686 | p-$[H_2N(CH_2)_8]C_6H_4CH_2$— | —$C(CH_3)_3$ | —$CO_2H$ |
| 687 | p-$[H_2N(CH_2)_8]C_6H_4CH_2$— | $HC{\equiv}CCH_2$— | —$CO_2H$ |
| 688 | p-$[H_2N(CH_2)_8]C_6H_4CH_2$— | $H_2C{=}CH$— | —$CO_2H$ |
| 689 | p-$[H_2N(CH_2)_8]C_6H_4CH_2$— | $H_2C{=}CHCH_2$— | —$CO_2H$ |
| 690 | p-$[H_2N(CH_2)_8]C_6H_4CH_2$— | —$CH_2F$ | —$CO_2H$ |
| 691 | p-$[H_2N(CH_2)_8]C_6H_4CH_2$— | —$CH_2C_6H_5$ | —$CO_2H$ |
| 692 | p-$[H_2N(CH_2)_8]C_6H_4CH_2$— | —$CH_2C_6H_4$-p-$OCH_3$ | —$CO_2H$ |
| 693 | p-$[H_2N(CH_2)_8]C_6H_4CH_2$— | —$CH_2C_6H_4$-p-$CH_3$ | —$CO_2H$ |
| 694 | p-$[H_2N(CH_2)_8]C_6H_4CH_2$— | —$CH_2C_6H_4$-p-F | —$CO_2H$ |
| 695 | p-$[H_2N(CH_2)_8]C_6H_4CH_2$— | —$CH_2CH_2C_6H_5$ | —$CO_2H$ |
| 696 | p-$[H_2N(CH_2)_8]C_6H_4CH_2$— | —$CH_2$-cyclo-$C_6H_{11}$ | —$CO_2H$ |
| 697 | p-$[H_2N(CH_2)_8]C_6H_4CH_2$— | —$CH_2$-cyclo-$C_6H_{10}$-4-F | —$CO_2H$ |
| 698 | p-$[H_2N(CH_2)_8]C_6H_4CH_2$— | —$CH_2$-cyclo-$C_6H_{10}$-4-$CH_3$ | —$CO_2H$ |
| 699 | p-$[H_2N(CH_2)_8]C_6H_4CH_2$— | —$CH_2$-cyclo-$C_6H_{10}$-4-$OCH_3$ | —$CO_2H$ |
| 700 | p-$[H_2N(CH_2)_8]C_6H_4CH_2$— | —$CH_2CH_2$-cyclo-$C_6H_{11}$ | —$CO_2H$ |
| 701 | p-$[H_2N(CH_2)_8]C_6H_4CH_2$— | —$CH_2$-cyclo-$C_5H_9$ | —$CO_2H$ |
| 702 | p-$[H_2N(CH_2)_8]C_6H_4CH_2$— | —$CH_2CH_2$-cyclo-$C_5H_9$ | —$CO_2H$ |
| 703 | p-$[H_2N(CH_2)_8]C_6H_4CH_2$— | —$CH_2$-2-naphthyl | —$CO_2H$ |
| 704 | p-$[H_2N(CH_2)_8]C_6H_4CH_2$— | —H | —$PO_3H_2$ |
| 705 | p-$[H_2N(CH_2)_8]C_6H_4CH_2$— | —$CH_3$ | —$PO_3H_2$ |
| 706 | p-$[H_2N(CH_2)_8]C_6H_4CH_2$— | —$CH_2CH_3$ | —$PO_3H_2$ |
| 707 | p-$[H_2N(CH_2)_8]C_6H_4CH_2$— | —$CH_2CH_2CH_3$ | —$PO_3H_2$ |
| 708 | p-$[H_2N(CH_2)_8]C_6H_4CH_2$— | —$CH_2CH_2CH_2CH_3$ | —$PO_3H_2$ |
| 709 | p-$[H_2N(CH_2)_8]C_6H_4CH_2$— | —$CH_2CH_2CH_2CH_2CH_3$ | —$PO_3H_2$ |
| 710 | p-$[H_2N(CH_2)_8]C_6H_4CH_2$— | —$CH_2CH_2CH_2CH_2CH_2CH_3$ | —$PO_3H_2$ |
| 711 | p-$[H_2N(CH_2)_8]C_6H_4CH_2$— | —$CH(CH_3)_2$ | —$PO_3H_2$ |
| 712 | p-$[H_2N(CH_2)_8]C_6H_4CH_2$— | —$CH_2CH(CH_3)_2$ | —$PO_3H_2$ |
| 713 | p-$[H_2N(CH_2)_8]C_6H_4CH_2$— | —$CH_2CH_2CH(CH_3)_2$ | —$PO_3H_2$ |
| 714 | p-$[H_2N(CH_2)_8]C_6H_4CH_2$— | -cyclo-$C_3H_5$ | —$PO_3H_2$ |
| 715 | p-$[H_2N(CH_2)_8]C_6H_4CH_2$— | -cyclo-$C_4H_7$ | —$PO_3H_2$ |
| 716 | p-$[H_2N(CH_2)_8]C_6H_4CH_2$— | -cyclo-$C_5H_9$ | —$PO_3H_2$ |
| 717 | p-$[H_2N(CH_2)_8]C_6H_4CH_2$— | -cyclo-$C_6H_{11}$ | —$PO_3H_2$ |

TABLE I-continued

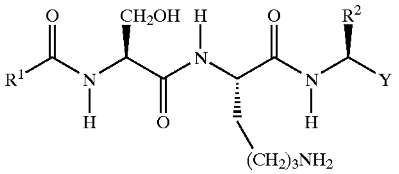

| Ex. No. | $R^1$ | $R^2$ | Y |
|---|---|---|---|
| 718 | p-$[H_2N(CH_2)_8]C_6H_4CH_2$— | -cyclo-$C_7H_{13}$ | —$PO_3H_2$ |
| 719 | p-$[H_2N(CH_2)_8]C_6H_4CH_2$— | -cyclo-$C_8H_{15}$ | —$PO_3H_2$ |
| 720 | p-$[H_2N(CH_2)_8]C_6H_4CH_2$— | —$CH(CH_3)(CH_2CH_3)$ | —$PO_3H_2$ |
| 721 | p-$[H_2N(CH_2)_8]C_6H_4CH_2$— | —$CH(CH_2CH_3)_2$ | —$PO_3H_2$ |
| 722 | p-$[H_2N(CH_2)_8]C_6H_4CH_2$— | —$CH(CH_3)(CH_2CH_2CH_3)$ | —$PO_3H_2$ |
| 723 | p-$[H_2N(CH_2)_8]C_6H_4CH_2$— | —$C(CH_3)_3$ | —$PO_3H_2$ |
| 724 | p-$[H_2N(CH_2)_8]C_6H_4CH_2$— | $HC{\equiv}CCH_2$— | —$PO_3H_2$ |
| 725 | p-$[H_2N(CH_2)_8]C_6H_4CH_2$— | $H_2C{=}CH$— | —$PO_3H_2$ |
| 726 | p-$[H_2N(CH_2)_8]C_6H_4CH_2$— | $H_2C{=}CHCH_2$— | —$PO_3H_2$ |
| 727 | p-$[H_2N(CH_2)_8]C_6H_4CH_2$— | —$CH_2F$ | —$PO_3H_2$ |
| 728 | p-$[H_2N(CH_2)_8]C_6H_4CH_2$— | —$CH_2C_6H_5$ | —$PO_3H_2$ |
| 729 | p-$[H_2N(CH_2)_8]C_6H_4CH_2$— | —$CH_2C_6H_4$-p-$OCH_3$ | —$PO_3H_2$ |
| 730 | p-$[H_2N(CH_2)_8]C_6H_4CH_2$— | —$CH_2C_6H_4$-p-$CH_3$ | —$PO_3H_2$ |
| 731 | p-$[H_2N(CH_2)_8]C_6H_4CH_2$— | —$CH_2C_6H_4$-p-F | —$PO_3H_2$ |
| 732 | p-$[H_2N(CH_2)_8]C_6H_4CH_2$— | —$CH_2CH_2C_6H_5$ | —$PO_3H_2$ |
| 733 | p-$[H_2N(CH_2)_8]C_6H_4CH_2$— | —$CH_2$-cyclo-$C_6H_{11}$ | —$PO_3H_2$ |
| 734 | p-$[H_2N(CH_2)_8]C_6H_4CH_2$— | —$CH_2$-cyclo-$C_6H_{10}$-4-F | —$PO_3H_2$ |
| 735 | p-$[H_2N(CH_2)_8]C_6H_4CH_2$— | —$CH_2$-cyclo-$C_6H_{10}$-4-$CH_3$ | —$PO_3H_2$ |
| 736 | p-$[H_2N(CH_2)_8]C_6H_4CH_2$— | —$CH_2$-cyclo-$C_6H_{10}$-4-$OCH_3$ | —$PO_3H_2$ |
| 737 | p-$[H_2N(CH_2)_8]C_6H_4CH_2$— | —$CH_2CH_2$-cyclo-$C_6H_{11}$ | —$PO_3H_2$ |
| 738 | p-$[H_2N(CH_2)_8]C_6H_4CH_2$— | —$CH_2$-cyclo-$C_5H_9$ | —$PO_3H_2$ |
| 739 | p-$[H_2N(CH_2)_8]C_6H_4CH_2$— | —$CH_2CH_2$-cyclo-$C_5H_9$ | —$PO_3H_2$ |
| 740 | p-$[H_2N(CH_2)_8]C_6H_4CH_2$— | —$CH_2$-2-naphthyl | —$PO_3H_2$ |
| 741 | p-$[H_2N(CH_2)_8]C_6H_4CH_2$— | —H | -5-Tet |
| 742 | p-$[H_2N(CH_2)_8]C_6H_4CH_2$— | —$CH_3$ | -5-Tet |
| 743 | p-$[H_2N(CH_2)_8]C_6H_4CH_2$— | —$CH_2CH_3$ | -5-Tet |
| 744 | p-$[H_2N(CH_2)_8]C_6H_4CH_2$— | —$CH_2CH_2CH_3$ | -5-Tet |
| 745 | p-$[H_2N(CH_2)_8]C_6H_4CH_2$— | —$CH_2CH_2CH_2CH_3$ | -5-Tet |
| 746 | p-$[H_2N(CH_2)_8]C_6H_4CH_2$— | —$CH_2CH_2CH_2CH_2CH_3$ | -5-Tet |
| 747 | p-$[H_2N(CH_2)_8]C_6H_4CH_2$— | —$CH_2CH_2CH_2CH_2CH_2CH_3$ | -5-Tet |
| 748 | p-$[H_2N(CH_2)_8]C_6H_4CH_2$— | —$CH(CH_3)_2$ | -5-Tet |
| 749 | p-$[H_2N(CH_2)_8]C_6H_4CH_2$— | —$CH_2CH(CH_3)_2$ | -5-Tet |
| 750 | p-$[H_2N(CH_2)_8]C_6H_4CH_2$— | —$CH_2CH_2CH(CH_3)_2$ | -5-Tet |
| 751 | p-$[H_2N(CH_2)_8]C_6H_4CH_2$— | -cyclo-$C_3H_5$ | -5-Tet |
| 752 | p-$[H_2N(CH_2)_8]C_6H_4CH_2$— | -cyclo-$C_4H_7$ | -5-Tet |
| 753 | p-$[H_2N(CH_2)_8]C_6H_4CH_2$— | -cyclo-$C_5H_9$ | -5-Tet |
| 754 | p-$[H_2N(CH_2)_8]C_6H_4CH_2$— | -cyclo-$C_6H_{11}$ | -5-Tet |
| 755 | p-$[H_2N(CH_2)_8]C_6H_4CH_2$— | -cyclo-$C_7H_{13}$ | -5-Tet |
| 756 | p-$[H_2N(CH_2)_8]C_6H_4CH_2$— | -cyclo-$C_8H_{15}$ | -5-Tet |
| 757 | p-$[H_2N(CH_2)_8]C_6H_4CH_2$— | —$CH(CH_3)(CH_2CH_3)$ | -5-Tet |
| 758 | p-$[H_2N(CH_2)_8]C_6H_4CH_2$— | —$CH(CH_2CH_3)_2$ | -5-Tet |
| 759 | p-$[H_2N(CH_2)_8]C_6H_4CH_2$— | —$CH(CH_3)(CH_2CH_2CH_3)$ | -5-Tet |
| 760 | p-$[H_2N(CH_2)_8]C_6H_4CH_2$— | —$C(CH_3)_3$ | -5-Tet |
| 761 | p-$[H_2N(CH_2)_8]C_6H_4CH_2$— | $HC{\equiv}CCH_2$— | -5-Tet |
| 762 | p-$[H_2N(CH_2)_8]C_6H_4CH_2$— | $H_2C{=}CH$— | -5-Tet |
| 763 | p-$[H_2N(CH_2)_8]C_6H_4CH_2$— | $H_2C{=}CHCH_2$— | -5-Tet |
| 764 | p-$[H_2N(CH_2)_8]C_6H_4CH_2$— | —$CH_2F$ | -5-Tet |
| 765 | p-$[H_2N(CH_2)_8]C_6H_4CH_2$— | —$CH_2C_6H_5$ | -5-Tet |
| 766 | p-$[H_2N(CH_2)_8]C_6H_4CH_2$— | —$CH_2C_6H_4$-p-$OCH_3$ | -5-Tet |
| 767 | p-$[H_2N(CH_2)_8]C_6H_4CH_2$— | —$CH_2C_6H_4$-p-$CH_3$ | -5-Tet |
| 768 | p-$[H_2N(CH_2)_8]C_6H_4CH_2$— | —$CH_2C_6H_4$-p-F | -5-Tet |
| 769 | p-$[H_2N(CH_2)_8]C_6H_4CH_2$— | —$CH_2CH_2C_6H_5$ | -5-Tet |
| 770 | p-$[H_2N(CH_2)_8]C_6H_4CH_2$— | —$CH_2$-cyclo-$C_6H_{11}$ | -5-Tet |
| 771 | p-$[H_2N(CH_2)_8]C_6H_4CH_2$— | —$CH_2$-cyclo-$C_6H_{10}$-4-F | -5-Tet |
| 772 | p-$[H_2N(CH_2)_8]C_6H_4CH_2$— | —$CH_2$-cyclo-$C_6H_{10}$-4-$CH_3$ | -5-Tet |
| 773 | p-$[H_2N(CH_2)_8]C_6H_4CH_2$— | —$CH_2$-cyclo-$C_6H_{10}$-4-$OCH_3$ | -5-Tet |
| 774 | p-$[H_2N(CH_2)_8]C_6H_4CH_2$— | —$CH_2CH_2$-cyclo-$C_6H_{11}$ | -5-Tet |
| 775 | p-$[H_2N(CH_2)_8]C_6H_4CH_2$— | —$CH_2$-cyclo-$C_5H_9$ | -5-Tet |
| 776 | p-$[H_2N(CH_2)_8]C_6H_4CH_2$— | —$CH_2CH_2$-cyclo-$C_5H_9$ | -5-Tet |
| 777 | p-$[H_2N(CH_2)_8]C_6H_4CH_2$— | —$CH_2$-2-naphthyl | -5-Tet |
| 778 | p-$[H_2N(CH_2)_9]C_6H_4CH_2$— | —H | —$CO_2H$ |
| 779 | p-$[H_2N(CH_2)_9]C_6H_4CH_2$— | —$CH_3$ | —$CO_2H$ |
| 780 | p-$[H_2N(CH_2)_9]C_6H_4CH_2$— | —$CH_2CH_3$ | —$CO_2H$ |
| 781 | p-$[H_2N(CH_2)_9]C_6H_4CH_2$— | —$CH_2CH_2CH_3$ | —$CO_2H$ |
| 782 | p-$[H_2N(CH_2)_9]C_6H_4CH_2$— | —$CH_2CH_2CH_2CH_3$ | —$CO_2H$ |
| 783 | p-$[H_2N(CH_2)_9]C_6H_4CH_2$— | —$CH_2CH_2CH_2CH_2CH_3$ | —$CO_2H$ |

TABLE I-continued

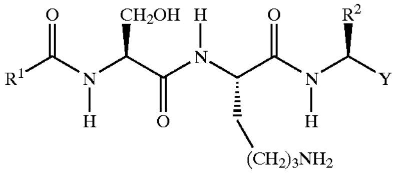

| Ex. No. | $R^1$ | $R^2$ | Y |
|---|---|---|---|
| 784 | p-[$H_2N(CH_2)_9$]$C_6H_4CH_2$— | —$CH_2CH_2CH_2CH_2CH_2CH_3$ | —$CO_2H$ |
| 785 | p-[$H_2N(CH_2)_9$]$C_6H_4CH_2$— | —$CH(CH_3)_2$ | —$CO_2H$ |
| 786 | p-[$H_2N(CH_2)_9$]$C_6H_4CH_2$— | —$CH_2CH(CH_3)_2$ | —$CO_2H$ |
| 787 | p-[$H_2N(CH_2)_9$]$C_6H_4CH_2$— | —$CH_2CH_2CH(CH_3)_2$ | —$CO_2H$ |
| 788 | p-[$H_2N(CH_2)_9$]$C_6H_4CH_2$— | -cyclo-$C_3H_5$ | —$CO_2H$ |
| 789 | p-[$H_2N(CH_2)_9$]$C_6H_4CH_2$— | -cyclo-$C_4H_7$ | —$CO_2H$ |
| 790 | p-[$H_2N(CH_2)_9$]$C_6H_4CH_2$— | -cyclo-$C_5H_9$ | —$CO_2H$ |
| 791 | p-[$H_2N(CH_2)_9$]$C_6H_4CH_2$— | -cyclo-$C_6H_{11}$ | —$CO_2H$ |
| 792 | p-[$H_2N(CH_2)_9$]$C_6H_4CH_2$— | -cyclo-$C_7H_{13}$ | —$CO_2H$ |
| 793 | p-[$H_2N(CH_2)_9$]$C_6H_4CH_2$— | -cyclo-$C_8H_{15}$ | —$CO_2H$ |
| 794 | p-[$H_2N(CH_2)_9$]$C_6H_4CH_2$— | —$CH(CH_3)(CH_2CH_3)$ | —$CO_2H$ |
| 795 | p-[$H_2N(CH_2)_9$]$C_6H_4CH_2$— | —$CH(CH_2CH_3)_2$ | —$CO_2H$ |
| 796 | p-[$H_2N(CH_2)_9$]$C_6H_4CH_2$— | —$CH(CH_3)(CH_2CH_2CH_3)$ | —$CO_2H$ |
| 797 | p-[$H_2N(CH_2)_9$]$C_6H_4CH_2$— | —$C(CH_3)_3$ | —$CO_2H$ |
| 798 | p-[$H_2N(CH_2)_9$]$C_6H_4CH_2$— | $HC{\equiv}CCH_2$— | —$CO_2H$ |
| 799 | p-[$H_2N(CH_2)_9$]$C_6H_4CH_2$— | $H_2C{=}CH$— | —$CO_2H$ |
| 800 | p-[$H_2N(CH_2)_9$]$C_6H_4CH_2$— | $H_2C{=}CHCH_2$— | —$CO_2H$ |
| 801 | p-[$H_2N(CH_2)_9$]$C_6H_4CH_2$— | —$CH_2F$ | —$CO_2H$ |
| 802 | p-[$H_2N(CH_2)_9$]$C_6H_4CH_2$— | —$CH_2C_6H_5$ | —$CO_2H$ |
| 803 | p-[$H_2N(CH_2)_9$]$C_6H_4CH_2$— | —$CH_2C_6H_4$-p-$OCH_3$ | —$CO_2H$ |
| 804 | p-[$H_2N(CH_2)_9$]$C_6H_4CH_2$— | —$CH_2C_6H_4$-p-$CH_3$ | —$CO_2H$ |
| 805 | p-[$H_2N(CH_2)_9$]$C_6H_4CH_2$— | —$CH_2C_6H_4$-p-F | —$CO_2H$ |
| 806 | p-[$H_2N(CH_2)_9$]$C_6H_4CH_2$— | —$CH_2CH_2C_6H_5$ | —$CO_2H$ |
| 807 | p-[$H_2N(CH_2)_9$]$C_6H_4CH_2$— | —$CH_2$-cyclo-$C_6H_{11}$ | —$CO_2H$ |
| 808 | p-[$H_2N(CH_2)_9$]$C_6H_4CH_2$— | —$CH_2$-cyclo-$C_6H_{10}$-4-F | —$CO_2H$ |
| 809 | p-[$H_2N(CH_2)_9$]$C_6H_4CH_2$— | —$CH_2$-cyclo-$C_6H_{10}$-4-$CH_3$ | —$CO_2H$ |
| 810 | p-[$H_2N(CH_2)_9$]$C_6H_4CH_2$— | —$CH_2$-cyclo-$C_6H_{10}$-4-$OCH_3$ | —$CO_2H$ |
| 811 | p-[$H_2N(CH_2)_9$]$C_6H_4CH_2$— | —$CH_2CH_2$-cyclo-$C_6H_{11}$ | —$CO_2H$ |
| 812 | p-[$H_2N(CH_2)_9$]$C_6H_4CH_2$— | —$CH_2$-cyclo-$C_5H_9$ | —$CO_2H$ |
| 813 | p-[$H_2N(CH_2)_9$]$C_6H_4CH_2$— | —$CH_2CH_2$-cyclo-$C_5H_9$ | —$CO_2H$ |
| 814 | p-[$H_2N(CH_2)_9$]$C_6H_4CH_2$— | —$CH_2$-2-naphthyl | —$CO_2H$ |
| 815 | p-[$H_2N(CH_2)_9$]$C_6H_4CH_2$— | —H | —$PO_3H_2$ |
| 816 | p-[$H_2N(CH_2)_9$]$C_6H_4CH_2$— | —$CH_3$ | —$PO_3H_2$ |
| 817 | p-[$H_2N(CH_2)_9$]$C_6H_4CH_2$— | —$CH_2CH_3$ | —$PO_3H_2$ |
| 818 | p-[$H_2N(CH_2)_9$]$C_6H_4CH_2$— | —$CH_2CH_2CH_3$ | —$PO_3H_2$ |
| 819 | p-[$H_2N(CH_2)_9$]$C_6H_4CH_2$— | —$CH_2CH_2CH_2CH_3$ | —$PO_3H_2$ |
| 820 | p-[$H_2N(CH_2)_9$]$C_6H_4CH_2$— | —$CH_2CH_2CH_2CH_2CH_3$ | —$PO_3H_2$ |
| 821 | p-[$H_2N(CH_2)_9$]$C_6H_4CH_2$— | —$CH_2CH_2CH_2CH_2CH_2CH_3$ | —$PO_3H_2$ |
| 822 | p-[$H_2N(CH_2)_9$]$C_6H_4CH_2$— | —$CH(CH_3)_2$ | —$PO_3H_2$ |
| 823 | p-[$H_2N(CH_2)_9$]$C_6H_4CH_2$— | —$CH_2CH(CH_3)_2$ | —$PO_3H_2$ |
| 824 | p-[$H_2N(CH_2)_9$]$C_6H_4CH_2$— | —$CH_2CH_2CH(CH_3)_2$ | —$PO_3H_2$ |
| 825 | p-[$H_2N(CH_2)_9$]$C_6H_4CH_2$— | -cyclo-$C_3H_5$ | —$PO_3H_2$ |
| 826 | p-[$H_2N(CH_2)_9$]$C_6H_4CH_2$— | -cyclo-$C_4H_7$ | —$PO_3H_2$ |
| 827 | p-[$H_2N(CH_2)_9$]$C_6H_4CH_2$— | -cyclo-$C_5H_9$ | —$PO_3H_2$ |
| 828 | p-[$H_2N(CH_2)_9$]$C_6H_4CH_2$— | -cyclo-$C_6H_{11}$ | —$PO_3H_2$ |
| 829 | p-[$H_2N(CH_2)_9$]$C_6H_4CH_2$— | -cyclo-$C_7H_{13}$ | —$PO_3H_2$ |
| 830 | p-[$H_2N(CH_2)_9$]$C_6H_4CH_2$— | -cyclo-$C_8H_{15}$ | —$PO_3H_2$ |
| 831 | p-[$H_2N(CH_2)_9$]$C_6H_4CH_2$— | —$CH(CH_3)(CH_2CH_3)$ | —$PO_3H_2$ |
| 832 | p-[$H_2N(CH_2)_9$]$C_6H_4CH_2$— | —$CH(CH_2CH_3)_2$ | —$PO_3H_2$ |
| 833 | p-[$H_2N(CH_2)_9$]$C_6H_4CH_2$— | —$CH(CH_3)(CH_2CH_2CH_3)$ | —$PO_3H_2$ |
| 834 | p-[$H_2N(CH_2)_9$]$C_6H_4CH_2$— | —$C(CH_3)_3$ | —$PO_3H_2$ |
| 835 | p-[$H_2N(CH_2)_9$]$C_6H_4CH_2$— | $HC{\equiv}CCH_2$— | —$PO_3H_2$ |
| 836 | p-[$H_2N(CH_2)_9$]$C_6H_4CH_2$— | $H_2C{=}CH$— | —$PO_3H_2$ |
| 837 | p-[$H_2N(CH_2)_9$]$C_6H_4CH_2$— | $H_2C{=}CHCH_2$— | —$PO_3H_2$ |
| 838 | p-[$H_2N(CH_2)_9$]$C_6H_4CH_2$— | —$CH_2F$ | —$PO_3H_2$ |
| 839 | p-[$H_2N(CH_2)_9$]$C_6H_4CH_2$— | —$CH_2C_6H_5$ | —$PO_3H_2$ |
| 840 | p-[$H_2N(CH_2)_9$]$C_6H_4CH_2$— | —$CH_2C_6H_4$-p-$OCH_3$ | —$PO_3H_2$ |
| 841 | p-[$H_2N(CH_2)_9$]$C_6H_4CH_2$— | —$CH_2C_6H_4$-p-$CH_3$ | —$PO_3H_2$ |
| 842 | p-[$H_2N(CH_2)_9$]$C_6H_4CH_2$— | —$CH_2C_6H_4$-p-F | —$PO_3H_2$ |
| 843 | p-[$H_2N(CH_2)_9$]$C_6H_4CH_2$— | —$CH_2CH_2C_6H_5$ | —$PO_3H_2$ |
| 844 | p-[$H_2N(CH_2)_9$]$C_6H_4CH_2$— | —$CH_2$-cyclo-$C_6H_{11}$ | —$PO_3H_2$ |
| 845 | p-[$H_2N(CH_2)_9$]$C_6H_4CH_2$— | —$CH_2$-cyclo-$C_6H_{10}$-4-F | —$PO_3H_2$ |
| 846 | p-[$H_2N(CH_2)_9$]$C_6H_4CH_2$— | —$CH_2$-cyclo-$C_6H_{10}$-4-$CH_3$ | —$PO_3H_2$ |
| 847 | p-[$H_2N(CH_2)_9$]$C_6H_4CH_2$— | —$CH_2$-cyclo-$C_6H_{10}$-4-$OCH_3$ | —$PO_3H_2$ |
| 848 | p-[$H_2N(CH_2)_9$]$C_6H_4CH_2$— | —$CH_2CH_2$-cyclo-$C_6H_{11}$ | —$PO_3H_2$ |
| 849 | p-[$H_2N(CH_2)_9$]$C_6H_4CH_2$— | —$CH_2$-cyclo-$C_5H_9$ | —$PO_3H_2$ |

TABLE I-continued

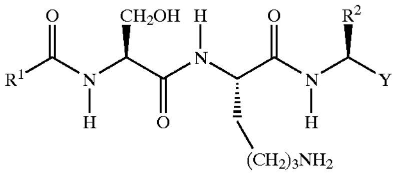

| Ex. No. | $R^1$ | $R^2$ | Y |
|---|---|---|---|
| 850 | p-$[H_2N(CH_2)_9]C_6H_4CH_2$— | —$CH_2CH_2$-cyclo-$C_5H_9$ | —$PO_3H_2$ |
| 851 | p-$[H_2N(CH_2)_9]C_6H_4CH_2$— | —$CH_2$-2-naphthyl | —$PO_3H_2$ |
| 852 | p-$[H_2N(CH_2)_9]C_6H_4CH_2$— | —H | -5-Tet |
| 853 | p-$[H_2N(CH_2)_9]C_6H_4CH_2$— | —$CH_3$ | -5-Tet |
| 854 | p-$[H_2N(CH_2)_9]C_6H_4CH_2$— | —$CH_2CH_3$ | -5-Tet |
| 855 | p-$[H_2N(CH_2)_9]C_6H_4CH_2$— | —$CH_2CH_2CH_3$ | -5-Tet |
| 856 | p-$[H_2N(CH_2)_9]C_6H_4CH_2$— | —$CH_2CH_2CH_2CH_3$ | -5-Tet |
| 857 | p-$[H_2N(CH_2)_9]C_6H_4CH_2$— | —$CH_2CH_2CH_2CH_2CH_3$ | -5-Tet |
| 858 | p-$[H_2N(CH_2)_9]C_6H_4CH_2$— | —$CH_2CH_2CH_2CH_2CH_2CH_3$ | -5-Tet |
| 859 | p-$[H_2N(CH_2)_9]C_6H_4CH_2$— | —$CH(CH_3)_2$ | -5-Tet |
| 860 | p-$[H_2N(CH_2)_9]C_6H_4CH_2$— | —$CH_2CH(CH_3)_2$ | -5-Tet |
| 861 | p-$[H_2N(CH_2)_9]C_6H_4CH_2$— | —$CH_2CH_2CH(CH_3)_2$ | -5-Tet |
| 862 | p-$[H_2N(CH_2)_9]C_6H_4CH_2$— | -cyclo-$C_3H_5$ | -5-Tet |
| 863 | p-$[H_2N(CH_2)_9]C_6H_4CH_2$— | -cyclo-$C_4H_7$ | -5-Tet |
| 864 | p-$[H_2N(CH_2)_9]C_6H_4CH_2$— | -cyclo-$C_5H_9$ | -5-Tet |
| 865 | p-$[H_2N(CH_2)_9]C_6H_4CH_2$— | -cyclo-$C_6H_{11}$ | -5-Tet |
| 866 | p-$[H_2N(CH_2)_9]C_6H_4CH_2$— | -cyclo-$C_7H_{13}$ | -5-Tet |
| 867 | p-$[H_2N(CH_2)_9]C_6H_4CH_2$— | -cyclo-$C_8H_{15}$ | -5-Tet |
| 868 | p-$[H_2N(CH_2)_9]C_6H_4CH_2$— | —$CH(CH_3)(CH_2CH_3)$ | -5-Tet |
| 869 | p-$[H_2N(CH_2)_9]C_6H_4CH_2$— | —$CH(CH_2CH_3)_2$ | -5-Tet |
| 870 | p-$[H_2N(CH_2)_9]C_6H_4CH_2$— | —$CH(CH_3)(CH_2CH_2CH_3)$ | -5-Tet |
| 871 | p-$[H_2N(CH_2)_9]C_6H_4CH_2$— | —$C(CH_3)_3$ | -5-Tet |
| 872 | p-$[H_2N(CH_2)_9]C_6H_4CH_2$— | $HC{\equiv}CCH_2$— | -5-Tet |
| 873 | p-$[H_2N(CH_2)_9]C_6H_4CH_2$— | $H_2C{=}CH$— | -5-Tet |
| 874 | p-$[H_2N(CH_2)_9]C_6H_4CH_2$— | $H_2C{=}CHCH_2$— | -5-Tet |
| 875 | p-$[H_2N(CH_2)_9]C_6H_4CH_2$— | —$CH_2F$ | -5-Tet |
| 876 | p-$[H_2N(CH_2)_9]C_6H_4CH_2$— | —$CH_2C_6H_5$ | -5-Tet |
| 877 | p-$[H_2N(CH_2)_9]C_6H_4CH_2$— | —$CH_2C_6H_4$-p-$OCH_3$ | -5-Tet |
| 878 | p-$[H_2N(CH_2)_9]C_6H_4CH_2$— | —$CH_2C_6H_4$-p-$CH_3$ | -5-Tet |
| 879 | p-$[H_2N(CH_2)_9]C_6H_4CH_2$— | —$CH_2C_6H_4$-p-F | -5-Tet |
| 880 | p-$[H_2N(CH_2)_9]C_6H_4CH_2$— | —$CH_2CH_2C_6H_5$ | -5-Tet |
| 881 | p-$[H_2N(CH_2)_9]C_6H_4CH_2$— | —$CH_2$-cyclo-$C_6H_{11}$ | -5-Tet |
| 882 | p-$[H_2N(CH_2)_9]C_6H_4CH_2$— | —$CH_2$-cyclo-$C_6H_{10}$-4-F | -5-Tet |
| 883 | p-$[H_2N(CH_2)_9]C_6H_4CH_2$— | —$CH_2$-cyclo-$C_6H_{10}$-4-$CH_3$ | -5-Tet |
| 884 | p-$[H_2N(CH_2)_9]C_6H_4CH_2$— | —$CH_2$-cyclo-$C_6H_{10}$-4-$OCH_3$ | -5-Tet |
| 885 | p-$[H_2N(CH_2)_9]C_6H_4CH_2$— | —$CH_2CH_2$-cyclo-$C_6H_{11}$ | -5-Tet |
| 886 | p-$[H_2N(CH_2)_9]C_6H_4CH_2$— | —$CH_2$-cyclo-$C_5H_9$ | -5-Tet |
| 887 | p-$[H_2N(CH_2)_9]C_6H_4CH_2$— | —$CH_2CH_2$-cyclo-$C_5H_9$ | -5-Tet |
| 888 | p-$[H_2N(CH_2)_9]C_6H_4CH_2$— | —$CH_2$-2-naphthyl | -5-Tet |
| 889 | p-$[H_2N(CH_2)_{10}]C_6H_4CH_2$— | —H | —$CO_2H$ |
| 890 | p-$[H_2N(CH_2)_{10}]C_6H_4CH_2$— | —$CH_3$ | —$CO_2H$ |
| 891 | p-$[H_2N(CH_2)_{10}]C_6H_4CH_2$— | —$CH_2CH_3$ | —$CO_2H$ |
| 892 | p-$[H_2N(CH_2)_{10}]C_6H_4CH_2$— | —$CH_2CH_2CH_3$ | —$CO_2H$ |
| 893 | p-$[H_2N(CH_2)_{10}]C_6H_4CH_2$— | —$CH_2CH_2CH_2CH_3$ | —$CO_2H$ |
| 894 | p-$[H_2N(CH_2)_{10}]C_6H_4CH_2$— | —$CH_2CH_2CH_2CH_2CH_3$ | —$CO_2H$ |
| 895 | p-$[H_2N(CH_2)_{10}]C_6H_4CH_2$— | —$CH_2CH_2CH_2CH_2CH_2CH_3$ | —$CO_2H$ |
| 896 | p-$[H_2N(CH_2)_{10}]C_6H_4CH_2$— | —$CH(CH_3)_2$ | —$CO_2H$ |
| 897 | p-$[H_2N(CH_2)_{10}]C_6H_4CH_2$— | —$CH_2CH(CH_3)_2$ | —$CO_2H$ |
| 898 | p-$[H_2N(CH_2)_{10}]C_6H_4CH_2$— | —$CH_2CH_2CH(CH_3)_2$ | —$CO_2H$ |
| 899 | p-$[H_2N(CH_2)_{10}]C_6H_4CH_2$— | -cyclo-$C_3H_5$ | —$CO_2H$ |
| 900 | p-$[H_2N(CH_2)_{10}]C_6H_4CH_2$— | -cyclo-$C_4H_7$ | —$CO_2H$ |
| 901 | p-$[H_2N(CH_2)_{10}]C_6H_4CH_2$— | -cyclo-$C_5H_9$ | —$CO_2H$ |
| 902 | p-$[H_2N(CH_2)_{10}]C_6H_4CH_2$— | -cyclo-$C_6H_{11}$ | —$CO_2H$ |
| 903 | p-$[H_2N(CH_2)_{10}]C_6H_4CH_2$— | -cyclo-$C_7H_{13}$ | —$CO_2H$ |
| 904 | p-$[H_2N(CH_2)_{10}]C_6H_4CH_2$— | -cyclo-$C_8H_{15}$ | —$CO_2H$ |
| 905 | p-$[H_2N(CH_2)_{10}]C_6H_4CH_2$— | —$CH(CH_3)(CH_2CH_3)$ | —$CO_2H$ |
| 906 | p-$[H_2N(CH_2)_{10}]C_6H_4CH_2$— | —$CH(CH_2CH_3)_2$ | —$CO_2H$ |
| 907 | p-$[H_2N(CH_2)_{10}]C_6H_4CH_2$— | —$CH(CH_3)(CH_2CH_2CH_3)$ | —$CO_2H$ |
| 908 | p-$[H_2N(CH_2)_{10}]C_6H_4CH_2$— | —$C(CH_3)_3$ | —$CO_2H$ |
| 909 | p-$[H_2N(CH_2)_{10}]C_6H_4CH_2$— | $HC{\equiv}CCH_2$— | —$CO_2H$ |
| 910 | p-$[H_2N(CH_2)_{10}]C_6H_4CH_2$— | $H_2C{=}CH$— | —$CO_2H$ |
| 911 | p-$[H_2N(CH_2)_{10}]C_6H_4CH_2$— | $H_2C{=}CHCH_2$— | —$CO_2H$ |
| 912 | p-$[H_2N(CH_2)_{10}]C_6H_4CH_2$— | —$CH_2F$ | —$CO_2H$ |
| 913 | p-$[H_2N(CH_2)_{10}]C_6H_4CH_2$— | —$CH_2C_6H_5$ | —$CO_2H$ |
| 914 | p-$[H_2N(CH_2)_{10}]C_6H_4CH_2$— | —$CH_2C_6H_4$-p-$OCH_3$ | —$CO_2H$ |
| 915 | p-$[H_2N(CH_2)_{10}]C_6H_4CH_2$— | —$CH_2C_6H_4$-p-$CH_3$ | —$CO_2H$ |

TABLE I-continued

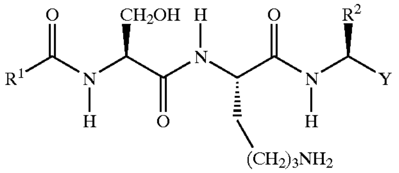

| Ex. No. | $R^1$ | $R^2$ | Y |
|---|---|---|---|
| 916 | p-$[H_2N(CH_2)_{10}]C_6H_4CH_2$— | —$CH_2C_6H_4$-p-F | —$CO_2H$ |
| 917 | p-$[H_2N(CH_2)_{10}]C_6H_4CH_2$— | —$CH_2CH_2C_6H_5$ | —$CO_2H$ |
| 918 | p-$[H_2N(CH_2)_{10}]C_6H_4CH_2$— | —$CH_2$-cyclo-$C_6H_{11}$ | —$CO_2H$ |
| 919 | p-$[H_2N(CH_2)_{10}]C_6H_4CH_2$— | —$CH_2$-cyclo-$C_6H_{10}$-4-F | —$CO_2H$ |
| 920 | p-$[H_2N(CH_2)_{10}]C_6H_4CH_2$— | —$CH_2$-cyclo-$C_6H_{10}$-4-$CH_3$ | —$CO_2H$ |
| 921 | p-$[H_2N(CH_2)_{10}]C_6H_4CH_2$— | —$CH_2$-cyclo-$C_6H_{10}$-4-$OCH_3$ | —$CO_2H$ |
| 922 | p-$[H_2N(CH_2)_{10}]C_6H_4CH_2$— | —$CH_2CH_2$-cyclo-$C_6H_{11}$ | —$CO_2H$ |
| 923 | p-$[H_2N(CH_2)_{10}]C_6H_4CH_2$— | —$CH_2$-cyclo-$C_5H_9$ | —$CO_2H$ |
| 924 | p-$[H_2N(CH_2)_{10}]C_6H_4CH_2$— | —$CH_2CH_2$-cyclo-$C_5H_9$ | —$CO_2H$ |
| 925 | p-$[H_2N(CH_2)_{10}]C_6H_4CH_2$— | —$CH_2$-2-naphthyl | —$CO_2H$ |
| 926 | p-$[H_2N(CH_2)_{10}]C_6H_4CH_2$— | —H | —$PO_3H_2$ |
| 927 | p-$[H_2N(CH_2)_{10}]C_6H_4CH_2$— | —$CH_3$ | —$PO_3H_2$ |
| 928 | p-$[H_2N(CH_2)_{10}]C_6H_4CH_2$— | —$CH_2CH_3$ | —$PO_3H_2$ |
| 929 | p-$[H_2N(CH_2)_{10}]C_6H_4CH_2$— | —$CH_2CH_2CH_3$ | —$PO_3H_2$ |
| 930 | p-$[H_2N(CH_2)_{10}]C_6H_4CH_2$— | —$CH_2CH_2CH_2CH_3$ | —$PO_3H_2$ |
| 931 | p-$[H_2N(CH_2)_{10}]C_6H_4CH_2$— | —$CH_2CH_2CH_2CH_2CH_3$ | —$PO_3H_2$ |
| 932 | p-$[H_2N(CH_2)_{10}]C_6H_4CH_2$— | —$CH_2CH_2CH_2CH_2CH_2CH_3$ | —$PO_3H_2$ |
| 933 | p-$[H_2N(CH_2)_{10}]C_6H_4CH_2$— | —$CH(CH_3)_2$ | —$PO_3H_2$ |
| 934 | p-$[H_2N(CH_2)_{10}]C_6H_4CH_2$— | —$CH_2CH(CH_3)_2$ | —$PO_3H_2$ |
| 935 | p-$[H_2N(CH_2)_{10}]C_6H_4CH_2$— | —$CH_2CH_2CH(CH_3)_2$ | —$PO_3H_2$ |
| 936 | p-$[H_2N(CH_2)_{10}]C_6H_4CH_2$— | -cyclo-$C_3H_5$ | —$PO_3H_2$ |
| 937 | p-$[H_2N(CH_2)_{10}]C_6H_4CH_2$— | -cyclo-$C_4H_7$ | —$PO_3H_2$ |
| 938 | p-$[H_2N(CH_2)_{10}]C_6H_4CH_2$— | -cyclo-$C_5H_9$ | —$PO_3H_2$ |
| 939 | p-$[H_2N(CH_2)_{10}]C_6H_4CH_2$— | -cyclo-$C_6H_{11}$ | —$PO_3H_2$ |
| 940 | p-$[H_2N(CH_2)_{10}]C_6H_4CH_2$— | -cyclo-$C_7H_{13}$ | —$PO_3H_2$ |
| 941 | p-$[H_2N(CH_2)_{10}]C_6H_4CH_2$— | -cyclo-$C_8H_{15}$ | —$PO_3H_2$ |
| 942 | p-$[H_2N(CH_2)_{10}]C_6H_4CH_2$— | —$CH(CH_3)(CH_2CH_3)$ | —$PO_3H_2$ |
| 943 | p-$[H_2N(CH_2)_{10}]C_6H_4CH_2$— | —$CH(CH_2CH_3)_2$ | —$PO_3H_2$ |
| 944 | p-$[H_2N(CH_2)_{10}]C_6H_4CH_2$— | —$CH(CH_3)(CH_2CH_2CH_3)$ | —$PO_3H_2$ |
| 945 | p-$[H_2N(CH_2)_{10}]C_6H_4CH_2$— | —$C(CH_3)_3$ | —$PO_3H_2$ |
| 946 | p-$[H_2N(CH_2)_{10}]C_6H_4CH_2$— | $HC{\equiv}CCH_2$— | —$PO_3H_2$ |
| 947 | p-$[H_2N(CH_2)_{10}]C_6H_4CH_2$— | $H_2C{=}CH$— | —$PO_3H_2$ |
| 948 | p-$[H_2N(CH_2)_{10}]C_6H_4CH_2$— | $H_2C{=}CHCH_2$— | —$PO_3H_2$ |
| 949 | p-$[H_2N(CH_2)_{10}]C_6H_4CH_2$— | —$CH_2F$ | —$PO_3H_2$ |
| 950 | p-$[H_2N(CH_2)_{10}]C_6H_4CH_2$— | —$CH_2C_6H_5$ | —$PO_3H_2$ |
| 951 | p-$[H_2N(CH_2)_{10}]C_6H_4CH_2$— | —$CH_2C_6H_4$-p-$OCH_3$ | —$PO_3H_2$ |
| 952 | p-$[H_2N(CH_2)_{10}]C_6H_4CH_2$— | —$CH_2C_6H_4$-p-$CH_3$ | —$PO_3H_2$ |
| 953 | p-$[H_2N(CH_2)_{10}]C_6H_4CH_2$— | —$CH_2C_6H_4$-p-F | —$PO_3H_2$ |
| 954 | p-$[H_2N(CH_2)_{10}]C_6H_4CH_2$— | —$CH_2CH_2C_6H_5$ | —$PO_3H_2$ |
| 955 | p-$[H_2N(CH_2)_{10}]C_6H_4CH_2$— | —$CH_2$-cyclo-$C_6H_{11}$ | —$PO_3H_2$ |
| 956 | p-$[H_2N(CH_2)_{10}]C_6H_4CH_2$— | —$CH_2$-cyclo-$C_6H_{10}$-4-F | —$PO_3H_2$ |
| 957 | p-$[H_2N(CH_2)_{10}]C_6H_4CH_2$— | —$CH_2$-cyclo-$C_6H_{10}$-4-$CH_3$ | —$PO_3H_2$ |
| 958 | p-$[H_2N(CH_2)_{10}]C_6H_4CH_2$— | —$CH_2$-cyclo-$C_6H_{10}$-4-$OCH_3$ | —$PO_3H_2$ |
| 959 | p-$[H_2N(CH_2)_{10}]C_6H_4CH_2$— | —$CH_2CH_2$-cyclo-$C_6H_{11}$ | —$PO_3H_2$ |
| 960 | p-$[H_2N(CH_2)_{10}]C_6H_4CH_2$— | —$CH_2$-cyclo-$C_5H_9$ | —$PO_3H_2$ |
| 961 | p-$[H_2N(CH_2)_{10}]C_6H_4CH_2$— | —$CH_2CH_2$-cyclo-$C_5H_9$ | —$PO_3H_2$ |
| 962 | p-$[H_2N(CH_2)_{10}]C_6H_4CH_2$— | —$CH_2$-2-naphthyl | —$PO_3H_2$ |
| 963 | p-$[H_2N(CH_2)_{10}]C_6H_4CH_2$— | —H | -5-Tet |
| 964 | p-$[H_2N(CH_2)_{10}]C_6H_4CH_2$— | —$CH_3$ | -5-Tet |
| 965 | p-$[H_2N(CH_2)_{10}]C_6H_4CH_2$— | —$CH_2CH_3$ | -5-Tet |
| 966 | p-$[H_2N(CH_2)_{10}]C_6H_4CH_2$— | —$CH_2CH_2CH_3$ | -5-Tet |
| 967 | p-$[H_2N(CH_2)_{10}]C_6H_4CH_2$— | —$CH_2CH_2CH_2CH_3$ | -5-Tet |
| 968 | p-$[H_2N(CH_2)_{10}]C_6H_4CH_2$— | —$CH_2CH_2CH_2CH_2CH_3$ | -5-Tet |
| 969 | p-$[H_2N(CH_2)_{10}]C_6H_4CH_2$— | —$CH_2CH_2CH_2CH_2CH_2CH_3$ | -5-Tet |
| 970 | p-$[H_2N(CH_2)_{10}]C_6H_4CH_2$— | —$CH(CH_3)_2$ | -5-Tet |
| 971 | p-$[H_2N(CH_2)_{10}]C_6H_4CH_2$— | —$CH_2CH(CH_3)_2$ | -5-Tet |
| 972 | p-$[H_2N(CH_2)_{10}]C_6H_4CH_2$— | —$CH_2CH_2CH(CH_3)_2$ | -5-Tet |
| 973 | p-$[H_2N(CH_2)_{10}]C_6H_4CH_2$— | -cyclo-$C_3H_5$ | -5-Tet |
| 974 | p-$[H_2N(CH_2)_{10}]C_6H_4CH_2$— | -cyclo-$C_4H_7$ | -5-Tet |
| 975 | p-$[H_2N(CH_2)_{10}]C_6H_4CH_2$— | -cyclo-$C_5H_9$ | -5-Tet |
| 976 | p-$[H_2N(CH_2)_{10}]C_6H_4CH_2$— | -cyclo-$C_6H_{11}$ | -5-Tet |
| 977 | p-$[H_2N(CH_2)_{10}]C_6H_4CH_2$— | -cyclo-$C_7H_{13}$ | -5-Tet |
| 978 | p-$[H_2N(CH_2)_{10}]C_6H_4CH_2$— | -cyclo-$C_8H_{15}$ | -5-Tet |
| 979 | p-$[H_2N(CH_2)_{10}]C_6H_4CH_2$— | —$CH(CH_3)(CH_2CH_3)$ | -5-Tet |
| 980 | p-$[H_2N(CH_2)_{10}]C_6H_4CH_2$— | —$CH(CH_2CH_3)_2$ | -5-Tet |
| 981 | p-$[H_2N(CH_2)_{10}]C_6H_4CH_2$— | —$CH(CH_3)(CH_2CH_2CH_3)$ | -5-Tet |

TABLE I-continued

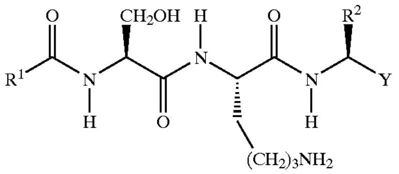

| Ex. No. | $R^1$ | $R^2$ | Y |
|---|---|---|---|
| 982 | p-$[H_2N(CH_2)_{10}]C_6H_4CH_2$— | —$C(CH_3)_3$ | -5-Tet |
| 983 | p-$[H_2N(CH_2)_{10}]C_6H_4CH_2$— | HC≡$CCH_2$— | -5-Tet |
| 984 | p-$[H_2N(CH_2)_{10}]C_6H_4CH_2$— | $H_2C$=CH— | -5-Tet |
| 985 | p-$[H_2N(CH_2)_{10}]C_6H_4CH_2$— | $H_2C$=$CHCH_2$— | -5-Tet |
| 986 | p-$[H_2N(CH_2)_{10}]C_6H_4CH_2$— | —$CH_2F$ | -5-Tet |
| 987 | p-$[H_2N(CH_2)_{10}]C_6H_4CH_2$— | —$CH_2C_6H_5$ | -5-Tet |
| 988 | p-$[H_2N(CH_2)_{10}]C_6H_4CH_2$— | —$CH_2C_6H_4$-p-$OCH_3$ | -5-Tet |
| 989 | p-$[H_2N(CH_2)_{10}]C_6H_4CH_2$— | —$CH_2C_6H_4$-p-$CH_3$ | -5-Tet |
| 990 | p-$[H_2N(CH_2)_{10}]C_6H_4CH_2$— | —$CH_2C_6H_4$-p-F | -5-Tet |
| 991 | p-$[H_2N(CH_2)_{10}]C_6H_4CH_2$— | —$CH_2CH_2C_6H_5$ | -5-Tet |
| 992 | p-$[H_2N(CH_2)_{10}]C_6H_4CH_2$— | —$CH_2$-cyclo-$C_6H_{11}$ | -5-Tet |
| 993 | p-$[H_2N(CH_2)_{10}]C_6H_4CH_2$— | —$CH_2$-cyclo-$C_6H_{10}$-4-F | -5-Tet |
| 994 | p-$[H_2N(CH_2)_{10}]C_6H_4CH_2$— | —$CH_2$-cyclo-$C_6H_{10}$-4-$CH_3$ | -5-Tet |
| 995 | p-$[H_2N(CH_2)_{10}]C_6H_4CH_2$— | —$CH_2$-cyclo-$C_6H_{10}$-4-$OCH_3$ | -5-Tet |
| 996 | p-$[H_2N(CH_2)_{10}]C_6H_4CH_2$— | —$CH_2CH_2$-cyclo-$C_6H_{11}$ | -5-Tet |
| 997 | p-$[H_2N(CH_2)_{10}]C_6H_4CH_2$— | —$CH_2$-cyclo-$C_5H_9$ | -5-Tet |
| 998 | p-$[H_2N(CH_2)_{10}]C_6H_4CH_2$— | —$CH_2CH_2$-cyclo-$C_5H_9$ | -5-Tet |
| 999 | p-$[H_2N(CH_2)_{10}]C_6H_4CH_2$— | —$CH_2$-2-naphthyl | -5-Tet |
| 1000 | p-$[H_2N(CH_2)_6]C_6H_4CH(CH_3)$— | —H | —$CO_2H$ |
| 1001 | p-$[H_2N(CH_2)_6]C_6H_4CH(CH_3)$— | —$CH_3$ | —$CO_2H$ |
| 1002 | p-$[H_2N(CH_2)_6]C_6H_4CH(CH_3)$— | —$CH_2CH_3$ | —$CO_2H$ |
| 1003 | p-$[H_2N(CH_2)_6]C_6H_4CH(CH_3)$— | —$CH_2CH_2CH_3$ | —$CO_2H$ |
| 1004 | p-$[H_2N(CH_2)_6]C_6H_4CH(CH_3)$— | —$CH_2CH_2CH_2CH_3$ | —$CO_2H$ |
| 1005 | p-$[H_2N(CH_2)_6]C_6H_4CH(CH_3)$— | —$CH_2CH_2CH_2CH_2CH_3$ | —$CO_2H$ |
| 1006 | p-$[H_2N(CH_2)_6]C_6H_4CH(CH_3)$— | —$CH_2CH_2CH_2CH_2CH_2CH_3$ | —$CO_2H$ |
| 1007 | p-$[H_2N(CH_2)_6]C_6H_4CH(CH_3)$— | —$CH(CH_3)_2$ | —$CO_2H$ |
| 1008 | p-$[H_2N(CH_2)_6]C_6H_4CH(CH_3)$— | —$CH_2CH(CH_3)_2$ | —$CO_2H$ |
| 1009 | p-$[H_2N(CH_2)_6]C_6H_4CH(CH_3)$— | —$CH_2CH_2CH(CH_3)_2$ | —$CO_2H$ |
| 1010 | p-$[H_2N(CH_2)_6]C_6H_4CH(CH_3)$— | -cyclo-$C_3H_5$ | —$CO_2H$ |
| 1011 | p-$[H_2N(CH_2)_6]C_6H_4CH(CH_3)$— | -cyclo-$C_4H_7$ | —$CO_2H$ |
| 1012 | p-$[H_2N(CH_2)_6]C_6H_4CH(CH_3)$— | -cyclo-$C_5H_9$ | —$CO_2H$ |
| 1013 | p-$[H_2N(CH_2)_6]C_6H_4CH(CH_3)$— | -cyclo-$C_6H_{11}$ | —$CO_2H$ |
| 1014 | p-$[H_2N(CH_2)_6]C_6H_4CH(CH_3)$— | -cyclo-$C_7H_{13}$ | —$CO_2H$ |
| 1015 | p-$[H_2N(CH_2)_6]C_6H_4CH(CH_3)$— | -cyclo-$C_8H_{15}$ | —$CO_2H$ |
| 1016 | p-$[H_2N(CH_2)_6]C_6H_4CH(CH_3)$— | —$CH(CH_3)(CH_2CH_3)$ | —$CO_2H$ |
| 1017 | p-$[H_2N(CH_2)_6]C_6H_4CH(CH_3)$— | —$CH(CH_2CH_3)_2$ | —$CO_2H$ |
| 1018 | p-$[H_2N(CH_2)_6]C_6H_4CH(CH_3)$— | —$CH(CH_3)(CH_2CH_2CH_3)$ | —$CO_2H$ |
| 1019 | p-$[H_2N(CH_2)_6]C_6H_4CH(CH_3)$— | —$C(CH_3)_3$ | —$CO_2H$ |
| 1020 | p-$[H_2N(CH_2)_6]C_6H_4CH(CH_3)$— | HC≡$CCH_2$— | —$CO_2H$ |
| 1021 | p-$[H_2N(CH_2)_6]C_6H_4CH(CH_3)$— | $H_2C$=CH— | —$CO_2H$ |
| 1022 | p-$[H_2N(CH_2)_6]C_6H_4CH(CH_3)$— | $H_2C$=$CHCH_2$— | —$CO_2H$ |
| 1023 | p-$[H_2N(CH_2)_6]C_6H_4CH(CH_3)$— | —$CH_2F$ | —$CO_2H$ |
| 1024 | p-$[H_2N(CH_2)_6]C_6H_4CH(CH_3)$— | —$CH_2C_6H_5$ | —$CO_2H$ |
| 1025 | p-$[H_2N(CH_2)_6]C_6H_4CH(CH_3)$— | —$CH_2C_6H_4$-p-$OCH_3$ | —$CO_2H$ |
| 1026 | p-$[H_2N(CH_2)_6]C_6H_4CH(CH_3)$— | —$CH_2C_6H_4$-p-$CH_3$ | —$CO_2H$ |
| 1027 | p-$[H_2N(CH_2)_6]C_6H_4CH(CH_3)$— | —$CH_2C_6H_4$-p-F | —$CO_2H$ |
| 1028 | p-$[H_2N(CH_2)_6]C_6H_4CH(CH_3)$— | —$CH_2CH_2C_6H_5$ | —$CO_2H$ |
| 1029 | p-$[H_2N(CH_2)_6]C_6H_4CH(CH_3)$— | —$CH_2$-cyclo-$C_6H_{11}$ | —$CO_2H$ |
| 1030 | p-$[H_2N(CH_2)_6]C_6H_4CH(CH_3)$— | —$CH_2$-cyclo-$C_6H_{10}$-4-F | —$CO_2H$ |
| 1031 | p-$[H_2N(CH_2)_6]C_6H_4CH(CH_3)$— | —$CH_2$-cyclo-$C_6H_{10}$-4-$CH_3$ | —$CO_2H$ |
| 1032 | p-$[H_2N(CH_2)_6]C_6H_4CH(CH_3)$— | —$CH_2$-cyclo-$C_6H_{10}$-4-$OCH_3$ | —$CO_2H$ |
| 1033 | p-$[H_2N(CH_2)_6]C_6H_4CH(CH_3)$— | —$CH_2CH_2$-cyclo-$C_6H_{11}$ | —$CO_2H$ |
| 1034 | p-$[H_2N(CH_2)_6]C_6H_4CH(CH_3)$— | —$CH_2$-cyclo-$C_5H_9$ | —$CO_2H$ |
| 1035 | p-$[H_2N(CH_2)_6]C_6H_4CH(CH_3)$— | —$CH_2CH_2$-cyclo-$C_5H_9$ | —$CO_2H$ |
| 1036 | p-$[H_2N(CH_2)_6]C_6H_4CH(CH_3)$— | —$CH_2$-2-naphthyl | —$CO_2H$ |
| 1037 | p-$[H_2N(CH_2)_6]C_6H_4CH(CH_3)$— | —H | —$PO_3H_2$ |
| 1038 | p-$[H_2N(CH_2)_6]C_6H_4CH(CH_3)$— | —$CH_3$ | —$PO_3H_2$ |
| 1039 | p-$[H_2N(CH_2)_6]C_6H_4CH(CH_3)$— | —$CH_2CH_3$ | —$PO_3H_2$ |
| 1040 | p-$[H_2N(CH_2)_6]C_6H_4CH(CH_3)$— | —$CH_2CH_2CH_3$ | —$PO_3H_2$ |
| 1041 | p-$[H_2N(CH_2)_6]C_6H_4CH(CH_3)$— | —$CH_2CH_2CH_2CH_3$ | —$PO_3H_2$ |
| 1042 | p-$[H_2N(CH_2)_6]C_6H_4CH(CH_3)$— | —$CH_2CH_2CH_2CH_2CH_3$ | —$PO_3H_2$ |
| 1043 | p-$[H_2N(CH_2)_6]C_6H_4CH(CH_3)$— | —$CH_2CH_2CH_2CH_2CH_2CH_3$ | —$PO_3H_2$ |
| 1044 | p-$[H_2N(CH_2)_6]C_6H_4CH(CH_3)$— | —$CH(CH_3)_2$ | —$PO_3H_2$ |
| 1045 | p-$[H_2N(CH_2)_6]C_6H_4CH(CH_3)$— | —$CH_2CH(CH_3)_2$ | —$PO_3H_2$ |
| 1046 | p-$[H_2N(CH_2)_6]C_6H_4CH(CH_3)$— | —$CH_2CH_2CH(CH_3)_2$ | —$PO_3H_2$ |
| 1047 | p-$[H_2N(CH_2)_6]C_6H_4CH(CH_3)$— | -cyclo-$C_3H_5$ | —$PO_3H_2$ |

TABLE I-continued

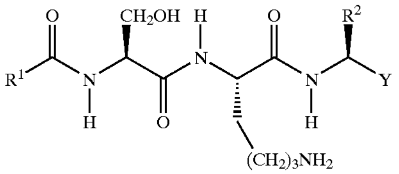

| Ex. No. | $R^1$ | $R^2$ | Y |
|---|---|---|---|
| 1048 | p-$[H_2N(CH_2)_6]C_6H_4CH(CH_3)$— | -cyclo-$C_4H_7$ | —$PO_3H_2$ |
| 1049 | p-$[H_2N(CH_2)_6]C_6H_4CH(CH_3)$— | -cyclo-$C_5H_9$ | —$PO_3H_2$ |
| 1050 | p-$[H_2N(CH_2)_6]C_6H_4CH(CH_3)$— | -cyclo-$C_6H_{11}$ | —$PO_3H_2$ |
| 1051 | p-$[H_2N(CH_2)_6]C_6H_4CH(CH_3)$— | -cyclo-$C_7H_{13}$ | —$PO_3H_2$ |
| 1052 | p-$[H_2N(CH_2)_6]C_6H_4CH(CH_3)$— | -cyclo-$C_8H_{15}$ | —$PO_3H_2$ |
| 1053 | p-$[H_2N(CH_2)_6]C_6H_4CH(CH_3)$— | —$CH(CH_3)(CH_2CH_3)$ | —$PO_3H_2$ |
| 1054 | p-$[H_2N(CH_2)_6]C_6H_4CH(CH_3)$— | —$CH(CH_2CH_3)_2$ | —$PO_3H_2$ |
| 1055 | p-$[H_2N(CH_2)_6]C_6H_4CH(CH_3)$— | —$CH(CH_3)(CH_2CH_2CH_3)$ | —$PO_3H_2$ |
| 1056 | p-$[H_2N(CH_2)_6]C_6H_4CH(CH_3)$— | —$C(CH_3)_3$ | —$PO_3H_2$ |
| 1057 | p-$[H_2N(CH_2)_6]C_6H_4CH(CH_3)$— | $HC{\equiv}CCH_2$— | —$PO_3H_2$ |
| 1058 | p-$[H_2N(CH_2)_6]C_6H_4CH(CH_3)$— | $H_2C{=}CH$— | —$PO_3H_2$ |
| 1059 | p-$[H_2N(CH_2)_6]C_6H_4CH(CH_3)$— | $H_2C{=}CHCH_2$— | —$PO_3H_2$ |
| 1060 | p-$[H_2N(CH_2)_6]C_6H_4CH(CH_3)$— | —$CH_2F$ | —$PO_3H_2$ |
| 1061 | p-$[H_2N(CH_2)_6]C_6H_4CH(CH_3)$— | —$CH_2C_6H_5$ | —$PO_3H_2$ |
| 1062 | p-$[H_2N(CH_2)_6]C_6H_4CH(CH_3)$— | —$CH_2C_6H_4$-p-$OCH_3$ | —$PO_3H_2$ |
| 1063 | p-$[H_2N(CH_2)_6]C_6H_4CH(CH_3)$— | —$CH_2C_6H_4$-p-$CH_3$ | —$PO_3H_2$ |
| 1064 | p-$[H_2N(CH_2)_6]C_6H_4CH(CH_3)$— | —$CH_2C_6H_4$-p-F | —$PO_3H_2$ |
| 1065 | p-$[H_2N(CH_2)_6]C_6H_4CH(CH_3)$— | —$CH_2CH_2C_6H_5$ | —$PO_3H_2$ |
| 1066 | p-$[H_2N(CH_2)_6]C_6H_4CH(CH_3)$— | —$CH_2$-cyclo-$C_6H_{11}$ | —$PO_3H_2$ |
| 1067 | p-$[H_2N(CH_2)_6]C_6H_4CH(CH_3)$— | —$CH_2$-cyclo-$C_6H_{10}$-4-F | —$PO_3H_2$ |
| 1068 | p-$[H_2N(CH_2)_6]C_6H_4CH(CH_3)$— | —$CH_2$-cyclo-$C_6H_{10}$-4-$CH_3$ | —$PO_3H_2$ |
| 1069 | p-$[H_2N(CH_2)_6]C_6H_4CH(CH_3)$— | —$CH_2$-cyclo-$C_6H_{10}$-4-$OCH_3$ | —$PO_3H_2$ |
| 1070 | p-$[H_2N(CH_2)_6]C_6H_4CH(CH_3)$— | —$CH_2CH_2$-cyclo-$C_6H_{11}$ | —$PO_3H_2$ |
| 1071 | p-$[H_2N(CH_2)_6]C_6H_4CH(CH_3)$— | —$CH_2$-cyclo-$C_5H_9$ | —$PO_3H_2$ |
| 1072 | p-$[H_2N(CH_2)_6]C_6H_4CH(CH_3)$— | —$CH_2CH_2$-cyclo-$C_5H_9$ | —$PO_3H_2$ |
| 1073 | p-$[H_2N(CH_2)_6]C_6H_4CH(CH_3)$— | —$CH_2$-2-naphthyl | —$PO_3H_2$ |
| 1074 | p-$[H_2N(CH_2)_6]C_6H_4CH(CH_3)$— | —H | -5-Tet |
| 1075 | p-$[H_2N(CH_2)_6]C_6H_4CH(CH_3)$— | —$CH_3$ | -5-Tet |
| 1076 | p-$[H_2N(CH_2)_6]C_6H_4CH(CH_3)$— | —$CH_2CH_3$ | -5-Tet |
| 1077 | p-$[H_2N(CH_2)_6]C_6H_4CH(CH_3)$— | —$CH_2CH_2CH_3$ | -5-Tet |
| 1078 | p-$[H_2N(CH_2)_6]C_6H_4CH(CH_3)$— | —$CH_2CH_2CH_2CH_3$ | -5-Tet |
| 1079 | p-$[H_2N(CH_2)_6]C_6H_4CH(CH_3)$— | —$CH_2CH_2CH_2CH_2CH_3$ | -5-Tet |
| 1080 | p-$[H_2N(CH_2)_6]C_6H_4CH(CH_3)$— | —$CH_2CH_2CH_2CH_2CH_2CH_3$ | -5-Tet |
| 1081 | p-$[H_2N(CH_2)_6]C_6H_4CH(CH_3)$— | —$CH(CH_3)_2$ | -5-Tet |
| 1082 | p-$[H_2N(CH_2)_6]C_6H_4CH(CH_3)$— | —$CH_2CH(CH_3)_2$ | -5-Tet |
| 1083 | p-$[H_2N(CH_2)_6]C_6H_4CH(CH_3)$— | —$CH_2CH_2CH(CH_3)_2$ | -5-Tet |
| 1084 | p-$[H_2N(CH_2)_6]C_6H_4CH(CH_3)$— | -cyclo-$C_3H_5$ | -5-Tet |
| 1085 | p-$[H_2N(CH_2)_6]C_6H_4CH(CH_3)$— | -cyclo-$C_4H_7$ | -5-Tet |
| 1086 | p-$[H_2N(CH_2)_6]C_6H_4CH(CH_3)$— | -cyclo-$C_5H_9$ | -5-Tet |
| 1087 | p-$[H_2N(CH_2)_6]C_6H_4CH(CH_3)$— | -cyclo-$C_6H_{11}$ | -5-Tet |
| 1088 | p-$[H_2N(CH_2)_6]C_6H_4CH(CH_3)$— | -cyclo-$C_7H_{13}$ | -5-Tet |
| 1089 | p-$[H_2N(CH_2)_6]C_6H_4CH(CH_3)$— | -cyclo-$C_8H_{15}$ | -5-Tet |
| 1090 | p-$[H_2N(CH_2)_6]C_6H_4CH(CH_3)$— | —$CH(CH_3)(CH_2CH_3)$ | -5-Tet |
| 1091 | p-$[H_2N(CH_2)_6]C_6H_4CH(CH_3)$— | —$CH(CH_2CH_3)_2$ | -5-Tet |
| 1092 | p-$[H_2N(CH_2)_6]C_6H_4CH(CH_3)$— | —$CH(CH_3)(CH_2CH_2CH_3)$ | -5-Tet |
| 1093 | p-$[H_2N(CH_2)_6]C_6H_4CH(CH_3)$— | —$C(CH_3)_3$ | -5-Tet |
| 1094 | p-$[H_2N(CH_2)_6]C_6H_4CH(CH_3)$— | $HC{\equiv}CCH_2$— | -5-Tet |
| 1095 | p-$[H_2N(CH_2)_6]C_6H_4CH(CH_3)$— | $H_2C{=}CH$— | -5-Tet |
| 1096 | p-$[H_2N(CH_2)_6]C_6H_4CH(CH_3)$— | $H_2C{=}CHCH_2$— | -5-Tet |
| 1097 | p-$[H_2N(CH_2)_6]C_6H_4CH(CH_3)$— | —$CH_2F$ | -5-Tet |
| 1098 | p-$[H_2N(CH_2)_6]C_6H_4CH(CH_3)$— | —$CH_2C_6H_5$ | -5-Tet |
| 1099 | p-$[H_2N(CH_2)_6]C_6H_4CH(CH_3)$— | —$CH_2C_6H_4$-p-$OCH_3$ | -5-Tet |
| 1100 | p-$[H_2N(CH_2)_6]C_6H_4CH(CH_3)$— | —$CH_2C_6H_4$-p-$CH_3$ | -5-Tet |
| 1101 | p-$[H_2N(CH_2)_6]C_6H_4CH(CH_3)$— | —$CH_2C_6H_4$-p-F | -5-Tet |
| 1102 | p-$[H_2N(CH_2)_6]C_6H_4CH(CH_3)$— | —$CH_2CH_2C_6H_5$ | -5-Tet |
| 1103 | p-$[H_2N(CH_2)_6]C_6H_4CH(CH_3)$— | —$CH_2$-cyclo-$C_6H_{11}$ | -5-Tet |
| 1104 | p-$[H_2N(CH_2)_6]C_6H_4CH(CH_3)$— | —$CH_2$-cyclo-$C_6H_{10}$-4-F | -5-Tet |
| 1105 | p-$[H_2N(CH_2)_6]C_6H_4CH(CH_3)$— | —$CH_2$-cyclo-$C_6H_{10}$-4-$CH_3$ | -5-Tet |
| 1106 | p-$[H_2N(CH_2)_6]C_6H_4CH(CH_3)$— | —$CH_2$-cyclo-$C_6H_{10}$-4-$OCH_3$ | -5-Tet |
| 1107 | p-$[H_2N(CH_2)_6]C_6H_4CH(CH_3)$— | —$CH_2CH_2$-cyclo-$C_6H_{11}$ | -5-Tet |
| 1108 | p-$[H_2N(CH_2)_6]C_6H_4CH(CH_3)$— | —$CH_2$-cyclo-$C_5H_9$ | -5-Tet |
| 1109 | p-$[H_2N(CH_2)_6]C_6H_4CH(CH_3)$— | —$CH_2CH_2$-cyclo-$C_5H_9$ | -5-Tet |
| 1110 | p-$[H_2N(CH_2)_6]C_6H_4CH(CH_3)$— | —$CH_2$-2-naphthyl | -5-Tet |
| 1111 | p-$[H_2N(CH_2)_8]C_6H_4CH(CH_3)$— | —H | —$CO_2H$ |
| 1112 | p-$[H_2N(CH_2)_8]C_6H_4CH(CH_3)$— | —$CH_3$ | —$CO_2H$ |
| 1113 | p-$[H_2N(CH_2)_8]C_6H_4CH(CH_3)$— | —$CH_2CH_3$ | —$CO_2H$ |

TABLE I-continued

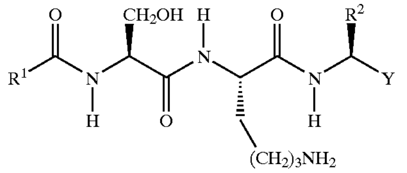

| Ex. No. | $R^1$ | $R^2$ | Y |
|---|---|---|---|
| 1114 | p-$[H_2N(CH_2)_8]C_6H_4CH(CH_3)$— | —$CH_2CH_2CH_3$ | —$CO_2H$ |
| 1115 | p-$[H_2N(CH_2)_8]C_6H_4CH(CH_3)$— | —$CH_2CH_2CH_2CH_3$ | —$CO_2H$ |
| 1116 | p-$[H_2N(CH_2)_8]C_6H_4CH(CH_3)$— | —$CH_2CH_2CH_2CH_2CH_3$ | —$CO_2H$ |
| 1117 | p-$[H_2N(CH_2)_8]C_6H_4CH(CH_3)$— | —$CH_2CH_2CH_2CH_2CH_2CH_3$ | —$CO_2H$ |
| 1118 | p-$[H_2N(CH_2)_8]C_6H_4CH(CH_3)$— | —$CH(CH_3)_2$ | —$CO_2H$ |
| 1119 | p-$[H_2N(CH_2)_8]C_6H_4CH(CH_3)$— | —$CH_2CH(CH_3)_2$ | —$CO_2H$ |
| 1120 | p-$[H_2N(CH_2)_8]C_6H_4CH(CH_3)$— | —$CH_2CH_2CH(CH_3)_2$ | —$CO_2H$ |
| 1121 | p-$[H_2N(CH_2)_8]C_6H_4CH(CH_3)$— | -cyclo-$C_3H_5$ | —$CO_2H$ |
| 1122 | p-$[H_2N(CH_2)_8]C_6H_4CH(CH_3)$— | -cyclo-$C_4H_7$ | —$CO_2H$ |
| 1123 | p-$[H_2N(CH_2)_8]C_6H_4CH(CH_3)$— | -cyclo-$C_5H_9$ | —$CO_2H$ |
| 1124 | p-$[H_2N(CH_2)_8]C_6H_4CH(CH_3)$— | -cyclo-$C_6H_{11}$ | —$CO_2H$ |
| 1125 | p-$[H_2N(CH_2)_8]C_6H_4CH(CH_3)$— | -cyclo-$C_7H_{13}$ | —$CO_2H$ |
| 1126 | p-$[H_2N(CH_2)_8]C_6H_4CH(CH_3)$— | -cyclo-$C_8H_{15}$ | —$CO_2H$ |
| 1127 | p-$[H_2N(CH_2)_8]C_6H_4CH(CH_3)$— | —$CH(CH_3)(CH_2CH_3)$ | —$CO_2H$ |
| 1128 | p-$[H_2N(CH_2)_8]C_6H_4CH(CH_3)$— | —$CH(CH_2CH_3)_2$ | —$CO_2H$ |
| 1129 | p-$[H_2N(CH_2)_8]C_6H_4CH(CH_3)$— | —$CH(CH_3)(CH_2CH_2CH_3)$ | —$CO_2H$ |
| 1130 | p-$[H_2N(CH_2)_8]C_6H_4CH(CH_3)$— | —$C(CH_3)_3$ | —$CO_2H$ |
| 1131 | p-$[H_2N(CH_2)_8]C_6H_4CH(CH_3)$— | $HC{\equiv}CCH_2$— | —$CO_2H$ |
| 1132 | p-$[H_2N(CH_2)_8]C_6H_4CH(CH_3)$— | $H_2C{=}CH$— | —$CO_2H$ |
| 1133 | p-$[H_2N(CH_2)_8]C_6H_4CH(CH_3)$— | $H_2C{=}CHCH_2$— | —$CO_2H$ |
| 1134 | p-$[H_2N(CH_2)_8]C_6H_4CH(CH_3)$— | —$CH_2F$ | —$CO_2H$ |
| 1135 | p-$[H_2N(CH_2)_8]C_6H_4CH(CH_3)$— | —$CH_2C_6H_5$ | —$CO_2H$ |
| 1136 | p-$[H_2N(CH_2)_8]C_6H_4CH(CH_3)$— | —$CH_2C_6H_4$-p-$OCH_3$ | —$CO_2H$ |
| 1137 | p-$[H_2N(CH_2)_8]C_6H_4CH(CH_3)$— | —$CH_2C_6H_4$-p-$CH_3$ | —$CO_2H$ |
| 1138 | p-$[H_2N(CH_2)_8]C_6H_4CH(CH_3)$— | —$CH_2C_6H_4$-p-F | —$CO_2H$ |
| 1139 | p-$[H_2N(CH_2)_8]C_6H_4CH(CH_3)$— | —$CH_2CH_2C_6H_5$ | —$CO_2H$ |
| 1140 | p-$[H_2N(CH_2)_8]C_6H_4CH(CH_3)$— | —$CH_2$-cyclo-$C_6H_{11}$ | —$CO_2H$ |
| 1141 | p-$[H_2N(CH_2)_8]C_6H_4CH(CH_3)$— | —$CH_2$-cyclo-$C_6H_{10}$-4-F | —$CO_2H$ |
| 1142 | p-$[H_2N(CH_2)_8]C_6H_4CH(CH_3)$— | —$CH_2$-cyclo-$C_6H_{10}$-4-$CH_3$ | —$CO_2H$ |
| 1143 | p-$[H_2N(CH_2)_8]C_6H_4CH(CH_3)$— | —$CH_2$-cyclo-$C_6H_{10}$-4-$OCH_3$ | —$CO_2H$ |
| 1144 | p-$[H_2N(CH_2)_8]C_6H_4CH(CH_3)$— | —$CH_2CH_2$-cyclo-$C_6H_{11}$ | —$CO_2H$ |
| 1145 | p-$[H_2N(CH_2)_8]C_6H_4CH(CH_3)$— | —$CH_2$-cyclo-$C_5H_9$ | —$CO_2H$ |
| 1146 | p-$[H_2N(CH_2)_8]C_6H_4CH(CH_3)$— | —$CH_2CH_2$-cyclo-$C_5H_9$ | —$CO_2H$ |
| 1147 | p-$[H_2N(CH_2)_8]C_6H_4CH(CH_3)$— | —$CH_2$-2-naphthyl | —$CO_2H$ |
| 1148 | p-$[H_2N(CH_2)_8]C_6H_4CH(CH_3)$— | —H | —$PO_3H_2$ |
| 1149 | p-$[H_2N(CH_2)_8]C_6H_4CH(CH_3)$— | —$CH_3$ | —$PO_3H_2$ |
| 1150 | p-$[H_2N(CH_2)_8]C_6H_4CH(CH_3)$— | —$CH_2CH_3$ | —$PO_3H_2$ |
| 1151 | p-$[H_2N(CH_2)_8]C_6H_4CH(CH_3)$— | —$CH_2CH_2CH_3$ | —$PO_3H_2$ |
| 1152 | p-$[H_2N(CH_2)_8]C_6H_4CH(CH_3)$— | —$CH_2CH_2CH_2CH_3$ | —$PO_3H_2$ |
| 1153 | p-$[H_2N(CH_2)_8]C_6H_4CH(CH_3)$— | —$CH_2CH_2CH_2CH_2CH_3$ | —$PO_3H_2$ |
| 1154 | p-$[H_2N(CH_2)_8]C_6H_4CH(CH_3)$— | —$CH_2CH_2CH_2CH_2CH_2CH_3$ | —$PO_3H_2$ |
| 1155 | p-$[H_2N(CH_2)_8]C_6H_4CH(CH_3)$— | —$CH(CH_3)_2$ | —$PO_3H_2$ |
| 1156 | p-$[H_2N(CH_2)_8]C_6H_4CH(CH_3)$— | —$CH_2CH(CH_3)_2$ | —$PO_3H_2$ |
| 1157 | p-$[H_2N(CH_2)_8]C_6H_4CH(CH_3)$— | —$CH_2CH_2CH(CH_3)_2$ | —$PO_3H_2$ |
| 1158 | p-$[H_2N(CH_2)_8]C_6H_4CH(CH_3)$— | -cyclo-$C_3H_5$ | —$PO_3H_2$ |
| 1159 | p-$[H_2N(CH_2)_8]C_6H_4CH(CH_3)$— | -cyclo-$C_4H_7$ | —$PO_3H_2$ |
| 1160 | p-$[H_2N(CH_2)_8]C_6H_4CH(CH_3)$— | -cyclo-$C_5H_9$ | —$PO_3H_2$ |
| 1161 | p-$[H_2N(CH_2)_8]C_6H_4CH(CH_3)$— | -cyclo-$C_6H_{11}$ | —$PO_3H_2$ |
| 1162 | p-$[H_2N(CH_2)_8]C_6H_4CH(CH_3)$— | -cyclo-$C_7H_{13}$ | —$PO_3H_2$ |
| 1163 | p-$[H_2N(CH_2)_8]C_6H_4CH(CH_3)$— | -cyclo-$C_8H_{15}$ | —$PO_3H_2$ |
| 1164 | p-$[H_2N(CH_2)_8]C_6H_4CH(CH_3)$— | —$CH(CH_3)(CH_2CH_3)$ | —$PO_3H_2$ |
| 1165 | p-$[H_2N(CH_2)_8]C_6H_4CH(CH_3)$— | —$CH(CH_2CH_3)_2$ | —$PO_3H_2$ |
| 1166 | p-$[H_2N(CH_2)_8]C_6H_4CH(CH_3)$— | —$CH(CH_3)(CH_2CH_2CH_3)$ | —$PO_3H_2$ |
| 1167 | p-$[H_2N(CH_2)_8]C_6H_4CH(CH_3)$— | —$C(CH_3)_3$ | —$PO_3H_2$ |
| 1168 | p-$[H_2N(CH_2)_8]C_6H_4CH(CH_3)$— | $HC{\equiv}CCH_2$— | —$PO_3H_2$ |
| 1169 | p-$[H_2N(CH_2)_8]C_6H_4CH(CH_3)$— | $H_2C{=}CH$— | —$PO_3H_2$ |
| 1170 | p-$[H_2N(CH_2)_8]C_6H_4CH(CH_3)$— | $H_2C{=}CHCH_2$— | —$PO_3H_2$ |
| 1171 | p-$[H_2N(CH_2)_8]C_6H_4CH(CH_3)$— | —$CH_2F$ | —$PO_3H_2$ |
| 1172 | p-$[H_2N(CH_2)_8]C_6H_4CH(CH_3)$— | —$CH_2C_6H_5$ | —$PO_3H_2$ |
| 1173 | p-$[H_2N(CH_2)_8]C_6H_4CH(CH_3)$— | —$CH_2C_6H_4$-p-$OCH_3$ | —$PO_3H_2$ |
| 1174 | p-$[H_2N(CH_2)_8]C_6H_4CH(CH_3)$— | —$CH_2C_6H_4$-p-$CH_3$ | —$PO_3H_2$ |
| 1175 | p-$[H_2N(CH_2)_8]C_6H_4CH(CH_3)$— | —$CH_2C_6H_4$-p-F | —$PO_3H_2$ |
| 1176 | p-$[H_2N(CH_2)_8]C_6H_4CH(CH_3)$— | —$CH_2CH_2C_6H_5$ | —$PO_3H_2$ |
| 1177 | p-$[H_2N(CH_2)_8]C_6H_4CH(CH_3)$— | —$CH_2$-cyclo-$C_6H_{11}$ | —$PO_3H_2$ |
| 1178 | p-$[H_2N(CH_2)_8]C_6H_4CH(CH_3)$— | —$CH_2$-cyclo-$C_6H_{10}$-4-F | —$PO_3H_2$ |
| 1179 | p-$[H_2N(CH_2)_8]C_6H_4CH(CH_3)$— | —$CH_2$-cyclo-$C_6H_{10}$-4-$CH_3$ | —$PO_3H_2$ |

TABLE I-continued

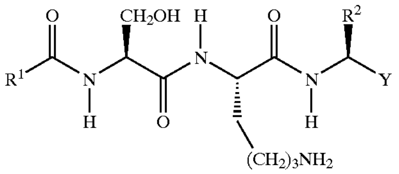

| Ex. No. | $R^1$ | $R^2$ | Y |
|---|---|---|---|
| 1180 | p-[$H_2N(CH_2)_8$]$C_6H_4CH(CH_3)$— | —$CH_2$-cyclo-$C_6H_{10}$-4-$OCH_3$ | —$PO_3H_2$ |
| 1181 | p-[$H_2N(CH_2)_8$]$C_6H_4CH(CH_3)$— | —$CH_2CH_2$-cyclo-$C_6H_{11}$ | —$PO_3H_2$ |
| 1182 | p-[$H_2N(CH_2)_8$]$C_6H_4CH(CH_3)$— | —$CH_2$-cyclo-$C_5H_9$ | —$PO_3H_2$ |
| 1183 | p-[$H_2N(CH_2)_8$]$C_6H_4CH(CH_3)$— | —$CH_2CH_2$-cyclo-$C_5H_9$ | —$PO_3H_2$ |
| 1184 | p-[$H_2N(CH_2)_8$]$C_6H_4CH(CH_3)$— | —$CH_2$-2-naphthyl | —$PO_3H_2$ |
| 1185 | p-[$H_2N(CH_2)_8$]$C_6H_4CH(CH_3)$— | —H | -5-Tet |
| 1186 | p-[$H_2N(CH_2)_8$]$C_6H_4CH(CH_3)$— | —$CH_3$ | -5-Tet |
| 1187 | p-[$H_2N(CH_2)_8$]$C_6H_4CH(CH_3)$— | —$CH_2CH_3$ | -5-Tet |
| 1188 | p-[$H_2N(CH_2)_8$]$C_6H_4CH(CH_3)$— | —$CH_2CH_2CH_3$ | -5-Tet |
| 1189 | p-[$H_2N(CH_2)_8$]$C_6H_4CH(CH_3)$— | —$CH_2CH_2CH_2CH_3$ | -5-Tet |
| 1190 | p-[$H_2N(CH_2)_8$]$C_6H_4CH(CH_3)$— | —$CH_2CH_2CH_2CH_2CH_3$ | -5-Tet |
| 1191 | p-[$H_2N(CH_2)_8$]$C_6H_4CH(CH_3)$— | —$CH_2CH_2CH_2CH_2CH_2CH_3$ | -5-Tet |
| 1192 | p-[$H_2N(CH_2)_8$]$C_6H_4CH(CH_3)$— | —$CH(CH_3)_2$ | -5-Tet |
| 1193 | p-[$H_2N(CH_2)_8$]$C_6H_4CH(CH_3)$— | —$CH_2CH(CH_3)_2$ | -5-Tet |
| 1194 | p-[$H_2N(CH_2)_8$]$C_6H_4CH(CH_3)$— | —$CH_2CH_2CH(CH_3)_2$ | -5-Tet |
| 1195 | p-[$H_2N(CH_2)_8$]$C_6H_4CH(CH_3)$— | -cyclo-$C_3H_5$ | -5-Tet |
| 1196 | p-[$H_2N(CH_2)_8$]$C_6H_4CH(CH_3)$— | -cyclo-$C_4H_7$ | -5-Tet |
| 1197 | p-[$H_2N(CH_2)_8$]$C_6H_4CH(CH_3)$— | -cyclo-$C_5H_9$ | -5-Tet |
| 1198 | p-[$H_2N(CH_2)_8$]$C_6H_4CH(CH_3)$— | -cyclo-$C_6H_{11}$ | -5-Tet |
| 1199 | p-[$H_2N(CH_2)_8$]$C_6H_4CH(CH_3)$— | -cyclo-$C_7H_{13}$ | -5-Tet |
| 1200 | p-[$H_2N(CH_2)_8$]$C_6H_4CH(CH_3)$— | -cyclo-$C_8H_{15}$ | -5-Tet |
| 1201 | p-[$H_2N(CH_2)_8$]$C_6H_4CH(CH_3)$— | —$CH(CH_3)(CH_2CH_3)$ | -5-Tet |
| 1202 | p-[$H_2N(CH_2)_8$]$C_6H_4CH(CH_3)$— | —$CH(CH_2CH_3)_2$ | -5-Tet |
| 1203 | p-[$H_2N(CH_2)_8$]$C_6H_4CH(CH_3)$— | —$CH(CH_3)(CH_2CH_2CH_3)$ | -5-Tet |
| 1204 | p-[$H_2N(CH_2)_8$]$C_6H_4CH(CH_3)$— | —$C(CH_3)_3$ | -5-Tet |
| 1205 | p-[$H_2N(CH_2)_8$]$C_6H_4CH(CH_3)$— | $HC{\equiv}CCH_2$— | -5-Tet |
| 1206 | p-[$H_2N(CH_2)_8$]$C_6H_4CH(CH_3)$— | $H_2C{=}CH$— | -5-Tet |
| 1207 | p-[$H_2N(CH_2)_8$]$C_6H_4CH(CH_3)$— | $H_2C{=}CHCH_2$— | -5-Tet |
| 1208 | p-[$H_2N(CH_2)_8$]$C_6H_4CH(CH_3)$— | —$CH_2F$ | -5-Tet |
| 1209 | p-[$H_2N(CH_2)_8$]$C_6H_4CH(CH_3)$— | —$CH_2C_6H_5$ | -5-Tet |
| 1210 | p-[$H_2N(CH_2)_8$]$C_6H_4CH(CH_3)$— | —$CH_2C_6H_4$-p-$OCH_3$ | -5-Tet |
| 1211 | p-[$H_2N(CH_2)_8$]$C_6H_4CH(CH_3)$— | —$CH_2C_6H_4$-p-$CH_3$ | -5-Tet |
| 1212 | p-[$H_2N(CH_2)_8$]$C_6H_4CH(CH_3)$— | —$CH_2C_6H_4$-p-F | -5-Tet |
| 1213 | p-[$H_2N(CH_2)_8$]$C_6H_4CH(CH_3)$— | —$CH_2CH_2C_6H_5$ | -5-Tet |
| 1214 | p-[$H_2N(CH_2)_8$]$C_6H_4CH(CH_3)$— | —$CH_2$-cyclo-$C_6H_{11}$ | -5-Tet |
| 1215 | p-[$H_2N(CH_2)_8$]$C_6H_4CH(CH_3)$— | —$CH_2$-cyclo-$C_6H_{10}$-4-F | -5-Tet |
| 1216 | p-[$H_2N(CH_2)_8$]$C_6H_4CH(CH_3)$— | —$CH_2$-cyclo-$C_6H_{10}$-4-$CH_3$ | -5-Tet |
| 1217 | p-[$H_2N(CH_2)_8$]$C_6H_4CH(CH_3)$— | —$CH_2$-cyclo-$C_6H_{10}$-4-$OCH_3$ | -5-Tet |
| 1218 | p-[$H_2N(CH_2)_8$]$C_6H_4CH(CH_3)$— | —$CH_2CH_2$-cyclo-$C_6H_{11}$ | -5-Tet |
| 1219 | p-[$H_2N(CH_2)_8$]$C_6H_4CH(CH_3)$— | —$CH_2$-cyclo-$C_5H_9$ | -5-Tet |
| 1220 | p-[$H_2N(CH_2)_8$]$C_6H_4CH(CH_3)$— | —$CH_2CH_2$-cyclo-$C_5H_9$ | -5-Tet |
| 1221 | p-[$H_2N(CH_2)_8$]$C_6H_4CH(CH_3)$— | —$CH_2$-2-naphthyl | -5-Tet |
| 1222 | p-[$H_2N(CH_2)_9$]$C_6H_4CH(CH_3)$— | —H | —$CO_2H$ |
| 1223 | p-[$H_2N(CH_2)_9$]$C_6H_4CH(CH_3)$— | —$CH_3$ | —$CO_2H$ |
| 1224 | p-[$H_2N(CH_2)_9$]$C_6H_4CH(CH_3)$— | —$CH_2CH_3$ | —$CO_2H$ |
| 1225 | p-[$H_2N(CH_2)_9$]$C_6H_4CH(CH_3)$— | —$CH_2CH_2CH_3$ | —$CO_2H$ |
| 1226 | p-[$H_2N(CH_2)_9$]$C_6H_4CH(CH_3)$— | —$CH_2CH_2CH_2CH_3$ | —$CO_2H$ |
| 1227 | p-[$H_2N(CH_2)_9$]$C_6H_4CH(CH_3)$— | —$CH_2CH_2CH_2CH_2CH_3$ | —$CO_2H$ |
| 1228 | p-[$H_2N(CH_2)_9$]$C_6H_4CH(CH_3)$— | —$CH_2CH_2CH_2CH_2CH_2CH_3$ | —$CO_2H$ |
| 1229 | p-[$H_2N(CH_2)_9$]$C_6H_4CH(CH_3)$— | —$CH(CH_3)_2$ | —$CO_2H$ |
| 1230 | p-[$H_2N(CH_2)_9$]$C_6H_4CH(CH_3)$— | —$CH_2CH(CH_3)_2$ | —$CO_2H$ |
| 1231 | p-[$H_2N(CH_2)_9$]$C_6H_4CH(CH_3)$— | —$CH_2CH_2CH(CH_3)_2$ | —$CO_2H$ |
| 1232 | p-[$H_2N(CH_2)_9$]$C_6H_4CH(CH_3)$— | -cyclo-$C_3H_5$ | —$CO_2H$ |
| 1233 | p-[$H_2N(CH_2)_9$]$C_6H_4CH(CH_3)$— | -cyclo-$C_4H_7$ | —$CO_2H$ |
| 1234 | p-[$H_2N(CH_2)_9$]$C_6H_4CH(CH_3)$— | -cyclo-$C_5H_9$ | —$CO_2H$ |
| 1235 | p-[$H_2N(CH_2)_9$]$C_6H_4CH(CH_3)$— | -cyclo-$C_6H_{11}$ | —$CO_2H$ |
| 1236 | p-[$H_2N(CH_2)_9$]$C_6H_4CH(CH_3)$— | -cyclo-$C_7H_{13}$ | —$CO_2H$ |
| 1237 | p-[$H_2N(CH_2)_9$]$C_6H_4CH(CH_3)$— | -cyclo-$C_8H_{15}$ | —$CO_2H$ |
| 1238 | p-[$H_2N(CH_2)_9$]$C_6H_4CH(CH_3)$— | —$CH(CH_3)(CH_2CH_3)$ | —$CO_2H$ |
| 1239 | p-[$H_2N(CH_2)_9$]$C_6H_4CH(CH_3)$— | —$CH(CH_2CH_3)_2$ | —$CO_2H$ |
| 1240 | p-[$H_2N(CH_2)_9$]$C_6H_4CH(CH_3)$— | —$CH(CH_3)(CH_2CH_2CH_3)$ | —$CO_2H$ |
| 1241 | p-[$H_2N(CH_2)_9$]$C_6H_4CH(CH_3)$— | —$C(CH_3)_3$ | —$CO_2H$ |
| 1242 | p-[$H_2N(CH_2)_9$]$C_6H_4CH(CH_3)$— | $HC{\equiv}CCH_2$— | —$CO_2H$ |
| 1243 | p-[$H_2N(CH_2)_9$]$C_6H_4CH(CH_3)$— | $H_2C{=}CH$— | —$CO_2H$ |
| 1244 | p-[$H_2N(CH_2)_9$]$C_6H_4CH(CH_3)$— | $H_2C{=}CHCH_2$— | —$CO_2H$ |
| 1245 | p-[$H_2N(CH_2)_9$]$C_6H_4CH(CH_3)$— | —$CH_2F$ | —$CO_2H$ |

TABLE I-continued

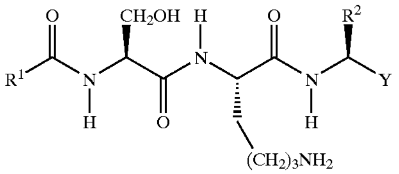

| Ex. No. | $R^1$ | $R^2$ | Y |
|---|---|---|---|
| 1246 | p-$[H_2N(CH_2)_9]C_6H_4CH(CH_3)$— | —$CH_2C_6H_5$ | —$CO_2H$ |
| 1247 | p-$[H_2N(CH_2)_9]C_6H_4CH(CH_3)$— | —$CH_2C_6H_4$-p-$OCH_3$ | —$CO_2H$ |
| 1248 | p-$[H_2N(CH_2)_9]C_6H_4CH(CH_3)$— | —$CH_2C_6H_4$-p-$CH_3$ | —$CO_2H$ |
| 1249 | p-$[H_2N(CH_2)_9]C_6H_4CH(CH_3)$— | —$CH_2C_6H_4$-p-F | —$CO_2H$ |
| 1250 | p-$[H_2N(CH_2)_9]C_6H_4CH(CH_3)$— | —$CH_2CH_2C_6H_5$ | —$CO_2H$ |
| 1251 | p-$[H_2N(CH_2)_9]C_6H_4CH(CH_3)$— | —$CH_2$-cyclo-$C_6H_{11}$ | —$CO_2H$ |
| 1252 | p-$[H_2N(CH_2)_9]C_6H_4CH(CH_3)$— | —$CH_2$-cyclo-$C_6H_{10}$-4-F | —$CO_2H$ |
| 1253 | p-$[H_2N(CH_2)_9]C_6H_4CH(CH_3)$— | —$CH_2$-cyclo-$C_6H_{10}$-4-$CH_3$ | —$CO_2H$ |
| 1254 | p-$[H_2N(CH_2)_9]C_6H_4CH(CH_3)$— | —$CH_2$-cyclo-$C_6H_{10}$-4-$OCH_3$ | —$CO_2H$ |
| 1255 | p-$[H_2N(CH_2)_9]C_6H_4CH(CH_3)$— | —$CH_2CH_2$-cyclo-$C_6H_{11}$ | —$CO_2H$ |
| 1256 | p-$[H_2N(CH_2)_9]C_6H_4CH(CH_3)$— | —$CH_2$-cyclo-$C_5H_9$ | —$CO_2H$ |
| 1257 | p-$[H_2N(CH_2)_9]C_6H_4CH(CH_3)$— | —$CH_2CH_2$-cyclo-$C_5H_9$ | —$CO_2H$ |
| 1258 | p-$[H_2N(CH_2)_9]C_6H_4CH(CH_3)$— | —$CH_2$-2-naphthyl | —$CO_2H$ |
| 1259 | p-$[H_2N(CH_2)_9]C_6H_4CH(CH_3)$— | —H | —$PO_3H_2$ |
| 1260 | p-$[H_2N(CH_2)_9]C_6H_4CH(CH_3)$— | —$CH_3$ | —$PO_3H_2$ |
| 1261 | p-$[H_2N(CH_2)_9]C_6H_4CH(CH_3)$— | —$CH_2CH_3$ | —$PO_3H_2$ |
| 1262 | p-$[H_2N(CH_2)_9]C_6H_4CH(CH_3)$— | —$CH_2CH_2CH_3$ | —$PO_3H_2$ |
| 1263 | p-$[H_2N(CH_2)_9]C_6H_4CH(CH_3)$— | —$CH_2CH_2CH_2CH_3$ | —$PO_3H_2$ |
| 1264 | p-$[H_2N(CH_2)_9]C_6H_4CH(CH_3)$— | —$CH_2CH_2CH_2CH_2CH_3$ | —$PO_3H_2$ |
| 1265 | p-$[H_2N(CH_2)_9]C_6H_4CH(CH_3)$— | —$CH_2CH_2CH_2CH_2CH_2CH_3$ | —$PO_3H_2$ |
| 1266 | p-$[H_2N(CH_2)_9]C_6H_4CH(CH_3)$— | —$CH(CH_3)_2$ | —$PO_3H_2$ |
| 1267 | p-$[H_2N(CH_2)_9]C_6H_4CH(CH_3)$— | —$CH_2CH(CH_3)_2$ | —$PO_3H_2$ |
| 1268 | p-$[H_2N(CH_2)_9]C_6H_4CH(CH_3)$— | —$CH_2CH_2CH(CH_3)_2$ | —$PO_3H_2$ |
| 1269 | p-$[H_2N(CH_2)_9]C_6H_4CH(CH_3)$— | -cyclo-$C_3H_5$ | —$PO_3H_2$ |
| 1270 | p-$[H_2N(CH_2)_9]C_6H_4CH(CH_3)$— | -cyclo-$C_4H_7$ | —$PO_3H_2$ |
| 1271 | p-$[H_2N(CH_2)_9]C_6H_4CH(CH_3)$— | -cyclo-$C_5H_9$ | —$PO_3H_2$ |
| 1272 | p-$[H_2N(CH_2)_9]C_6H_4CH(CH_3)$— | -cyclo-$C_6H_{11}$ | —$PO_3H_2$ |
| 1273 | p-$[H_2N(CH_2)_9]C_6H_4CH(CH_3)$— | -cyclo-$C_7H_{13}$ | —$PO_3H_2$ |
| 1274 | p-$[H_2N(CH_2)_9]C_6H_4CH(CH_3)$— | -cyclo-$C_8H_{15}$ | —$PO_3H_2$ |
| 1275 | p-$[H_2N(CH_2)_9]C_6H_4CH(CH_3)$— | —$CH(CH_3)(CH_2CH_3)$ | —$PO_3H_2$ |
| 1276 | p-$[H_2N(CH_2)_9]C_6H_4CH(CH_3)$— | —$CH(CH_2CH_3)_2$ | —$PO_3H_2$ |
| 1277 | p-$[H_2N(CH_2)_9]C_6H_4CH(CH_3)$— | —$CH(CH_3)(CH_2CH_2CH_3)$ | —$PO_3H_2$ |
| 1278 | p-$[H_2N(CH_2)_9]C_6H_4CH(CH_3)$— | —$C(CH_3)_3$ | —$PO_3H_2$ |
| 1279 | p-$[H_2N(CH_2)_9]C_6H_4CH(CH_3)$— | $HC{\equiv}CCH_2$— | —$PO_3H_2$ |
| 1280 | p-$[H_2N(CH_2)_9]C_6H_4CH(CH_3)$— | $H_2C{=}CH$— | —$PO_3H_2$ |
| 1281 | p-$[H_2N(CH_2)_9]C_6H_4CH(CH_3)$— | $H_2C{=}CHCH_2$— | —$PO_3H_2$ |
| 1282 | p-$[H_2N(CH_2)_9]C_6H_4CH(CH_3)$— | —$CH_2F$ | —$PO_3H_2$ |
| 1283 | p-$[H_2N(CH_2)_9]C_6H_4CH(CH_3)$— | —$CH_2C_6H_5$ | —$PO_3H_2$ |
| 1284 | p-$[H_2N(CH_2)_9]C_6H_4CH(CH_3)$— | —$CH_2C_6H_4$-p-$OCH_3$ | —$PO_3H_2$ |
| 1285 | p-$[H_2N(CH_2)_9]C_6H_4CH(CH_3)$— | —$CH_2C_6H_4$-p-$CH_3$ | —$PO_3H_2$ |
| 1286 | p-$[H_2N(CH_2)_9]C_6H_4CH(CH_3)$— | —$CH_2C_6H_4$-p-F | —$PO_3H_2$ |
| 1287 | p-$[H_2N(CH_2)_9]C_6H_4CH(CH_3)$— | —$CH_2CH_2C_6H_5$ | —$PO_3H_2$ |
| 1288 | p-$[H_2N(CH_2)_9]C_6H_4CH(CH_3)$— | —$CH_2$-cyclo-$C_6H_{11}$ | —$PO_3H_2$ |
| 1289 | p-$[H_2N(CH_2)_9]C_6H_4CH(CH_3)$— | —$CH_2$-cyclo-$C_6H_{10}$-4-F | —$PO_3H_2$ |
| 1290 | p-$[H_2N(CH_2)_9]C_6H_4CH(CH_3)$— | —$CH_2$-cyclo-$C_6H_{10}$-4-$CH_3$ | —$PO_3H_2$ |
| 1291 | p-$[H_2N(CH_2)_9]C_6H_4CH(CH_3)$— | —$CH_2$-cyclo-$C_6H_{10}$-4-$OCH_3$ | —$PO_3H_2$ |
| 1292 | p-$[H_2N(CH_2)_9]C_6H_4CH(CH_3)$— | —$CH_2CH_2$-cyclo-$C_6H_{11}$ | —$PO_3H_2$ |
| 1293 | p-$[H_2N(CH_2)_9]C_6H_4CH(CH_3)$— | —$CH_2$-cyclo-$C_5H_9$ | —$PO_3H_2$ |
| 1294 | p-$[H_2N(CH_2)_9]C_6H_4CH(CH_3)$— | —$CH_2CH_2$-cyclo-$C_5H_9$ | —$PO_3H_2$ |
| 1295 | p-$[H_2N(CH_2)_9]C_6H_4CH(CH_3)$— | —$CH_2$-2-naphthyl | —$PO_3H_2$ |
| 1296 | p-$[H_2N(CH_2)_9]C_6H_4CH(CH_3)$— | —H | -5-Tet |
| 1297 | p-$[H_2N(CH_2)_9]C_6H_4CH(CH_3)$— | —$CH_3$ | -5-Tet |
| 1298 | p-$[H_2N(CH_2)_9]C_6H_4CH(CH_3)$— | —$CH_2CH_3$ | -5-Tet |
| 1299 | p-$[H_2N(CH_2)_9]C_6H_4CH(CH_3)$— | —$CH_2CH_2CH_3$ | -5-Tet |
| 1300 | p-$[H_2N(CH_2)_9]C_6H_4CH(CH_3)$— | —$CH_2CH_2CH_2CH_3$ | -5-Tet |
| 1301 | p-$[H_2N(CH_2)_9]C_6H_4CH(CH_3)$— | —$CH_2CH_2CH_2CH_2CH_3$ | -5-Tet |
| 1302 | p-$[H_2N(CH_2)_9]C_6H_4CH(CH_3)$— | —$CH_2CH_2CH_2CH_2CH_2CH_3$ | -5-Tet |
| 1303 | p-$[H_2N(CH_2)_9]C_6H_4CH(CH_3)$— | —$CH(CH_3)_2$ | -5-Tet |
| 1304 | p-$[H_2N(CH_2)_9]C_6H_4CH(CH_3)$— | —$CH_2CH(CH_3)_2$ | -5-Tet |
| 1305 | p-$[H_2N(CH_2)_9]C_6H_4CH(CH_3)$— | —$CH_2CH_2CH(CH_3)_2$ | -5-Tet |
| 1306 | p-$[H_2N(CH_2)_9]C_6H_4CH(CH_3)$— | -cyclo-$C_3H_5$ | -5-Tet |
| 1307 | p-$[H_2N(CH_2)_9]C_6H_4CH(CH_3)$— | -cyclo-$C_4H_7$ | -5-Tet |
| 1308 | p-$[H_2N(CH_2)_9]C_6H_4CH(CH_3)$— | -cyclo-$C_5H_9$ | -5-Tet |
| 1309 | p-$[H_2N(CH_2)_9]C_6H_4CH(CH_3)$— | -cyclo-$C_6H_{11}$ | -5-Tet |
| 1310 | p-$[H_2N(CH_2)_9]C_6H_4CH(CH_3)$— | -cyclo-$C_7H_{13}$ | -5-Tet |
| 1311 | p-$[H_2N(CH_2)_9]C_6H_4CH(CH_3)$— | -cyclo-$C_8H_{15}$ | -5-Tet |

TABLE I-continued

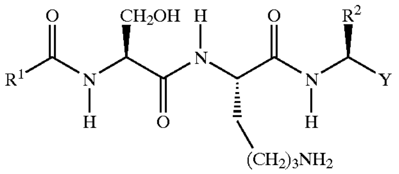

| Ex. No. | $R^1$ | $R^2$ | Y |
|---|---|---|---|
| 1312 | p-$[H_2N(CH_2)_9]C_6H_4CH(CH_3)$— | —$CH(CH_3)(CH_2CH_3)$ | -5-Tet |
| 1313 | p-$[H_2N(CH_2)_9]C_6H_4CH(CH_3)$— | —$CH(CH_2CH_3)_2$ | -5-Tet |
| 1314 | p-$[H_2N(CH_2)_9]C_6H_4CH(CH_3)$— | —$CH(CH_3)(CH_2CH_2CH_3)$ | -5-Tet |
| 1315 | p-$[H_2N(CH_2)_9]C_6H_4CH(CH_3)$— | —$C(CH_3)_3$ | -5-Tet |
| 1316 | p-$[H_2N(CH_2)_9]C_6H_4CH(CH_3)$— | $HC{\equiv}CCH_2$— | -5-Tet |
| 1317 | p-$[H_2N(CH_2)_9]C_6H_4CH(CH_3)$— | $H_2C{=}CH$— | -5-Tet |
| 1318 | p-$[H_2N(CH_2)_9]C_6H_4CH(CH_3)$— | $H_2C{=}CHCH_2$— | -5-Tet |
| 1319 | p-$[H_2N(CH_2)_9]C_6H_4CH(CH_3)$— | —$CH_2F$ | -5-Tet |
| 1320 | p-$[H_2N(CH_2)_9]C_6H_4CH(CH_3)$— | —$CH_2C_6H_5$ | -5-Tet |
| 1321 | p-$[H_2N(CH_2)_9]C_6H_4CH(CH_3)$— | —$CH_2C_6H_4$-p-$OCH_3$ | -5-Tet |
| 1322 | p-$[H_2N(CH_2)_9]C_6H_4CH(CH_3)$— | —$CH_2C_6H_4$-p-$CH_3$ | -5-Tet |
| 1323 | p-$[H_2N(CH_2)_9]C_6H_4CH(CH_3)$— | —$CH_2C_6H_4$-p-F | -5-Tet |
| 1324 | p-$[H_2N(CH_2)_9]C_6H_4CH(CH_3)$— | —$CH_2CH_2C_6H_5$ | -5-Tet |
| 1325 | p-$[H_2N(CH_2)_9]C_6H_4CH(CH_3)$— | —$CH_2$-cyclo-$C_6H_{11}$ | -5-Tet |
| 1326 | p-$[H_2N(CH_2)_9]C_6H_4CH(CH_3)$— | —$CH_2$-cyclo-$C_6H_{10}$-4-F | -5-Tet |
| 1327 | p-$[H_2N(CH_2)_9]C_6H_4CH(CH_3)$— | —$CH_2$-cyclo-$C_6H_{10}$-4-$CH_3$ | -5-Tet |
| 1328 | p-$[H_2N(CH_2)_9]C_6H_4CH(CH_3)$— | —$CH_2$-cyclo-$C_6H_{10}$-4-$OCH_3$ | -5-Tet |
| 1329 | p-$[H_2N(CH_2)_9]C_6H_4CH(CH_3)$— | —$CH_2CH_2$-cyclo-$C_6H_{11}$ | -5-Tet |
| 1330 | p-$[H_2N(CH_2)_9]C_6H_4CH(CH_3)$— | —$CH_2$-cyclo-$C_5H_9$ | -5-Tet |
| 1331 | p-$[H_2N(CH_2)_9]C_6H_4CH(CH_3)$— | —$CH_2CH_2$-cyclo-$C_5H_9$ | -5-Tet |
| 1332 | p-$[H_2N(CH_2)_9]C_6H_4CH(CH_3)$— | —$CH_2$-2-naphthyl | -5-Tet |
| 1333 | p-$[H_2N(CH_2)_{10}]C_6H_4CH(CH_3)$— | —H | —$CO_2H$ |
| 1334 | p-$[H_2N(CH_2)_{10}]C_6H_4CH(CH_3)$— | —$CH_3$ | —$CO_2H$ |
| 1335 | p-$[H_2N(CH_2)_{10}]C_6H_4CH(CH_3)$— | —$CH_2CH_3$ | —$CO_2H$ |
| 1336 | p-$[H_2N(CH_2)_{10}]C_6H_4CH(CH_3)$— | —$CH_2CH_2CH_3$ | —$CO_2H$ |
| 1337 | p-$[H_2N(CH_2)_{10}]C_6H_4CH(CH_3)$— | —$CH_2CH_2CH_2CH_3$ | —$CO_2H$ |
| 1338 | p-$[H_2N(CH_2)_{10}]C_6H_4CH(CH_3)$— | —$CH_2CH_2CH_2CH_2CH_3$ | —$CO_2H$ |
| 1339 | p-$[H_2N(CH_2)_{10}]C_6H_4CH(CH_3)$— | —$CH_2CH_2CH_2CH_2CH_2CH_3$ | —$CO_2H$ |
| 1340 | p-$[H_2N(CH_2)_{10}]C_6H_4CH(CH_3)$— | —$CH(CH_3)_2$ | —$CO_2H$ |
| 1341 | p-$[H_2N(CH_2)_{10}]C_6H_4CH(CH_3)$— | —$CH_2CH(CH_3)_2$ | —$CO_2H$ |
| 1342 | p-$[H_2N(CH_2)_{10}]C_6H_4CH(CH_3)$— | —$CH_2CH_2CH(CH_3)_2$ | —$CO_2H$ |
| 1343 | p-$[H_2N(CH_2)_{10}]C_6H_4CH(CH_3)$— | -cyclo-$C_3H_5$ | —$CO_2H$ |
| 1344 | p-$[H_2N(CH_2)_{10}]C_6H_4CH(CH_3)$— | -cyclo-$C_4H_7$ | —$CO_2H$ |
| 1345 | p-$[H_2N(CH_2)_{10}]C_6H_4CH(CH_3)$— | -cyclo-$C_5H_9$ | —$CO_2H$ |
| 1346 | p-$[H_2N(CH_2)_{10}]C_6H_4CH(CH_3)$— | -cyclo-$C_6H_{11}$ | —$CO_2H$ |
| 1347 | p-$[H_2N(CH_2)_{10}]C_6H_4CH(CH_3)$— | -cyclo-$C_7H_{13}$ | —$CO_2H$ |
| 1348 | p-$[H_2N(CH_2)_{10}]C_6H_4CH(CH_3)$— | -cyclo-$C_8H_{15}$ | —$CO_2H$ |
| 1349 | p-$[H_2N(CH_2)_{10}]C_6H_4CH(CH_3)$— | —$CH(CH_3)(CH_2CH_3)$ | —$CO_2H$ |
| 1350 | p-$[H_2N(CH_2)_{10}]C_6H_4CH(CH_3)$— | —$CH(CH_2CH_3)_2$ | —$CO_2H$ |
| 1351 | p-$[H_2N(CH_2)_{10}]C_6H_4CH(CH_3)$— | —$CH(CH_3)(CH_2CH_2CH_3)$ | —$CO_2H$ |
| 1352 | p-$[H_2N(CH_2)_{10}]C_6H_4CH(CH_3)$— | —$C(CH_3)_3$ | —$CO_2H$ |
| 1353 | p-$[H_2N(CH_2)_{10}]C_6H_4CH(CH_3)$— | $HC{\equiv}CCH_2$— | —$CO_2H$ |
| 1354 | p-$[H_2N(CH_2)_{10}]C_6H_4CH(CH_3)$— | $H_2C{=}CH$— | —$CO_2H$ |
| 1355 | p-$[H_2N(CH_2)_{10}]C_6H_4CH(CH_3)$— | $H_2C{=}CHCH_2$— | —$CO_2H$ |
| 1356 | p-$[H_2N(CH_2)_{10}]C_6H_4CH(CH_3)$— | —$CH_2F$ | —$CO_2H$ |
| 1357 | p-$[H_2N(CH_2)_{10}]C_6H_4CH(CH_3)$— | —$CH_2C_6H_5$ | —$CO_2H$ |
| 1358 | p-$[H_2N(CH_2)_{10}]C_6H_4CH(CH_3)$— | —$CH_2C_6H_4$-p-$OCH_3$ | —$CO_2H$ |
| 1359 | p-$[H_2N(CH_2)_{10}]C_6H_4CH(CH_3)$— | —$CH_2C_6H_4$-p-$CH_3$ | —$CO_2H$ |
| 1360 | p-$[H_2N(CH_2)_{10}]C_6H_4CH(CH_3)$— | —$CH_2C_6H_4$-p-F | —$CO_2H$ |
| 1361 | p-$[H_2N(CH_2)_{10}]C_6H_4CH(CH_3)$— | —$CH_2CH_2C_6H_5$ | —$CO_2H$ |
| 1362 | p-$[H_2N(CH_2)_{10}]C_6H_4CH(CH_3)$— | —$CH_2$-cyclo-$C_6H_{11}$ | —$CO_2H$ |
| 1363 | p-$[H_2N(CH_2)_{10}]C_6H_4CH(CH_3)$— | —$CH_2$-cyclo-$C_6H_{10}$-4-F | —$CO_2H$ |
| 1364 | p-$[H_2N(CH_2)_{10}]C_6H_4CH(CH_3)$— | —$CH_2$-cyclo-$C_6H_{10}$-4-$CH_3$ | —$CO_2H$ |
| 1365 | p-$[H_2N(CH_2)_{10}]C_6H_4CH(CH_3)$— | —$CH_2$-cyclo-$C_6H_{10}$-4-$OCH_3$ | —$CO_2H$ |
| 1366 | p-$[H_2N(CH_2)_{10}]C_6H_4CH(CH_3)$— | —$CH_2CH_2$-cyclo-$C_6H_{11}$ | —$CO_2H$ |
| 1367 | p-$[H_2N(CH_2)_{10}]C_6H_4CH(CH_3)$— | —$CH_2$-cyclo-$C_5H_9$ | —$CO_2H$ |
| 1368 | p-$[H_2N(CH_2)_{10}]C_6H_4CH(CH_3)$— | —$CH_2CH_2$-cyclo-$C_5H_9$ | —$CO_2H$ |
| 1369 | p-$[H_2N(CH_2)_{10}]C_6H_4CH(CH_3)$— | —$CH_2$-2-naphthyl | —$CO_2H$ |
| 1370 | p-$[H_2N(CH_2)_{10}]C_6H_4CH(CH_3)$— | —H | —$PO_3H_2$ |
| 1371 | p-$[H_2N(CH_2)_{10}]C_6H_4CH(CH_3)$— | —$CH_3$ | —$PO_3H_2$ |
| 1372 | p-$[H_2N(CH_2)_{10}]C_6H_4CH(CH_3)$— | —$CH_2CH_3$ | —$PO_3H_2$ |
| 1373 | p-$[H_2N(CH_2)_{10}]C_6H_4CH(CH_3)$— | —$CH_2CH_2CH_3$ | —$PO_3H_2$ |
| 1374 | p-$[H_2N(CH_2)_{10}]C_6H_4CH(CH_3)$— | —$CH_2CH_2CH_2CH_3$ | —$PO_3H_2$ |
| 1375 | p-$[H_2N(CH_2)_{10}]C_6H_4CH(CH_3)$— | —$CH_2CH_2CH_2CH_2CH_3$ | —$PO_3H_2$ |
| 1376 | p-$[H_2N(CH_2)_{10}]C_6H_4CH(CH_3)$— | —$CH_2CH_2CH_2CH_2CH_2CH_3$ | —$PO_3H_2$ |
| 1377 | p-$[H_2N(CH_2)_{10}]C_6H_4CH(CH_3)$— | —$CH(CH_3)_2$ | —$PO_3H_2$ |

TABLE I-continued

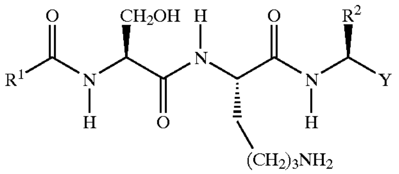

| Ex. No. | $R^1$ | $R^2$ | Y |
|---|---|---|---|
| 1378 | p-$[H_2N(CH_2)_{10}]C_6H_4CH(CH_3)$— | —$CH_2CH(CH_3)_2$ | —$PO_3H_2$ |
| 1379 | p-$[H_2N(CH_2)_{10}]C_6H_4CH(CH_3)$— | —$CH_2CH_2CH(CH_3)_2$ | —$PO_3H_2$ |
| 1380 | p-$[H_2N(CH_2)_{10}]C_6H_4CH(CH_3)$— | -cyclo-$C_3H_5$ | —$PO_3H_2$ |
| 1381 | p-$[H_2N(CH_2)_{10}]C_6H_4CH(CH_3)$— | -cyclo-$C_4H_7$ | —$PO_3H_2$ |
| 1382 | p-$[H_2N(CH_2)_{10}]C_6H_4CH(CH_3)$— | -cyclo-$C_5H_9$ | —$PO_3H_2$ |
| 1383 | p-$[H_2N(CH_2)_{10}]C_6H_4CH(CH_3)$— | -cyclo-$C_6H_{11}$ | —$PO_3H_2$ |
| 1384 | p-$[H_2N(CH_2)_{10}]C_6H_4CH(CH_3)$— | -cyclo-$C_7H_{13}$ | —$PO_3H_2$ |
| 1385 | p-$[H_2N(CH_2)_{10}]C_6H_4CH(CH_3)$— | -cyclo-$C_8H_{15}$ | —$PO_3H_2$ |
| 1386 | p-$[H_2N(CH_2)_{10}]C_6H_4CH(CH_3)$— | —$CH(CH_3)(CH_2CH_3)$ | —$PO_3H_2$ |
| 1387 | p-$[H_2N(CH_2)_{10}]C_6H_4CH(CH_3)$— | —$CH(CH_2CH_3)_2$ | —$PO_3H_2$ |
| 1388 | p-$[H_2N(CH_2)_{10}]C_6H_4CH(CH_3)$— | —$CH(CH_3)(CH_2CH_2CH_3)$ | —$PO_3H_2$ |
| 1389 | p-$[H_2N(CH_2)_{10}]C_6H_4CH(CH_3)$— | —$C(CH_3)_3$ | —$PO_3H_2$ |
| 1390 | p-$[H_2N(CH_2)_{10}]C_6H_4CH(CH_3)$— | $HC{\equiv}CCH_2$— | —$PO_3H_2$ |
| 1391 | p-$[H_2N(CH_2)_{10}]C_6H_4CH(CH_3)$— | $H_2C{=}CH$— | —$PO_3H_2$ |
| 1392 | p-$[H_2N(CH_2)_{10}]C_6H_4CH(CH_3)$— | $H_2C{=}CHCH_2$— | —$PO_3H_2$ |
| 1393 | p-$[H_2N(CH_2)_{10}]C_6H_4CH(CH_3)$— | —$CH_2F$ | —$PO_3H_2$ |
| 1394 | p-$[H_2N(CH_2)_{10}]C_6H_4CH(CH_3)$— | —$CH_2C_6H_5$ | —$PO_3H_2$ |
| 1395 | p-$[H_2N(CH_2)_{10}]C_6H_4CH(CH_3)$— | —$CH_2C_6H_4$-p-$OCH_3$ | —$PO_3H_2$ |
| 1396 | p-$[H_2N(CH_2)_{10}]C_6H_4CH(CH_3)$— | —$CH_2C_6H_4$-p-$CH_3$ | —$PO_3H_2$ |
| 1397 | p-$[H_2N(CH_2)_{10}]C_6H_4CH(CH_3)$— | —$CH_2C_6H_4$-p-F | —$PO_3H_2$ |
| 1398 | p-$[H_2N(CH_2)_{10}]C_6H_4CH(CH_3)$— | —$CH_2CH_2C_6H_5$ | —$PO_3H_2$ |
| 1399 | p-$[H_2N(CH_2)_{10}]C_6H_4CH(CH_3)$— | —$CH_2$-cyclo-$C_6H_{11}$ | —$PO_3H_2$ |
| 1400 | p-$[H_2N(CH_2)_{10}]C_6H_4CH(CH_3)$— | —$CH_2$-cyclo-$C_6H_{10}$-4-F | —$PO_3H_2$ |
| 1401 | p-$[H_2N(CH_2)_{10}]C_6H_4CH(CH_3)$— | —$CH_2$-cyclo-$C_6H_{10}$-4-$CH_3$ | —$PO_3H_2$ |
| 1402 | p-$[H_2N(CH_2)_{10}]C_6H_4CH(CH_3)$— | —$CH_2$-cyclo-$C_6H_{10}$-4-$OCH_3$ | —$PO_3H_2$ |
| 1403 | p-$[H_2N(CH_2)_{10}]C_6H_4CH(CH_3)$— | —$CH_2CH_2$-cyclo-$C_6H_{11}$ | —$PO_3H_2$ |
| 1404 | p-$[H_2N(CH_2)_{10}]C_6H_4CH(CH_3)$— | —$CH_2$-cyclo-$C_5H_9$ | —$PO_3H_2$ |
| 1405 | p-$[H_2N(CH_2)_{10}]C_6H_4CH(CH_3)$— | —$CH_2CH_2$-cyclo-$C_5H_9$ | —$PO_3H_2$ |
| 1406 | p-$[H_2N(CH_2)_{10}]C_6H_4CH(CH_3)$— | —$CH_2$-2-naphthyl | —$PO_3H_2$ |
| 1407 | p-$[H_2N(CH_2)_{10}]C_6H_4CH(CH_3)$— | —H | -5-Tet |
| 1408 | p-$[H_2N(CH_2)_{10}]C_6H_4CH(CH_3)$— | —$CH_3$ | -5-Tet |
| 1409 | p-$[H_2N(CH_2)_{10}]C_6H_4CH(CH_3)$— | —$CH_2CH_3$ | -5-Tet |
| 1410 | p-$[H_2N(CH_2)_{10}]C_6H_4CH(CH_3)$— | —$CH_2CH_2CH_3$ | -5-Tet |
| 1411 | p-$[H_2N(CH_2)_{10}]C_6H_4CH(CH_3)$— | —$CH_2CH_2CH_2CH_3$ | -5-Tet |
| 1412 | p-$[H_2N(CH_2)_{10}]C_6H_4CH(CH_3)$— | —$CH_2CH_2CH_2CH_2CH_3$ | -5-Tet |
| 1413 | p-$[H_2N(CH_2)_{10}]C_6H_4CH(CH_3)$— | —$CH_2CH_2CH_2CH_2CH_2CH_3$ | -5-Tet |
| 1414 | p-$[H_2N(CH_2)_{10}]C_6H_4CH(CH_3)$— | —$CH(CH_3)_2$ | -5-Tet |
| 1415 | p-$[H_2N(CH_2)_{10}]C_6H_4CH(CH_3)$— | —$CH_2CH(CH_3)_2$ | -5-Tet |
| 1416 | p-$[H_2N(CH_2)_{10}]C_6H_4CH(CH_3)$— | —$CH_2CH_2CH(CH_3)_2$ | -5-Tet |
| 1417 | p-$[H_2N(CH_2)_{10}]C_6H_4CH(CH_3)$— | -cyclo-$C_3H_5$ | -5-Tet |
| 1418 | p-$[H_2N(CH_2)_{10}]C_6H_4CH(CH_3)$— | -cyclo-$C_4H_7$ | -5-Tet |
| 1419 | p-$[H_2N(CH_2)_{10}]C_6H_4CH(CH_3)$— | -cyclo-$C_5H_9$ | -5-Tet |
| 1420 | p-$[H_2N(CH_2)_{10}]C_6H_4CH(CH_3)$— | -cyclo-$C_6H_{11}$ | -5-Tet |
| 1421 | p-$[H_2N(CH_2)_{10}]C_6H_4CH(CH_3)$— | -cyclo-$C_7H_{13}$ | -5-Tet |
| 1422 | p-$[H_2N(CH_2)_{10}]C_6H_4CH(CH_3)$— | -cyclo-$C_8H_{15}$ | -5-Tet |
| 1423 | p-$[H_2N(CH_2)_{10}]C_6H_4CH(CH_3)$— | —$CH(CH_3)(CH_2CH_3)$ | -5-Tet |
| 1424 | p-$[H_2N(CH_2)_{10}]C_6H_4CH(CH_3)$— | —$CH(CH_2CH_3)_2$ | -5-Tet |
| 1425 | p-$[H_2N(CH_2)_{10}]C_6H_4CH(CH_3)$— | —$CH(CH_3)(CH_2CH_2CH_3)$ | -5-Tet |
| 1426 | p-$[H_2N(CH_2)_{10}]C_6H_4CH(CH_3)$— | —$C(CH_3)_3$ | -5-Tet |
| 1427 | p-$[H_2N(CH_2)_{10}]C_6H_4CH(CH_3)$— | $HC{\equiv}CCH_2$— | -5-Tet |
| 1428 | p-$[H_2N(CH_2)_{10}]C_6H_4CH(CH_3)$— | $H_2C{=}CH$— | -5-Tet |
| 1429 | p-$[H_2N(CH_2)_{10}]C_6H_4CH(CH_3)$— | $H_2C{=}CHCH_2$— | -5-Tet |
| 1430 | p-$[H_2N(CH_2)_{10}]C_6H_4CH(CH_3)$— | —$CH_2F$ | -5-Tet |
| 1431 | p-$[H_2N(CH_2)_{10}]C_6H_4CH(CH_3)$— | —$CH_2C_6H_5$ | -5-Tet |
| 1432 | p-$[H_2N(CH_2)_{10}]C_6H_4CH(CH_3)$— | —$CH_2C_6H_4$-p-$OCH_3$ | -5-Tet |
| 1433 | p-$[H_2N(CH_2)_{10}]C_6H_4CH(CH_3)$— | —$CH_2C_6H_4$-p-$CH_3$ | -5-Tet |
| 1434 | p-$[H_2N(CH_2)_{10}]C_6H_4CH(CH_3)$— | —$CH_2C_6H_4$-p-F | -5-Tet |
| 1435 | p-$[H_2N(CH_2)_{10}]C_6H_4CH(CH_3)$— | —$CH_2CH_2C_6H_5$ | -5-Tet |
| 1436 | p-$[H_2N(CH_2)_{10}]C_6H_4CH(CH_3)$— | —$CH_2$-cyclo-$C_6H_{11}$ | -5-Tet |
| 1437 | p-$[H_2N(CH_2)_{10}]C_6H_4CH(CH_3)$— | —$CH_2$-cyclo-$C_6H_{10}$-4-F | -5-Tet |
| 1438 | p-$[H_2N(CH_2)_{10}]C_6H_4CH(CH_3)$— | —$CH_2$-cyclo-$C_6H_{10}$-4-$CH_3$ | -5-Tet |
| 1439 | p-$[H_2N(CH_2)_{10}]C_6H_4CH(CH_3)$— | —$CH_2$-cyclo-$C_6H_{10}$-4-$OCH_3$ | -5-Tet |
| 1440 | p-$[H_2N(CH_2)_{10}]C_6H_4CH(CH_3)$— | —$CH_2CH_2$-cyclo-$C_6H_{11}$ | -5-Tet |
| 1441 | p-$[H_2N(CH_2)_{10}]C_6H_4CH(CH_3)$— | —$CH_2$-cyclo-$C_5H_9$ | -5-Tet |
| 1442 | p-$[H_2N(CH_2)_{10}]C_6H_4CH(CH_3)$— | —$CH_2CH_2$-cyclo-$C_5H_9$ | -5-Tet |
| 1443 | p-$[H_2N(CH_2)_{10}]C_6H_4CH(CH_3)$— | —$CH_2$-2-naphthyl | -5-Tet |

TABLE I-continued
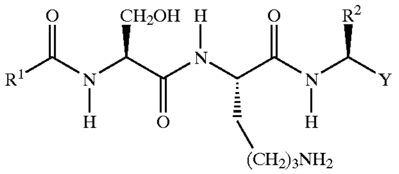
| Ex. No. | $R^1$ | $R^2$ | Y |
|---|---|---|---|
| 1444 | 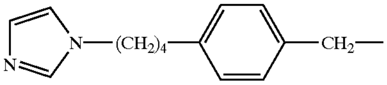 | —H | $—CO_2H$ |
| 1445 | 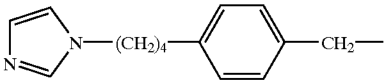 | $—CH_3$ | $—CO_2H$ |
| 1446 | 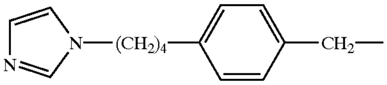 | $—CH_2CH_3$ | $—CO_2H$ |
| 1447 | 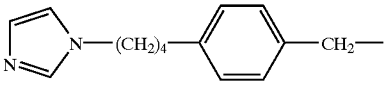 | $—CH_2CH_2CH_3$ | $—CO_2H$ |
| 1448 | 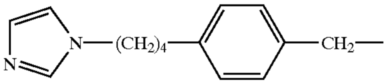 | $—CH_2CH_2CH_2CH_3$ | $—CO_2H$ |
| 1449 | 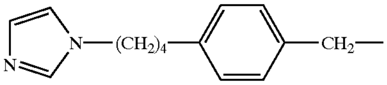 | $—CH_2CH_2CH_2CH_2CH_3$ | $—CO_2H$ |
| 1450 | 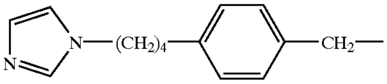 | $—CH_2CH_2CH_2CH_2CH_2CH_3$ | $—CO_2H$ |
| 1451 | 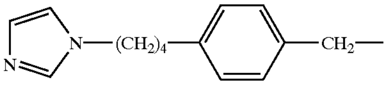 | $—CH(CH_3)_2$ | $—CO_2H$ |
| 1452 | 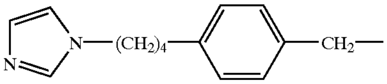 | $—CH_2CH(CH_3)_2$ | $—CO_2H$ |
| 1453 | 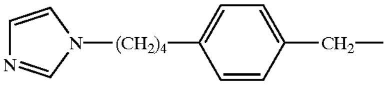 | $—CH_2CH_2CH(CH_3)_2$ | $—CO_2H$ |
| 1454 | 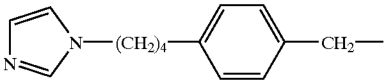 | $\text{-cyclo-}C_3H_5$ | $—CO_2H$ |
| 1455 | 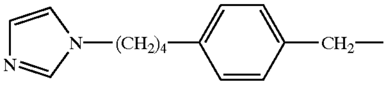 | $\text{-cyclo-}C_4H_7$ | $—CO_2H$ |
| 1456 | 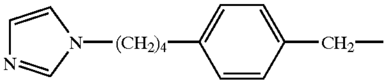 | $\text{-cyclo-}C_5H_9$ | $—CO_2H$ |

TABLE I-continued
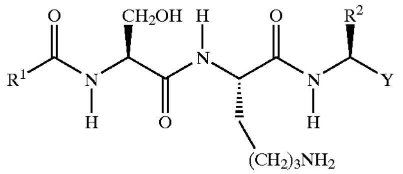
| Ex. No. | $R^1$ | $R^2$ | Y |
|---|---|---|---|
| 1457 | 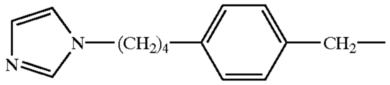 | -cyclo-$C_6H_{11}$ | —$CO_2H$ |
| 1458 | 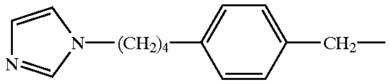 | -cyclo-$C_7H_{13}$ | —$CO_2H$ |
| 1459 | 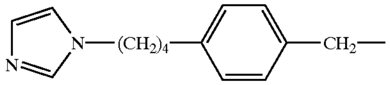 | -cyclo-$C_8H_{15}$ | —$CO_2H$ |
| 1460 | 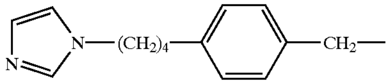 | —$CH(CH_3)(CH_2CH_3)$ | —$CO_2H$ |
| 1461 | 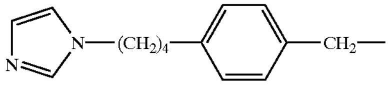 | —$CH(CH_2CH_3)_2$ | —$CO_2H$ |
| 1462 | 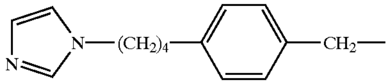 | —$CH(CH_3)(CH_2CH_2CH_3)$ | —$CO_2H$ |
| 1463 | 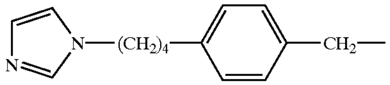 | —$C(CH_3)_3$ | —$CO_2H$ |
| 1464 | 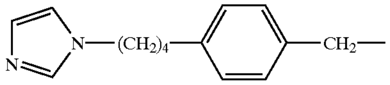 | $HC{\equiv}CCH_2$— | —$CO_2H$ |
| 1465 | 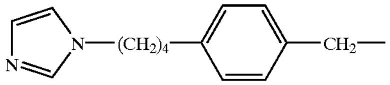 | $H_2C{=}CH$— | —$CO_2H$ |
| 1466 | 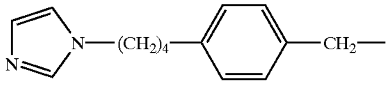 | $H_2C{=}CHCH_2$— | —$CO_2H$ |
| 1467 | 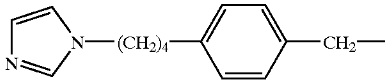 | —$CH_2F$ | —$CO_2H$ |
| 1468 | 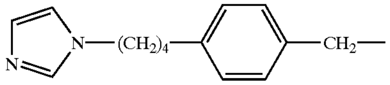 | —$CH_2C_6H_5$ | —$CO_2H$ |
| 1469 | 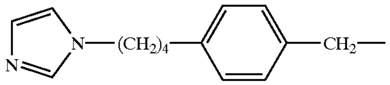 | —$CH_2C_6H_4$-p-$OCH_3$ | —$CO_2H$ |

TABLE I-continued
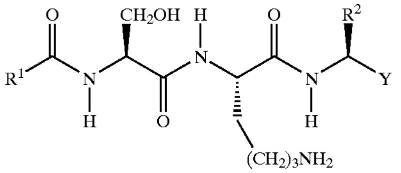
| Ex. No. | $R^1$ | $R^2$ | Y |
|---|---|---|---|
| 1470 | 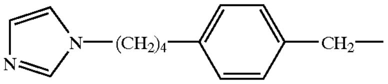 | $—CH_2C_6H_4$-p-$CH_3$ | $—CO_2H$ |
| 1471 | 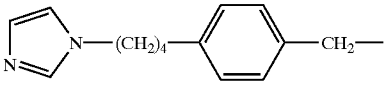 | $—CH_2C_6H_4$-p-F | $—CO_2H$ |
| 1472 | 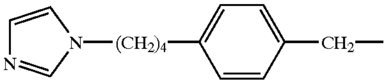 | $—CH_2CH_2C_6H_5$ | $—CO_2H$ |
| 1473 | 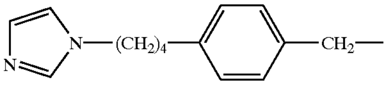 | $—CH_2$-cyclo-$C_6H_{11}$ | $—CO_2H$ |
| 1474 | 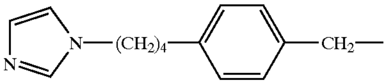 | $—CH_2$-cyclo-$C_6H_{10}$-4-F | $—CO_2H$ |
| 1475 | 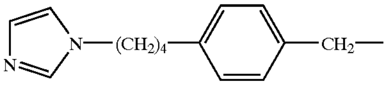 | $—CH_2$-cyclo-$C_6H_{10}$-4-$CH_3$ | $—CO_2H$ |
| 1476 | 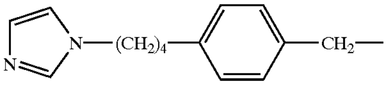 | $—CH_2$-cyclo-$C_6H_{10}$-4-$OCH_3$ | $—CO_2H$ |
| 1477 | 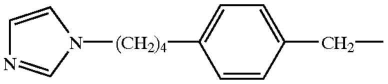 | $—CH_2CH_2$-cyclo-$C_6H_{11}$ | $—CO_2H$ |
| 1478 | 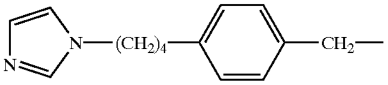 | $—CH_2$-cyclo-$C_5H_9$ | $—CO_2H$ |
| 1479 | 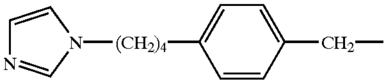 | $—CH_2CH_2$-cyclo-$C_5H_9$ | $—CO_2H$ |
| 1480 | 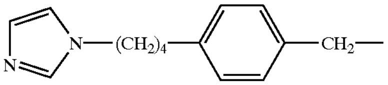 | $—CH_2$-2-naphthyl | $—CO_2H$ |
| 1481 | 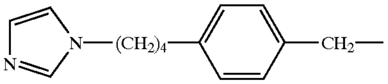 | —H | $—PO_3H_2$ |
| 1482 | 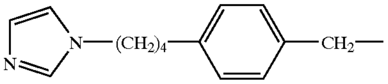 | $—CH_3$ | $—PO_3H_2$ |

TABLE I-continued
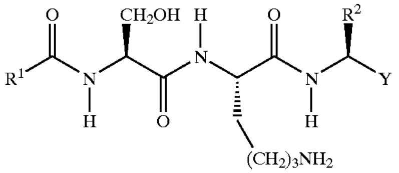
| Ex. No. | $R^1$ | $R^2$ | Y |
|---|---|---|---|
| 1483 | 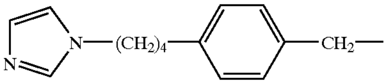 | $—CH_2CH_3$ | $—PO_3H_2$ |
| 1484 | 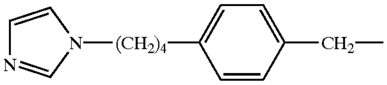 | $—CH_2CH_2CH_3$ | $—PO_3H_2$ |
| 1485 | 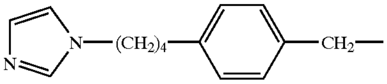 | $—CH_2CH_2CH_2CH_3$ | $—PO_3H_2$ |
| 1486 | 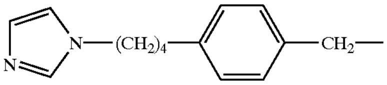 | $—CH_2CH_2CH_2CH_2CH_3$ | $—PO_3H_2$ |
| 1487 | 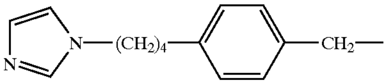 | $—CH_2CH_2CH_2CH_2CH_2CH_3$ | $—PO_3H_2$ |
| 1488 | 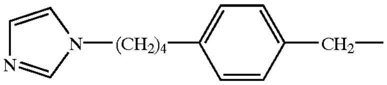 | $—CH(CH_3)_2$ | $—PO_3H_2$ |
| 1489 | 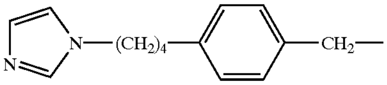 | $—CH_2CH(CH_3)_2$ | $—PO_3H_2$ |
| 1490 | 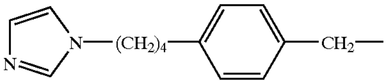 | $—CH_2CH_2CH(CH_3)_2$ | $—PO_3H_2$ |
| 1491 | 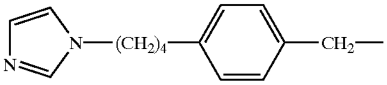 | -cyclo-$C_3H_5$ | $—PO_3H_2$ |
| 1492 | 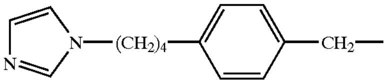 | -cyclo-$C_4H_7$ | $—PO_3H_2$ |
| 1493 | 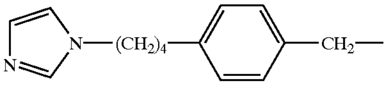 | -cyclo-$C_5H_9$ | $—PO_3H_2$ |
| 1494 | 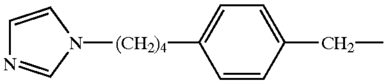 | -cyclo-$C_6H_{11}$ | $—PO_3H_2$ |
| 1495 | 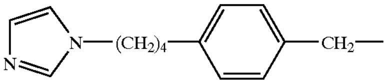 | -cyclo-$C_7H_{13}$ | $—PO_3H_2$ |

TABLE I-continued
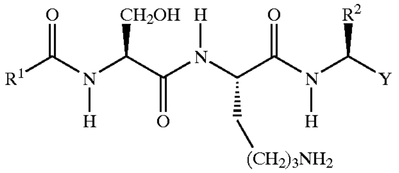
| Ex. No. | $R^1$ | $R^2$ | Y |
|---|---|---|---|
| 1496 | 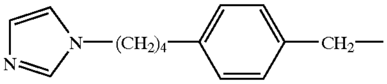 | -cyclo-$C_8H_{15}$ | $—PO_3H_2$ |
| 1497 | 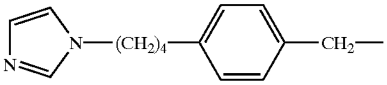 | $—CH(CH_3)(CH_2CH_3)$ | $—PO_3H_2$ |
| 1498 | 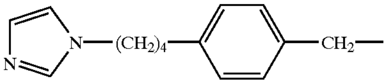 | $—CH(CH_2CH_3)_2$ | $—PO_3H_2$ |
| 1499 | 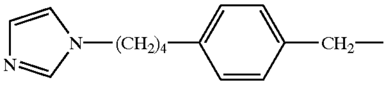 | $—CH(CH_3)(CH_2CH_2CH_3)$ | $—PO_3H_2$ |
| 1500 | 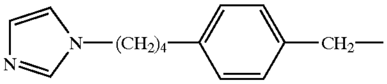 | $—C(CH_3)_3$ | $—PO_3H_2$ |
| 1501 | 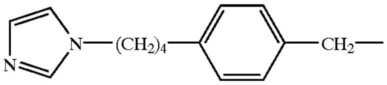 | $HC{\equiv}CCH_2—$ | $—PO_3H_2$ |
| 1502 | 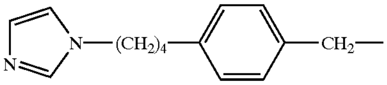 | $H_2C{=}CH—$ | $—PO_3H_2$ |
| 1503 | 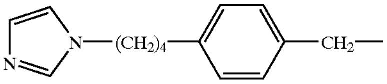 | $H_2C{=}CHCH_2—$ | $—PO_3H_2$ |
| 1504 | 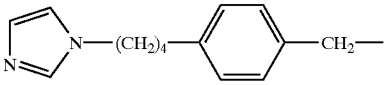 | $—CH_2F$ | $—PO_3H_2$ |
| 1505 | 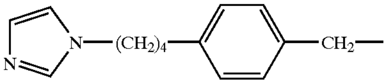 | $—CH_2C_6H_5$ | $—PO_3H_2$ |
| 1506 | 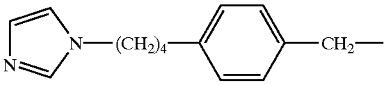 | $—CH_2C_6H_4$-p-$OCH_3$ | $—PO_3H_2$ |
| 1507 | 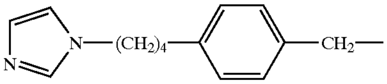 | $—CH_2C_6H_4$-p-$CH_3$ | $—PO_3H_2$ |
| 1508 | 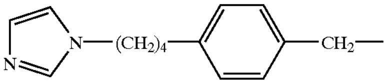 | $—CH_2C_6H_4$-p-F | $—PO_3H_2$ |

TABLE I-continued
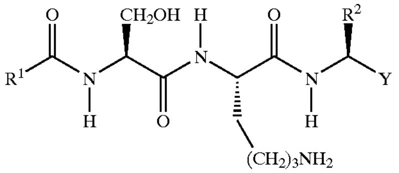
| Ex. No. | $R^1$ | $R^2$ | Y |
| --- | --- | --- | --- |
| 1509 | 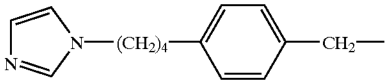 | $—CH_2CH_2C_6H_5$ | $—PO_3H_2$ |
| 1510 | 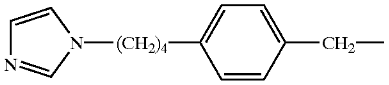 | $—CH_2$-cyclo-$C_6H_{11}$ | $—PO_3H_2$ |
| 1511 | 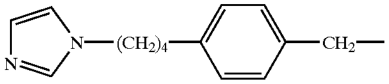 | $—CH_2$-cyclo-$C_6H_{10}$-4-F | $—PO_3H_2$ |
| 1512 | 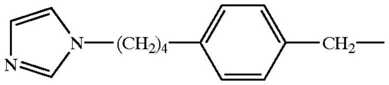 | $—CH_2$-cyclo-$C_6H_{10}$-4-$CH_3$ | $—PO_3H_2$ |
| 1513 | 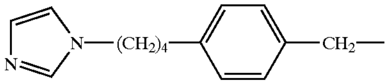 | $—CH_2$-cyclo-$C_6H_{10}$-4-$OCH_3$ | $—PO_3H_2$ |
| 1514 | 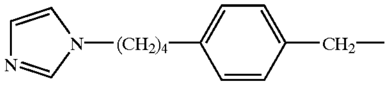 | $—CH_2CH_2$-cyclo-$C_6H_{11}$ | $—PO_3H_2$ |
| 1515 | 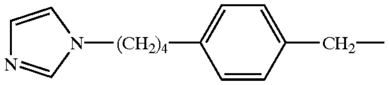 | $—CH_2$-cyclo-$C_5H_9$ | $—PO_3H_2$ |
| 1516 | 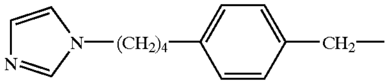 | $—CH_2CH_2$-cyclo-$C_5H_9$ | $—PO_3H_2$ |
| 1517 | 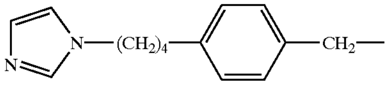 | $—CH_2$-2-naphthyl | $—PO_3H_2$ |
| 1518 | 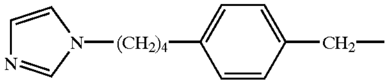 | —H | -5-Tet |
| 1519 | 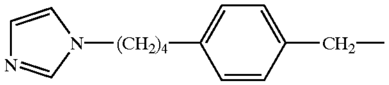 | $—CH_3$ | -5-Tet |
| 1520 | 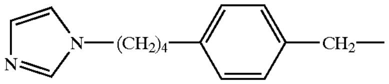 | $—CH_2CH_3$ | -5-Tet |
| 1521 | 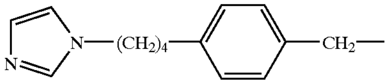 | $—CH_2CH_2CH_3$ | -5-Tet |

TABLE I-continued
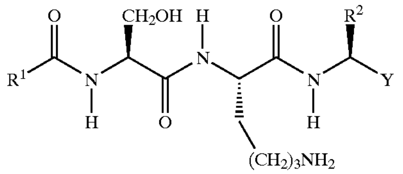
| Ex. No. | $R^1$ | $R^2$ | Y |
|---|---|---|---|
| 1522 | 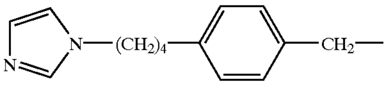 | $—CH_2CH_2CH_2CH_3$ | -5-Tet |
| 1523 | 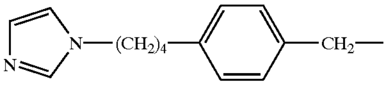 | $—CH_2CH_2CH_2CH_2CH_3$ | -5-Tet |
| 1524 | 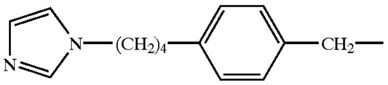 | $—CH_2CH_2CH_2CH_2CH_2CH_3$ | -5-Tet |
| 1525 | 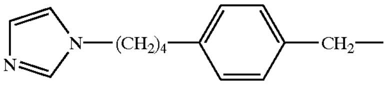 | $—CH(CH_3)_2$ | -5-Tet |
| 1526 | 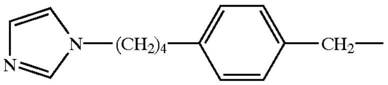 | $—CH_2CH(CH_3)_2$ | -5-Tet |
| 1527 | 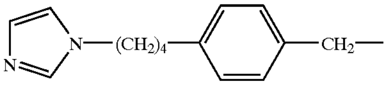 | $—CH_2CH_2CH(CH_3)_2$ | -5-Tet |
| 1528 | 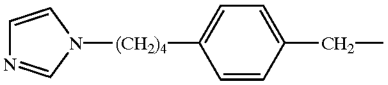 | -cyclo-$C_3H_5$ | -5-Tet |
| 1529 | 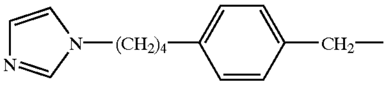 | -cyclo-$C_4H_7$ | -5-Tet |
| 1530 | 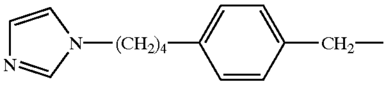 | -cyclo-$C_5H_9$ | -5-Tet |
| 1531 | 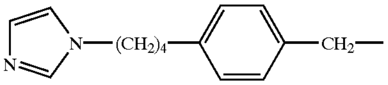 | -cyclo-$C_6H_{11}$ | -5-Tet |
| 1532 | 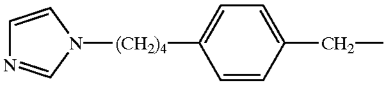 | -cyclo-$C_7H_{13}$ | -5-Tet |
| 1533 | 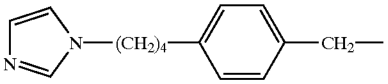 | -cyclo-$C_8H_{15}$ | -5-Tet |
| 1534 | 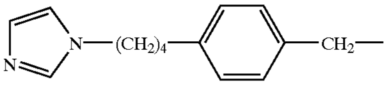 | $—CH(CH_3)(CH_2CH_3)$ | -5-Tet |

TABLE I-continued
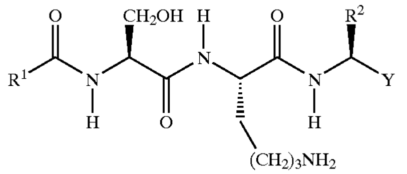
| Ex. No. | $R^1$ | $R^2$ | Y |
|---|---|---|---|
| 1535 | 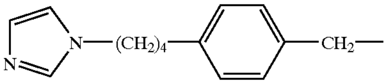 | $—CH(CH_2CH_3)_2$ | -5-Tet |
| 1536 | 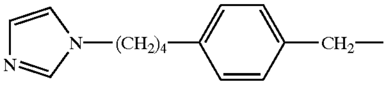 | $—CH(CH_3)(CH_2CH_2CH_3)$ | -5-Tet |
| 1537 | 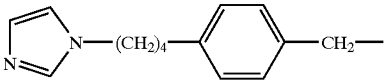 | $—C(CH_3)_3$ | -5-Tet |
| 1538 | 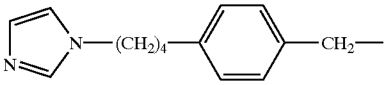 | $HC{\equiv}CCH_2—$ | -5-Tet |
| 1539 | 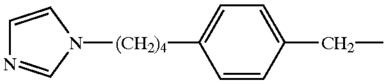 | $H_2C{=}CH—$ | -5-Tet |
| 1540 | 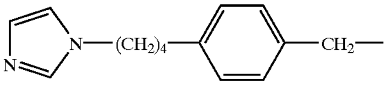 | $H_2C{=}CHCH_2—$ | -5-Tet |
| 1541 | 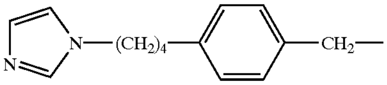 | $—CH_2F$ | -5-Tet |
| 1542 | 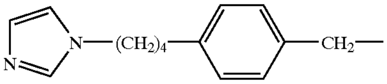 | $—CH_2C_6H_5$ | -5-Tet |
| 1543 | 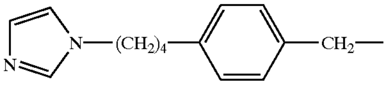 | $—CH_2C_6H_4$-p-$OCH_3$ | -5-Tet |
| 1544 | 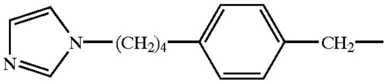 | $—CH_2C_6H_4$-p-$CH_3$ | -5-Tet |
| 1545 | 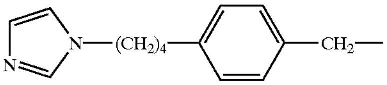 | $—CH_2C_6H_4$-p-F | -5-Tet |
| 1546 | 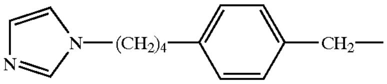 | $—CH_2CH_2C_6H_5$ | -5-Tet |
| 1547 | 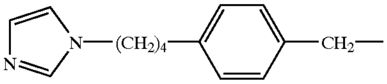 | $—CH_2$-cyclo-$C_6H_{11}$ | -5-Tet |

TABLE I-continued
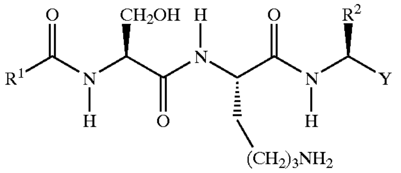
| Ex. No. | $R^1$ | $R^2$ | Y |
|---|---|---|---|
| 1548 | 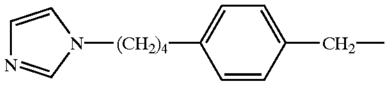 | $—CH_2$-cyclo-$C_6H_{10}$-4-F | -5-Tet |
| 1549 | 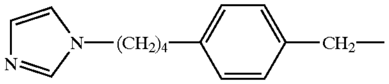 | $—CH_2$-cyclo-$C_6H_{10}$-4-$CH_3$ | -5-Tet |
| 1550 | 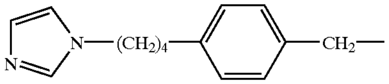 | $—CH_2$-cyclo-$C_6H_{10}$-4-$OCH_3$ | -5-Tet |
| 1551 | 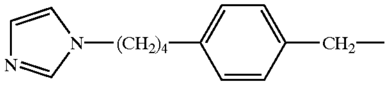 | $—CH_2CH_2$-cyclo-$C_6H_{11}$ | -5-Tet |
| 1552 | 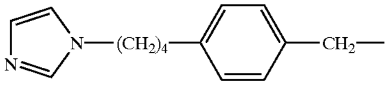 | $—CH_2$-cyclo-$C_5H_9$ | -5-Tet |
| 1553 | 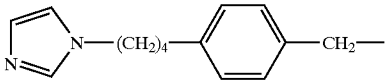 | $—CH_2CH_2$-cyclo-$C_5H_9$ | -5-Tet |
| 1554 | 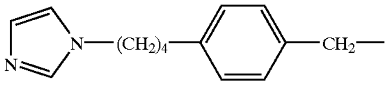 | $—CH_2$-2-naphthyl | -5-Tet |
| 1555 | 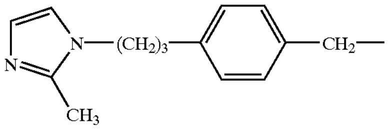 | —H | $—CO_2H$ |
| 1556 | 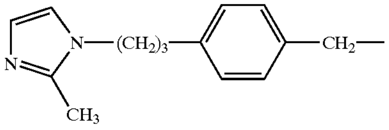 | $—CH_3$ | $—CO_2H$ |
| 1557 | 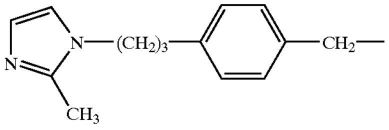 | $—CH_2CH_3$ | $—CO_2H$ |
| 1558 | 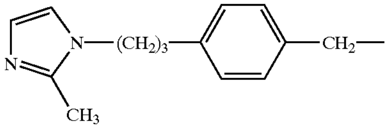 | $—CH_2CH_2CH_3$ | $—CO_2H$ |

TABLE I-continued
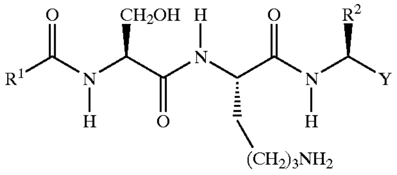
| Ex. No. | $R^1$ | $R^2$ | Y |
|---|---|---|---|
| 1559 | 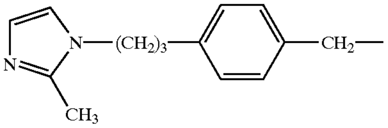 | $—CH_2CH_2CH_2CH_3$ | $—CO_2H$ |
| 1560 | 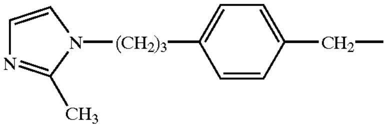 | $—CH_2CH_2CH_2CH_2CH_3$ | $—CO_2H$ |
| 1561 | 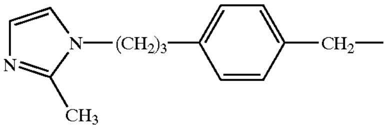 | $—CH_2CH_2CH_2CH_2CH_2CH_3$ | $—CO_2H$ |
| 1562 | 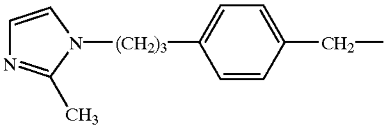 | $—CH(CH_3)_2$ | $—CO_2H$ |
| 1563 | 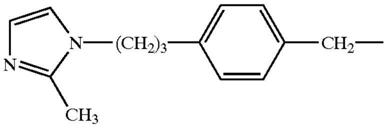 | $—CH_2CH(CH_3)_2$ | $—CO_2H$ |
| 1564 | 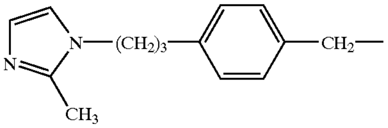 | $—CH_2CH_2CH(CH_3)_2$ | $—CO_2H$ |
| 1565 | 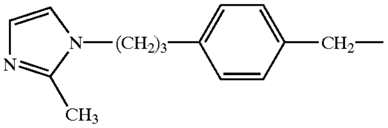 | -cyclo-$C_3H_5$ | $—CO_2H$ |
| 1566 | 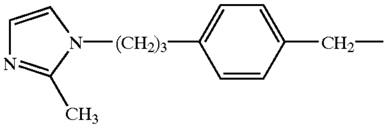 | -cyclo-$C_4H_7$ | $—CO_2H$ |
| 1567 | 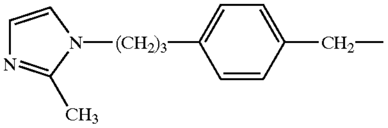 | -cyclo-$C_5H_9$ | $—CO_2H$ |

TABLE I-continued
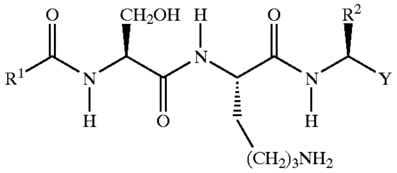
| Ex. No. | $R^1$ | $R^2$ | Y |
|---|---|---|---|
| 1568 | 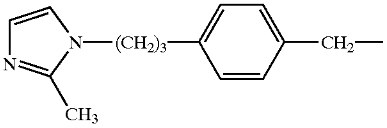 | -cyclo-$C_6H_{11}$ | —$CO_2H$ |
| 1569 | 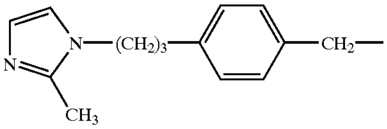 | -cyclo-$C_7H_{13}$ | —$CO_2H$ |
| 1570 | 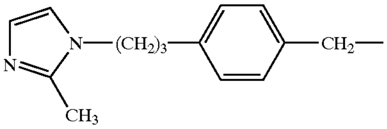 | -cyclo-$C_8H_{15}$ | —$CO_2H$ |
| 1571 | 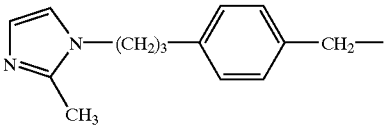 | —$CH(CH_3)(CH_2CH_3)$ | —$CO_2H$ |
| 1572 | 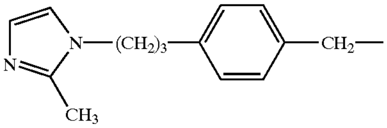 | —$CH(CH_2CH_3)_2$ | —$CO_2H$ |
| 1573 | 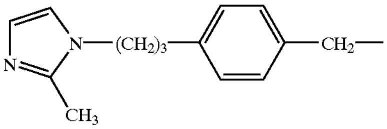 | —$CH(CH_3)(CH_2CH_2CH_3)$ | —$CO_2H$ |
| 1574 | 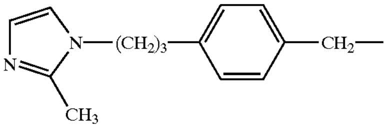 | —$C(CH_3)_3$ | —$CO_2H$ |
| 1575 | 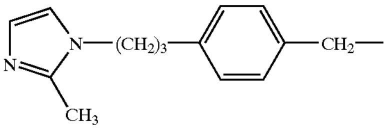 | $HC{\equiv}CCH_2$— | —$CO_2H$ |
| 1576 | 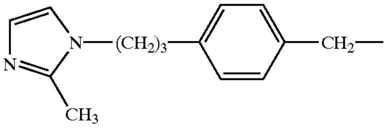 | $H_2C{=}CH$— | —$CO_2H$ |

TABLE I-continued
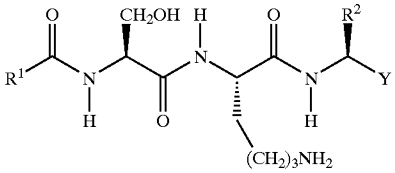
| Ex. No. | $R^1$ | $R^2$ | Y |
|---|---|---|---|
| 1577 | 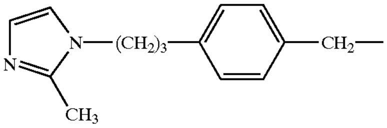 | $H_2C{=}CHCH_2$— | —$CO_2H$ |
| 1578 | 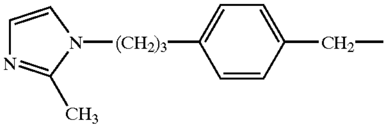 | —$CH_2F$ | —$CO_2H$ |
| 1579 | 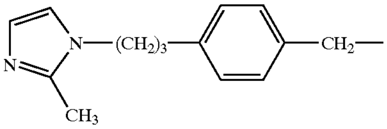 | —$CH_2C_6H_5$ | —$CO_2H$ |
| 1580 | 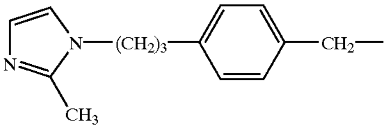 | —$CH_2C_6H_4$-p-$OCH_3$ | —$CO_2H$ |
| 1581 | 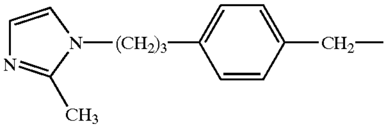 | —$CH_2C_6H_4$-p-$CH_3$ | —$CO_2H$ |
| 1582 | 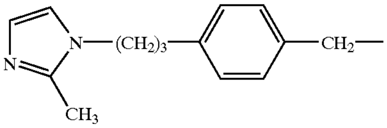 | —$CH_2C_6H_4$-p-F | —$CO_2H$ |
| 1583 | 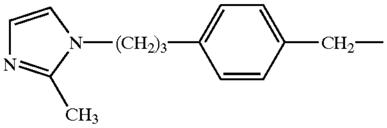 | —$CH_2CH_2C_6H_5$ | —$CO_2H$ |
| 1584 | 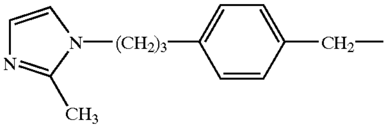 | —$CH_2$-cyclo-$C_6H_{11}$ | —$CO_2H$ |
| 1585 | 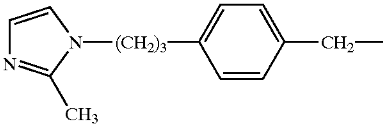 | —$CH_2$-cyclo-$C_6H_{10}$-4-F | —$CO_2H$ |

TABLE I-continued
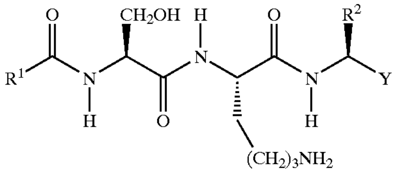
| Ex. No. | $R^1$ | $R^2$ | Y |
|---|---|---|---|
| 1586 | 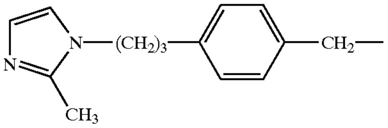 | $—CH_2$-cyclo-$C_6H_{10}$-4-$CH_3$ | $—CO_2H$ |
| 1587 | 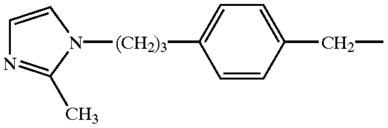 | $—CH_2$-cyclo-$C_6H_{10}$-4-$OCH_3$ | $—CO_2H$ |
| 1588 | 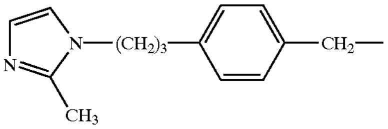 | $—CH_2CH_2$-cyclo-$C_6H_{11}$ | $—CO_2H$ |
| 1589 | 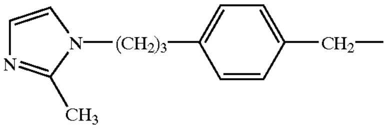 | $—CH_2$-cyclo-$C_5H_9$ | $—CO_2H$ |
| 1590 | 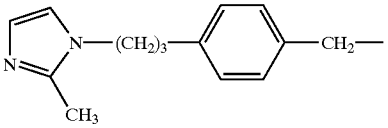 | $—CH_2CH_2$-cyclo-$C_5H_9$ | $—CO_2H$ |
| 1591 | 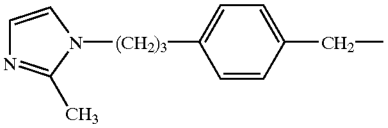 | $—CH_2$-2-naphthyl | $—CO_2H$ |
| 1592 | 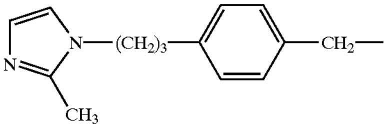 | —H | $—PO_3H_2$ |
| 1593 | 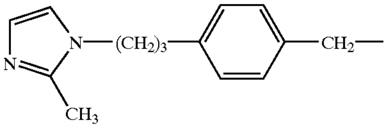 | $—CH_3$ | $—PO_3H_2$ |
| 1594 | 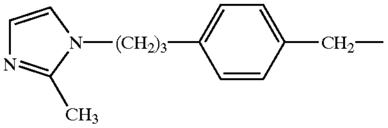 | $—CH_2CH_3$ | $—PO_3H_2$ |

TABLE I-continued
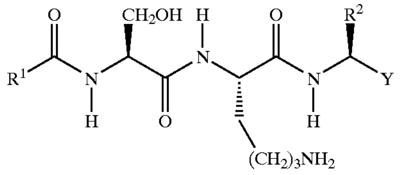
| Ex. No. | $R^1$ | $R^2$ | Y |
|---|---|---|---|
| 1595 | 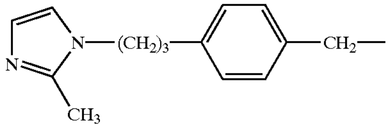 | $—CH_2CH_2CH_3$ | $—PO_3H_2$ |
| 1596 | 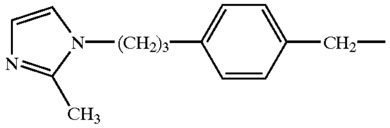 | $—CH_2CH_2CH_2CH_3$ | $—PO_3H_2$ |
| 1597 | 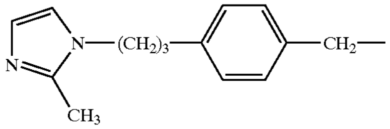 | $—CH_2CH_2CH_2CH_2CH_3$ | $—PO_3H_2$ |
| 1598 | 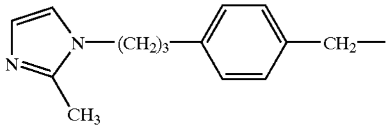 | $—CH_2CH_2CH_2CH_2CH_2CH_3$ | $—PO_3H_2$ |
| 1599 | 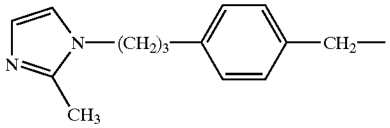 | $—CH(CH_3)_2$ | $—PO_3H_2$ |
| 1600 | 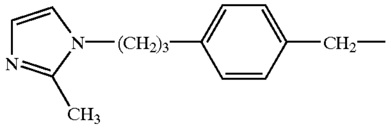 | $—CH_2CH(CH_3)_2$ | $—PO_3H_2$ |
| 1601 | 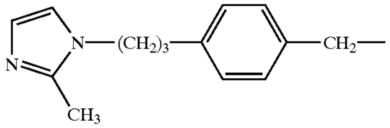 | $—CH_2CH_2CH(CH_3)_2$ | $—PO_3H_2$ |
| 1602 | 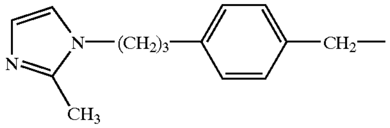 | -cyclo-$C_3H_5$ | $—PO_3H_2$ |
| 1603 | 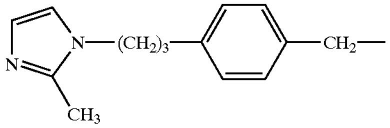 | -cyclo-$C_4H_7$ | $—PO_3H_2$ |

TABLE I-continued
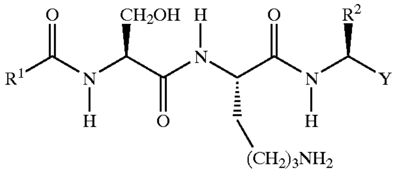
| Ex. No. | $R^1$ | $R^2$ | Y |
|---|---|---|---|
| 1604 | 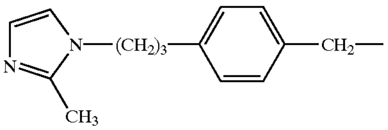 | -cyclo-$C_5H_9$ | —$PO_3H_2$ |
| 1605 | 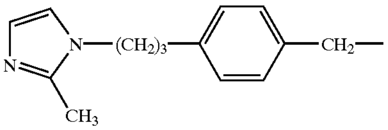 | -cyclo-$C_6H_{11}$ | —$PO_3H_2$ |
| 1606 | 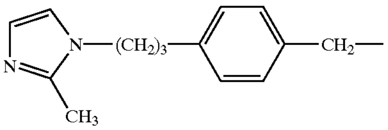 | -cyclo-$C_7H_{13}$ | —$PO_3H_2$ |
| 1607 | 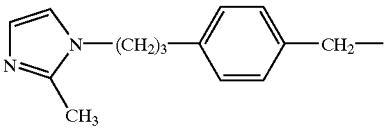 | -cyclo-$C_8H_{15}$ | —$PO_3H_2$ |
| 1608 | 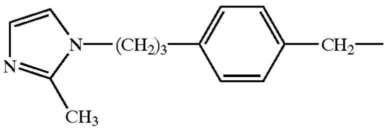 | —$CH(CH_3)(CH_2CH_3)$ | —$PO_3H_2$ |
| 1609 | 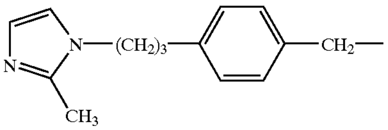 | —$CH(CH_2CH_3)_2$ | —$PO_3H_2$ |
| 1610 | 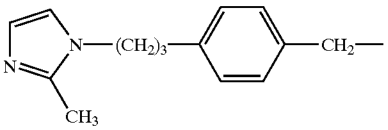 | —$CH(CH_3)(CH_2CH_2CH_3)$ | —$PO_3H_2$ |
| 1611 | 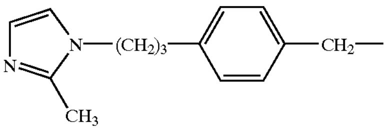 | —$C(CH_3)_3$ | —$PO_3H_2$ |
| 1612 | 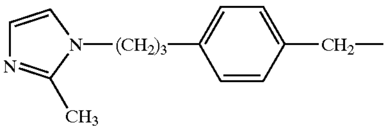 | $HC{\equiv}CCH_2$— | —$PO_3H_2$ |

TABLE I-continued
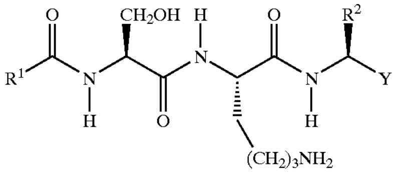
| Ex. No. | $R^1$ | $R^2$ | Y |
|---|---|---|---|
| 1613 | 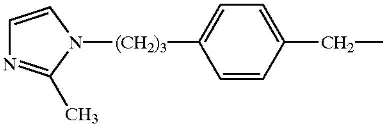 | $H_2C{=}CH—$ | $—PO_3H_2$ |
| 1614 | 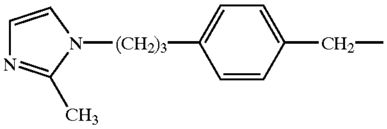 | $H_2C{=}CHCH_2—$ | $—PO_3H_2$ |
| 1615 | 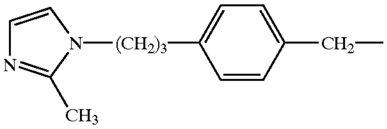 | $—CH_2F$ | $—PO_3H_2$ |
| 1616 | 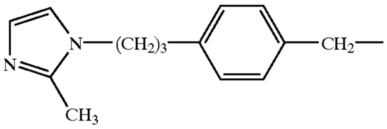 | $—CH_2C_6H_5$ | $—PO_3H_2$ |
| 1617 | 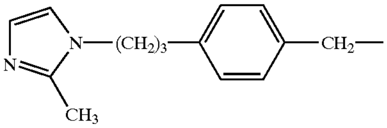 | $—CH_2C_6H_4$-p-$OCH_3$ | $—PO_3H_2$ |
| 1618 | 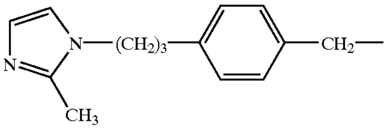 | $—CH_2C_6H_4$-p-$CH_3$ | $—PO_3H_2$ |
| 1619 | 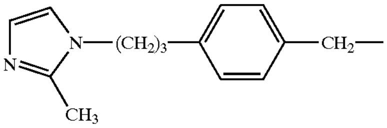 | $—CH_2C_6H_4$-p-F | $—PO_3H_2$ |
| 1620 | 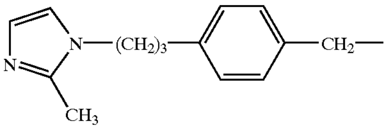 | $—CH_2CH_2C_6H_5$ | $—PO_3H_2$ |
| 1621 | 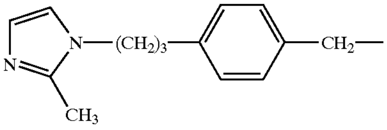 | $—CH_2$-cyclo-$C_6H_{11}$ | $—PO_3H_2$ |

TABLE I-continued
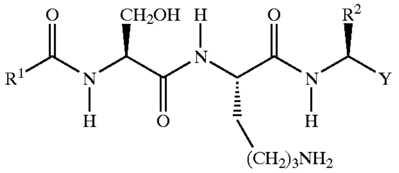
| Ex. No. | $R^1$ | $R^2$ | Y |
|---|---|---|---|
| 1622 | 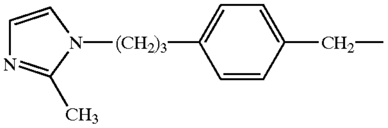 | $—CH_2$-cyclo-$C_6H_{10}$-4-F | $—PO_3H_2$ |
| 1623 | 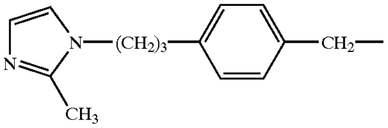 | $—CH_2$-cyclo-$C_6H_{10}$-4-$CH_3$ | $—PO_3H_2$ |
| 1624 | 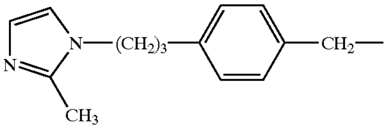 | $—CH_2$-cyclo-$C_6H_{10}$-4-$OCH_3$ | $—PO_3H_2$ |
| 1625 | 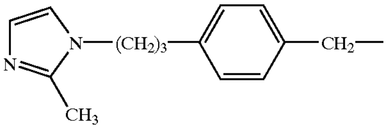 | $—CH_2CH_2$-cyclo-$C_6H_{11}$ | $—PO_3H_2$ |
| 1626 | 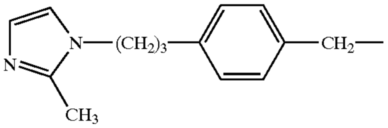 | $—CH_2$-cyclo-$C_5H_9$ | $—PO_3H_2$ |
| 1627 | 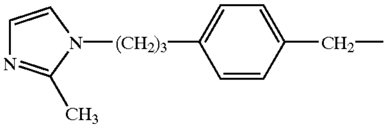 | $—CH_2CH_2$-cyclo-$C_5H_9$ | $—PO_3H_2$ |
| 1628 | 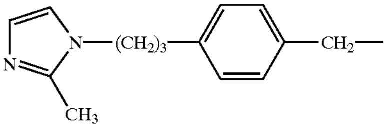 | $—CH_2$-2-naphthyl | $—PO_3H_2$ |
| 1629 | 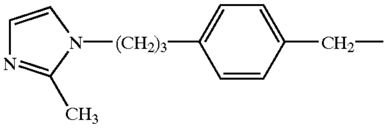 | —H | -5-Tet |
| 1630 | 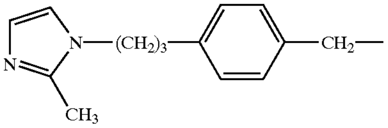 | $—CH_3$ | -5-Tet |

TABLE I-continued
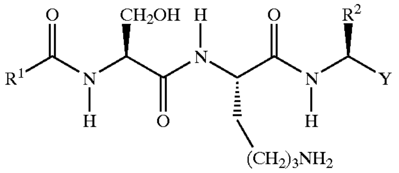
| Ex. No. | $R^1$ | $R^2$ | Y |
|---|---|---|---|
| 1631 | 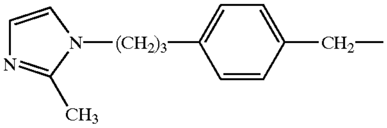 | $—CH_2CH_3$ | -5-Tet |
| 1632 | 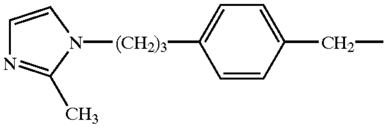 | $—CH_2CH_2CH_3$ | -5-Tet |
| 1633 | 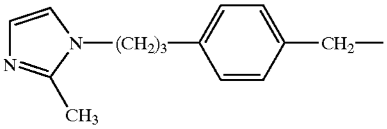 | $—CH_2CH_2CH_2CH_3$ | -5-Tet |
| 1634 | 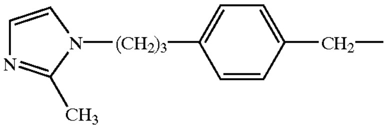 | $—CH_2CH_2CH_2CH_2CH_3$ | -5-Tet |
| 1635 | 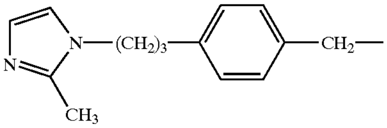 | $—CH_2CH_2CH_2CH_2CH_2CH_3$ | -5-Tet |
| 1636 | 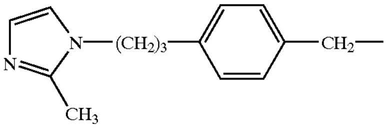 | $—CH(CH_3)_2$ | -5-Tet |
| 1637 | 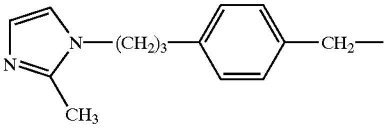 | $—CH_2CH(CH_3)_2$ | -5-Tet |
| 1638 | 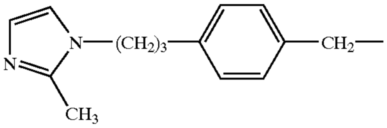 | $—CH_2CH_2CH(CH_3)_2$ | -5-Tet |
| 1639 | 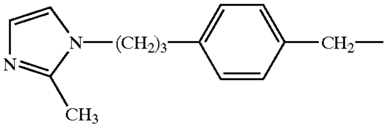 | -cyclo-$C_3H_5$ | -5-Tet |

TABLE I-continued
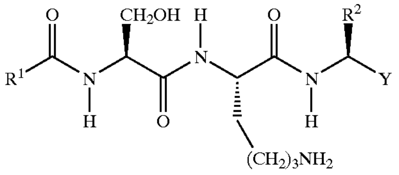
| Ex. No. | $R^1$ | $R^2$ | Y |
|---|---|---|---|
| 1640 | 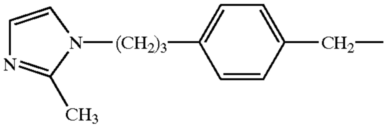 | -cyclo-$C_4H_7$ | -5-Tet |
| 1641 | 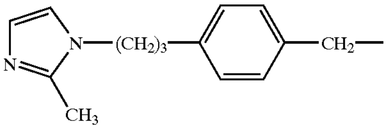 | -cyclo-$C_5H_9$ | -5-Tet |
| 1642 | 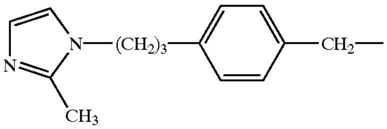 | -cyclo-$C_6H_{11}$ | -5-Tet |
| 1643 | 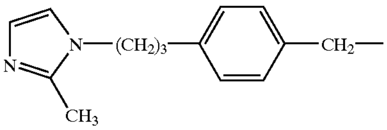 | -cyclo-$C_7H_{13}$ | -5-Tet |
| 1644 | 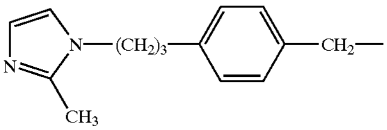 | -cyclo-$C_8H_{15}$ | -5-Tet |
| 1645 | 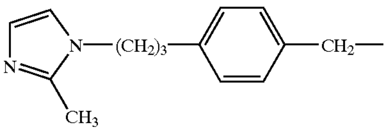 | —$CH(CH_3)(CH_2CH_3)$ | -5-Tet |
| 1646 | 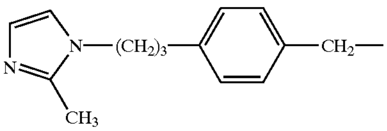 | —$CH(CH_2CH_3)_2$ | -5-Tet |
| 1647 | 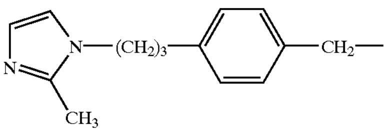 | —$CH(CH_3)(CH_2CH_2CH_3)$ | -5-Tet |
| 1648 | 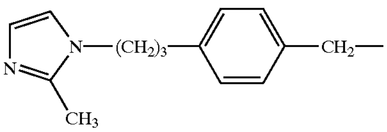 | —$C(CH_3)_3$ | -5-Tet |

TABLE I-continued
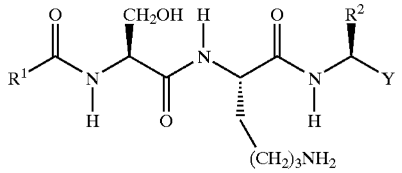
| Ex. No. | $R^1$ | $R^2$ | Y |
|---|---|---|---|
| 1649 | 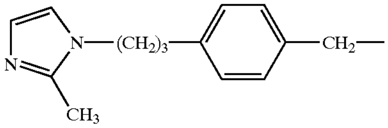 | $HC \equiv CCH_2$— | -5-Tet |
| 1650 | 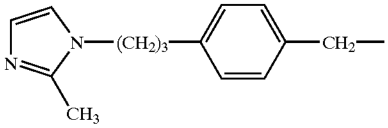 | $H_2C{=}CH$— | -5-Tet |
| 1651 | 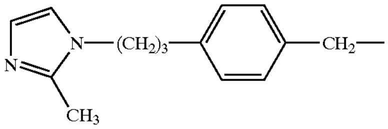 | $H_2C{=}CHCH_2$— | -5-Tet |
| 1652 | 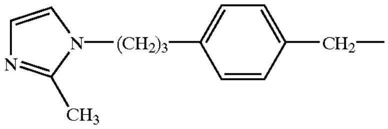 | —$CH_2F$ | -5-Tet |
| 1653 | 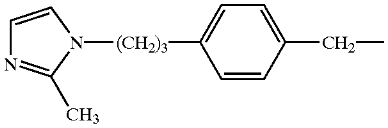 | —$CH_2C_6H_5$ | -5-Tet |
| 1654 | 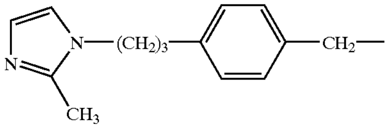 | —$CH_2C_6H_4$-p-$OCH_3$ | -5-Tet |
| 1655 | 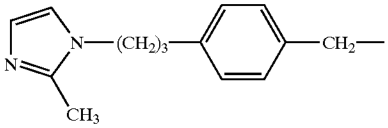 | —$CH_2C_6H_4$-p-$CH_3$ | -5-Tet |
| 1656 | 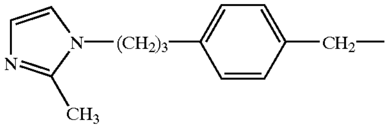 | —$CH_2C_6H_4$-p-F | -5-Tet |
| 1657 | 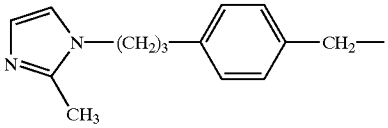 | —$CH_2CH_2C_6H_5$ | -5-Tet |

TABLE I-continued
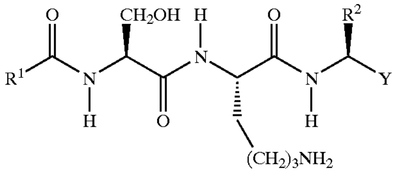
| Ex. No. | $R^1$ | $R^2$ | Y |
|---|---|---|---|
| 1658 | 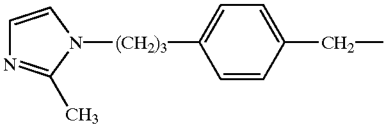 | $—CH_2$-cyclo-$C_6H_{11}$ | -5-Tet |
| 1659 | 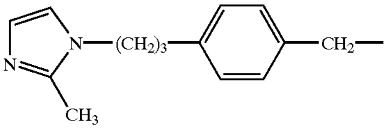 | $—CH_2$-cyclo-$C_6H_{10}$-4-F | -5-Tet |
| 1660 | 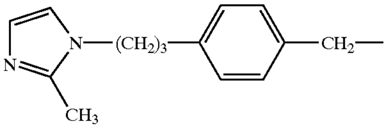 | $—CH_2$-cyclo-$C_6H_{10}$-4-$CH_3$ | -5-Tet |
| 1661 | 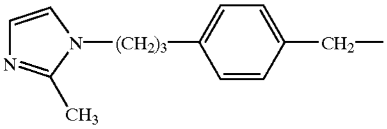 | $—CH_2$-cyclo-$C_6H_{10}$-4-$OCH_3$ | -5-Tet |
| 1662 | 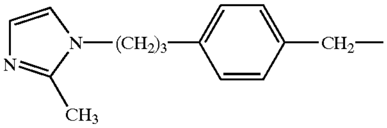 | $—CH_2CH_2$-cyclo-$C_6H_{11}$ | -5-Tet |
| 1663 | 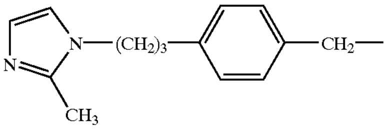 | $—CH_2$-cyclo-$C_5H_9$ | -5-Tet |
| 1664 | 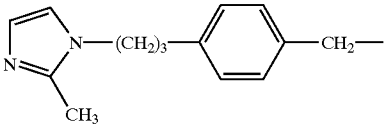 | $—CH_2CH_2$-cyclo-$C_5H_9$ | -5-Tet |
| 1665 | 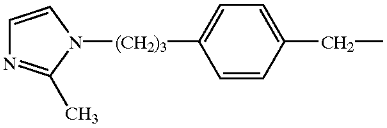 | $—CH_2$-2-naphthyl | -5-Tet |
| 1666 | 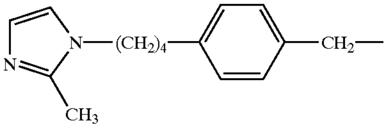 | —H | $—CO_2H$ |

TABLE I-continued
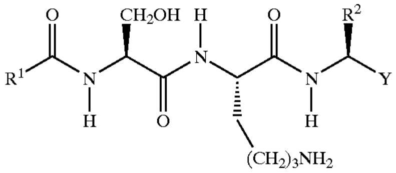
| Ex. No. | R[1] | R[2] | Y |
|---|---|---|---|
| 1667 | 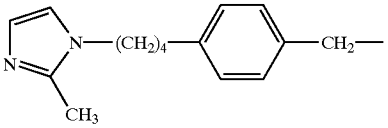 | $—CH_3$ | —CONHOH |
| 1668 | 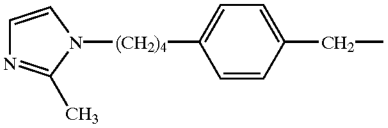 | $—CH_2CH_3$ | $—CO_2H$ |
| 1669 | 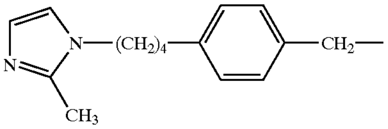 | $—CH_2CH_2CH_3$ | $—CO_2H$ |
| 1670 | 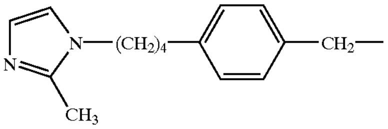 | $—CH_2CH_2CH_2CH_3$ | $—CO_2H$ |
| 1671 | 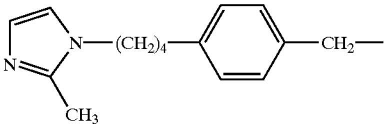 | $—CH_2CH_2CH_2CH_2CH_3$ | $—CO_2H$ |
| 1672 | 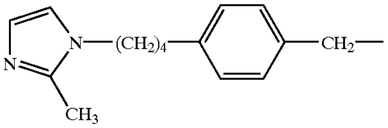 | $—CH_2CH_2CH_2CH_2CH_2CH_3$ | $—CO_2H$ |
| 1673 | 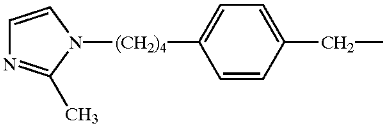 | $—CH(CH_3)_2$ | $—CO_2H$ |
| 1674 | 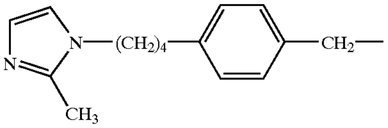 | $—CH_2CH(CH_3)_2$ | —CONHOH |
| 1675 | 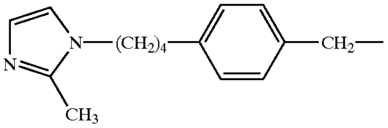 | $—CH_2CH_2CH(CH_3)_2$ | $—CO_2H$ |

TABLE I-continued
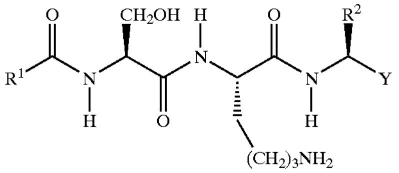
| Ex. No. | $R^1$ | $R^2$ | Y |
|---|---|---|---|
| 1676 | 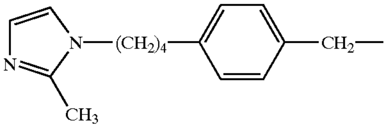 | -cyclo-$C_3H_5$ | —$CO_2H$ |
| 1677 | 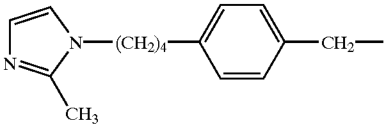 | -cyclo-$C_4H_7$ | —$CO_2H$ |
| 1678 | 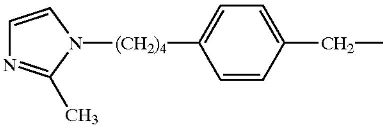 | -cyclo-$C_5H_9$ | —$CO_2H$ |
| 1679 | 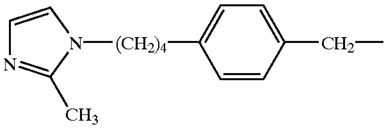 | -cyclo-$C_6H_{11}$ | —CONHOH |
| 1680 | 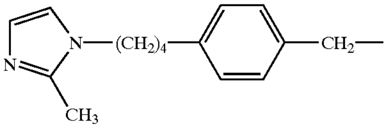 | -cyclo-$C_7H_{13}$ | —$CO_2H$ |
| 1681 | 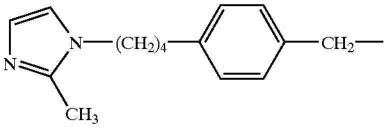 | -cyclo-$C_8H_{15}$ | —CONHOH |
| 1682 | 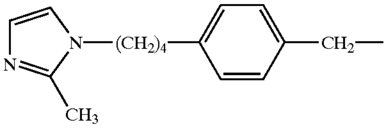 | —$CH(CH_3)(CH_2CH_3)$ | —CONHOH |
| 1683 | 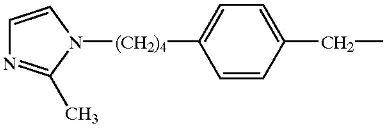 | —$CH(CH_2CH_3)_2$ | —$CO_2H$ |
| 1684 | 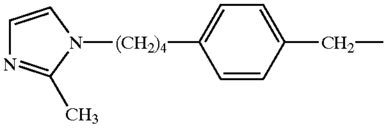 | —$CH(CH_3)(CH_2CH_2CH_3)$ | —$CO_2H$ |

TABLE I-continued
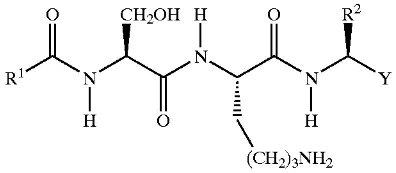
| Ex. No. | $R^1$ | $R^2$ | Y |
| --- | --- | --- | --- |
| 1685 | 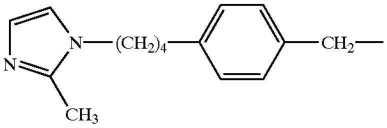 | $—C(CH_3)_3$ | $—CO_2H$ |
| 1686 | 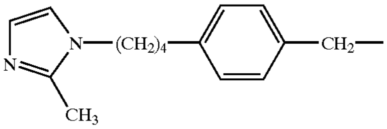 | $HC≡CCH_2—$ | $—CO_2H$ |
| 1687 | 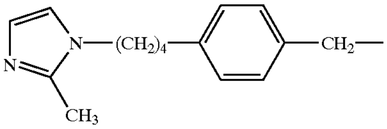 | $H_2C═CH—$ | $—CO_2H$ |
| 1688 | 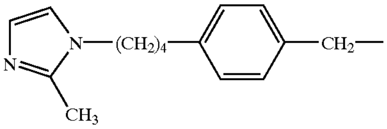 | $H_2C═CHCH_2—$ | $—CO_2H$ |
| 1689 | 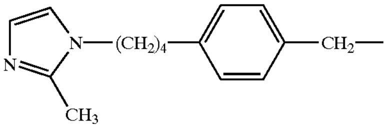 | $—CH_2F$ | $—CO_2H$ |
| 1690 | 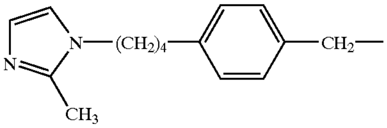 | $—CH_2C_6H_5$ | —CONHOH |
| 1691 | 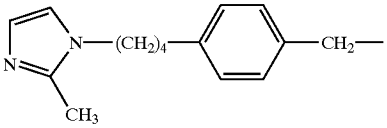 | $—CH_2C_6H_4$-p-$OCH_3$ | $—CO_2H$ |
| 1692 | 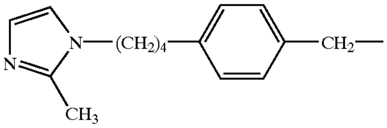 | $—CH_2C_6H_4$-p-$CH_3$ | $—CO_2H$ |
| 1693 | 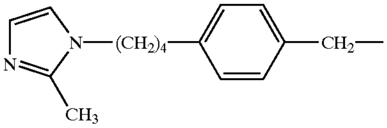 | $—CH_2C_6H_4$-p-F | $—CO_2H$ |

TABLE I-continued
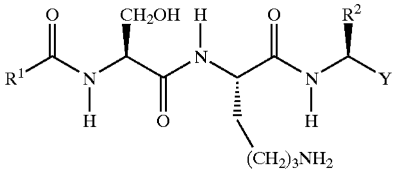
| Ex. No. | $R^1$ | $R^2$ | Y |
|---|---|---|---|
| 1694 | 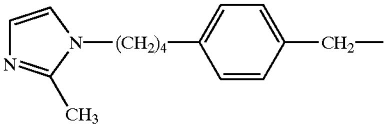 | $—CH_2CH_2C_6H_5$ | $—CO_2H$ |
| 1695 | 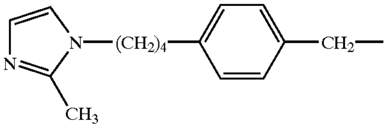 | $—CH_2$-cyclo-$C_6H_{11}$ | —CONHOH |
| 1696 | 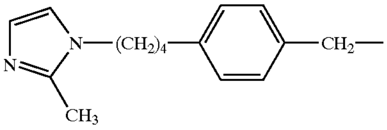 | $—CH_2$-cyclo-$C_6H_{10}$-4-F | $—CO_2H$ |
| 1697 | 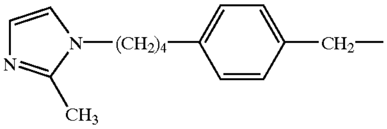 | $—CH_2$-cyclo-$C_6H_{10}$-4-$CH_3$ | $—CO_2H$ |
| 1698 | 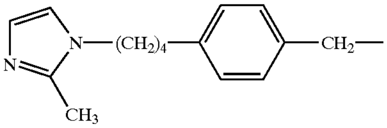 | $—CH_2$-cyclo-$C_6H_{10}$-4-$OCH_3$ | $—CO_2H$ |
| 1699 | 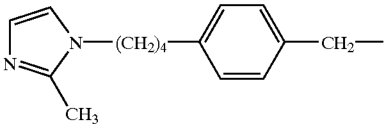 | $—CH_2CH_2$-cyclo-$C_6H_{11}$ | $—CO_2H$ |
| 1700 | 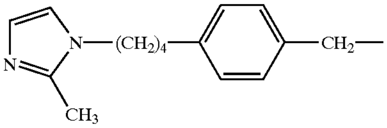 | $—CH_2$-cyclo-$C_5H_9$ | $—CO_2H$ |
| 1701 | 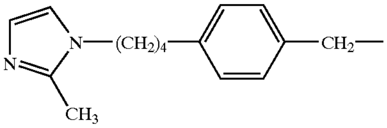 | $—CH_2CH_2$-cyclo-$C_5H_9$ | $—CO_2H$ |
| 1702 | 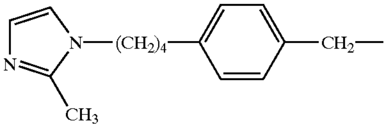 | $—CH_2$-2-naphthyl | $—CO_2H$ |

TABLE I-continued
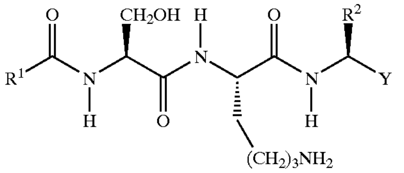
| Ex. No. | $R^1$ | $R^2$ | Y |
|---|---|---|---|
| 1703 | 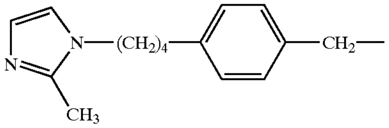 | $—H$ | $—PO_3H_2$ |
| 1704 | 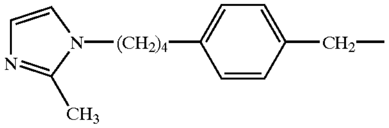 | $—CH_3$ | $—PO_3H_2$ |
| 1705 | 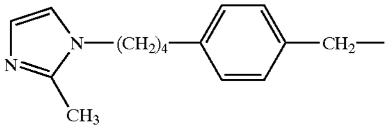 | $—CH_2CH_3$ | $—PO_3H_2$ |
| 1706 | 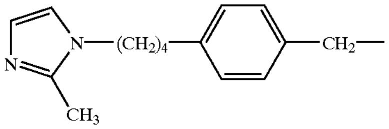 | $—CH_2CH_2CH_3$ | $—PO_3H_2$ |
| 1707 | 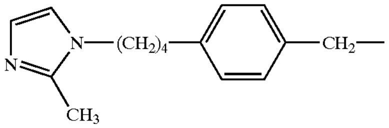 | $—CH_2CH_2CH_2CH_3$ | $—PO_3H_2$ |
| 1708 | 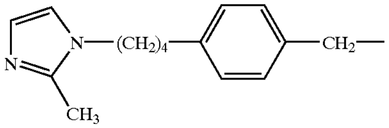 | $—CH_2CH_2CH_2CH_2CH_3$ | $—PO_3H_2$ |
| 1709 | 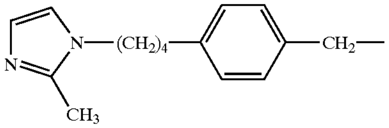 | $—CH_2CH_2CH_2CH_2CH_2CH_3$ | $—PO_3H_2$ |
| 1710 | 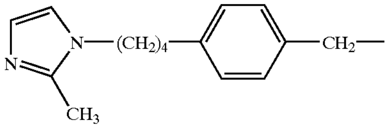 | $—CH(CH_3)_2$ | $—PO_3H_2$ |
| 1711 | 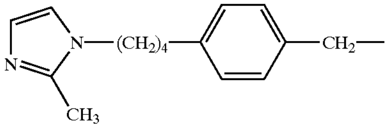 | $—CH_2CH(CH_3)_2$ | $—PO_3H_2$ |

TABLE I-continued
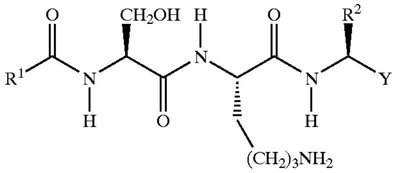
| Ex. No. | $R^1$ | $R^2$ | Y |
|---|---|---|---|
| 1712 | 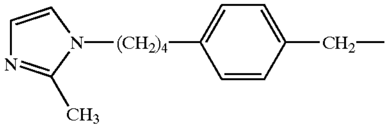 | $—CH_2CH_2CH(CH_3)_2$ | $—PO_3H_2$ |
| 1713 | 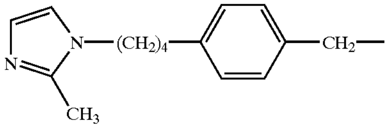 | -cyclo-$C_3H_5$ | $—PO_3H_2$ |
| 1714 | 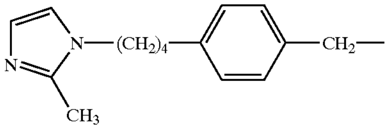 | -cyclo-$C_4H_7$ | $—PO_3H_2$ |
| 1715 | 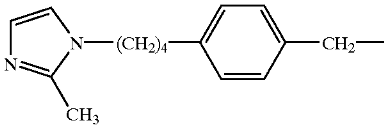 | -cyclo-$C_5H_9$ | $—PO_3H_2$ |
| 1716 | 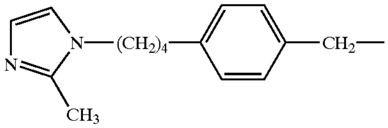 | -cyclo-$C_6H_{11}$ | $—PO_3H_2$ |
| 1717 | 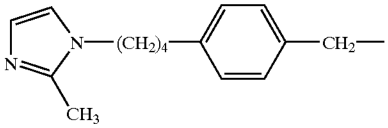 | -cyclo-$C_7H_{13}$ | $—PO_3H_2$ |
| 1718 | 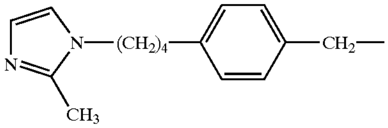 | -cyclo-$C_8H_{15}$ | $—PO_3H_2$ |
| 1719 | 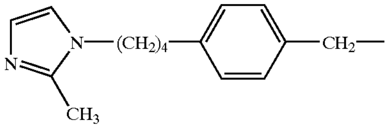 | $—CH(CH_3)(CH_2CH_3)$ | $—PO_3H_2$ |
| 1720 | 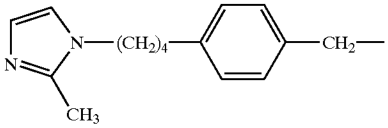 | $—CH(CH_2CH_3)_2$ | $—PO_3H_2$ |

TABLE I-continued
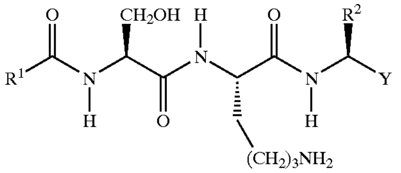
| Ex. No. | $R^1$ | $R^2$ | Y |
|---|---|---|---|
| 1721 | 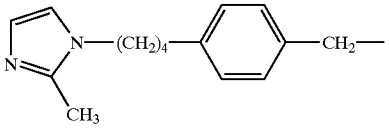 | $—CH(CH_3)(CH_2CH_2CH_3)$ | $—PO_3H_2$ |
| 1722 | 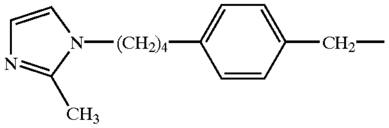 | $—C(CH_3)_3$ | $—PO_3H_2$ |
| 1723 | 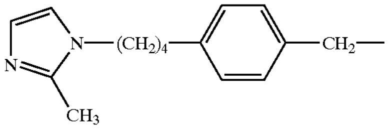 | $HC{\equiv}CCH_2—$ | $—PO_3H_2$ |
| 1724 | 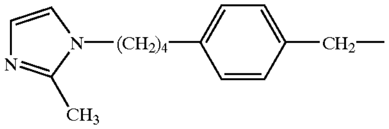 | $H_2C{=}CH—$ | $—PO_3H_2$ |
| 1725 | 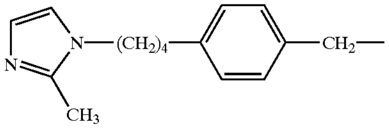 | $H_2C{=}CHCH_2—$ | $—PO_3H_2$ |
| 1726 | 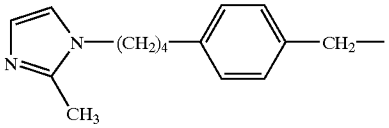 | $—CH_2F$ | $—PO_3H_2$ |
| 1727 | 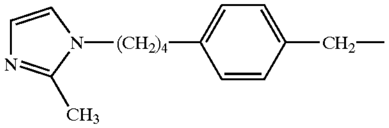 | $—CH_2C_6H_5$ | $—PO_3H_2$ |
| 1728 | 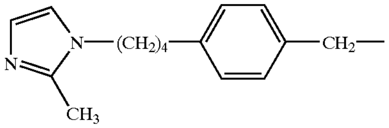 | $—CH_2C_6H_4$-p-$OCH_3$ | $—PO_3H_2$ |
| 1729 | 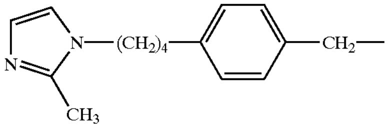 | $—CH_2C_6H_4$-p-$CH_3$ | $—PO_3H_2$ |

TABLE I-continued
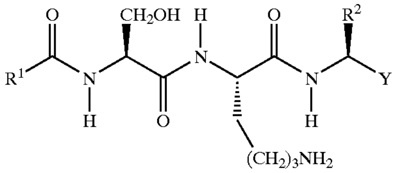
| Ex. No. | $R^1$ | $R^2$ | Y |
|---|---|---|---|
| 1730 | 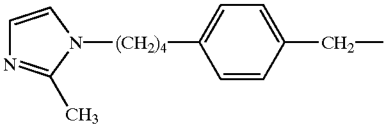 | $—CH_2C_6H_4$-p-F | $—PO_3H_2$ |
| 1731 | 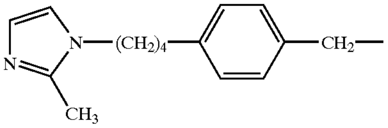 | $—CH_2CH_2C_6H_5$ | $—PO_3H_2$ |
| 1732 | 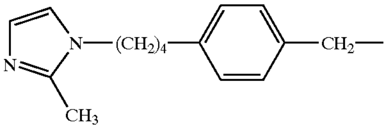 | $—CH_2$-cyclo-$C_6H_{11}$ | $—PO_3H_2$ |
| 1733 | 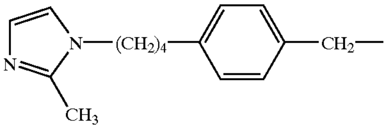 | $—CH_2$-cyclo-$C_6H_{10}$-4-F | $—PO_3H_2$ |
| 1734 | 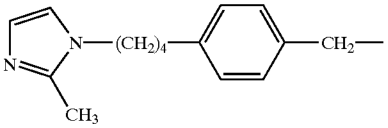 | $—CH_2$-cyclo-$C_6H_{10}$-4-$CH_3$ | $—PO_3H_2$ |
| 1735 | 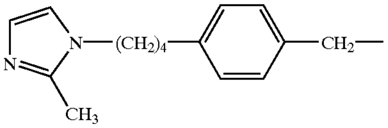 | $—CH_2$-cyclo-$C_6H_{10}$-4-$OCH_3$ | $—PO_3H_2$ |
| 1736 | 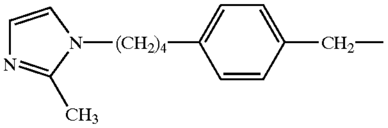 | $—CH_2CH_2$-cyclo-$C_6H_{11}$ | $—PO_3H_2$ |
| 1737 | 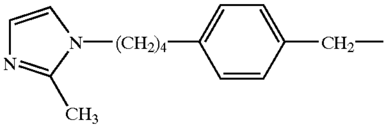 | $—CH_2$-cyclo-$C_5H_9$ | $—PO_3H_2$ |
| 1738 | 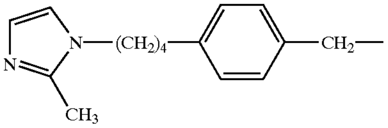 | $—CH_2CH_2$-cyclo-$C_5H_9$ | $—PO_3H_2$ |

TABLE I-continued
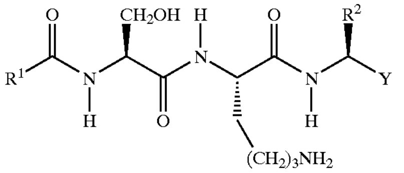
| Ex. No. | $R^1$ | $R^2$ | Y |
|---|---|---|---|
| 1739 | 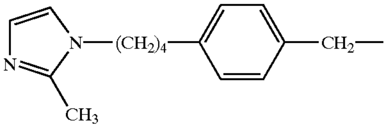 | —$CH_2$-2-naphthyl | —$PO_3H_2$ |
| 1740 | 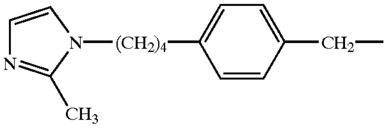 | —H | -5-Tet |
| 1741 | 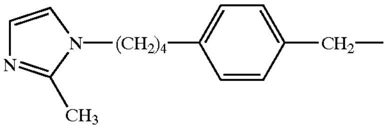 | —$CH_3$ | -5-Tet |
| 1742 | 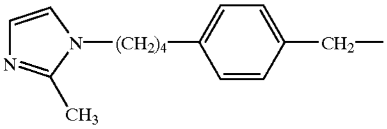 | —$CH_2CH_3$ | -5-Tet |
| 1743 | 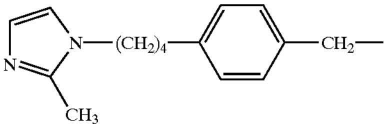 | —$CH_2CH_2CH_3$ | -5-Tet |
| 1744 | 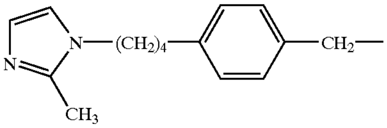 | —$CH_2CH_2CH_2CH_3$ | -5-Tet |
| 1745 | 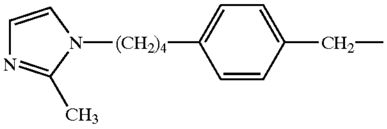 | —$CH_2CH_2CH_2CH_2CH_3$ | -5-Tet |
| 1746 | 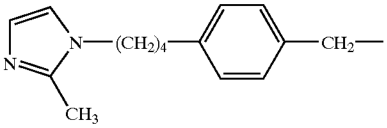 | —$CH_2CH_2CH_2CH_2CH_2CH_3$ | -5-Tet |
| 1747 | 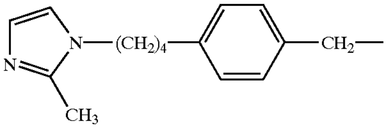 | —$CH(CH_3)_2$ | -5-Tet |

TABLE I-continued
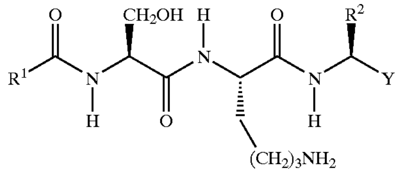
| Ex. No. | $R^1$ | $R^2$ | Y |
|---|---|---|---|
| 1748 | 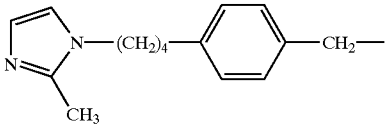 | $—CH_2CH(CH_3)_2$ | -5-Tet |
| 1749 | 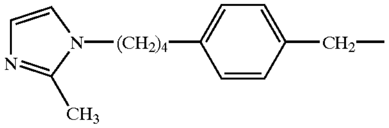 | $—CH_2CH_2CH(CH_3)_2$ | -5-Tet |
| 1750 | 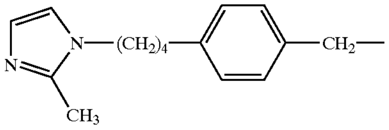 | -cyclo-$C_3H_5$ | -5-Tet |
| 1751 | 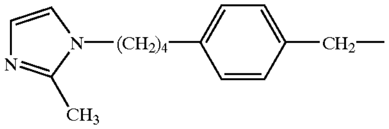 | -cyclo-$C_4H_7$ | -5-Tet |
| 1752 | 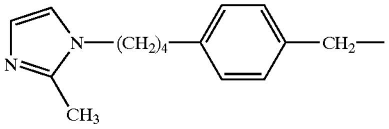 | -cyclo-$C_5H_9$ | -5-Tet |
| 1753 | 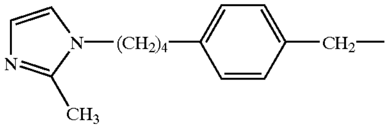 | -cyclo-$C_6H_{11}$ | -5-Tet |
| 1754 | 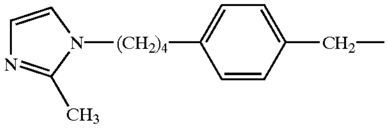 | -cyclo-$C_7H_{13}$ | -5-Tet |
| 1755 | 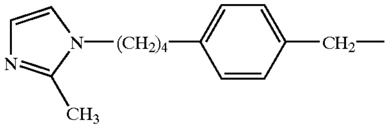 | -cyclo-$C_8H_{15}$ | -5-Tet |
| 1756 | 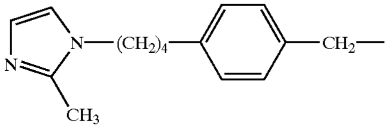 | $—CH(CH_3)(CH_2CH_3)$ | -5-Tet |

TABLE I-continued
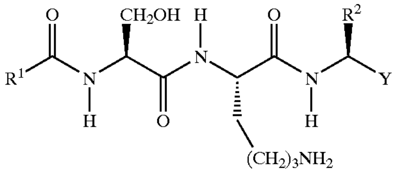
| Ex. No. | $R^1$ | $R^2$ | Y |
|---|---|---|---|
| 1757 | 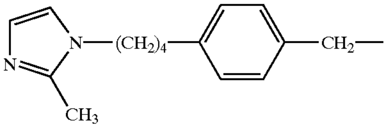 | $—CH(CH_2CH_3)_2$ | -5-Tet |
| 1758 | 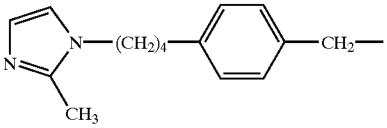 | $—CH(CH_3)(CH_2CH_2CH_3)$ | -5-Tet |
| 1759 | 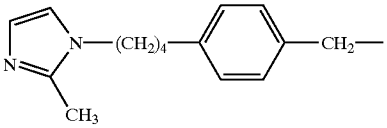 | $—C(CH_3)_3$ | -5-Tet |
| 1760 | 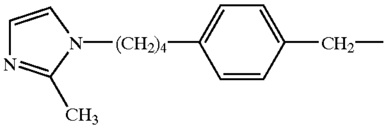 | $HC{\equiv}CCH_2—$ | -5-Tet |
| 1761 | 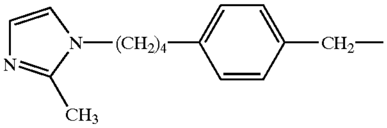 | $H_2C{=}CH—$ | -5-Tet |
| 1762 | 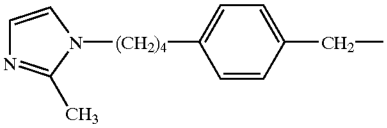 | $H_2C{=}CHCH_2—$ | -5-Tet |
| 1763 | 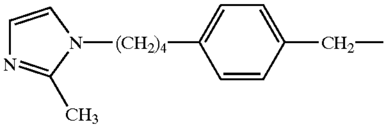 | $—CH_2F$ | -5-Tet |
| 1764 | 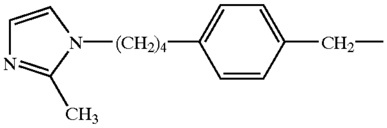 | $—CH_2C_6H_5$ | -5-Tet |
| 1765 | 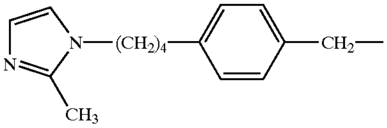 | $—CH_2C_6H_4$-p-$OCH_3$ | -5-Tet |

TABLE I-continued
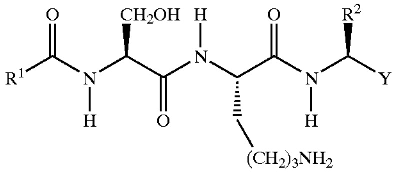
| Ex. No. | $R^1$ | $R^2$ | Y |
|---|---|---|---|
| 1766 | 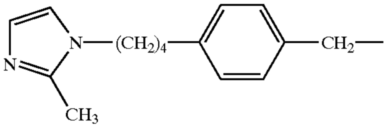 | $—CH_2C_6H_4$-p-$CH_3$ | -5-Tet |
| 1767 | 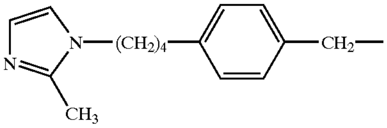 | $—CH_2C_6H_4$-p-F | -5-Tet |
| 1768 | 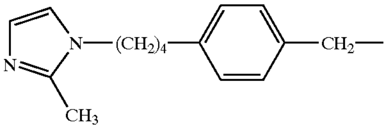 | $—CH_2CH_2C_6H_5$ | -5-Tet |
| 1769 | 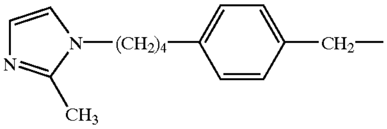 | $—CH_2$-cyclo-$C_6H_{11}$ | -5-Tet |
| 1770 | 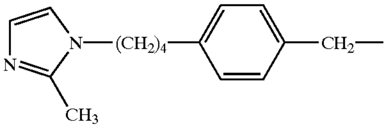 | $—CH_2$-cyclo-$C_6H_{10}$-4-F | -5-Tet |
| 1771 | 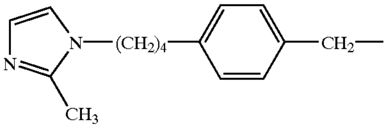 | $—CH_2$-cyclo-$C_6H_{10}$-4-$CH_3$ | -5-Tet |
| 1772 | 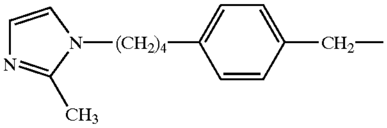 | $—CH_2$-cyclo-$C_6H_{10}$-4-$OCH_3$ | -5-Tet |
| 1773 | 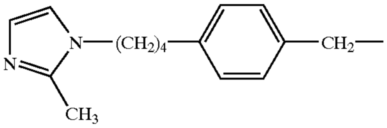 | $—CH_2CH_2$-cyclo-$C_6H_{11}$ | -5-Tet |
| 1774 | 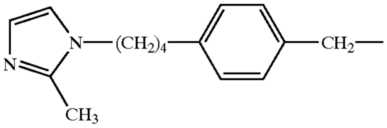 | $—CH_2$-cyclo-$C_5H_9$ | -5-Tet |

TABLE I-continued
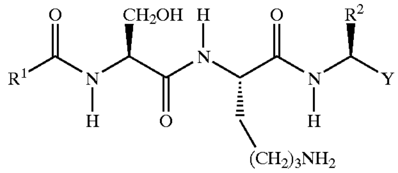
| Ex. No. | $R^1$ | $R^2$ | Y |
| --- | --- | --- | --- |
| 1775 | 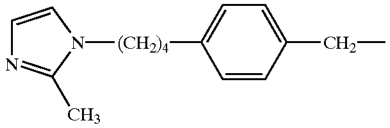 | $—CH_2CH_2$-cyclo-$C_5H_9$ | -5-Tet |
| 1776 | 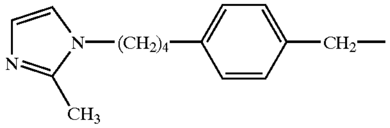 | $—CH_2$-2-naphthyl | -5-Tet |
| 1777 | 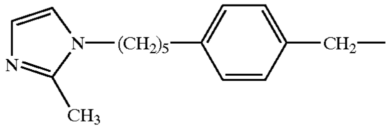 | —H | $—CO_2H$ |
| 1778 | 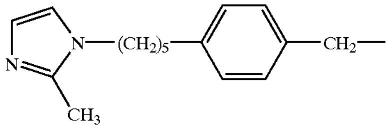 | $—CH_3$ | $—CO_2H$ |
| 1779 | 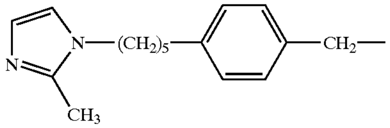 | $—CH_2CH_3$ | $—CO_2H$ |
| 1780 | 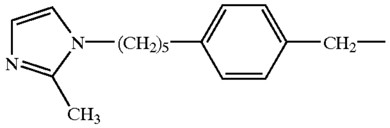 | $—CH_2CH_2CH_3$ | $—CO_2H$ |
| 1781 | 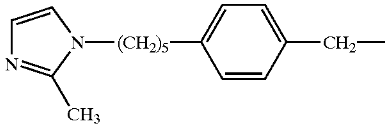 | $—CH_2CH_2CH_2CH_3$ | $—CO_2H$ |
| 1782 | 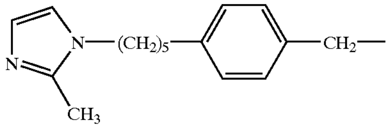 | $—CH_2CH_2CH_2CH_2CH_3$ | $—CO_2H$ |
| 1783 | 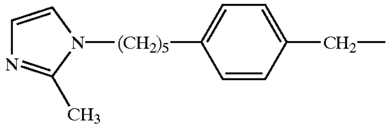 | $—CH_2CH_2CH_2CH_2CH_2CH_3$ | $—CO_2H$ |

TABLE I-continued
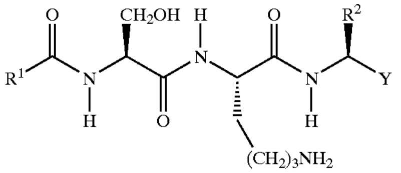
| Ex. No. | $R^1$ | $R^2$ | Y |
|---|---|---|---|
| 1784 | 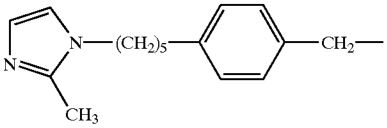 | $-CH(CH_3)_2$ | $-CO_2H$ |
| 1785 | 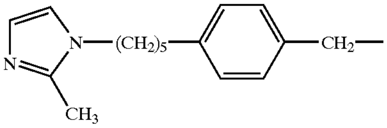 | $-CH_2CH(CH_3)_2$ | $-CO_2H$ |
| 1786 | 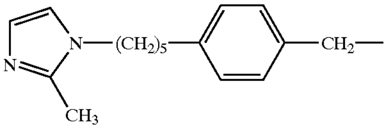 | $-CH_2CH_2CH(CH_3)_2$ | $-CO_2H$ |
| 1787 | 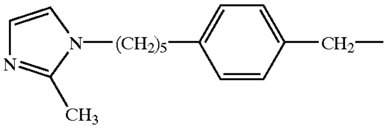 | -cyclo-$C_3H_5$ | $-CO_2H$ |
| 1788 | 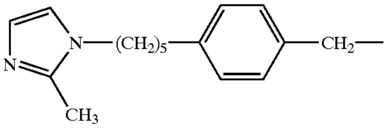 | -cyclo-$C_4H_7$ | $-CO_2H$ |
| 1789 | 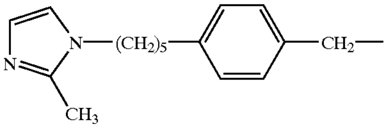 | -cyclo-$C_5H_9$ | $-CO_2H$ |
| 1790 | 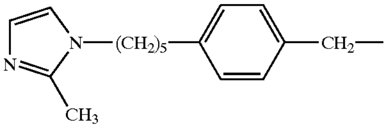 | -cyclo-$C_6H_{11}$ | $-CO_2H$ |
| 1791 | 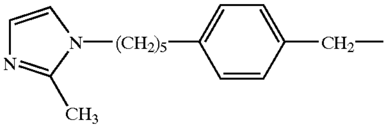 | -cyclo-$C_7H_{13}$ | $-CO_2H$ |
| 1792 | 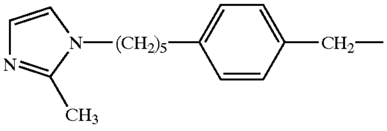 | -cyclo-$C_8H_{15}$ | $-CO_2H$ |

TABLE I-continued
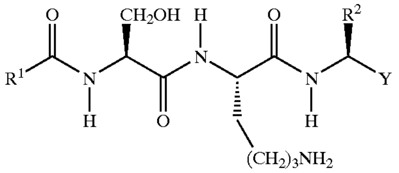
| Ex. No. | $R^1$ | $R^2$ | Y |
|---|---|---|---|
| 1793 | 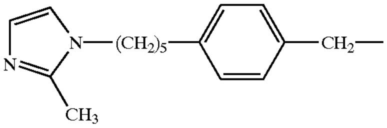 | $—CH(CH_3)(CH_2CH_3)$ | $—CO_2H$ |
| 1794 | 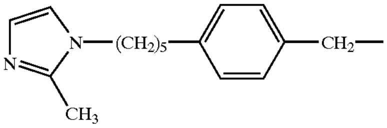 | $—CH(CH_2CH_3)_2$ | $—CO_2H$ |
| 1795 | 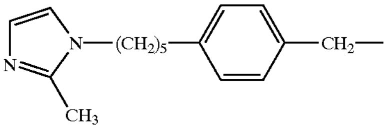 | $—CH(CH_3)(CH_2CH_2CH_3)$ | $—CO_2H$ |
| 1796 | 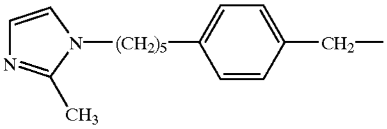 | $—C(CH_3)_3$ | $—CO_2H$ |
| 1797 | 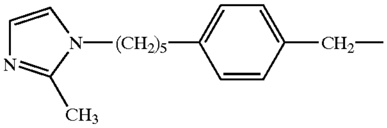 | $HC{\equiv}CCH_2—$ | $—CO_2H$ |
| 1798 | 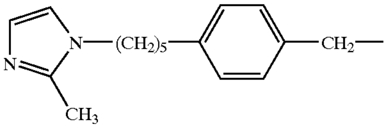 | $H_2C{=}CH—$ | $—CO_2H$ |
| 1799 | 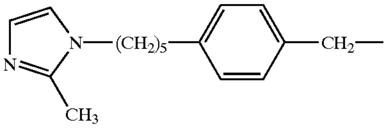 | $H_2C{=}CHCH_2—$ | $—CO_2H$ |
| 1800 | 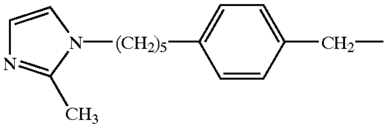 | $—CH_2F$ | $—CO_2H$ |
| 1801 | 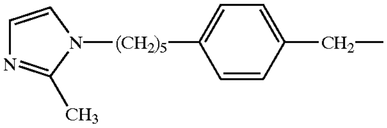 | $—CH_2C_6H_5$ | $—CO_2H$ |

TABLE I-continued
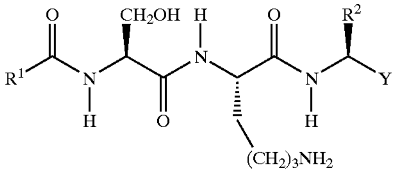
| Ex. No. | $R^1$ | $R^2$ | Y |
|---|---|---|---|
| 1802 | 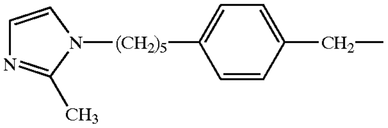 | $—CH_2C_6H_4$-p-$OCH_3$ | $—CO_2H$ |
| 1803 | 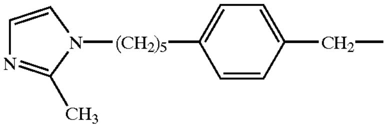 | $—CH_2C_6H_4$-p-$CH_3$ | $—CO_2H$ |
| 1804 | 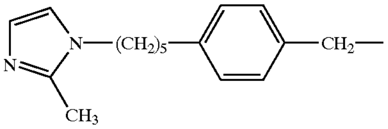 | $—CH_2C_6H_4$-p-F | $—CO_2H$ |
| 1805 | 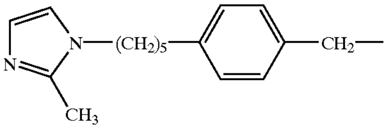 | $—CH_2CH_2C_6H_5$ | $—CO_2H$ |
| 1806 | 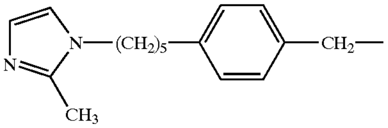 | $—CH_2$-cyclo-$C_6H_{11}$ | $—CO_2H$ |
| 1807 | 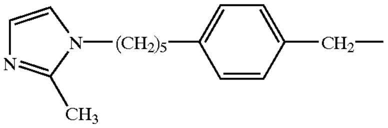 | $—CH_2$-cyclo-$C_6H_{10}$-4-F | $—CO_2H$ |
| 1808 | 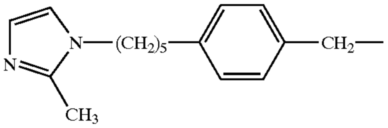 | $—CH_2$-cyclo-$C_6H_{10}$-4-$CH_3$ | $—CO_2H$ |
| 1809 | 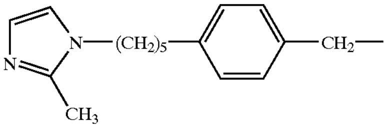 | $—CH_2$-cyclo-$C_6H_{10}$-4-$OCH_3$ | $—CO_2H$ |
| 1810 | 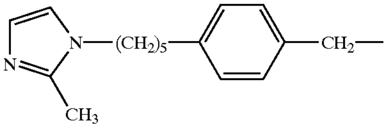 | $—CH_2CH_2$-cyclo-$C_6H_{11}$ | $—CO_2H$ |

TABLE I-continued
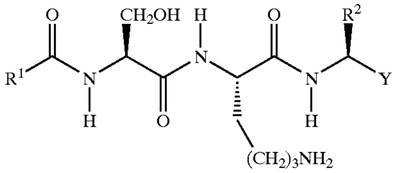
| Ex. No. | $R^1$ | $R^2$ | Y |
|---|---|---|---|
| 1811 | 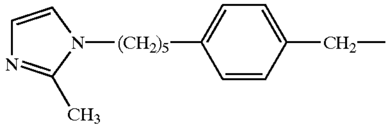 | —$CH_2$-cyclo-$C_5H_9$ | —$CO_2H$ |
| 1812 | 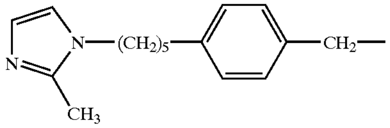 | —$CH_2CH_2$-cyclo-$C_5H_9$ | —$CO_2H$ |
| 1813 | 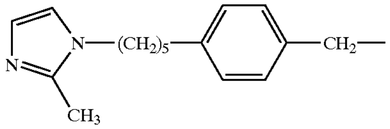 | —$CH_2$-2-naphthyl | —$CO_2H$ |
| 1814 | 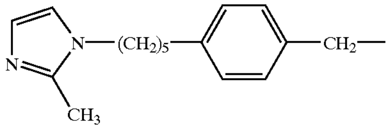 | —H | —$PO_3H_2$ |
| 1815 | 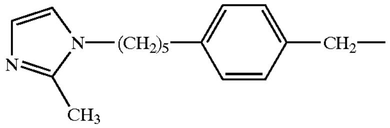 | —$CH_3$ | —$PO_3H_2$ |
| 1816 | 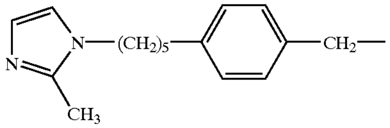 | —$CH_2CH_3$ | —$PO_3H_2$ |
| 1817 | 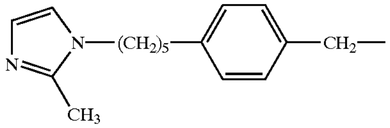 | —$CH_2CH_2CH_3$ | —$PO_3H_2$ |
| 1818 | 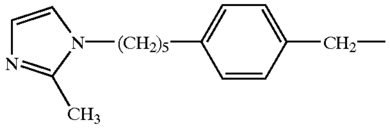 | —$CH_2CH_2CH_2CH_3$ | —$PO_3H_2$ |
| 1819 | 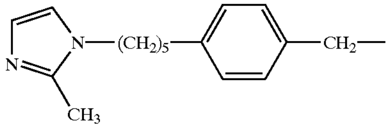 | —$CH_2CH_2CH_2CH_2CH_3$ | —$PO_3H_2$ |

TABLE I-continued
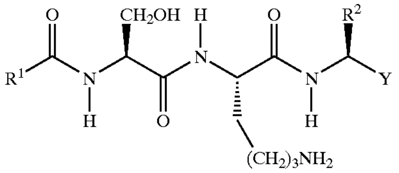
| Ex. No. | $R^1$ | $R^2$ | Y |
|---|---|---|---|
| 1820 | 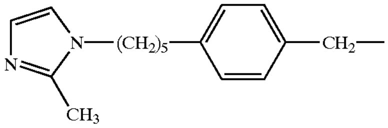 | $—CH_2CH_2CH_2CH_2CH_2CH_3$ | $—PO_3H_2$ |
| 1821 | 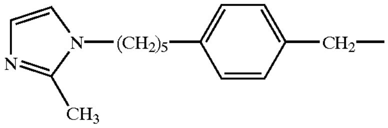 | $—CH(CH_3)_2$ | $—PO_3H_2$ |
| 1822 | 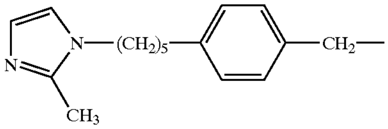 | $—CH_2CH(CH_3)_2$ | $—PO_3H_2$ |
| 1823 | 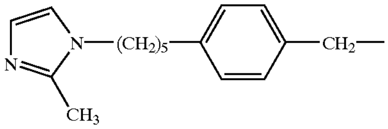 | $—CH_2CH_2CH(CH_3)_2$ | $—PO_3H_2$ |
| 1824 | 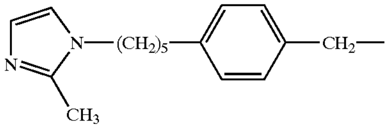 | -cyclo-$C_3H_5$ | $—PO_3H_2$ |
| 1825 | 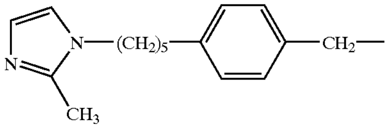 | -cyclo-$C_4H_7$ | $—PO_3H_2$ |
| 1826 | 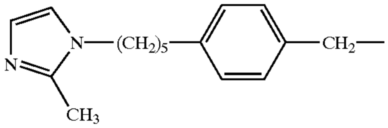 | -cyclo-$C_5H_9$ | $—PO_3H_2$ |
| 1827 | 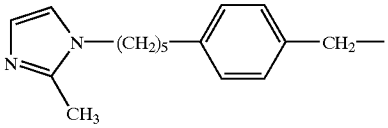 | -cyclo-$C_6H_{11}$ | $—PO_3H_2$ |
| 1828 | 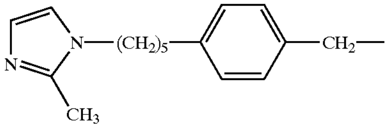 | -cyclo-$C_7H_{13}$ | $—PO_3H_2$ |

TABLE I-continued
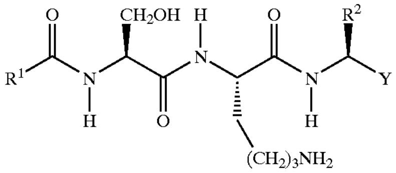
| Ex. No. | $R^1$ | $R^2$ | Y |
|---|---|---|---|
| 1829 | 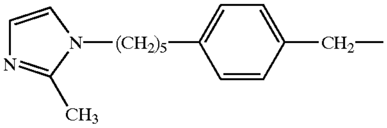 | -cyclo-$C_8H_{15}$ | $—PO_3H_2$ |
| 1830 | 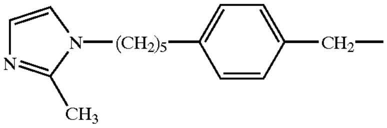 | $—CH(CH_3)(CH_2CH_3)$ | $—PO_3H_2$ |
| 1831 | 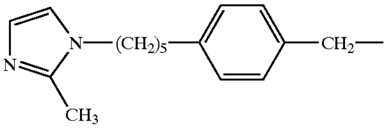 | $—CH(CH_2CH_3)_2$ | $—PO_3H_2$ |
| 1832 | 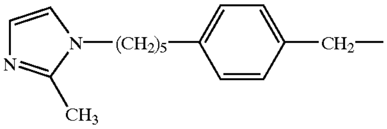 | $—CH(CH_3)(CH_2CH_2CH_3)$ | $—PO_3H_2$ |
| 1833 | 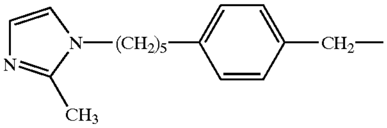 | $—C(CH_3)_3$ | $—PO_3H_2$ |
| 1834 | 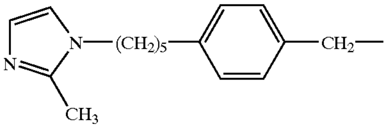 | $HC{\equiv}CCH_2—$ | $—PO_3H_2$ |
| 1835 | 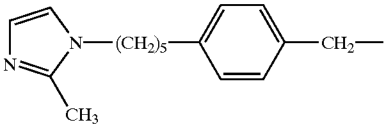 | $H_2C{=}CH—$ | $—PO_3H_2$ |
| 1836 | 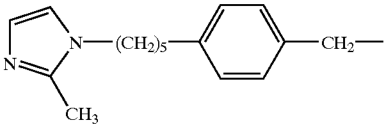 | $H_2C{=}CHCH_2—$ | $—PO_3H_2$ |
| 1837 | 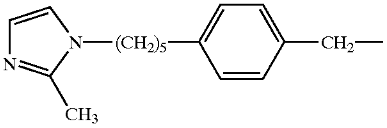 | $—CH_2F$ | $—PO_3H_2$ |

TABLE I-continued
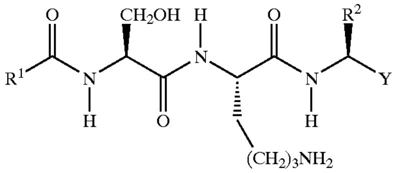
| Ex. No. | $R^1$ | $R^2$ | Y |
|---|---|---|---|
| 1838 | 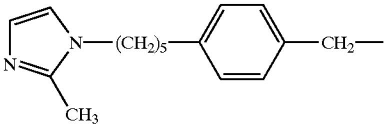 | $—CH_2C_6H_5$ | $—PO_3H_2$ |
| 1839 | 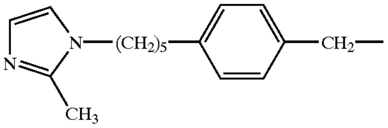 | $—CH_2C_6H_4$-p-$OCH_3$ | $—PO_3H_2$ |
| 1840 | 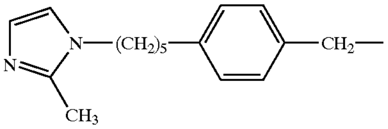 | $—CH_2C_6H_4$-p-$CH_3$ | $—PO_3H_2$ |
| 1841 | 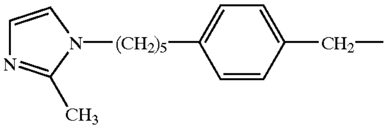 | $—CH_2C_6H_4$-p-F | $—PO_3H_2$ |
| 1842 | 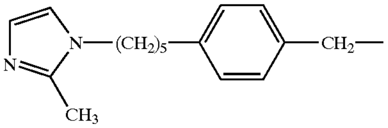 | $—CH_2CH_2C_6H_5$ | $—PO_3H_2$ |
| 1843 | 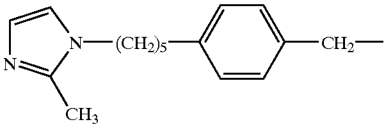 | $—CH_2$-cyclo-$C_6H_{11}$ | $—PO_3H_2$ |
| 1844 | 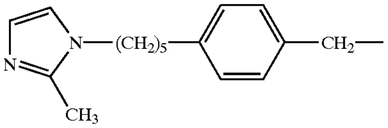 | $—CH_2$-cyclo-$C_6H_{10}$-4-F | $—PO_3H_2$ |
| 1845 | 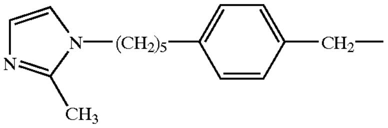 | $—CH_2$-cyclo-$C_6H_{10}$-4-$CH_3$ | $—PO_3H_2$ |
| 1846 | 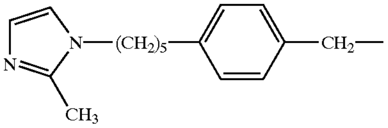 | $—CH_2$-cyclo-$C_6H_{10}$-4-$OCH_3$ | $—PO_3H_2$ |

TABLE I-continued
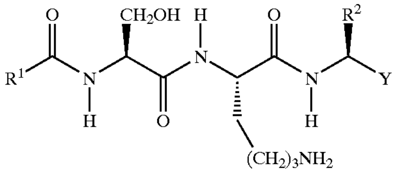
| Ex. No. | $R^1$ | $R^2$ | Y |
|---|---|---|---|
| 1847 | 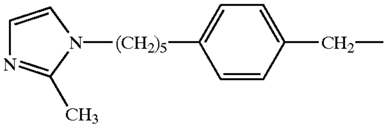 | $—CH_2CH_2$-cyclo-$C_6H_{11}$ | $—PO_3H_2$ |
| 1848 | 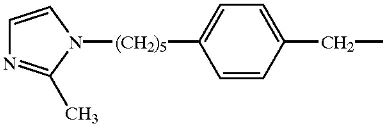 | $—CH_2$-cyclo-$C_5H_9$ | $—PO_3H_2$ |
| 1849 | 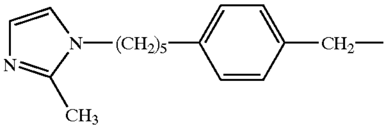 | $—CH_2CH_2$-cyclo-$C_5H_9$ | $—PO_3H_2$ |
| 1850 | 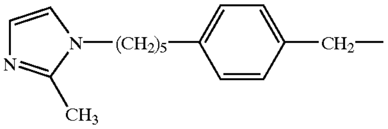 | $—CH_2$-2-naphthyl | $—PO_3H_2$ |
| 1851 | 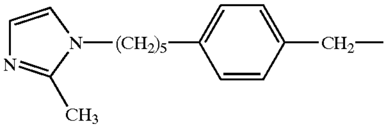 | —H | -5-Tet |
| 1852 | 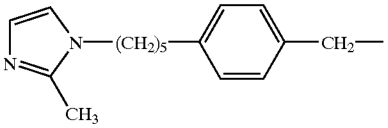 | $—CH_3$ | -5-Tet |
| 1853 | 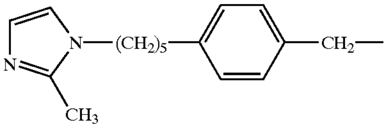 | $—CH_2CH_3$ | -5-Tet |
| 1854 | 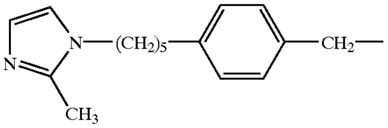 | $—CH_2CH_2CH_3$ | -5-Tet |
| 1855 | 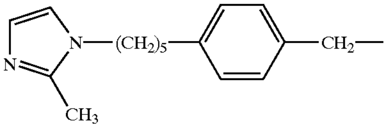 | $—CH_2CH_2CH_2CH_3$ | -5-Tet |

TABLE I-continued
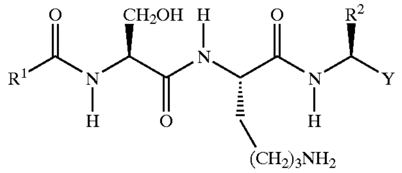
| Ex. No. | $R^1$ | $R^2$ | Y |
|---|---|---|---|
| 1856 | 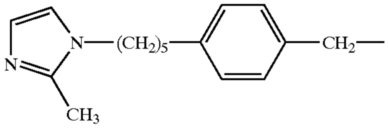 | $—CH_2CH_2CH_2CH_2CH_3$ | -5-Tet |
| 1857 | 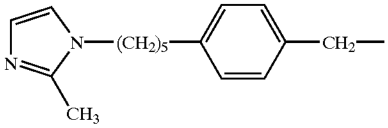 | $—CH_2CH_2CH_2CH_2CH_2CH_3$ | -5-Tet |
| 1858 | 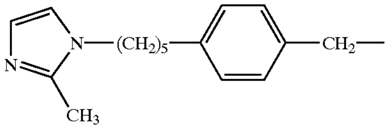 | $—CH(CH_3)_2$ | -5-Tet |
| 1859 | 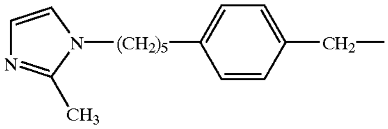 | $—CH_2CH(CH_3)_2$ | -5-Tet |
| 1860 | 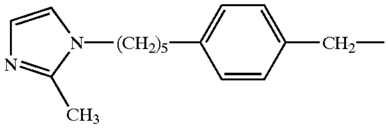 | $—CH_2CH_2CH(CH_3)_2$ | -5-Tet |
| 1861 | 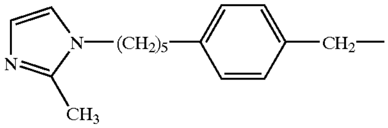 | -cyclo-$C_3H_5$ | -5-Tet |
| 1862 | 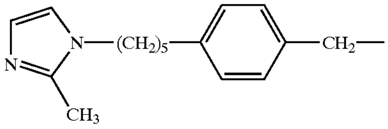 | -cyclo-$C_4H_7$ | -5-Tet |
| 1863 | 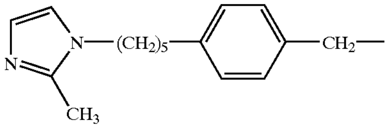 | -cyclo-$C_5H_9$ | -5-Tet |
| 1864 | 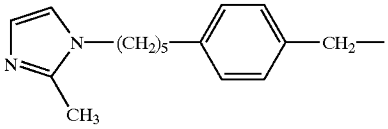 | -cyclo-$C_6H_{11}$ | -5-Tet |

TABLE I-continued
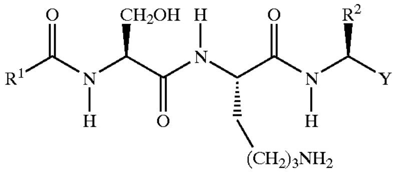
| Ex. No. | $R^1$ | $R^2$ | Y |
|---|---|---|---|
| 1865 | 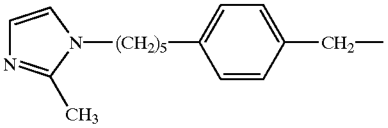 | -cyclo-$C_7H_{13}$ | -5-Tet |
| 1866 | 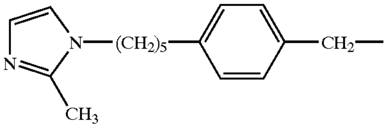 | -cyclo-$C_8H_{15}$ | -5-Tet |
| 1867 | 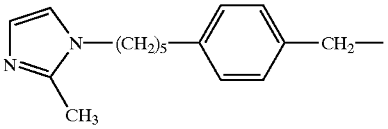 | —$CH(CH_3)(CH_2CH_3)$ | -5-Tet |
| 1868 | 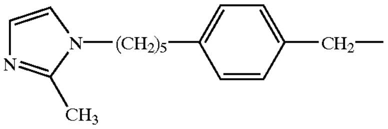 | —$CH(CH_2CH_3)_2$ | -5-Tet |
| 1869 | 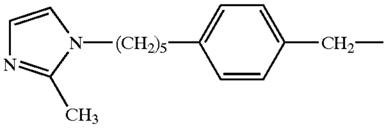 | —$CH(CH_3)(CH_2CH_2CH_3)$ | -5-Tet |
| 1870 | 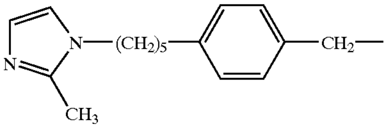 | —$C(CH_3)_3$ | -5-Tet |
| 1871 | 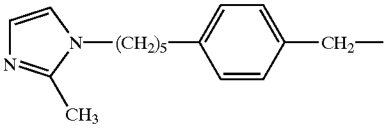 | $HC{\equiv}CCH_2$— | -5-Tet |
| 1872 | 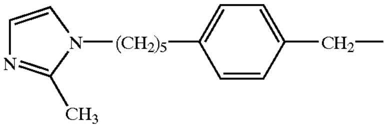 | $H_2C{=}CH$— | -5-Tet |
| 1873 | 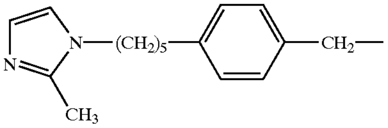 | $H_2C{=}CHCH_2$— | -5-Tet |

TABLE I-continued
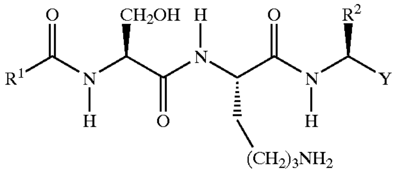
| Ex. No. | $R^1$ | $R^2$ | Y |
|---|---|---|---|
| 1874 | 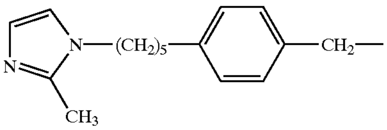 | $—CH_2F$ | -5-Tet |
| 1875 | 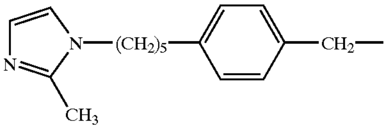 | $—CH_2C_6H_5$ | -5-Tet |
| 1876 | 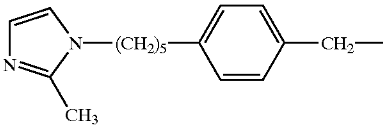 | $—CH_2C_6H_4$-p-$OCH_3$ | -5-Tet |
| 1877 | 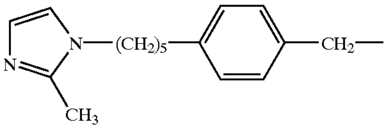 | $—CH_2C_6H_4$-p-$CH_3$ | -5-Tet |
| 1878 | 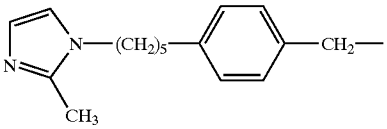 | $—CH_2C_6H_4$-p-F | -5-Tet |
| 1879 | 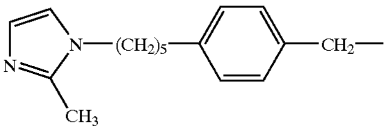 | $—CH_2CH_2C_6H_5$ | -5-Tet |
| 1880 | 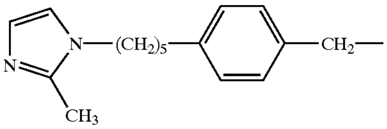 | $—CH_2$-cyclo-$C_6H_{11}$ | -5-Tet |
| 1881 | 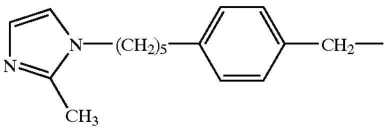 | $—CH_2$-cyclo-$C_6H_{10}$-4-F | -5-Tet |
| 1882 | 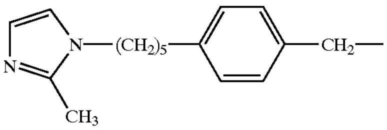 | $—CH_2$-cyclo-$C_6H_{10}$-4-$CH_3$ | -5-Tet |

TABLE I-continued
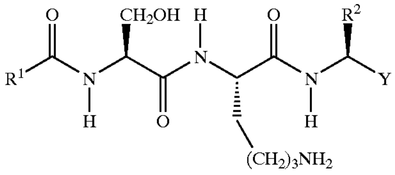
| Ex. No. | $R^1$ | $R^2$ | Y |
|---|---|---|---|
| 1883 | 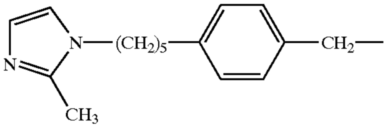 | $—CH_2$-cyclo-$C_6H_{10}$-4-$OCH_3$ | -5-Tet |
| 1884 | 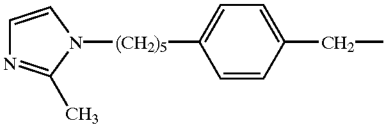 | $—CH_2CH_2$-cyclo-$C_6H_{11}$ | -5-Tet |
| 1885 | 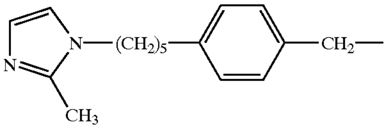 | $—CH_2$-cyclo-$C_5H_9$ | -5-Tet |
| 1886 | 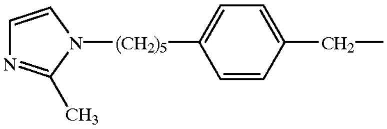 | $—CH_2CH_2$-cyclo-$C_5H_9$ | -5-Tet |
| 1887 | 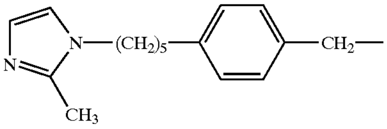 | $—CH_2$-2-naphthyl | -5-Tet |
| 1888 | 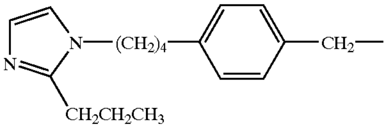 | —H | $—CO_2H$ |
| 1889 | 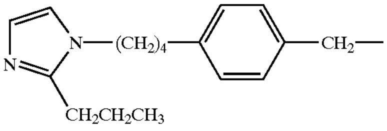 | $—CH_3$ | $—CO_2H$ |
| 1890 | 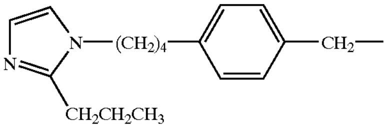 | $—CH_2CH_3$ | $—CO_2H$ |
| 1891 | 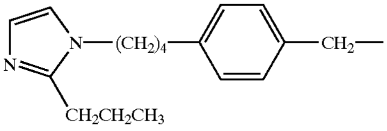 | $—CH_2CH_2CH_3$ | $—CO_2H$ |

TABLE I-continued
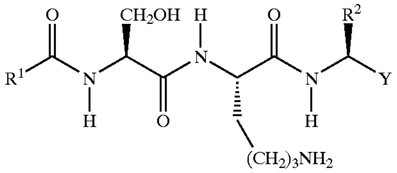
| Ex. No. | $R^1$ | $R^2$ | Y |
|---|---|---|---|
| 1892 | 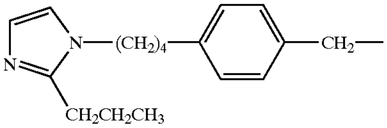 | $—CH_2CH_2CH_2CH_3$ | $—CO_2H$ |
| 1893 | 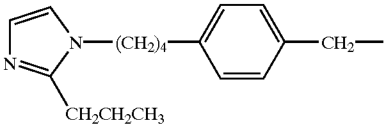 | $—CH_2CH_2CH_2CH_2CH_3$ | $—CO_2H$ |
| 1894 | 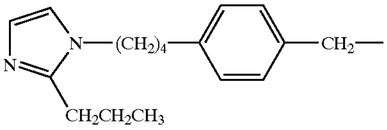 | $—CH_2CH_2CH_2CH_2CH_2CH_3$ | $—CO_2H$ |
| 1895 | 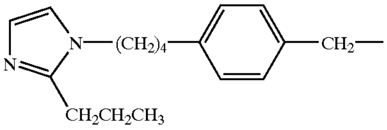 | $—CH(CH_3)_2$ | $—CO_2H$ |
| 1896 | 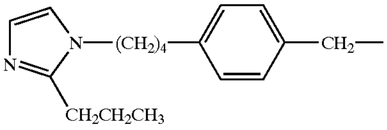 | $—CH_2CH(CH_3)_2$ | $—CO_2H$ |
| 1897 | 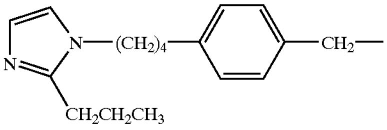 | $—CH_2CH_2CH(CH_3)_2$ | $—CO_2H$ |
| 1898 | 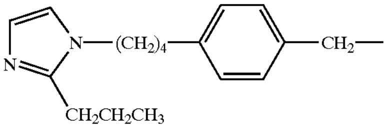 | -cyclo-$C_3H_5$ | $—CO_2H$ |
| 1899 | 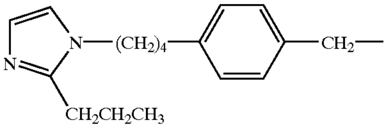 | -cyclo-$C_4H_7$ | $—CO_2H$ |
| 1900 | 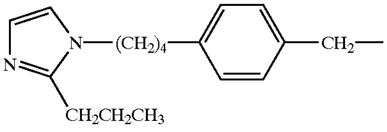 | -cyclo-$C_5H_9$ | $—CO_2H$ |

TABLE I-continued
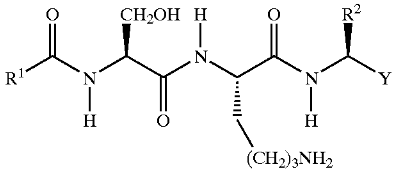
| Ex. No. | $R^1$ | $R^2$ | Y |
|---|---|---|---|
| 1901 | 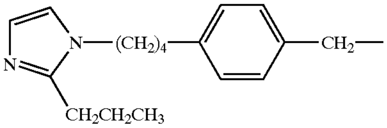 | -cyclo-$C_6H_{11}$ | —$CO_2H$ |
| 1902 | 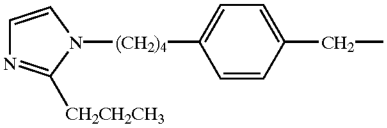 | -cyclo-$C_7H_{13}$ | —$CO_2H$ |
| 1903 | 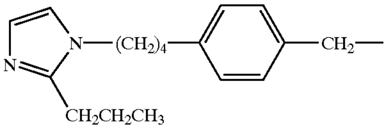 | -cyclo-$C_8H_{15}$ | —$CO_2H$ |
| 1904 | 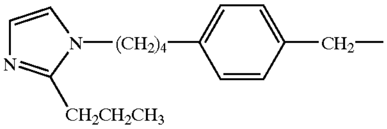 | —$CH(CH_3)(CH_2CH_3)$ | —$CO_2H$ |
| 1905 | 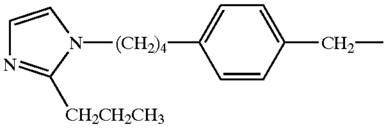 | —$CH(CH_2CH_3)_2$ | —$CO_2H$ |
| 1906 | 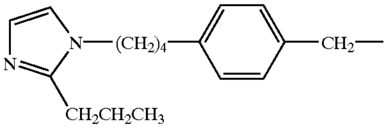 | —$CH(CH_3)(CH_2CH_2CH_3)$ | —$CO_2H$ |
| 1907 | 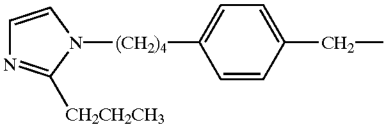 | —$C(CH_3)_3$ | —$CO_2H$ |
| 1908 | 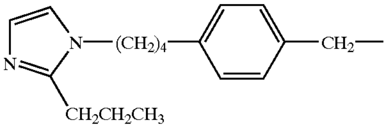 | $HC{\equiv}CCH_2$— | —$CO_2H$ |
| 1909 | 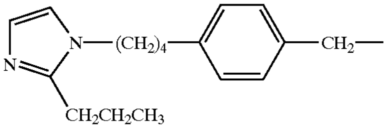 | $H_2C{=}CH$— | —$CO_2H$ |

TABLE I-continued
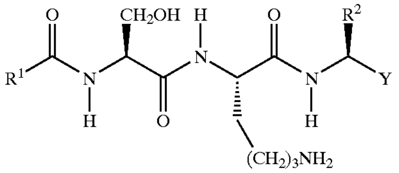
| Ex. No. | $R^1$ | $R^2$ | Y |
|---|---|---|---|
| 1910 | 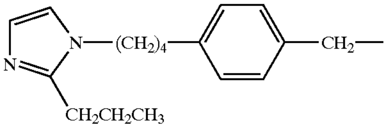 | $H_2C{=}CHCH_2$— | —$CO_2H$ |
| 1911 | 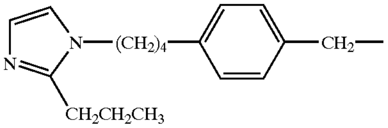 | —$CH_2F$ | —$CO_2H$ |
| 1912 | 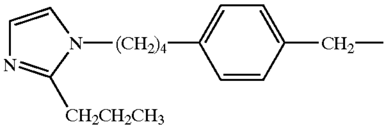 | —$CH_2C_6H_5$ | —$CO_2H$ |
| 1913 | 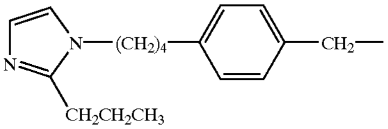 | —$CH_2C_6H_4$-p-$OCH_3$ | —$CO_2H$ |
| 1914 | 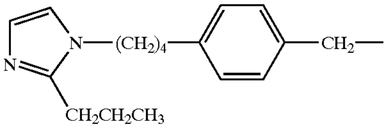 | —$CH_2C_6H_4$-p-$CH_3$ | —$CO_2H$ |
| 1915 | 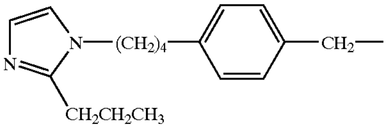 | —$CH_2C_6H_4$-p-F | —$CO_2H$ |
| 1916 | 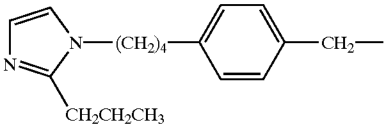 | —$CH_2CH_2C_6H_5$ | —$CO_2H$ |
| 1917 | 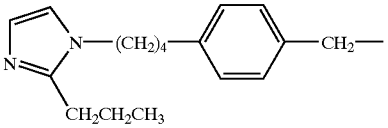 | —$CH_2$-cyclo-$C_6H_{11}$ | —$CO_2H$ |
| 1918 | 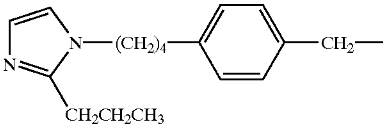 | —$CH_2$-cyclo-$C_6H_{10}$-4-F | —$CO_2H$ |

TABLE I-continued
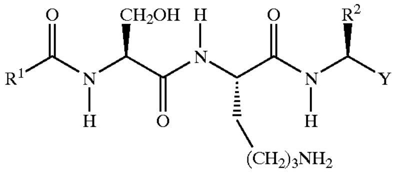
| Ex. No. | $R^1$ | $R^2$ | Y |
|---|---|---|---|
| 1919 | 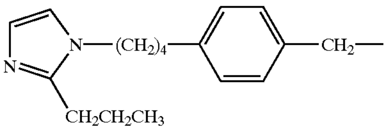 | $—CH_2$-cyclo-$C_6H_{10}$-4-$CH_3$ | $—CO_2H$ |
| 1920 | 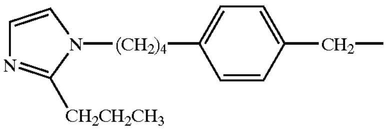 | $—CH_2$-cyclo-$C_6H_{10}$-4-$OCH_3$ | $—CO_2H$ |
| 1921 | 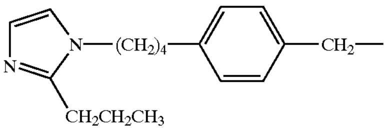 | $—CH_2CH_2$-cyclo-$C_6H_{11}$ | $—CO_2H$ |
| 1922 | 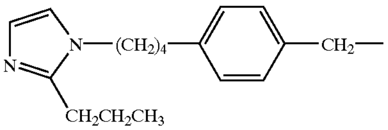 | $—CH_2$-cyclo-$C_5H_9$ | $—CO_2H$ |
| 1923 | 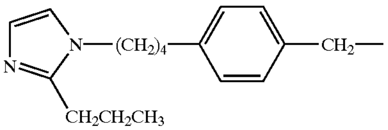 | $—CH_2CH_2$-cyclo-$C_5H_9$ | $—CO_2H$ |
| 1924 | 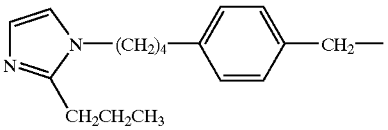 | $—CH_2$-2-naphthyl | $—CO_2H$ |
| 1925 | 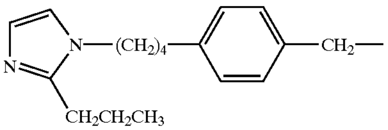 | —H | $—PO_3H_2$ |
| 1926 | 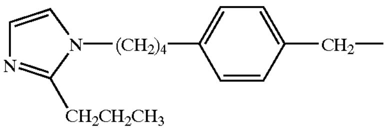 | $—CH_3$ | $—PO_3H_2$ |
| 1927 | 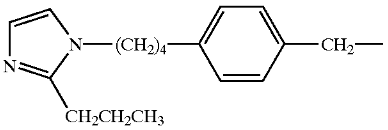 | $—CH_2CH_3$ | $—PO_3H_2$ |

TABLE I-continued
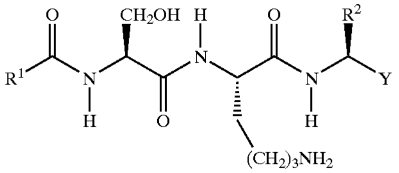
| Ex. No. | $R^1$ | $R^2$ | Y |
|---|---|---|---|
| 1928 | 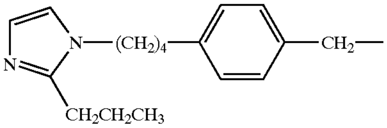 | $—CH_2CH_2CH_3$ | $—PO_3H_2$ |
| 1929 | 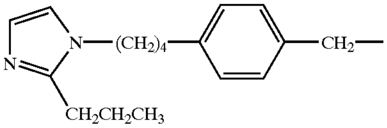 | $—CH_2CH_2CH_2CH_3$ | $—PO_3H_2$ |
| 1930 | 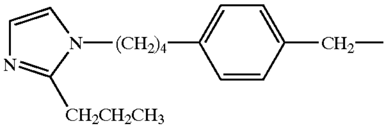 | $—CH_2CH_2CH_2CH_2CH_3$ | $—PO_3H_2$ |
| 1931 | 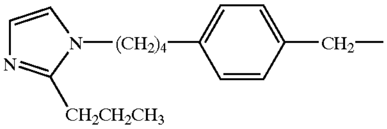 | $—CH_2CH_2CH_2CH_2CH_2CH_3$ | $—PO_3H_2$ |
| 1932 | 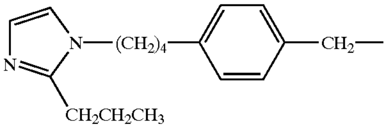 | $—CH(CH_3)_2$ | $—PO_3H_2$ |
| 1933 | 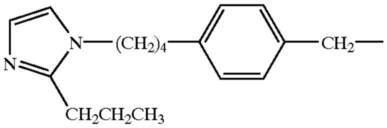 | $—CH_2CH(CH_3)_2$ | $—PO_3H_2$ |
| 1934 | 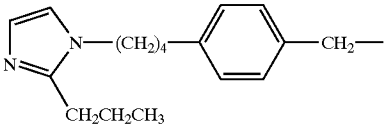 | $—CH_2CH_2CH(CH_3)_2$ | $—PO_3H_2$ |
| 1935 | 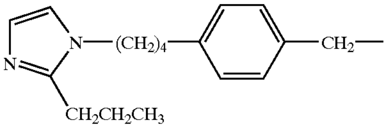 | -cyclo-$C_3H_5$ | $—PO_3H_2$ |
| 1936 | 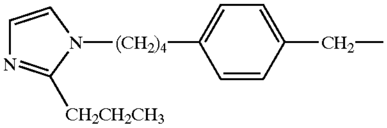 | -cyclo-$C_4H_7$ | $—PO_3H_2$ |

TABLE I-continued
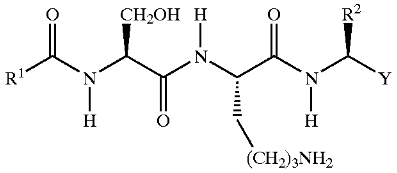
| Ex. No. | $R^1$ | $R^2$ | Y |
|---|---|---|---|
| 1937 | 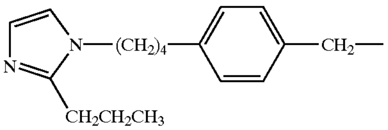 | -cyclo-$C_5H_9$ | —$PO_3H_2$ |
| 1938 | 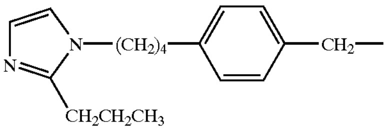 | -cyclo-$C_6H_{11}$ | —$PO_3H_2$ |
| 1939 | 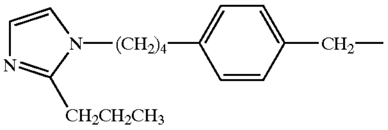 | -cyclo-$C_7H_{13}$ | —$PO_3H_2$ |
| 1940 | 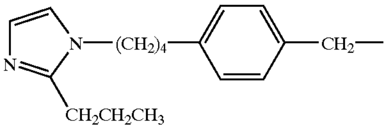 | -cyclo-$C_8H_{15}$ | —$PO_3H_2$ |
| 1941 | 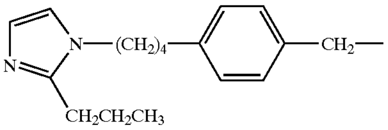 | —$CH(CH_3)(CH_2CH_3)$ | —$PO_3H_2$ |
| 1942 | 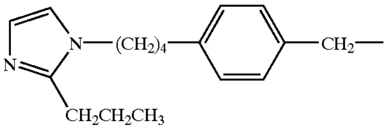 | —$CH(CH_2CH_3)_2$ | —$PO_3H_2$ |
| 1943 | 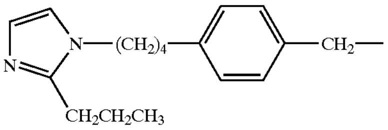 | —$CH(CH_3)(CH_2CH_2CH_3)$ | —$PO_3H_2$ |
| 1944 | 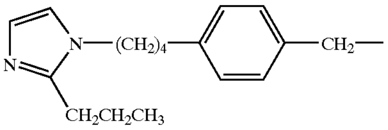 | —$C(CH_3)_3$ | —$PO_3H_2$ |
| 1945 | 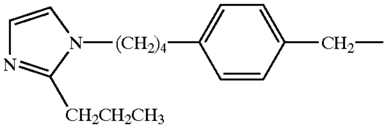 | $HC{\equiv}CCH_2$— | —$PO_3H_2$ |

TABLE I-continued
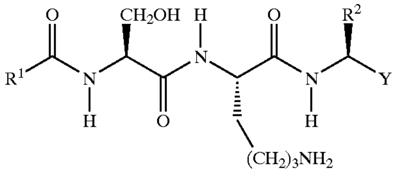
| Ex. No. | $R^1$ | $R^2$ | Y |
|---|---|---|---|
| 1946 | 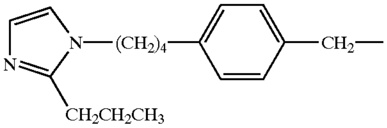 | $H_2C{=}CH—$ | $—PO_3H_2$ |
| 1947 | 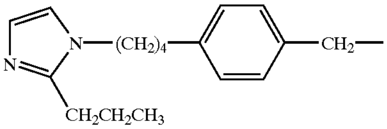 | $H_2C{=}CHCH_2—$ | $—PO_3H_2$ |
| 1948 | 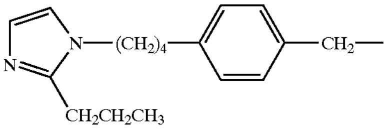 | $—CH_2F$ | $—PO_3H_2$ |
| 1949 | 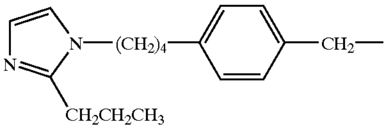 | $—CH_2C_6H_5$ | $—PO_3H_2$ |
| 1950 | 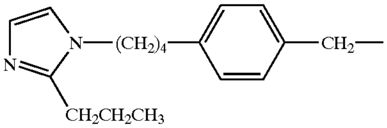 | $—CH_2C_6H_4$-p-$OCH_3$ | $—PO_3H_2$ |
| 1951 | 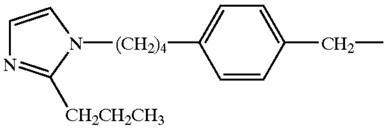 | $—CH_2C_6H_4$-p-$CH_3$ | $—PO_3H_2$ |
| 1952 | 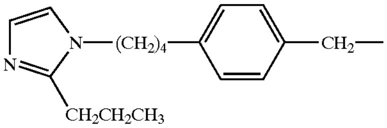 | $—CH_2C_6H_4$-p-F | $—PO_3H_2$ |
| 1953 | 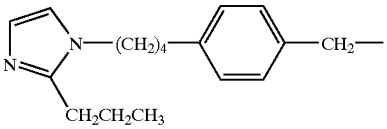 | $—CH_2CH_2C_6H_5$ | $—PO_3H_2$ |
| 1954 | 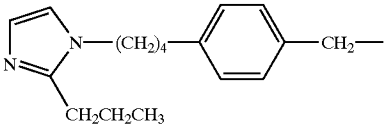 | $—CH_2$-cyclo-$C_6H_{11}$ | $—PO_3H_2$ |

TABLE I-continued
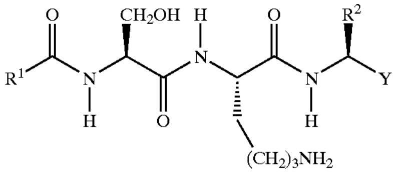
| Ex. No. | $R^1$ | $R^2$ | Y |
|---|---|---|---|
| 1955 | 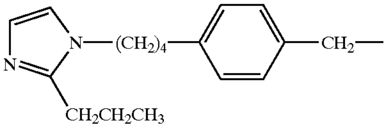 | $—CH_2$-cyclo-$C_6H_{10}$-4-F | $—PO_3H_2$ |
| 1956 | 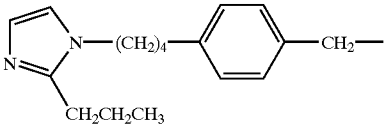 | $—CH_2$-cyclo-$C_6H_{10}$-4-$CH_3$ | $—PO_3H_2$ |
| 1957 | 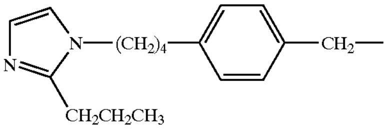 | $—CH_2$-cyclo-$C_6H_{10}$-4-$OCH_3$ | $—PO_3H_2$ |
| 1958 | 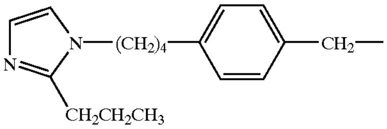 | $—CH_2CH_2$-cyclo-$C_6H_{11}$ | $—PO_3H_2$ |
| 1959 | 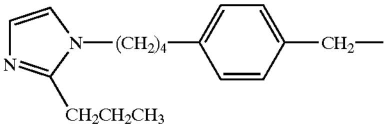 | $—CH_2$-cyclo-$C_5H_9$ | $—PO_3H_2$ |
| 1960 | 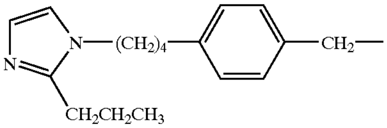 | $—CH_2CH_2$-cyclo-$C_5H_9$ | $—PO_3H_2$ |
| 1961 | 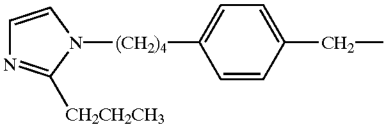 | $—CH_2$-2-naphthyl | $—PO_3H_2$ |
| 1962 | 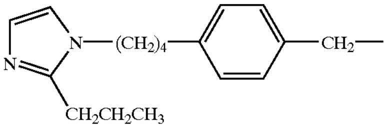 | —H | -5-Tet |
| 1963 | 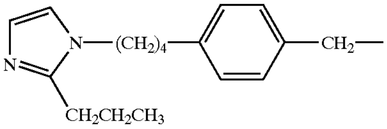 | $—CH_3$ | -5-Tet |

TABLE I-continued
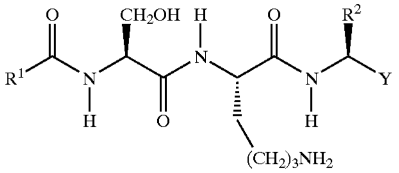
| Ex. No. | $R^1$ | $R^2$ | Y |
|---|---|---|---|
| 1964 | 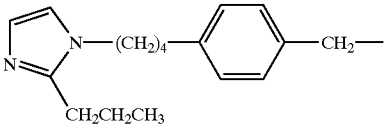 | $—CH_2CH_3$ | -5-Tet |
| 1965 | 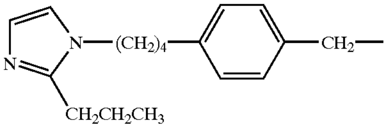 | $—CH_2CH_2CH_3$ | -5-Tet |
| 1966 | 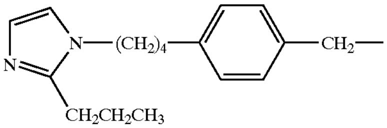 | $—CH_2CH_2CH_2CH_3$ | -5-Tet |
| 1967 | 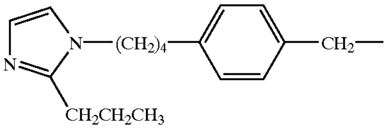 | $—CH_2CH_2CH_2CH_2CH_3$ | -5-Tet |
| 1968 | 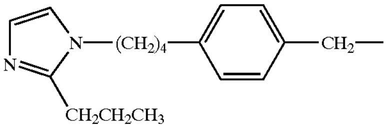 | $—CH_2CH_2CH_2CH_2CH_2CH_3$ | -5-Tet |
| 1969 | 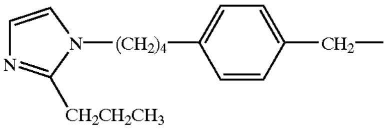 | $—CH(CH_3)_2$ | -5-Tet |
| 1970 | 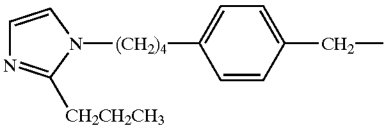 | $—CH_2CH(CH_3)_2$ | -5-Tet |
| 1971 | 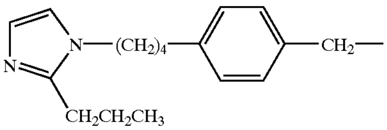 | $—CH_2CH_2CH(CH_3)_2$ | -5-Tet |
| 1972 | 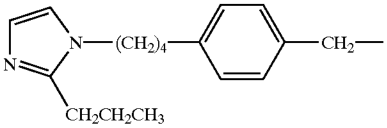 | -cyclo-$C_3H_5$ | -5-Tet |

TABLE I-continued
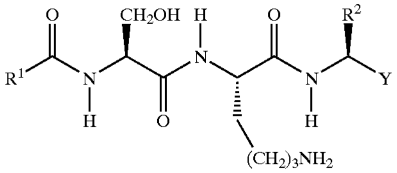
| Ex. No. | $R^1$ | $R^2$ | Y |
| --- | --- | --- | --- |
| 1973 | 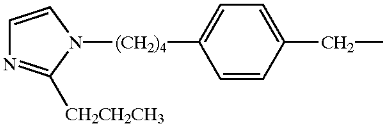 | -cyclo-$C_4H_7$ | -5-Tet |
| 1974 | 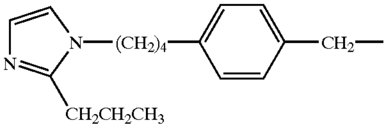 | -cyclo-$C_5H_9$ | -5-Tet |
| 1975 | 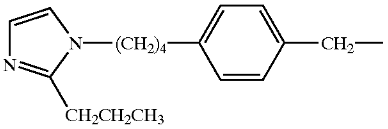 | -cyclo-$C_6H_{11}$ | -5-Tet |
| 1976 | 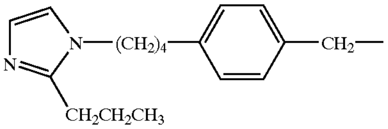 | -cyclo-$C_7H_{13}$ | -5-Tet |
| 1977 | 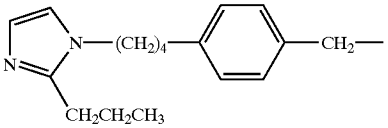 | -cyclo-$C_8H_{15}$ | -5-Tet |
| 1978 | 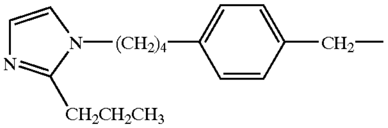 | $—CH(CH_3)(CH_2CH_3)$ | -5-Tet |
| 1979 | 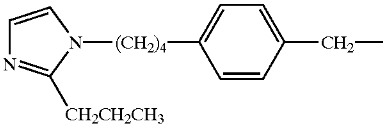 | $—CH(CH_2CH_3)_2$ | -5-Tet |
| 1980 | 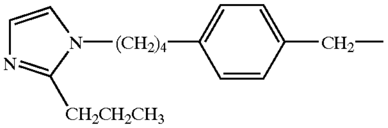 | $—CH(CH_3)(CH_2CH_2CH_3)$ | -5-Tet |
| 1981 | 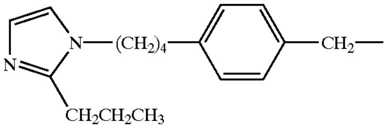 | $—C(CH_3)_3$ | -5-Tet |

TABLE I-continued
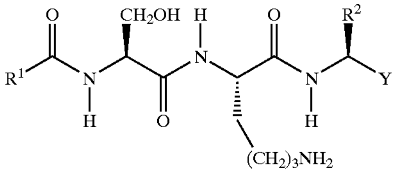
| Ex. No. | $R^1$ | $R^2$ | Y |
|---|---|---|---|
| 1982 | 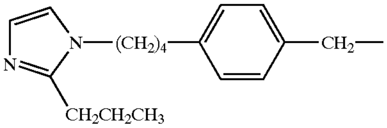 | $HC\equiv CCH_2$— | -5-Tet |
| 1983 | 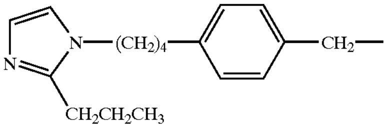 | $H_2C{=}CH$— | -5-Tet |
| 1984 | 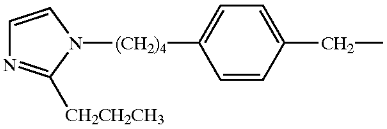 | $H_2C{=}CHCH_2$— | -5-Tet |
| 1985 | 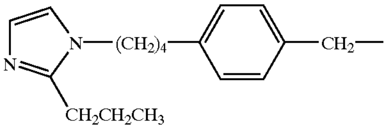 | —$CH_2F$ | -5-Tet |
| 1986 | 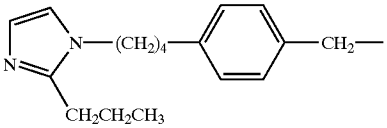 | —$CH_2C_6H_5$ | -5-Tet |
| 1987 | 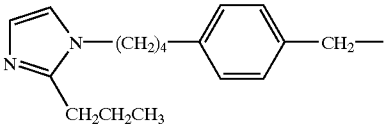 | —$CH_2C_6H_4$-p-$OCH_3$ | -5-Tet |
| 1988 | 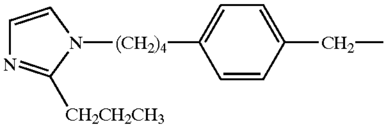 | —$CH_2C_6H_4$-p-$CH_3$ | -5-Tet |
| 1989 | 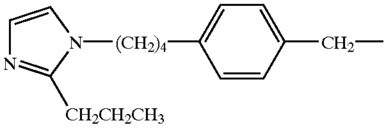 | —$CH_2C_6H_4$-p-F | -5-Tet |
| 1990 | 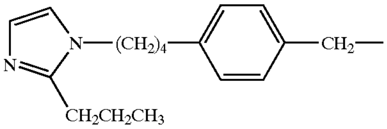 | —$CH_2CH_2C_6H_5$ | -5-Tet |

TABLE I-continued
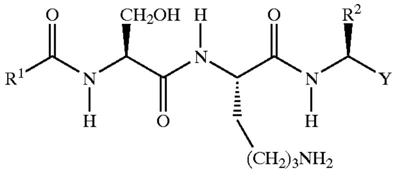
| Ex. No. | $R^1$ | $R^2$ | Y |
|---|---|---|---|
| 1991 | 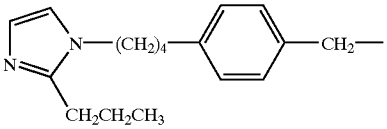 | $—CH_2$-cyclo-$C_6H_{11}$ | -5-Tet |
| 1992 | 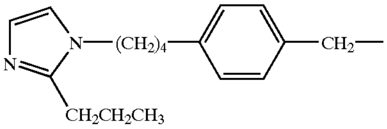 | $—CH_2$-cyclo-$C_6H_{10}$-4-F | -5-Tet |
| 1993 | 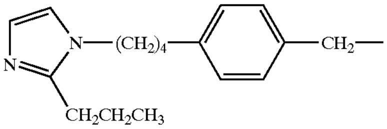 | $—CH_2$-cyclo-$C_6H_{10}$-4-$CH_3$ | -5-Tet |
| 1994 | 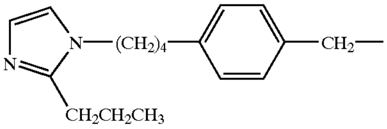 | $—CH_2$-cyclo-$C_6H_{10}$-4-$OCH_3$ | -5-Tet |
| 1995 | 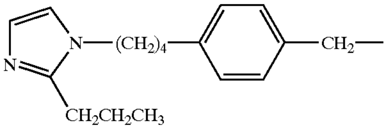 | $—CH_2CH_2$-cyclo-$C_6H_{11}$ | -5-Tet |
| 1996 | 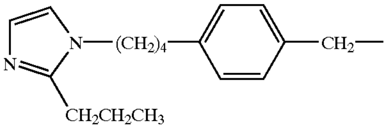 | $—CH_2$-cyclo-$C_5H_9$ | -5-Tet |
| 1997 | 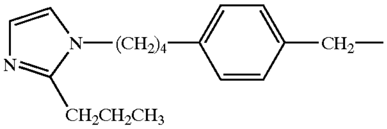 | $—CH_2CH_2$-cyclo-$C_5H_9$ | -5-Tet |
| 1998 | 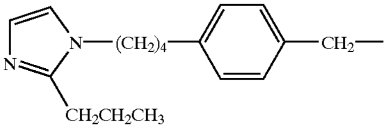 | $—CH_2$-2-naphthyl | -5-Tet |
| 1999 | 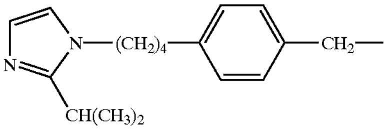 | —H | $—CO_2H$ |

TABLE I-continued
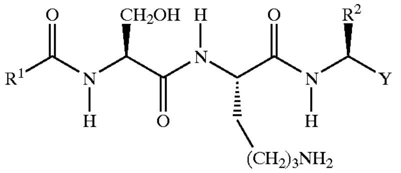
| Ex. No. | $R^1$ | $R^2$ | Y |
|---|---|---|---|
| 2000 | 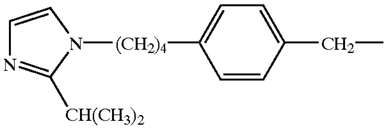 | $—CH_3$ | $—CO_2H$ |
| 2001 | 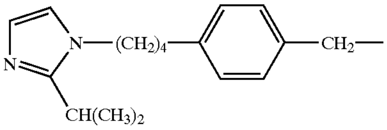 | $—CH_2CH_3$ | $—CO_2H$ |
| 2002 | 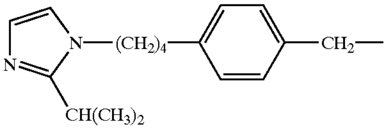 | $—CH_2CH_2CH_3$ | $—CO_2H$ |
| 2003 | 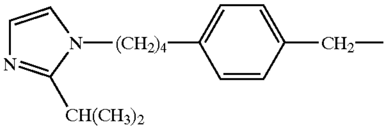 | $—CH_2CH_2CH_2CH_3$ | $—CO_2H$ |
| 2004 | 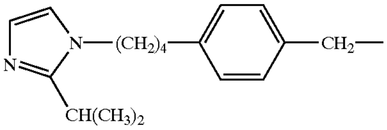 | $—CH_2CH_2CH_2CH_2CH_3$ | $—CO_2H$ |
| 2005 | 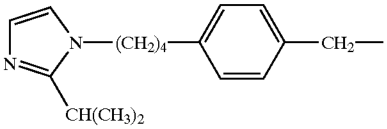 | $—CH_2CH_2CH_2CH_2CH_2CH_3$ | $—CO_2H$ |
| 2006 | 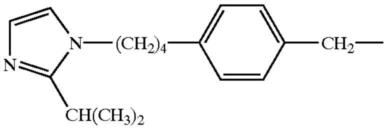 | $—CH(CH_3)_2$ | $—CO_2H$ |
| 2007 | 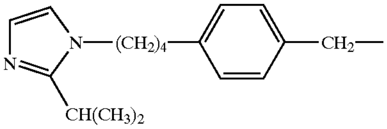 | $—CH_2CH(CH_3)_2$ | $—CO_2H$ |
| 2008 | 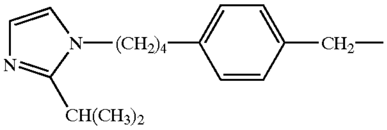 | $—CH_2CH_2CH(CH_3)_2$ | $—CO_2H$ |

TABLE I-continued
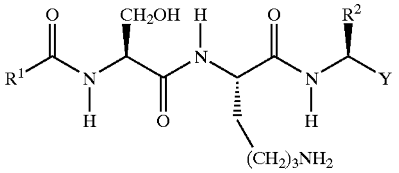
| Ex. No. | $R^1$ | $R^2$ | Y |
|---|---|---|---|
| 2009 | 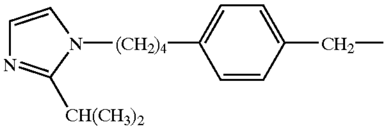 | —cyclo-$C_3H_5$ | —$CO_2H$ |
| 2010 | 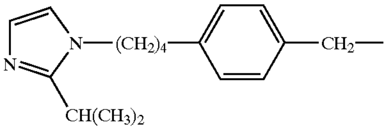 | -cyclo-$C_4H_7$ | —$CO_2H$ |
| 2011 | 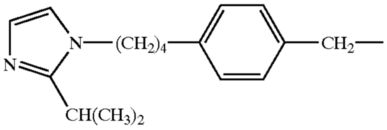 | -cyclo-$C_5H_9$ | —$CO_2H$ |
| 2012 | 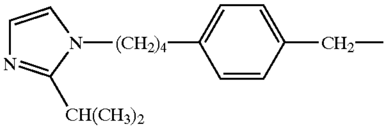 | -cyclo-$C_6H_{11}$ | —$CO_2H$ |
| 2013 | 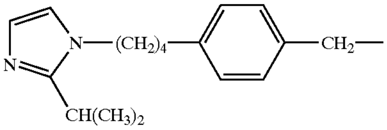 | -cyclo-$C_7H_{13}$ | —$CO_2H$ |
| 2014 | 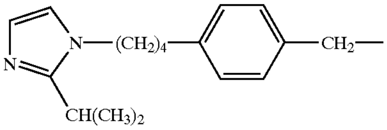 | -cyclo-$C_8H_{15}$ | —$CO_2H$ |
| 2015 | 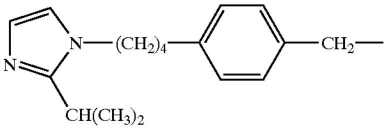 | —$CH(CH_3)(CH_2CH_3)$ | —$CO_2H$ |
| 2016 | 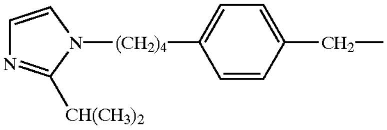 | —$CH(CH_2CH_3)_2$ | —$CO_2H$ |
| 2017 | 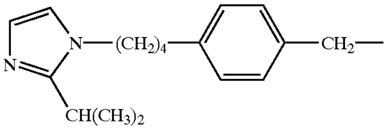 | —$CH(CH_3)(CH_2CH_2CH_3)$ | —$CO_2H$ |

TABLE I-continued
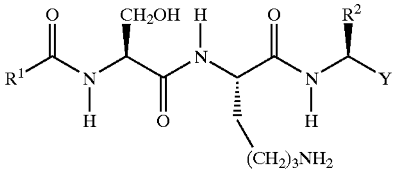
| Ex. No. | $R^1$ | $R^2$ | Y |
|---|---|---|---|
| 2018 | 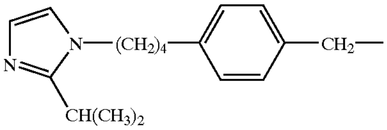 | $—C(CH_3)_3$ | $—CO_2H$ |
| 2019 | 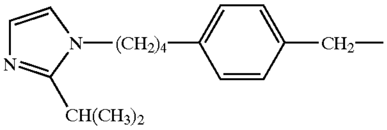 | $HC{\equiv}CCH_2—$ | $—CO_2H$ |
| 2020 | 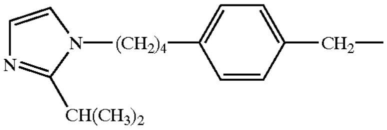 | $H_2C{=}CH—$ | $—CO_2H$ |
| 2021 | 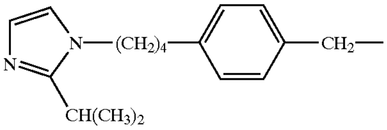 | $H_2C{=}CHCH_2—$ | $—CO_2H$ |
| 2022 | 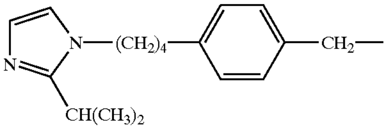 | $—CH_2F$ | $—CO_2H$ |
| 2023 | 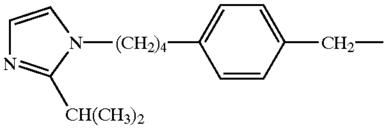 | $—CH_2C_6H_5$ | $—CO_2H$ |
| 2024 | 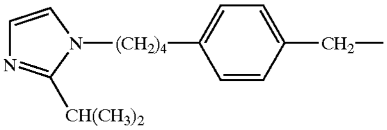 | $—CH_2C_6H_4$-p-$OCH_3$ | $—CO_2H$ |
| 2025 | 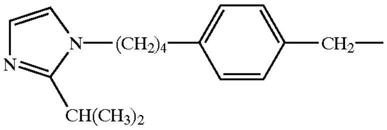 | $—CH_2C_6H_4$-p-$CH_3$ | $—CO_2H$ |
| 2026 | 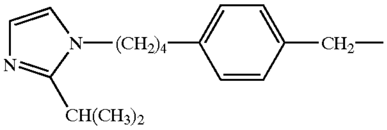 | $—CH_2C_6H_4$-p-F | $—CO_2H$ |

TABLE I-continued
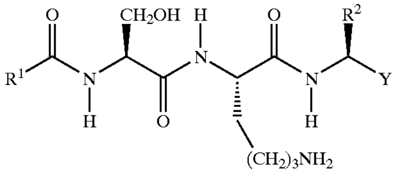
| Ex. No. | $R^1$ | $R^2$ | Y |
|---|---|---|---|
| 2027 | 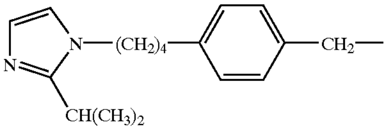 | $—CH_2CH_2C_6H_5$ | $—CO_2H$ |
| 2028 | 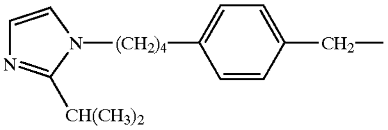 | $—CH_2$-cyclo-$C_6H_{11}$ | $—CO_2H$ |
| 2029 | 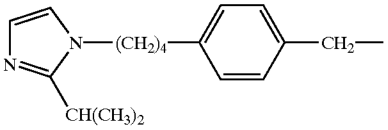 | $—CH_2$-cyclo-$C_6H_{10}$-4-F | $—CO_2H$ |
| 2030 | 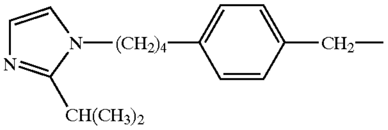 | $—CH_2$-cyclo-$C_6H_{10}$-4-$CH_3$ | $—CO_2H$ |
| 2031 | 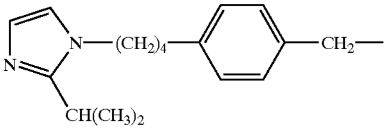 | $—CH_2$-cyclo-$C_6H_{10}$-4-$OCH_3$ | $—CO_2H$ |
| 2032 | 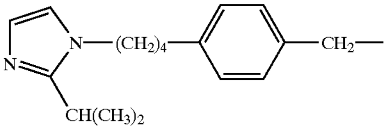 | $—CH_2CH_2$-cyclo-$C_6H_{11}$ | $—CO_2H$ |
| 2033 | 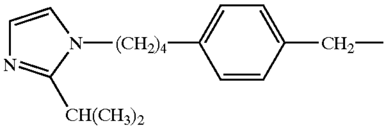 | $—CH_2$-cyclo-$C_5H_9$ | $—CO_2H$ |
| 2034 | 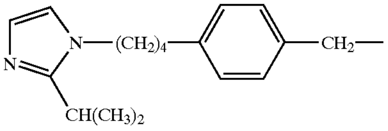 | $—CH_2CH_2$-cyclo-$C_5H_9$ | $—CO_2H$ |
| 2035 | 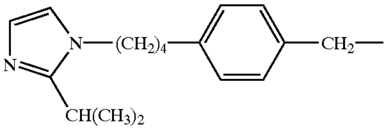 | $—CH_2$-2-naphthyl | $—CO_2H$ |

TABLE I-continued
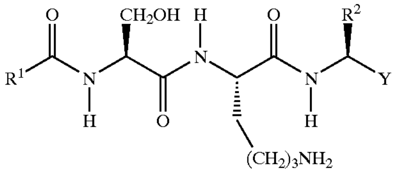
| Ex. No. | $R^1$ | $R^2$ | Y |
|---|---|---|---|
| 2036 | 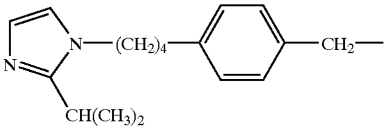 | —H | $—PO_3H_2$ |
| 2037 | 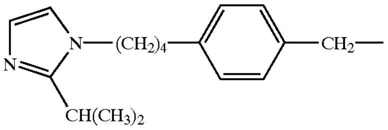 | $—CH_3$ | $—PO_3H_2$ |
| 2038 | 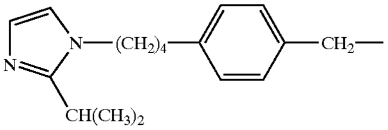 | $—CH_2CH_3$ | $—PO_3H_2$ |
| 2039 | 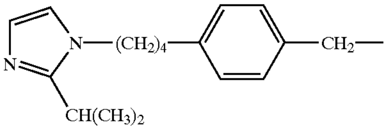 | $—CH_2CH_2CH_3$ | $—PO_3H_2$ |
| 2040 | 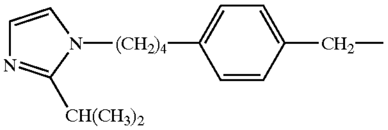 | $—CH_2CH_2CH_2CH_3$ | $—PO_3H_2$ |
| 2041 | 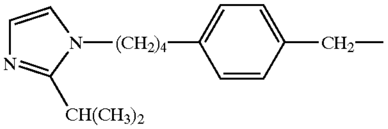 | $—CH_2CH_2CH_2CH_2CH_3$ | $—PO_3H_2$ |
| 2042 | 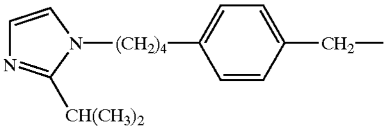 | $—CH_2CH_2CH_2CH_2CH_2CH_3$ | $—PO_3H_2$ |
| 2043 | 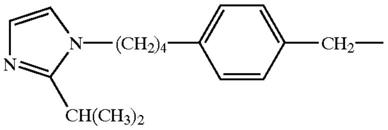 | $—CH(CH_3)_2$ | $—PO_3H_2$ |
| 2044 | 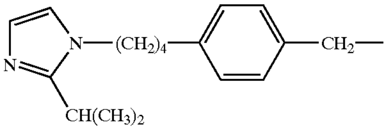 | $—CH_2CH(CH_3)_2$ | $—PO_3H_2$ |

TABLE I-continued
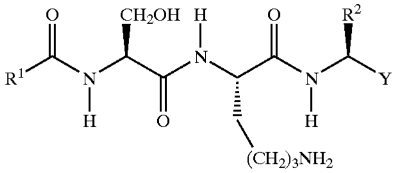
| Ex. No. | $R^1$ | $R^2$ | Y |
|---|---|---|---|
| 2045 | 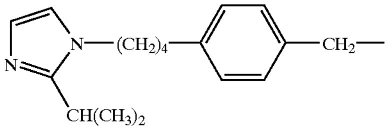 | $—CH_2CH_2CH(CH_3)_2$ | $—PO_3H_2$ |
| 2046 | 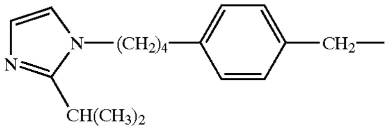 | $-cyclo-C_3H_5$ | $—PO_3H_2$ |
| 2047 | 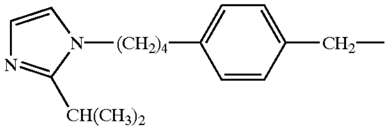 | $-cyclo-C_4H_7$ | $—PO_3H_2$ |
| 2048 | 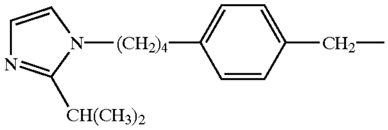 | $-cyclo-C_5H_9$ | $—PO_3H_2$ |
| 2049 | 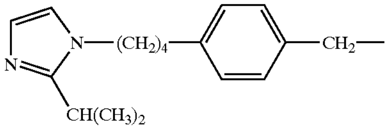 | $-cyclo-C_6H_{11}$ | $—PO_3H_2$ |
| 2050 | 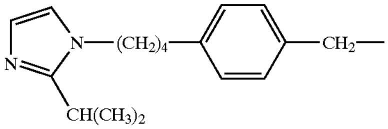 | $-cyclo-C_7H_{13}$ | $—PO_3H_2$ |
| 2051 | 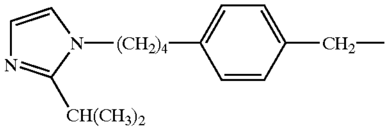 | $-cyclo-C_8H_{15}$ | $—PO_3H_2$ |
| 2052 | 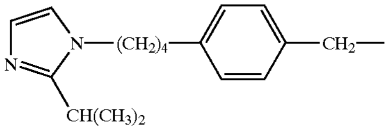 | $—CH(CH_3)(CH_2CH_3)$ | $—PO_3H_2$ |
| 2053 | 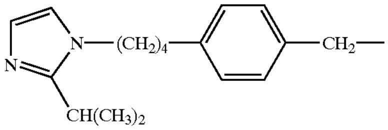 | $—CH(CH_2CH_3)_2$ | $—PO_3H_2$ |

TABLE I-continued
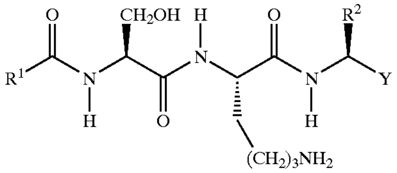
| Ex. No. | $R^1$ | $R^2$ | Y |
|---|---|---|---|
| 2054 | 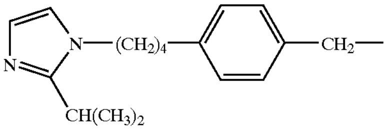 | $-CH(CH_3)(CH_2CH_2CH_3)$ | $-PO_3H_2$ |
| 2055 | 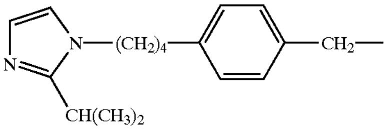 | $-C(CH_3)_3$ | $-PO_3H_2$ |
| 2056 | 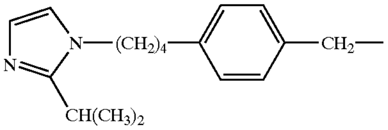 | $HC{\equiv}CCH_2-$ | $-PO_3H_2$ |
| 2057 | 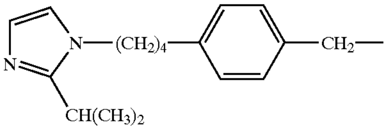 | $H_2C{=}CH-$ | $-PO_3H_2$ |
| 2058 | 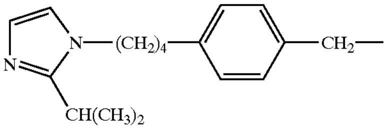 | $H_2C{=}CHCH_2-$ | $-PO_3H_2$ |
| 2059 | 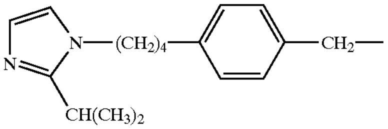 | $-CH_2F$ | $-PO_3H_2$ |
| 2060 | 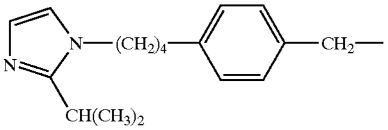 | $-CH_2C_6H_5$ | $-PO_3H_2$ |
| 2061 | 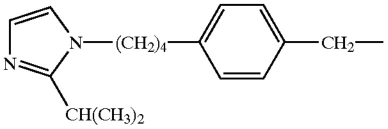 | $-CH_2C_6H_4$-p-$OCH_3$ | $-PO_3H_2$ |
| 2062 | 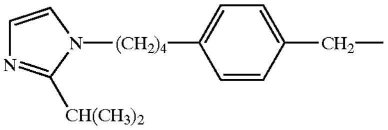 | $-CH_2C_6H_4$-p-$CH_3$ | $-PO_3H_2$ |

TABLE I-continued
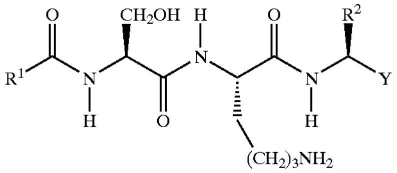
| Ex. No. | $R^1$ | $R^2$ | Y |
|---|---|---|---|
| 2063 | 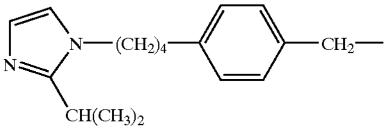 | $—CH_2C_6H_4$-p-F | $—PO_3H_2$ |
| 2064 | 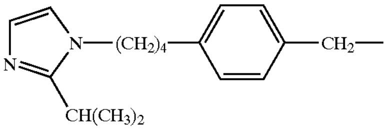 | $—CH_2CH_2C_6H_5$ | $—PO_3H_2$ |
| 2065 | 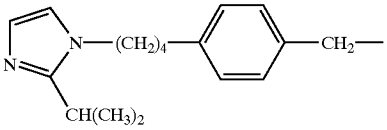 | $—CH_2$-cyclo-$C_6H_{11}$ | $—PO_3H_2$ |
| 2066 | 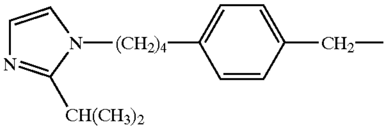 | $—CH_2$-cyclo-$C_6H_{10}$-4-F | $—PO_3H_2$ |
| 2067 | 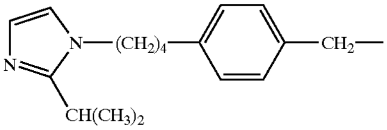 | $—CH_2$-cyclo-$C_6H_{10}$-4-$CH_3$ | $—PO_3H_2$ |
| 2068 | 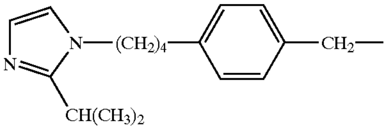 | $—CH_2$-cyclo-$C_6H_{10}$-4-$OCH_3$ | $—PO_3H_2$ |
| 2069 | 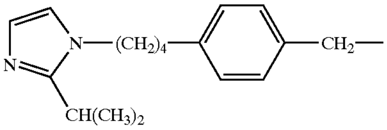 | $—CH_2CH_2$-cyclo-$C_6H_{11}$ | $—PO_3H_2$ |
| 2070 | 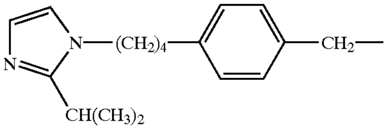 | $—CH_2$-cyclo-$C_5H_9$ | $—PO_3H_2$ |
| 2071 | 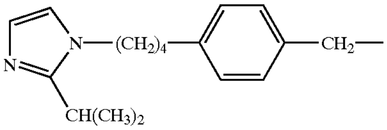 | $—CH_2CH_2$-cyclo-$C_5H_9$ | $—PO_3H_2$ |

TABLE I-continued
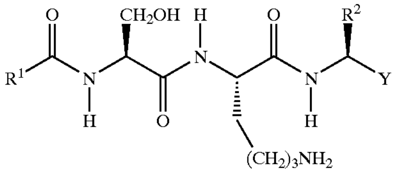
| Ex. No. | $R^1$ | $R^2$ | Y |
|---|---|---|---|
| 2072 | 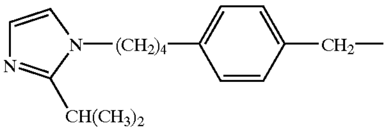 | $-CH_2$-2-naphthyl | $-PO_3H_2$ |
| 2073 | 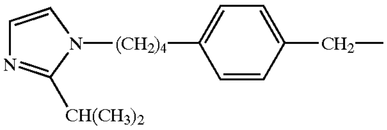 | —H | -5-Tet |
| 2074 | 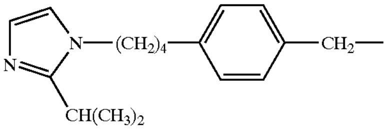 | $-CH_3$ | -5-Tet |
| 2075 | 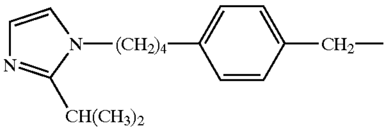 | $-CH_2CH_3$ | -5-Tet |
| 2076 | 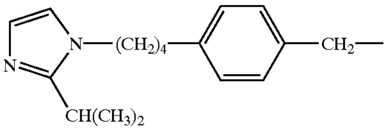 | $-CH_2CH_2CH_3$ | -5-Tet |
| 2077 | 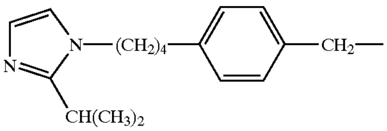 | $-CH_2CH_2CH_2CH_3$ | -5-Tet |
| 2078 | 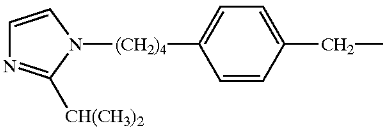 | $-CH_2CH_2CH_2CH_2CH_3$ | -5-Tet |
| 2079 | 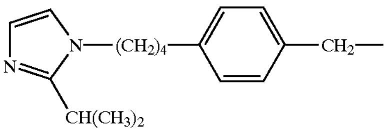 | $-CH_2CH_2CH_2CH_2CH_2CH_3$ | -5-Tet |
| 2080 | 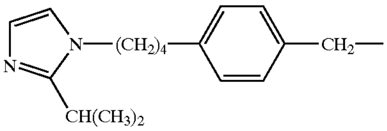 | $-CH(CH_3)_2$ | -5-Tet |

TABLE I-continued
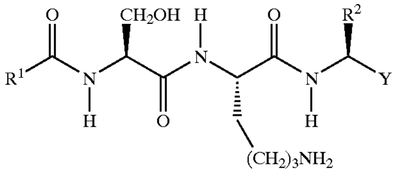
| Ex. No. | $R^1$ | $R^2$ | Y |
|---|---|---|---|
| 2081 | 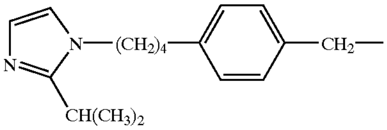 | $—CH_2CH(CH_3)_2$ | -5-Tet |
| 2082 | 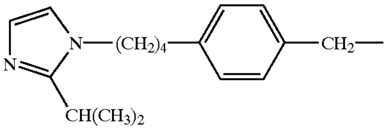 | $—CH_2CH_2CH(CH_3)_2$ | -5-Tet |
| 2083 | 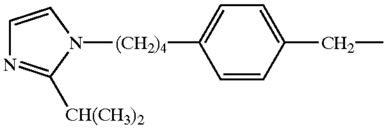 | -cyclo-$C_3H_5$ | -5-Tet |
| 2084 | 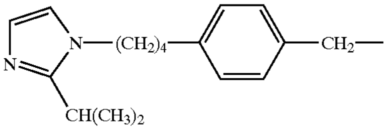 | -cyclo-$C_4H_7$ | -5-Tet |
| 2085 | 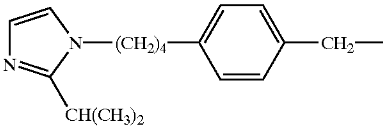 | -cyclo-$C_5H_9$ | -5-Tet |
| 2086 | 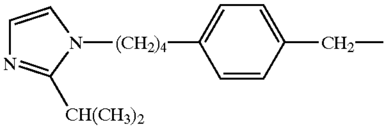 | -cyclo-$C_6H_{11}$ | -5-Tet |
| 2087 | 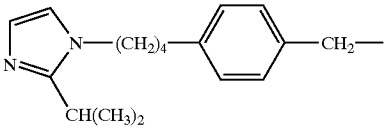 | -cyclo-$C_7H_{13}$ | -5-Tet |
| 2088 | 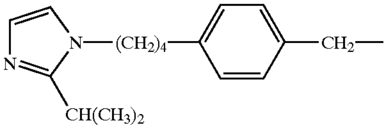 | -cyclo-$C_8H_{15}$ | -5-Tet |
| 2089 | 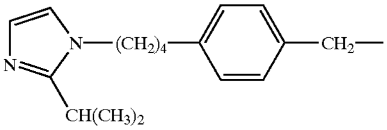 | $—CH(CH_3)(CH_2CH_3)$ | -5-Tet |

TABLE I-continued
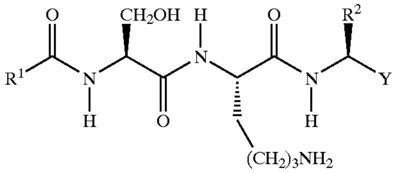
| Ex. No. | $R^1$ | $R^2$ | Y |
|---|---|---|---|
| 2090 | 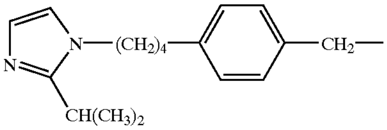 | $—CH(CH_2CH_3)_2$ | -5-Tet |
| 2091 | 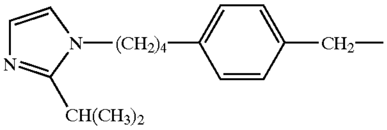 | $—CH(CH_3)(CH_2CH_2CH_3)$ | -5-Tet |
| 2092 | 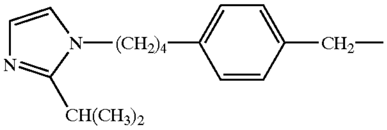 | $—C(CH_3)_3$ | -5-Tet |
| 2093 | 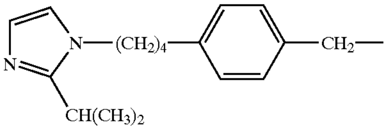 | $HC{\equiv}CCH_2—$ | -5-Tet |
| 2094 | 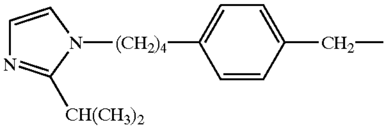 | $H_2C{=}CH—$ | -5-Tet |
| 2095 | 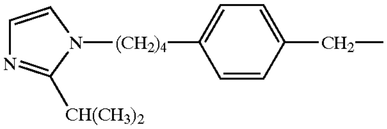 | $H_2C{=}CHCH_2—$ | -5-Tet |
| 2096 | 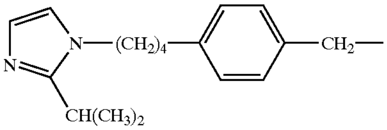 | $—CH_2F$ | -5-Tet |
| 2097 | 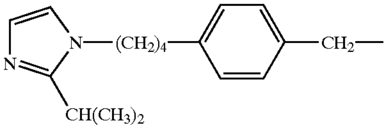 | $—CH_2C_6H_5$ | -5-Tet |
| 2098 | 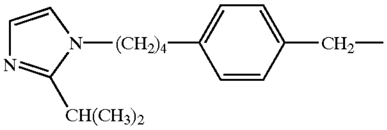 | $—CH_2C_6H_4$-p-$OCH_3$ | -5-Tet |

TABLE I-continued
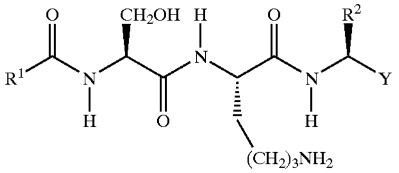
| Ex. No. | $R^1$ | $R^2$ | Y |
|---|---|---|---|
| 2099 | 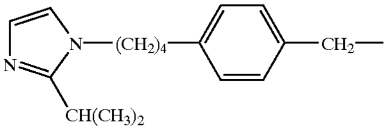 | $—CH_2C_6H_4$-p-$CH_3$ | -5-Tet |
| 2100 | 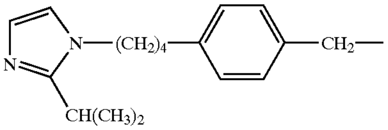 | $—CH_2C_6H_4$-p-F | -5-Tet |
| 2101 | 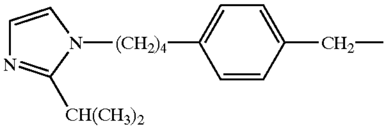 | $—CH_2CH_2C_6H_5$ | -5-Tet |
| 2102 | 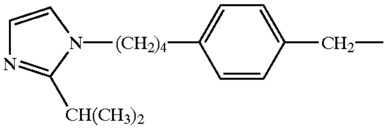 | $—CH_2$-cyclo-$C_6H_{11}$ | -5-Tet |
| 2103 | 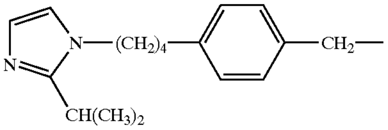 | $—CH_2$-cyclo-$C_6H_{10}$-4-F | -5-Tet |
| 2104 | 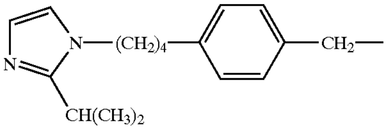 | $—CH_2$-cyclo-$C_6H_{10}$-4-$CH_3$ | -5-Tet |
| 2105 | 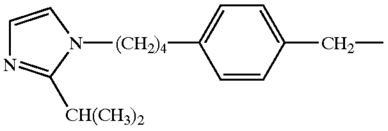 | $—CH_2$-cyclo-$C_6H_{10}$-4-$OCH_3$ | -5-Tet |
| 2106 | 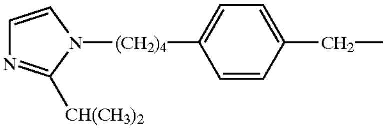 | $—CH_2CH_2$-cyclo-$C_6H_{11}$ | -5-Tet |
| 2107 | 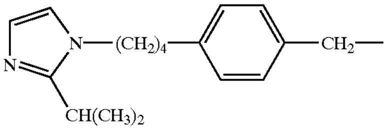 | $—CH_2$-cyclo-$C_5H_9$ | -5-Tet |

TABLE I-continued
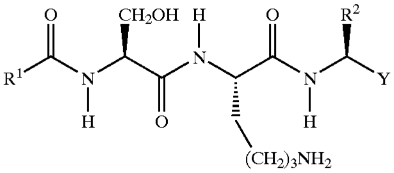
| Ex. No. | $R^1$ | $R^2$ | Y |
|---|---|---|---|
| 2108 | 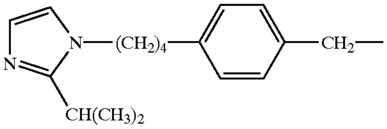 | $—CH_2CH_2$-cyclo-$C_5H_9$ | -5-Tet |
| 2109 | 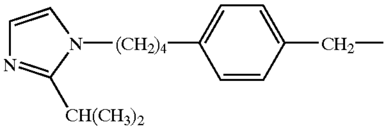 | $—CH_2$-2-naphthyl | -5-Tet |
| 2110 | 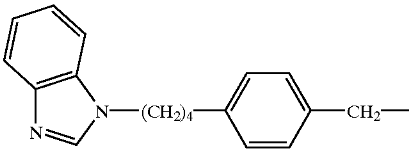 | —H | $—CO_2H$ |
| 2111 | 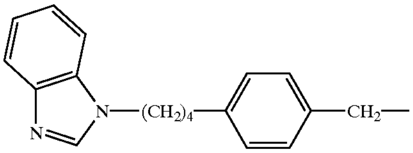 | $—CH_3$ | $—CO_2H$ |
| 2112 | 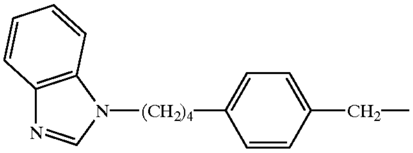 | $—CH_2CH_3$ | $—CO_2H$ |
| 2113 | 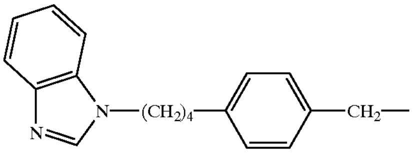 | $—CH_2CH_2CH_3$ | $—CO_2H$ |
| 2114 | 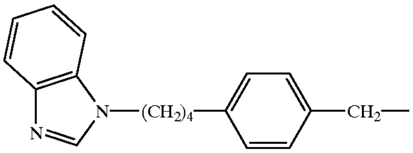 | $—CH_2CH_2CH_2CH_3$ | $—CO_2H$ |
| 2115 | 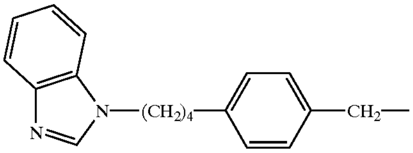 | $—CH_2CH_2CH_2CH_2CH_3$ | $—CO_2H$ |

TABLE I-continued
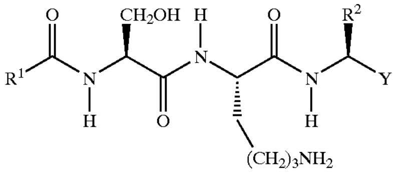
| Ex. No. | $R^1$ | $R^2$ | Y |
|---|---|---|---|
| 2116 | 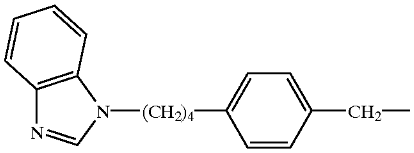 | $—CH_2CH_2CH_2CH_2CH_2CH_3$ | $—CO_2H$ |
| 2117 | 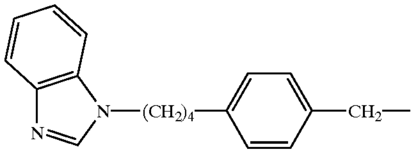 | $—CH(CH_3)_2$ | $—CO_2H$ |
| 2118 | 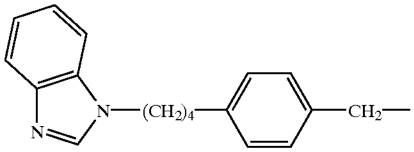 | $—CH_2CH(CH_3)_2$ | $—CO_2H$ |
| 2119 | 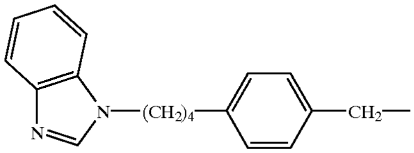 | $—CH_2CH_2CH(CH_3)_2$ | $—CO_2H$ |
| 2120 | 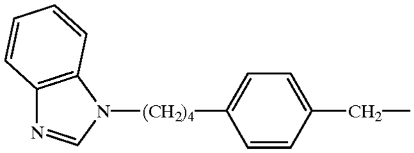 | —cyclo-$C_3H_5$ | $—CO_2H$ |
| 2121 | 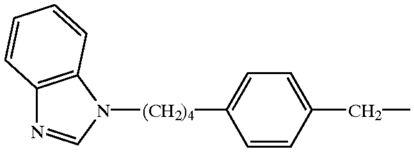 | -cyclo-$C_4H_7$ | $—CO_2H$ |
| 2122 | 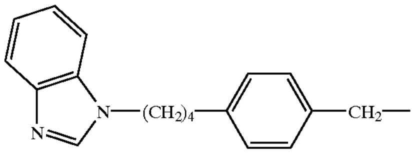 | -cyclo-$C_5H_9$ | $—CO_2H$ |
| 2123 | 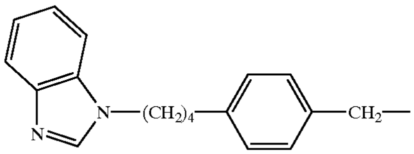 | -cyclo-$C_6H_{11}$ | $—CO_2H$ |

TABLE I-continued
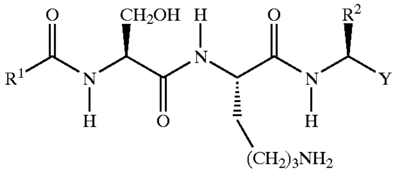
| Ex. No. | $R^1$ | $R^2$ | Y |
|---|---|---|---|
| 2124 | 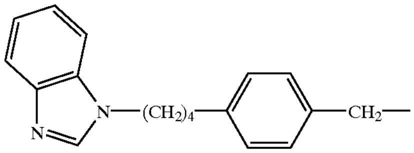 | -cyclo-$C_7H_{13}$ | —$CO_2H$ |
| 2125 | 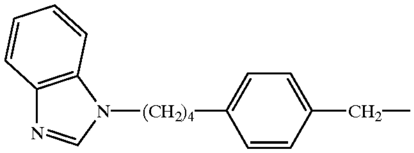 | -cyclo-$C_8H_{15}$ | —$CO_2H$ |
| 2126 | 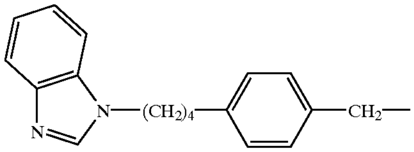 | —$CH(CH_3)(CH_2CH_3)$ | —$CO_2H$ |
| 2127 | 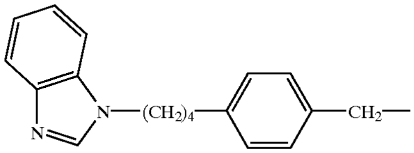 | —$CH(CH_2CH_3)_2$ | —$CO_2H$ |
| 2128 | 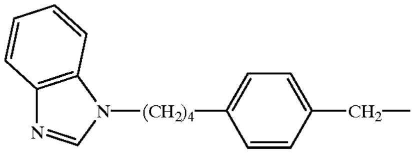 | —$CH(CH_3)(CH_2CH_2CH_3)$ | —$CO_2H$ |
| 2129 | 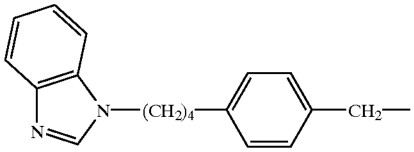 | —$C(CH_3)_3$ | —$CO_2H$ |
| 2130 | 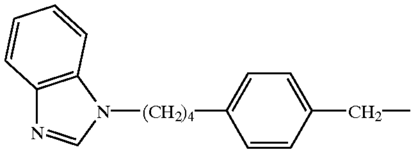 | $HC{\equiv}CCH_2$— | —$CO_2H$ |
| 2131 | 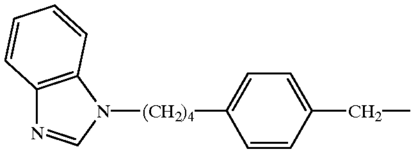 | $H_2C{=}CH$— | —$CO_2H$ |

TABLE I-continued
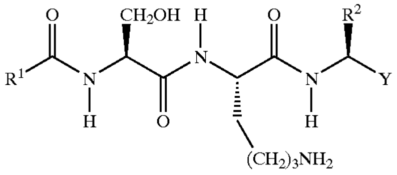
| Ex. No. | $R^1$ | $R^2$ | Y |
|---|---|---|---|
| 2132 | 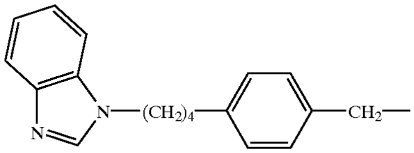 | $H_2C{=}CHCH_2$— | —$CO_2H$ |
| 2133 | 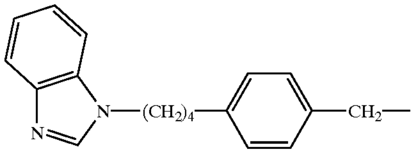 | —$CH_2F$ | —$CO_2H$ |
| 2134 | 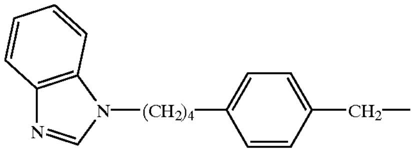 | —$CH_2C_6H_5$ | —$CO_2H$ |
| 2135 | 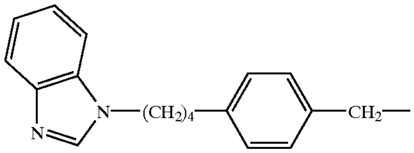 | —$CH_2C_6H_4$-p-$OCH_3$ | —$CO_2H$ |
| 2136 | 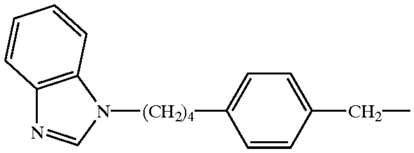 | —$CH_2C_6H_4$-p-$CH_3$ | —$CO_2H$ |
| 2137 | 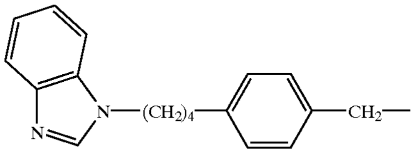 | —$CH_2C_6H_4$-p-F | —$CO_2H$ |
| 2138 | 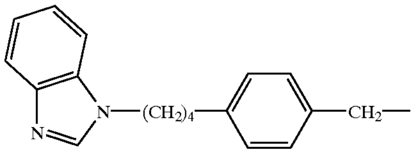 | —$CH_2CH_2C_6H_5$ | —$CO_2H$ |
| 2139 | 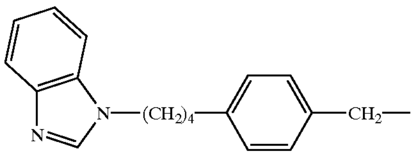 | —$CH_2$-cyclo-$C_6H_{11}$ | —$CO_2H$ |

TABLE I-continued
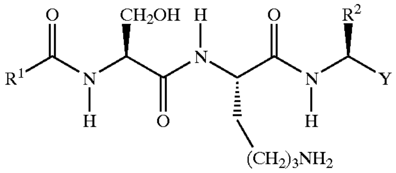
| Ex. No. | $R^1$ | $R^2$ | Y |
|---|---|---|---|
| 2140 | 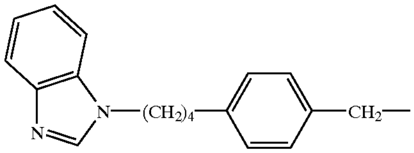 | $—CH_2$-cyclo-$C_6H_{10}$-4-F | $—CO_2H$ |
| 2141 | 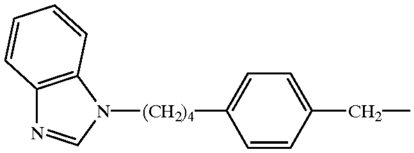 | $—CH_2$-cyclo-$C_6H_{10}$-4-$CH_3$ | $—CO_2H$ |
| 2142 | 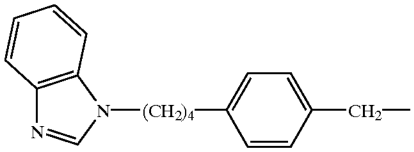 | $—CH_2$-cyclo-$C_6H_{10}$-4-$OCH_3$ | $—CO_2H$ |
| 2143 | 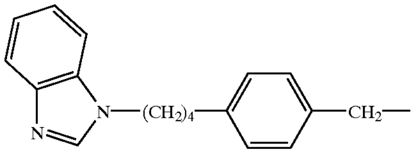 | $—CH_2CH_2$-cyclo-$C_6H_{11}$ | $—CO_2H$ |
| 2144 | 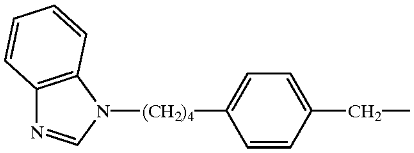 | $—CH_2$-cyclo-$C_5H_9$ | $—CO_2H$ |
| 2145 | 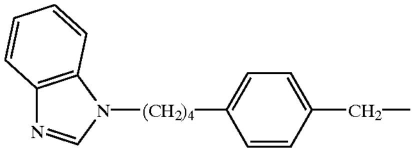 | $—CH_2CH_2$-cyclo-$C_5H_9$ | $—CO_2H$ |
| 2146 | 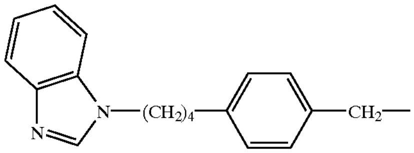 | $—CH_2$-2-naphthyl | $—CO_2H$ |
| 2147 | 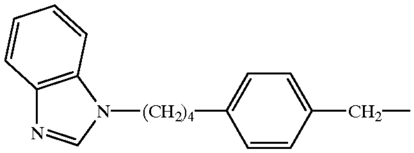 | —H | $—PO_3H_2$ |

TABLE I-continued
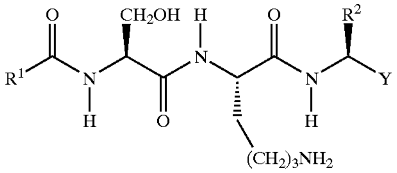
| Ex. No. | $R^1$ | $R^2$ | Y |
|---|---|---|---|
| 2148 | 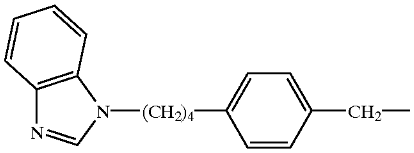 | $-CH_3$ | $-PO_3H_2$ |
| 2149 | 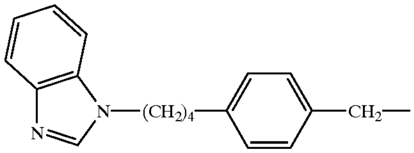 | $-CH_2CH_3$ | $-PO_3H_2$ |
| 2150 | 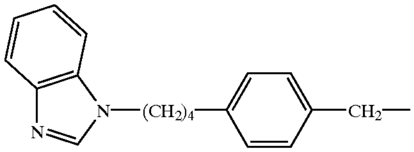 | $-CH_2CH_2CH_3$ | $-PO_3H_2$ |
| 2151 | 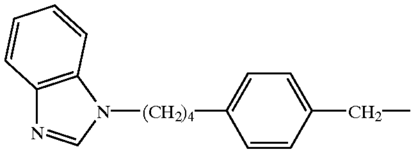 | $-CH_2CH_2CH_2CH_3$ | $-PO_3H_2$ |
| 2152 | 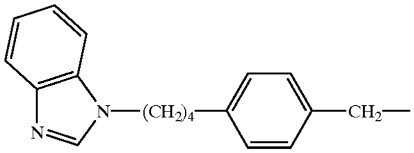 | $-CH_2CH_2CH_2CH_2CH_3$ | $-PO_3H_2$ |
| 2153 | 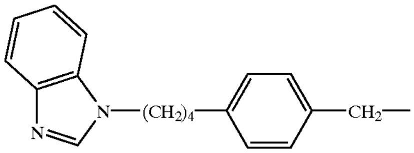 | $-CH_2CH_2CH_2CH_2CH_2CH_3$ | $-PO_3H_2$ |
| 2154 | 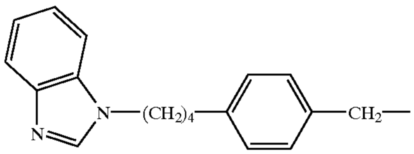 | $-CH(CH_3)_2$ | $-PO_3H_2$ |
| 2155 | 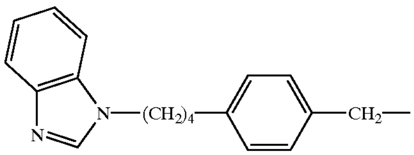 | $-CH_2CH(CH_3)_2$ | $-PO_3H_2$ |

TABLE I-continued
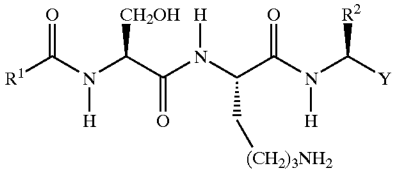
| Ex. No. | $R^1$ | $R^2$ | Y |
|---|---|---|---|
| 2156 | 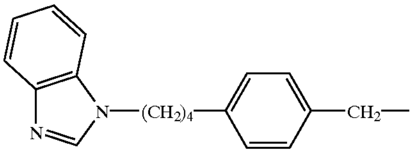 | $—CH_2CH_2CH(CH_3)_2$ | $—PO_3H_2$ |
| 2157 | 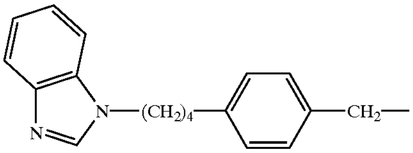 | -cyclo-$C_3H_5$ | $—PO_3H_2$ |
| 2158 | 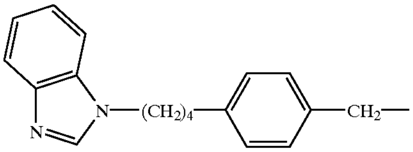 | -cyclo-$C_4H_7$ | $—PO_3H_2$ |
| 2159 | 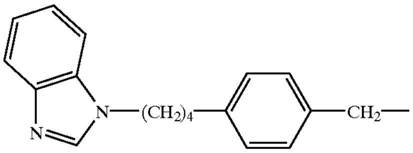 | -cyclo-$C_5H_9$ | $—PO_3H_2$ |
| 2160 | 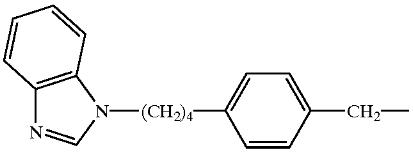 | -cyclo-$C_6H_{11}$ | $—PO_3H_2$ |
| 2161 | 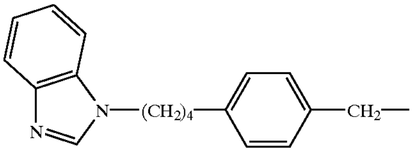 | -cyclo-$C_7H_{13}$ | $—PO_3H_2$ |
| 2162 | 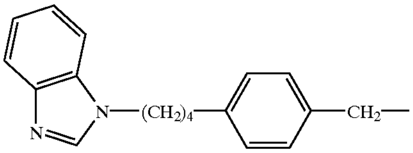 | -cyclo-$C_8H_{15}$ | $—PO_3H_2$ |
| 2163 | 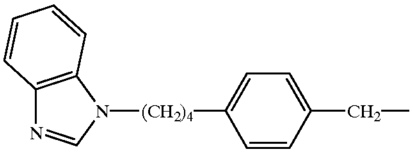 | $—CH(CH_3)(CH_2CH_3)$ | $—PO_3H_2$ |

TABLE I-continued
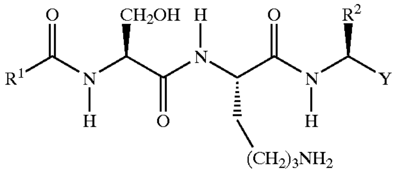
| Ex. No. | $R^1$ | $R^2$ | Y |
|---|---|---|---|
| 2164 | 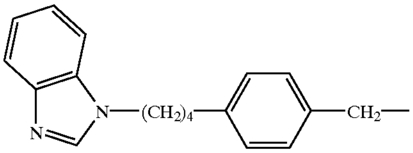 | $—CH(CH_2CH_3)_2$ | $—PO_3H_2$ |
| 2165 | 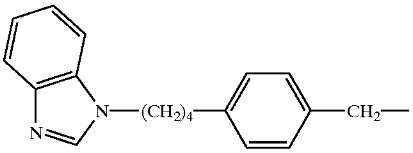 | $—CH(CH_3)(CH_2CH_2CH_3)$ | $—PO_3H_2$ |
| 2166 | 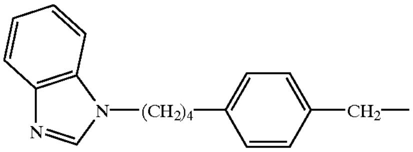 | $—C(CH_3)_3$ | $—PO_3H_2$ |
| 2167 | 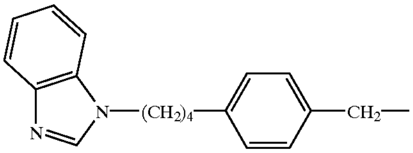 | $HC{\equiv}CCH_2—$ | $—PO_3H_2$ |
| 2168 | 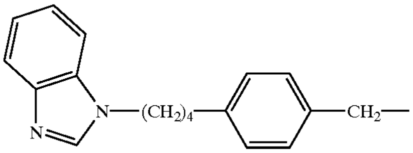 | $H_2C{=}CH—$ | $—PO_3H_2$ |
| 2169 | 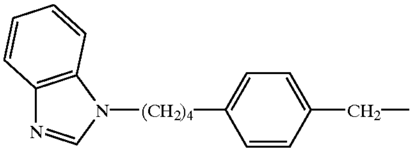 | $H_2C{=}CHCH_2—$ | $—PO_3H_2$ |
| 2170 | 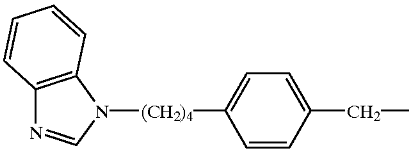 | $—CH_2F$ | $—PO_3H_2$ |
| 2171 | 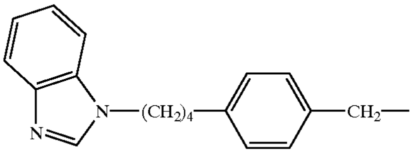 | $—CH_2C_6H_5$ | $—PO_3H_2$ |

TABLE I-continued
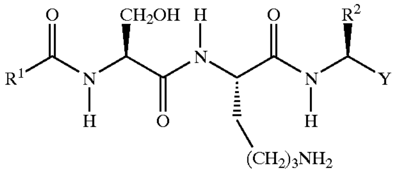
| Ex. No. | $R^1$ | $R^2$ | Y |
|---|---|---|---|
| 2172 | 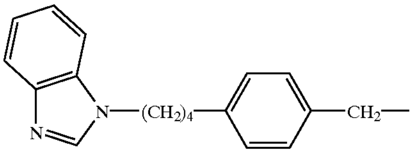 | $—CH_2C_6H_4$-p-$OCH_3$ | $—PO_3H_2$ |
| 2173 | 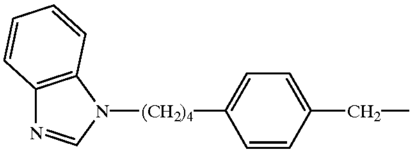 | $—CH_2C_6H_4$-p-$CH_3$ | $—PO_3H_2$ |
| 2174 | 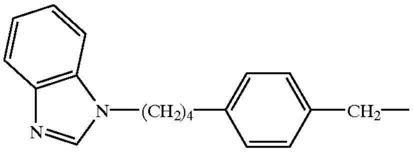 | $—CH_2C_6H_4$-p-F | $—PO_3H_2$ |
| 2175 | 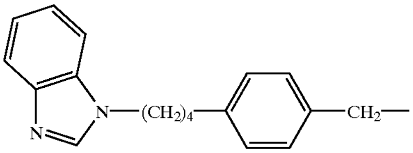 | $—CH_2CH_2C_6H_5$ | $—PO_3H_2$ |
| 2176 | 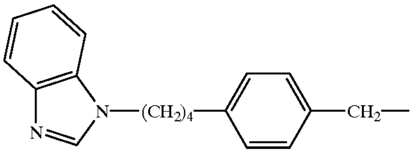 | $—CH_2$-cyclo-$C_6H_{11}$ | $—PO_3H_2$ |
| 2177 | 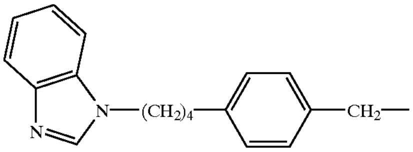 | $—CH_2$-cyclo-$C_6H_{10}$-4-F | $—PO_3H_2$ |
| 2178 | 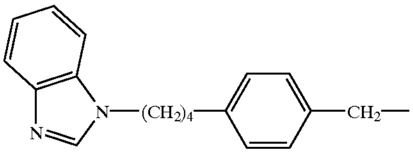 | $—CH_2$-cyclo-$C_6H_{10}$-4-$CH_3$ | $—PO_3H_2$ |
| 2179 | 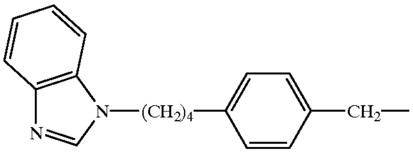 | $—CH_2$-cyclo-$C_6H_{10}$-4-$OCH_3$ | $—PO_3H_2$ |

TABLE I-continued
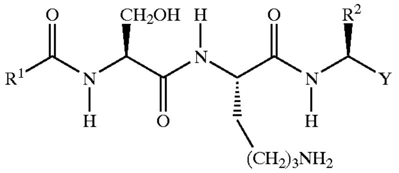
| Ex. No. | $R^1$ | $R^2$ | Y |
|---|---|---|---|
| 2180 | 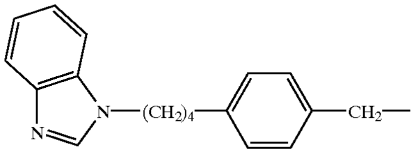 | $—CH_2CH_2$-cyclo-$C_6H_{11}$ | $—PO_3H_2$ |
| 2181 | 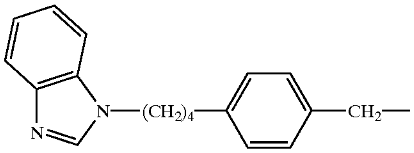 | $—CH_2$-cyclo-$C_5H_9$ | $—PO_3H_2$ |
| 2182 | 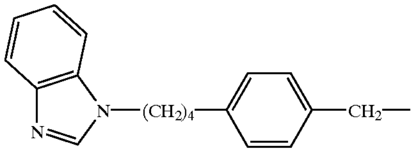 | $—CH_2CH_2$-cyclo-$C_5H_9$ | $—PO_3H_2$ |
| 2183 | 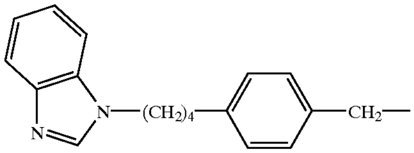 | $—CH_2$-2-naphthyl | $—PO_3H_2$ |
| 2184 | 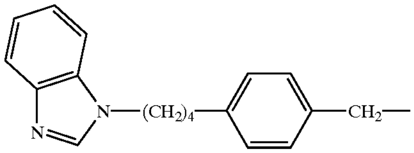 | —H | -5-Tet |
| 2185 | 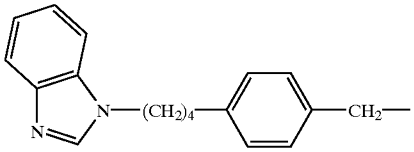 | $—CH_3$ | -5-Tet |
| 2186 | 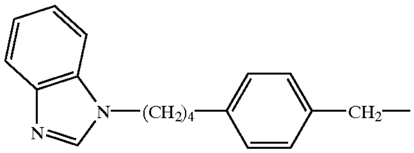 | $—CH_2CH_3$ | -5-Tet |
| 2187 | 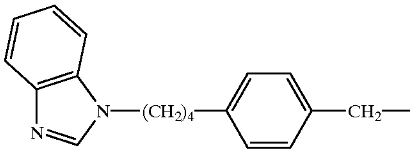 | $—CH_2CH_2CH_3$ | -5-Tet |

TABLE I-continued
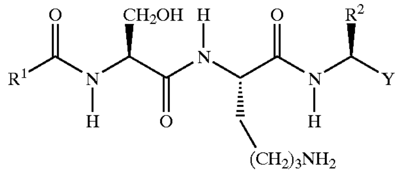
| Ex. No. | $R^1$ | $R^2$ | Y |
|---|---|---|---|
| 2188 | 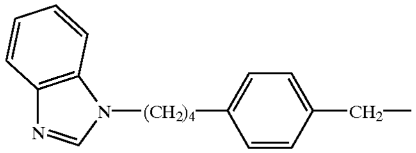 | $-CH_2CH_2CH_2CH_3$ | -5-Tet |
| 2189 | 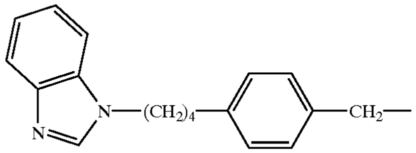 | $-CH_2CH_2CH_2CH_2CH_3$ | -5-Tet |
| 2190 | 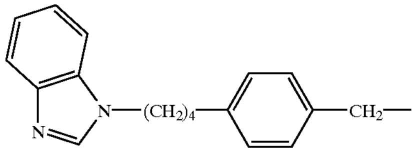 | $-CH_2CH_2CH_2CH_2CH_2CH_3$ | -5-Tet |
| 2191 | 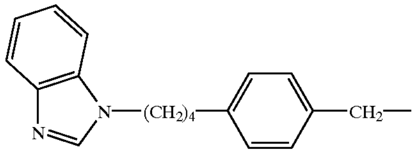 | $-CH(CH_3)_2$ | -5-Tet |
| 2192 | 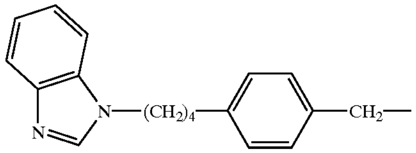 | $-CH_2CH(CH_3)_2$ | -5-Tet |
| 2193 | 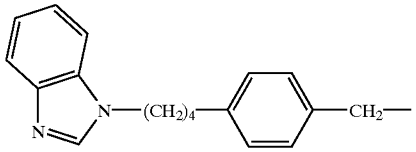 | $-CH_2CH_2CH(CH_3)_2$ | -5-Tet |
| 2194 | 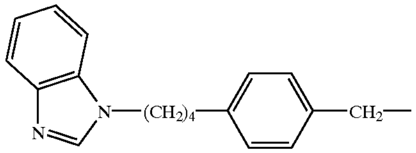 | -cyclo-$C_3H_5$ | -5-Tet |
| 2195 | 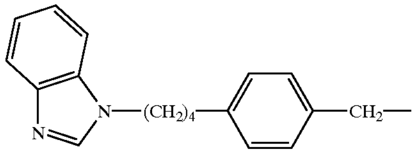 | -cyclo-$C_4H_7$ | -5-Tet |

TABLE I-continued
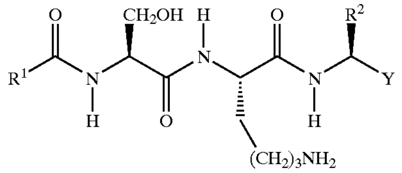
| Ex. No. | $R^1$ | $R^2$ | Y |
|---|---|---|---|
| 2196 | 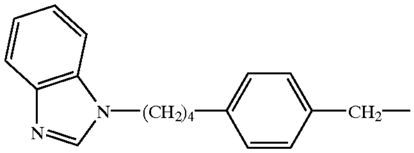 | -cyclo-$C_5H_9$ | -5-Tet |
| 2197 | 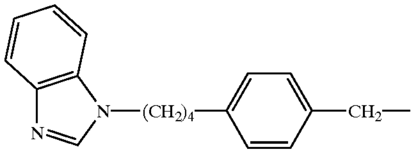 | -cyclo-$C_6H_{11}$ | -5-Tet |
| 2198 | 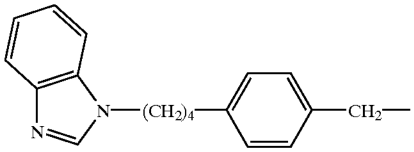 | -cyclo-$C_7H_{13}$ | -5-Tet |
| 2199 | 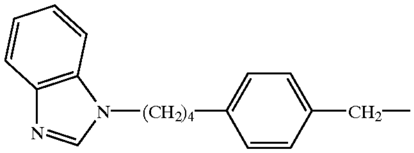 | -cyclo-$C_8H_{15}$ | -5-Tet |
| 2200 | 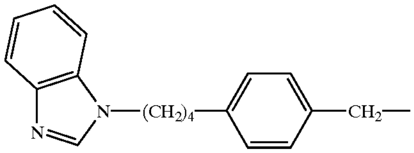 | $-CH(CH_3)(CH_2CH_3)$ | -5-Tet |
| 2201 | 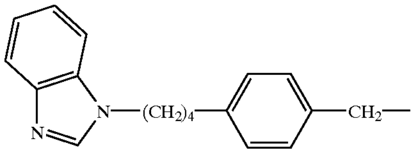 | $-CH(CH_2CH_3)_2$ | -5-Tet |
| 2202 | 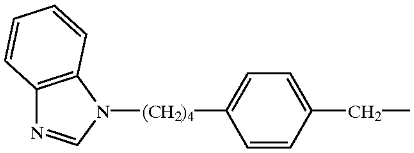 | $-CH(CH_3)(CH_2CH_2CH_3)$ | -5-Tet |
| 2203 | 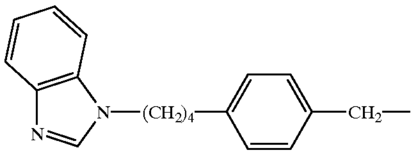 | $-C(CH_3)_3$ | -5-Tet |

TABLE I-continued
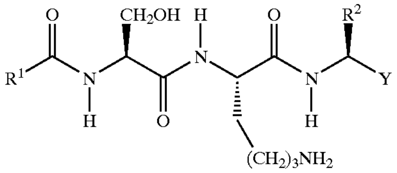
| Ex. No. | $R^1$ | $R^2$ | Y |
|---|---|---|---|
| 2204 | 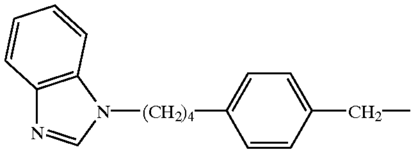 | $HC{\equiv}CCH_2$— | -5-Tet |
| 2205 | 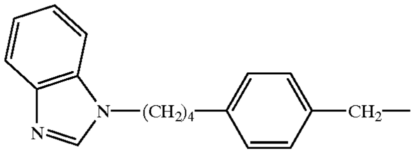 | $H_2C{=}CH$— | -5-Tet |
| 2206 | 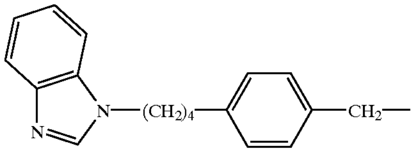 | $H_2C{=}CHCH_2$— | -5-Tet |
| 2207 | 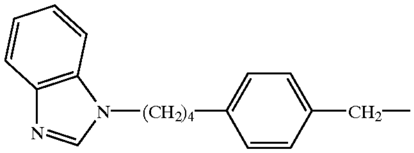 | —$CH_2F$ | -5-Tet |
| 2208 | 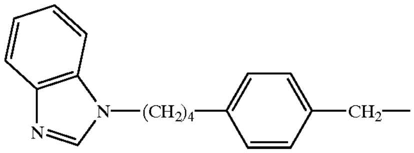 | —$CH_2C_6H_5$ | -5-Tet |
| 2209 | 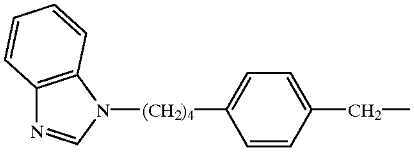 | —$CH_2C_6H_4$-p-$OCH_3$ | -5-Tet |
| 2210 | 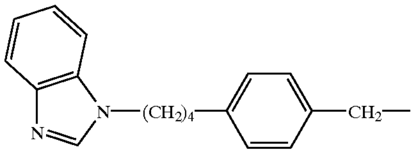 | —$CH_2C_6H_4$-p-$CH_3$ | -5-Tet |
| 2211 | 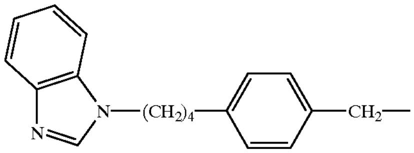 | —$CH_2C_6H_4$-p-F | -5-Tet |

TABLE I-continued
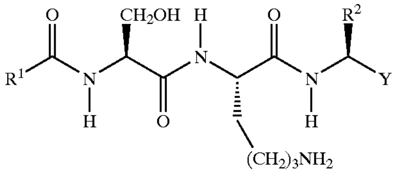
| Ex. No. | $R^1$ | $R^2$ | Y |
|---|---|---|---|
| 2212 | 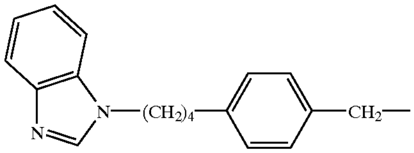 | $—CH_2CH_2C_6H_5$ | -5-Tet |
| 2213 | 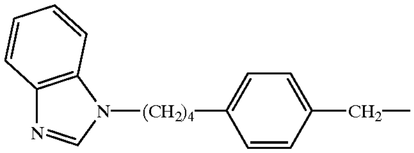 | $—CH_2$-cyclo-$C_6H_{11}$ | -5-Tet |
| 2214 | 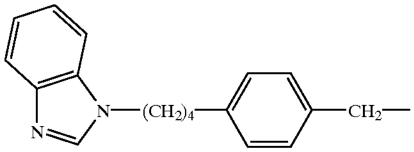 | $—CH_2$-cyclo-$C_6H_{10}$-4-F | -5-Tet |
| 2215 | 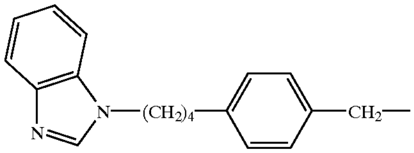 | $—CH_2$-cyclo-$C_6H_{10}$-4-$CH_3$ | -5-Tet |
| 2216 | 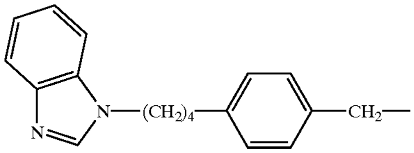 | $—CH_2$-cyclo-$C_6H_{10}$-4-$OCH_3$ | -5-Tet |
| 2217 | 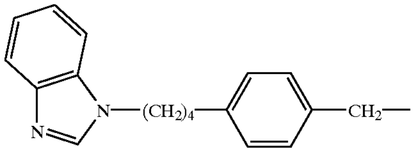 | $—CH_2CH_2$-cyclo-$C_6H_{11}$ | -5-Tet |
| 2218 | 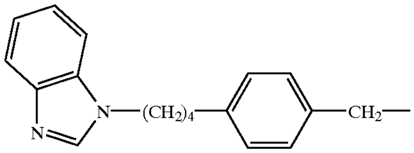 | $—CH_2$-cyclo-$C_5H_9$ | -5-Tet |
| 2219 | 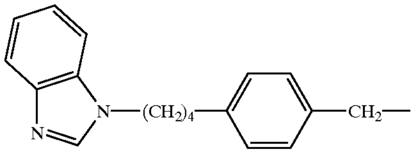 | $—CH_2CH_2$-cyclo-$C_5H_9$ | -5-Tet |

TABLE I-continued
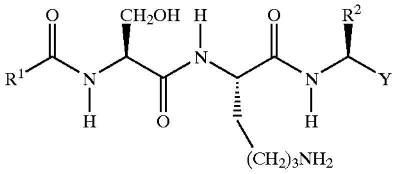
| Ex. No. | $R^1$ | $R^2$ | Y |
|---|---|---|---|
| 2220 | 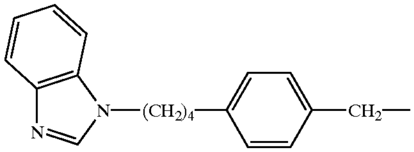 | —$CH_2$-2-naphthyl | -5-Tet |
| 2221 | 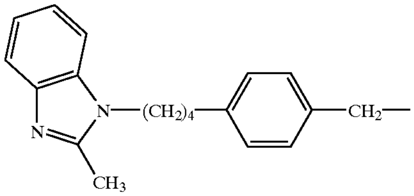 | —H | —$CO_2H$ |
| 2222 | 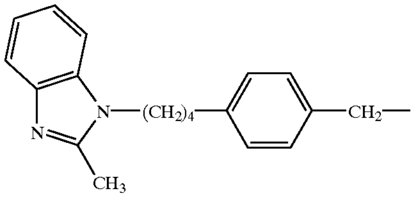 | —$CH_3$ | —$CO_2H$ |
| 2223 | 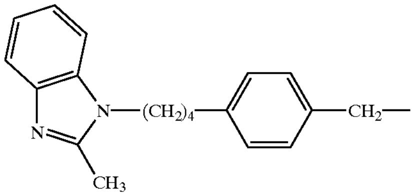 | —$CH_2CH_3$ | —$CO_2H$ |
| 2224 | 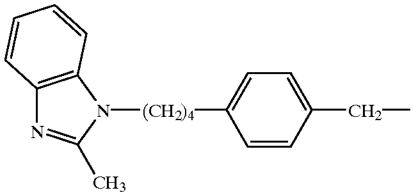 | —$CH_2CH_2CH_3$ | —$CO_2H$ |
| 2225 | 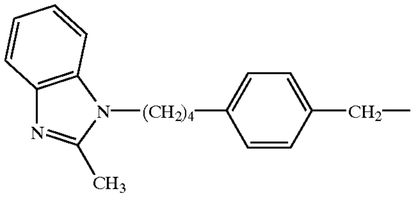 | —$CH_2CH_2CH_2CH_3$ | —$CO_2H$ |

TABLE I-continued
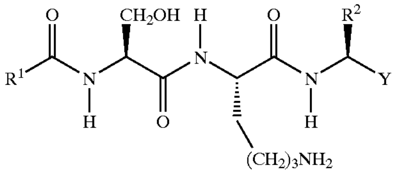
| Ex. No. | $R^1$ | $R^2$ | Y |
|---|---|---|---|
| 2226 | 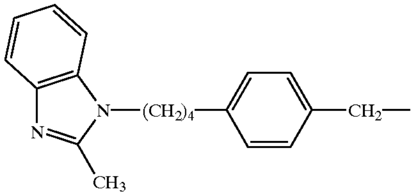 | $—CH_2CH_2CH_2CH_2CH_3$ | $—CO_2H$ |
| 2227 | 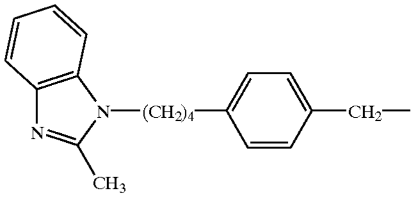 | $—CH_2CH_2CH_2CH_2CH_2CH_3$ | $—CO_2H$ |
| 2228 | 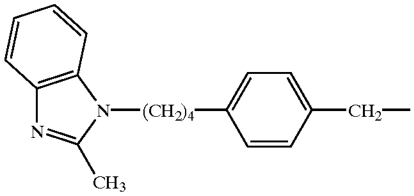 | $—CH(CH_3)_2$ | $—CO_2H$ |
| 2229 | 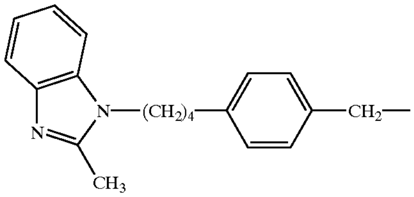 | $—CH_2CH(CH_3)_2$ | $—CO_2H$ |
| 2230 | 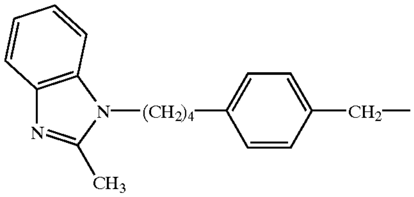 | $—CH_2CH_2CH(CH_3)_2$ | $—CO_2H$ |
| 2231 | 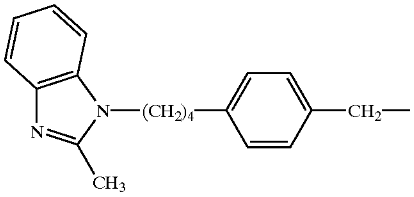 | —cyclo-$C_3H_5$ | $—CO_2H$ |

TABLE I-continued
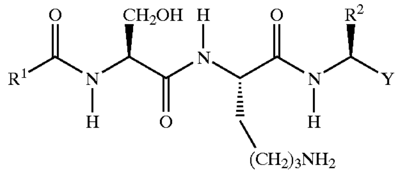
| Ex. No. | $R^1$ | $R^2$ | Y |
|---|---|---|---|
| 2232 | 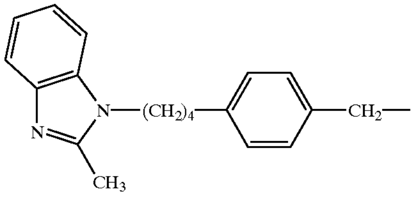 | -cyclo-$C_4H_7$ | —$CO_2H$ |
| 2233 | 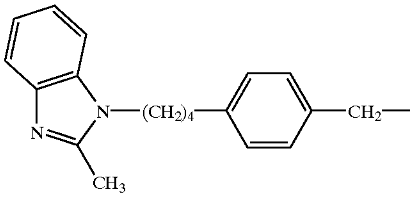 | -cyclo-$C_5H_9$ | —$CO_2H$ |
| 2234 | 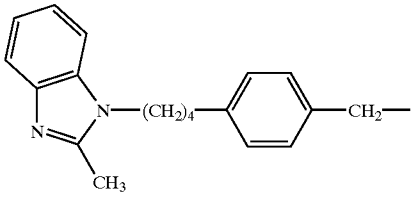 | -cyclo-$C_6H_{11}$ | —$CO_2H$ |
| 2235 | 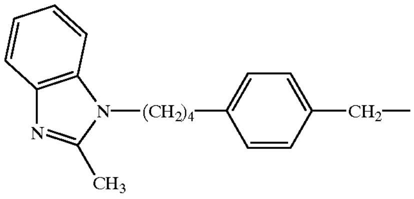 | -cyclo-$C_7H_{13}$ | —$CO_2H$ |
| 2236 | 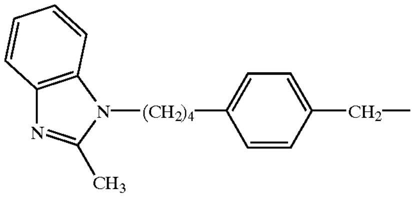 | -cyclo-$C_8H_{15}$ | —$CO_2H$ |
| 2237 | 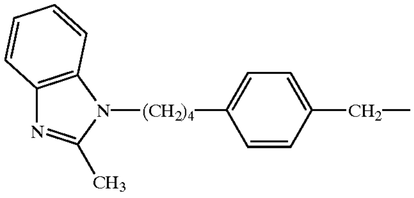 | —$CH(CH_3)(CH_2CH_3)$ | —$CO_2H$ |

TABLE I-continued
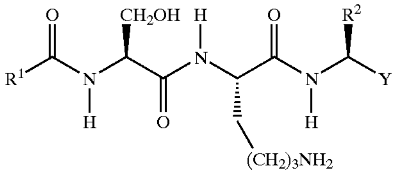
| Ex. No. | $R^1$ | $R^2$ | Y |
|---|---|---|---|
| 2238 | 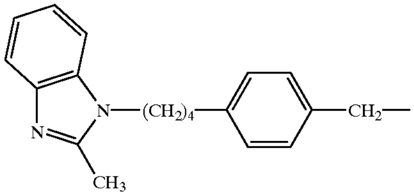 | $—CH(CH_2CH_3)_2$ | $—CO_2H$ |
| 2239 | 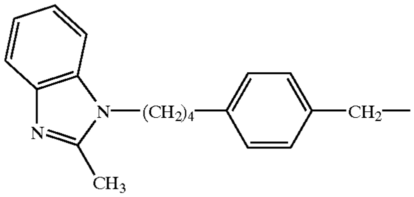 | $—CH(CH_3)(CH_2CH_2CH_3)$ | $—CO_2H$ |
| 2240 | 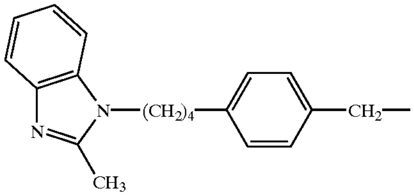 | $—C(CH_3)_3$ | $—CO_2H$ |
| 2241 | 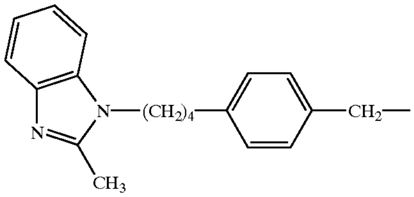 | $HC{\equiv}CCH_2—$ | $—CO_2H$ |
| 2242 | 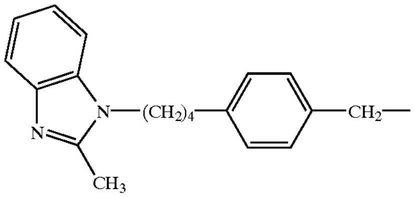 | $H_2C{=}CH—$ | $—CO_2H$ |
| 2243 | 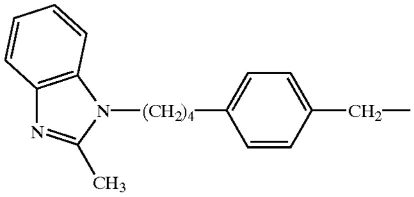 | $H_2C{=}CHCH_2—$ | $—CO_2H$ |

TABLE I-continued
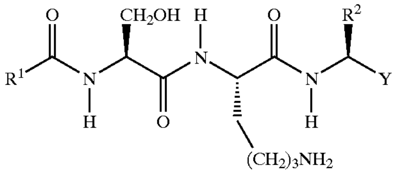
| Ex. No. | $R^1$ | $R^2$ | Y |
|---|---|---|---|
| 2244 | 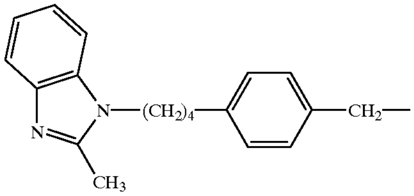 | $—CH_2F$ | $—CO_2H$ |
| 2245 | 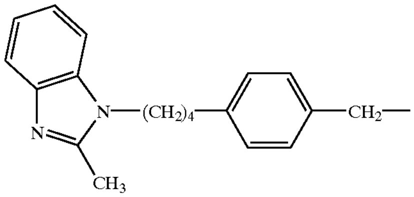 | $—CH_2C_6H_5$ | $—CO_2H$ |
| 2246 | 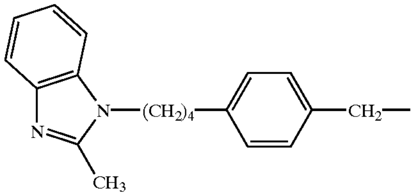 | $—CH_2C_6H_4$-p-$OCH_3$ | $—CO_2H$ |
| 2247 | 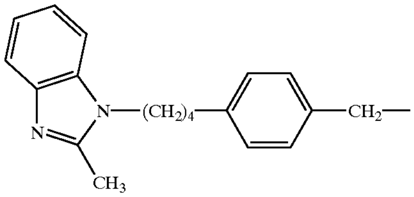 | $—CH_2C_6H_4$-p-$CH_3$ | $—CO_2H$ |
| 2248 | 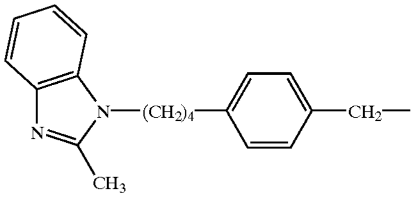 | $—CH_2C_6H_4$-p-F | $—CO_2H$ |
| 2249 | 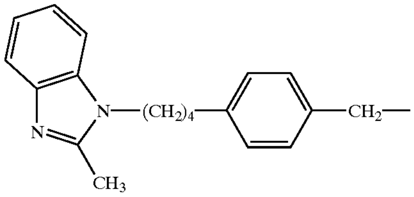 | $—CH_2CH_2C_6H_5$ | $—CO_2H$ |

TABLE I-continued
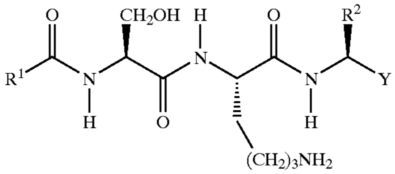
| Ex. No. | $R^1$ | $R^2$ | Y |
|---|---|---|---|
| 2250 | 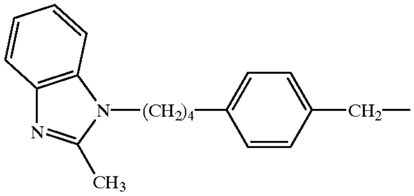 | $—CH_2$-cyclo-$C_6H_{11}$ | $—CO_2H$ |
| 2251 | 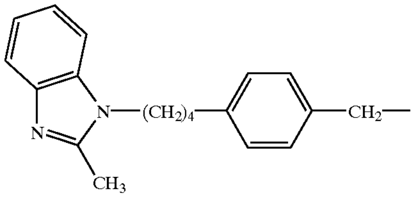 | $—CH_2$-cyclo-$C_6H_{10}$-4-F | $—CO_2H$ |
| 2252 | 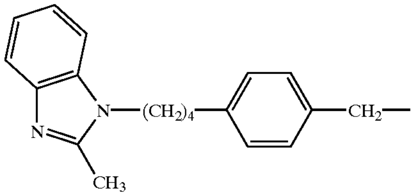 | $—CH_2$-cyclo-$C_6H_{10}$-4-$CH_3$ | $—CO_2H$ |
| 2253 | 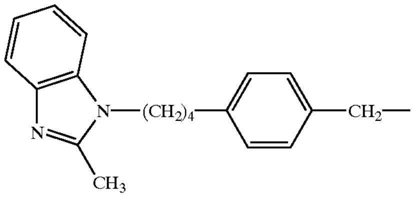 | $—CH_2$-cyclo-$C_6H_{10}$-4-$OCH_3$ | $—CO_2H$ |
| 2254 | 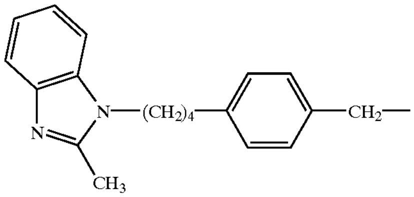 | $—CH_2CH_2$-cyclo-$C_6H_{11}$ | $—CO_2H$ |
| 2255 | 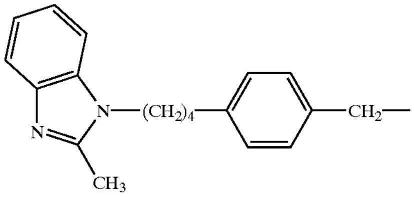 | $—CH_2$-cyclo-$C_5H_9$ | $—CO_2H$ |

TABLE I-continued
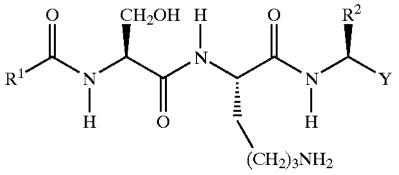
| Ex. No. | $R^1$ | $R^2$ | Y |
|---|---|---|---|
| 2256 | 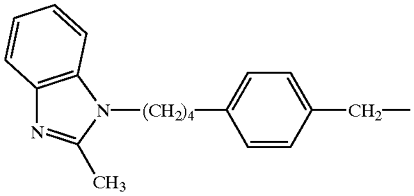 | $—CH_2CH_2$-cyclo-$C_5H_9$ | $—CO_2H$ |
| 2257 | 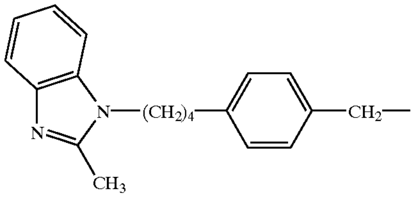 | $—CH_2$-2-naphthyl | $—CO_2H$ |
| 2258 | 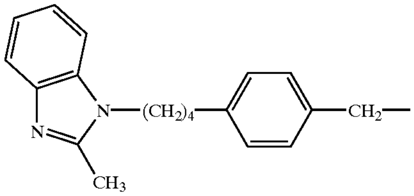 | —H | $—PO_3H_2$ |
| 2259 | 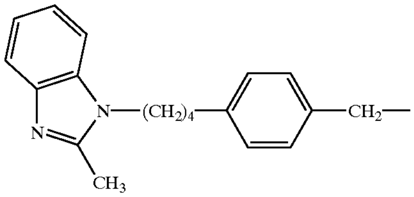 | $—CH_3$ | $—PO_3H_2$ |
| 2260 | 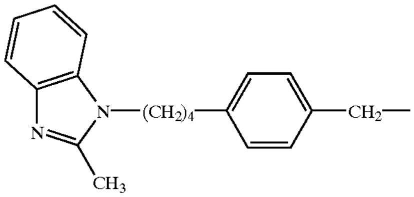 | $—CH_2CH_3$ | $—PO_3H_2$ |
| 2261 | 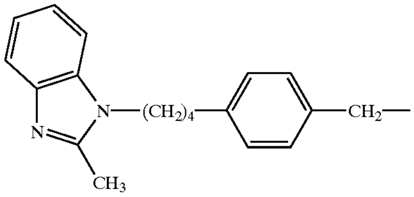 | $—CH_2CH_2CH_3$ | $—PO_3H_2$ |

TABLE I-continued
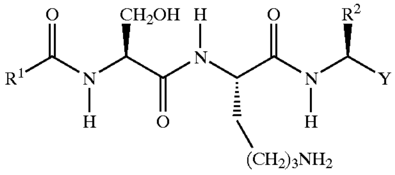
| Ex. No. | $R^1$ | $R^2$ | Y |
|---|---|---|---|
| 2262 | 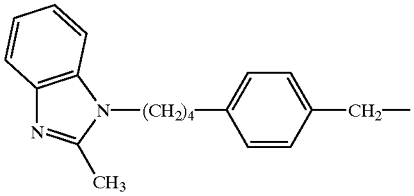 | $—CH_2CH_2CH_2CH_3$ | $—PO_3H_2$ |
| 2263 | 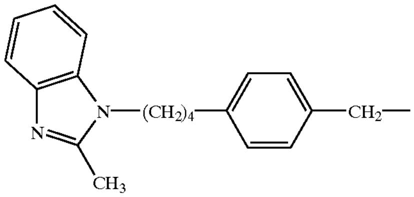 | $—CH_2CH_2CH_2CH_2CH_3$ | $—PO_3H_2$ |
| 2264 | 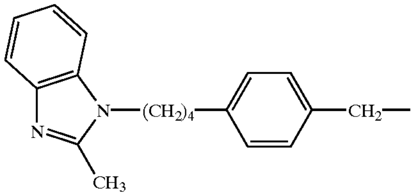 | $—CH_2CH_2CH_2CH_2CH_2CH_3$ | $—PO_3H_2$ |
| 2265 | 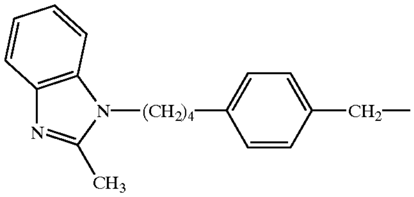 | $—CH(CH_3)_2$ | $—PO_3H_2$ |
| 2266 | 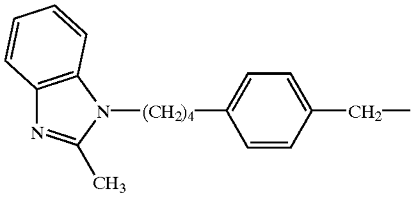 | $—CH_2CH(CH_3)_2$ | $—PO_3H_2$ |
| 2267 | 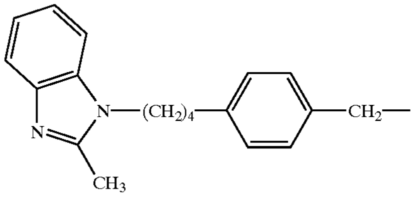 | $—CH_2CH_2CH(CH_3)_2$ | $—PO_3H_2$ |

TABLE I-continued
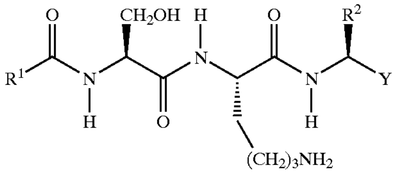
| Ex. No. | $R^1$ | $R^2$ | Y |
| --- | --- | --- | --- |
| 2268 | 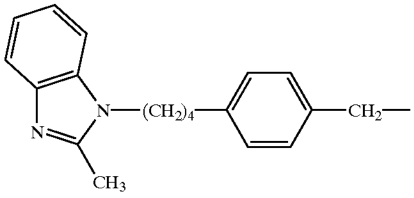 | -cyclo-$C_3H_5$ | —$PO_3H_2$ |
| 2269 | 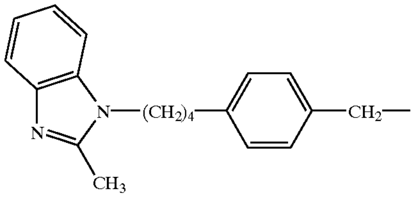 | -cyclo-$C_4H_7$ | —$PO_3H_2$ |
| 2270 | 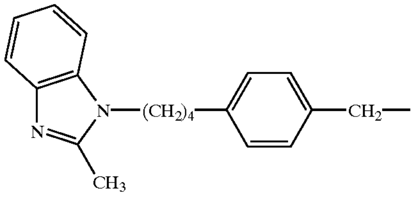 | -cyclo-$C_5H_9$ | —$PO_3H_2$ |
| 2271 | 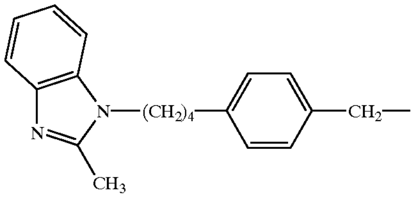 | -cyclo-$C_6H_{11}$ | —$PO_3H_2$ |
| 2272 | 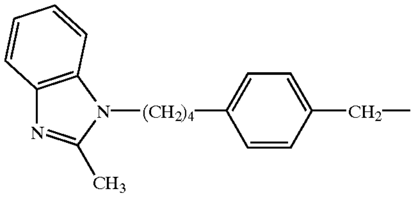 | -cyclo-$C_7H_{13}$ | —$PO_3H_2$ |
| 2273 | 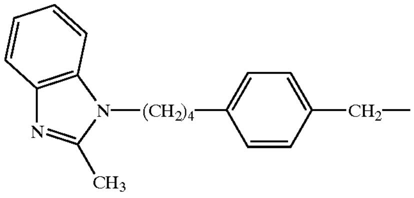 | -cyclo-$C_8H_{15}$ | —$PO_3H_2$ |

TABLE I-continued
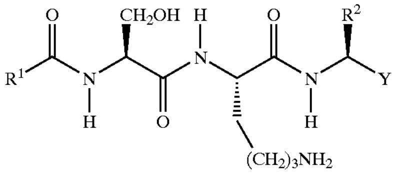
| Ex. No. | $R^1$ | $R^2$ | Y |
|---|---|---|---|
| 2274 | 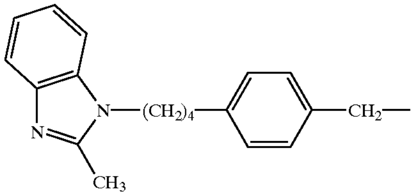 | $—CH(CH_3)(CH_2CH_3)$ | $—PO_3H_2$ |
| 2275 | 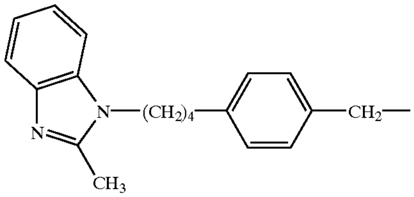 | $—CH(CH_2CH_3)_2$ | $—PO_3H_2$ |
| 2276 | 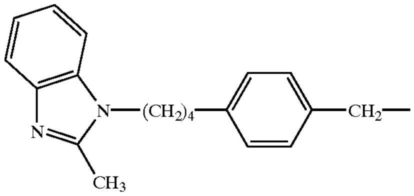 | $—CH(CH_3)(CH_2CH_2CH_3)$ | $—PO_3H_2$ |
| 2277 | 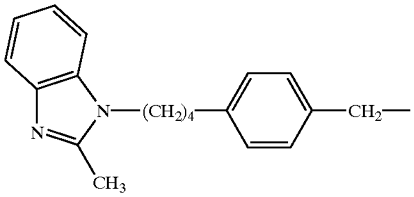 | $—C(CH_3)_3$ | $—PO_3H_2$ |
| 2278 | 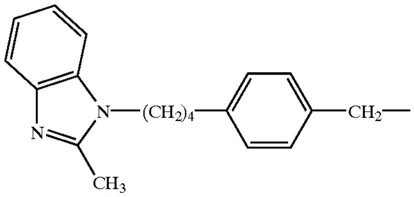 | $HC{\equiv}CCH_2—$ | $—PO_3H_2$ |
| 2279 | 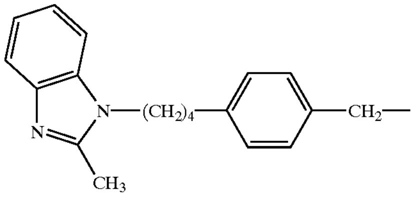 | $H_2C{=}CH—$ | $—PO_3H_2$ |

TABLE I-continued
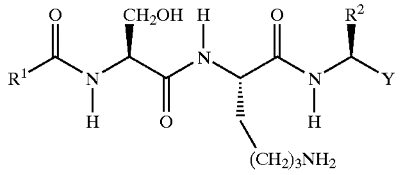
| Ex. No. | $R^1$ | $R^2$ | Y |
|---|---|---|---|
| 2280 | 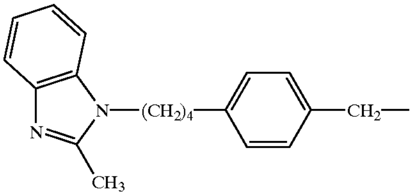 | $H_2C{=}CHCH_2—$ | $—PO_3H_2$ |
| 2281 | 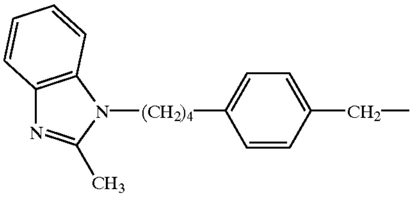 | $—CH_2F$ | $—PO_3H_2$ |
| 2282 | 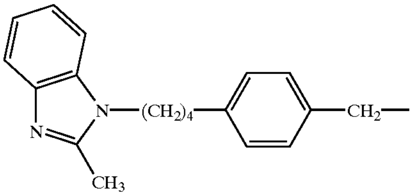 | $—CH_2C_6H_5$ | $—PO_3H_2$ |
| 2283 | 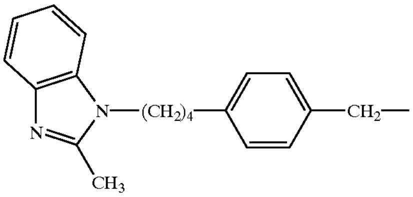 | $—CH_2C_6H_4$-p-$OCH_3$ | $—PO_3H_2$ |
| 2284 | 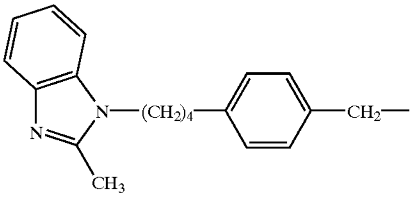 | $—CH_2C_6H_4$-p-$CH_3$ | $—PO_3H_2$ |
| 2285 | 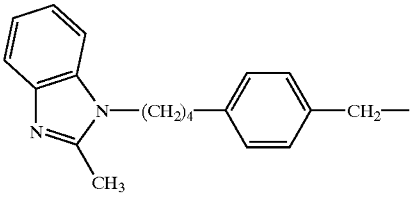 | $—CH_2C_6H_4$-p-F | $—PO_3H_2$ |

TABLE I-continued
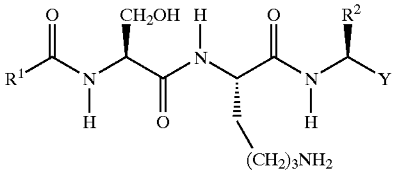
| Ex. No. | $R^1$ | $R^2$ | Y |
|---|---|---|---|
| 2286 | 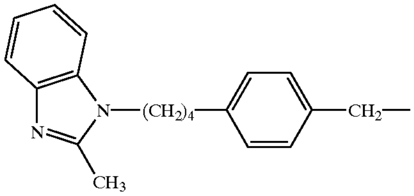 | $—CH_2CH_2C_6H_5$ | $—PO_3H_2$ |
| 2287 | 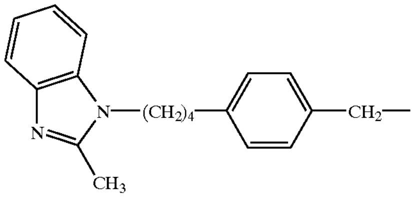 | $—CH_2$-cyclo-$C_6H_{11}$ | $—PO_3H_2$ |
| 2288 | 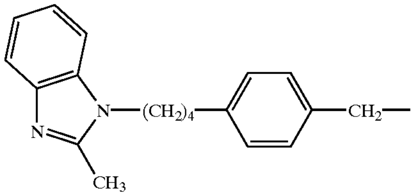 | $—CH_2$-cyclo-$C_6H_{10}$-4-F | $—PO_3H_2$ |
| 2289 | 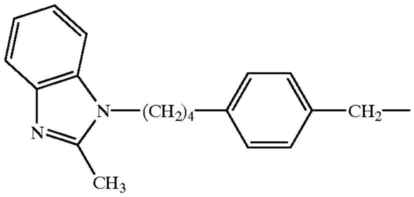 | $—CH_2$-cyclo-$C_6H_{10}$-4-$CH_3$ | $—PO_3H_2$ |
| 2290 | 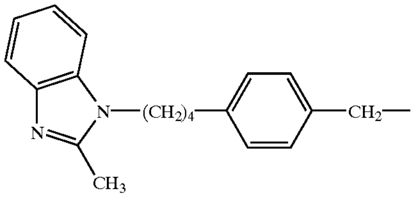 | $—CH_2$-cyclo-$C_6H_{10}$-4-$OCH_3$ | $—PO_3H_2$ |
| 2291 | 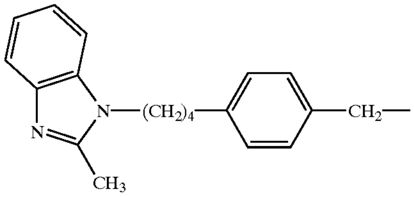 | $—CH_2CH_2$-cyclo-$C_6H_{11}$ | $—PO_3H_2$ |

TABLE I-continued
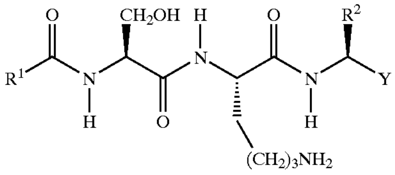
| Ex. No. | $R^1$ | $R^2$ | Y |
|---|---|---|---|
| 2292 | 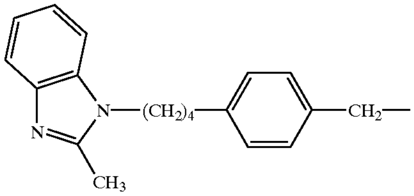 | $—CH_2$-cyclo-$C_5H_9$ | $—PO_3H_2$ |
| 2293 | 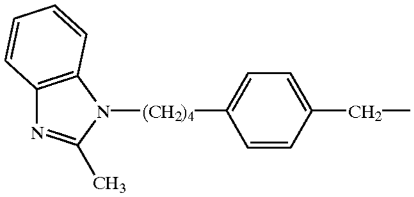 | $—CH_2CH_2$-cyclo-$C_5H_9$ | $—PO_3H_2$ |
| 2294 | 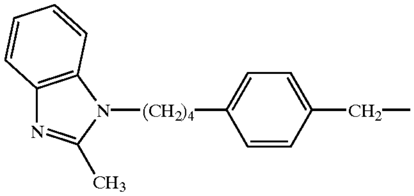 | $—CH_2$-2-naphthyl | $—PO_3H_2$ |
| 2295 | 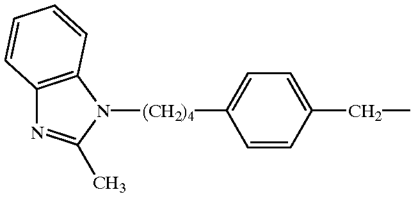 | —H | -5-Tet |
| 2296 | 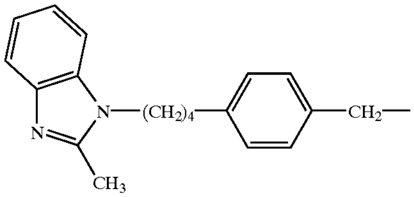 | $—CH_3$ | -5-Tet |
| 2297 | 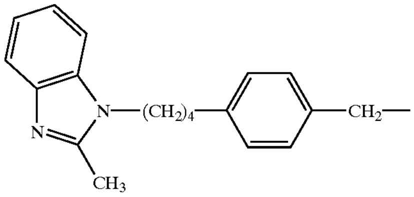 | $—CH_2CH_3$ | -5-Tet |

TABLE I-continued
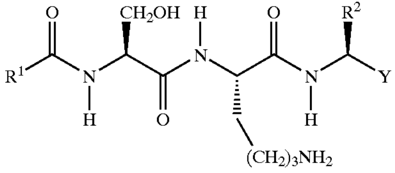
| Ex. No. | $R^1$ | $R^2$ | Y |
|---|---|---|---|
| 2298 | 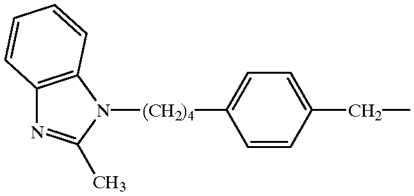 | $—CH_2CH_2CH_3$ | -5-Tet |
| 2299 | 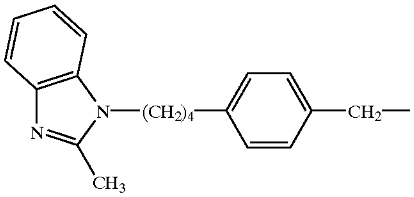 | $—CH_2CH_2CH_2CH_3$ | -5-Tet |
| 2300 | 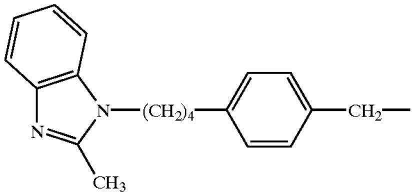 | $—CH_2CH_2CH_2CH_2CH_3$ | -5-Tet |
| 2301 | 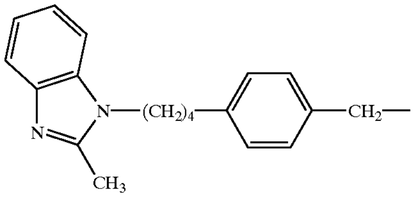 | $—CH_2CH_2CH_2CH_2CH_2CH_3$ | -5-Tet |
| 2302 | 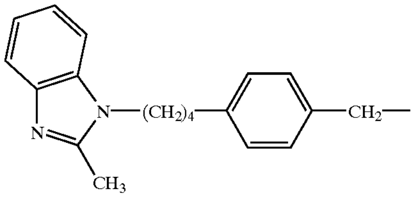 | $—CH(CH_3)_2$ | -5-Tet |
| 2303 | 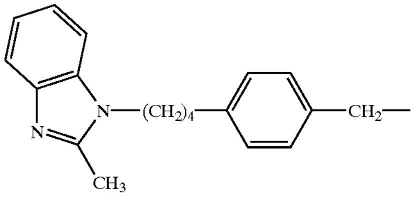 | $—CH_2CH(CH_3)_2$ | -5-Tet |

TABLE I-continued
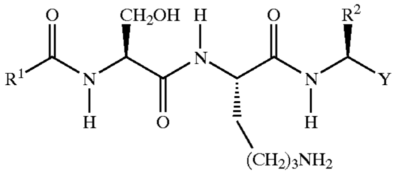
| Ex. No. | $R^1$ | $R^2$ | Y |
|---|---|---|---|
| 2304 | 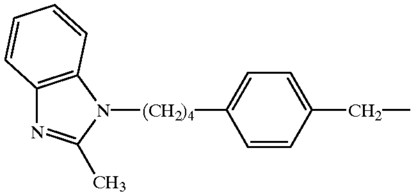 | $-CH_2CH_2CH(CH_3)_2$ | -5-Tet |
| 2305 | 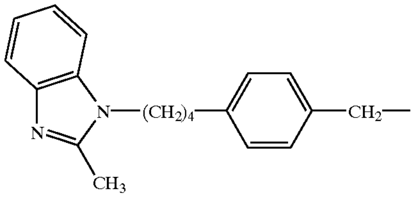 | -cyclo-$C_3H_5$ | -5-Tet |
| 2306 | 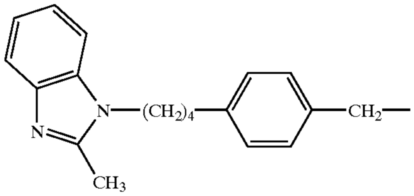 | -cyclo-$C_4H_7$ | -5-Tet |
| 2307 | 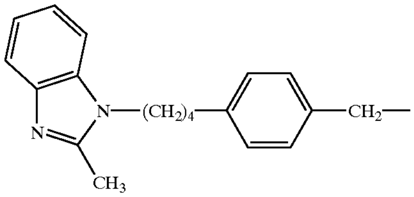 | -cyclo-$C_5H_9$ | -5-Tet |
| 2308 | 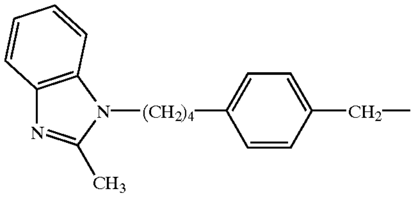 | -cyclo-$C_6H_{11}$ | -5-Tet |
| 2309 | 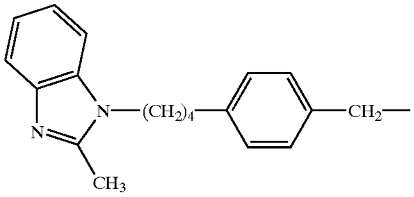 | -cyclo-$C_7H_{13}$ | -5-Tet |

TABLE I-continued
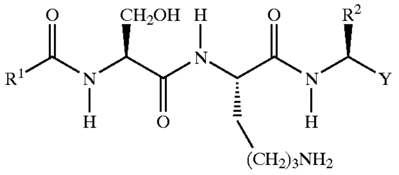
| Ex. No. | $R^1$ | $R^2$ | Y |
|---|---|---|---|
| 2310 | 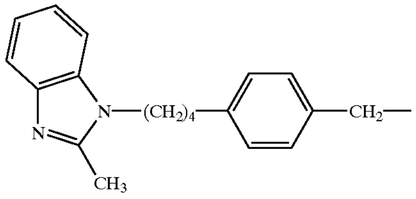 | -cyclo-$C_8H_{15}$ | -5-Tet |
| 2311 | 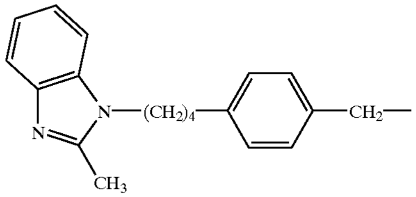 | —$CH(CH_3)(CH_2CH_3)$ | -5-Tet |
| 2312 | 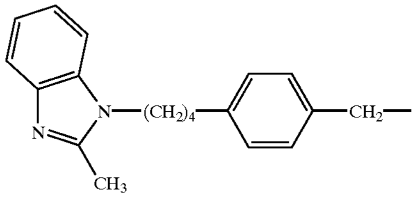 | —$CH(CH_2CH_3)_2$ | -5-Tet |
| 2313 | 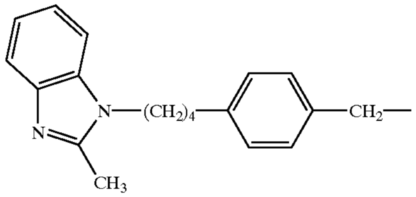 | —$CH(CH_3)(CH_2CH_2CH_3)$ | -5-Tet |
| 2314 | 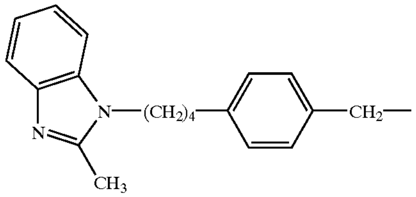 | —$C(CH_3)_3$ | -5-Tet |
| 2315 | 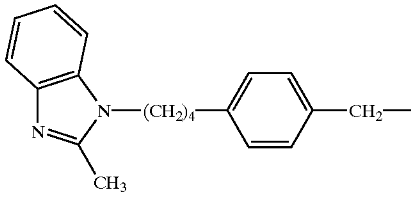 | $HC{\equiv}CCH_2$— | -5-Tet |

TABLE I-continued
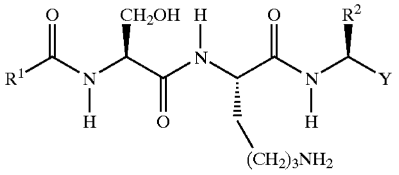
| Ex. No. | $R^1$ | $R^2$ | Y |
|---|---|---|---|
| 2316 | 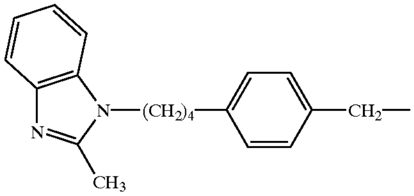 | $H_2C{=}CH-$ | -5-Tet |
| 2317 | 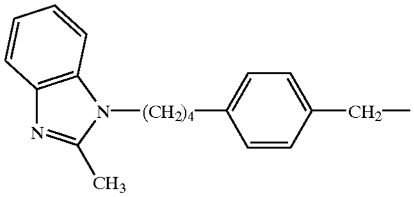 | $H_2C{=}CHCH_2-$ | -5-Tet |
| 2318 | 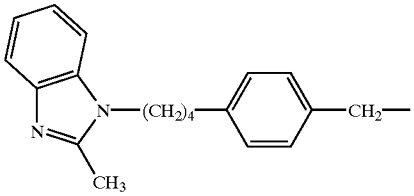 | $-CH_2F$ | -5-Tet |
| 2319 | 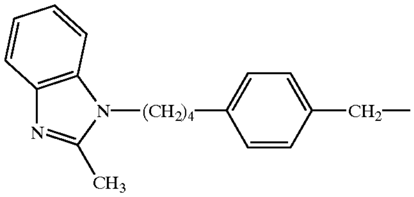 | $-CH_2C_6H_5$ | -5-Tet |
| 2320 | 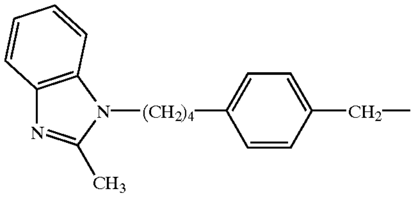 | $-CH_2C_6H_4$-p-$OCH_3$ | -5-Tet |
| 2321 | 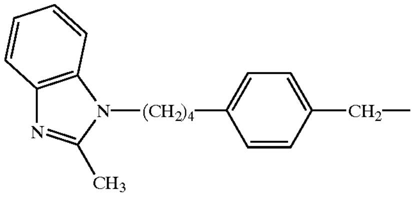 | $-CH_2C_6H_4$-p-$CH_3$ | -5-Tet |

TABLE I-continued
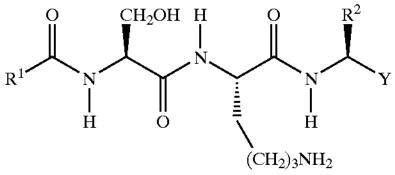
| Ex. No. | $R^1$ | $R^2$ | Y |
|---|---|---|---|
| 2322 | 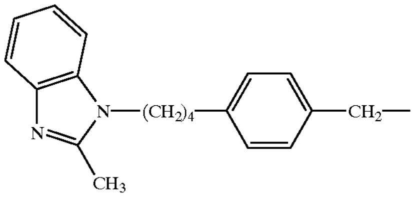 | $—CH_2C_6H_4$-p-F | -5-Tet |
| 2323 | 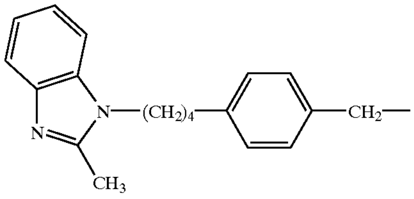 | $—CH_2CH_2C_6H_5$ | -5-Tet |
| 2324 | 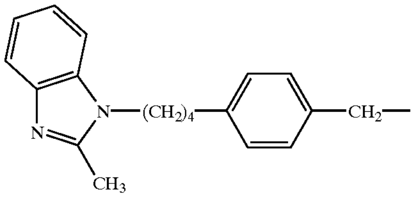 | $—CH_2$-cyclo-$C_6H_{11}$ | -5-Tet |
| 2325 | 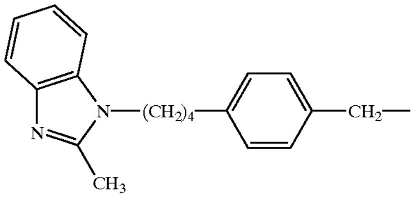 | $—CH_2$-cyclo-$C_6H_{10}$-4-F | -5-Tet |
| 2326 | 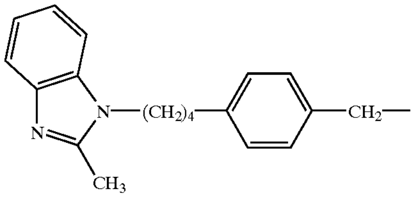 | $—CH_2$-cyclo-$C_6H_{10}$-4-$CH_3$ | -5-Tet |
| 2327 | 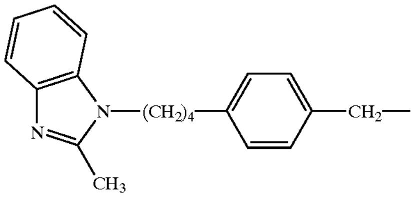 | $—CH_2$-cyclo-$C_6H_{10}$-4-$OCH_3$ | -5-Tet |

TABLE I-continued
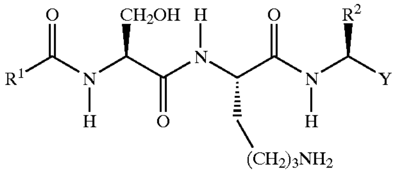
| Ex. No. | $R^1$ | $R^2$ | Y |
|---|---|---|---|
| 2328 | 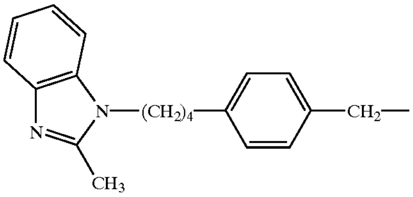 | $—CH_2CH_2$-cyclo-$C_6H_{11}$ | -5-Tet |
| 2329 | 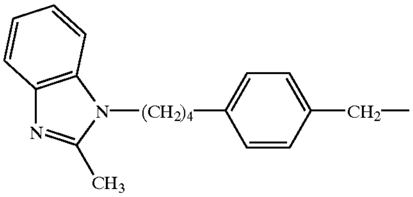 | $—CH_2$-cyclo-$C_5H_9$ | -5-Tet |
| 2330 | 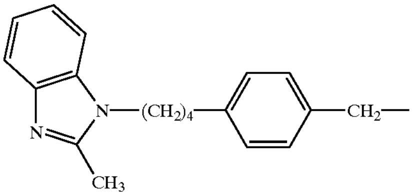 | $—CH_2CH_2$-cyclo-$C_5H_9$ | -5-Tet |
| 2331 | 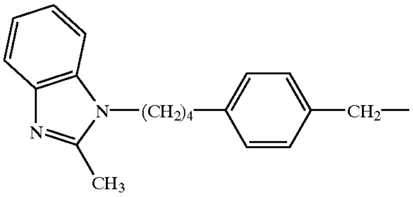 | $—CH_2$-2-naphthyl | -5-Tet |
| 2332 | 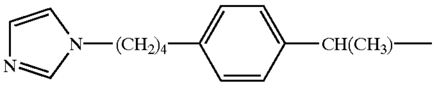 | —H | $—CO_2H$ |
| 2333 | 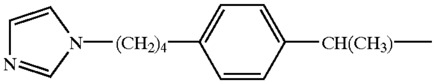 | $—CH_3$ | $—CO_2H$ |
| 2334 | 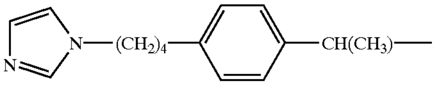 | $—CH_2CH_3$ | $—CO_2H$ |
| 2335 | 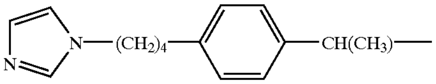 | $—CH_2CH_2CH_3$ | $—CO_2H$ |
| 2336 | 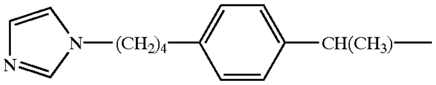 | $—CH_2CH_2CH_2CH_3$ | $—CO_2H$ |

TABLE I-continued
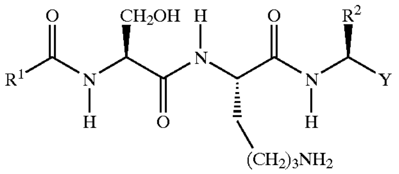
| Ex. No. | $R^1$ | $R^2$ | Y |
|---|---|---|---|
| 2337 | 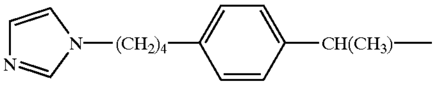 | $—CH_2CH_2CH_2CH_2CH_3$ | $—CO_2H$ |
| 2338 | 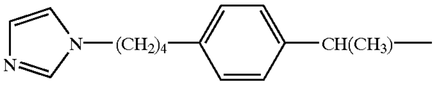 | $—CH_2CH_2CH_2CH_2CH_2CH_3$ | $—CO_2H$ |
| 2339 | 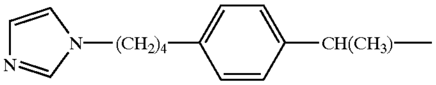 | $—CH(CH_3)_2$ | $—CO_2H$ |
| 2340 | 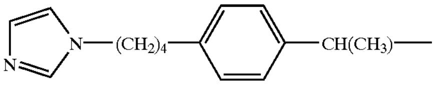 | $—CH_2CH(CH_3)_2$ | $—CO_2H$ |
| 2341 | 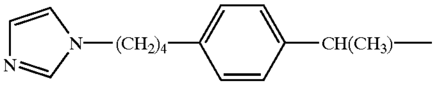 | $—CH_2CH_2CH(CH_3)_2$ | $—CO_2H$ |
| 2342 | 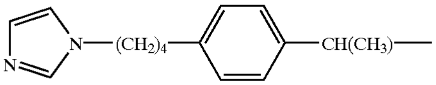 | —cyclo-$C_3H_5$ | $—CO_2H$ |
| 2343 | 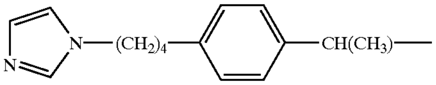 | -cyclo-$C_4H_7$ | $—CO_2H$ |
| 2344 | 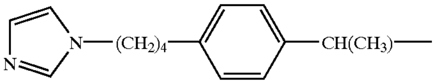 | -cyclo-$C_5H_9$ | $—CO_2H$ |
| 2345 | 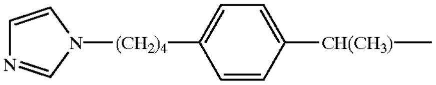 | -cyclo-$C_6H_{11}$ | $—CO_2H$ |
| 2346 | 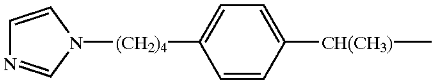 | -cyclo-$C_7H_{13}$ | $—CO_2H$ |
| 2347 | 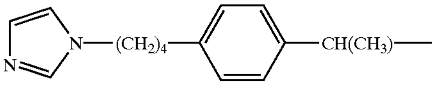 | -cyclo-$C_8H_{15}$ | $—CO_2H$ |
| 2348 | 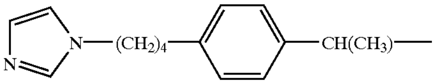 | $—CH(CH_3)(CH_2CH_3)$ | $—CO_2H$ |
| 2349 | 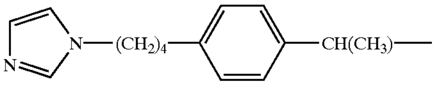 | $—CH(CH_2CH_3)_2$ | $—CO_2H$ |

TABLE I-continued
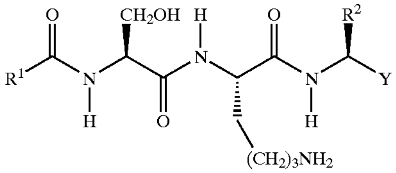
| Ex. No. | $R^1$ | $R^2$ | Y |
|---|---|---|---|
| 2350 | 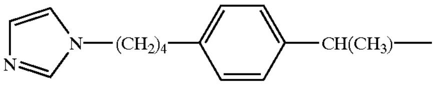 | $—CH(CH_3)(CH_2CH_2CH_3)$ | $—CO_2H$ |
| 2351 | 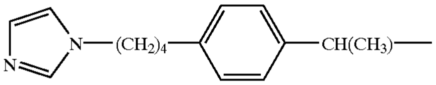 | $—C(CH_3)_3$ | $—CO_2H$ |
| 2352 | 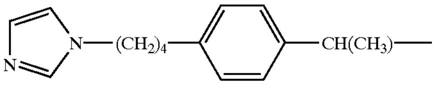 | $HC{\equiv}CCH_2—$ | $—CO_2H$ |
| 2353 | 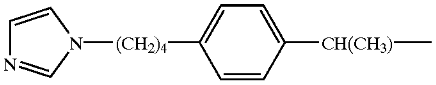 | $H_2C{=}CH—$ | $—CO_2H$ |
| 2354 | 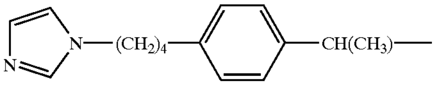 | $H_2C{=}CHCH_2—$ | $—CO_2H$ |
| 2355 | 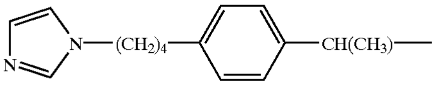 | $—CH_2F$ | $—CO_2H$ |
| 2356 | 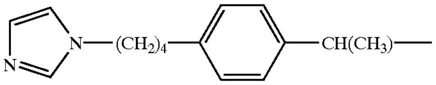 | $—CH_2C_6H_5$ | $—CO_2H$ |
| 2357 | 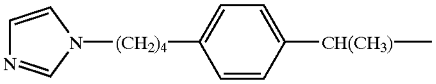 | $—CH_2C_6H_4$-p-$OCH_3$ | $—CO_2H$ |
| 2358 | 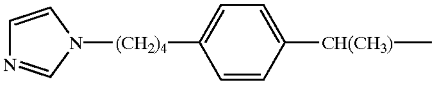 | $—CH_2C_6H_4$-p-$CH_3$ | $—CO_2H$ |
| 2359 | 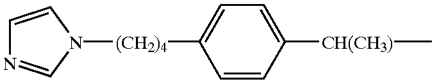 | $—CH_2C_6H_4$-p-F | $—CO_2H$ |
| 2360 | 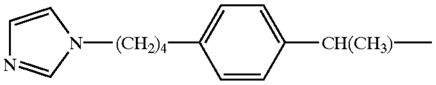 | $—CH_2CH_2C_6H_5$ | $—CO_2H$ |
| 2361 | 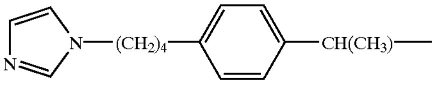 | $—CH_2$-cyclo-$C_6H_{11}$ | $—CO_2H$ |
| 2362 | 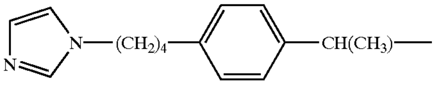 | $—CH_2$-cyclo-$C_6H_{10}$-4-F | $—CO_2H$ |

TABLE I-continued
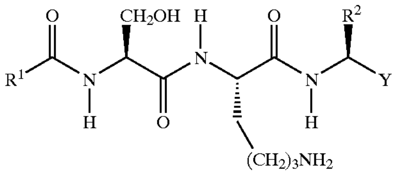
| Ex. No. | $R^1$ | $R^2$ | Y |
|---|---|---|---|
| 2363 | 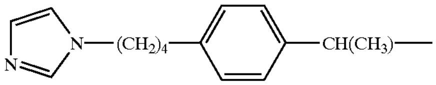 | $—CH_2$-cyclo-$C_6H_{10}$-4-$CH_3$ | $—CO_2H$ |
| 2364 | 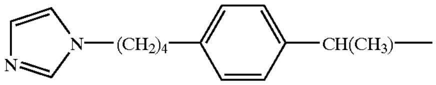 | $—CH_2$-cyclo-$C_6H_{10}$-4-$OCH_3$ | $—CO_2H$ |
| 2365 | 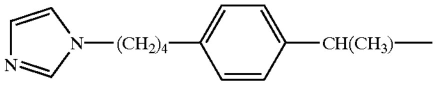 | $—CH_2CH_2$-cyclo-$C_6H_{11}$ | $—CO_2H$ |
| 2366 | 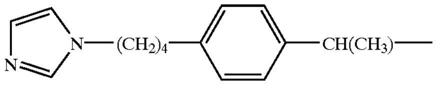 | $—CH_2$-cyclo-$C_5H_9$ | $—CO_2H$ |
| 2367 | 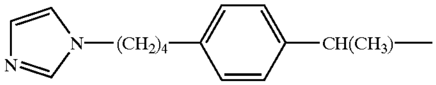 | $—CH_2CH_2$-cyclo-$C_5H_9$ | $—CO_2H$ |
| 2368 | 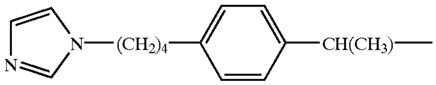 | $—CH_2$-2-naphthyl | $—CO_2H$ |
| 2369 | 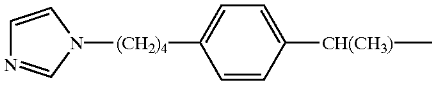 | —H | $—PO_3H_2$ |
| 2370 | 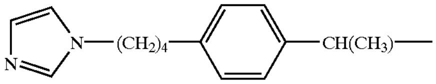 | $—CH_3$ | $—PO_3H_2$ |
| 2371 | 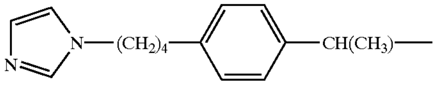 | $—CH_2CH_3$ | $—PO_3H_2$ |
| 2372 | 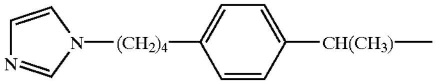 | $—CH_2CH_2CH_3$ | $—PO_3H_2$ |
| 2373 | 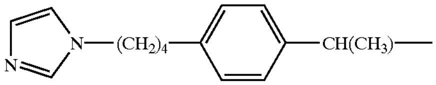 | $—CH_2CH_2CH_2CH_3$ | $—PO_3H_2$ |
| 2374 | 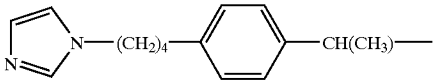 | $—CH_2CH_2CH_2CH_2CH_3$ | $—PO_3H_2$ |
| 2375 | 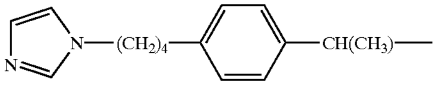 | $—CH_2CH_2CH_2CH_2CH_2CH_3$ | $—PO_3H_2$ |

TABLE I-continued
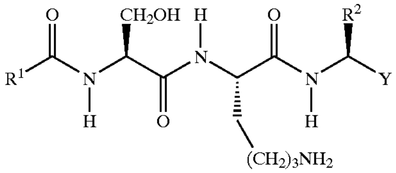
| Ex. No. | $R^1$ | $R^2$ | Y |
| --- | --- | --- | --- |
| 2376 | 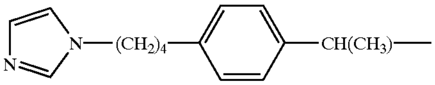 | $—CH(CH_3)_2$ | $—PO_3H_2$ |
| 2377 | 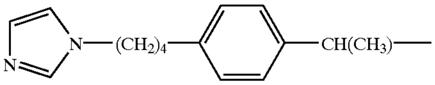 | $—CH_2CH(CH_3)_2$ | $—PO_3H_2$ |
| 2378 | 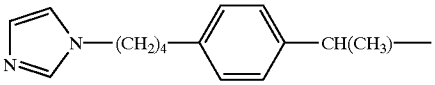 | $—CH_2CH_2CH(CH_3)_2$ | $—PO_3H_2$ |
| 2379 | 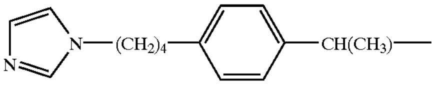 | -cyclo-$C_3H_5$ | $—PO_3H_2$ |
| 2380 | 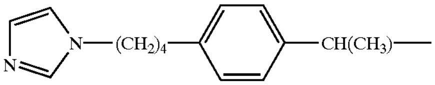 | -cyclo-$C_4H_7$ | $—PO_3H_2$ |
| 2381 | 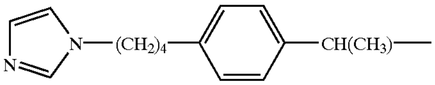 | -cyclo-$C_5H_9$ | $—PO_3H_2$ |
| 2382 | 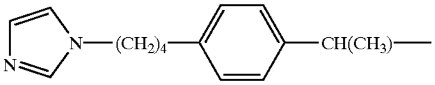 | -cyclo-$C_6H_{11}$ | $—PO_3H_2$ |
| 2383 | 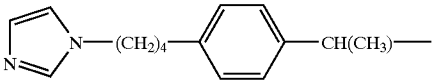 | -cyclo-$C_7H_{13}$ | $—PO_3H_2$ |
| 2384 | 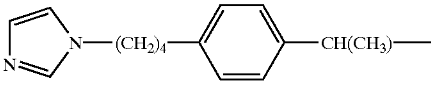 | -cyclo-$C_8H_{15}$ | $—PO_3H_2$ |
| 2385 | 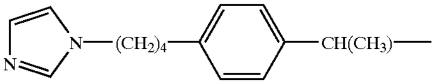 | $—CH(CH_3)(CH_2CH_3)$ | $—PO_3H_2$ |
| 2386 | 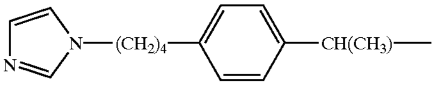 | $—CH(CH_2CH_3)_2$ | $—PO_3H_2$ |
| 2387 | 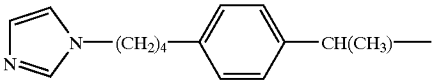 | $—CH(CH_3)(CH_2CH_2CH_3)$ | $—PO_3H_2$ |
| 2388 | 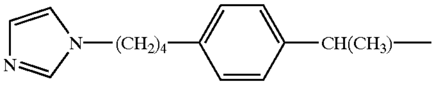 | $—C(CH_3)_3$ | $—PO_3H_2$ |

TABLE I-continued
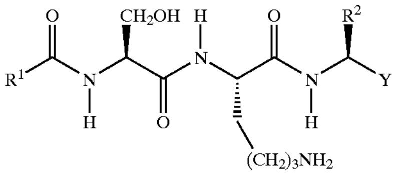
| Ex. No. | $R^1$ | $R^2$ | Y |
|---|---|---|---|
| 2389 | 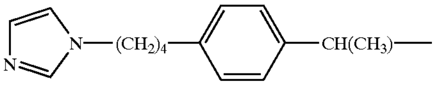 | $HC{\equiv}CCH_2$— | —$PO_3H_2$ |
| 2390 | 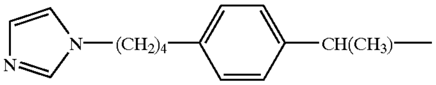 | $H_2C{=}CH$— | —$PO_3H_2$ |
| 2391 | 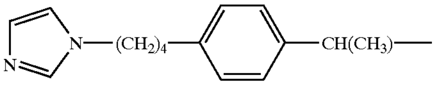 | $H_2C{=}CHCH_2$— | —$PO_3H_2$ |
| 2392 | 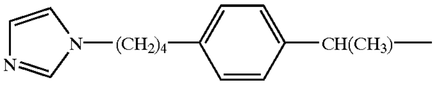 | —$CH_2F$ | —$PO_3H_2$ |
| 2393 | 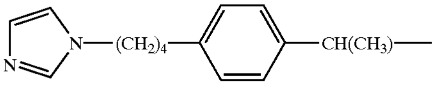 | —$CH_2C_6H_5$ | —$PO_3H_2$ |
| 2394 | 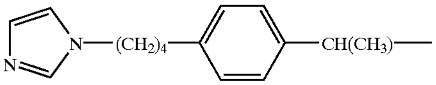 | —$CH_2C_6H_4$-p-$OCH_3$ | —$PO_3H_2$ |
| 2395 | 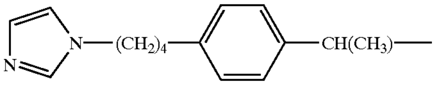 | —$CH_2C_6H_4$-p-$CH_3$ | —$PO_3H_2$ |
| 2396 | 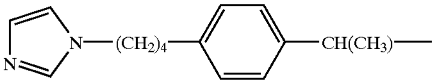 | —$CH_2C_6H_4$-p-F | —$PO_3H_2$ |
| 2397 | 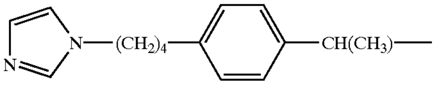 | —$CH_2CH_2C_6H_5$ | —$PO_3H_2$ |
| 2398 | 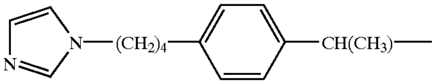 | —$CH_2$-cyclo-$C_6H_{11}$ | —$PO_3H_2$ |
| 2399 | 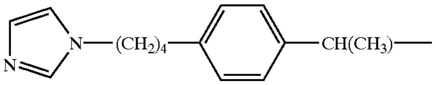 | —$CH_2$-cyclo-$C_6H_{10}$-4-F | —$PO_3H_2$ |
| 2400 | 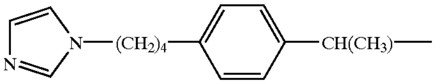 | —$CH_2$-cyclo-$C_6H_{10}$-4-$CH_3$ | —$PO_3H_2$ |
| 2401 | 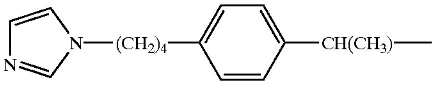 | —$CH_2$-cyclo-$C_6H_{10}$-4-$OCH_3$ | —$PO_3H_2$ |

TABLE I-continued
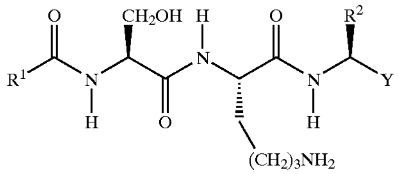
| Ex. No. | $R^1$ | $R^2$ | Y |
|---|---|---|---|
| 2402 | 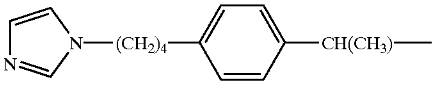 | $—CH_2CH_2$-cyclo-$C_6H_{11}$ | $—PO_3H_2$ |
| 2403 | 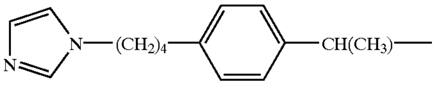 | $—CH_2$-cyclo-$C_5H_9$ | $—PO_3H_2$ |
| 2404 | 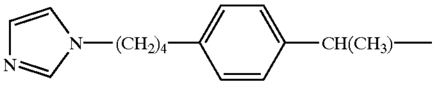 | $—CH_2CH_2$-cyclo-$C_5H_9$ | $—PO_3H_2$ |
| 2405 | 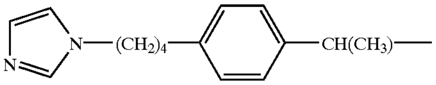 | $—CH_2$-2-naphthyl | $—PO_3H_2$ |
| 2406 | 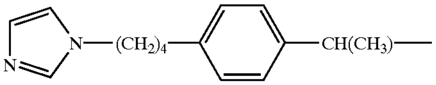 | —H | -5-Tet |
| 2407 | 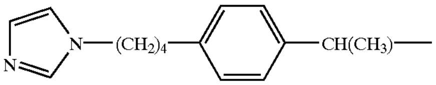 | $—CH_3$ | -5-Tet |
| 2408 | 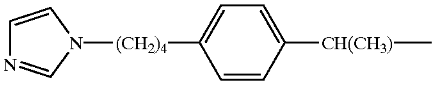 | $—CH_2CH_3$ | -5-Tet |
| 2409 | 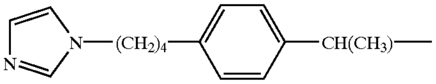 | $—CH_2CH_2CH_3$ | -5-Tet |
| 2410 | 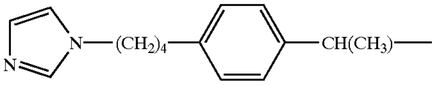 | $—CH_2CH_2CH_2CH_3$ | -5-Tet |
| 2411 | 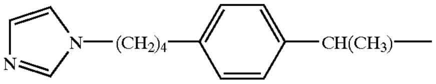 | $—CH_2CH_2CH_2CH_2CH_3$ | -5-Tet |
| 2412 | 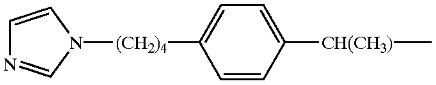 | $—CH_2CH_2CH_2CH_2CH_2CH_3$ | -5-Tet |
| 2413 | 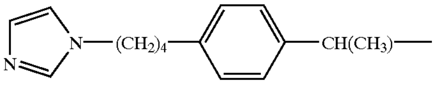 | $—CH(CH_3)_2$ | -5-Tet |
| 2414 | 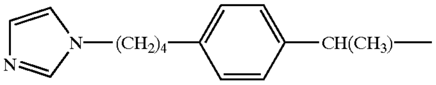 | $—CH_2CH(CH_3)_2$ | -5-Tet |

TABLE I-continued
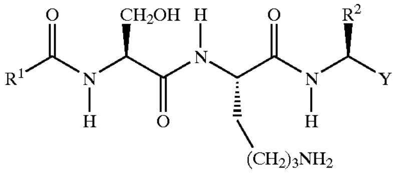
| Ex. No. | $R^1$ | $R^2$ | Y |
|---|---|---|---|
| 2415 | 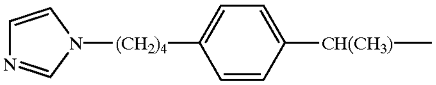 | $-CH_2CH_2CH(CH_3)_2$ | -5-Tet |
| 2416 | 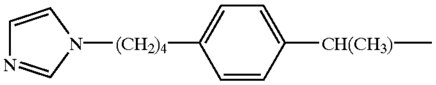 | -cyclo-$C_3H_5$ | -5-Tet |
| 2417 | 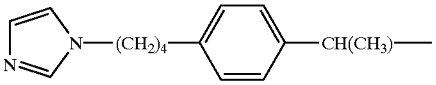 | -cyclo-$C_4H_7$ | -5-Tet |
| 2418 | 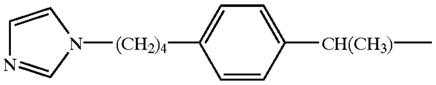 | -cyclo-$C_5H_9$ | -5-Tet |
| 2419 | 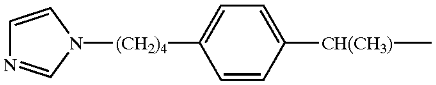 | -cyclo-$C_6H_{11}$ | -5-Tet |
| 2420 | 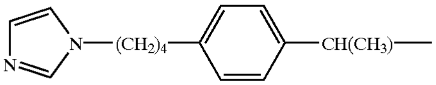 | -cyclo-$C_7H_{13}$ | -5-Tet |
| 2421 | 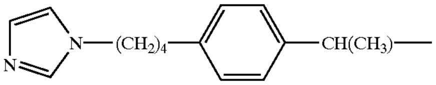 | -cyclo-$C_8H_{15}$ | -5-Tet |
| 2422 | 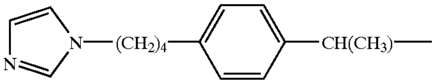 | $-CH(CH_3)(CH_2CH_3)$ | -5-Tet |
| 2423 | 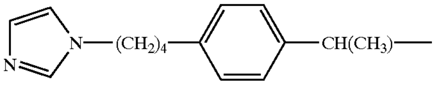 | $-CH(CH_2CH_3)_2$ | -5-Tet |
| 2424 | 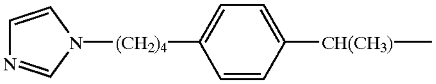 | $-CH(CH_3)(CH_2CH_2CH_3)$ | -5-Tet |
| 2425 | 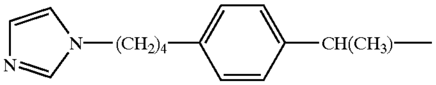 | $-C(CH_3)_3$ | -5-Tet |
| 2426 | 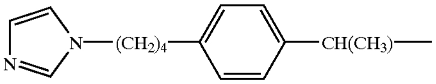 | $HC{\equiv}CCH_2-$ | -5-Tet |
| 2427 | 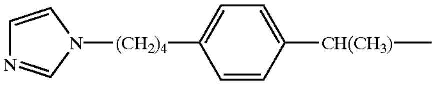 | $H_2C{=}CH-$ | -5-Tet |

TABLE I-continued
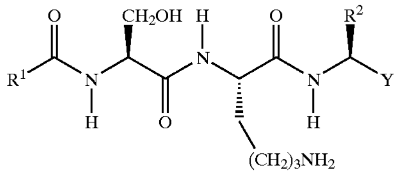
| Ex. No. | $R^1$ | $R^2$ | Y |
|---|---|---|---|
| 2428 | 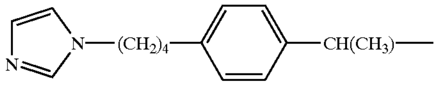 | $H_2C{=}CHCH_2$— | -5-Tet |
| 2429 | 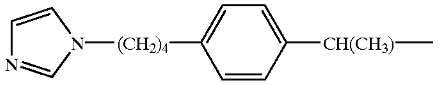 | —$CH_2F$ | -5-Tet |
| 2430 | 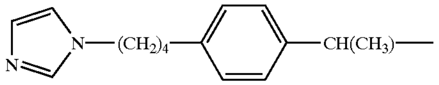 | —$CH_2C_6H_5$ | -5-Tet |
| 2431 | 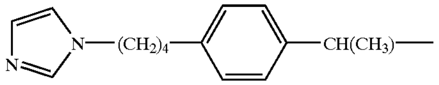 | —$CH_2C_6H_4$-p-$OCH_3$ | -5-Tet |
| 2432 | 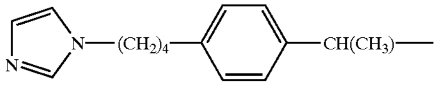 | —$CH_2C_6H_4$-p-$CH_3$ | -5-Tet |
| 2433 | 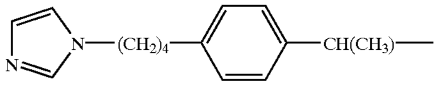 | —$CH_2C_6H_4$-p-F | -5-Tet |
| 2434 | 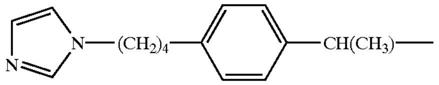 | —$CH_2CH_2C_6H_5$ | -5-Tet |
| 2435 | 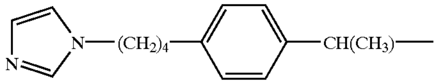 | —$CH_2$-cyclo-$C_6H_{11}$ | -5-Tet |
| 2436 | 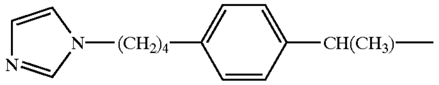 | —$CH_2$-cyclo-$C_6H_{10}$-4-F | -5-Tet |
| 2437 | 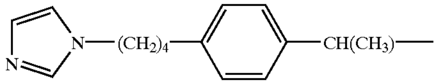 | —$CH_2$-cyclo-$C_6H_{10}$-4-$CH_3$ | -5-Tet |
| 2438 | 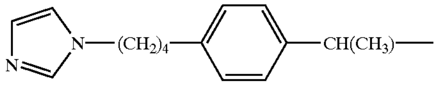 | —$CH_2$-cyclo-$C_6H_{10}$-4-$OCH_3$ | -5-Tet |
| 2439 | 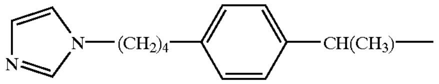 | —$CH_2CH_2$-cyclo-$C_6H_{11}$ | -5-Tet |
| 2440 | 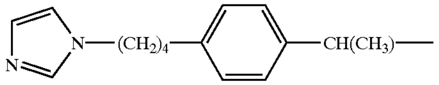 | —$CH_2$-cyclo-$C_5H_9$ | -5-Tet |

TABLE I-continued
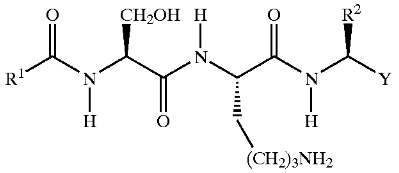
| Ex. No. | $R^1$ | $R^2$ | Y |
|---|---|---|---|
| 2441 | 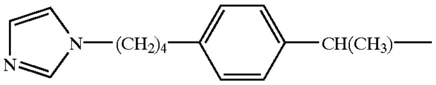 | $—CH_2CH_2$-cyclo-$C_5H_9$ | -5-Tet |
| 2442 | 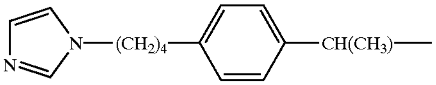 | $—CH_2$-2-naphthyl | -5-Tet |
| 2443 | 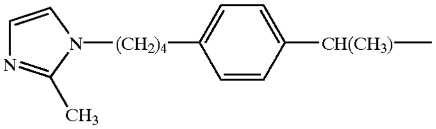 | —H | $—CO_2H$ |
| 2444 | 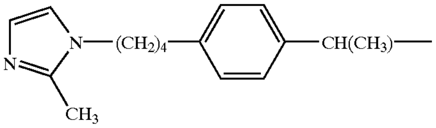 | $—CH_3$ | $—CO_2H$ |
| 2445 | 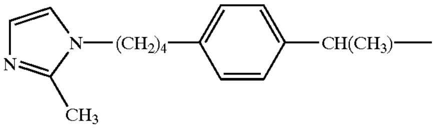 | $—CH_2CH_3$ | $—CO_2H$ |
| 2446 | 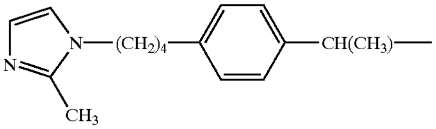 | $—CH_2CH_2CH_3$ | $—CO_2H$ |
| 2447 | 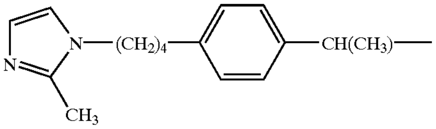 | $—CH_2CH_2CH_2CH_3$ | $—CO_2H$ |
| 2448 | 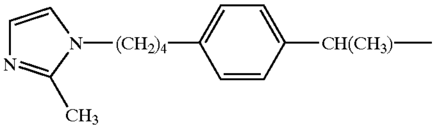 | $—CH_2CH_2CH_2CH_2CH_3$ | $—CO_2H$ |
| 2449 | 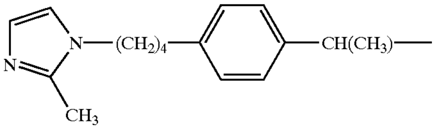 | $—CH_2CH_2CH_2CH_2CH_2CH_3$ | $—CO_2H$ |
| 2450 | 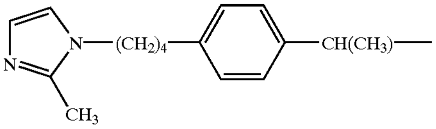 | $—CH(CH_3)_2$ | $—CO_2H$ |

TABLE I-continued
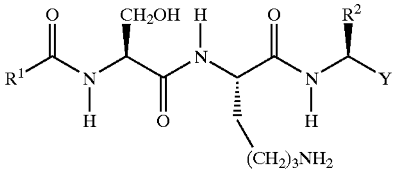
| Ex. No. | $R^1$ | $R^2$ | Y |
|---|---|---|---|
| 2451 | 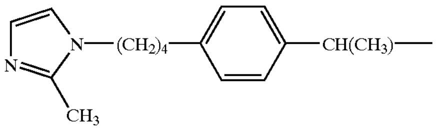 | $—CH_2CH(CH_3)_2$ | $—CO_2H$ |
| 2452 | 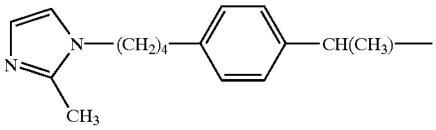 | $—CH_2CH_2CH(CH_3)_2$ | $—CO_2H$ |
| 2453 | 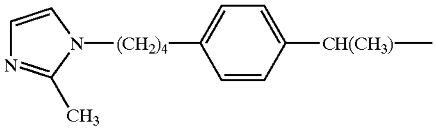 | —cyclo-$C_3H_5$ | $—CO_2H$ |
| 2454 | 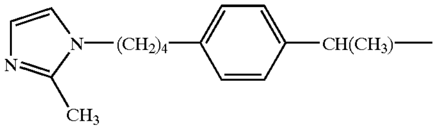 | -cyclo-$C_4H_7$ | $—CO_2H$ |
| 2455 | 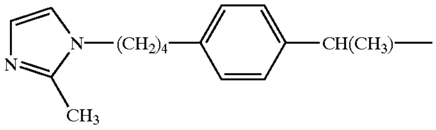 | -cyclo-$C_5H_9$ | $—CO_2H$ |
| 2456 | 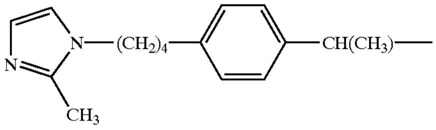 | -cyclo-$C_6H_{11}$ | $—CO_2H$ |
| 2457 | 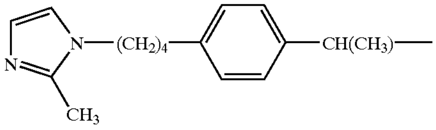 | -cyclo-$C_7H_{13}$ | $—CO_2H$ |
| 2458 | 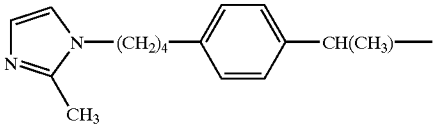 | -cyclo-$C_8H_{15}$ | $—CO_2H$ |
| 2459 | 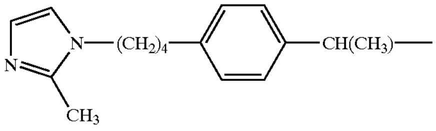 | $—CH(CH_3)(CH_2CH_3)$ | $—CO_2H$ |

TABLE I-continued
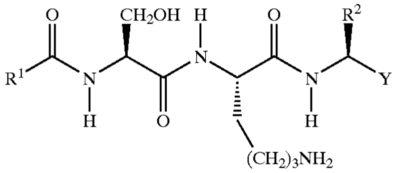
| Ex. No. | $R^1$ | $R^2$ | Y |
|---|---|---|---|
| 2460 | 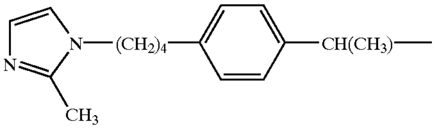 | $—CH(CH_2CH_3)_2$ | $—CO_2H$ |
| 2461 | 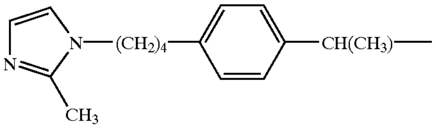 | $—CH(CH_3)(CH_2CH_2CH_3)$ | $—CO_2H$ |
| 2462 | 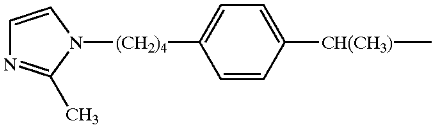 | $—C(CH_3)_3$ | $—CO_2H$ |
| 2463 | 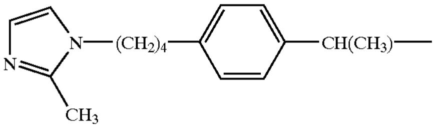 | $HC{\equiv}CCH_2—$ | $—CO_2H$ |
| 2464 | 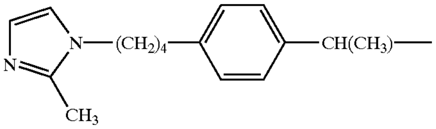 | $H_2C{=}CH—$ | $—CO_2H$ |
| 2465 | 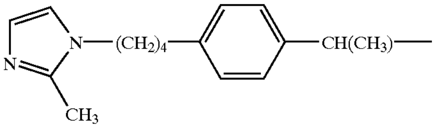 | $H_2C{=}CHCH_2—$ | $—CO_2H$ |
| 2466 | 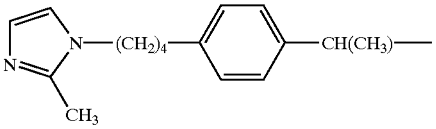 | $—CH_2F$ | $—CO_2H$ |
| 2467 | 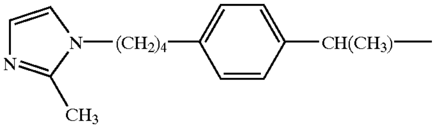 | $—CH_2C_6H_5$ | $—CO_2H$ |
| 2468 | 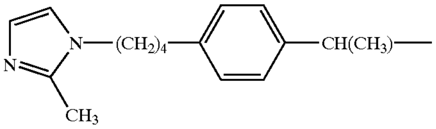 | $—CH_2C_6H_4$-p-$OCH_3$ | $—CO_2H$ |

TABLE I-continued
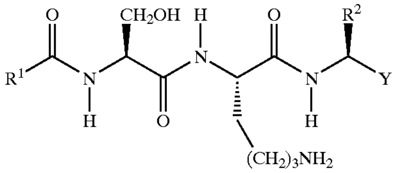
| Ex. No. | $R^1$ | $R^2$ | Y |
|---|---|---|---|
| 2469 | 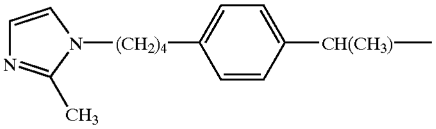 | $-CH_2C_6H_4$-p-$CH_3$ | $-CO_2H$ |
| 2470 | 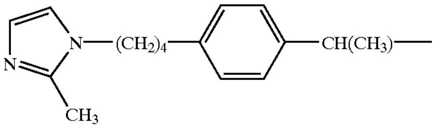 | $-CH_2C_6H_4$-p-F | $-CO_2H$ |
| 2471 | 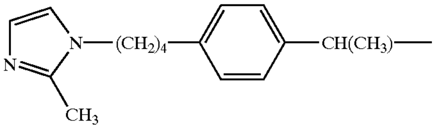 | $-CH_2CH_2C_6H_5$ | $-CO_2H$ |
| 2472 | 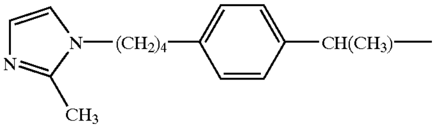 | $-CH_2$-cyclo-$C_6H_{11}$ | —CONHOH |
| 2473 | 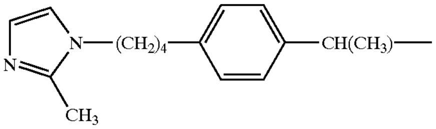 | $-CH_2$-cyclo-$C_6H_{10}$-4-F | $-CO_2H$ |
| 2474 | 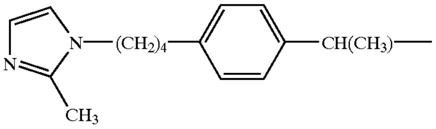 | $-CH_2$-cyclo-$C_6H_{10}$-4-$CH_3$ | $-CO_2H$ |
| 2475 | 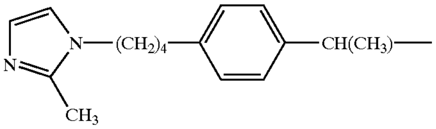 | $-CH_2$-cyclo-$C_6H_{10}$-4-$OCH_3$ | $-CO_2H$ |
| 2476 | 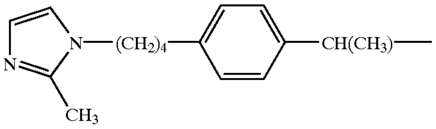 | $-CH_2CH_2$-cyclo-$C_6H_{11}$ | $-CO_2H$ |
| 2477 | 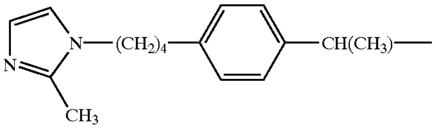 | $-CH_2$-cyclo-$C_5H_9$ | $-CO_2H$ |

TABLE I-continued
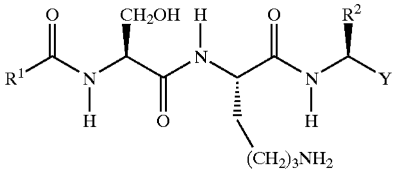
| Ex. No. | $R^1$ | $R^2$ | Y |
|---|---|---|---|
| 2478 | 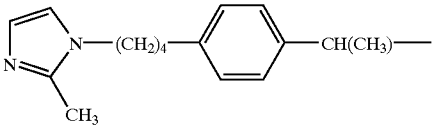 | $—CH_2CH_2$-cyclo-$C_5H_9$ | $—CO_2H$ |
| 2479 | 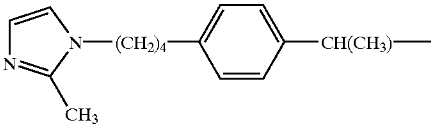 | $—CH_2$-2-naphthyl | $—CO_2H$ |
| 2480 | 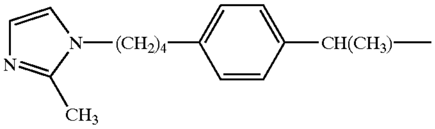 | —H | $—PO_3H_2$ |
| 2481 | 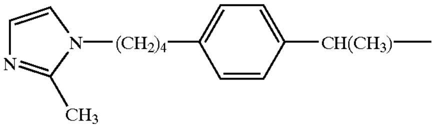 | $—CH_3$ | $—PO_3H_2$ |
| 2482 | 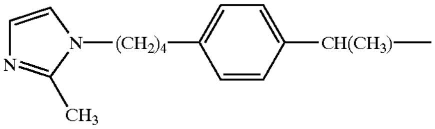 | $—CH_2CH_3$ | $—PO_3H_2$ |
| 2483 | 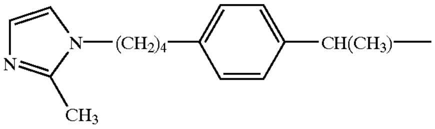 | $—CH_2CH_2CH_3$ | $—PO_3H_2$ |
| 2484 | 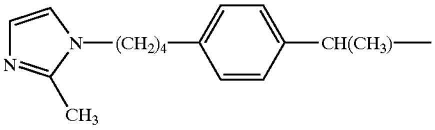 | $—CH_2CH_2CH_2CH_3$ | $—PO_3H_2$ |
| 2485 | 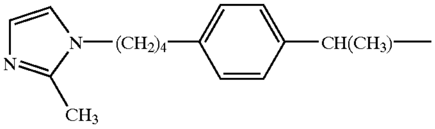 | $—CH_2CH_2CH_2CH_2CH_3$ | $—PO_3H_2$ |
| 2486 | 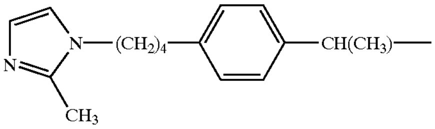 | $—CH_2CH_2CH_2CH_2CH_2CH_3$ | $—PO_3H_2$ |

TABLE I-continued
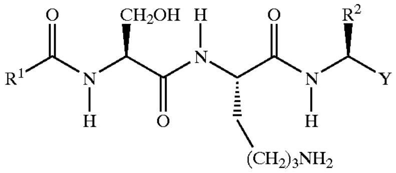
| Ex. No. | $R^1$ | $R^2$ | Y |
|---|---|---|---|
| 2487 | 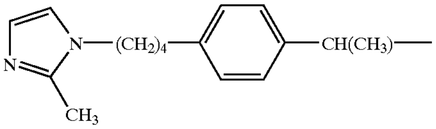 | $—CH(CH_3)_2$ | $—PO_3H_2$ |
| 2488 | 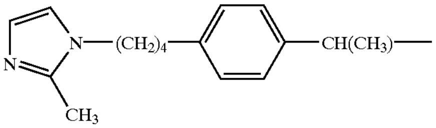 | $—CH_2CH(CH_3)_2$ | $—PO_3H_2$ |
| 2489 | 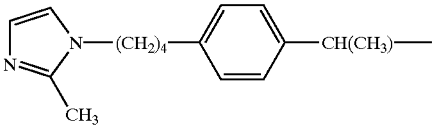 | $—CH_2CH_2CH(CH_3)_2$ | $—PO_3H_2$ |
| 2490 | 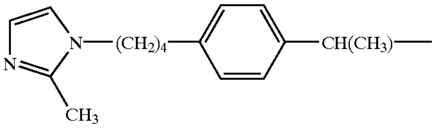 | -cyclo-$C_3H_5$ | $—PO_3H_2$ |
| 2491 | 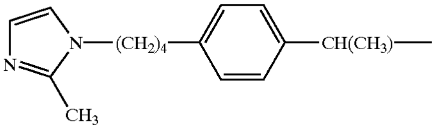 | -cyclo-$C_4H_7$ | $—PO_3H_2$ |
| 2492 | 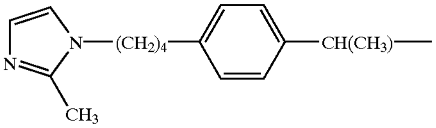 | -cyclo-$C_5H_9$ | $—PO_3H_2$ |
| 2493 | 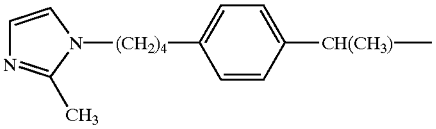 | -cyclo-$C_6H_{11}$ | $—PO_3H_2$ |
| 2494 | 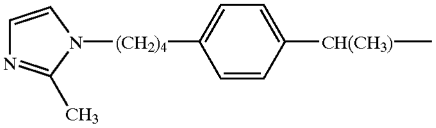 | -cyclo-$C_7H_{13}$ | $—PO_3H_2$ |
| 2495 | 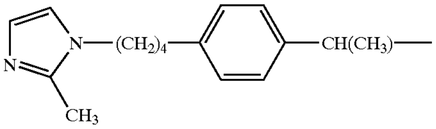 | -cyclo-$C_8H_{15}$ | $—PO_3H_2$ |

TABLE I-continued
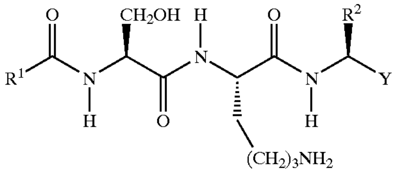
| Ex. No. | $R^1$ | $R^2$ | Y |
|---|---|---|---|
| 2496 | 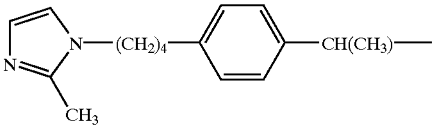 | $—CH(CH_3)(CH_2CH_3)$ | $—PO_3H_2$ |
| 2497 | 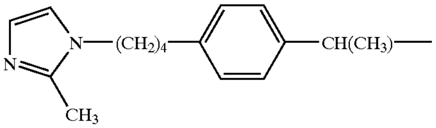 | $—CH(CH_2CH_3)_2$ | $—PO_3H_2$ |
| 2498 | 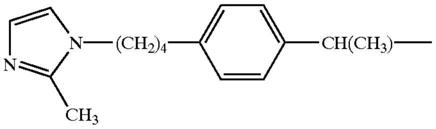 | $—CH(CH_3)(CH_2CH_2CH_3)$ | $—PO_3H_2$ |
| 2499 | 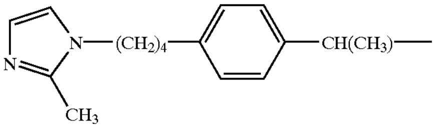 | $—C(CH_3)_3$ | $—PO_3H_2$ |
| 2500 | 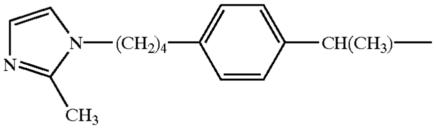 | $HC{\equiv}CCH_2—$ | $—PO_3H_2$ |
| 2501 | 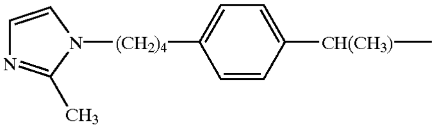 | $H_2C{=}CH—$ | $—PO_3H_2$ |
| 2502 | 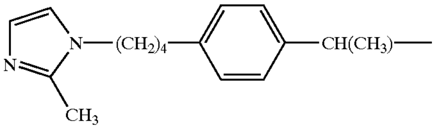 | $H_2C{=}CHCH_2—$ | $—PO_3H_2$ |
| 2503 | 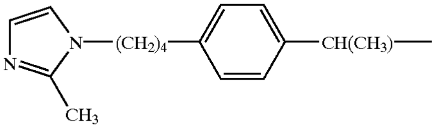 | $—CH_2F$ | $—PO_3H_2$ |
| 2504 | 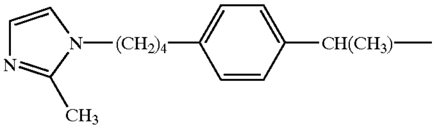 | $—CH_2C_6H_5$ | $—PO_3H_2$ |

TABLE I-continued
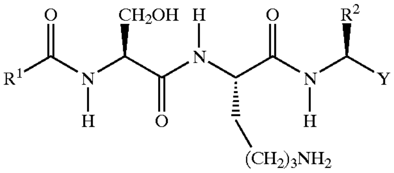
| Ex. No. | $R^1$ | $R^2$ | Y |
|---|---|---|---|
| 2505 | 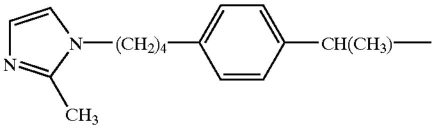 | $—CH_2C_6H_4$-p-$OCH_3$ | $—PO_3H_2$ |
| 2506 | 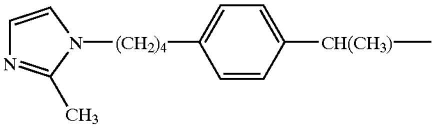 | $—CH_2C_6H_4$-p-$CH_3$ | $—PO_3H_2$ |
| 2507 | 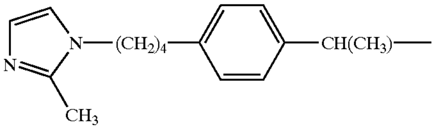 | $—CH_2C_6H_4$-p-F | $—PO_3H_2$ |
| 2508 | 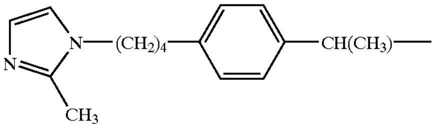 | $—CH_2CH_2C_6H_5$ | $—PO_3H_2$ |
| 2509 | 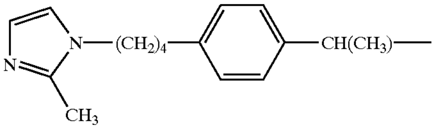 | $—CH_2$-cyclo-$C_6H_{11}$ | $—PO_3H_2$ |
| 2510 | 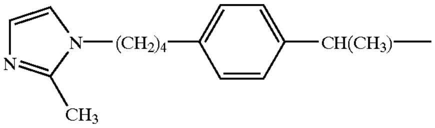 | $—CH_2$-cyclo-$C_6H_{10}$-4-F | $—PO_3H_2$ |
| 2511 | 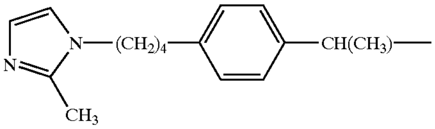 | $—CH_2$-cyclo-$C_6H_{10}$-4-$CH_3$ | $—PO_3H_2$ |
| 2512 | 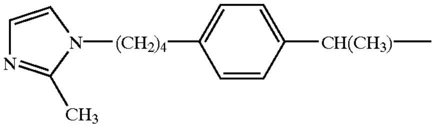 | $—CH_2$-cyclo-$C_6H_{10}$-4-$OCH_3$ | $—PO_3H_2$ |
| 2513 | 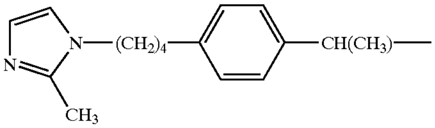 | $—CH_2CH_2$-cyclo-$C_6H_{11}$ | $—PO_3H_2$ |

TABLE I-continued
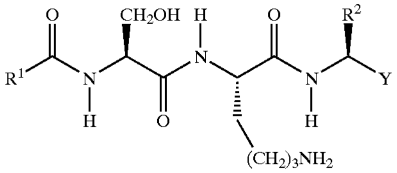
| Ex. No. | $R^1$ | $R^2$ | Y |
|---|---|---|---|
| 2514 | 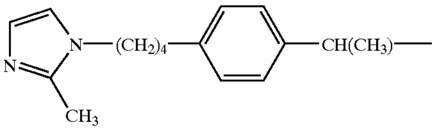 | $—CH_2$-cyclo-$C_5H_9$ | $—PO_3H_2$ |
| 2515 | 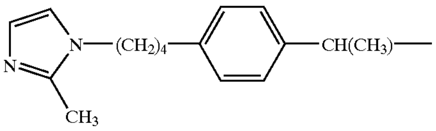 | $—CH_2CH_2$-cyclo-$C_5H_9$ | $—PO_3H_2$ |
| 2516 | 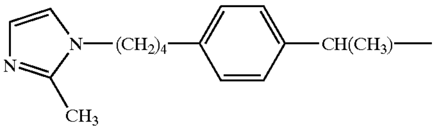 | $—CH_2$-2-naphthyl | $—PO_3H_2$ |
| 2517 | 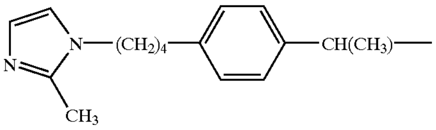 | —H | -5-Tet |
| 2518 | 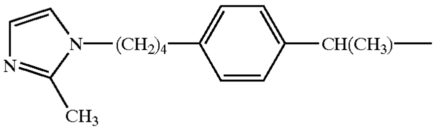 | $—CH_3$ | -5-Tet |
| 2519 | 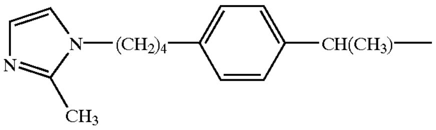 | $—CH_2CH_3$ | -5-Tet |
| 2520 | 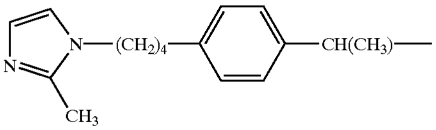 | $—CH_2CH_2CH_3$ | -5-Tet |
| 2521 | 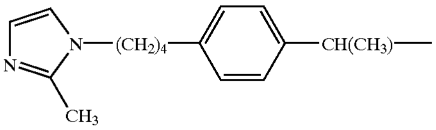 | $—CH_2CH_2CH_2CH_3$ | -5-Tet |
| 2522 | 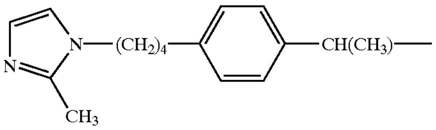 | $—CH_2CH_2CH_2CH_2CH_3$ | -5-Tet |

TABLE I-continued
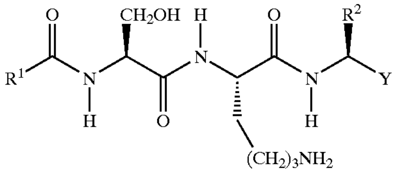
| Ex. No. | $R^1$ | $R^2$ | Y |
|---|---|---|---|
| 2523 | 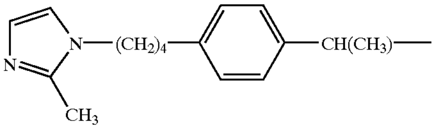 | $—CH_2CH_2CH_2CH_2CH_2CH_3$ | -5-Tet |
| 2524 | 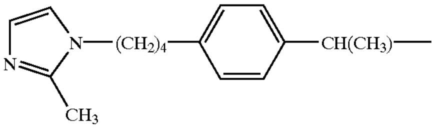 | $—CH(CH_3)_2$ | -5-Tet |
| 2525 | 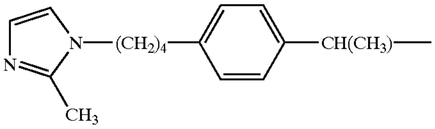 | $—CH_2CH(CH_3)_2$ | -5-Tet |
| 2526 | 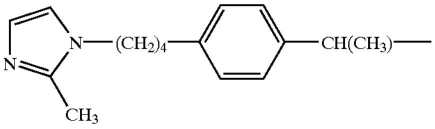 | $—CH_2CH_2CH(CH_3)_2$ | -5-Tet |
| 2527 | 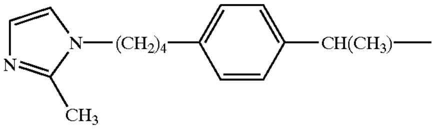 | -cyclo-$C_3H_5$ | -5-Tet |
| 2528 | 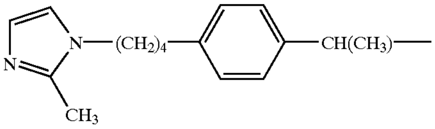 | -cyclo-$C_4H_7$ | -5-Tet |
| 2529 | 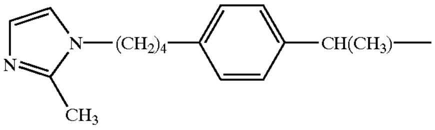 | -cyclo-$C_5H_9$ | -5-Tet |
| 2530 | 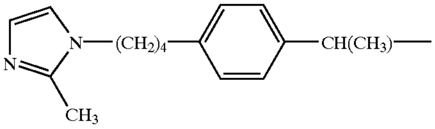 | -cyclo-$C_6H_{11}$ | -5-Tet |
| 2531 | 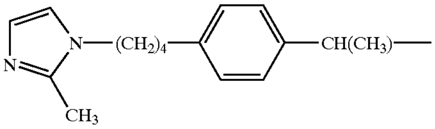 | -cyclo-$C_7H_{13}$ | -5-Tet |

TABLE I-continued
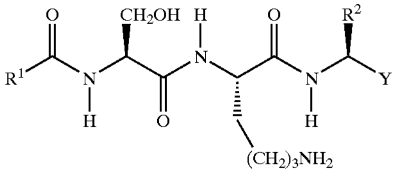
| Ex. No. | $R^1$ | $R^2$ | Y |
|---|---|---|---|
| 2532 | 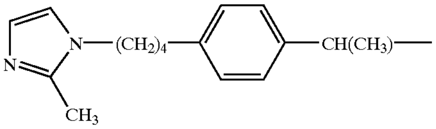 | -cyclo-$C_8H_{15}$ | -5-Tet |
| 2533 | 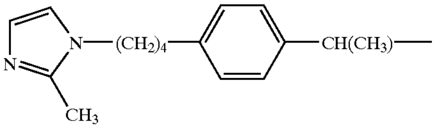 | $—CH(CH_3)(CH_2CH_3)$ | -5-Tet |
| 2534 | 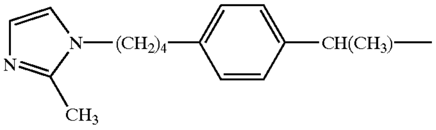 | $—CH(CH_2CH_3)_2$ | -5-Tet |
| 2535 | 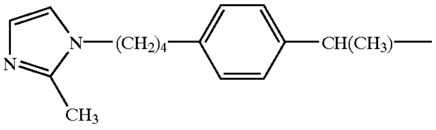 | $—CH(CH_3)(CH_2CH_2CH_3)$ | -5-Tet |
| 2536 | 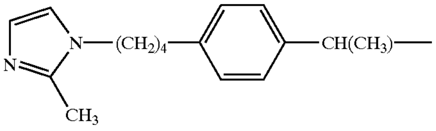 | $—C(CH_3)_3$ | -5-Tet |
| 2537 | 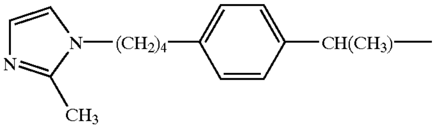 | $HC{\equiv}CCH_2—$ | -5-Tet |
| 2538 | 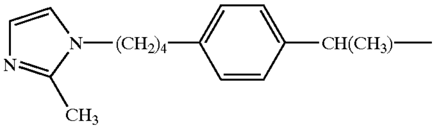 | $H_2C{=}CH—$ | -5-Tet |
| 2539 | 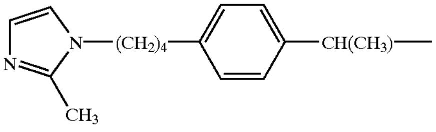 | $H_2C{=}CHCH_2—$ | -5-Tet |
| 2540 | 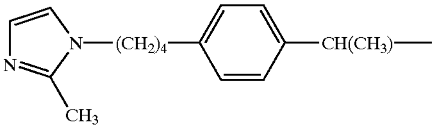 | $—CH_2F$ | -5-Tet |

TABLE I-continued
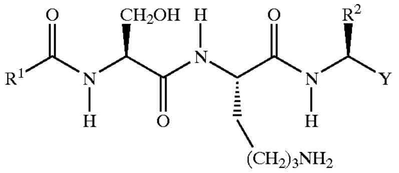
| Ex. No. | $R^1$ | $R^2$ | Y |
|---|---|---|---|
| 2541 | 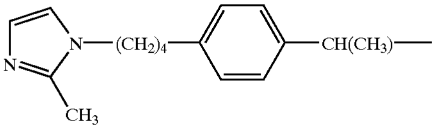 | $—CH_2C_6H_5$ | -5-Tet |
| 2542 | 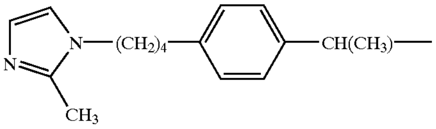 | $—CH_2C_6H_4$-p-$OCH_3$ | -5-Tet |
| 2543 | 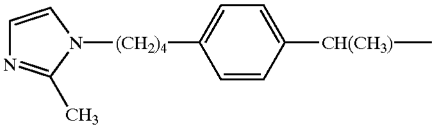 | $—CH_2C_6H_4$-p-$CH_3$ | -5-Tet |
| 2544 | 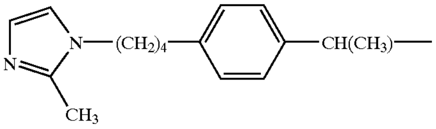 | $—CH_2C_6H_4$-p-F | -5-Tet |
| 2545 | 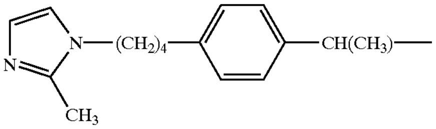 | $—CH_2CH_2C_6H_5$ | -5-Tet |
| 2546 | 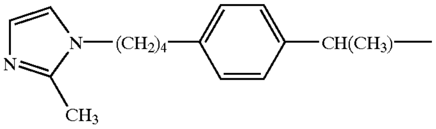 | $—CH_2$-cyclo-$C_6H_{11}$ | -5-Tet |
| 2547 | 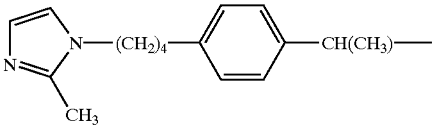 | $—CH_2$-cyclo-$C_6H_{10}$-4-F | -5-Tet |
| 2548 | 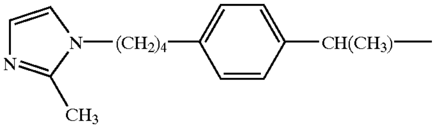 | $—CH_2$-cyclo-$C_6H_{10}$-4-$CH_3$ | -5-Tet |
| 2549 | 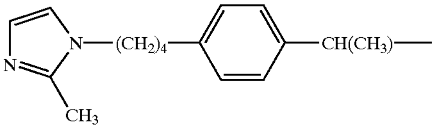 | $—CH_2$-cyclo-$C_6H_{10}$-4-$OCH_3$ | -5-Tet |

TABLE I-continued
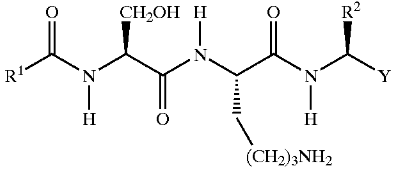
| Ex. No. | $R^1$ | $R^2$ | Y |
|---|---|---|---|
| 2550 | 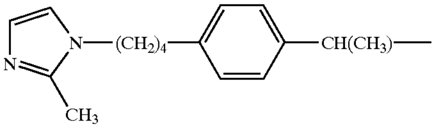 | $—CH_2CH_2$-cyclo-$C_6H_{11}$ | -5-Tet |
| 2551 | 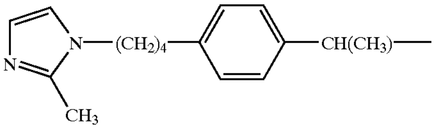 | $—CH_2$-cyclo-$C_5H_9$ | -5-Tet |
| 2552 | 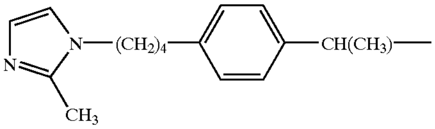 | $—CH_2CH_2$-cyclo-$C_5H_9$ | -5-Tet |
| 2553 | 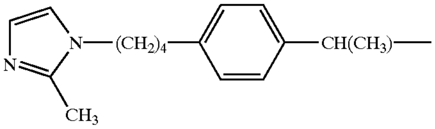 | $—CH_2$-2-naphthyl | -5-Tet |
| 2554 | 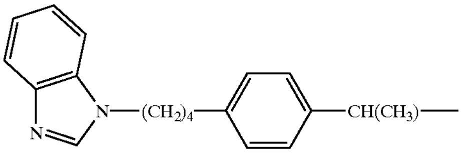 | —H | $—CO_2H$ |
| 2555 | 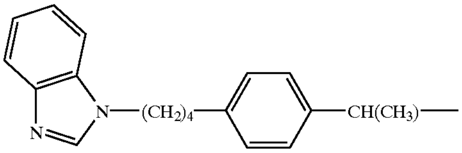 | $—CH_3$ | $—CO_2H$ |
| 2556 | 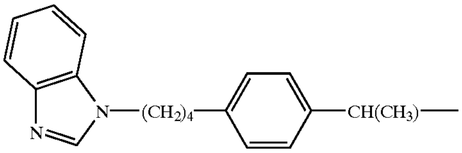 | $—CH_2CH_3$ | $—CO_2H$ |
| 2557 | 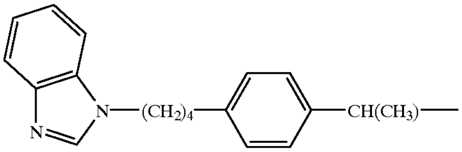 | $—CH_2CH_2CH_3$ | $—CO_2H$ |

TABLE I-continued
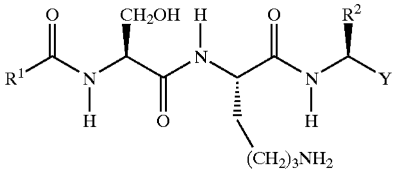
| Ex. No. | $R^1$ | $R^2$ | Y |
|---|---|---|---|
| 2558 | 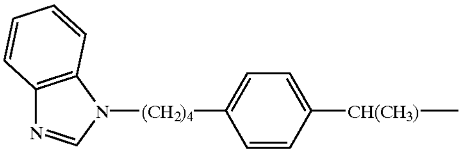 | $—CH_2CH_2CH_2CH_3$ | $—CO_2H$ |
| 2559 | 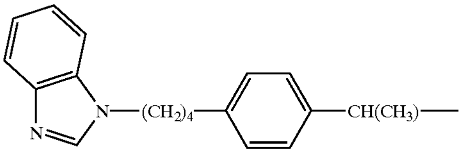 | $—CH_2CH_2CH_2CH_2CH_3$ | $—CO_2H$ |
| 2560 | 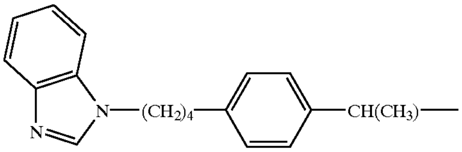 | $—CH_2CH_2CH_2CH_2CH_2CH_3$ | $—CO_2H$ |
| 2561 | 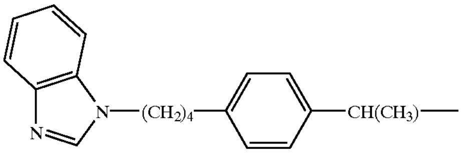 | $—CH(CH_3)_2$ | $—CO_2H$ |
| 2562 | 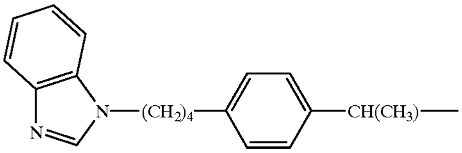 | $—CH_2CH(CH_3)_2$ | $—CO_2H$ |
| 2563 | 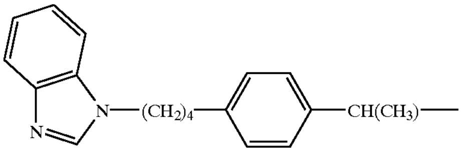 | $—CH_2CH_2CH(CH_3)_2$ | $—CO_2H$ |
| 2564 | 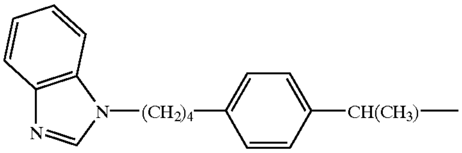 | -cyclo-$C_3H_5$ | $—CO_2H$ |
| 2565 | 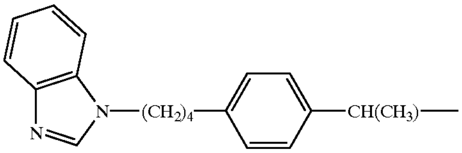 | -cyclo-$C_4H_7$ | $—CO_2H$ |

TABLE I-continued
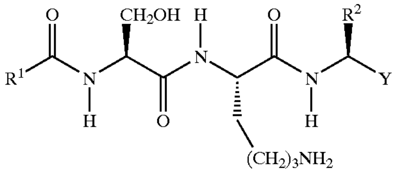
| Ex. No. | $R^1$ | $R^2$ | Y |
|---|---|---|---|
| 2566 | 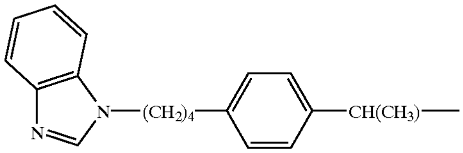 | -cyclo-$C_5H_9$ | —$CO_2H$ |
| 2567 | 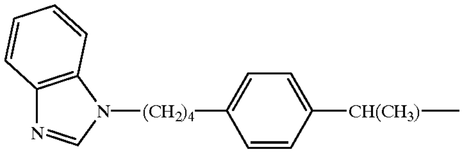 | -cyclo-$C_6H_{11}$ | —$CO_2H$ |
| 2568 | 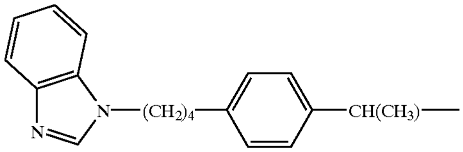 | -cyclo-$C_7H_{13}$ | —$CO_2H$ |
| 2569 | 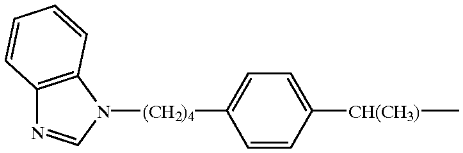 | -cyclo-$C_8H_{15}$ | —$CO_2H$ |
| 2570 | 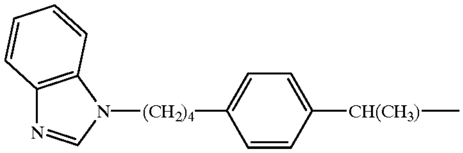 | —$CH(CH_3)(CH_2CH_3)$ | —$CO_2H$ |
| 2571 | 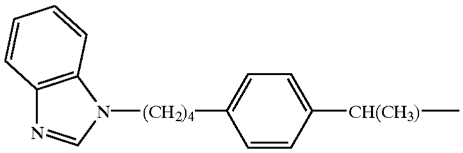 | —$CH(CH_2CH_3)_2$ | —$CO_2H$ |
| 2572 | 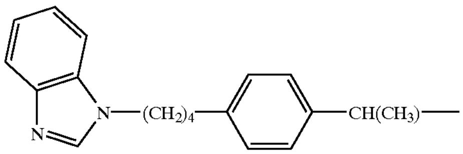 | —$CH(CH_3)(CH_2CH_2CH_3)$ | —$CO_2H$ |
| 2573 | 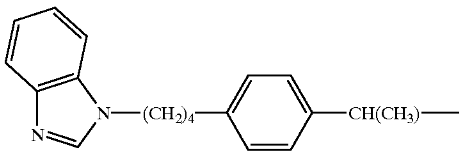 | —$C(CH_3)_3$ | —$CO_2H$ |

TABLE I-continued
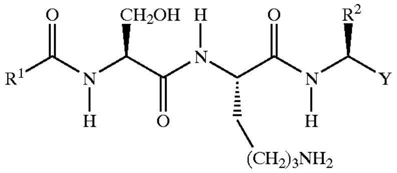
| Ex. No. | $R^1$ | $R^2$ | Y |
|---|---|---|---|
| 2574 | 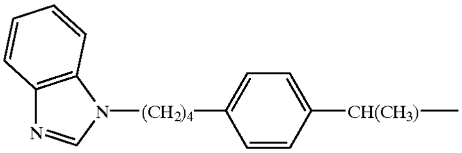 | HC≡CCH$_2$— | —CO$_2$H |
| 2575 | 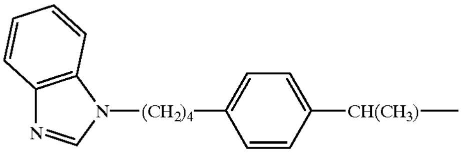 | H$_2$C═CH— | —CO$_2$H |
| 2576 | 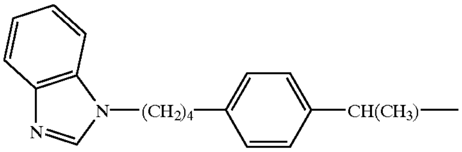 | H$_2$C═CHCH$_2$— | —CO$_2$H |
| 2577 | 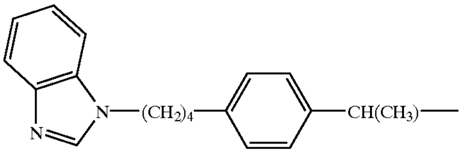 | —CH$_2$F | —CO$_2$H |
| 2578 | 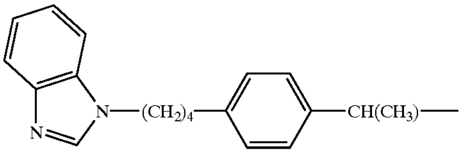 | —CH$_2$C$_6$H$_5$ | —CO$_2$H |
| 2579 | 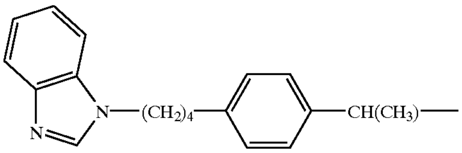 | —CH$_2$C$_6$H$_4$-p-OCH$_3$ | —CO$_2$H |
| 2580 | 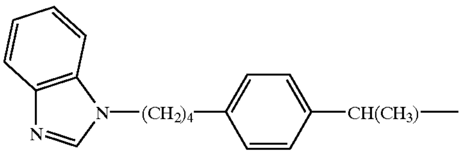 | —CH$_2$C$_6$H$_4$-p-CH$_3$ | —CO$_2$H |
| 2581 | 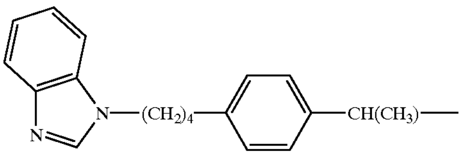 | —CH$_2$C$_6$H$_4$-p-F | —CO$_2$H |

TABLE I-continued
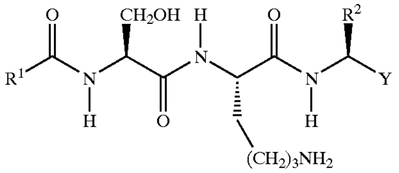
| Ex. No. | R¹ | R² | Y |
|---|---|---|---|
| 2582 | 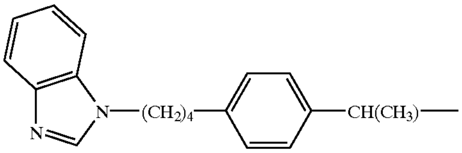 | —$CH_2CH_2C_6H_5$ | —$CO_2H$ |
| 2583 | 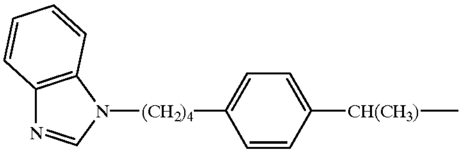 | —$CH_2$-cyclo-$C_6H_{11}$ | —$CO_2H$ |
| 2584 | 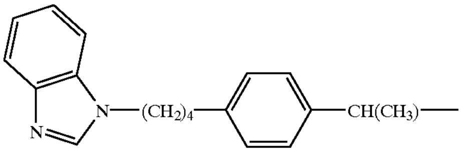 | —$CH_2$-cyclo-$C_6H_{10}$-4-F | —$CO_2H$ |
| 2585 | 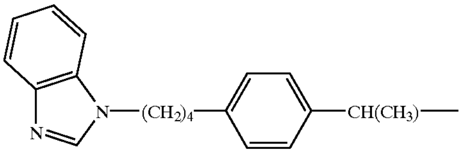 | —$CH_2$-cyclo-$C_6H_{10}$-4-$CH_3$ | —$CO_2H$ |
| 2586 | 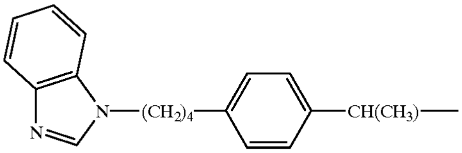 | —$CH_2$-cyclo-$C_6H_{10}$-4-$OCH_3$ | —$CO_2H$ |
| 2587 | 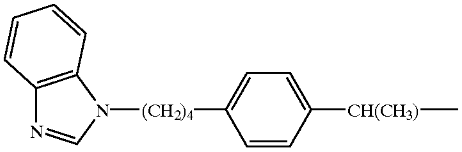 | —$CH_2CH_2$-cyclo-$C_6H_{11}$ | —$CO_2H$ |
| 2588 | 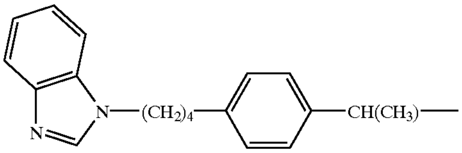 | —$CH_2$-cyclo-$C_5H_9$ | —$CO_2H$ |
| 2589 | 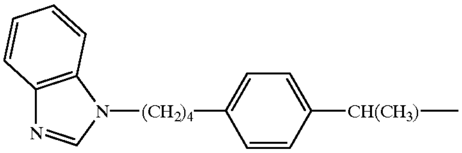 | —$CH_2CH_2$-cyclo-$C_5H_9$ | —$CO_2H$ |

TABLE I-continued
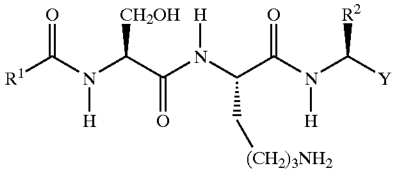
| Ex. No. | $R^1$ | $R^2$ | Y |
|---|---|---|---|
| 2590 | 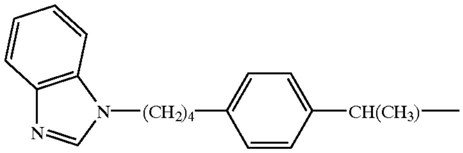 | $—CH_2$-2-naphthyl | $—CO_2H$ |
| 2591 | 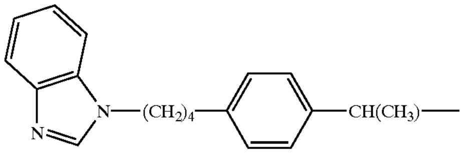 | —H | $—PO_3H_2$ |
| 2592 | 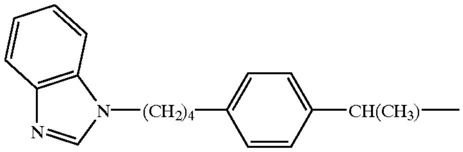 | $—CH_3$ | $—PO_3H_2$ |
| 2593 | 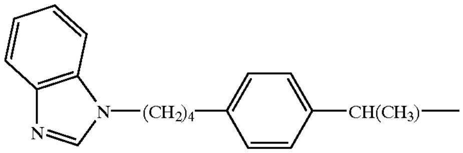 | $—CH_2CH_3$ | $—PO_3H_2$ |
| 2594 | 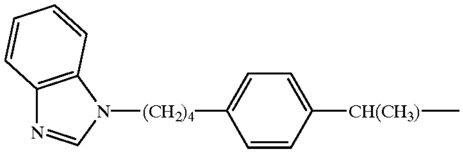 | $—CH_2CH_2CH_3$ | $—PO_3H_2$ |
| 2595 | 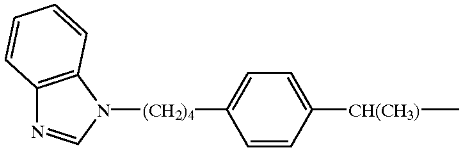 | $—CH_2CH_2CH_2CH_3$ | $—PO_3H_2$ |
| 2596 | 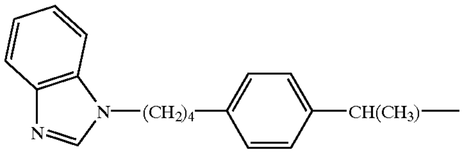 | $—CH_2CH_2CH_2CH_2CH_3$ | $—PO_3H_2$ |
| 2597 | 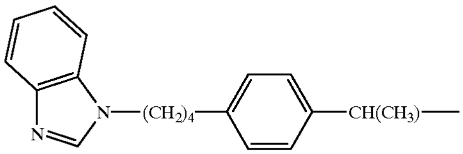 | $—CH_2CH_2CH_2CH_2CH_2CH_3$ | $—PO_3H_2$ |

TABLE I-continued
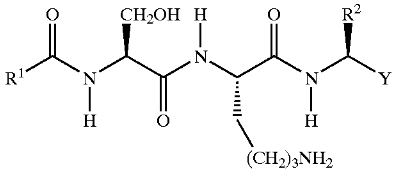
| Ex. No. | $R^1$ | $R^2$ | Y |
|---|---|---|---|
| 2598 | 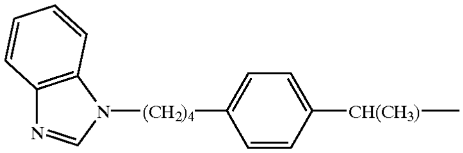 | $—CH(CH_3)_2$ | $—PO_3H_2$ |
| 2599 | 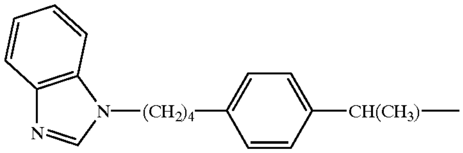 | $—CH_2CH(CH_3)_2$ | $—PO_3H_2$ |
| 2600 | 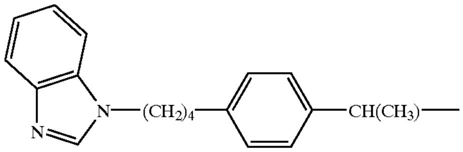 | $—CH_2CH_2CH(CH_3)_2$ | $—PO_3H_2$ |
| 2601 | 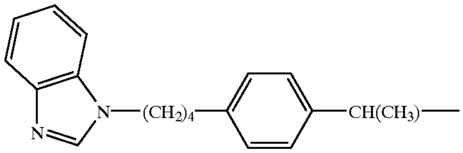 | -cyclo-$C_3H_5$ | $—PO_3H_2$ |
| 2602 | 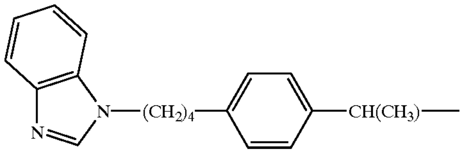 | -cyclo-$C_4H_7$ | $—PO_3H_2$ |
| 2603 | 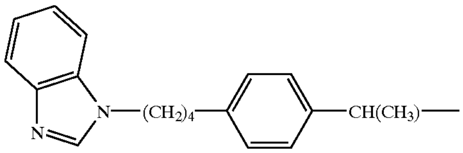 | -cyclo-$C_5H_9$ | $—PO_3H_2$ |
| 2604 | 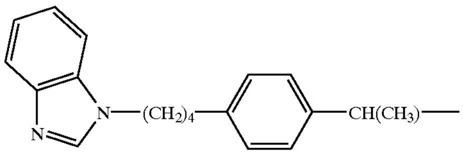 | -cyclo-$C_6H_{11}$ | $—PO_3H_2$ |
| 2605 | 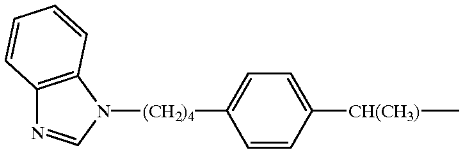 | -cyclo-$C_7H_{13}$ | $—PO_3H_2$ |

TABLE I-continued
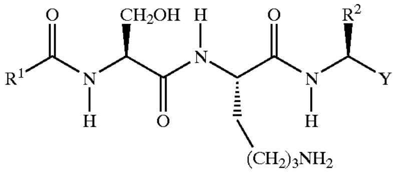
| Ex. No. | $R^1$ | $R^2$ | Y |
| --- | --- | --- | --- |
| 2606 | 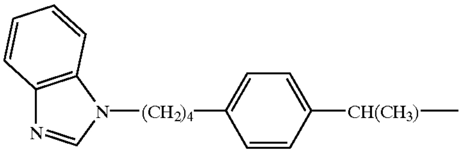 | -cyclo-$C_8H_{15}$ | $—PO_3H_2$ |
| 2607 | 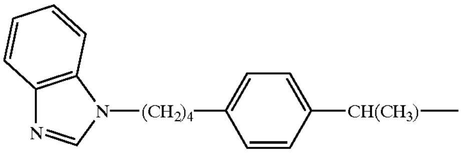 | $—CH(CH_3)(CH_2CH_3)$ | $—PO_3H_2$ |
| 2608 | 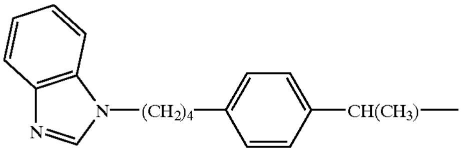 | $—CH(CH_2CH_3)_2$ | $—PO_3H_2$ |
| 2609 | 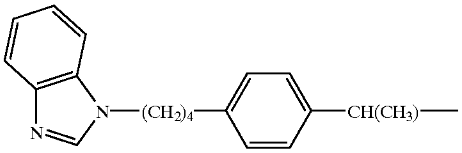 | $—CH(CH_3)(CH_2CH_2CH_3)$ | $—PO_3H_2$ |
| 2610 | 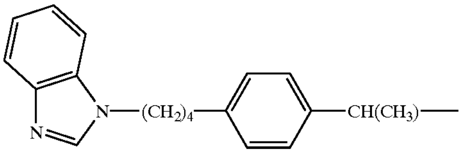 | $—C(CH_3)_3$ | $—PO_3H_2$ |
| 2611 | 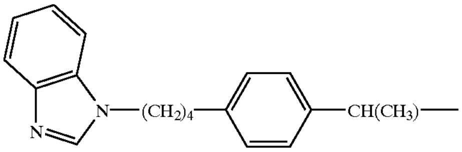 | $HC{\equiv}CCH_2—$ | $—PO_3H_2$ |
| 2612 | 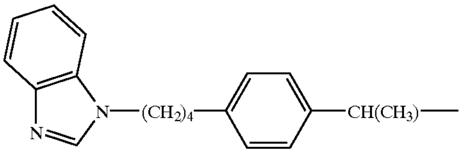 | $H_2C{=}CH—$ | $—PO_3H_2$ |
| 2613 | 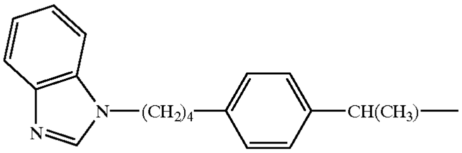 | $H_2C{=}CHCH_2—$ | $—PO_3H_2$ |

TABLE I-continued
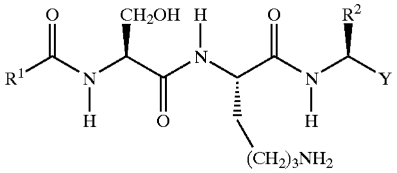
| Ex. No. | $R^1$ | $R^2$ | Y |
|---|---|---|---|
| 2614 | 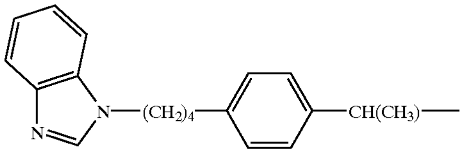 | $—CH_2F$ | $—PO_3H_2$ |
| 2615 | 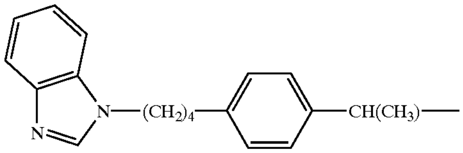 | $—CH_2C_6H_5$ | $—PO_3H_2$ |
| 2616 | 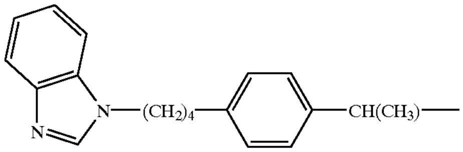 | $—CH_2C_6H_4$-p-$OCH_3$ | $—PO_3H_2$ |
| 2617 | 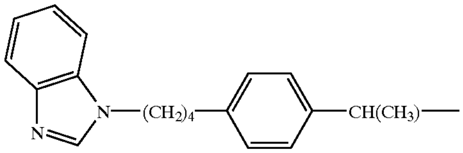 | $—CH_2C_6H_4$-p-$CH_3$ | $—PO_3H_2$ |
| 2618 | 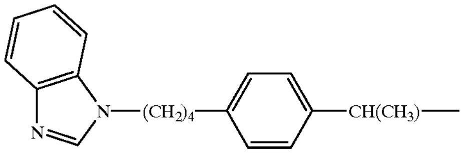 | $—CH_2C_6H_4$-p-F | $—PO_3H_2$ |
| 2619 | 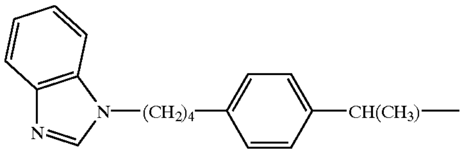 | $—CH_2CH_2C_6H_5$ | $—PO_3H_2$ |
| 2620 | 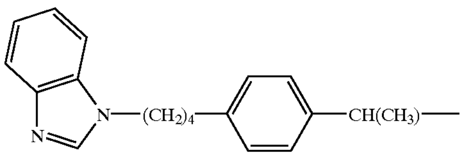 | $—CH_2$-cyclo-$C_6H_{11}$ | $—PO_3H_2$ |
| 2621 | 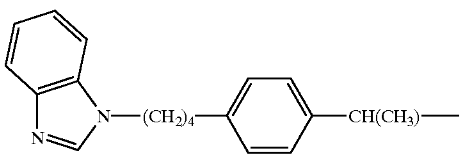 | $—CH_2$-cyclo-$C_6H_{10}$-4-F | $—PO_3H_2$ |

TABLE I-continued
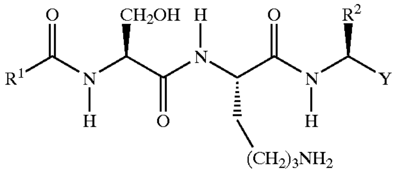
| Ex. No. | $R^1$ | $R^2$ | Y |
|---|---|---|---|
| 2622 | 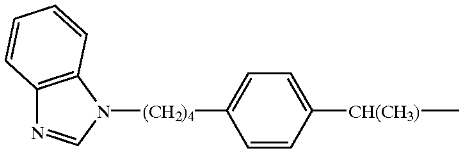 | $—CH_2$-cyclo-$C_6H_{10}$-4-$CH_3$ | $—PO_3H_2$ |
| 2623 | 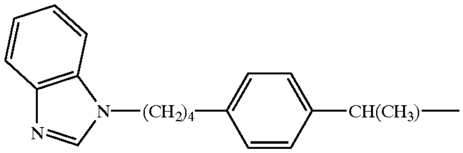 | $—CH_2$-cyclo-$C_6H_{10}$-4-$OCH_3$ | $—PO_3H_2$ |
| 2624 | 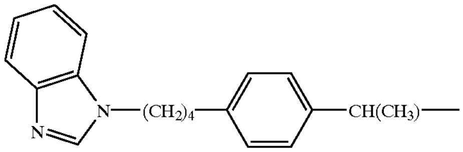 | $—CH_2CH_2$-cyclo-$C_6H_{11}$ | $—PO_3H_2$ |
| 2625 | 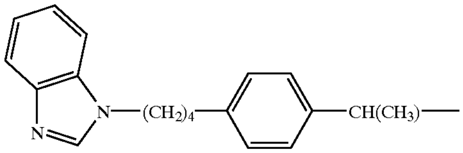 | $—CH_2$-cyclo-$C_5H_9$ | $—PO_3H_2$ |
| 2626 | 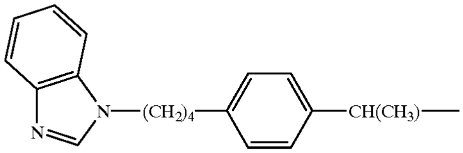 | $—CH_2CH_2$-cyclo-$C_5H_9$ | $—PO_3H_2$ |
| 2627 | 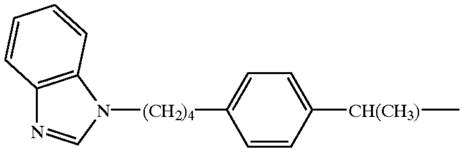 | $—CH_2$-2-naphthyl | $—PO_3H_2$ |
| 2628 | 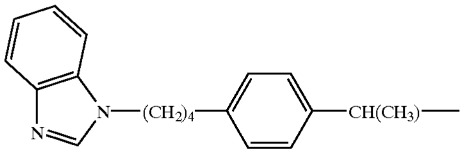 | —H | -5-Tet |
| 2629 | 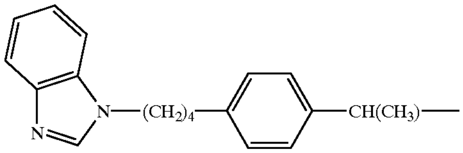 | $—CH_3$ | -5-Tet |

TABLE I-continued
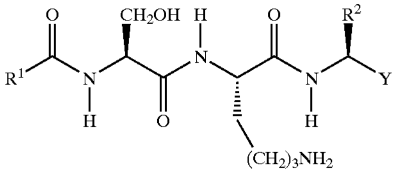
| Ex. No. | $R^1$ | $R^2$ | Y |
|---|---|---|---|
| 2630 | 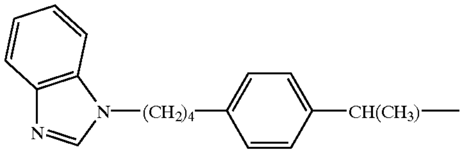 | $—CH_2CH_3$ | -5-Tet |
| 2631 | 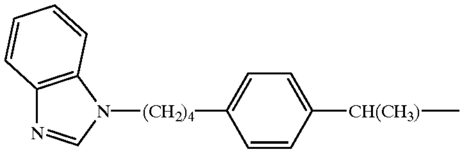 | $—CH_2CH_2CH_3$ | -5-Tet |
| 2632 | 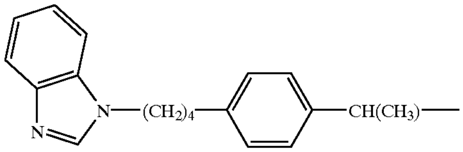 | $—CH_2CH_2CH_2CH_3$ | -5-Tet |
| 2633 | 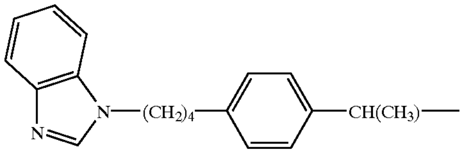 | $—CH_2CH_2CH_2CH_2CH_3$ | -5-Tet |
| 2634 | 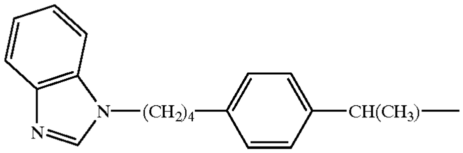 | $—CH_2CH_2CH_2CH_2CH_2CH_3$ | -5-Tet |
| 2635 | 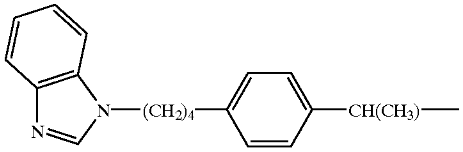 | $—CH(CH_3)_2$ | -5-Tet |
| 2636 | 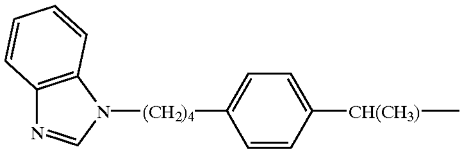 | $—CH_2CH(CH_3)_2$ | -5-Tet |
| 2637 | 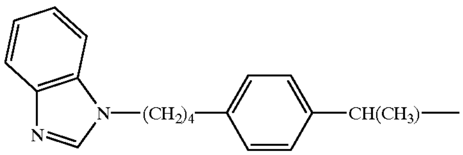 | $—CH_2CH_2CH(CH_3)_2$ | -5-Tet |

TABLE I-continued
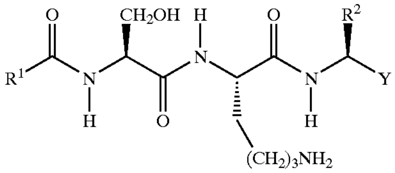
| Ex. No. | $R^1$ | $R^2$ | Y |
|---|---|---|---|
| 2638 | 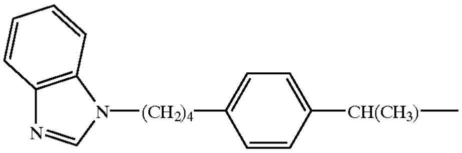 | -cyclo-$C_3H_5$ | -5-Tet |
| 2639 | 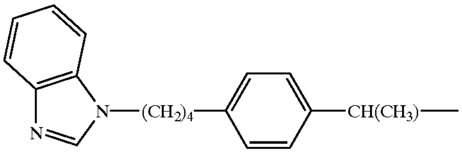 | -cyclo-$C_4H_7$ | -5-Tet |
| 2640 | 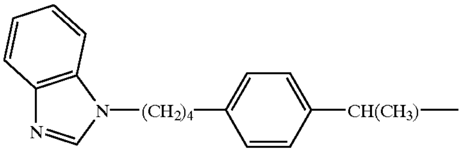 | -cyclo-$C_5H_9$ | -5-Tet |
| 2641 | 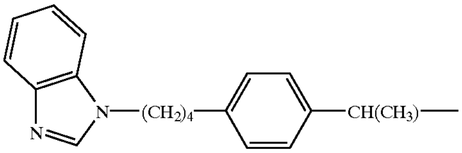 | -cyclo-$C_6H_{11}$ | -5-Tet |
| 2642 | 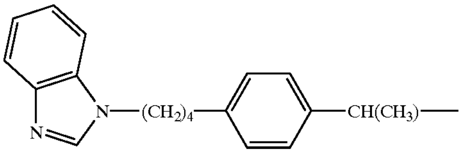 | -cyclo-$C_7H_{13}$ | -5-Tet |
| 2643 | 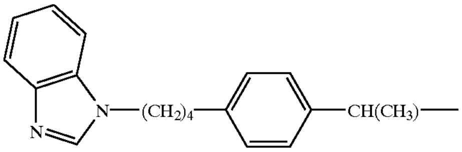 | -cyclo-$C_8H_{15}$ | -5-Tet |
| 2644 | 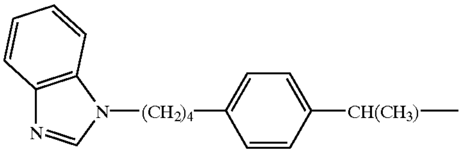 | $—CH(CH_3)(CH_2CH_3)$ | -5-Tet |
| 2645 | 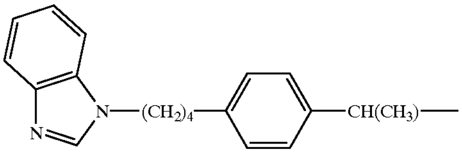 | $—CH(CH_2CH_3)_2$ | -5-Tet |

TABLE I-continued
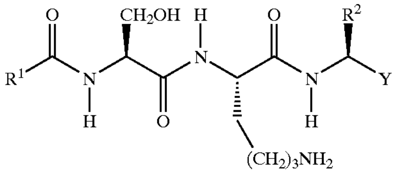
| Ex. No. | R[1] | R[2] | Y |
|---|---|---|---|
| 2646 | 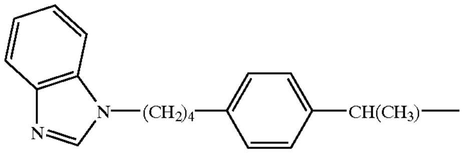 | $—CH(CH_3)(CH_2CH_2CH_3)$ | -5-Tet |
| 2647 | 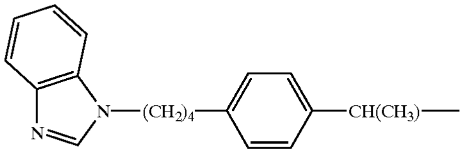 | $—C(CH_3)_3$ | -5-Tet |
| 2648 | 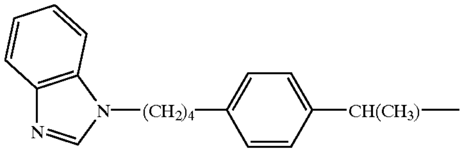 | $HC\equiv CCH_2—$ | -5-Tet |
| 2649 | 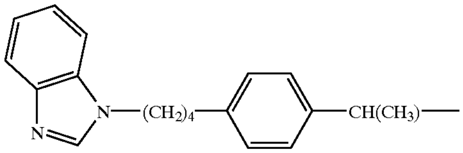 | $H_2C=CH—$ | -5-Tet |
| 2650 | 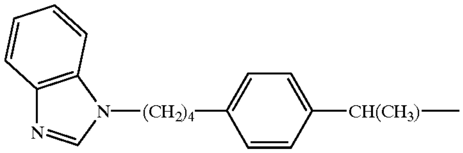 | $H_2C=CHCH_2—$ | -5-Tet |
| 2651 | 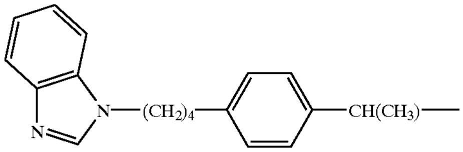 | $—CH_2F$ | -5-Tet |
| 2652 | 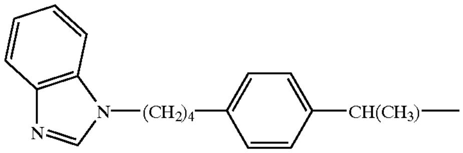 | $—CH_2C_6H_5$ | -5-Tet |
| 2653 | 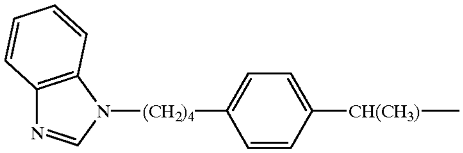 | $—CH_2C_6H_4$-p-$OCH_3$ | -5-Tet |

TABLE I-continued
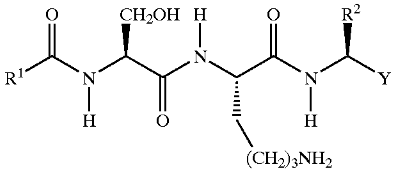
| Ex. No. | $R^1$ | $R^2$ | Y |
|---|---|---|---|
| 2654 | 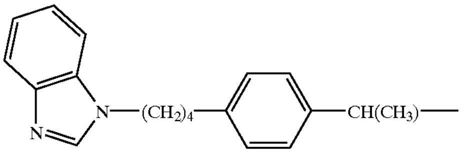 | $—CH_2C_6H_4$-p-$CH_3$ | -5-Tet |
| 2655 | 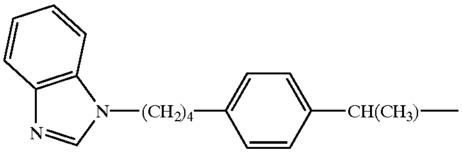 | $—CH_2C_6H_4$-p-F | -5-Tet |
| 2656 | 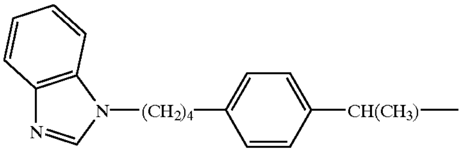 | $—CH_2CH_2C_6H_5$ | -5-Tet |
| 2657 | 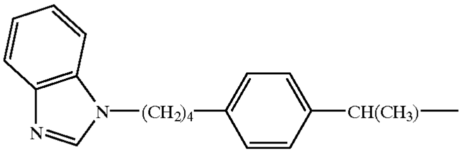 | $—CH_2$-cyclo-$C_6H_{11}$ | -5-Tet |
| 2658 | 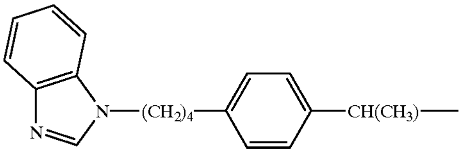 | $—CH_2$-cyclo-$C_6H_{10}$-4-F | -5-Tet |
| 2659 | 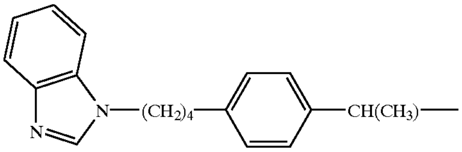 | $—CH_2$-cyclo-$C_6H_{10}$-4-$CH_3$ | -5-Tet |
| 2660 | 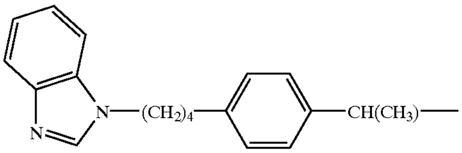 | $—CH_2$-cyclo-$C_6H_{10}$-4-$OCH_3$ | -5-Tet |
| 2661 | 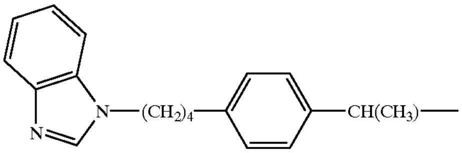 | $—CH_2CH_2$-cyclo-$C_6H_{11}$ | -5-Tet |

TABLE I-continued
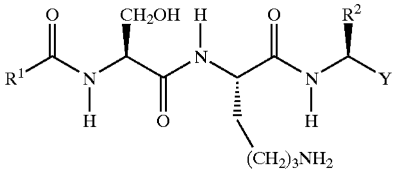
| Ex. No. | $R^1$ | $R^2$ | Y |
|---|---|---|---|
| 2662 | 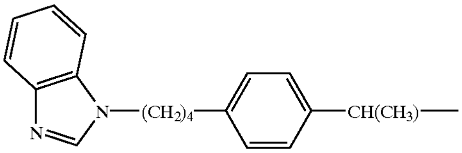 | $—CH_2$-cyclo-$C_5H_9$ | -5-Tet |
| 2663 | 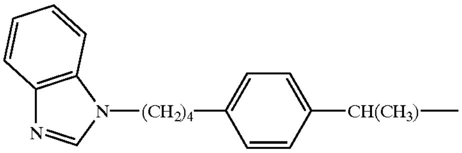 | $—CH_2CH_2$-cyclo-$C_5H_9$ | -5-Tet |
| 2664 | 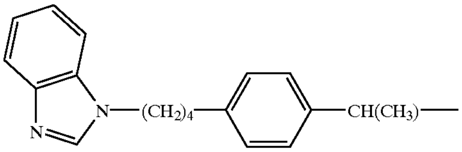 | $—CH_2$-2-naphthyl | -5-Tet |
| 2665 | 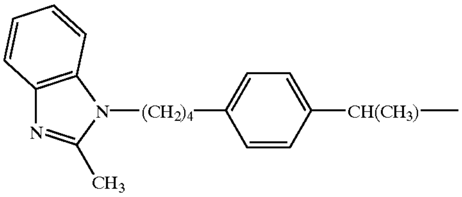 | —H | $—CO_2H$ |
| 2666 | 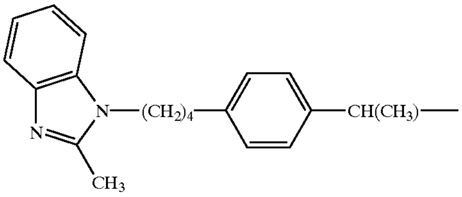 | $—CH_3$ | $—CO_2H$ |
| 2667 | 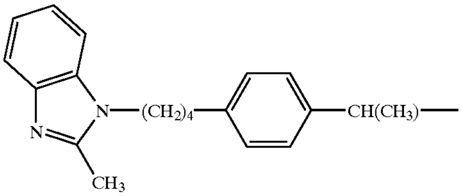 | $—CH_2CH_3$ | $—CO_2H$ |
| 2668 | 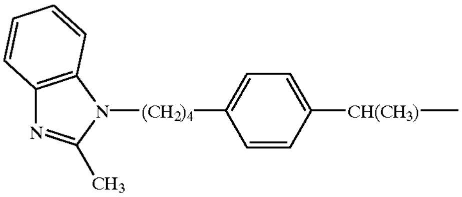 | $—CH_2CH_2CH_3$ | $—CO_2H$ |

TABLE I-continued
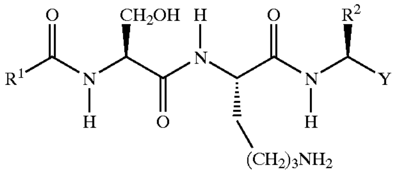
| Ex. No. | $R^1$ | $R^2$ | Y |
|---|---|---|---|
| 2669 | 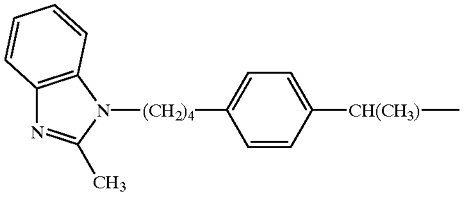 | $—CH_2CH_2CH_2CH_3$ | $—CO_2H$ |
| 2670 | 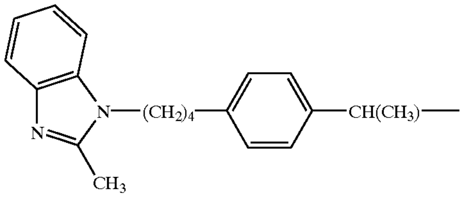 | $—CH_2CH_2CH_2CH_2CH_3$ | $—CO_2H$ |
| 2671 | 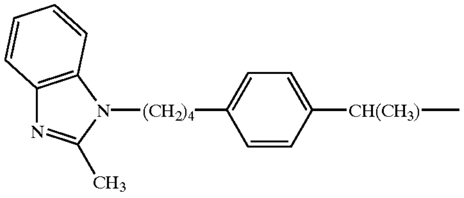 | $—CH_2CH_2CH_2CH_2CH_2CH_3$ | $—CO_2H$ |
| 2672 | 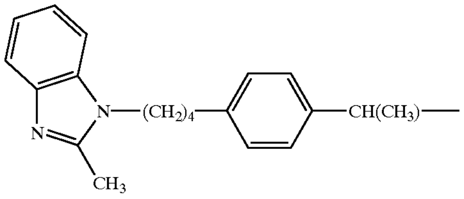 | $—CH(CH_3)_2$ | $—CO_2H$ |
| 2673 | 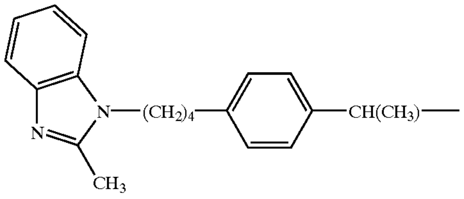 | $—CH_2CH(CH_3)_2$ | $—CO_2H$ |
| 2674 | 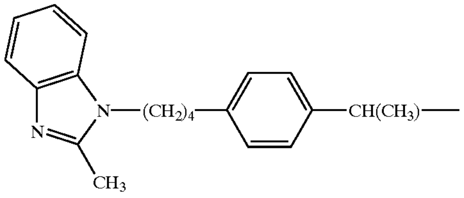 | $—CH_2CH_2CH(CH_3)_2$ | $—CO_2H$ |

TABLE I-continued
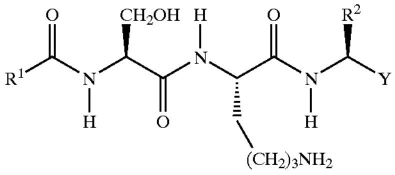
| Ex. No. | $R^1$ | $R^2$ | Y |
|---|---|---|---|
| 2675 | 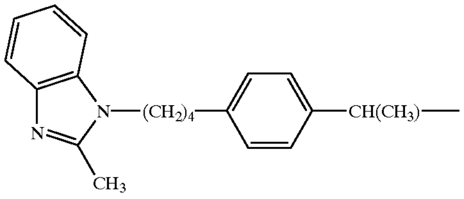 | -cyclo-$C_3H_5$ | —$CO_2H$ |
| 2676 | 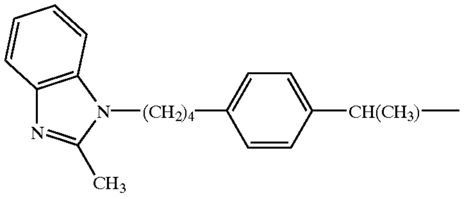 | -cyclo-$C_4H_7$ | —$CO_2H$ |
| 2677 | 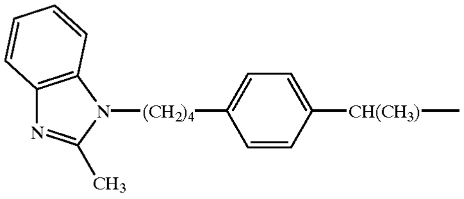 | -cyclo-$C_5H_9$ | —$CO_2H$ |
| 2678 | 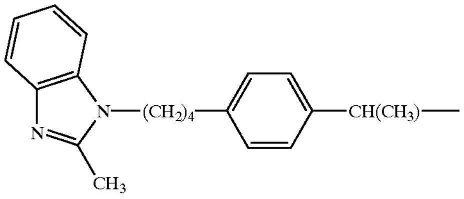 | -cyclo-$C_6H_{11}$ | —$CO_2H$ |
| 2679 | 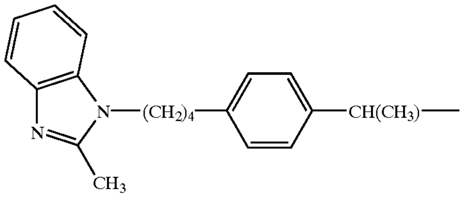 | -cyclo-$C_7H_{13}$ | —$CO_2H$ |
| 2680 | 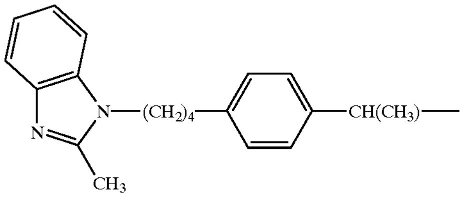 | -cyclo-$C_8H_{15}$ | —$CO_2H$ |

TABLE I-continued
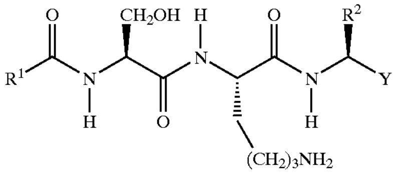
| Ex. No. | $R^1$ | $R^2$ | Y |
|---|---|---|---|
| 2681 | 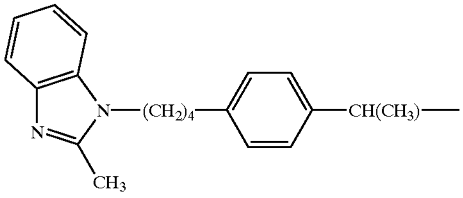 | $—CH(CH_3)(CH_2CH_3)$ | $—CO_2H$ |
| 2682 | 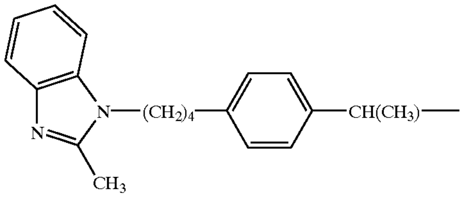 | $—CH(CH_2CH_3)_2$ | $—CO_2H$ |
| 2683 | 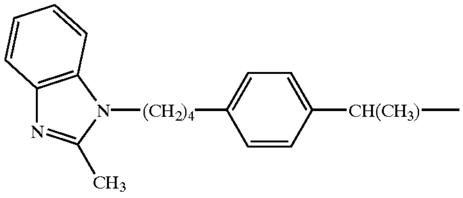 | $—CH(CH_3)(CH_2CH_2CH_3)$ | $—CO_2H$ |
| 2684 | 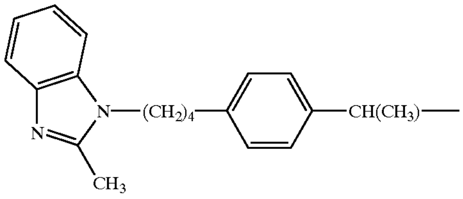 | $—C(CH_3)_3$ | $—CO_2H$ |
| 2685 | 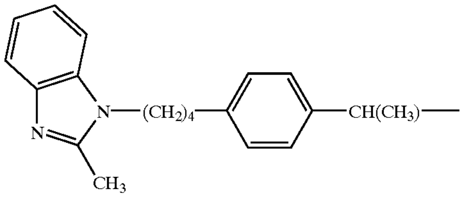 | $HC{\equiv}CCH_2—$ | $—CO_2H$ |
| 2686 | 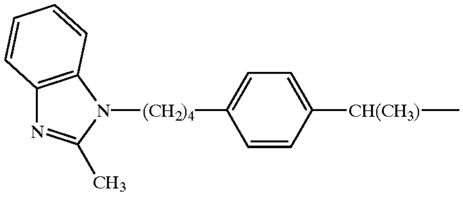 | $H_2C{=}CH—$ | $—CO_2H$ |

TABLE I-continued
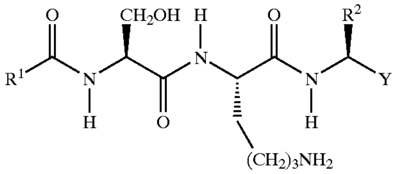
| Ex. No. | $R^1$ | $R^2$ | Y |
| --- | --- | --- | --- |
| 2687 | 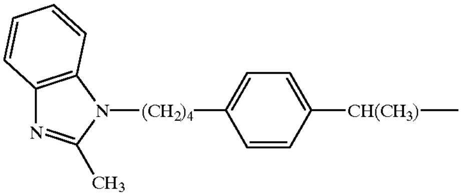 | $H_2C{=}CHCH_2$— | —$CO_2H$ |
| 2688 | 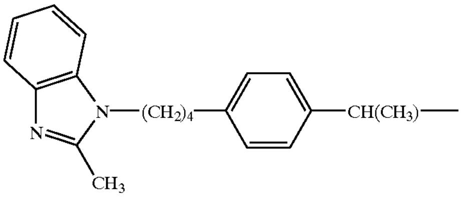 | —$CH_2F$ | —$CO_2H$ |
| 2689 | 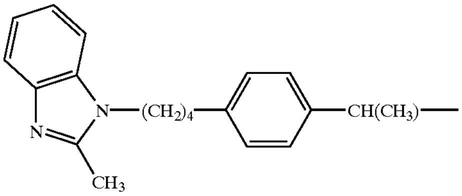 | —$CH_2C_6H_5$ | —$CO_2H$ |
| 2690 | 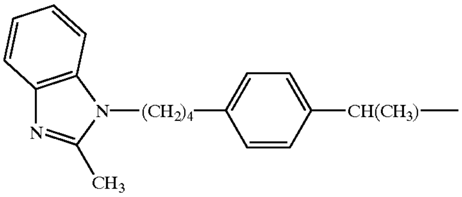 | —$CH_2C_6H_4$-p-$OCH_3$ | —$CO_2H$ |
| 2691 | 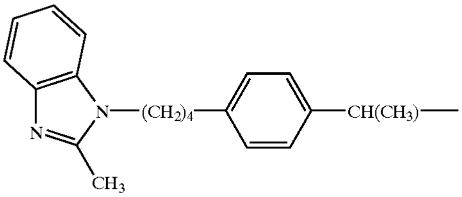 | —$CH_2C_6H_4$-p-$CH_3$ | —$CO_2H$ |
| 2692 | 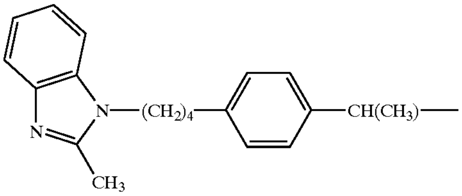 | —$CH_2C_6H_4$-p-F | —$CO_2H$ |

TABLE I-continued
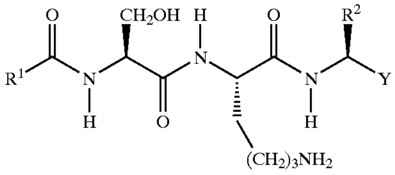
| Ex. No. | $R^1$ | $R^2$ | Y |
|---|---|---|---|
| 2693 | 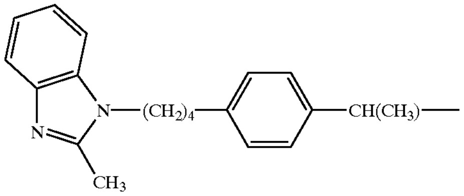 | $-CH_2CH_2C_6H_5$ | $-CO_2H$ |
| 2694 | 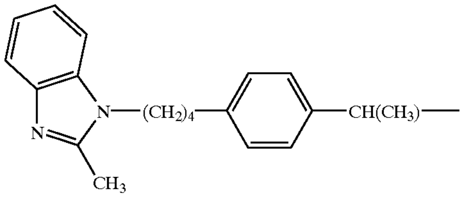 | $-CH_2$-cyclo-$C_6H_{11}$ | $-CO_2H$ |
| 2695 | 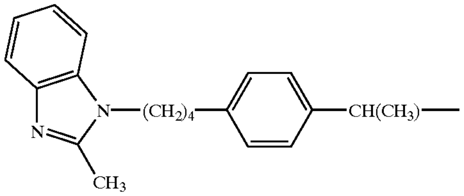 | $-CH_2$-cyclo-$C_6H_{10}$-4-F | $-CO_2H$ |
| 2696 | 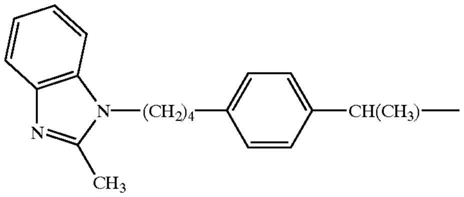 | $-CH_2$-cyclo-$C_6H_{10}$-4-$CH_3$ | $-CO_2H$ |
| 2697 | 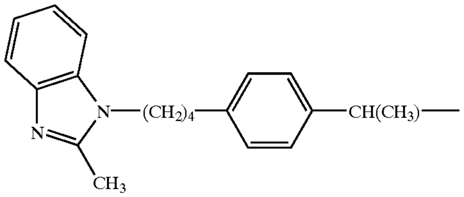 | $-CH_2$-cyclo-$C_6H_{10}$-4-$OCH_3$ | $-CO_2H$ |
| 2698 | 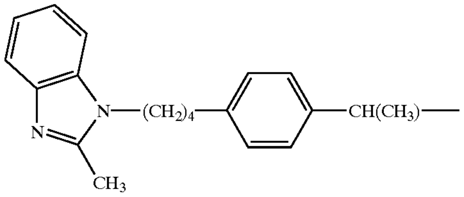 | $-CH_2CH_2$-cyclo-$C_6H_{11}$ | $-CO_2H$ |

TABLE I-continued
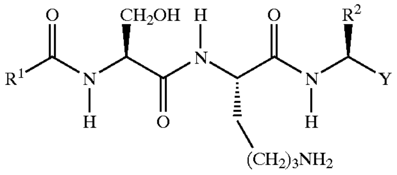
| Ex. No. | $R^1$ | $R^2$ | Y |
|---|---|---|---|
| 2699 | 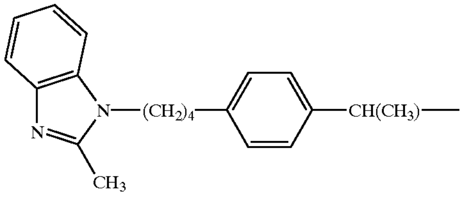 | $-CH_2$-cyclo-$C_5H_9$ | $-CO_2H$ |
| 2700 | 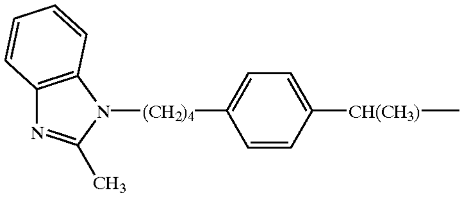 | $-CH_2CH_2$-cyclo-$C_5H_9$ | $-CO_2H$ |
| 2701 | 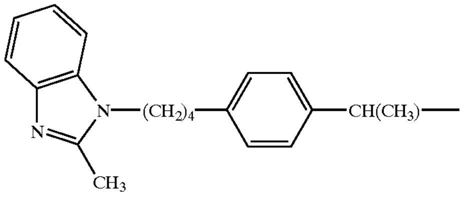 | $-CH_2$-2-naphthyl | $-CO_2H$ |
| 2702 | 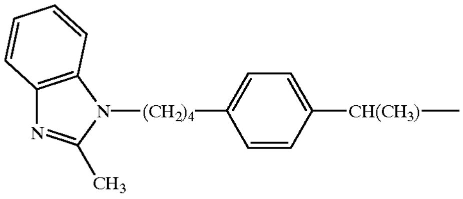 | —H | $-PO_3H_2$ |
| 2703 | 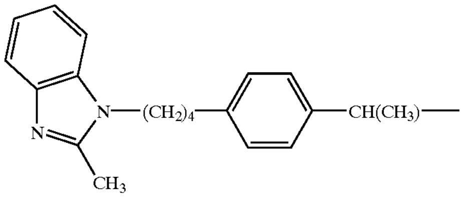 | $-CH_3$ | $-PO_3H_2$ |
| 2704 | 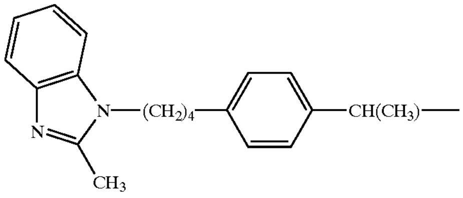 | $-CH_2CH_3$ | $-PO_3H_2$ |

TABLE I-continued
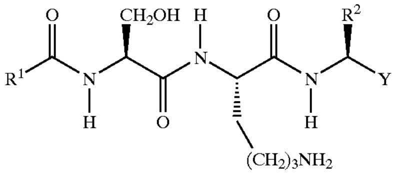
| Ex. No. | $R^1$ | $R^2$ | Y |
|---|---|---|---|
| 2705 | 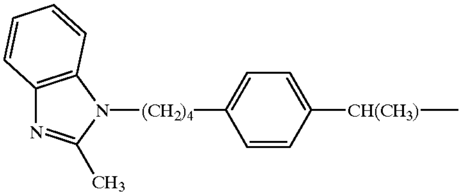 | $—CH_2CH_2CH_3$ | $—PO_3H_2$ |
| 2706 | 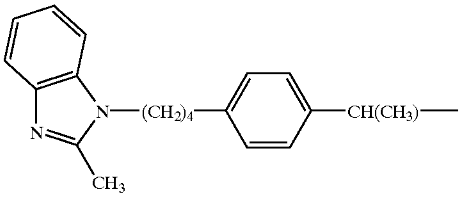 | $—CH_2CH_2CH_2CH_3$ | $—PO_3H_2$ |
| 2707 | 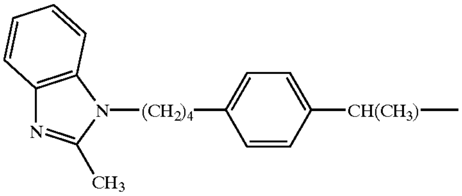 | $—CH_2CH_2CH_2CH_2CH_3$ | $—PO_3H_2$ |
| 2708 | 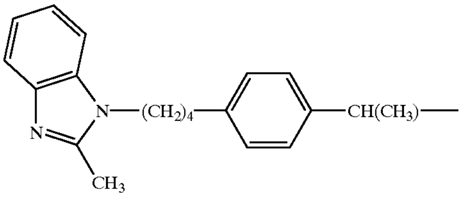 | $—CH_2CH_2CH_2CH_2CH_2CH_3$ | $—PO_3H_2$ |
| 2709 | 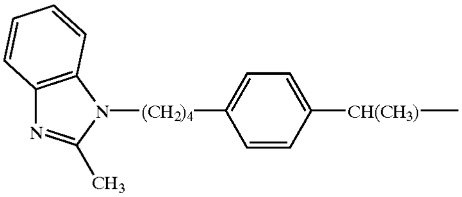 | $—CH(CH_3)_2$ | $—PO_3H_2$ |
| 2710 | 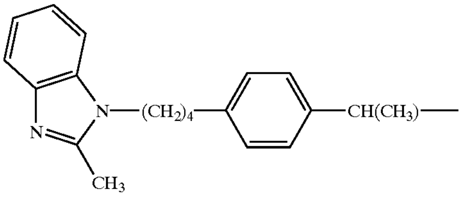 | $—CH_2CH(CH_3)_2$ | $—PO_3H_2$ |

TABLE I-continued
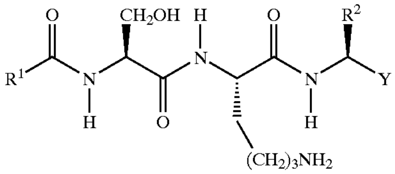
| Ex. No. | $R^1$ | $R^2$ | Y |
|---|---|---|---|
| 2711 | 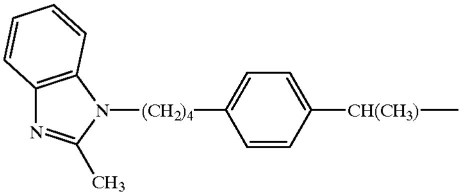 | $—CH_2CH_2CH(CH_3)_2$ | $—PO_3H_2$ |
| 2712 | 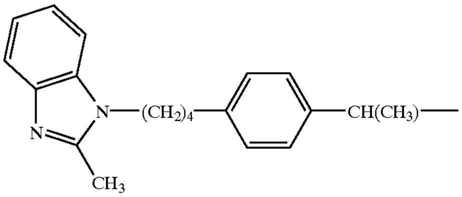 | -cyclo-$C_3H_5$ | $—PO_3H_2$ |
| 2713 | 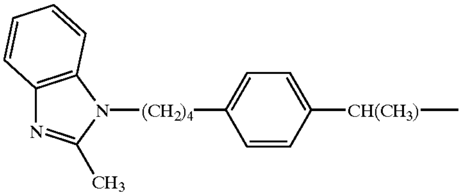 | -cyclo-$C_4H_7$ | $—PO_3H_2$ |
| 2714 | 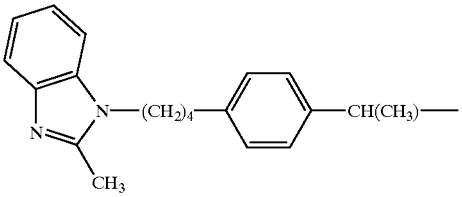 | -cyclo-$C_5H_9$ | $—PO_3H_2$ |
| 2715 | 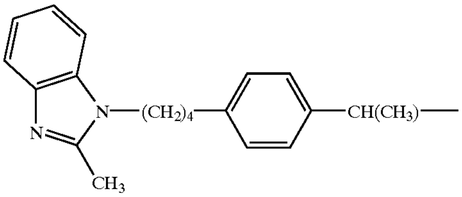 | -cyclo-$C_6H_{11}$ | $—PO_3H_2$ |
| 2716 | 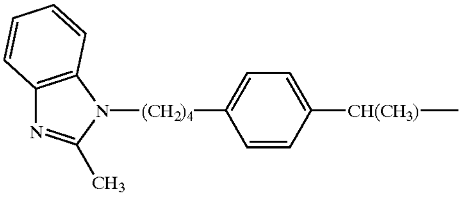 | -cyclo-$C_7H_{13}$ | $—PO_3H_2$ |

TABLE I-continued
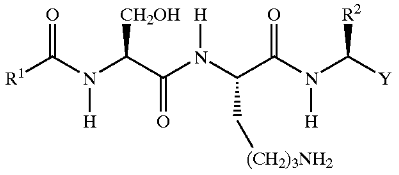
| Ex. No. | $R^1$ | $R^2$ | Y |
|---|---|---|---|
| 2717 | 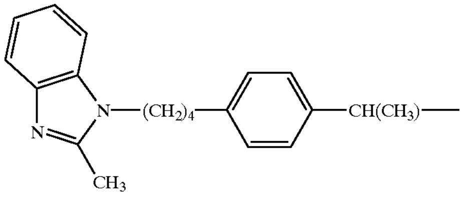 | -cyclo-$C_8H_{15}$ | —$PO_3H_2$ |
| 2718 | 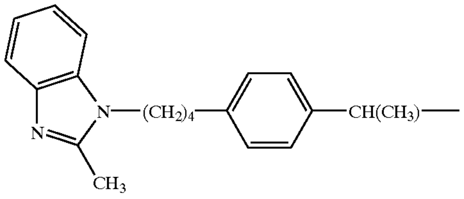 | —$CH(CH_3)(CH_2CH_3)$ | —$PO_3H_2$ |
| 2719 | 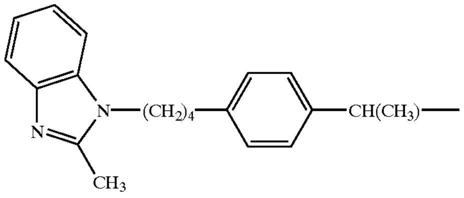 | —$CH(CH_2CH_3)_2$ | —$PO_3H_2$ |
| 2720 | 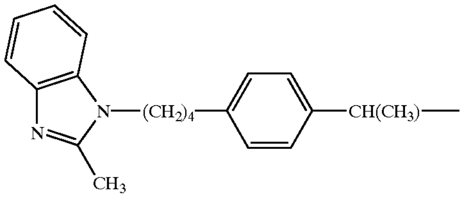 | —$CH(CH_3)(CH_2CH_2CH_3)$ | —$PO_3H_2$ |
| 2721 | 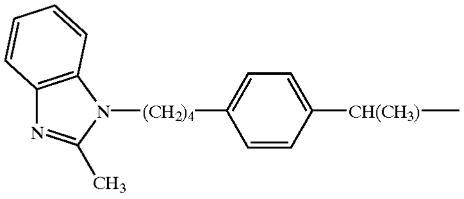 | —$C(CH_3)_3$ | —$PO_3H_2$ |
| 2722 | 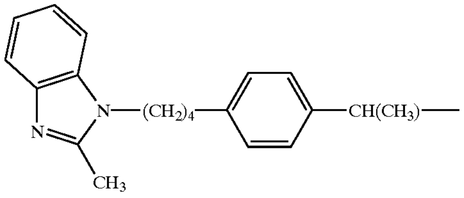 | $HC{\equiv}CCH_2$— | —$PO_3H_2$ |

TABLE I-continued
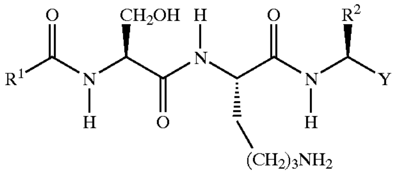
| Ex. No. | $R^1$ | $R^2$ | Y |
|---|---|---|---|
| 2723 | 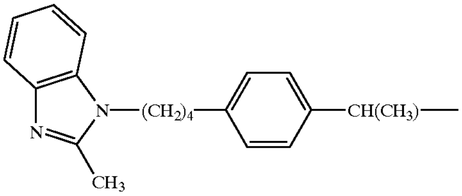 | $H_2C{=}CH—$ | $—PO_3H_2$ |
| 2724 | 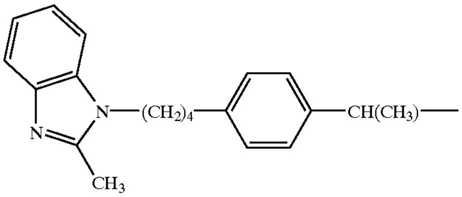 | $H_2C{=}CHCH_2—$ | $—PO_3H_2$ |
| 2725 | 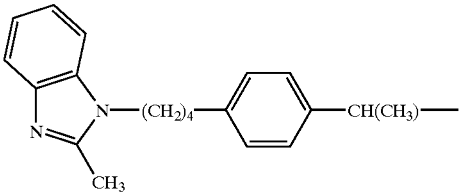 | $—CH_2F$ | $—PO_3H_2$ |
| 2726 | 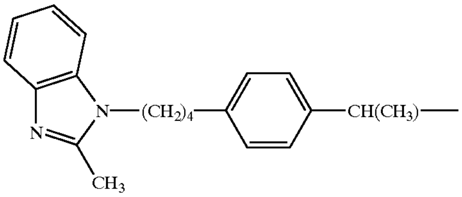 | $—CH_2C_6H_5$ | $—PO_3H_2$ |
| 2727 | 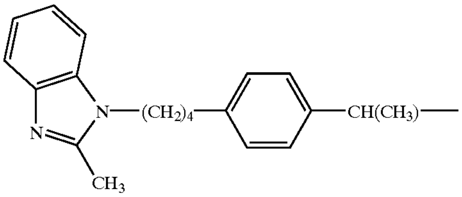 | $—CH_2C_6H_4$-p-$OCH_3$ | $—PO_3H_2$ |
| 2728 | 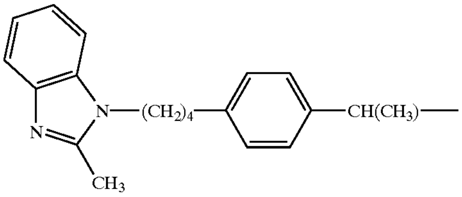 | $—CH_2C_6H_4$-p-$CH_3$ | $—PO_3H_2$ |

TABLE I-continued
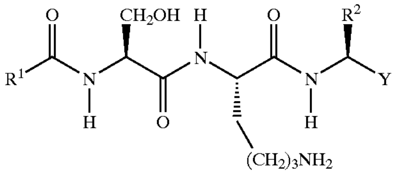
| Ex. No. | $R^1$ | $R^2$ | Y |
|---|---|---|---|
| 2729 | 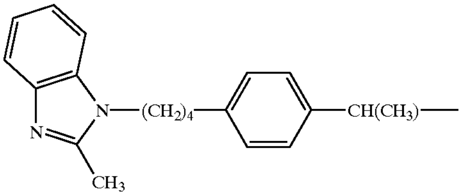 | $—CH_2C_6H_4$-p-F | $—PO_3H_2$ |
| 2730 | 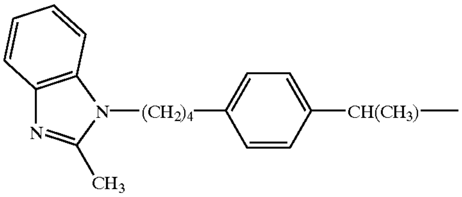 | $—CH_2CH_2C_6H_5$ | $—PO_3H_2$ |
| 2731 | 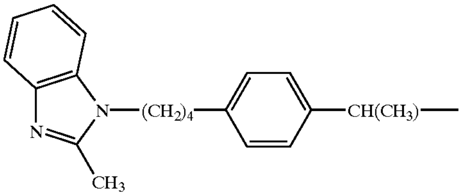 | $—CH_2$-cyclo-$C_6H_{11}$ | $—PO_3H_2$ |
| 2732 | 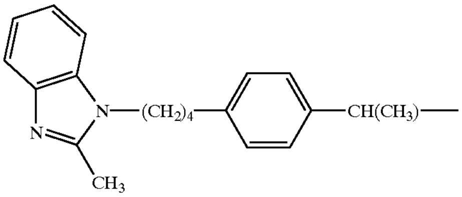 | $—CH_2$-cyclo-$C_6H_{10}$-4-F | $—PO_3H_2$ |
| 2733 | 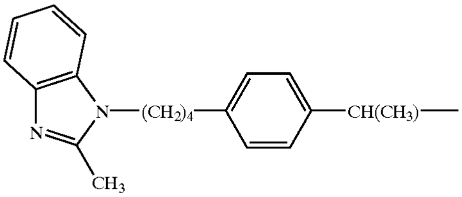 | $—CH_2$-cyclo-$C_6H_{10}$-4-$CH_3$ | $—PO_3H_2$ |
| 2734 | 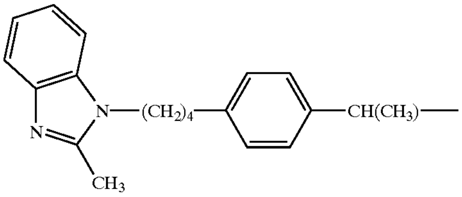 | $—CH_2$-cyclo-$C_6H_{10}$-4-$OCH_3$ | $—PO_3H_2$ |

TABLE I-continued
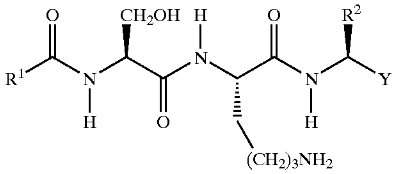
| Ex. No. | $R^1$ | $R^2$ | Y |
|---|---|---|---|
| 2735 | 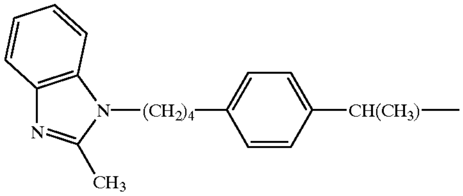 | $-CH_2CH_2$-cyclo-$C_6H_{11}$ | $-PO_3H_2$ |
| 2736 | 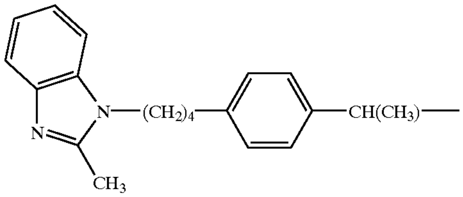 | $-CH_2$-cyclo-$C_5H_9$ | $-PO_3H_2$ |
| 2737 | 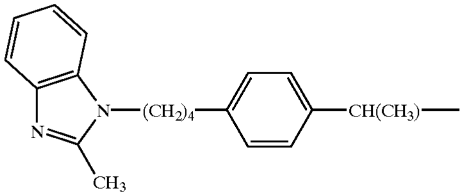 | $-CH_2CH_2$-cyclo-$C_5H_9$ | $-PO_3H_2$ |
| 2738 | 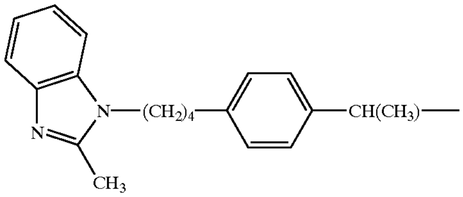 | $-CH_2$-2-naphthyl | $-PO_3H_2$ |
| 2739 | 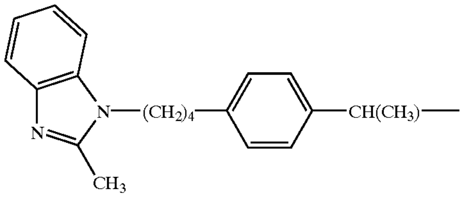 | —H | -5-Tet |
| 2740 | 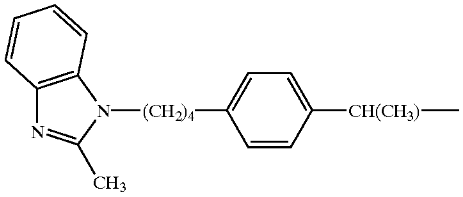 | $-CH_3$ | -5-Tet |

TABLE I-continued
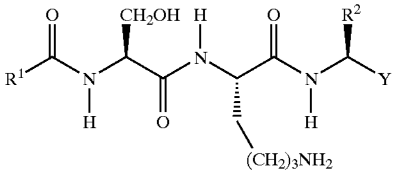
| Ex. No. | $R^1$ | $R^2$ | Y |
|---|---|---|---|
| 2741 | 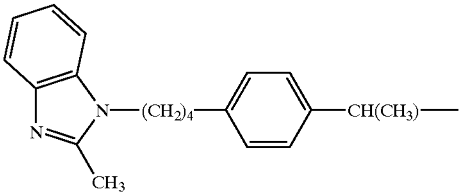 | $—CH_2CH_3$ | -5-Tet |
| 2742 | 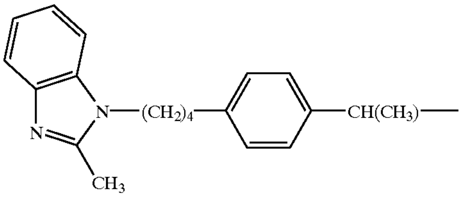 | $—CH_2CH_2CH_3$ | -5-Tet |
| 2743 | 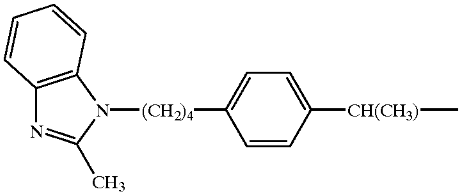 | $—CH_2CH_2CH_2CH_3$ | -5-Tet |
| 2744 | 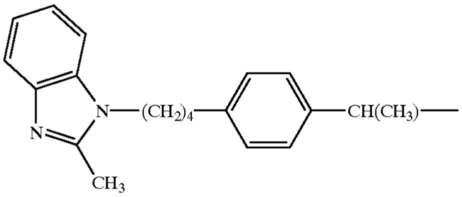 | $—CH_2CH_2CH_2CH_2CH_3$ | -5-Tet |
| 2745 | 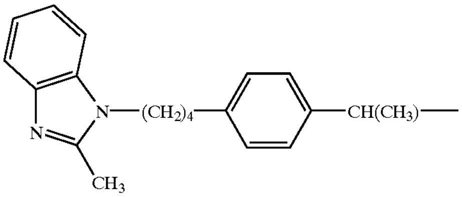 | $—CH_2CH_2CH_2CH_2CH_2CH_3$ | -5-Tet |
| 2746 | 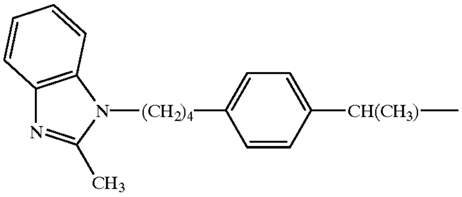 | $—CH(CH_3)_2$ | -5-Tet |

TABLE I-continued
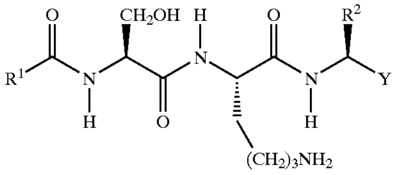
| Ex. No. | $R^1$ | $R^2$ | Y |
|---|---|---|---|
| 2747 | 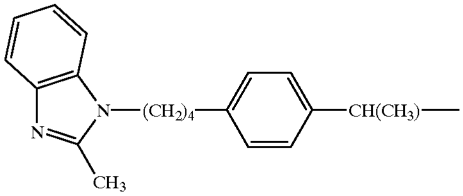 | $-CH_2CH(CH_3)_2$ | -5-Tet |
| 2748 | 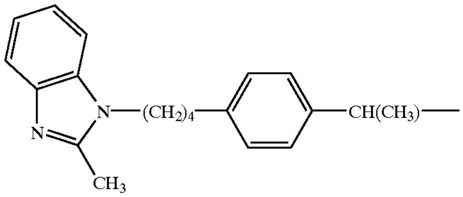 | $-CH_2CH_2CH(CH_3)_2$ | -5-Tet |
| 2749 | 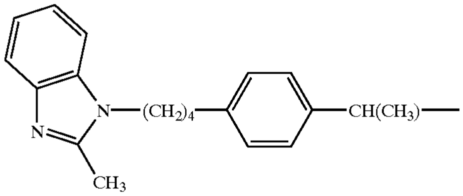 | -cyclo-$C_3H_5$ | -5-Tet |
| 2750 | 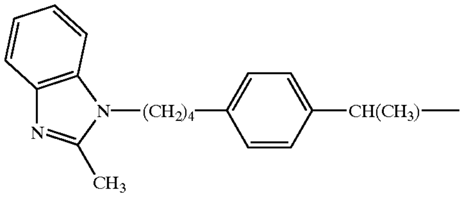 | -cyclo-$C_4H_7$ | -5-Tet |
| 2751 | 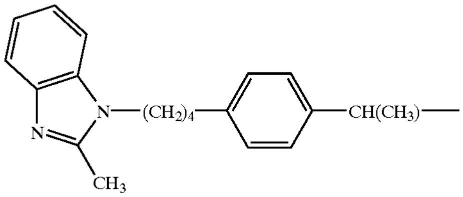 | -cyclo-$C_5H_9$ | -5-Tet |
| 2752 | 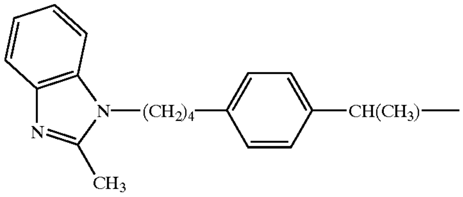 | -cyclo-$C_6H_{11}$ | -5-Tet |

TABLE I-continued
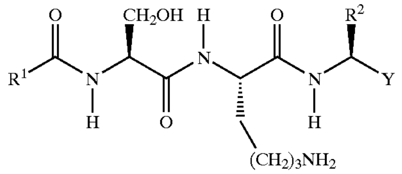
| Ex. No. | $R^1$ | $R^2$ | Y |
|---|---|---|---|
| 2753 | 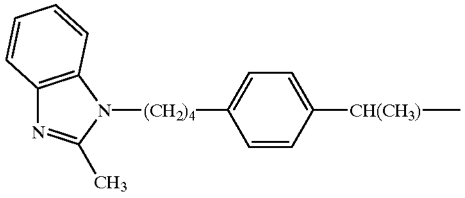 | -cyclo-$C_7H_{13}$ | -5-Tet |
| 2754 | 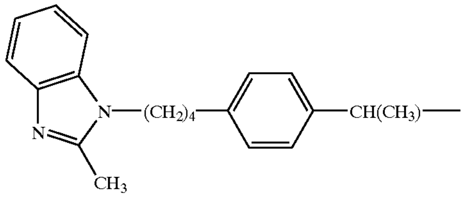 | -cyclo-$C_8H_{15}$ | -5-Tet |
| 2755 | 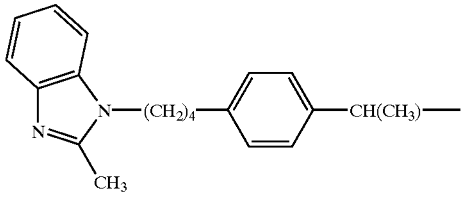 | $—CH(CH_3)(CH_2CH_3)$ | -5-Tet |
| 2756 | 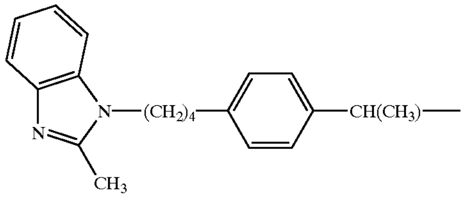 | $—CH(CH_2CH_3)_2$ | -5-Tet |
| 2757 | 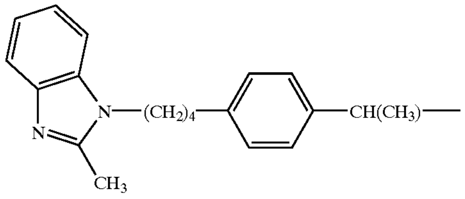 | $—CH(CH_3)(CH_2CH_2CH_3)$ | -5-Tet |
| 2758 | 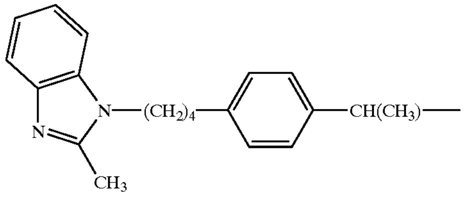 | $—C(CH_3)_3$ | -5-Tet |

TABLE I-continued
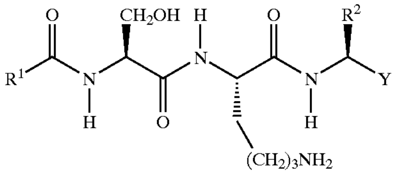
| Ex. No. | $R^1$ | $R^2$ | Y |
| --- | --- | --- | --- |
| 2759 | 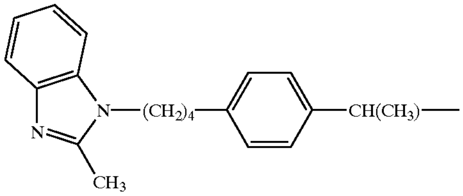 | $HC\equiv CCH_2$— | -5-Tet |
| 2760 | 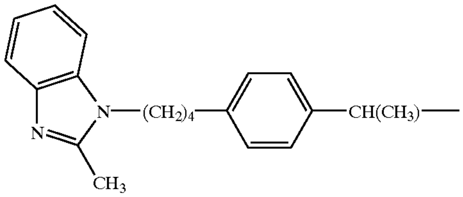 | $H_2C=CH$— | -5-Tet |
| 2761 | 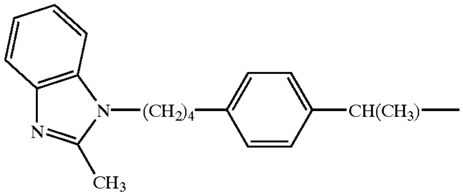 | $H_2C=CHCH_2$— | -5-Tet |
| 2762 | 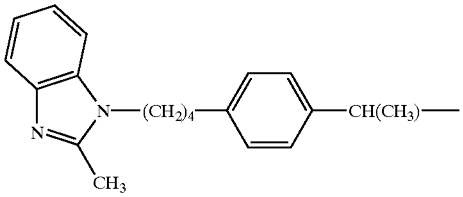 | —$CH_2F$ | -5-Tet |
| 2763 | 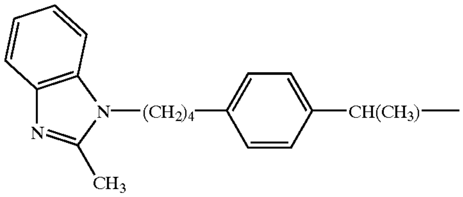 | —$CH_2C_6H_5$ | -5-Tet |
| 2764 | 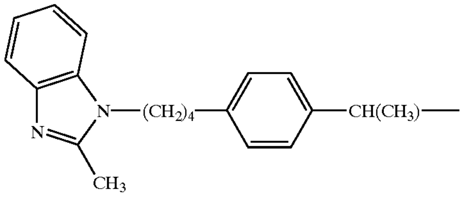 | —$CH_2C_6H_4$-p-$OCH_3$ | -5-Tet |

TABLE I-continued
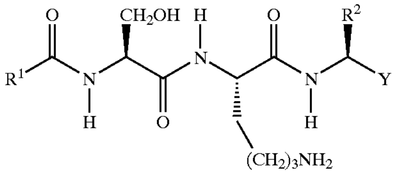
| Ex. No. | $R^1$ | $R^2$ | Y |
|---|---|---|---|
| 2765 | 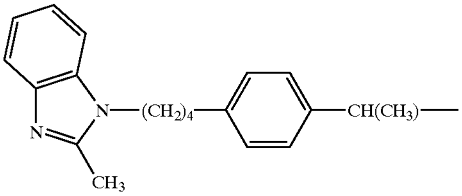 | —$CH_2C_6H_4$-p-$CH_3$ | -5-Tet |
| 2766 | 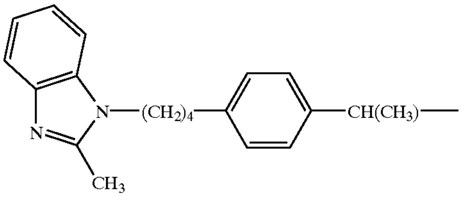 | —$CH_2C_6H_4$-p-F | -5-Tet |
| 2767 | 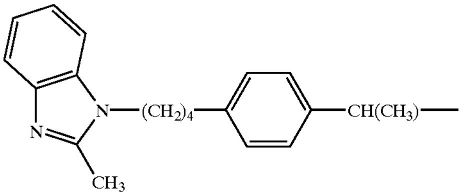 | —$CH_2CH_2C_6H_5$ | -5-Tet |
| 2768 | 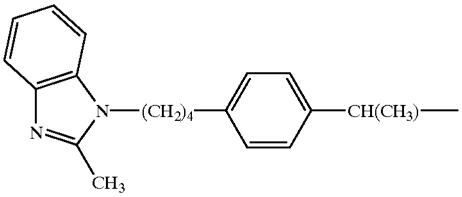 | —$CH_2$-cyclo-$C_6H_{11}$ | -5-Tet |
| 2769 | 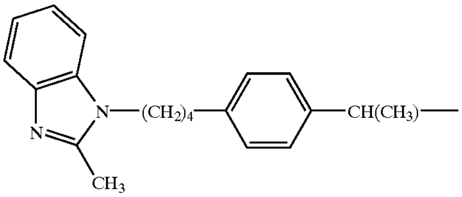 | —$CH_2$-cyclo-$C_6H_{10}$-4-F | -5-Tet |
| 2770 | 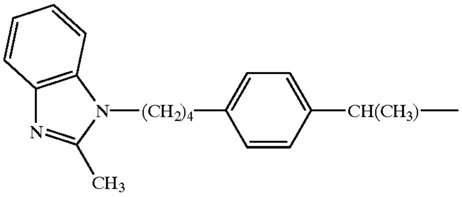 | —$CH_2$-cyclo-$C_6H_{10}$-4-$CH_3$ | -5-Tet |

TABLE I-continued

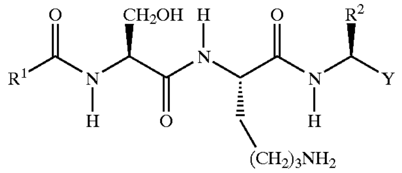

| Ex. No. | $R^1$ | $R^2$ | Y |
|---|---|---|---|
| 2771 | 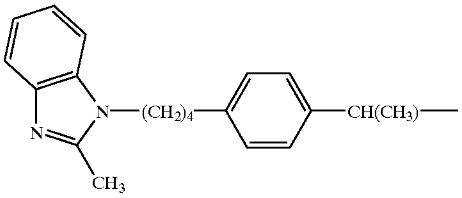 | $—CH_2$-cyclo-$C_6H_{10}$-4-$OCH_3$ | -5-Tet |
| 2772 | 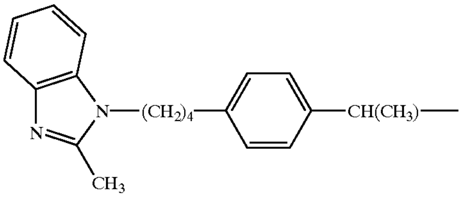 | $—CH_2CH_2$-cyclo-$C_6H_{11}$ | -5-Tet |
| 2773 | 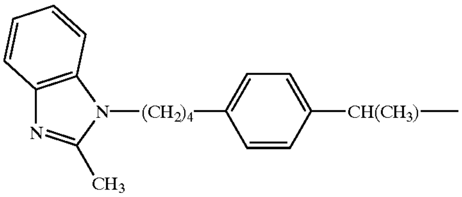 | $—CH_2$-cyclo-$C_5H_9$ | -5-Tet |
| 2774 | 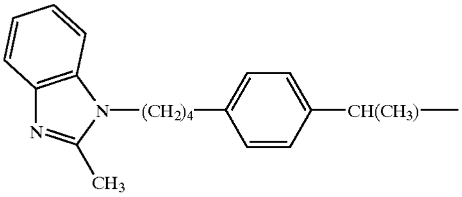 | $—CH_2CH_2$-cyclo-$C_5H_9$ | -5-Tet |
| 2775 | 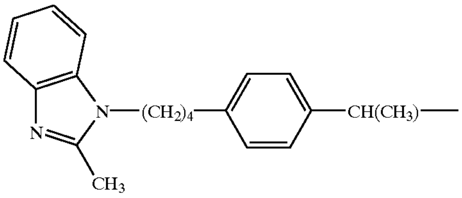 | $—CH_2$-2-naphthyl | -5-Tet |
| 2776 | $H_2N(CH_2)_9—$ | —H | $—CO_2H$ |
| 2777 | $H_2N(CH_2)_9—$ | $—CH_3$ | $—CO_2H$ |
| 2778 | $H_2N(CH_2)_9—$ | $—CH_2CH_3$ | $—CO_2H$ |
| 2779 | $H_2N(CH_2)_9—$ | $—CH_2CH_2CH_3$ | $—CO_2H$ |
| 2780 | $H_2N(CH_2)_9—$ | $—CH_2CH_2CH_2CH_3$ | $—CO_2H$ |
| 2781 | $H_2N(CH_2)_9—$ | $—CH_2CH_2CH_2CH_2CH_3$ | $—CO_2H$ |
| 2782 | $H_2N(CH_2)_9—$ | $—CH_2CH_2CH_2CH_2CH_2CH_3$ | $—CO_2H$ |
| 2783 | $H_2N(CH_2)_9—$ | $—CH(CH_3)_2$ | $—CO_2H$ |
| 2784 | $H_2N(CH_2)_9—$ | $—CH_2CH(CH_3)_2$ | $—CO_2H$ |
| 2785 | $H_2N(CH_2)_9—$ | $—CH_2CH_2CH(CH_3)_2$ | $—CO_2H$ |
| 2786 | $H_2N(CH_2)_9—$ | -cyclo-$C_3H_5$ | $—CO_2H$ |

BIOLOGICAL EVALUATION

Assay A: NMT Enzyme Inhibition Assays

Recombinant *Candida albicans* and human NMTs were expressed and purified from *E. coli* using previously described protocols. [D. A. Towler et al, *Proc. Natl. Acad. Sci. USA*, 84, 2707–2712 (1987); R. C. Weigand et al, *J. Biol. Chem.*, 267, 8591–8598 (1992); R. J. Duronio et al, *Proc. Natl. Acad. Sci. USA*, 89, 4129–4133 (1992)] The ability of compounds to inhibit Candida NMT enzymatic activity was assessed using a radiochemical HPLC end-point assay as described previously for *Saccharomyces cerevisiae* and human NMTs. [D. Towler et al, *Proc. Natl. Acad. Sci. USA*, 83, 2812–2816 (1986); W. J. Rocque et al, J. Biol. Chem., 268, 9964–9971 (1991)] The donor substrate [$^3$H] myristoyl-coenzyme A was enzymatically synthesized from [$^3$H]myristic acid (50 Ci/mmol, Amersham, Arlington Heights, Ill.) and coenzyme A (Fluka Chemical Corp., Ronkonkoma, N.Y.), and purified as described previously. [W. J. Rocque et al, J. Biol. Chem., 268, 9964–9971 (1991)] The peptide acceptor substrate GNAASARR-$NH_2$ was prepared by solid-phase peptide synthesis using the t-Boc amino acid methodology, followed by HF treatment and reverse-phase HPLC purification. Inhibitor stock solutions were prepared at 22 mM in DMSO; the final concentration of DMSO in each assay was 0.5% (v/v). Inhibition assays were carried out by combining variable amounts of inhibitor or buffer with 0.11 mmoles of [$^3$H]myristoyl-coenzyme A (1 $\mu$Ci, 9.09 Ci/mmol) and 2.2 nmoles of GNAASARR-$NH_2$ in a total volume of 60 $\mu$L of 0.2 M N-[2-hydroxy-ethyl] piperazine-N'-[2-ethanesulfonic acid], pH 7.4, 2 mM DL-dithiothreitol, 0.2 mM ethylene glycol-bis-(β-aminoethyl ether) N,N,N',N'-tetraacetic acid, and initiating the reaction by the addition of 50 $\mu$L of a Candida NMT solution (7–12 ng/50 $\mu$L). Assays with human NMT were identical except that they used 60–75 ng/50 $\mu$L of enzyme solution and 0.22 nmoles of GNAASARR-$NH_2$. The reaction was quenched after 10 minutes at 24° C. by the addition of ice-cold MeOH, and the reaction products were separated and measured using C4 reverse-phase HPLC (Vydac $214TP_{10415}$; Separations Group, Hesperia, Calif.) and in-line scintillation counting using a Radiomatic A250 (Packard Instruments, Downers Grove, Ill.) and Ecolite(+) (ICN Biomedical, Costa Mesa, Calif.) as the scintillant. Selectivity was determined by calculating the ratio of the $IC_{50}$ against human NMT to the $IC_{50}$ against *C. albicans* NMT.

Organism-culture and Source:

Antifungal Screens were set up initially against *Candida albicans*, strain B311, and *Cryotococcus neoformans*, strain L210425. Both pathogens, (originally from the stock culture collection, Medical mycology research center, Washington university-Barnes hospital), were obtained from Dr.Kobayashi, Prof.of infectious diseases, Washington University, St.Louis, Mo.

All cultures are maintained at 30° C. on Sabouraud's dextrose agar slants and subcultured at monthly intervals to fresh medium. All inocula for susceptibility testing are prepared in yeast nitogen base(YNB, Difco) broth.

A loopful of growth from Sabouraud dextrose agar slant is inoculated into 4 ml of YNB broth media and incubated at 30° C. overnight (18–24 hrs) with constant agitation (Gyratory Shaker, New Brunswick Scientific). Prior to setting up susceptibility testing, the organisms are counted in a hemocytometer, and diluted as needed into assay media.

Antifungal Susceptibility Testing:

1) (Assay at DH 5.4/30° C. Incubation/YNB Media).

Antifungal assays were carried out initially by a modification of the method published by Jones, et. al; (1), and communicated to Searle by Dr. Kobayashi, Washington University. [R. N. Jones et al, *Manual of Clinical Microbiology*, 4th ed., (1985)]

The antifungal susceptibility testing consists of a microdilution broth procedure performed in 96 well microtiter plates (Costar, cat#3799). Briefly, test compounds from a 20 mM stock solution in DMSO are diluted into sterile, deionized water (final DMSO concentration not exceeding 1%), to yield 2× the desired concentration (100 uM, 10 uM and 1 uM for an initial screen, or a selected concentration range in serial 2 fold dilutions for $EC_{50}$ determination). One hundred microliters (100 ul) of each concentration is dispensed into triplicate wells of a 96 well microtiter plate. Appropriate dilutions of a suspension of *C.albicans* (1x10$^6$ cells/ml) in 2× YNB is distributed into each of the wells, including growth control wells containing no test compound as well as control wells with 0.5% DMSO. Amphotericin B at 0.05, 1 and 5 ug/ml is included in each assay plate as a positive control. The plates are incubated at 30° C. and cell growth is scored by reading the absorbance at 590 nm on an Elisa plate reader(Dynatech, MR.5000). $EC_{50}$, the concentration of compound inhibiting growth by 50% compared to untreated controls, is calculated for 24 hrs and 48 hrs.

To determine MFC (minimal fungicidal concentration), all wells that have no visible growth are subcultured on to Sabouraud dextrose agar. These subcultures are incubated at 30° C. and examined for growth at daily intervals upto four days. The MFC is defined as the lowest concentration of compound showing<than 10 cfu on subculture. Parallel, identical assays are set up simultaneously to test compound effect on *Crytococcus neoformans.*

2) Assay at pH 7.0/35° C. Incubation/(Candida Strains Only).

Based on several papers published during 1990–1993 regarding the standardization of testing procedures at multiple research centers, and the finding that, inoculum size, pH of media, and the temperature of incubation drastically affect the antifungal activity of several compounds, particularly in the Azole class of antifungals, an additional assay was configured at pH 7.0 for *Candida albicans*. [M. A. Pfaller et al, *Antimicrobial Agents and Chemotherapy*, 34, 1648–1654 (1990); F. C. Odds et al, *Antimicrobial Agents and Chemotherapy*, 36, 1727–1737 (1992); R. A. Cook et al, *Antimicrobial Agents and Chemotherapy*, 34, 1542–1545 (1990)]

The assay format is identical to the first one with the following modifications: *C.albicans* cells are diluted to 1x10$^3$ cells/ml into 2× buffered YNB (YNB buffered with 1.65 mM MOPS, pH 7.0, with the addition of 2% Dextrose and 0.08% casamino acids mixture, bio 101. inc,cat #10420-100). Incubation is carried out at 35° C. instead of 30° C., and cell growth is monitored at 590 nm at 24 and 48 hrs as described. All other aspects of the assay are identical. This assay was validated with amphotericin B, fluconazole, cilofungin (Ly-121019), Nikkomycin and terbinafine using the following Candida strains- (*C.albicans*, B311, *C.parasilosis, C.tropicalis, C.lusitaniae, C.glabrata*, and *C. albicans* 516)-Table II. All strains were from Dr. Kobayashi, Washington university. Antifungal activity is expressed as $EC_{50}$-($\mu$M) at 24 hr and 48 hr for both sets of assay conditions for *Candida albicans*, and pH 5.4 assay only for *Cryrtococcus neoformans*.

TABLE II:

ANTIFUNGAL ACTIVITY OF KNOWN COMPOUNDS AGAINST CANDIDA STRAINS-(pH 7.0/35° C. / 1X $10^3$ CELLS/mL)/ $EC_{50}$ - 48 HRS

| | *C.albicans* | | | | | |
|---|---|---|---|---|---|---|
| Compound | (b311) | (516) | *C.para* | *C.trop.* | *C.lusi.* | *C.glab.* |
| Amphotericin (μg/mL) | 0.11 | 0.14 | 0.31 | 0.44 | 0.42 | 0.47 |
| Fluconazole (μg/mL) | 0.71 | 0.65 | 0.91 | 2.6 | 0.6 | 26 |
| Terbinafine (μM) | 4.4 | 3.2 | 0.2 | >100 | 0.4 | >100 |
| Ly 12109 (μM) | 0.6 | 0.6 | 32 | 0.6 | 6.6 | 6.1 |
| Nikkomycin (μM) | 4.5 | 11 | 13 | >100 | 28 | >100 |

TABLE III:

ANTIFUNGAL ACTIVITY OF NMT INHIBITORS

| | pH 5.4 ASSAY | | |
|---|---|---|---|
| COMPOUND EX. # | *C.albicans* | *C.neoformans* $EC_{50}$ -μM | pH 7.0 ASSAY *C. albicans* |
| 1 | 24h 33 | >100 | >100 |
| | 48h 77 | >100 | >100 |
| 2 | 24h 35 | >100 | >100 |
| | 48h 70 | >100 | >100 |
| 3 | 24h 33 | >100 | >100 |
| | 48h 58 | >100 | >100 |
| 4 | 24h 63 | >100 | >100 |
| | 48h >100 | >100 | >100 |
| 5 | 24h 68 | >100 | >100 |
| | 48h 81 | >100 | >100 |
| 6 | 24h 80 | >100 | >100 |
| | 48h >100 | >100 | >100 |
| 7 | 24h 97 | >100 | >100 |
| | 48h >100 | >100 | >100 |
| 9 | 24h >100 | >100 | >100 |
| | 48h >100 | >100 | >100 |
| 10 | 24h >100 | >100 | >100 |
| | 48h >100 | >100 | >100 |
| Comp. A | 24h >400 | >100 | >100 |
| | 48h >400 | >100 | >100 |

TABLE IV:

ACTIVITY ($EC_{50}$) OF EXAMPLE #2 and COMPARATOR COMPOUND A AGAINST DIFFERENT STRAINS OF CANDIDA (pH 5.4 assay) / 24 hr)

| Strain Compound | *C.alb* (B311) | *C.para.* | *C.trop.* | *C.lusi.* | *C.glab.* | *C.alb* (516) |
|---|---|---|---|---|---|---|
| Ex. #2 | 35 | 40 | >250 | >250 | >250 | >250 |
| Compar. Comp. A | >400 | >250 | >250 | >250 | >250 | >250 |

TABLE V

Biological Activity of Example #1–11 Compounds

| Ex. No. | $IC_{50}$ caNMT (μM) | $IC_{50}$ hNMT (μM) | Selectivity | $caEC_{50}$ 24 hours (μM) |
|---|---|---|---|---|
| 1 | 0.4 | 850 | 2200 | 33 |
| 2 | 1.4 | 810 | 560 | 35 |

TABLE V-continued

Biological Activity of Example #1–11 Compounds

| Ex. No. | $IC_{50}$ caNMT (μM) | $IC_{50}$ hNMT (μM) | Selectivity | $caEC_{50}$ 24 hours (μM) |
|---|---|---|---|---|
| 3 | 80% @ 11 μM | NT | ND | 33 |
| 4 | 6.7 | NT | ND | 63 |
| 5 | 27% @ 10 μM | NT | ND | 68 |
| 6 | 36% @ 10 μM | NT | ND | 80 |
| 7 | 100 | NT | ND | 97 |
| 8 | 78% @ 10 μM | NT | ND | >100 |
| 9 | 6 | NT | ND | >100 |
| 10 | 40% @ 10 μM | NT | ND | >100 |
| 11 | 18 | NT | ND | >100 |

caNMT = *Candida albicans* NMT;
hNMT = human NMT;
$IC_{50}$ reported or % inhibition at ~10 μM.
ca = *Candida albicans*
NT = Not tested;
ND = not determined.

Assay B: Gel Shift Assay for Assessing the Degree of N-myristoylation of Arf1p in Strains Containing Wild Type or Mutant NMTs Rationale N-myristoylation of *C. albicans* ADP ribosylation factor (Arf), produces a change in its electrophoretic mobility during SDS-polyacrylamide gel electrophoresis. The acylated species migrates more rapidly than the nonmyristoylated species [J. K. Lodge et al, *J. Biol. Chem.*, 269, 2996–3009 (1994)].

Recent genetic studies have shown that NMT is essential for vegetative growth of *Candida albicans* [R. A Weinberg et al, *Mol. Micro.*, in press, (1995)]. This conclusion was based on the following set of observations. A strain of *C. albicans* was constructed in which one copy of NMT was partially deleted and disrupted. A $Gly^{447}$→Asp mutation was introduced into the second MMT allele. This mutation produces marked reductions in catalytic efficiency at 24 and 37° C., as judged by in vitro kinetic studies of the purified wild type and mutant enzymes. The growth characteristics of isogenic VMT/IMT, NMT/Δnmt, and nmtΔ/nmtG447D *C. albicans* strains were subsequently assessed under a variety of conditions. Only the nmtΔ/nmtG447D strain requires myristate for growth on YPD medium at 24 or 37° C. When nmtΔ/nmtG447D cells are switched from YPD supplemented with 500 μM myristate to YPD that does not contain any supplemental myristate, 60% of the cells die within 4 h (assay=the ability to form colonies on YPD/500 μM myristate). Protein gel shift assays of Arf N-myristoylation indicated that when exponentially growing nmtΔ/nmtG447D cells were incubated at 24° C. in the presence of myristate, 100% of Arf is N-myristoylated. After 4 h of incubation in the absence of myristate, nonmyristoyalted Arf represents ~40–50% of total cellular Arf.

Based on these findings, acylation of *C. albicans* Arf, measured using this protein gel shift assay, was used to define the effects of peptide analog inhibitors of *C. albicans* NMT on the efficiency of protein N-myristoylation in cultures of this fungal pathogen.

The assay was performed as follows. A single colony of *Candida albicans* strain MONCA105 NMT, [R. A Weinberg et al, *Mol. Micro*., in press, (1995)] was innoculated into YPD medium (YPD=1% yeast extract, 2% peptone, 2% dextrose). Cultures were shaken at 24° C. for 12–16 h. Cells were recovered by centrifugation, washed 3 times with sterile PBS, pH 7.4 and resuspended in YPD at an $OD_{600}$ of 1.0–1.5. Fifty microliters of a 20 mM stock solution of peptide analog (prepared in sterile deionized $H_2O$) were added to a sterile polypropylene tube containing 4.5 mL of fresh YPD medium. Five hundred microliters of the *C. albicans* culture was then added to the tubes. Controls consisted of no added peptide analog (i.e. water alone).The tubes were incubated at 24° C. with vigorous shaking for 2 hr or 4 hr. For each experiment, duplicate tubes were assayed for each condition and at each time point. Cells were recovered by centrifugation, resuspended in 200 μL of Lysis Buffer (0.125M Tris-HCl, pH 6.8/4% SDS), and transferred to microfuge tubes containing 200 μL of glass beads (bead diameter=425–600 μm, Sigma).The slurry was vortexed 3 times for 1 min each. Between each cycle of vortexing, the tubes were placed on ice for 1 min. The mixture was then placed in a boiling water bath for 10 min, vortexed once again for 1 min and subsequently spun at 10,000×g for 2 min. The cleared supernatant fraction was removed, spun again at 10,000×g for 5 min and the total protein concentration determined. Equal masses of protein from each sample (100 μg) were reduced, denatured, fractionated by electrophoresis through a 12% polyacrylamide gel containing 0.1% SDS [U. K. Laemmli, *Nature*, 227, 680–685 (1970)] and transferred to PVDF membranes (Millipore). The resulting Western blots were probed with rabbit antiserum R23 which was raised against a peptide (SNSLKNST) encompassing the C-terminal 8 residues of *S. cerevisiae* Arf1p (kindly supplied by Richard Kahn, Lab of Biological Chemistry, NCI, NIH; final dilution=1:4000 in I-Block buffer from Tropix). Antigen-antibody complexes were visualized using the Western-Light Immunoblotting System (Tropix). The secondary antibody was an alkaline phosphatase-conjugated goat-anti-Rabbit IgG. 200 μM Example #2 produces ~10% reduction in Arf N-myristoylation within 2 h. The optical isomer (Comparator Compound A) is not an inhibitor of purified *C. albicans* Nmt in vitro. 200 μM of this compound produces no detectable reduction of Arf acylation in vivo at either the 2 h or the 4 h time point.

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present. invention may be administered by any suitable route, preferably in the form of a pharmaceutical composition adapted to such a route, and in a dose effective.for the treatment intended. Therapeutically effective doses of the compounds of the present invention required to prevent or arrest the progress of the medical condition are readily ascertained by one of ordinary skill in the art. The compounds and compositions may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 500 mg, preferably from about 10 to 250 mg. A suitable daily dose may vary widely depending on the condition of the patient and other factors. However, a dose of from about 0.01 to about 15 mg/kg body weight, particularly from about 0.1 to 10 mg/kg body weight, may be appropriate.

The active ingredient may also be administered by injection as a composition wherein, for example, saline, dextrose or water may be used as a suitable carrier. A suitable daily dose may range from about 0.01 to 15 mg/kg body weight injected per day in multiple doses depending on the disease being treated. A preferred daily dose would be from about 0.5 to about 10 mg/kg body weight. Compounds indicated for prophylactic therapy will preferably be administered in a daily dose generally in a range from about 0.01 mg to about 15 mg per kilogram of body weight per day. A more preferred dosage will be a range from about 0.1 mg to about 10 mg per kilogram of body weight. Most preferred is a dosage in a range from about 0.5 to about 5 mg per kilogram of body weight per day.

A suitable dose can be administered, in multiple sub-doses per day. These sub-doses may be administered in unit dosage forms. Typically, a dose or sub-dose may contain from about 1 mg to about 500 mg of active compound per unit dosage form. A more preferred dosage will contain from about 10 mg to about 250 mg of active compound per unit dosage form. Most preferred is a dosage form containing from about 20 mg to about 150 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

A preferred method of treatment includes administering a compound of the invention topically to treat primary infections occurring in the vaginal tract. Another preferred method of treatment includes administering a compound of the invention by gastrointestinal absorption, either by oral ingestion or by suppository, to treat a systemic fungal infection.

Although this invention has been described with respect to specific embodiments, the details of these embodiments are not to be construed as limitations.

What is claimed is:

1. A method of inhibiting growth of *Candida Albicans* in a subject afflicted therewith comprising administering to said subject a compound, for a time and under conditions effective to inhibit growth of *Candida Albicans*, selected from compounds of Formula II:

(II)

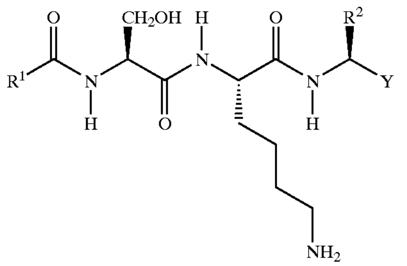

wherein $R^1$ is selected from aminoalkyl, aminoalkylcycloalkyl, aminoalkylcycloalkylalkyl, monoalkylaminoalkyl, dialkylaminoalkyl, monoalkylaminocycloalkylalkyl, dialkylaminocycloalkylalkyl, aminoalkylarylalkyl, monoalkylaminoalkylarylalkyl, dialkylaminoalkylarylalkyl,. aminocycloalkyl, monocycloalkylaminoalkyl, monoalkylaminocycloalkyl, monocycloalkylaminocycloalkyl, dialkylaminocycloalkyl, aminocycloalkylarylalkyl, aminoalkylarylcycloalkyl, aminocycloalkylarylcycloalkyl, monocycloalkylaminoalkylarylalkyl, monoalkylaminocycloalkylarylalkyl, monoalkylaminoalkylarylcycloalkyl, monocycloalkylaminocycloalkylarylalkyl, monocycloalkylaminoalkylarylcycloalkyl, monoalkylaminocycloalkylarylcycloalkyl, monocycloalkylaminocycloalkylarylcycloalkyl, dialkylaminocycloalkylarylalkyl, dialkylaminoalkylarylcycloalkyl, dialkylaminocycloalkylarylcycloalkyl, heterocyclic-A-alkyl, heterocyclic-A-alkylarylalkyl, heterocyclic-A-cycloalkyl, heterocyclic-A-cycloalkylarylalkyl, heterocyclic-A-alkylarylcycloalkyl, heterocyclic-A-cycloalkylarylcycloalkyl, heteroaryl-A-alkyl, heteroaryl-A-alkylarylalkyl, heteroaryl-A-cycloalkyl, heteroaryl-A-cycloalkylarylalkyl, hetergaryl-A-alkylarylcycloalkyl and heteroaryl-A-cycloalkylarylcycloalkyl, wherein A is either a covalent bond or is a moiety selected from

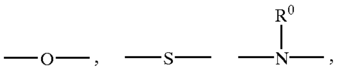

wherein $R^0$ is selected from hydrido, alkyl, cycloalkyl and cycloalkylalkyl; wherein any foregoing heterocyclic-containing moiety may be fused to an aryl ring to form an arylheterocyclic moiety, and wherein any foregoing heteroaryl-containing moiety may be fused to an aryl ring to form an arylheteroaryl moiety, and wherein any of said heterocyclic moiety, heteroaryl moiety, arylheterocyclic moiety and arylheteroaryl moiety may be independently substituted at one or more substitutable positions with one or more radicals selected from halo, alkyl, haloalkyl, cycloalkyl, cycloalkylalkyl, amino, aminoacyl, aminocarbonylalkoxy, monoalkylamino, dialkylamino, alkoxy, alkylthio, aralkyl and aryl, with the proviso that said heterocyclic moiety is selected from morpholino, thiomorpholino, piperazinyl, piperidinyl and pyrrolidinyl, and with the further proviso that said heteroaryl moiety is selected from imidazolyl and pyridinyl;

wherein $R^2$ is a radical selected from hydrido, alkyl, cycloalkyl, cycloalkylalkyl, bicycloalkyl, alkenyl, cycloalkenyl, fused bicycloalkenyl, cycloalkyl fused to cycloalkenyl, alkenylalkyl, alkynyl, aralkyl and aryl, wherein any of said $R^2$ radicals having a substitutable position may be substituted by one or more radicals selected from alkyl, cycloalkyl, cycloalkylalkyl, alkenyl, cycloalkenyl, fused bicycloalkenyl, cycloalkyl fused to cycloalkenyl, alkenylalkyl, alkynyl, halo, haloalkyl, alkoxy, alkoxyalkyl, alkylthio, aralkoxy, aryloxy, arylthio, aralkyl, aryl, alkoxycarbonyl, cycloalkoxycarbonyl, alkoxycarbonylalkyl and cycloalkoxycarbonylcycloalkyl;

wherein Y is selected from hydroxyalkyl, hydroxycycloalkyl, hydroxycycloalkylalkyl, hydroxyaryl, hydroxyaminocarbonylaralkyl, hydroxyaminocarbonyl, hydroxyaminocarbonylalkyl, hydroxyaminocarbonylcycloalkyl, hydroxyaminocarbonylcycloalkylalkyl, hydroxyaminocarbonylaryl, carboxyl, carboxyalkyl, carboxycycloalkyl, carboxycyloalkylalkyl, tetrazolyl, tetrazolylalkyl, tetrazolylcycloalkyl, tetrazolylcycloalkylalkyl, phosphinic acid, monoalkylphosphinic acid, dialkylphosphinic acid, monocycloalkylphosphinic acid, dicycloalkylphosphinic acid, monocycloalkylalkylphosphinic acid, dicycloalkylalkylphosphinic acid, mixed monoalkylmonocycloalkylphosphinic acid, mixed monoalkylmonocycloalkylalkylphosphinic acid, mixed monocycloalkylmonocycloalkylalkylphosphinic acid, monoarylphosphinic acid, diarylphosphinic acid, mixed monoalkyl-monoarylphosphinic acid, mixed monocycloalkyl-monoarylphosphinic acid, mixed monocycloalkylalkyl-monoarylphosphinic acid, phosphonic acid, alkylphosphonic acid, cycloalkylphosphonic acid, cycloalkylalkylphosphonic acid, aralkylphosphonic acid and arylphosphonic acid;

or an acceptable ester, amide, or salt thereof.

2. The method of claim 1 wherein $R^1$ is selected from aminoalkyl, monoalkylaminoalkyl, dialkylaminoalkyl, aminoalkylphenylalkyl, monoalkylaminoalkylphenylalkyl, dialkylaminoalkylphenylalkyl, heterocyclicalkyl, heterocyclicalkylphenylalkyl, heteroarylalkyl, heteroarylalkylphenylalkyl, heterocycliccylcoalkyl, heterocycliccycloalkylalkyl, heteroarylcycloalkyl and heteroarylcycloalkylalkyl wherein any foregoing heterocyclic moiety may be fused to a phenyl ring to form a benzoheterocyclic moiety and wherein any foregoing heteroaryl moiety may be fused to a phenyl ring to form a benzoheteroaryl moiety, and wherein any of said heterocyclic moiety, benzoheterocyclic moiety, heteroaryl moiety and benzoheteroaryl moiety may be substituted at one or more substitutable positions with one or more radicals selected from halo, alkyl, haloalkyl, cycloalkyl, cycloalkylalkyl, alkoxy, alkylthio, phenylalkyl and phenyl; with the proviso that said heterocyclic moiety is selected from morpholino, thiomorpholino, piperazinyl, piperidinyl and pyrrolidinyl, and with the further proviso that said heteroaryl is selected from imidazolyl and pyridinyl;

wherein $R^2$ is a radical selected from hydrido, alkyl, cycloalkyl, cycloalkylalkyl, phenylalkyl and phenyl, wherein any of said $R^2$ radicals having a substitutable position may be substituted by one or more radicals selected from alkyl, cycloalkyl, cycloalkylalkyl, alkenyl, alkynyl, halo, haloalkyl, alkoxy, alkylthio, phenylalkyl, phenyl, naphthyl, tetrahydronaphthyl, decahydronaphthyl, naphthylalkyl, tetrahydronaphthylalkyl, decahydronaphthylalkyl, naphthylcycloalkyl, tetrahydronaphthylcycloalkyl, decahydronaphthylalkyl, alkoxycarbonyl and alkoxycarbonylalkyl;

wherein Y is selected from

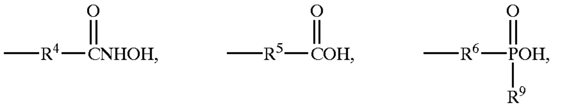

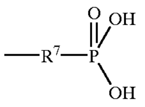

and

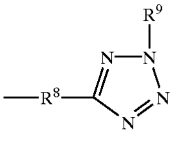

wherein each of $R^4$ through $R^8$ is either a covalent bond or is a divalent radical of the general structure

wherein X is selected from alkyl, cycloalkyl, cycloalkylalkyl, phenylalkyl and phenyl;

wherein $R^9$ is selected from hydrido, alkyl, cycloalkyl, cycloalkylalkyl, phenylalkyl and phenyl;

or an acceptable ester, amide, or salt thereof.

3. The method of claim 2 wherein $R^1$ is selected from

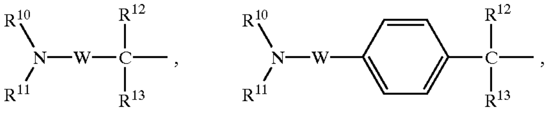

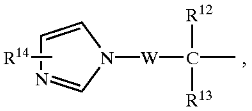

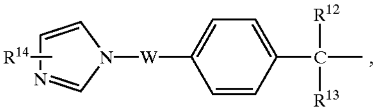

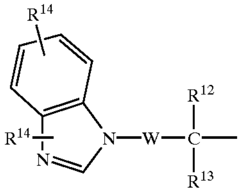

and

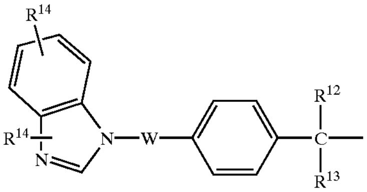

wherein W is a divalent radical of the general structure

wherein W is selected from alkyl and cycloalkyl;

wherein each of $R^{10}$ and $R^{11}$ is independently selected from hydrido, alkyl, cycloalkyl, cycloalkylalkyl, phenylalkyl and phenyl; wherein further $R^{10}$ and $R^{11}$ may be taken together to form a saturated heterocyclic ring system having five or six ring members and having at least one nitrogen atom as a ring member and optionally having a second heteroatom selected from an oxygen, nitrogen or sulfur atom as a ring member, said heterocyclic ring system selected from morpholino, thiomorpholino, piperazinyl, piperidinyl and pyrrolidinyl; wherein each of $R^{12}$ and $R^{13}$ is independently selected from hydrido, alkyl and haloalkyl; wherein $R^{14}$ is selected from hydrido, alkyl, haloalkyl, halo, cycloalkyl, alkoxy, alkylthio, phenylalkyl and phenyl;

wherein $R^2$ is a moiety selected from hydrido, alkyl, cycloalkyl, cycloalkylalkyl, alkenyl, alkynyl, haloalkyl, naphthyl, tetrahydronaphthyl, decahydronaphthyl, naphthylalkyl, tetrahydronaphthylalkyl, decahydronaphthylalkyl, naphthylcycloalkyl, tetrahydronaphthylcycloalkyl, decahydronaphthylalkyl, phenylalkyl and phenyl, wherein any said $R^2$ moiety may be substituted at a substitutable position by one or more radicals selected from alkyl, halo and alkoxy;

wherein Y is selected from

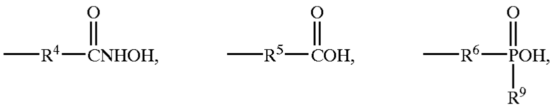

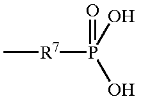

and

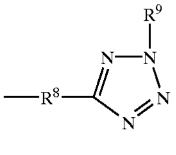

wherein each of $R^4$ through $R^8$ is either a covalent bond or is a divalent radical of the general structure

with each of $R^4$ through $R^8$ independently selected from $—CH_2—$, $—CH_2CH_2—$ and $—CH_2CH_2CH_2—$;

wherein $R^9$ is selected from hydrido, alkyl, cycloalkyl, cycloalkylalkyl, phenylalkyl and phenyl;

or an acceptable ester, amide, or salt thereof.

4. The method of claim 3 wherein $R^1$ is selected from

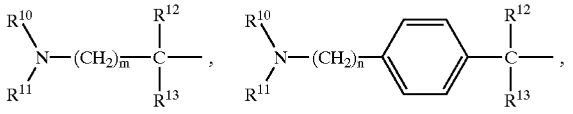

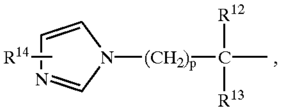

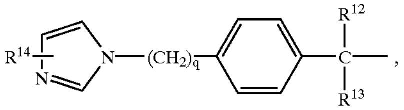

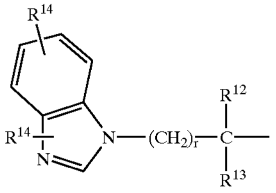

and

-continued

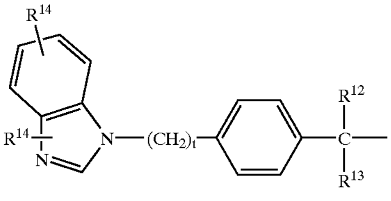

wherein each of $R^{10}$ and $R^{11}$ is independently selected from hydrido, alkyl, cycloalkyl, cycloalkylalkyl, phenylalkyl and phenyl; wherein further $R^{10}$ and $R^{11}$ may be taken together to form a saturated heterocyclic ring system having five or six ring members and having at least one nitrogen atom as a ring member and optionally having a second heteroatom selected from an oxygen, nitrogen or sulfur atom as a ring member, said heterocyclic ring system selected from morpholino, thiomorpholino, piperazinyl, piperidinyl and pyrrolidinyl; wherein each of $R^{12}$ and $R^{13}$ is independently selected from hydrido, alkyl and haloalkyl; wherein $R^{14}$ is selected from hydrido, alkyl, haloalkyl, halo, cycloalkyl, alkoxy, alkylthio, phenylalkyl and phenyl;

wherein each of m, n, p and r is a whole number independently selected from 3 through 15; wherein each of q and t is a whole number independently selected from 1 through 6;

wherein $R^2$ is a moiety selected from hydrido, alkyl, cycloalkyl, cycloalkylalkyl, alkenyl, alkynyl, haloalkyl, naphthyl, tetrahydronaphthyl, decahydronaphthyl, naphthylalkyl, tetrahydronaphthylalkyl, decahydronaphthylalkyl, naphthylcycloalkyl, tetrahydronaphthylcycloalkyl, decahydronaphthylalkyl, phenylalkyl, and phenyl, wherein any said $R^2$ moiety may be substituted at a substitutable position by one or more radicals selected from alkyl, halo and alkoxy;

wherein Y is selected from

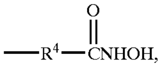 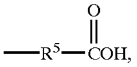 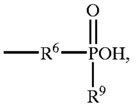

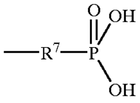 and 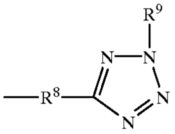

wherein each of $R^4$ through $R^8$ is either a covalent bond or is a divalent radical of the general structure $$-[X]-$$

with each of $R^4$ through $R^8$ independently selected from $-CH_2-$, $-CH_2CH_2-$ and $-CH_2CH_2CH_2$;

wherein $R^9$ is selected from hydrido, alkyl, cycloalkyl, cycloalkylalkyl and benzyl;

or an acceptable ester, amide, or salt thereof.

5. The method of claim 4 wherein $R^1$ is selected from

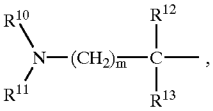 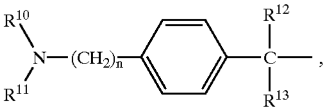

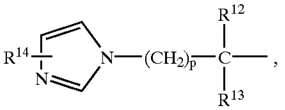

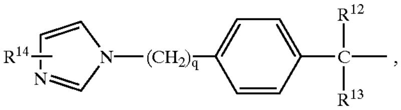

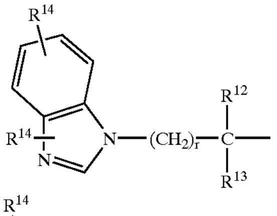 and

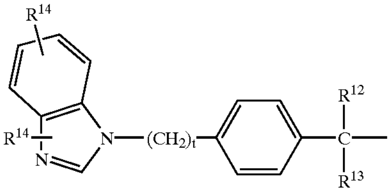

wherein each of $R^{10}$ and $R^{11}$ is independently selected from hydrido and alkyl; wherein further $R^{10}$ and $R^{11}$ may be taken together to form a saturated heterocyclic ring system having five or six ring members and having at least one nitrogen atom as a ring member and optionally having a second hetero atom selected from an oxygen, nitrogen or sulfur atom as a ring member, said heterocyclic ring system selected from morpholino, thiomorpholino, piperazinyl, piperidinyl and pyrrolidinyl;

wherein each of $R^{12}$ and $R^{13}$ is independently selected from hydrido, alkyl and haloalkyl; wherein $R^{14}$ is selected from hydrido, alkyl, haloalkyl, halo, cycloalkyl, alkoxy, alkylthio, phenylalkyl and phenyl;

wherein each of m, n, p and r is a whole number independently selected from 6 through 14; wherein each of q and t is a whole number independently selected from 3 through 6;

wherein $R^2$ is a moiety selected from hydrido, alkyl, cycloalkyl, cycloalkylalkyl, alkenyl, alkynyl, haloalkyl, naphthyl, tetrahydronaphthyl, decahydronaphthyl, naphthylalkyl, tetrahydronaphthylalkyl, decahydronaphthylalkyl, naphthylcycloalkyl, tetrahydronaphthylcycloalkyl, decahydronaphthylalkyl, phenylalkyl, and phenyl, wherein any said $R^2$ moiety may be substituted at a substitutable position by one or more radicals selected from alkyl, halo and alkoxy;

wherein Y is selected from

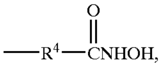 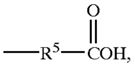 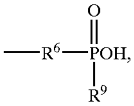

-continued

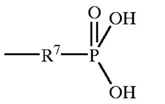

and

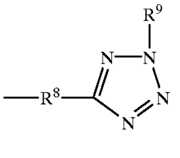

wherein each of $R^4$ through $R^8$ is either a covalent bond or is a divalent radical of the general structure

—[X]— with each of $R^4$ through $R^8$ independently selected from $—CH_2—$, $—CH_2CH_2—$ and $—CH_2CH_2CH_2;$ wherein $R^9$ is selected from hydrido, alkyl and benzyl;

or an acceptable ester, amide, or salt thereof.

6. The method of claim 5 wherein $R^1$ is selected from

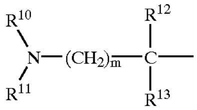

,

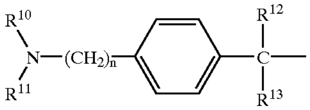

,

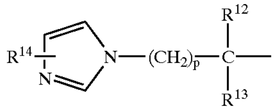

,

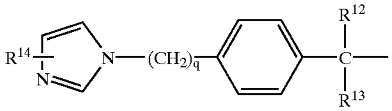

,

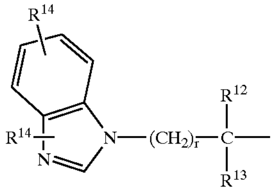

and

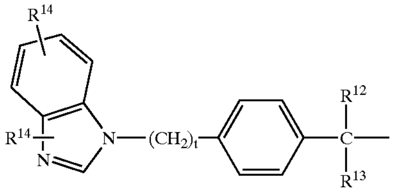

wherein each of $R^{10}$ and $R^{11}$ is independently selected from hydrido and alkyl; wherein each of $R^{12}$ and $R^{13}$ is independently selected from hydrido and alkyl; wherein $R^{14}$ is selected from hydrido, alkyl, haloalkyl, alkoxy and alkylthio;

wherein each of m, n, p and r is a whole number independently selected from 6 through 14; wherein each of q and t is a whole number independently selected from 3 through 6;

wherein $R^2$ is a moiety selected from hydrido, alkyl, cycloalkyl, cycloalkylalkyl, alkenyl, alkynyl, haloalkyl, naphthyl, naphthylalkyl, phenylalkyl, and phenyl, wherein any said $R^2$ moiety may be substituted at a substitutable position by one or more radicals selected from alkyl, halo and alkoxy;

wherein Y is selected from

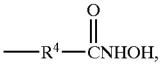

,

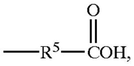

,

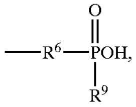

,

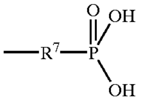

and

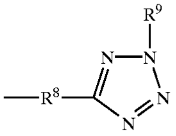

wherein each of $R^4$ through $R^8$ is either a covalent bond or is $—CH_2;$ wherein $R^9$ is selected from hydrido, alkyl and benzyl;

or an acceptable ester, amide, or salt thereof.

7. The method of claim 6 wherein $R^1$ is selected from $H_2N(CH_2)_9—$, $H_2N(CH_2)_{10}—$, $H_2N(CH_2)_{11}—$, $CH_3NH(CH_2)_{10}—$, $(CH_3)_2N(CH_2)_{10}—$, p-$[H_2N(CH_2)_6]C_6H_4CH_2—$, p-$[H_2N(CH_2)_8]C_6H_4CH_2—$, p-$[H_2N(CH_2)_9]C_6H_4CH_2—$, p-$[H_2N(CH_2)_{10}]C_6H_4CH_2—$, p-$[H_2N(CH_2)_6]C_6H_4CH(CH_3)—$, p-$[H_2N(CH_2)_8]C_6H_4CH(CH_3)—$, p-$[H_2N(CH_2)_9]C_6H_4CH(CH_3)—$, p-$[H_2N(CH_2)_{10}]C_6H_4CH(CH_3)—$,

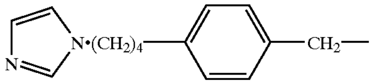

,

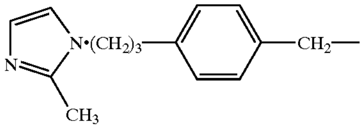

,

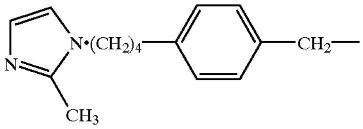

,

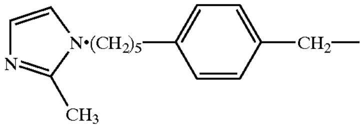

,

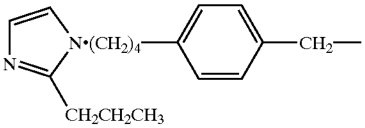

,

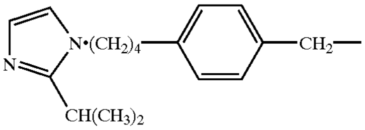

,

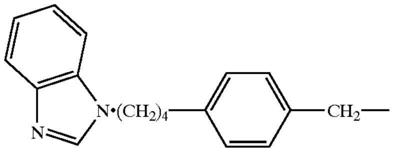

,

-continued

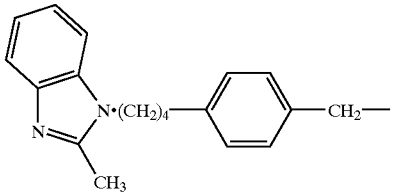,

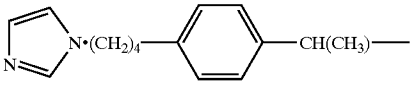,

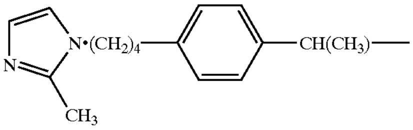,

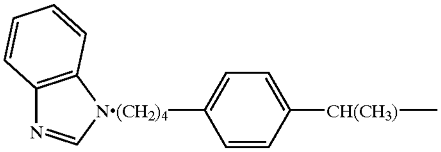 and

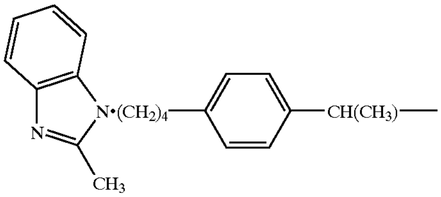;

wherein $R^2$ is selected from —H, —$CH_3$, —$CH_2CH_3$, -$CH_2CH_2CH_3$, —$CH_2CH_2CH_2CH_3$, —$CH_2CH_2CH_2CH_2CH_3$, —$CH_2CH_2CH_2CH_2CH_3$, —CH$(CH_3)_2$, —$CH_2CH(CH_3)_2$, —$CH_2CH_2CH(CH_3)_2$, -cyclo-$C_3H_5$, -cyclo-$C_4H_7$, -cyclo-$C_5H_9$, -cyclo-$C_6H_{11}$, -cyclo-$C_7H_{13}$, -cyclo-$C_8H_{15}$, —$CH(CH_3)(CH_2CH_3)$, —CH$(CH_2CH_3)_2$, —$CH(CH_3)(CH_2CH_2CH_3)$, —$C(CH_3)_3$, HC≡$CCH_2$—, $H_2C$=CH—, $H_2C$=$CHCH_2$—, —$CH_2F$, —$CH_2C_6H_5$, —$CH_2C_6H_4$-p-$OCH_3$, —$CH_2C_6H_4$-p-$CH_3$, —$CH_2C_6H_4$-p-F, —$CH_2CH_2C_6H_5$, —$CH_2$-cyclo-$C_6H_{11}$, —$CH_2$-cyclo-$C_6H_{10}$-4-F, —$CH_2$-cyclo-$C_6H_{10}$-4-$CH_3$, —$CH_2$-cyclo-$C_6H_{10}$-4-$OCH_3$, —$CH_2CH_2$-cyclo-$C_6H_{11}$, —$CH_2$-cyclo-$C_5H_9$, —$CH_2CH_2$-cyclo-$C_5H_9$ and —$CH_2$-2-naphthyl;

wherein Y is selected from —$CO_2H$, —$CH_2CO_2H$, CONHOH, —$PO_3H_2$, and

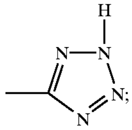;

or an acceptable ester, amide, or salt thereof.

8. The method of claim 7 wherein said compound is selected from compounds and their diastereoisomers of the group consisting of L-Alanine, 3-cyclohexyl-N-[$N^2$-[N-[2-[4-[4-(2-methyl-1H-imidazol-1-yl)butyl]phenyl]oxopropyl]-L-seryl]-L-lysyl]-, (±), bis-trifluoroacetate;

L-Alanine, 3-cyclohexyl-N-[$N^2$-[N-[[4-[4-(2-methyl-1H-imidazol-1-yl)butyl]phenyl]acetyl]-L-seryl]-L-lysyl]-, bis-trifluoroacetate;

L-Alanine, 3-cyclohexyl-N-[[(11-amino-undecanoyl)-L-seryl]-L-lysyl]-, bis-trifluoroacetate;

L-Leucine, N-[[(11-amino-undecanoyl)-L-seryl]-L-lysyl]-, bis-trifluoroacetate;

L-Alanine, N-[$N^2$-[N-[[4-[4-(2-methyl-1H-imidazol-1-yl)butyl]phenyl]acetyl]-L-seryl]-L-lysyl]-, bis-trifluoroacetate;

L-Alanine, 3-phenyl-N-[$N^2$-[N-[[4-[4-(2-methyl-1H-imidazol-1-yl)butyl]phenyl]acetyl]-L-seryl]-L-lysyl]-, bis-trifluoroacetate;

L-iso-Leucine, N-[$N^2$-[N-[[4-[4-(2-methyl-1H-imidazol-1-yl)butyl]phenyl]acetyl]-L-seryl]-L-lysyl]-, bis-trifluoroacetate;

L-Leucine, N-[$N^2$-[N-[[4-[4-(2-methyl-1H-imidazol-1-yl)butyl]phenyl]acetyl]-L-seryl]-L-lysyl]-, bis-trifluoroacetate;

Lysinamide, N-[1-cyclohexyl-2-carboxyethyl]-$N^2$-[N-[[4-[4-(2-methyl-1H-imidazol-1-yl)butyl]phenyl]acetyl]-L-seryl]-, ±, bis-trifluoroacetate;

Lysinamide, N-[1-cyclooctyl-2-carboxyethyl]-$N^2$-[N-[[4-[4-(2-methyl-1H-imidazol-1-yl)butyl]phenyl]acetyl]-L-seryl]-, ±, bis-trifluoroacetate; and D-Alanine, 3-cyclohexyl-N-[$N^2$-[N-[[4-[4-(2-methyl-1H-imidazol-1-yl)butyl]phenyl]acetyl]-L-seryl]-L-lysyl]-, bis-trifluoroacetate.

9. The method of claim 8 wherein said compound is L-Alanine, 3-cyclohexyl-N-[$N^2$-[N-[2-[4-[4-[2-methyl-1H-imidazol-1-yl)butyl]phenyl] oxopropyl]-L-seryl]-L-lysyl]-, (±), bis-trifluoroacetate.

10. The method of claim 8 wherein said compound is L-Alanine, 3-cyclohexyl-N-[$N^2$-[N-[[4-[4-(2-methyl-1H-imidazol-1-yl)butyl]phenyl]acetyl]-L-seryl]-L-lysyl]-, bis-trifluoroacetate.

11. The method of claim 1 wherein said compound is administered topically.

12. The method of claim 1 wherein said compound is administered by gastrointestinal absorption to inhibit systemic growth of *Candida Albicans*.

* * * * *